(12) United States Patent
Damude et al.

(10) Patent No.: US 7,645,604 B2
(45) Date of Patent: *Jan. 12, 2010

(54) DELTA-9 ELONGASES AND THEIR USE IN MAKING POLYUNSATURATED FATTY ACIDS

(75) Inventors: Howard Glenn Damude, Hockessin, DE (US); Brian McGonigle, Wilmington, DE (US); Zhixiong Xue, Chadds Ford, PA (US); Quinn Qun Zhu, West Chester, PA (US)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 280 days.

This patent is subject to a terminal disclaimer.

(21) Appl. No.: 11/601,564

(22) Filed: Nov. 16, 2006

(65) Prior Publication Data

US 2007/0117190 A1 May 24, 2007

Related U.S. Application Data

(60) Provisional application No. 60/739,989, filed on Nov. 23, 2005.

(51) Int. Cl.
*C12N 9/10* (2006.01)
*C12P 7/64* (2006.01)
*C12N 9/00* (2006.01)
*C12N 1/20* (2006.01)
*C12N 15/00* (2006.01)
*C07H 21/04* (2006.01)

(52) U.S. Cl. .................. 435/193; 435/134; 435/183; 435/252.3; 435/320.1; 536/23.2

(58) Field of Classification Search .................. None
See application file for complete search history.

(56) References Cited

U.S. PATENT DOCUMENTS 6,825,017 B1   11/2004   Browse et al.

FOREIGN PATENT DOCUMENTS

| WO | WO 00/34439 A1 | 6/2000 |
|---|---|---|
| WO | 02/077213 A2 | 10/2002 |
| WO | WO 02/077213 A2 | 10/2002 |
| WO | 2004/057001 A1 | 7/2004 |
| WO | WO 2004/057001 A2 | 7/2004 |
| WO | WO 2004/071178 A2 | 8/2004 |
| WO | WO 2004/071467 A2 | 8/2004 |
| WO | WO 2004/101753 A2 | 11/2004 |
| WO | WO 2004/101757 A2 | 11/2004 |
| WO | WO 2005/012316 A2 | 2/2005 |
| WO | WO 2005/083093 A2 | 9/2005 |
| WO | WO 2005/103253 A1 | 11/2005 |
| WO | WO 2006/012325 A1 | 2/2006 |
| WO | WO 2006/012326 A1 | 2/2006 |
| WO | WO 2006/052870 A2 | 5/2006 |
| WO | WO 2006/052871 A2 | 5/2006 |
| WO | WO 2006/055322 A2 | 5/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Qi, Baoxiu et al., Identification of a cDNA encoding a novel C18-Delta9 polyunsaturated fatty acid-specific elongating activity from the docosahexaenoic acid (DHA)-producing microalga, Isochrysis galbana1, FEBS Letters, 2002, p. 159-165, vol. 510.
Qi, Baoxiu et al, Production of very long chain polyunsaturated omega-3 and omega-6 fatty acids in plants, Nature Biotechnology, Jun. 2004, p. 739-745, vol. 22, No. 6.
Beaudoin, Frederic et al., Heterologous reconstitution in yeast of the polyunsaturated fatty acid biosynthetic pathway, PNAS, Jun. 6, 2000, p. 6421-6426, vol. 97, No. 12.
Barsanti, Laura et al., Fatty acid content in wild type and WZSL mutant of Euglena gracilis, Journal of Applied Phycology, 2000, p. 515-520, vol. 12, Kluwer Academic Publishers.
Drexler, Hjordis et al., Metabolic engineering of fatty acids for breeding of new oilseed crops: strategies, problems and first results, Journal of Plant Physiology, 2003, p. 779-802, Urban & Fischer Verlag.
U.S. Appl. No. 11/264,737, filed May 25, 2006, Howard Glenn Damude et al.
U.S. Appl. No. 11/265,761, filed Jun. 1, 2006, Howard Glenn Damude et al.
U.S. Appl. No. 60/739,989, filed Nov. 23, 2005, Howard Glenn Damude et al.
U.S. Appl. No. 60/795,810, filed Apr. 28, 2006, Howard Glenn Damude et al.
U.S. Appl. No. 60/793,575, filed Apr. 20, 2006, Zhixiong Xue et al.
U.S. Appl. No. 60/796,637, filed May 1, 2006, Narendra S. Yadav et al.
U.S. Appl. No. 60/801,172, filed May 17, 2006, Howard Glenn Damude et al.
U.S. Appl. No. 60/801,119, filed May 17, 2006, Howard Glenn Damude et al.
U.S. Appl. No. 60/853,563, filed Oct. 23, 2006, Howard Glenn Damude et al.
U.S. Appl. No. 60/855,177, filed Oct. 30, 2006, Zhixiong Xue et al.
U.S. Appl. No. 10/776,311, filed Sep. 2, 2004, Edgar Benjamin Cahoon et al.
U.S. Appl. No. 10/776,889, filed Feb. 11, 2004, Anthony J. Kinnay et al.
U.S. Appl. No. 11/166,003, filed Aug. 31, 2006, Howard Glenn Damude et al.
U.S. Appl. No. 10/840,478, filed Dec. 16, 2004, Stephen K. Picataggio et al.
U.S. Appl. No. 10/840,579, filed Jun. 23, 2005, Stephen K. Picataggio et al.
U.S. Appl. No. 10/840,325, filed Feb. 24, 2005, Narendra S. Yadav et al.
U.S. Appl. No. 10/869,630, filed Jan. 20, 2005, Stephen K. Picataggio et al.

(Continued)

Primary Examiner—Christian L Fronda
(74) Attorney, Agent, or Firm—Lynne M. Christenbury

(57) ABSTRACT

The present invention relates to Δ9 elongases, which have the ability to convert linoleic acid [18:2, LA] to eicosadienoic acid [20:2, EDA]. Isolated nucleic acid fragments and recombinant constructs comprising such fragments encoding Δ9 elongase along with methods of making long-chain polyunsaturated fatty acids (PUFAs) using these Δ9 elongases in plants and oleaginous yeast are disclosed.

14 Claims, 17 Drawing Sheets

OTHER PUBLICATIONS

U.S. Appl. No. 10/882,760, filed Jul. 20, 2006, Narendra S. Yadav et al.
U.S. Appl. No. 10/985,109, filed Jun. 16, 2005, Howard Glenn Damude et al.
U.S. Appl. No. 10/985,691, filed Sep. 29, 2005, Narendra S. Yadav et al.
U.S. Appl. No. 10/987,548, filed Jun. 16, 2005, Dana M. Walters Pollak.
U.S. Appl. No. 11/024,545, filed May 4, 2006, Zhixiong Xue et al.
U.S. Appl. No. 11/024,544, filed May 4, 2006, Narendra S. Yadav et al.
U.S. Appl. No. 11/166,993, filed Dec. 29, 2005, Howard Glenn Damude et al.
U.S. Appl. No. 11/183,664, filed Jan. 26, 2006, Stephen K. Picataggio et al.
U.S. Appl. No. 11/185,301, filed May 4, 2006, Zhixiong Xue et al.
U.S. Appl. No. 11/190,750, filed May 4, 2006, Stephen K. Picataggio et al.
U.S. Appl. No. 11/198,975, filed Aug. 8, 2005, Quinn Qun et al.
U.S. Appl. No. 11/225,354, filed Mar. 16, 2006, Zhixiong Xue et al.
U.S. Appl. No. 11/251,466, filed May 4, 2006, Howard Glenn Damude et al.
U.S. Appl. No. 11/254,173, filed May 4, 2006, Daniel Joseph Macool et al.
U.S. Appl. No. 11/253,882, filed Apr. 19, 2007, Daniel Joseph Macool et al.
U.S. Appl. No. 11/264,784, filed May 4, 2006, Howard Glenn Damude et al.
J. Dyerberg et. al., Fatty Acid Composition of the Plasma Lipids in Greenland Eskimos, Amer. J. Clin. Nutr., 1975, vol. 28:958-966.
J. Dyerberg et. al., Eicosapentaenoic Acid and Prevention of Thrombosis and Atherosclerosis, Lancet, 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. Schacky et. al., 3 Fatty Acids—From Eskimos to Clinical Cardiology—What Took Us So Long? World Rev. Nutr. Dirt. 2001, vol. 88:90-99.
National Center for Biotechnology Information General Identifier No. AAL37626, Mar. 9, 2006, B. Qi et. al., Identification of a CDNA Encoding a Novel C18-Delta (9) Polyunsaturated Fatty Acid-Specific Elongating Activity From the Docosahexaenoic Acid (DHA)-Producing Microalga, Isochrysis Galbana.
Browse et. al., Polyunsaturated Fatty Acids Synthesis: What Will They Think of Next?, Trends in Biochemical Sciences, 2002, vol. 27:467-473.
Napier, Plumbing the Depths of PUFA Biosynthesis: A Novel Polyketide Synthase-Like Pathway From Marine Organisms, Trends in Plant Sciences, 2002, vol. 7:51-54.
Wallis et. al., The Desaturase of Euglena Gracilis: An Alternate Pathway for Synthesis of 20-Carbon Polyunsaturated Fatty Acids, Arch. Biochem. and Biophys., 1999, vol. 365:307-316.
Sayanova et. al., The Alternative Pathway C20, 8 Desaturase From the Non-Photosynthetic Organism Acanthamoeba Castellanii an Atypical Cytochrome B5-Fusion Destaurase, FEBS LETT., 2006, vol. 580:1946-1952.

\* cited by examiner

FIG. 2

```
       M....N................W.........E.L.........LK..L....G                      Consensus #1
                 10        20        30        40        50
  1    MEVVNEIVSIGQEVLPKVDYAQLWSDASHCEVLYLSIAFVILKFTLGPLG                SEQ ID NO:2 (EgD9e)
  1    MALANDAGE---------RIWAAVTDPEILIGTFSYLLLKPLLRNSG                   SEQ ID NO:8 (IgD9e)

..............YN.L.....S...SF...A.A.....Y..G.......               Consensus #1
                 60        70        80        90       100
 51    PKGQSRMKF--VFTNYNLLMSIYSLGSFLSMAYAM--YTIGV----MS                  SEQ ID NO:2 (EgD9e)
 39    LVDEKKGAYRTSMIWYNVLLALFSALSFYVTATALGWDYGTGAWLRRQTG                SEQ ID NO:8 (IgD9e)

D.....F............D.....F..T.....FY.SK..EY.D...L.L.GK......L    Consensus #1
                110       120       130       140       150
 91    DNCEKAF-----DNNVFRITTQLFYLSKFLEYIDSFYLPLMGKPLTWL                  SEQ ID NO:2 (EgD9e)
 89    DTPQPLFQCPSPVWDSKLFTWTAKAFYYSKYVEYLDTAWLVLKGKRVSFL                SEQ ID NO:8 (IgD9e)

Q.FHH.GAP.D...L........NE.VWIF......N.FIH.IMY.YY............KF   Consensus #1
                160       170       180       190       200
134    QFFHHLGAPMDMWLFYNYRNEAVWIFVLLNGFIHWIMYGYYWTRLIKLKF                SEQ ID NO:2 (EgD9e)
139    QAFHHFGAPWDVYLGIRLHNEGVWIFMFFNSFIHTIMYTYYGLTAAGYKF                SEQ ID NO:8 (IgD9e)

...K.LIT.MQI.QF...GF...VW.Y.N.PC.......D.....F.W.FNY.YVG.        Consensus #1
                210       220       230       240       250
184    PMPKSLIITSMQIIQFNVGFYIVWKYRNIPCYRQDGMRMFGWFFNYFYVGT              SEQ ID NO:2 (EgD9e)
189    -KAKPLITAMQICQFVGGFLLVWDYINVPCFNSDKGKLFSWAFNYAYVGS               SEQ ID NO:8 (IgD9e)

V...LF..F..Q........K......A.K..                                  Consensus #1
                260       270
234    VLCLFLNFYVQTYIVRKHKG-AKKIQ                                        SEQ ID NO:2 (EgD9e)
238    VFLLFCHFFYQDNLATKKSAKAGKQL                                        SEQ ID NO:8 (IgD9e)
```

FIG. 4

| Sample Name | Fatty Acid | 16:0 | 16:1 (9) | 18:0 | 18:1 (9) | LA | GLA | ALA | STA | EDA | DGLA | ARA | ErA | ETA | EPA | 22:2 (13, 16) | 22:4 (7, 10,13, 16) | DPA | 24:1 | % Eo |
|---|---|---|---|---|---|---|---|---|---|---|---|---|---|---|---|---|---|---|---|---|
| pY75 | None | 12.8 | 54.4 | 3.4 | 28.5 | 0.0 | 0.0 | 0.0 | 0.0 | 0.5 | 0.0 | 0.0 | 0.0 | 0.0 | 0.1 | 0.0 | 0.0 | 0.0 | 0.3 | |
| pY119-5 | | 12.5 | 55.2 | 3.5 | 27.3 | 0.0 | 0.0 | 0.0 | 0.0 | 0.6 | 0.0 | 0.0 | 0.0 | 0.0 | 0.0 | 0.0 | 0.0 | 0.0 | 0.7 | |
| pY119-6 | | 13.0 | 53.8 | 3.6 | 28.3 | 0.0 | 0.0 | 0.0 | 0.0 | 0.5 | 0.0 | 0.0 | 0.0 | 0.0 | 0.0 | 0.0 | 0.0 | 0.0 | 0.6 | |
| pY119-8 | | 12.5 | 52.8 | 3.5 | 30.2 | 0.0 | 0.0 | 0.0 | 0.0 | 0.5 | 0.0 | 0.0 | 0.0 | 0.0 | 0.1 | 0.0 | 0.0 | 0.0 | 0.5 | |
| pY75 | LA | 17.4 | 20.5 | 4.6 | 11.1 | | | 0.0 | 0.0 | | 0.0 | 0.0 | 0.0 | 0.0 | 0.0 | 0.0 | 0.0 | 0.0 | 0.5 | 1.2 |
| pY119-5 | | 13.6 | 30.9 | 3.1 | 12.2 | | | 0.0 | 0.0 | | 0.0 | 0.0 | 0.0 | 0.0 | 0.0 | 0.0 | 0.0 | 0.0 | 0.5 | 19.3 |
| pY119-6 | | 15.2 | 26.7 | 4.0 | 13.4 | | | 0.0 | 0.0 | | 0.0 | 0.0 | 0.5 | 0.0 | 0.0 | 0.2 | 0.0 | 0.0 | 0.6 | 22.1 |
| pY119-8 | | 14.0 | 29.1 | 3.9 | 15.2 | | | 0.0 | 0.0 | | 0.0 | 0.0 | 0.0 | 0.0 | 0.0 | 0.2 | 0.0 | 0.0 | 0.4 | 27.2 |
| pY75 | ALA | 11.1 | 6.2 | 4.4 | 4.4 | 0.2 | 0.0 | | 0.0 | 0.4 | 0.0 | 0.0 | 0.0 | 0.0 | 0.0 | 0.0 | 0.0 | 0.0 | 0.3 | 0.4 |
| pY119-5 | | 11.7 | 17.0 | 4.9 | 13.3 | 0.1 | 0.0 | | 0.0 | 0.3 | 0.0 | 0.0 | 0.0 | 0.0 | 0.0 | 0.1 | 0.0 | 0.0 | 0.4 | 21.4 |
| pY119-6 | | 11.7 | 16.1 | 5.0 | 12.6 | 0.1 | 0.0 | | 0.0 | 0.3 | 0.0 | 0.0 | 0.2 | 0.0 | 0.0 | 0.4 | 0.0 | 0.0 | 0.4 | 21.7 |
| pY119-8 | | 11.1 | 17.0 | 4.7 | 13.1 | 0.1 | 0.0 | | 0.0 | 0.2 | 0.0 | 0.0 | 0.0 | 0.0 | 0.0 | 0.5 | 0.0 | 0.0 | 0.4 | 22.9 |
| pY75 | GLA | 16.4 | 7.8 | 5.4 | 6.0 | 0.0 | | 0.0 | 0.0 | 0.4 | 0.0 | 0.0 | 0.0 | 0.0 | 0.0 | 0.6 | 0.0 | 0.0 | 0.6 | 0.6 |
| pY119-5 | | 16.4 | 10.1 | 5.8 | 8.4 | 0.0 | | 0.0 | 0.2 | 0.4 | 0.1 | 0.0 | 0.0 | 0.0 | 0.0 | 0.5 | 0.0 | 0.0 | 0.7 | 0.8 |
| pY119-6 | | 14.6 | 9.8 | 4.7 | 7.0 | 0.0 | | 0.0 | 0.2 | 0.3 | 0.1 | 0.0 | 0.0 | 0.0 | 0.0 | 0.6 | 0.0 | 0.0 | 0.5 | 0.7 |
| pY119-8 | | 16.4 | 8.0 | 4.9 | 6.1 | 0.0 | | 0.0 | 0.2 | 0.2 | 0.1 | 0.0 | 0.0 | 0.0 | 0.0 | 0.5 | 0.0 | 0.0 | 0.5 | 0.9 |
| pY75 | STA | 11.5 | 5.9 | 4.9 | 5.9 | 0.0 | 0.0 | 0.0 | | 0.3 | 0.0 | 0.0 | 0.0 | 0.0 | 0.0 | 0.0 | 0.0 | 0.0 | 0.5 | 0.5 |
| pY119-5 | | 12.5 | 5.4 | 5.0 | 5.0 | 0.0 | 0.1 | 0.0 | | 0.3 | 0.1 | 0.0 | 0.0 | 0.0 | 0.0 | 0.0 | 0.0 | 0.0 | 0.7 | 0.7 |
| pY119-6 | | 11.4 | 6.6 | 5.2 | 7.0 | 0.0 | 0.1 | 0.0 | | 0.3 | 0.1 | 0.0 | 0.0 | 0.0 | 0.0 | 0.0 | 0.0 | 0.0 | 0.5 | 0.6 |
| pY119-8 | | 11.3 | 5.0 | 3.9 | 4.5 | 0.0 | 0.0 | 0.0 | | 0.2 | 0.1 | 0.0 | 0.0 | 0.0 | 0.0 | 0.0 | 0.0 | 0.0 | 0.5 | 0.6 |
| pY75 | ARA | 19.2 | 33.2 | 4.9 | 17.3 | 0.0 | 0.0 | 0.0 | 0.0 | 0.6 | 0.0 | | 0.0 | 0.0 | 0.0 | 0.0 | 0.0 | 0.0 | 0.7 | 0.0 |
| pY119-5 | | 18.6 | 34.4 | 4.8 | 19.0 | 0.0 | 0.0 | 0.0 | 0.0 | 0.5 | 0.1 | | 0.0 | 0.0 | 0.0 | 0.0 | 0.0 | 0.0 | 0.8 | 0.5 |
| pY119-6 | | 16.9 | 34.4 | 5.5 | 24.4 | 0.0 | 0.0 | 0.0 | 0.0 | 0.3 | 0.1 | | 0.0 | 0.0 | 0.0 | 0.0 | 0.0 | 0.0 | 0.6 | 0.6 |
| pY119-8 | | 17.7 | 36.5 | 4.4 | 18.7 | 0.0 | 0.0 | 0.0 | 0.0 | 0.5 | 0.1 | | 0.0 | 0.0 | 0.0 | 0.0 | 0.0 | 0.0 | 0.5 | 0.5 |
| pY75 | EPA | 16.7 | 27.7 | 4.7 | 16.4 | 0.0 | 0.0 | 0.0 | 0.0 | 0.4 | 0.0 | 0.0 | 0.0 | 0.0 | | 0.0 | 0.0 | 0.0 | 0.4 | 0.0 |
| pY119-5 | | 16.0 | 29.9 | 5.0 | 18.7 | 0.0 | 0.0 | 0.0 | 0.0 | 0.0 | 0.0 | 0.1 | 0.0 | 0.0 | | 0.0 | 0.0 | | 0.5 | 0.4 |
| pY119-6 | | 17.4 | 27.3 | 6.0 | 20.8 | 0.0 | 0.0 | 0.0 | 0.0 | 0.0 | 0.0 | 0.1 | 0.0 | 0.0 | | 0.1 | 0.0 | | 0.5 | 0.4 |
| pY119-8 | | 16.5 | 28.8 | 5.9 | 22.1 | 0.0 | 0.0 | 0.0 | 0.0 | 0.0 | 0.0 | 0.1 | 0.0 | 0.0 | | 0.0 | 0.0 | | 0.6 | 0.4 |

SEQUENCE LISTING

<160> NUMBER OF SEQ ID NOS: 129

<210> SEQ ID NO 1
<211> LENGTH: 777
<212> TYPE: DNA
<213> ORGANISM: Euglena gracilis

<400> SEQUENCE: 1

```
atggaggtgg tgaatgaaat agtctcaatt gggcaggaag ttttacccaa agttgattat      60
gcccaactct ggagtgatgc cagtcactgt gaggtgcttt acttgtccat cgcatttgtc     120
atcttgaagt tcactcttgg ccccttggt ccaaaaggtc agtctcgtat gaagtttgtt     180
ttcaccaatt acaaccttct catgtccatt tattcgttgg gatcattcct ctcaatggca     240
tatgccatgt acaccatcgg tgttatgtct gacaactgcg agaaggcttt tgacaacaac     300
gtcttcagga tcaccacgca gttgttctat ttgagcaagt tcctggagta tattgactcc     360
ttctatttgc cactgatggg caagcctctg acctggttgc aattcttcca tcatttgggg     420
gcaccgatgg atatgtggct gttctataat taccgaaatg aagctgtttg gattttttgtg    480
ctgttgaatg gtttcatcca ctggatcatg tacggttatt attggaccag attgatcaag     540
ctgaagttcc ccatgccaaa atccctgatt acatcaatgc agatcattca attcaatgtt     600
ggtttctaca ttgtctggaa gtacaggaac attcctgtt atcgccaaga tgggatgagg     660
atgtttggct ggttcttcaa ttactttat gttggcacag tcttgtgttt gttcttgaat      720
ttctatgtgc aaacgtatat cgtcaggaag cacaagggag ccaaaaagat tcagtga       777
```

<210> SEQ ID NO 2
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: delta-9 elongase (EgD9e)

<400> SEQUENCE: 2

```
Met Glu Val Val Asn Glu Ile Val Ser Ile Gly Gln Glu Val Leu Pro
1               5                  10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160
```

```
Leu Leu Asn Gly Phe Ile His Trp Ile Met Tyr Gly Tyr Tyr Trp Thr
            165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
            195                 200                 205

Arg Asn Ile Pro Cys Tyr Arg Gln Asp Gly Met Arg Met Phe Gly Trp
            210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 3
<211> LENGTH: 777
<212> TYPE: DNA
<213> ORGANISM: Artificial Sequence
<220> FEATURE:
<223> OTHER INFORMATION: EgD9eS: synthetic delta-9 elongase derived from
    Euglena gracilis and codon-optimized for expression in Yarrowia
    lipolytica

<400> SEQUENCE: 3

```
atggaggtcg tgaacgaaat cgtctccatt ggccaggagg ttcttcccaa ggtcgactat      60
gctcagctct ggtctgatgc ctcgcactgc gaggtgctgt acctctccat cgccttcgtc     120
atcctgaagt tcacccttgg tcctctcgga cccaagggtc agtctcgaat gaagtttgtg     180
ttcaccaact acaacctgct catgtccatc tactcgctgg ctccttcct ctctatggcc      240 tacgccatgt acaccattgg tgtcatgtcc gacaactgcg agaaggcttt cgacaacaat     300
gtcttccgaa tcaccactca gctgttctac ctcagcaagt tcctcgagta cattgactcc     360
ttctatctgc ccctcatggg caagcctctg acctggttgc agttctttca ccatctcgga     420
gctcctatgg acatgtggct gttctacaac taccgaaacg aagccgtttg gatctttgtg     480
ctgctcaacg gcttcattca ctggatcatg tacggctact attggacccg actgatcaag     540
ctcaagttcc ctatgcccaa gtccctgatt acttctatgc agatcattca gttcaacgtt     600
ggcttctaca tcgtctggaa gtaccggaac attcctgct accgacaaga tggaatgaga      660
atgtttggct ggttttcaa ctacttctac gttggtactg tcctgtgtct gttcctcaac      720
ttctacgtgc agacctacat cgtccgaaag cacaagggag ccaaaaagat tcagtga       777
```

<210> SEQ ID NO 4
<211> LENGTH: 792
<212> TYPE: DNA
<213> ORGANISM: Eutreptiella sp. CCMP389

<400> SEQUENCE: 4

```
atggctgcgg tgatagaggt cgccaacgag tttgtagcca tcacggcaga aacgctcccc      60
aaagttgact atcaacgact atggcgagac atttacagtt gtgagctact gtatttctcc     120
attgccttcg tgatcttgaa gtttacgttg ggcgagttga gcgacagcgg aaaaaagatt     180
ttgagagtgt tgttcaagtg gtacaatctc ttcatgtccg tgttctcctt ggtgtctttc     240
ctttgcatgg gctatgccat ttataccgtg ggcctatact ctaacgaatg cgacagggct     300
ttcgacaact cgttgttccg ctttgcaaca aaggtgttct actacagtaa gttttttggag    360
```

```
tacatcgact cttttatct tccgctcatg gccaagccgc tgtctttcct gcaattcttc    420
catcacttgg gagccccat ggacatgtgg ctctttgtcc aatattctgg ggaatctatt    480
tggatctttg tgttttgaa tgggttcatt cactttgtta tgtacgggta ctactggact    540
cggctgatga agttcaattt cccaatgccc aagcagttga ttaccgcgat gcagatcacg    600
cagttcaacg ttggtttcta cctcgtgtgg tggtacaaag atattccctg ctaccgaaag    660
gatcccatgc gaatgttggc ctggatcttc aattactggt atgttgggac tgtcttgctg    720
ctgttcatta atttcttcgt caaatcctat gtgttcccaa agccgaagac tgcagataaa    780
aaggtccaat ag                                                       792
```

<210> SEQ ID NO 5
<211> LENGTH: 263
<212> TYPE: PRT
<213> ORGANISM: Eutreptiella sp. CCMP389
<220> FEATURE:
<221> NAME/KEY: MISC_FEATURE
<222> LOCATION: (1)..(263)
<223> OTHER INFORMATION: delta-9 elongase (E389D9e)

<400> SEQUENCE: 5

```
Met Ala Ala Val Ile Glu Val Ala Asn Glu Phe Val Ala Ile Thr Ala
 1               5                  10                  15

Glu Thr Leu Pro Lys Val Asp Tyr Gln Arg Leu Trp Arg Asp Ile Tyr
             20                  25                  30

Ser Cys Glu Leu Leu Tyr Phe Ser Ile Ala Phe Val Ile Leu Lys Phe
         35                  40                  45

Thr Leu Gly Glu Leu Ser Asp Ser Gly Lys Lys Ile Leu Arg Val Leu
     50                  55                  60

Phe Lys Trp Tyr Asn Leu Phe Met Ser Val Phe Ser Leu Val Ser Phe
 65                  70                  75                  80

Leu Cys Met Gly Tyr Ala Ile Tyr Thr Val Gly Leu Tyr Ser Asn Glu
                 85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260
```

<210> SEQ ID NO 6
<211> LENGTH: 792
<212> TYPE: DNA
<213> ORGANISM: Artificial Sequence
<220> FEATURE:
<223> OTHER INFORMATION: E389D9eS: synthetic delta-9 elongase derived
      from Eutreptiella sp. CCMP389 and codon-optimized for expression
      in Yarrowia lipolytica

<400> SEQUENCE: 6

| | |
|---|---|
| atggctgccg tcatcgaggt ggccaacgag ttcgtcgcta tcactgccga gacccttccc | 60 |
| aaggtggact atcagcgact ctggcgagac atctactcct gcgagctcct gtacttctcc | 120 |
| attgctttcg tcatcctcaa gtttacccct ggcgagctct cggattctgg caaaaagatt | 180 |
| ctgcgagtgc tgttcaagtg gtacaacctc ttcatgtccg tctttcgct ggtgtccttc | 240 |
| ctctgtatgg gttacgccat ctacaccgtt ggactgtact ccaacgaatg cgacagagct | 300 |
| ttcgacaaca gcttgttccg atttgccacc aaggtcttct actattccaa gtttctggag | 360 |
| tacatcgact ctttctacct tcccctcatg gccaagcctc tgtcctttct gcagttcttt | 420 |
| catcacttgg gagctcctat ggacatgtgg ctcttcgtgc agtactctgg cgaatccatt | 480 |
| tggatctttg tgttcctgaa cggattcatt cactttgtca tgtacggcta ctattggaca | 540 |
| cggctgatga gttcaacttt cccatgccc aagcagctca ttaccgcaat gcagatcacc | 600 |
| cagttcaacg ttggcttcta cctcgtgtgg tggtacaagg acattccctg ttaccgaaag | 660 |
| gatcccatgc gaatgctggc ctggatcttc aactactggt acgtcggtac cgttcttctg | 720 |
| ctcttcatca acttctttgt caagtcctac gtgtttccca gcctaagac tgccgacaaa | 780 |
| aaggtccagt ag | 792 |

<210> SEQ ID NO 7
<211> LENGTH: 1064
<212> TYPE: DNA
<213> ORGANISM: Isochrysis galbana (GenBank Accession No. AF390174)
<220> FEATURE:
<221> NAME/KEY: CDS
<222> LOCATION: (2)..(793)
<223> OTHER INFORMATION: delta-9 elongase (IgD9e)

<400> SEQUENCE: 7

```
g atg gcc ctc gca aac gac gcg gga gag cgc atc tgg gcg gct gtg acc        49
  Met Ala Leu Ala Asn Asp Ala Gly Glu Arg Ile Trp Ala Ala Val Thr
  1               5                  10                  15 gac ccg gaa atc ctc att ggc acc ttc tcg tac ttg cta ctc aaa ccg           97
Asp Pro Glu Ile Leu Ile Gly Thr Phe Ser Tyr Leu Leu Leu Lys Pro
             20                  25                  30 ctg ctc cgc aat tcc ggg ctg gtg gat gag aag aag ggc gca tac agg          145
Leu Leu Arg Asn Ser Gly Leu Val Asp Glu Lys Lys Gly Ala Tyr Arg
         35                  40                  45 acg tcc atg atc tgg tac aac gtt ctg ctg gcg ctc ttc tct gcg ctg          193
Thr Ser Met Ile Trp Tyr Asn Val Leu Leu Ala Leu Phe Ser Ala Leu
     50                  55                  60 agc ttc tac gtg acg gcg acc gcc ctc ggc tgg gac tat ggt acg ggc          241
Ser Phe Tyr Val Thr Ala Thr Ala Leu Gly Trp Asp Tyr Gly Thr Gly
 65                  70                  75                  80 gcg tgg ctg cgc agg caa acc ggc gac aca ccg cag ccg ctc ttc cag          289
Ala Trp Leu Arg Arg Gln Thr Gly Asp Thr Pro Gln Pro Leu Phe Gln
                 85                  90                  95 tgc ccg tcc ccg gtt tgg gac tcg aag ctc ttc aca tgg acc gcc aag          337
Cys Pro Ser Pro Val Trp Asp Ser Lys Leu Phe Thr Trp Thr Ala Lys
            100                 105                 110
```

```
gca ttc tat tac tcc aag tac gtg gag tac ctc gac acg gcc tgg ctg      385
Ala Phe Tyr Tyr Ser Lys Tyr Val Glu Tyr Leu Asp Thr Ala Trp Leu
        115                 120                 125 gtg ctc aag ggc aag agg gtc tcc ttt ctc cag gcc ttc cac cac ttt      433
Val Leu Lys Gly Lys Arg Val Ser Phe Leu Gln Ala Phe His His Phe
130                 135                 140 ggc gcg ccg tgg gat gtg tac ctc ggc att cgg ctg cac aac gag ggc      481
Gly Ala Pro Trp Asp Val Tyr Leu Gly Ile Arg Leu His Asn Glu Gly
145                 150                 155                 160 gta tgg atc ttc atg ttt ttc aac tcg ttc att cac acc atc atg tac      529
Val Trp Ile Phe Met Phe Phe Asn Ser Phe Ile His Thr Ile Met Tyr
                165                 170                 175 acc tac tac ggc ctc acc gcc gcc ggg tat aag ttc aag gcc aag ccg      577
Thr Tyr Tyr Gly Leu Thr Ala Ala Gly Tyr Lys Phe Lys Ala Lys Pro
            180                 185                 190 ctc atc acc gcg atg cag atc tgc cag ttc gtg ggc ggc ttc ctg ttg      625
Leu Ile Thr Ala Met Gln Ile Cys Gln Phe Val Gly Gly Phe Leu Leu
        195                 200                 205 gtc tgg gac tac atc aac gtc ccc tgc ttc aac tcg gac aaa ggg aag      673
Val Trp Asp Tyr Ile Asn Val Pro Cys Phe Asn Ser Asp Lys Gly Lys
210                 215                 220 ttg ttc agc tgg gct ttc aac tat gca tac gtc ggc tcg gtc ttc ttg      721
Leu Phe Ser Trp Ala Phe Asn Tyr Ala Tyr Val Gly Ser Val Phe Leu
225                 230                 235                 240 ctc ttc tgc cac ttt ttc tac cag gac aac ttg gca acg aag aaa tcg      769
Leu Phe Cys His Phe Phe Tyr Gln Asp Asn Leu Ala Thr Lys Lys Ser
                245                 250                 255 gcc aag gcg ggc aag cag ctc tag gcctcgagcc ggctcgcggg ttcaaggagg     823
Ala Lys Ala Gly Lys Gln Leu
            260 gcgacacggg ggtgggacgt ttgcatggag atggattgtg gatgtcctta cgccttactc    883 atcaatgtcc tcccatctct cccctctaga ccttctacta gccatctaga agggcagctc    943 agagacggat accgttcccc ctcccttcc ttttcgtctt tgctttgcca ttgtttgttt    1003 gtctctattt tttaaactat tgacgctaac gcgttacgct cgcaaaaaaa aaaaaaaaa    1063 a                                                                   1064

<210> SEQ ID NO 8
<211> LENGTH: 263
<212> TYPE: PRT
<213> ORGANISM: Isochrysis galbana (GenBank Accession No. AF390174)

<400> SEQUENCE: 8

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110
```

```
Ala Phe Tyr Tyr Ser Lys Tyr Val Glu Tyr Leu Asp Thr Ala Trp Leu
            115                 120                 125

Val Leu Lys Gly Lys Arg Val Ser Phe Leu Gln Ala Phe His His Phe
        130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 9
<211> LENGTH: 792
<212> TYPE: DNA
<213> ORGANISM: Artificial Sequence
<220> FEATURE:
<223> OTHER INFORMATION: IgD9eS: synthetic delta-9 elongase derived from
      Isochrysis galbana and codon-optimized for expression in Yarrowia
      lipolytica

<400> SEQUENCE: 9
atggctctgg ccaacgacgc tggcgagcga atctgggctg ccgtcaccga tcccgaaatc      60
ctcattggca ccttctccta cctgctcctg aagcctctcc tgcgaaactc tggtctcgtg     120
gacgagaaga aggagcctta ccgaacctcc atgatctggt acaacgtcct cctggctctc     180
ttctctgccc tgtccttcta cgtgactgcc accgctctcg gctgggacta cggtactgga     240
gcctggctgc gaagacagac cggtgatact ccccagcctc tctttcagtg tccctctcct     300
gtctgggact ccaagctgtt cacctggact gccaaggcct tctactattc taagtacgtg     360
gagtacctcg acaccgcttg gctggtcctc aagggcaagc gagtgtcctt ctgcaggcc     420 ttccatcact tggagctcc ctgggacgtc tacctcggca ttcgactgca caacgagggt     480
gtgtggatct tcatgttctt taactcgttc attcacacca tcatgtacac ctactatgga     540
ctgactgccg ctggctacaa gttcaaggcc aagcctctga tcactgccat gcagatttgc     600
cagttcgtcg gtggctttct cctggtctgg gactacatca acgttccctg cttcaactct     660
gacaagggca agctgttctc ctgggctttc aactacgcct acgtcggatc tgtctttctc     720
ctgttctgtc acttcttta ccaggacaac ctggccacca gaaatccgc taaggctggt     780 aagcagcttt ag                                                          792

<210> SEQ ID NO 10
<211> LENGTH: 757
<212> TYPE: DNA
<213> ORGANISM: Euglena gracilis
<220> FEATURE:
<221> NAME/KEY: misc_feature
<222> LOCATION: (677)..(677)
```

<223> OTHER INFORMATION: n is a, c, g, or t

<400> SEQUENCE: 10

| | | | | | |
|---|---|---|---|---|---|
| ttttttttcg | aacacttaat | ggaggtggtg | aatgaaatag | tctcaattgg | gcaggaagtt | 60 |
| ttacccaaag | ttgattatgc | ccaactctgg | agtgatgcca | gtcactgtga | ggtgctttac | 120 |
| ttgtccatcg | catttgtcat | cttgaagttc | actcttggcc | cccttggtcc | aaaaggtcag | 180 |
| tctcgtatga | agtttgtttt | caccaattac | aaccttctca | tgtccattta | ttcgttggga | 240 |
| tcattcctct | caatggcata | tgccatgtac | accatcggtg | ttatgtctga | caactgcgag | 300 |
| aaggcttttg | acaacaacgt | cttcaggatc | accacgcagt | tgttctattt | gagcaagttc | 360 |
| ctggagtata | ttgactcctt | ctatttgcca | ctgatgggca | agcctctgac | ctggttgcaa | 420 |
| ttcttccatc | atttggggc | accgatggat | atgtggctgt | tctataatta | ccgaaatgaa | 480 |
| gctgtttgga | tttttgtgct | gttgaatggt | ttcatccact | ggatcatgta | cggttattat | 540 |
| tggaccagat | tgatcaagct | gaagttcccc | atgccaaaat | ccctgattac | atcaatgcag | 600 |
| atcattcaat | tcaatgttgg | tttctacatt | gtctggaagt | acaggaacat | tccctgttat | 660 |
| cgccaagatg | ggatgangat | gtttggctgg | ttcttcaatt | acttttatgt | tggcacagtc | 720 |
| ttgtgtttgt | tcttgaattt | ctatgtgcaa | acgtata | | | 757 |

<210> SEQ ID NO 11
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 11

| | | | | | |
|---|---|---|---|---|---|
| tcaggatcac | cacgcagttg | ttctatttga | gcangttcct | ggagtatatt | gactccttct | 60 |
| atttgccant | gatgggcaag | cntctgacct | ggttgcaatt | cttccatcat | tnggggcac | 120 |
| cgatggatat | gtggctgttc | tataattacc | gaaatgaagc | tgtttggatt | tttgtgctgt | 180 |
| tgaatggttt | catccactgg | atcatgtacg | gttattannn | gaccagattg | atcaagctga | 240 |
| agttccccat | gccaaaatcc | ctgattacat | caatgcagat | cattcaattc | aatgttggtt | 300 |
| tctacattgt | ctggaagtac | aggaacattc | cctgttatcg | ccaagatggg | atgaggatgt | 360 |
| ttggctggtt | cttcaattac | ttttatgttg | gcacagtctt | gtgtttgttc | ttgaatttct | 420 |

```
atgtgcaaac gtatatcgtc aggaagcaca agggagccaa aaagattcag tgatatttcc      480
tcctctgcgg tggcctcttt tgacctcccc ttgacaccta taatgtggag gtgtcgggct      540
ctctccgtct caccagcact tgactctgca ggtgctcact tttatttttt acccatcttt      600
gcttgttgac cattcacctc tcccacttcc acatagtcca ttctaactgt tgcagactgc      660
ggtccatttt ttccagagct cccaatgacc atacgcgaca ccttgtnnnc ncccagccca      720
ttgtgcacaa ttcatagtgg catcgttttg ccttgatacg tgtgcatcca gcgg            774

<210> SEQ ID NO 12
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 12
gacatggcaa ctatgatttt attttgactg atagtgacct gttcgttgca acaaattgat       60
gagcaatgct tttttataat gccaactttg tacaaaaaag ttggattttt tttcgaacac      120
ttaatggagg tggtgaatga aatagtctca attgggcagg aagttttacc caaagttgat      180
tatgcccaac tctggagtga tgccagtcac tgtgaggtgc tttacttgtc catcgcattt      240
gtcatcttga agttcactct tggccccctt ggtccaaaag gtcagtctcg tatgaagttt      300
gttttcacca attacaacct tctcatgtcc atttattcgt tgggatcatt cctctcaatg      360
gcatatgcca tgtacaccat cggtgttatg tctgacaact gcgagaaggc ttttgacaac      420
aacgtcttca ggatcaccac gcagttgttc tatttgagca agttcctgga gtatattgac      480
tccttctatt tgccactgat gggcaagcct ctgacctggt tgcaattctt ccatcatttg      540
ggggcaccga tggatatgtg gctgttctat aattaccgaa atgaagctgt ttggattttt      600
gtgctgttga atggtttcat ccactggatc atgtacggtt attattggac cagattgatc      660
aagctgaagt tccccatgcc aaaatccctg attacatcaa tgcagatcat tcaattcaat      720
gttggtttct acattgtctg gaagtacagg aacattccct gttatcgcca agatgggatg      780
aggatgtttg gctggttctt caattacttt tatgttggca cagtcttgtg tttgttcttg      840
aatttctatg tgcaaacgta tatcgtcagg aagcacaagg gagccaaaaa gattcagtga      900
tatttcctcc tctgcggtgg cctcttttga cctccccttg acacctataa tgtggaggtg      960
tcgggctctc tccgtctcac cagcacttga ctctgcaggt gctcactttt attttttacc     1020
catctttgct tgttgaccat tcacctctcc cacttccaca tagtccattc taactgttgc     1080
agactgcggt ccattttttc cagagctccc aatgaccata cgcgacacct tgtnnncncc     1140
cagcccattg tgcacaattc atagtggcat cgttttgcct tgatacgtgt gcatccagcg     1200
g                                                                     1201

<210> SEQ ID NO 13
<211> LENGTH: 200
<212> TYPE: DNA
<213> ORGANISM: Eutreptiella sp. CCMP389

<400> SEQUENCE: 13
```

-continued

| ttacagttct tccaccactt gggagccccc atggacatgt ggctctttgt ccaatattct | 60 |
| gggaatcta tttggatctt tgtgttttg aatgggttca ttcactttgt tatgtacggg | 120 |
| tactactgga ctcggctgat gaagttcaat ttcccaatgc ccaagcagtt gattaccgcg | 180 |
| atgcagatca tccaattcaa | 200 |

<210> SEQ ID NO 14
<211> LENGTH: 406
<212> TYPE: DNA
<213> ORGANISM: Eutreptiella sp. CCMP389

<400> SEQUENCE: 14

| atggcgagac atttacagtt gtgagctact gtatttctcc attgccttcg tgatcttgaa | 60 |
| gtttacgttg ggcgagttga gcgacagcgg aaaaaagatt ttgagagtgt tgttcaagtg | 120 |
| gtacaatctc ttcatgtccg tgttctcctt ggtgtctttc ctttgcatgg gctatgccat | 180 |
| ttataccgtg ggcctatact ctaacgaatg cgacagggct ttcgacaact cgttgttccg | 240 |
| ctttgcaaca aggtgttct actacagtaa gttttttggag tacatcgact cttttatct | 300 |
| tccgctcatg gccaagccgc tgtctttcct gcaattcttc catcacttgg gagcccccat | 360 |
| ggacatgtgg ctctttgtcc aatattctgg ggaatctatt tggatc | 406 |

<210> SEQ ID NO 15
<211> LENGTH: 197
<212> TYPE: DNA
<213> ORGANISM: Eutreptiella sp. CCMP389

<400> SEQUENCE: 15

| tccatttcgc ccgtcaagcc agagtggcca ttacggctgg tcggacacaa catggctgcg | 60 |
| gtgatagagg tcgccaacga gtttgtagcc atcacggcag aaacgctccc caaagttgac | 120 |
| tatcaacgac tatggcgaga catttacagt tgtgagctac tgtatttctc cattgccttc | 180 |
| gtgatcttga agtttac | 197 |

<210> SEQ ID NO 16
<211> LENGTH: 920
<212> TYPE: DNA
<213> ORGANISM: Eutreptiella sp. CCMP389

<400> SEQUENCE: 16

| ctggactcgg ctgatgaagt tcaatttccc aatgcccaag cagttgatta ccgcgatgca | 60 |
| gatcacgcag ttcaacgttg gtttctacct cgtgtggtgg tacaaagata ttccctgcta | 120 |
| ccgaaaggat cccatgcgaa tgttggcctg atcttcaat tactggtatg ttgggactgt | 180 |
| cttgctgctg ttcattaatt tcttcgtcaa atcctatgtg ttcccaaagc cgaagactgc | 240 |
| agataaaaag gtccaatagc tgcacacaca caattatgca gctccccacc actttctccc | 300 |
| caaaacagcc agccagcccc cttcccatga acaagaacc tacccctcc ctgctcctct | 360 |
| ttttttaatc tcttattcca ccatacactt gatgacaaca gttgccgtgc agtggagcta | 420 |
| tgtggtgcat gctgcaatgc actggggcat catattaaga ttattgttat tagtggtgcc | 480 |
| cttgcttctc tgctttgtgc ccctggtacc agggtgcacc catgatgcag tacacaagtt | 540 |
| gttcaatgtg tgcactgtgg tattctctga attccttgag gagccattta gtttaaccaa | 600 |
| gcatgactcg gctggattgg ctcgaggtca ttgcggaagc aaaagtttg cgaggcagct | 660 |
| gccgaaggtg ctgctaagtt cggcttcaaa ctggcctttg cacacccagg tacccaggga | 720 |
| ttccaagtct catggctggc atattttagg tttcatgcat ccgcagtggc gtttatgcaa | 780 |

```
ggcacagacg tttatattta tggatatgcg agtgaaggtt ggcttgccag cattggcatc    840
gcctgcctgc atactgagtt tgttgtaaa agtacaaact cagtatcaac aatacaattt    900
ttktttgaaa aaaaaaaaaa                                                920

<210> SEQ ID NO 17
<211> LENGTH: 1504
<212> TYPE: DNA
<213> ORGANISM: Eutreptiella sp. CCMP389
<220> FEATURE:
<221> NAME/KEY: misc_feature
<222> LOCATION: (1487)..(1487)
<223> OTHER INFORMATION: n is a, c, g, or t

<400> SEQUENCE: 17
tccatttcgc ccgtcaagcc agagtggcca ttacggctgg tcggacacaa catggctgcg     60
gtgatagagg tcgccaacga gtttgtagcc atcacggcag aaacgctccc caaagttgac    120
tatcaacgac tatggcgaga catttacagt tgtgagctac tgtatttctc cattgccttc    180
gtgatcttga agtttacgtt gggcgagttg agcgacagcg gaaaaaagat tttgagagtg    240
ttgttcaagt ggtacaatct cttcatgtcc gtgttctcct tggtgtcttt cctttgcatg    300
ggctatgcca tttataccgt gggcctatac tctaacgaat gcgacagggc tttcgacaac    360
tcgttgttcc gctttgcaac aaaggtgttc tactacagta agttttttgga gtacatcgac    420 tcttttatc ttccgctcat ggccaagccg ctgtctttcc tgcaattctt ccatcacttg    480
ggagccccca tggacatgtg gctctttgtc caatattctg gggaatctat ttggatcttt    540 gtgttttttga atgggttcat tcactttgtt atgtacgggt actactggac tcggctgatg    600
aagttcaatt tcccaatgcc caagcagttg attaccgcga tgcagatcac gcagttcaac    660 gttggttttct acctcgtgtg gtggtacaaa gatattccct gctaccgaaa ggatcccatg    720
cgaatgttgg cctggatctt caattactgg tatgttggga ctgtcttgct gctgttcatt    780
aatttcttcg tcaaatccta tgtgttccca agccgaaga ctgcagataa aaaggtccaa    840
tagctgcaca cacacaatta tgcagctccc caccactttc tccccaaaac agccagccag    900
cccccttccc atgaaacaag aacctacccc ctccctgctc ctcttttttt aatctcttat    960
tccaccatac acttgatgac aacagttgcc gtgcagtgga gctatgtggt gcatgctgca   1020
atgcactggg gcatcatatt aagattattg ttattagtgg tgcccttgct tctctgcttt   1080
gtgcccctgg taccagggtg cacccatgat gcagtacaca agttgttcaa tgtgtgcact   1140
gtggtattct ctgaattcct tgaggagcca tttagtttaa ccaagcatga ctcggctgga   1200
ttggctcgag gtcattgcgg aagcaaaagt tttgcgaggc agctgccgaa ggtgctgcta   1260
agttcggctt caaactggcc tttgcacacc caggtaccca gggattccaa gtctcatggc   1320
tggcatattt taggtttcat gcatccgcag tggcgtttat gcaaggcaca gacgtttata   1380
tttatggata tgcgagtgaa ggttggcttg ccagcattgg catcgcctgc ctgcatactg   1440
agttttgttg taaagtaca aactcagtat caacaataca attttntttt gaaaaaaaaa   1500
aaaa                                                                1504

<210> SEQ ID NO 18
<211> LENGTH: 18
<212> TYPE: DNA
<213> ORGANISM: Artificial Sequence
<220> FEATURE:
<223> OTHER INFORMATION: M13F universal primer
```

```
<400> SEQUENCE: 18
tgtaaaacga cggccagt                                                   18

<210> SEQ ID NO 19
<211> LENGTH: 30
<212> TYPE: DNA
<213> ORGANISM: Artificial Sequence
<220> FEATURE:
<223> OTHER INFORMATION: Primer oEugEL1-1

<400> SEQUENCE: 19
agcggccgca ccatggaggt ggtgaatgaa                                      30

<210> SEQ ID NO 20
<211> LENGTH: 30
<212> TYPE: DNA
<213> ORGANISM: Artificial Sequence
<220> FEATURE:
<223> OTHER INFORMATION: Primer oEugEL1-2

<400> SEQUENCE: 20
tgcggccgct cactgaatct ttttggctcc                                      30

<210> SEQ ID NO 21
<211> LENGTH: 8306
<212> TYPE: DNA
<213> ORGANISM: Artificial Sequence
<220> FEATURE:
<223> OTHER INFORMATION: Plasmid pY119

<400> SEQUENCE: 21
ggccgcaggg cggatccccc gggctgcagg aattcgatat caagcttatc gataccgtcg     60
acctcgaggg ggggcccggt acccaattcg ccctatagtg agtcgtatta cgcgcgctca    120
ctggccgtcg ttttacaacg tcgtgactgg gaaaaccctg gcgttaccca acttaatcgc    180
cttgcagcac atccccctttt cgccagctgg cgtaatagcg aagaggcccg caccgatcgc    240
ccttcccaac agttgcgcag cctgaatggc gaatggcgcg acgcgccctg tagcggcgca    300
ttaagcgcgg cgggtgtggt ggttacgcgc agcgtgaccg ctacacttgc cagcgcccta    360
gcgcccgctc ctttcgcttt cttcccttcc tttctcgcca cgttcgccgg ctttccccgt    420
caagctctaa atcgggggct ccctttaggg ttccgattta gtgctttacg gcacctcgac    480
cccaaaaaac ttgattaggg tgatggttca cgtagtgggc catcgccctg atagacggtt    540
tttcgccctt tgacgttgga gtccacgttc tttaatagtg gactcttgtt ccaaactgga    600
acaacactca accctatctc ggtctattct tttgatttat aagggatttt gccgatttcg    660
gcctattggt taaaaatga gctgatttaa caaaaattta cgcgaattt taacaaaata    720 ttaacgttta caatttcctg atgcggtatt ttctccttac gcatctgtgc ggtatttcac    780
accgcatatc gacggtcgag gagaacttct agtatatcca catacctaat attattgcct    840 tattaaaat ggaatcccaa caattacatc aaaatccaca ttctcttcaa atcaattgt    900 cctgtacttc cttgttcatg tgtgttcaaa acgttatat ttataggata attatactct    960
atttctcaac aagtaattgg ttgtttggcc gagcggtcta aggcgcctga ttcaagaaat   1020
atcttgaccg cagttaactg tgggaatact caggtatcgt aagatgcaag agttcgaatc   1080
tcttagcaac cattatttt ttcctcaaca taacgagaac acacagggc gctatcgcac   1140 agaatcaaat tcgatgactg gaaatttttt gttaatttca gaggtcgcct gacgcatata   1200 ccttttttcaa ctgaaaaatt gggagaaaaa ggaaaggtga gaggccggaa ccggcttttc   1260
```

```
atatagaata gagaagcgtt catgactaaa tgcttgcatc acaatacttg aagttgacaa    1320
tattatttaa ggacctattg ttttttccaa taggtggtta gcaatcgtct tactttctaa    1380
cttttcttac cttttacatt tcagcaatat atatatatat ttcaaggata taccattcta    1440
atgtctgccc ctatgtctgc ccctaagaag atcgtcgttt tgccaggtga ccacgttggt    1500
caagaaatca cagccgaagc cattaaggtt cttaaagcta tttctgatgt tcgttccaat    1560
gtcaagttcg atttcgaaaa tcatttaatt ggtggtgctg ctatcgatgc tacaggtgtc    1620
ccacttccag atgaggcgct ggaagcctcc aagaaggttg atgccgtttt gttaggtgct    1680
gtggctggtc ctaaatgggg taccggtagt gttagacctg aacaaggttt actaaaaatc    1740
cgtaaagaac ttcaattgta cgccaactta agaccatgta actttgcatc cgactctctt    1800
ttagacttat ctccaatcaa gccacaattt gctaaaggta ctgacttcgt tgttgtcaga    1860
gaattagtgg gaggtatttta ctttggtaag agaaaggaag acgatggtga tggtgtcgct    1920
tgggatagtg aacaatacac cgttccagaa gtgcaaagaa tcacaagaat ggccgctttc    1980
atggccctac aacatgagcc accattgcct atttggtcct tggataaagc taatcttttg    2040
gcctcttcaa gattatggag aaaaactgtg gaggaaacca tcaagaacga attccctaca    2100
ttgaaggttc aacatcaatt gattgattct gccgccatga tcctagttaa gaacccaacc    2160
cacctaaatg gtattataat caccagcaac atgtttggtg atatcatctc cgatgaagcc    2220
tccgttatcc caggttcctt gggtttgttg ccatctgcgt ccttggcctc tttgccagac    2280
aagaacaccg catttggttt gtacgaacca tgccacggtt ctgctccaga tttgccaaag    2340
aataaggttg accctatcgc cactatcttg tctgctgcaa tgatgttgaa attgtcattg    2400
aacttgcctg aagaaggtaa ggccattgaa gatgcagtta aaaaggtttt ggatgcaggt    2460
atcagaactg gtgatttagg tggttccaac agtaccaccg aagtcggtga tgctgtcgcc    2520
gaagaagtta agaaaatcct tgcttaaaaa gattctcttt ttttatgata tttgtacata    2580
aactttataa atgaaattca taatagaaac gacacgaaat tacaaaatgg aatatgttca    2640
tagggtagac gaaactatat acgcaatcta catacattta tcaagaagga gaaaaaggag    2700
gatagtaaag gaatacaggt aagcaaattg atactaatgg ctcaacgtga taaggaaaaa    2760
gaattgcact ttaacattaa tattgacaag gaggagggca ccacacaaaa agttaggtgt    2820
aacagaaaat catgaaacta cgattcctaa tttgatattg gaggattttc tctaaaaaaa    2880
aaaaaataca acaaataaaa aacactcaat gacctgacca tttgatggag tttaagtcaa    2940
taccttcttg aagcatttcc cataatggtg aaagttccct caagaatttt actctgtcag    3000 aaacggccctt acgacgtagt cgatatggtg cactctcagt acaatctgct ctgatgccgc    3060
atagttaagc cagccccgac acccgccaac acccgctgac gcgccctgac gggcttgtct    3120
gctcccggca tccgcttaca gacaagctgt gaccgtctcc gggagctgca tgtgtcagag    3180
gttttcaccg tcatcaccga aacgcgcgag acgaaagggc ctcgtgatac gcctattttt    3240
ataggttaat gtcatgataa taatggtttc ttagtatgat ccaatatcaa aggaaatgat    3300
agcattgaag gatgagacta atccaattga ggagtggcag catatagaac agctaaaggg    3360
tagtgctgaa ggaagcatac gatacccccgc atggaatggg ataatatcac aggaggtact    3420
agactacctt tcatcctaca taaatagacg catataagta cgcatttaag cataaacacg    3480
cactatgccg ttcttctcat gtatatatat atacaggcaa cacgcagata taggtgcgac    3540
gtgaacagtg agctgtatgt gcgcagctcg cgttgcattt tcggaagcgc tcgttttcgg    3600
```

```
aaacgctttg aagttcctat tccgaagttc ctattctcta gaaagtatag gaacttcaga   3660
gcgcttttga aaaccaaaag cgctctgaag acgcactttc aaaaaaccaa aaacgcaccg   3720
gactgtaacg agctactaaa atattgcgaa taccgcttcc acaaacattg ctcaaaagta   3780
tctctttgct atatatctct gtgctatatc cctatataac ctacccatcc acctttcgct   3840
ccttgaactt gcatctaaac tcgacctcta cattttttat gtttatctct agtattactc   3900
tttagacaaa aaaattgtag taagaactat tcatagagtg aatcgaaaac aatacgaaaa   3960
tgtaaacatt tcctatacgt agtatataga gacaaaatag aagaaaccgt tcataatttt   4020
ctgaccaatg aagaatcatc aacgctatca ctttctgttc acaaagtatg cgcaatccac   4080
atcggtatag aatataatcg gggatgcctt tatcttgaaa aaatgcaccc gcagcttcgc   4140
tagtaatcag taaacgcggg aagtggagtc aggcttttt tatggaagag aaaatagaca    4200
ccaaagtagc cttcttctaa ccttaacgga cctacagtgc aaaaagttat caagagactg   4260
cattatagag cgcacaaagg agaaaaaaag taatctaaga tgctttgtta gaaaaatagc   4320
gctctcggga tgcattttt g tagaacaaaa aagaagtata gattctttgt tggtaaaata   4380
gcgctctcgc gttgcatttc tgttctgtaa aaatgcagct cagattcttt gtttgaaaaa   4440
ttagcgctct cgcgttgcat ttttgtttta caaaaatgaa gcacagattc ttcgttggta   4500
aaatagcgct ttcgcgttgc atttctgttc tgtaaaaatg cagctcagat tctttgtttg   4560
aaaaattagc gctctcgcgt tgcattttg ttctacaaaa tgaagcacag atgcttcgtt    4620
caggtggcac ttttcgggga atgtgcgcg gaacccctat tgtttatttt tctaaaatac    4680
attcaaatat gtatccgctc atgagacaat aaccctgata aatgcttcaa taatattgaa   4740
aaaggaagag tatgagtatt caacatttcc gtgtcgccct tattccctt tttgcggcat    4800
tttgccttcc tgttttgct cacccagaaa cgctggtgaa agtaaaagat gctgaagatc   4860
agttgggtgc acgagtgggt tacatcgaac tggatctcaa cagcggtaag atccttgaga   4920
gttttcgccc cgaagaacgt tttccaatga tgagcacttt taaagttctg ctatgtggcg   4980
cggtattatc ccgtattgac gccgggcaag agcaactcgg tcgccgcata cactattctc   5040
agaatgactt ggttgagtac tcaccagtca cagaaaagca tcttacggat ggcatgacag   5100
taagagaatt atgcagtgct gccataacca tgagtgataa cactgcggcc aacttacttc   5160
tgacaacgat cggaggaccg aaggagctaa ccgcttttt gcacaacatg ggggatcatg   5220
taactcgcct tgatcgttgg gaaccggagc tgaatgaagc cataccaaac gacgagcgtg   5280
acaccacgat gcctgtagca atggcaacaa cgttgcgcaa actattaact ggcgaactac   5340
ttactctagc ttcccggcaa caattaatag actggatgga ggcggataaa gttgcaggac   5400
cacttctgcg ctcggccctt ccggctggct ggtttattgc tgataaatct ggagccggtg   5460
agcgtgggtc tcgcggtatc attgcagcac tggggccaga tggtaagccc tcccgtatcg   5520
tagttatcta cacgacgggg agtcaggcaa ctatggatga acgaaataga cagatcgctg   5580
agataggtgc ctcactgatt aagcattggt aactgtcaga ccaagtttac tcatatatac   5640
tttagattga tttaaaactt cattttaat ttaaaaggat ctaggtgaag atcctttttg    5700
ataatctcat gaccaaaatc ccttaacgtg agttttcgtt ccactgagcg tcagacccccg   5760
tagaaaagat caaaggatct tcttgagatc ctttttttct gcgcgtaatc tgctgcttgc   5820
aaacaaaaaa accaccgcta ccagcggtgg tttgtttgcc ggatcaagag ctaccaactc   5880
ttttccgaa ggtaactggc ttcagcagag cgcagatacc aaatactgtc cttctagtgt    5940
agccgtagtt aggccaccac ttcaagaact ctgtagcacc gcctacatac ctcgctctgc   6000
```

```
taatcctgtt accagtggct gctgccagtg gcgataagtc gtgtcttacc gggttggact   6060
caagacgata gttaccggat aaggcgcagc ggtcgggctg aacggggggt tcgtgcacac   6120
agcccagctt ggagcgaacg acctacaccg aactgagata cctacagcgt gagctatgag   6180
aaagcgccac gcttcccgaa gggagaaagg cggacaggta tccggtaagc ggcagggtcg   6240
gaacaggaga gcgcacgagg gagcttccag ggggaaacgc ctggtatctt tatagtcctg   6300
tcgggtttcg ccacctctga cttgagcgtc gattttttgtg atgctcgtca ggggggcgga   6360
gcctatggaa aaacgccagc aacgcggcct ttttacggtt cctggccttt tgctggcctt   6420
ttgctcacat gttctttcct gcgttatccc ctgattctgt ggataaccgt attaccgcct   6480
ttgagtgagc tgataccgct cgccgcagcc gaacgaccga gcgcagcgag tcagtgagcg   6540
aggaagcgga agagcgccca atacgcaaac cgcctctccc cgcgcgttgg ccgattcatt   6600
aatgcagctg gcacgacagg tttcccgact ggaaagcggg cagtgagcgc aacgcaatta   6660
atgtgagtta cctcactcat taggcacccc aggctttaca ctttatgctt ccggctccta   6720
tgttgtgtgg aattgtgagc ggataacaat ttcacacagg aaacagctat gaccatgatt   6780
acgccaagcg cgcaattaac cctcactaaa gggaacaaaa gctggagctc caccgcggga   6840
tttcgaaact aagttcttgg tgttttaaaa ctaaaaaaaa gactaactat aaaagtagaa   6900
tttaagaagt ttaagaaata gatttacaga attacaatca atacctaccg tctttatata   6960
cttattagtc aagtagggga ataatttcag ggaactggtt tcaaccttttt ttttcagctt   7020
tttccaaatc agagagagca gaaggtaata gaaggtgtaa gaaaatgaga tagatacatg   7080
cgtgggtcaa ttgccttgtg tcatcattta ctccaggcag gttgcatcac tccattgagg   7140
ttgtgcccgt tttttgcctg tttgtgcccc tgttctctgt agttgcgcta agagaatgga   7200
cctatgaact gatggttggt gaagaaaaca atattttggt gctgggattc tttttttttc   7260
tggatgccag cttaaaaagc gggctccatt atatttagtg gatgccagga ataaactgtt   7320
cacccagaca cctacgatgt tatatattct gtgtaacccg cccctatttt gggcatgta   7380
cgggttacag cagaattaaa aggctaattt tttgactaaa taaagttagg aaaatcacta   7440
ctattaatta tttacgtatt ctttgaaatg gcagtattga taatgataaa ctcgaaatca   7500
ctagtggatc cgcccagcgg ccgcaccatg gaggtggtga atgaaatagt ctcaattggg   7560
caggaagttt tacccaaagt tgattatgcc caactctgga gtgatgccag tcactgtgag   7620
gtgctttact tgtccatcgc atttgtcatc ttgaagttca ctcttggccc ccttggtcca   7680
aaaggtcagt ctcgtatgaa gtttgttttc accaattaca accttctcat gtccatttat   7740
tcgttgggat cattcctctc aatggcatat gccatgtaca ccatcggtgt tatgtctgac   7800
aactgcgaga aggcttttga caacaacgtc ttcaggatca ccacgcagtt gttctatttg   7860
agcaagttcc tggagtatat tgactccttc tatttgccac tgatgggcaa gcctctgacc   7920
tggttgcaat tcttccatca tttgggggca ccgatggata tgtggctgtt ctataattac   7980
cgaaatgaag ctgtttggat ttttgtgctg ttgaatggtt tcatccactg gatcatgtac   8040
ggttattatt ggaccagatt gatcaagctg aagttcccca tgccaaaatc cctgattaca   8100
tcaatgcaga tcattcaatt caatgttggt ttctacattg tctggaagta caggaacatt   8160
ccctgttatc gccaagatgg gatgaggatg tttggctggt tcttcaatta cttttatgtt   8220
ggcacagtct tgtgtttgtt cttgaatttc tatgtgcaaa cgtatatcgt caggaagcac   8280
aagggagcca aaaagattca gtgagc                                        8306
```

<210> SEQ ID NO 22
<211> LENGTH: 9472
<212> TYPE: DNA
<213> ORGANISM: Artificial Sequence
<220> FEATURE:
<223> OTHER INFORMATION: Plasmid pDMW263

<400> SEQUENCE: 22

| | | | | | |
|---|---|---|---|---|---|
| catggcatgg | atggtacgtc | ctgtagaaac | cccaacccgt | gaaatcaaaa | aactcgacgg | 60 |
| cctgtgggca | ttcagtctgg | atcgcgaaaa | ctgtggaatt | gatcagcgtt | ggtgggaaag | 120 |
| cgcgttacaa | gaaagccggg | caattgctgt | gccaggcagt | tttaacgatc | agttcgccga | 180 |
| tgcagatatt | cgtaattatg | cgggcaacgt | ctggtatcag | cgcgaagtct | ttataccgaa | 240 |
| aggttgggca | ggccagcgta | tcgtgctgcg | tttcgatgcg | gtcactcatt | acggcaaagt | 300 |
| gtgggtcaat | aatcaggaag | tgatggagca | tcagggcggc | tatacgccat | ttgaagccga | 360 |
| tgtcacgccg | tatgttattg | ccgggaaaag | tgtacgtatc | accgtttgtg | tgaacaacga | 420 |
| actgaactgg | cagactatcc | cgccgggaat | ggtgattacc | gacgaaaacg | gcaagaaaaa | 480 |
| gcagtcttac | ttccatgatt | tctttaacta | tgccgggatc | catcgcagcg | taatgctcta | 540 |
| caccacgccg | aacacctggg | tggacgatat | caccgtggtg | acgcatgtcg | cgcaagactg | 600 |
| taaccacgcg | tctgttgact | ggcaggtggt | ggccaatggt | gatgtcagcg | ttgaactgcg | 660 |
| tgatgcggat | caacaggtgg | ttgcaactgg | acaaggcact | agcgggactt | gcaagtggt | 720 |
| gaatccgcac | ctctgcaac | cgggtgaagg | ttatctctat | gaactgtgcg | tcacagccaa | 780 |
| aagccagaca | gagtgtgata | tctacccgct | tcgcgtcggc | atccggtcag | tggcagtgaa | 840 |
| gggcgaacag | ttcctgatta | ccacaaaacc | gttctacttt | actggctttg | gtcgtcatga | 900 |
| agatgcggac | ttacgtggca | aaggattcga | taacgtgctg | atggtgcacg | accacgcatt | 960 |
| aatggactgg | attggggcca | actcctaccg | tacctcgcat | tacccttacg | ctgaagagat | 1020 |
| gctcgactgg | gcagatgaac | atggcatcgt | ggtgattgat | gaaactgctg | ctgtcggctt | 1080 |
| taacctctct | ttaggcattg | gtttcgaagc | gggcaacaag | ccgaaagaac | tgtacgcga | 1140 |
| agaggcagtc | aacggggaaa | ctcagcaagc | gcacttacag | gcgattaaag | agctgatagc | 1200 |
| gcgtgacaaa | aaccacccaa | gcgtggtgat | gtggagtatt | gccaacgaac | cggatacccg | 1260 |
| tccgcaagtg | cacgggaata | tttcgccact | ggcggaagca | acgcgtaaac | tcgacccgac | 1320 |
| gcgtccgatc | acctgcgtca | atgtaatgtt | ctgcgacgct | cacaccgata | ccatcagcga | 1380 |
| tctctttgat | gtgctgtgcc | tgaaccgtta | ttacggatgg | tatgtccaaa | gcggcgattt | 1440 |
| ggaaacggca | gagaaggtac | tggaaaaaga | acttctggcc | tggcaggaga | aactgcatca | 1500 |
| gccgattatc | atcaccgaat | acggcgtgga | tacgttagcc | gggctgcact | caatgtacac | 1560 |
| cgacatgtgg | agtgaagagt | atcagtgtgc | atggctggat | atgtatcacc | gcgtctttga | 1620 |
| tcgcgtcagc | gccgtcgtcg | gtgaacaggt | atggaatttc | gccgatttg | cgacctcgca | 1680 |
| aggcatattg | cgcgttggcg | gtaacaagaa | agggatcttc | actcgcgacc | gcaaaccgaa | 1740 |
| gtcggcggct | tttctgctgc | aaaaacgctg | gactggcatg | aacttcggtg | aaaaaccgca | 1800 |
| gcagggaggc | aaacaatgat | taattaacta | gagcggccgc | caccgcggcc | cgagattccg | 1860 |
| gcctcttcgg | ccgccaagcg | acccgggtgg | acgtctagag | gtacctagca | attaacagat | 1920 |
| agtttgccgg | tgataattct | cttaacctcc | cacactcctt | tgacataacg | atttatgtaa | 1980 |
| cgaaactgaa | atttgaccag | atattgtgtc | cgcggtggag | ctccagcttt | tgttcccttt | 2040 |
| agtgagggtt | aatttcgagc | ttggcgtaat | catggtcata | gctgtttcct | gtgtgaaatt | 2100 |

```
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg cgctcttccg cttcctcgc tcactgactc gctgcgctcg tcgttcggc    2340 tgcggcgagc ggtatcagct cactcaaagg cggtaatacg gttatccaca gaatcagggg    2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga acccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg gtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
```

```
attagggtga tggttcacgt agtgggccat cgccctgata gacgttttt cgcccttga  4500
cgttggagtc cacgttcttt aatagtggac tcttgttcca aactggaaca acactcaacc  4560
ctatctcggt ctattctttt gatttataag ggattttgcc gatttcggcc tattggttaa  4620
aaaatgagct gatttaacaa aaatttaacg cgaattttaa caaaatatta acgcttacaa  4680
tttccattcg ccattcaggc tgcgcaactg ttgggaaggg cgatcggtgc gggcctcttc  4740
gctattacgc cagctggcga aagggggatg tgctgcaagg cgattaagtt gggtaacgcc  4800
agggttttcc cagtcacgac gttgtaaaac gacggccagt gaattgtaat acgactcact  4860
atagggcgaa ttgggtaccg gccccccct cgaggtcgat ggtgtcgata agcttgatat  4920
cgaattcatg tcacacaaac cgatcttcgc ctcaaggaaa cctaattcta catccgagag  4980
actgccgaga tccagtctac actgattaat tttcgggcca ataatttaaa aaaatcgtgt  5040
tatataatat tatatgtatt atatatatac atcatgatga tactgacagt catgtcccat  5100
tgctaaatag acagactcca tctgccgcct ccaactgatg ttctcaatat ttaaggggtc  5160
atctcgcatt gtttaataat aaacagactc catctaccgc ctccaaatga tgttctcaaa  5220
atatattgta tgaacttatt tttattactt agtattatta gacaacttac ttgctttatg  5280
aaaaacactt cctatttagg aaacaattta taatggcagt tcgttcattt aacaatttat  5340
gtagaataaa tgttataaat gcgtatggga aatcttaaat atggatagca taatgatat  5400
ctgcattgcc taattcgaaa tcaacagcaa cgaaaaaaat cccttgtaca acataaatag  5460
tcatcgagaa atatcaacta tcaaagaaca gctattcaca cgttactatt gagattatta  5520
ttggacgaga atcacacact caactgtctt tctctcttct agaaatacag gtacaagtat  5580
gtactattct cattgttcat acttctagtc atttcatccc acatattcct tggatttctc  5640
tccaatgaat gacattctat cttgcaaatt caacaattat aataagatat accaaagtag  5700
cggtatagtg gcaatcaaaa agcttctctg gtgtgcttct cgtatttatt tttattctaa  5760
tgatccatta aaggtatata tttatttctt gttatataat ccttttgttt attacatggg  5820
ctggatacat aaaggtattt tgatttaatt ttttgcttaa attcaatccc cctcgttca  5880
gtgtcaactg taatggtagg aaattaccat acttttgaag aagcaaaaaa aatgaaagaa  5940
aaaaaaaatc gtatttccag gttagacgtt ccgcagaatc tagaatgcgg tatgcggtac  6000
attgttcttc gaacgtaaaa gttgcgctcc ctgagatatt gtacattttt gcttttacaa  6060
gtacaagtac atcgtacaac tatgtactac tgttgatgca tccacaacag tttgttttgt  6120
ttttttttgt ttttttttt tctaatgatt cattaccgct atgtatacct acttgtactt  6180
gtagtaagcc gggttattgg cgttcaatta atcatagact tatgaatctg cacggtgtgc  6240
gctgcgagtt acttttagct tatgcatgct acttgggtgt aatattggga tctgttcgga  6300
aatcaacgga tgctcaaccg atttcgacag taataatttg aatcgaatcg gagcctaaaa  6360
tgaacccgag tatatctcat aaaattctcg gtgagaggtc tgtgactgtc agtacaaggt  6420
gccttcatta tgccctcaac cttaccatac ctcactgaat gtagtgtacc tctaaaaatg  6480
aaatacagtg ccaaaagcca aggcactgag ctcgtctaac ggacttgata tacaaccaat  6540
taaaacaaat gaaagaaat acagttcttt gtatcatttg taacaattac cctgtacaaa  6600
ctaaggtatt gaaatcccac aatattccca aagtccaccc ctttccaaat tgtcatgcct  6660
acaactcata taccaagcac taacctacca aacaccacta aaacccaca aaatatatct  6720
taccgaatat acagtaacaa gctaccacca cactcgttgg gtgcagtcgc cagcttaaag  6780
atatctatcc acatcagcca caactcccct tcctttaataa accgactaca cccttggcta  6840
```

```
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacgcagc ctcaacagcg tcaccggcgg gcttcatgtt aagagagaac     7260
ttgagcatca tggcggcaga cagaatggtg gcaatgggt tgaccttctg cttgccgaga    7320
tcggggcag atccgtgaca gggctcgtac agaccgaacg cctcgttggt gtcgggcaga    7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct aagggccag gaaggcggcc    7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccga aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
tagatgacaa attcaacaac tcacagctga ctttctgcca ttgccactag ggggggcct    8640
ttttatatgg ccaagccaag ctctccacgt cggttgggct gcacccaaca ataaatgggt   8700
agggttgcac caacaaaggg atgggatggg ggtagaaga tacgaggata acggggctca    8760
atggcacaaa taagaacgaa tactgccatt aagactcgtg atccagcgac tgacaccatt   8820
gcatcatcta agggcctcaa aactacctcg gaactgctgc gctgatctgg acaccacaga   8880
ggttccgagc actttaggtt gcaccaaatg tcccaccagg tgcaggcaga aaacgctgga   8940
acagcgtgta cagtttgtct taacaaaaag tgagggcgct gaggtcgagc agggtggtgt   9000
gacttgttat agcctttaga gctgcgaaag cgcgtatgga tttggctcat caggccagat   9060
tgagggtctg tggacacatg tcatgttagt gtacttcaat cgcccctgg atatagcccc    9120
gacaataggc cgtggcctca ttttttgcc ttccgcacat ttccattgct cgatacccac    9180
```

| | |
|---|---|
| accttgcttc tcctgcactt gccaaccttg atactggttt acattgacca acatcttaca | 9240 |
| agcgggggc ttgtctaggg tatatataaa cagtggctct cccaatcggt tgccagtctc | 9300 |
| tttttccttt tctttcccca cagattcgaa atctaaacta cacatcacag aattccgagc | 9360 |
| cgtgagtatc cacgacaaga tcagtgtcga gacgacgcgt tttgtgtaat gacacaatcc | 9420 |
| gaaagtcgct agcaacacac actctctaca caaactaacc cagctctggt ac | 9472 |

```
<210> SEQ ID NO 23
<211> LENGTH: 101
<212> TYPE: DNA
<213> ORGANISM: Artificial Sequence
<220> FEATURE:
<223> OTHER INFORMATION: Primer IL3-1A

<400> SEQUENCE: 23
```

| | |
|---|---|
| gccaacgacg ctggcgagcg aatctgggct gccgtcaccg atcccgaaat cctcattggc | 60 |
| accttctcct acctgctcct gaagcctctc ctgcgaaact c | 101 |

```
<210> SEQ ID NO 24
<211> LENGTH: 101
<212> TYPE: DNA
<213> ORGANISM: Artificial Sequence
<220> FEATURE:
<223> OTHER INFORMATION: Primer IL3-1B

<400> SEQUENCE: 24
```

| | |
|---|---|
| accagagttt cgcaggagag gcttcaggag caggtaggag aaggtgccaa tgaggatttc | 60 |
| gggatcggtg acggcagccc agattcgctc gccagcgtcg t | 101 |

```
<210> SEQ ID NO 25
<211> LENGTH: 100
<212> TYPE: DNA
<213> ORGANISM: Artificial Sequence
<220> FEATURE:
<223> OTHER INFORMATION: Primer IL3-2A

<400> SEQUENCE: 25
```

| | |
|---|---|
| tggtctcgtg gacgagaaga aaggagccta ccgaacctcc atgatctggt acaacgtcct | 60 |
| cctggctctc ttctctgccc tgtccttcta cgtgactgcc | 100 |

```
<210> SEQ ID NO 26
<211> LENGTH: 100
<212> TYPE: DNA
<213> ORGANISM: Artificial Sequence
<220> FEATURE:
<223> OTHER INFORMATION: Primer IL3-2B

<400> SEQUENCE: 26
```

| | |
|---|---|
| cggtggcagt cacgtagaag gacagggcag agaagagagc caggaggacg ttgtaccaga | 60 |
| tcatggaggt tcggtaggct cctttcttct cgtccacgag | 100 |

```
<210> SEQ ID NO 27
<211> LENGTH: 100
<212> TYPE: DNA
<213> ORGANISM: Artificial Sequence
<220> FEATURE:
<223> OTHER INFORMATION: Primer IL3-3A

<400> SEQUENCE: 27
```

| | |
|---|---|
| accgctctcg gctgggacta cggtactgga gcctggctgc gaagacagac cggtgatact | 60 |
| ccccagcctc tctttcagtg tccctctcct gtctgggact | 100 |

<210> SEQ ID NO 28
<211> LENGTH: 100
<212> TYPE: DNA
<213> ORGANISM: Artificial Sequence
<220> FEATURE:
<223> OTHER INFORMATION: Primer IL3-3B

<400> SEQUENCE: 28
ttggagtccc agacaggaga gggacactga aagagaggct ggggagtatc accggtctgt    60
cttcgcagcc aggctccagt accgtagtcc cagccgagag                         100

<210> SEQ ID NO 29
<211> LENGTH: 100
<212> TYPE: DNA
<213> ORGANISM: Artificial Sequence
<220> FEATURE:
<223> OTHER INFORMATION: Primer IL3-4A

<400> SEQUENCE: 29
ccaagctgtt cacctggact gccaaggcct tctactattc taagtacgtg gagtacctcg    60
acaccgcttg gctggtcctc aagggcaagc gagtgtcctt                         100

<210> SEQ ID NO 30
<211> LENGTH: 100
<212> TYPE: DNA
<213> ORGANISM: Artificial Sequence
<220> FEATURE:
<223> OTHER INFORMATION: Primer IL3-4B

<400> SEQUENCE: 30
cagaaaggac actcgcttgc ccttgaggac cagccaagcg gtgtcgaggt actccacgta    60
cttagaatag tagaaggcct tggcagtcca ggtgaacagc                         100

<210> SEQ ID NO 31
<211> LENGTH: 89
<212> TYPE: DNA
<213> ORGANISM: Artificial Sequence
<220> FEATURE:
<223> OTHER INFORMATION: Primer IL3-5A

<400> SEQUENCE: 31
ttccatcact ttggagctcc ctgggacgtc tacctcggca ttcgactgca caacgagggt    60
gtgtggatct tcatgttctt taactcgtt                                      89

<210> SEQ ID NO 32
<211> LENGTH: 89
<212> TYPE: DNA
<213> ORGANISM: Artificial Sequence
<220> FEATURE:
<223> OTHER INFORMATION: Primer IL3-5B

<400> SEQUENCE: 32
aatgaacgag ttaaagaaca tgaagatcca cacaccctcg ttgtgcagtc gaatgccgag    60
gtagacgtcc cagggagctc caaagtgat                                      89

<210> SEQ ID NO 33
<211> LENGTH: 91
<212> TYPE: DNA
<213> ORGANISM: Artificial Sequence
<220> FEATURE:
<223> OTHER INFORMATION: Primer IL3-6A -continued

```
<400> SEQUENCE: 33
cattcacacc atcatgtaca cctactatgg actgactgcc gctggctaca agttcaaggc      60
caagcctctg atcactgcca tgcagatttg c                                    91

<210> SEQ ID NO 34
<211> LENGTH: 91
<212> TYPE: DNA
<213> ORGANISM: Artificial Sequence
<220> FEATURE:
<223> OTHER INFORMATION: Primer IL3-6B

<400> SEQUENCE: 34
actggcaaat ctgcatggca gtgatcagag gcttggcctt gaacttgtag ccagcggcag      60
tcagtccata gtaggtgtac atgatggtgt g                                    91

<210> SEQ ID NO 35
<211> LENGTH: 94
<212> TYPE: DNA
<213> ORGANISM: Artificial Sequence
<220> FEATURE:
<223> OTHER INFORMATION: Primer IL3-7A

<400> SEQUENCE: 35
cagttcgtcg gtggctttct cctggtctgg gactacatca acgttccctg cttcaactct      60
gacaagggca agctgttctc ctgggctttc aact                                 94

<210> SEQ ID NO 36
<211> LENGTH: 94
<212> TYPE: DNA
<213> ORGANISM: Artificial Sequence
<220> FEATURE:
<223> OTHER INFORMATION: Primer IL3-7B

<400> SEQUENCE: 36
gcgtagttga aagcccagga gaacagcttg cccttgtcag agttgaagca gggaacgttg      60
atgtagtccc agaccaggag aaagccaccg acga                                 94

<210> SEQ ID NO 37
<211> LENGTH: 91
<212> TYPE: DNA
<213> ORGANISM: Artificial Sequence
<220> FEATURE:
<223> OTHER INFORMATION: Primer IL3-8A

<400> SEQUENCE: 37
acgcctacgt cggatctgtc tttctcctgt tctgtcactt cttttaccag gacaacctgg      60
ccaccaagaa atccgctaag gctggtaagc a                                    91

<210> SEQ ID NO 38
<211> LENGTH: 91
<212> TYPE: DNA
<213> ORGANISM: Artificial Sequence
<220> FEATURE:
<223> OTHER INFORMATION: Primer IL3-8B

<400> SEQUENCE: 38
aagctgctta ccagccttag cggatttctt ggtggccagg ttgtcctggt aaaagaagtg      60
acagaacagg agaaagacag atccgacgta g                                    91

<210> SEQ ID NO 39
<211> LENGTH: 41
```

<212> TYPE: DNA
<213> ORGANISM: Artificial Sequence
<220> FEATURE:
<223> OTHER INFORMATION: Primer IL3-1F

<400> SEQUENCE: 39
tttccatggc tctggccaac gacgctggcg agcgaatctg g              41

<210> SEQ ID NO 40
<211> LENGTH: 36
<212> TYPE: DNA
<213> ORGANISM: Artificial Sequence
<220> FEATURE:
<223> OTHER INFORMATION: Primer IL3-4R

<400> SEQUENCE: 40
tttctgcaga aaggacactc gcttgccctt gaggac                    36

<210> SEQ ID NO 41
<211> LENGTH: 41
<212> TYPE: DNA
<213> ORGANISM: Artificial Sequence
<220> FEATURE:
<223> OTHER INFORMATION: Primer IL3-5F

<400> SEQUENCE: 41
tttctgcagg ccttccatca ctttggagct ccctgggacg t              41

<210> SEQ ID NO 42
<211> LENGTH: 42
<212> TYPE: DNA
<213> ORGANISM: Artificial Sequence
<220> FEATURE:
<223> OTHER INFORMATION: Primer IL3-8R

<400> SEQUENCE: 42
tttgcggccg ctaaagctgc ttaccagcct tagcggattt ct             42

<210> SEQ ID NO 43
<211> LENGTH: 417
<212> TYPE: DNA
<213> ORGANISM: Artificial Sequence
<220> FEATURE:
<223> OTHER INFORMATION: 417 bp NcoI/PstI fragment pT9(1-4)

<400> SEQUENCE: 43
catggctctg ccaacgacg ctggcgagcg aatctgggct gccgtcaccg atcccgaaat    60
cctcattggc accttctcct acctgctcct gaagcctctc ctgcgaaact ctggtctcgt   120
ggacgagaag aaaggagcct accgaacctc catgatctgg tacaacgtcc tcctggctct   180
cttctctgcc ctgtccttct acgtgactgc caccgctctc ggctgggact acggtactgg   240
agcctggctg cgaagacaga ccggtgatac tccccagcct ctctttcagt gtccctctcc   300
tgtctgggac tccaagctgt tcacctggac tgccaaggcc ttctactatt ctaagtacgt   360
ggagtacctc gacaccgctt ggctggtcct caagggcaag cgagtgtcct ttctgca      417

<210> SEQ ID NO 44
<211> LENGTH: 377
<212> TYPE: DNA
<213> ORGANISM: Artificial Sequence
<220> FEATURE:
<223> OTHER INFORMATION: 377 bp PstI/Not1 fragment pT9(5-8)

<400> SEQUENCE: 44

| | |
|---|---:|
| ggccttccat cactttggag ctccctggga cgtctacctc ggcattcgac tgcacaacga | 60 |
| gggtgtgtgg atcttcatgt tctttaactc gttcattcac accatcatgt acacctacta | 120 |
| tggactgact gccgctggct acaagttcaa ggccaagcct ctgatcactg ccatgcagat | 180 |
| ttgccagttc gtcggtggct ttctcctggt ctgggactac atcaacgttc cctgcttcaa | 240 |
| ctctgacaag ggcaagctgt tctcctgggc tttcaactac gcctacgtcg gatctgtctt | 300 |
| tctcctgttc tgtcacttct tttaccagga caacctggcc accagaaaat ccgctaaggc | 360 |
| tggtaagcag ctttagc | 377 |

<210> SEQ ID NO 45
<211> LENGTH: 7783
<212> TYPE: DNA
<213> ORGANISM: Artificial Sequence
<220> FEATURE:
<223> OTHER INFORMATION: Plasmid pY115

<400> SEQUENCE: 45

| | |
|---|---:|
| catggctctg ccaacgacg ctggcgagcg aatctgggct gccgtcaccg atcccgaaat | 60 |
| cctcattggc accttctcct acctgctcct gaagcctctc ctgcgaaact ctggtctcgt | 120 |
| ggacgagaag aaaggagcct accgaacctc catgatctgg tacaacgtcc tcctggctct | 180 |
| cttctctgcc ctgtccttct acgtgactgc caccgctctc ggctgggact acggtactgg | 240 |
| agcctggctg cgaagacaga ccggtgatac tccccagcct ctctttcagt gtccctctcc | 300 |
| tgtctgggac tccaagctgt tcacctggac tgccaaggcc ttctactatt ctaagtacgt | 360 |
| ggagtacctc gacaccgctt ggctggtcct caagggcaag cgagtgtcct ttctgcaggc | 420 |
| cttccatcac tttggagctc cctgggacgt ctacctcggc attcgactgc acaacgaggg | 480 |
| tgtgtggatc ttcatgttct taactcgtt cattcacacc atcatgtaca cctactatgg | 540 |
| actgactgcc gctggctaca gttcaaggc caagcctctg atcactgcca tgcagatttg | 600 |
| ccagttcgtc ggtggctttc tcctggtctg ggactacatc aacgttccct gcttcaactc | 660 |
| tgacaagggc aagctgttct cctgggcttt caactacgcc tacgtcggat ctgtctttct | 720 |
| cctgttctgt cacttctttt accaggacaa cctggccacc agaaatccg ctaaggctgg | 780 |
| taagcagctt tagcggccgc aagtgtggat ggggaagtga gtgcccggtt ctgtgtgcac | 840 |
| aattggcaat ccaagatgga tggattcaac acagggatat agcgagctac gtggtggtgc | 900 |
| gaggatatag caacggatat ttatgtttga cacttgagaa tgtacgtac aagcactgtc | 960 |
| caagtacaat actaaacata ctgtacatac tcatactcgt acccgggcaa cggtttcact | 1020 |
| tgagtgcagt ggctagtgct cttactcgta cagtgtgcaa tactgcgtat catagtcttt | 1080 |
| gatgtatatc gtattcattc atgttagttg cgtacgagcc ggaagcataa agtgtaaagc | 1140 |
| ctggggtgcc taatgagtga gctaactcac attaattgcg ttgcgctcac tgcccgcttt | 1200 |
| ccagtcggga aacctgtcgt gccagctgca ttaatgaatc ggccaacgcg cggggagagg | 1260 |
| cggtttgcgt attgggcgct cttccgcttc ctcgctcact gactcgctgc gctcggtcgt | 1320 |
| tcggctgcgg cgagcggtat cagctcactc aaaggcggta atacggttat ccacagaatc | 1380 |
| aggggataac gcaggaaaga acatgtgagc aaaaggccag caaaaggcca ggaaccgtaa | 1440 |
| aaaggccgcg ttgctggcgt ttttccatag gctccgcccc cctgacgagc atcacaaaaa | 1500 |
| tcgacgctca agtcagaggt ggcgaaaccc gacaggacta taaagatacc aggcgtttcc | 1560 |
| ccctggaagc tccctcgtgc gctctcctgt tccgaccctg ccgcttaccg gatacctgtc | 1620 |
| cgcctttctc ccttcgggaa gcgtggcgct ttctcatagc tcacgctgta ggtatctcag | 1680 |

```
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta atcaatcta agtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaatagggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg ttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc ccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
```

```
cgtgttatat aatattatat gtattatata tatacatcat gatgatactg acagtcatgt    4080
cccattgcta aatagacaga ctccatctgc cgcctccaac tgatgttctc aatatttaag    4140
gggtcatctc gcattgttta ataataaaca gactccatct accgcctcca aatgatgttc    4200
tcaaaatata ttgtatgaac ttatttttat tacttagtat tattagacaa cttacttgct    4260
ttatgaaaaa cacttcctat ttaggaaaca atttataatg gcagttcgtt catttaacaa    4320
tttatgtaga ataaatgtta taaatgcgta tgggaaatct taaatatgga tagcataaat    4380
gatatctgca ttgcctaatt cgaaatcaac agcaacgaaa aaaatcccct gtacaacata    4440
aatagtcatc gagaaatatc aactatcaaa gaacagctat tcacacgtta ctattgagat    4500
tattattgga cgagaatcac acactcaact gtctttctct cttctagaaa tacaggtaca    4560
agtatgtact attctcattg ttcatacttc tagtcatttc atcccacata ttccttggat    4620
ttctctccaa tgaatgacat tctatcttgc aaattcaaca attataataa gatataccaa    4680
agtagcggta tagtggcaat caaaaagctt ctctggtgtg cttctcgtat ttatttttat    4740
tctaatgatc cattaaaggt atatatttat ttcttgttat ataatccttt tgtttattac    4800
atgggctgga tacataaagg tattttgatt taattttttg cttaaattca atcccccctc    4860
gttcagtgtc aactgtaatg gtaggaaatt accatacttt tgaagaagca aaaaaaatga    4920
aagaaaaaaa aaatcgtatt tccaggttag acgttccgca gaatctagaa tgcggtatgc    4980
ggtacattgt tcttcgaacg taaaagttgc gctccctgag atattgtaca ttttttgcttt   5040
tacaagtaca agtacatcgt acaactatgt actactgttg atgcatccac aacagtttgt    5100
tttgtttttt tttgttttt tttttctaa tgattcatta ccgctatgta tacctacttg      5160
tacttgtagt aagccgggtt attggcgttc aattaatcat agacttatga atctgcacgg    5220
tgtgcgctgc gagttacttt tagcttatgc atgctacttg ggtgtaatat tgggatctgt    5280
tcggaaatca acggatgctc aatcgatttc gacagtaatt aattaagtca tacacaagtc    5340
agctttcttc gagcctcata taagtataag tagttcaacg tattagcact gtacccagca    5400
tctccgtatc gagaaacaca acaacatgcc ccattggaca gatcatgcgg atacacaggt    5460
tgtgcagtat catacatact cgatcagaca ggtcgtctga ccatcataca agctgaacaa    5520
gcgctccata cttgcacgct ctctatatac acagttaaat tacatatcca tagtctaacc    5580
tctaacagtt aatcttctgg taagcctccc agccagcctt ctggtatcgc ttggcctcct    5640
caataggatc tcggttctgg ccgtacagac ctcggccgac aattatgata tccgttccgg    5700
tagacatgac atcctcaaca gttcggtact gctgtccgag agcgtctccc ttgtcgtcaa    5760
gacccacccc gggggtcaga ataagccagt cctcagagtc gcccttaggt cggttctggg    5820
caatgaagcc aaccacaaac tcggggtcgg atcgggcaag ctcaatggtc tgcttggagt    5880
actcgccagt ggccagagag cccttgcaag acagctcggc cagcatgagc agacctctgg    5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgagggggag cacagtgccg gcgtaggtga    6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
```

| | |
|---|---|
| cttcgtagga gggcattttg gtggtgaaga ggagactgaa ataaatttag tctgcagaac | 6480 |
| tttttatcgg aaccttatct ggggcagtga agtatatgtt atggtaatag ttacgagtta | 6540 |
| gttgaactta tagatagact ggactatacg gctatcggtc caaattagaa agaacgtcaa | 6600 |
| tggctctctg ggcgtcgcct ttgccgacaa aaatgtgatc atgatgaaag ccagcaatga | 6660 |
| cgttgcagct gatattgttg tcggccaacc gcgccgaaaa cgcagctgtc agacccacag | 6720 |
| cctccaacga agaatgtatc gtcaaagtga tccaagcaca ctcatagttg gagtcgtact | 6780 |
| ccaaaggcgg caatgacgag tcagacagat actcgtcgac gtttaaacag tgtacgcaga | 6840 |
| tctactatag aggaacattt aaattgcccc ggagaagacg gccaggccgc ctagatgaca | 6900 |
| aattcaacaa ctcacagctg actttctgcc attgccacta ggggggggcc tttttatatg | 6960 |
| gccaagccaa gctctccacg tcggttgggc tgcacccaac aataaatggg tagggttgca | 7020 |
| ccaacaaagg gatgggatgg ggggtagaag atacgaggat aacggggctc aatggcacaa | 7080 |
| ataagaacga atactgccat taagactcgt gatccagcga ctgacaccat tgcatcatct | 7140 |
| aagggcctca aaactacctc ggaactgctg cgctgatctg gacaccacag aggttccgag | 7200 |
| cactttaggt tgcaccaaat gtcccaccag gtgcaggcag aaaacgctgg aacagcgtgt | 7260 |
| acagtttgtc ttaacaaaaa gtgagggcgc tgaggtcgag cagggtggtg tgacttgtta | 7320 |
| tagcctttag agctgcgaaa gcgcgtatgg atttggctca tcaggccaga ttgagggtct | 7380 |
| gtggacacat gtcatgttag tgtacttcaa tcgcccctg gatatagccc cgacaatagg | 7440 |
| ccgtggcctc atttttttgc cttccgcaca tttccattgc tcgatccca caccttgctt | 7500 |
| ctcctgcact tgccaacctt aatactggtt tacattgacc aacatcttac aagcgggggg | 7560 |
| cttgtctagg gtatatataa acagtggctc tcccaatcgg ttgccagtct cttttttcct | 7620 |
| ttctttcccc acagattcga aatctaaact acacatcaca gaattccgag ccgtgagtat | 7680 |
| ccacgacaag atcagtgtcg agacgacgcg ttttgtgtaa tgacacaatc cgaaagtcgc | 7740 |
| tagcaacaca cactctctac acaaactaac ccagctctgg tac | 7783 |

<210> SEQ ID NO 46
<211> LENGTH: 7879
<212> TYPE: DNA
<213> ORGANISM: Artificial Sequence
<220> FEATURE:
<223> OTHER INFORMATION: Plasmid pDMW237

<400> SEQUENCE: 46

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgagccggaa gcataaagtg taaagcctgg ggtgcctaat | 360 |
| gagtgagcta actcacatta attgcgttgc gctcactgcc cgctttccag tcgggaaacc | 420 |
| tgtcgtgcca gctgcattaa tgaatcggcc aacgcgcggg gagaggcggt ttgcgtattg | 480 |
| ggcgctcttc cgcttcctcg ctcactgact cgctgcgctc ggtcgttcgg ctgcggcgag | 540 |
| cggtatcagc tcactcaaag gcggtaatac ggttatccac agaatcaggg gataacgcag | 600 |
| gaaagaacat gtgagcaaaa ggccagcaaa aggccaggaa ccgtaaaaag gccgcgttgc | 660 |

```
tggcgttttt ccataggctc cgccccctg acgagcatca caaaaatcga cgctcaagtc       720
agaggtggcg aaacccgaca ggactataaa gataccaggc gtttccccct ggaagctccc       780
tcgtgcgctc tcctgttccg accctgccgc ttaccggata cctgtccgcc tttctccctt       840
cgggaagcgt ggcgctttct catagctcac gctgtaggta tctcagttcg gtgtaggtcg       900
ttcgctccaa gctgggctgt gtgcacgaac ccccgttca gcccgaccgc tgcgccttat       960
ccggtaacta tcgtcttgag tccaacccgg taagacacga cttatcgcca ctggcagcag      1020
ccactggtaa caggattagc agagcgaggt atgtaggcgg tgctacagag ttcttgaagt      1080
ggtggcctaa ctacggctac actagaagga cagtatttgg tatctgcgct ctgctgaagc      1140
cagttacctt cggaaaaaga gttggtagct cttgatccgg caaacaaacc accgctggta      1200
gcggtggttt ttttgtttgc aagcagcaga ttacgcgcag aaaaaaagga tctcaagaag      1260
atcctttgat cttttctacg gggtctgacg ctcagtggaa cgaaaactca cgttaaggga      1320
ttttggtcat gagattatca aaaggatct tcacctagat ccttttaaat taaaaatgaa       1380
gttttaaatc aatctaaagt atatatgagt aaacttggtc tgacagttac caatgcttaa      1440
tcagtgaggc acctatctca gcgatctgtc tatttcgttc atccatagtt gcctgactcc      1500
ccgtcgtgta gataactacg atacgggagg gcttaccatc tggccccagt gctgcaatga      1560
taccgcgaga cccacgctca ccggctccag atttatcagc aataaaccag ccagccggaa      1620
gggccgagcg cagaagtggt cctgcaactt tatccgcctc catccagtct attaattgtt      1680
gccgggaagc tagagtaagt agttcgccag ttaatagttt gcgcaacgtt gttgccattg      1740
ctacaggcat cgtggtgtca cgctcgtcgt ttggtatggc ttcattcagc tccggttccc      1800
aacgatcaag gcgagttaca tgatccccca tgttgtgcaa aaaagcggtt agctccttcg      1860
gtcctccgat cgttgtcaga agtaagttgg ccgcagtgtt atcactcatg gttatggcag      1920
cactgcataa ttctcttact gtcatgccat ccgtaagatg cttttctgtg actggtgagt      1980
actcaaccaa gtcattctga aatagtgta tgcggcgacc gagttgctct tgcccggcgt       2040
caatacggga taataccgcg ccacatagca gaactttaaa agtgctcatc attggaaaac      2100
gttcttcggg gcgaaaactc tcaaggatct taccgctgtt gagatccagt tcgatgtaac      2160
ccactcgtgc acccaactga tcttcagcat cttttacttt caccagcgtt tctgggtgag      2220
caaaaacagg aaggcaaaat gccgcaaaaa agggaataag ggcgacacgg aaatgttgaa      2280
tactcatact cttcctttt caatattatt gaagcattta tcagggttat tgtctcatga      2340
gcggatacat atttgaatgt atttagaaaa ataaacaaat aggggttccg cgcacatttc      2400
cccgaaaagt gccacctgac gcgcctgta gcggcgcatt aagcgcggcg ggtgtggtgg      2460
ttacgcgcag cgtgaccgct acacttgcca gcgccctagc gcccgctcct ttcgctttct      2520
tcccttcctt tctcgccacg ttcgccggct ttccccgtca agctctaaat cggggggctcc      2580 ctttagggtt ccgatttagt gctttacggc acctcgaccc caaaaaactt gattagggtg      2640
atggttcacg tagtgggcca tcgccctgat agacggtttt tcgccctttg acgttggagt      2700
ccacgttctt taatagtgga ctcttgttcc aaactggaac aacactcaac cctatctcgg      2760
tctattcttt tgatttataa gggattttgc cgatttcggc ctattggtta aaaatgagc       2820 tgatttaaca aaaatttaac gcgaatttta acaaaatatt aacgcttaca atttccattc      2880
gccattcagg ctgcgcaact gttgggaagg gcgatcggtg cgggcctctt cgctattacg      2940
ccagctggcg aaagggggat gtgctgcaag gcgattaagt tgggtaacgc cagggttttc      3000
ccagtcacga cgttgtaaaa cgacggccag tgaattgtaa tacgactcac tatagggcga      3060
```

```
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaagggt catctcgcat    3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatccgac cactcggcga ttcggtgaca ccggtactgg   5340
tgcttgacag tgttgccaat atctgcgaac tttctgtcct cgaacaggaa gaaaccgtgc   5400
```

```
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgactcag gcgacgacgg aattcctgca gcccatctgc    6060
agaattcagg agagaccggg ttggcggcgt atttgtgtcc caaaaaacag ccccaattgc    6120
cccggagaag acggccaggc cgcctagatg acaaattcaa caactcacag ctgactttct    6180
gccattgcca ctagggggg gccttttat atggccaagc caagctctcc acgtcggttg    6240
ggctgcaccc aacaataaat gggtagggtt gcaccaacaa agggatggga tgggggtag    6300 aagatacgag gataacgggg ctcaatggca caaataagaa cgaatactgc cattaagact    6360
cgtgatccag cgactgacac cattgcatca tctaagggcc tcaaaactac ctcggaactg    6420
ctgcgctgat ctggacacca cagaggttcc gagcactta ggttgcacca aatgtcccac    6480
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcatttttt tgccttccgc    6720
acatttccat tgctcggtac ccacaccttg cttctcctgc acttgccaac cttaatactg    6780
gtttacattg accaacatct tacaagcggg gggcttgtct agggtatata taaacagtgg    6840
ctctcccaat cggttgccag tctcttttt cctttcttc cccacagatt cgaaatctaa    6900
actacacatc acacaatgcc tgttactgac gtccttaagc gaaagtccgg tgtcatcgtc    6960
ggcgacgatg tccgagccgt gagtatccac gacaagatca gtgtcgagac gacgcgtttt    7020
gtgtaatgac acaatccgaa agtcgctagc aacacacact ctctacacaa actaacccag    7080
ctctccatgg ctctggccaa cgacgctggc gagcgaatct gggctgccgt caccgatccc    7140
gaaatcctca ttggcacctt ctcctacctg ctcctgaagc ctctcctgcg aaactctggt    7200
ctcgtggacg agaagaaagg agcctaccga acctccatga tctggtacaa cgtcctcctg    7260
gctctcttct ctgccctgtc cttctacgtg actgccaccg ctctcggctg ggactacggt    7320
actggagcct ggctgcgaag acagaccggt gatactcccc agcctctctt tcagtgtccc    7380
tctcctgtct gggactccaa gctgttcacc tggactgcca aggccttcta ctattctaag    7440
tacgtggagt acctcgacac cgcttggctg gtcctcaagg gcaagcgagt gtcctttctg    7500
caggccttcc atcactttgg agctccctgg gacgtctacc tcggcattcg actgcacaac    7560
gagggtgtgt ggatcttcat gttctttaac tcgttcattc acaccatcat gtacacctac    7620
tatggactga ctgccgctgg ctacaagttc aaggccaagc ctctgatcac tgccatgcag    7680
atttgccagt cgtcggtgg ctttctcctg gtctgggact acatcaacgt tccctgcttc    7740
aactctgaca agggcaagct gttctcctgg gctttcaact acgcctacgt cggatctgtc    7800
```

```
tttctcctgt tctgtcactt cttttaccag gacaacctgg ccaccaagaa atccgctaag      7860
gctggtaagc agctttagc                                                   7879

<210> SEQ ID NO 47
<211> LENGTH: 8704
<212> TYPE: DNA
<213> ORGANISM: Artificial Sequence
<220> FEATURE:
<223> OTHER INFORMATION: Plasmid pBY1

<400> SEQUENCE: 47
ggccgcaagt gtggatgggg aagtgagtgc ccggttctgt gtgcacaatt ggcaatccaa        60
gatggatgga ttcaacacag ggatatagcg agctacgtgg tggtgcgagg atatagcaac      120
ggatatttat gtttgacact tgagaatgta cgatacaagc actgtccaag tacaatacta      180
aacatactgt acatactcat actcgtaccc gggcaacggt ttcacttgag tgcagtggct      240
agtgctctta ctcgtacagt gtgcaatact gcgtatcata gtctttgatg tatatcgtat      300
tcattcatgt tagttgcgta cgagccggaa gcataaagtg taaagcctgg ggtgcctaat      360
gagtgagcta actcacatta attgcgttgc gctcactgcc cgctttccag tcgggaaacc      420
tgtcgtgcca gctgcattaa tgaatcggcc aacgcgcggg gagaggcggt ttgcgtattg      480
ggcgctcttc cgcttcctcg ctcactgact cgctgcgctc ggtcgttcgg ctgcggcgag      540
cggtatcagc tcactcaaag gcggtaatac ggttatccac agaatcaggg gataacgcag      600
gaaagaacat gtgagcaaaa ggccagcaaa aggccaggaa ccgtaaaaag gccgcgttgc      660
tggcgttttt ccataggctc cgcccccctg acgagcatca caaaaatcga cgctcaagtc      720
agaggtggcg aaacccgaca ggactataaa gataccaggc gtttccccct ggaagctccc      780
tcgtgcgctc tcctgttccg accctgccgc ttaccggata cctgtccgcc tttctccctt      840
cgggaagcgt ggcgctttct catagctcac gctgtaggta tctcagttcg gtgtaggtcg      900
ttcgctccaa gctgggctgt gtgcacgaac cccccgttca gcccgaccgc tgcgccttat      960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg ggtctgacg ctcagtggaa cgaaaactca cgttaaggga     1320
ttttggtcat gagattatca aaaggatct cacctagat cctttaaat taaaatgaa     1380 gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt cgcaacgtt gttgccattg     1740 ctacaggcat cgtggtgtca cgctcgtcgt ttggtatggc ttcattcagc tccggttccc     1800
aacgatcaag gcgagttaca tgatccccca tgttgtgcaa aaaagcggtt agctccttcg     1860
gtcctccgat cgttgtcaga agtaagttgg ccgcagtgtt atcactcatg gttatggcag     1920
```

```
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgcctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca agctctaaat cgggggctcc    2580
ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt aatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat    3360 tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg ctggatacata    4020 taaaggtatt ttgatttaat tttttgctta aattcaatcc cccctcgttc agtgtcaact    4080
gtaatggtag gaaattacca tacttttgaa gaagcaaaaa aatgaaaga aaaaaaaaat    4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
```

```
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccegggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc ccctggata tagccccgac aataggccgt ggcctcattt    6660
```

-continued

```
ttttgccttc cgcacatttc cattgctcga tacccacacc ttgcttctcc tgcacttgcc      6720
aaccttaata ctggtttaca ttgaccaaca tcttacaagc gggggcttg tctagggtat       6780 atataaacag tggctctccc aatcggttgc cagtctcttt tttcctttct ttccccacag      6840
attcgaaatc taaactacac atcacagaat tccgagccgt gagtatccac gacaagatca     6900
gtgtcgagac gacgcgtttt gtgtaatgac acaatccgaa agtcgctagc aacacacact     6960
ctctacacaa actaacccag ctctggtacc atgatcacaa gtttgtacaa aaaagctgaa     7020
cgagaaacgt aaaatgatat aaatatcaat atattaaatt agattttgca taaaaaacag     7080
actacataat actgtaaaac acaacatatc cagtcatatt ggcggccgca ttaggcaccc     7140
caggctttac actttatgct tccggctcgt ataatgtgtg gattttgagt taggatccgt     7200
cgagattttc aggagctaag gaagctaaaa tggagaaaaa aatcactgga tataccaccg     7260
ttgatatatc ccaatggcat cgtaaagaac attttgaggc atttcagtca gttgctcaat     7320
gtacctataa ccagaccgtt cagctggata ttacggcctt tttaaagacc gtaaagaaaa     7380
ataagcacaa gttttatccg gcctttattc acattcttgc ccgcctgatg aatgctcatc     7440
cggaattccg tatggcaatg aaagacggtg agctggtgat atgggatagt gttcacccttt    7500 gttacaccgt tttccatgag caaactgaaa cgttttcatc gctctggagt gaataccacg     7560
acgatttccg gcagtttcta cacatatatt cgcaagatgt ggcgtgttac ggtgaaaacc     7620
tggcctattt ccctaaaggg tttattgaga atatgttttt cgtctcagcc aatccctggg     7680
tgagtttcac cagttttgat ttaaacgtgg ccaatatgga caacttcttc gcccccgttt     7740
tcaccatggg caaatattat acgcaaggcg acaaggtgct gatgccgctg gcgattcagg     7800
ttcatcatgc cgtttgtgat ggcttccatg tcggcagaat gcttaatgaa ttacaacagt     7860
actgcgatga gtggcagggc ggggcgtaaa cgcgtggatc cggcttacta aaagccagat     7920
aacagtatgc gtatttgcgc gctgattttt gcggtataag aatatatact gatatgtata     7980
cccgaagtat gtcaaaaaga ggtatgctat gaagcagcgt attacagtga cagttgacag     8040
cgacagctat cagttgctca aggcatatat gatgtcaata tctccggtct ggtaagcaca     8100
accatgcaga atgaagcccg tcgtctgcgt gccgaacgct ggaaagcgga aaatcaggaa     8160
gggatggctg aggtcgcccg gtttattgaa atgaacggct cttttgctga cgagaacagg     8220
ggctggtgaa atgcagttta aggtttacac ctataaaaga gagagccgtt atcgtctgtt     8280
tgtggatgta cagagtgata ttattgacac gcccgggcga cggatggtga tcccctggc    8340 cagtgcacgt ctgctgtcag ataaagtctc ccgtgaactt tacccggtgg tgcatatcgg     8400
ggatgaaagc tggcgcatga tgaccaccga tatggccagt gtgccggtct ccgttatcgg     8460
ggaagaagtg gctgatctca gccaccgcga aaatgacatc aaaaacgcca ttaacctgat     8520
gttctgggga atataaatgt caggctccct tatacacagc cagtctgcag gtcgaccata     8580
gtgactggat atgttgtgtt ttacagcatt atgtagtctg tttttatgc aaaatctaat      8640 ttaatatatt gatatttata tcattttacg tttctcgttc agctttcttg tacaaagtgg     8700
tgat                                                                   8704
```

<210> SEQ ID NO 48
<211> LENGTH: 8145
<212> TYPE: DNA
<213> ORGANISM: Artificial Sequence
<220> FEATURE:
<223> OTHER INFORMATION: Plasmid pBY2
<220> FEATURE:
<221> NAME/KEY: misc_feature

```
<222> LOCATION: (8028)..(8031)
<223> OTHER INFORMATION: n is a, c, g, or t
<220> FEATURE:
<221> NAME/KEY: misc_feature
<222> LOCATION: (8063)..(8065)
<223> OTHER INFORMATION: n is a, c, g, or t
<220> FEATURE:
<221> NAME/KEY: misc_feature
<222> LOCATION: (8067)..(8069)
<223> OTHER INFORMATION: n is a, c, g, or t
<220> FEATURE:
<221> NAME/KEY: misc_feature
<222> LOCATION: (8071)..(8073)
<223> OTHER INFORMATION: n is a, c, g, or t
<220> FEATURE:
<221> NAME/KEY: misc_feature
<222> LOCATION: (8075)..(8075)
<223> OTHER INFORMATION: n is a, c, g, or t
<220> FEATURE:
<221> NAME/KEY: misc_feature
<222> LOCATION: (8126)..(8135)
<223> OTHER INFORMATION: n is a, c, g, or t

<400> SEQUENCE: 48
cttgtacaaa gtggtgatgg ccgcaagtgt ggatggggaa gtgagtgccc ggttctgtgt      60
gcacaattgg caatccaaga tggatggatt caacacaggg atatagcgag ctacgtggtg    120
gtgcgaggat atagcaacgg atatttatgt ttgacacttg agaatgtacg atacaagcac    180
tgtccaagta caatactaaa catactgtac atactcatac tcgtacccgg caacggttt     240 cacttgagtg cagtggctag tgctcttact cgtacagtgt gcaatactgc gtatcatagt    300
cttggatgta tatcgtattc attcatgtta gttgcgtacg agccggaagc ataaagtgta    360
aagcctgggg tgcctaatga gtgagctaac tcacattaat tgcgttgcgc tcactgcccg    420
ctttccagtc gggaaacctg tcgtgccagc tgcattaatt aatcggccaa cgcgcgggga    480
gaggcggttt gcgtattggg cgctcttccg cttcctcgct cactgactcg ctgcgctcgg    540
tcgttcggct gcggcgagcg gtatcagctc actcaaaggc ggtaatacgg ttatccacag    600
aatcagggga taacgcagga agaacatgt gagcaaaagg ccagcaaaag gccaggaacc     660
gtaaaaaggc cgcgttgctg gcgttttcc ataggctccg ccccctgac gagcatcaca     720 aaaatcgacg ctcaagtcag aggtggcgaa acccgacagg actataaaga taccaggcgt    780
ttccccctgg aagctccctc gtgcgctctc ctgttccgac cctgccgctt accggatacc    840
tgtccgcctt tctcccttcg ggaagcgtgg cgctttctca tagctcacgc tgtaggtatc    900
tcagttcggt gtaggtcgtt cgctccaagc tgggctgtgt gcacgaaccc cccgttcagc    960
ccgaccgctg cgccttatcc ggtaactatc gtcttgagtc caacccggta agacacgact   1020
tatcgccact ggcagcagcc actggtaaca ggattagcag agcgaggtat gtaggcggtg   1080
ctacagagtt cttgaagtgg tggcctaact acggctacac tagaaggaca gtatttggta   1140
tctgcgctct gctgaagcca gttaccttcg gaaaaagagt tggtagctct tgatccggca   1200
aacaaaccac cgctggtagc ggtggttttt tgtttgcaa gcagcagatt acgcgcagaa    1260
aaaaaggatc tcaagaagat cctttgatct tttctacggg gtctgacgct cagtggaacg   1320
aaaactcacg ttaagggatt ttggtcatga gattatcaaa aaggatcttc acctagatcc   1380
ttttaaatta aaaatgaagt tttaaatcaa tctaaagtat atatgagtaa acttggtctg   1440
acagttacca atgcttaatc agtgaggcac ctatctcagc gatctgtcta tttcgttcat   1500
ccatagttgc ctgactcccc gtcgtgtaga taactacgat acgggagggc ttaccatctg   1560
gccccagtgc tgcaatgata ccgcgagacc cacgctcacc ggctccagat ttatcagcaa   1620
```

```
taaaccagcc agccggaagg gccgagcgca gaagtggtcc tgcaactttta tccgcctcca    1680 tccagtctat taattgttgc cgggaagcta gagtaagtag ttcgccagtt aatagtttgc    1740
gcaacgttgt tgccattgct acaggcatcg tggtgtcacg ctcgtcgttt ggtatggctt    1800
cattcagctc cggttcccaa cgatcaaggc gagttacatg atcccccatg ttgtgcaaaa    1860
aagcggttag ctccttcggt cctccgatcg ttgtcagaag taagttggcc gcagtgttat    1920
cactcatggt tatggcagca ctgcataatt ctcttactgt catgccatcc gtaagatgct    1980
tttctgtgac tggtgagtac tcaaccaagt cattctgaga atagtgtatg cggcgaccga    2040
gttgctcttg cccggcgtca atacgggata ataccgcgcc acatagcaga actttaaaag    2100
tgctcatcat tggaaaacgt tcttcggggc gaaaactctc aaggatctta ccgctgttga    2160
gatccagttc gatgtaaccc actcgtgcac ccaactgatc ttcagcatct tttactttca    2220
ccagcgtttc tgggtgagca aaaacaggaa ggcaaaatgc cgcaaaaaag gaataagggg    2280
cgacacggaa atgttgaata ctcatactct tcctttttca atattattga agcatttatc    2340
agggttattg tctcatgagc ggatacatat ttgaatgtat ttagaaaaat aaacaaatag    2400
gggttccgcg cacatttccc cgaaaagtgc cacctgacgc gccctgtagc ggcgcattaa    2460
gcgcggcggg tgtggtggtt acgcgcagcg tgaccgctac acttgccagc gccctagcgc    2520
ccgctccttt cgctttcttc ccttcctttc tcgccacgtt cgccggcttt ccccgtcaag    2580
ctctaaatcg ggggctccct ttagggttcc gatttagtgc tttacggcac ctcgacccca    2640
aaaaacttga ttagggtgat ggttcacgta gtgggccatc gccctgatag acggtttttc    2700
gccctttgac gttggagtcc acgttcttta atagtggact cttgttccaa actggaacaa    2760
cactcaaccc tatctcggtc tattcttttg atttataagg gattttgccg atttcggcct    2820
attggttaaa aaatgagctg atttaacaaa aatttaacgc gaattttaac aaaatattaa    2880
cgcttacaat ttccattcgc cattcaggct gcgcaactgt tgggaagggc gatcggtgcg    2940
ggcctcttcg ctattacgcc agctggcgaa agggggatgt gctgcaaggc gattaagttg    3000
ggtaacgcca gggttttccc agtcacgacg ttgtaaaacg acggccagtg aattgtaata    3060
cgactcacta tagggcgaat tgggtaccgg gccccccctc gaggtcgatg gtgtcgataa    3120
gcttgatatc gaattcatgt cacacaaacc gatcttcgcc tcaaggaaac ctaattctac    3180
atccgagaga ctgccgagat ccagtctaca ctgattaatt ttcgggccaa taatttaaaa    3240
aaatcgtgtt atataatatt atatgtatta tatatataca tcatgatgat actgacagtc    3300
atgtcccatt gctaaataga cagactccat ctgccgcctc caactgatgt tctcaatatt    3360 taagggtca tctcgcattg tttaataata aacagactcc atctaccgcc tccaaatgat    3420
gttctcaaaa tatattgtat gaacttattt ttattactta gtattattag acaacttact    3480
tgctttatga aaacacttc ctatttagga aacaatttat aatggcagtt cgttcattta    3540
acaatttatg tagaataaat gttataaatg cgtatgggaa atcttaaata tggatagcat    3600
aaatgatatc tgcattgcct aattcgaaat caacagcaac gaaaaaaatc ccttgtacaa    3660
cataaatagt catcgagaaa tatcaactat caaagaacag ctattcacac gttactattg    3720
agattattat tggacgagaa tcacacactc aactgtcttt ctctcttcta gaaatacagg    3780
tacaagtatg tactattctc attgttcata cttctagtca tttcatccca catattcctt    3840
ggatttctct ccaatgaatg acattctatc ttgcaaattc aacaattata ataagatata    3900
ccaaagtagc ggtatagtgg caatcaaaaa gcttctctgg tgtgcttctc gtatttattt    3960
ttattctaat gatccattaa aggtatatat ttatttcttg ttatataatc cttttgttta    4020
```

```
ttacatgggc tggatacata aaggtatttt gatttaattt tttgcttaaa ttcaatcccc    4080
cctcgttcag tgtcaactgt aatggtagga aattaccata cttttgaaga agcaaaaaaa    4140
atgaaagaaa aaaaaaatcg tatttccagg ttagacgttc cgcagaatct agaatgcggt    4200
atgcggtaca ttgttcttcg aacgtaaaag ttgcgctccc tgagatattg tacattttttg   4260 cttttacaag tacaagtaca tcgtacaact atgtactact gttgatgcat ccacaacagt    4320
ttgttttgtt ttttttttgtt ttttttttttt ctaatgattc attaccgcta tgtataccta   4380
cttgtacttg tagtaagccg ggttattggc gttcaattaa tcatagactt atgaatctgc    4440
acggtgtgcg ctgcgagtta cttttagctt atgcatgcta cttgggtgta atattgggat    4500
ctgttcggaa atcaacggat gctcaatcga tttcgacagt aattaattaa gtcatacaca    4560
agtcagcttt cttcgagcct catataagta taagtagttc aacgtattag cactgtaccc    4620
agcatctccg tatcgagaaa cacaacaaca tgccccattg acagatcat gcggatacac     4680 aggttgtgca gtatcataca tactcgatca gacaggtcgt ctgaccatca tacaagctga    4740
acaagcgctc catacttgca cgctctctat atacacagtt aaattacata tccatagtct    4800
aacctctaac agttaatctt ctggtaagcc tcccagccag ccttctggta tcgcttggcc    4860
tcctcaatag gatctcggtt ctggccgtac agacctcggc cgacaattat gatatccgtt    4920
ccggtagaca tgacatcctc aacagttcgg tactgctgtc cgagagcgtc tcccttgtcg    4980
tcaagaccca ccccggggt cagaataagc cagtcctcag agtcgcccctt aggtcggttc    5040 tgggcaatga agccaaccac aaactcgggg tcggatcggg caagctcaat ggtctgcttg    5100
gagtactcgc cagtggccag agagcccttg caagacagct cggccagcat gagcagacct    5160
ctggccagct tctcgttggg agaggggact aggaactcct tgtactggga gttctcgtag    5220
tcagagacgt cctccttctt ctgttcagag acagtttcct cggcaccagc tcgcaggcca    5280
gcaatgattc cggttccggg tacaccgtgg gcgttggtga tatcggacca ctcggcgatt    5340
cggtgacacc ggtactggtg cttgacagtg ttgccaatat ctgcgaactt tctgtcctcg    5400
aacaggaaga aaccgtgctt aagagcaagt tccttgaggg ggagcacagt gccggcgtag    5460
gtgaagtcgt caatgatgtc gatatgggtt ttgatcatgc acacataagg tccgacctta    5520
tcggcaagct caatgagctc cttggtggtg gtaacatcca gagaagcaca caggttggtt    5580
ttcttggctg ccacgagctt gagcactcga gcggcaaagg cggacttgtg gacgttagct    5640
cgagcttcgt aggagggcat tttggtggtg aagaggagac tgaaataaat ttagtctgca    5700
gaacttttta tcggaacctt atctggggca gtgaagtata tgttatggta atagttacga    5760
gttagttgaa cttatagata gactggacta tacggctatc ggtccaaatt agaaagaacg    5820
tcaatggctc tctgggcgtc gcctttgccg acaaaaatgt gatcatgatg aaagccagca    5880
atgacgttgc agctgatatt gttgtcggcc aaccgcgccg aaaacgcagc tgtcagaccc    5940
acagcctcca acgaagaatg tatcgtcaaa gtgatccaag cacactcata gttggagtcg    6000
tactccaaag gcggcaatga cgagtcagac agatactcgt cgacgtttaa acagtgtacg    6060
cagatctact atagaggaac atttaaattg ccccggagaa gacggccagg ccgcctagat    6120
gacaaattca acaactcaca gctgactttc tgccattgcc actaggggg ggcctttttta    6180 tatggccaag ccaagctctc cacgtcggtt gggctgcacc caacaataaa tgggtagggt    6240
tgcaccaaca aagggatggg atgggggta gaagatacga ggataacggg gctcaatggc    6300
acaaataaga acgaatactg ccattaagac tcgtgatcca gcgactgaca ccattgcatc    6360
```

```
atctaagggc ctcaaaacta cctcggaact gctgcgctga tctggacacc acagaggttc    6420
cgagcacttt aggttgcacc aaatgtccca ccaggtgcag gcagaaaacg ctggaacagc    6480
gtgtacagtt tgtcttaaca aaaagtgagg gcgctgaggt cgagcagggt ggtgtgactt    6540
gttatagcct ttagagctgc gaaagcgcgt atggatttgg ctcatcaggc cagattgagg    6600
gtctgtggac acatgtcatg ttagtgtact tcaatcgccc cctggatata gccccgacaa    6660
taggccgtgg cctcattttt ttgccttccg cacatttcca ttgctcgata cccacacctt    6720
gcttctcctg cacttgccaa ccttaatact ggtttacatt gaccaacatc ttacaagcgg    6780
ggggcttgtc tagggtatat ataaacagtg gctctcccaa tcggttgcca gtctcttttt    6840
tcctttcttt ccccacagat tcgaaatcta aactacacat cacagaattc cgagccgtga    6900
gtatccacga caagatcagt gtcgagacga cgcgttttgt gtaatgacac aatccgaaag    6960
tcgctagcaa cacacactct ctacacaaac taacccagct ctggtaccat gatcacaagt    7020
ttgtacaaaa aagttggatt ttttttcgaa cacttaatgg aggtggtgaa tgaaatagtc    7080
tcaattgggc aggaagtttt acccaaagtt gattatgccc aactctggag tgatgccagt    7140
cactgtgagt tgctttactt gtccatcgca tttgtcatct tgaagttcac tcttggcccc    7200
cttggtccaa aaggtcagtc tcgtatgaag tttgttttca ccaattacaa ccttctcatg    7260
tccatttatt cgttgggatc attcctctca atggcatatg ccatgtacac catcggtgtt    7320
atgtctgaca actgcgagaa ggcttttgac aacaacgtct tcaggatcac cacgcagttg    7380
ttctatttga gcaagttcct ggagtatatt gactccttct atttgccact gatgggcaag    7440
cctctgacct ggttgcaatt cttccatcat ttgggggcac cgatggatat gtggctgttc    7500
tataattacc gaaatgaagc tgtttggatt tttgtgctgt tgaatggttt catccactgg    7560
atcatgtacg gttattattg gaccagattg atcaagctga agttccccat gccaaaatcc    7620
ctgattacat caatgcagat cattcaattc aatgttggtt tctacattgt ctggaagtac    7680
aggaacattc cctgttatcg ccaagatggg atgaggatgt ttggctggtt cttcaattac    7740
ttttatgttg gcacagtctt gtgtttgttc ttgaatttct atgtgcaaac gtatatcgtc    7800
aggaagcaca agggagccaa aaagattcag tgatatttcc tcctctgcgg tggcctcttt    7860
tgacctcccc ttgacaccta taatgtggag gtgtcgggct ctctccgtct caccagcact    7920
tgactctgca ggtgctcact tttattttt acccatcttt gcttgttgac cattcacctc    7980
tcccacttcc acatagtcca ttctaactgt tgcagactgc ggtccatnnn ntccagagct    8040
cccaatgacc atacgcgaca ccnnntnnna nnncngccca ttgtgcacaa ttcatagtgg    8100
catcgttttg ccttgatacg tgtgcnnnnn nnnnnaccca acttt              8145
```

<210> SEQ ID NO 49
<211> LENGTH: 31
<212> TYPE: DNA
<213> ORGANISM: Artificial Sequence
<220> FEATURE:
<223> OTHER INFORMATION: Primer ig-s

<400> SEQUENCE: 49
caccatggct ctggccaacg acgctggcga g                                    31

<210> SEQ ID NO 50
<211> LENGTH: 26
<212> TYPE: DNA
<213> ORGANISM: Artificial Sequence
<220> FEATURE:
<223> OTHER INFORMATION: Primer ig-as

<400> SEQUENCE: 50
ctaaagctgc ttaccagcct tagcgg                                          26

<210> SEQ ID NO 51
<211> LENGTH: 7877
<212> TYPE: DNA
<213> ORGANISM: Artificial Sequence
<220> FEATURE:
<223> OTHER INFORMATION: Plasmid pBY1-FAE

<400> SEQUENCE: 51

| | | | | | |
|---|---|---|---|---|---|
| cttgtacaaa | gtggtgatgg | ccgcaagtgt | ggatggggaa | gtgagtgccc | ggttctgtgt | 60 |
| gcacaattgg | caatccaaga | tggatggatt | caacacaggg | atatagcgag | ctacgtggtg | 120 |
| gtgcgaggat | atagcaacgg | atatttatgt | ttgacacttg | agaatgtacg | atacaagcac | 180 |
| tgtccaagta | caatactaaa | catactgtac | atactcatac | tcgtacccgg | caacggttt | 240 |
| cacttgagtg | cagtggctag | tgctcttact | cgtacagtgt | gcaatactgc | gtatcatagt | 300 |
| ctttgatgta | tatcgtattc | attcatgtta | gttgcgtacg | agccggaagc | ataaagtgta | 360 |
| aagcctgggg | tgcctaatga | gtgagctaac | tcacattaat | tgcgttgcgc | tcactgcccg | 420 |
| ctttccagtc | gggaaacctg | tcgtgccagc | tgcattaatg | aatcggccaa | cgcgcgggga | 480 |
| gaggcggttt | gcgtattggg | cgctcttccg | cttcctcgct | cactgactcg | ctgcgctcgg | 540 |
| tcgttcggct | gcggcgagcg | gtatcagctc | actcaaaggc | ggtaatacgg | ttatccacag | 600 |
| aatcagggga | taacgcagga | aagaacatgt | gagcaaaagg | ccagcaaaag | gccaggaacc | 660 |
| gtaaaaaggc | cgcgttgctg | gcgtttttcc | ataggctccg | ccccctgac | gagcatcaca | 720 |
| aaaatcgacg | ctcaagtcag | aggtggcgaa | acccgacagg | actataaaga | taccaggcgt | 780 |
| ttccccctgg | aagctccctc | gtgcgctctc | ctgttccgac | cctgccgctt | accggatacc | 840 |
| tgtccgcctt | tctcccttcg | ggaagcgtgg | cgctttctca | tagctcacgc | tgtaggtatc | 900 |
| tcagttcggt | gtaggtcgtt | cgctccaagc | tgggctgtgt | gcacgaaccc | cccgttcagc | 960 |
| ccgaccgctg | cgccttatcc | ggtaactatc | gtcttgagtc | caacccggta | agacacgact | 1020 |
| tatcgccact | ggcagcagcc | actggtaaca | ggattagcag | agcgaggtat | gtaggcggtg | 1080 |
| ctacagagtt | cttgaagtgg | tggcctaact | acggctacac | tagaaggaca | gtatttggta | 1140 |
| tctgcgctct | gctgaagcca | gttaccttcg | gaaaaagagt | tggtagctct | tgatccggca | 1200 |
| aacaaaccac | cgctggtagc | ggtggttttt | ttgtttgcaa | gcagcagatt | acgcgcagaa | 1260 |
| aaaaaggatc | tcaagaagat | cctttgatct | tttctacggg | gtctgacgct | cagtggaacg | 1320 |
| aaaactcacg | ttaagggatt | ttggtcatga | gattatcaaa | aaggatcttc | acctagatcc | 1380 |
| ttttaaatta | aaaatgaagt | tttaaatcaa | tctaaagtat | atatgagtaa | acttggtctg | 1440 |
| acagttacca | atgcttaatc | agtgaggcac | ctatctcagc | gatctgtcta | tttcgttcat | 1500 |
| ccatagttgc | ctgactcccc | gtcgtgtaga | taactacgat | acgggagggc | ttaccatctg | 1560 |
| gccccagtgc | tgcaatgata | ccgcgagacc | cacgctcacc | ggctccagat | ttatcagcaa | 1620 |
| taaaccagcc | agccggaagg | gccgagcgca | gaagtggtcc | tgcaacttta | tccgcctcca | 1680 |
| tccagtctat | taattgttgc | cgggaagcta | gagtaagtag | ttcgccagtt | aatagtttgc | 1740 |
| gcaacgttgt | tgccattgct | acaggcatcg | tggtgtcacg | ctcgtcgttt | ggtatggctt | 1800 |
| cattcagctc | cggttcccaa | cgatcaaggc | gagttacatg | atcccccatg | ttgtgcaaaa | 1860 |
| aagcggttag | ctccttcggt | cctccgatcg | ttgtcagaag | taagttggcc | gcagtgttat | 1920 |

```
cactcatggt tatggcagca ctgcataatt ctcttactgt catgccatcc gtaagatgct    1980
tttctgtgac tggtgagtac tcaaccaagt cattctgaga atagtgtatg cggcgaccga    2040
gttgctcttg cccggcgtca atacgggata ataccgcgcc acatagcaga actttaaaag    2100
tgctcatcat tggaaaacgt tcttcggggc gaaaactctc aaggatctta ccgctgttga    2160
gatccagttc gatgtaaccc actcgtgcac ccaactgatc ttcagcatct tttactttca    2220
ccagcgtttc tgggtgagca aaaacaggaa ggcaaaatgc cgcaaaaaag gaataagggg    2280
cgacacggaa atgttgaata ctcatactct ccttttttca atattattga agcatttatc    2340
agggttattg tctcatgagc ggatacatat ttgaatgtat ttagaaaaat aaacaaatag    2400
gggttccgcg cacatttccc cgaaaagtgc cacctgacgc gccctgtagc ggcgcattaa    2460
gcgcggcggg tgtggtggtt acgcgcagcg tgaccgctac acttgccagc gccctagcgc    2520
ccgctccttt cgctttcttc ccttcctttc tcgccacgtt cgccggcttt ccccgtcaag    2580
ctctaaatcg ggggctccct ttagggttcc gatttagtgc tttacggcac ctcgacccca    2640
aaaaacttga ttagggtgat ggttcacgta gtgggccatc gccctgatag acggtttttc    2700
gccctttgac gttggagtcc acgttcttta atagtggact cttgttccaa actggaacaa    2760
cactcaaccc tatctcggtc tattcttttg atttataagg gattttgccg atttcggcct    2820
attggttaaa aaatgagctg atttaacaaa aatttaacgc gaattttaac aaaatattaa    2880
cgcttacaat ttccattcgc cattcaggct gcgcaactgt tgggaagggc gatcggtgcg    2940
ggcctcttcg ctattacgcc agctggcgaa agggggatgt gctgcaaggc gattaagttg    3000
ggtaacgcca gggttttccc agtcacgacg ttgtaaaacg acggccagtg aattgtaata    3060
cgactcacta tagggcgaat tgggtaccgg gccccccctc gaggtcgatg gtgtcgataa    3120
gcttgatatc gaattcatgt cacacaaacc gatcttcgcc tcaaggaaac ctaattctac    3180
atccgagaga ctgccgagat ccagtctaca ctgattaatt ttcgggccaa taatttaaaa    3240
aaatcgtgtt atataatatt atatgtatta tatatataca tcatgatgat actgacagtc    3300
atgtcccatt gctaaataga cagactccat ctgccgcctc caactgatgt tctcaatatt    3360 taagggtca tctcgcattg tttaataata acagactcc atctaccgcc tccaaatgat     3420
gttctcaaaa tatattgtat gaacttattt ttattactta gtattattag acaacttact    3480
tgctttatga aaaacacttc ctatttagga aacaatttat aatggcagtt cgttcattta    3540
acaatttatg tagaataaat gttataaatg cgtatgggaa atcttaaata tggatagcat    3600
aaatgatatc tgcattgcct aattcgaaat caacagcaac gaaaaaaatc ccttgtacaa    3660
cataaatagt catcgagaaa tatcaactat caaagaacag ctattcacac gttactattg    3720
agattattat tggacgagaa tcacacactc aactgtcttt ctctcttcta gaaatacagg    3780
tacaagtatg tactattctc attgttcata cttctagtca tttcatccca catattcctt    3840
ggatttctct ccaatgaatg acattctatc ttgcaaattc aacaattata ataagatata    3900
ccaaagtagc ggtatagtgg caatcaaaaa gcttctctgg tgtgcttctc gtatttattt    3960
ttattctaat gatccattaa aggtatatat ttatttcttg ttatataatc cttttgttta    4020
ttacatgggc tggatacata aaggtatttt gatttaattt tttgcttaaa ttcaatcccc    4080
cctcgttcag tgtcaactgt aatggtagga aattaccata cttttgaaga agcaaaaaaa    4140
atgaaagaaa aaaaaaatcg tatttccagg ttagacgttc cgcagaatct agaatgcggt    4200
atgcggtaca ttgttcttcg aacgtaaaag ttgcgctccc tgagatattg tacattttttg   4260 cttttacaag tacaagtaca tcgtacaact atgtactact gttgatgcat ccacaacagt    4320
```

```
ttgttttgtt ttttttttgtt tttttttttt ctaatgattc attaccgcta tgtatacctc    4380
cttgtacttg tagtaagccg ggttattggc gttcaattaa tcatagactt atgaatctgc    4440
acggtgtgcg ctgcgagtta cttttagctt atgcatgcta cttgggtgta atattgggat    4500
ctgttcggaa atcaacggat gctcaatcga tttcgacagt aattaattaa gtcatacaca    4560
agtcagcttt cttcgagcct catataagta taagtagttc aacgtattag cactgtaccc    4620
agcatctccg tatcgagaaa cacaacaaca tgccccattg gacagatcat gcggatacac    4680
aggttgtgca gtatcataca tactcgatca gacaggtcgt ctgaccatca tacaagctga    4740
acaagcgctc catacttgca cgctctctat atacacagtt aaattacata tccatagtct    4800
aacctctaac agttaatctt ctggtaagcc tcccagccag ccttctggta tcgcttggcc    4860
tcctcaatag gatctcggtt ctggccgtac agacctcggc cgacaattat gatatccgtt    4920
ccggtagaca tgacatcctc aacagttcgg tactgctgtc cgagagcgtc tcccttgtcg    4980
tcaagaccca ccccgggggt cagaataagc cagtcctcag agtcgccctt aggtcggttc    5040
tgggcaatga agccaaccac aaactcgggg tcggatcggg caagctcaat ggtctgcttg    5100
gagtactcgc cagtggccag agagcccttg caagacagct cggccagcat gagcagacct    5160
ctggccagct tctcgttggg agaggggact aggaactcct tgtactggga gttctcgtag    5220
tcagagacgt cctccttctt ctgttcagag acagtttcct cggcaccagc tcgcaggcca    5280
gcaatgattc cggttccggg tacaccgtgg gcgttggtga tatcggacca ctcggcgatt    5340
cggtgacacc ggtactggtg cttgacagtg ttgccaatat ctgcgaactt tctgtcctcg    5400
aacaggaaga aaccgtgctt aagagcaagt tccttgaggg ggagcacagt gccggcgtag    5460
gtgaagtcgt caatgatgtc gatatgggtt ttgatcatgc acacataagg tccgaccta    5520
tcggcaagct caatgagctc cttggtggtg gtaacatcca gagaagcaca caggttggtt    5580
ttcttggctg ccacgagctt gagcactcga gcggcaaagg cggacttgtg gacgttagct    5640
cgagcttcgt aggagggcat tttggtggtg aagaggagac tgaaataaat ttagtctgca    5700
gaactttta tcgaacctt atctggggca gtgaagtata tgttatggta atagttacga    5760
gttagttgaa cttatagata gactggacta tacggctatc ggtccaaatt agaaagaacg    5820
tcaatggctc tctgggcgtc gcctttgccg acaaaaatgt gatcatgatg aaagccagca    5880
atgacgttgc agctgatatt gttgtcggcc aaccgcgccg aaaacgcagc tgtcagaccc    5940
acagcctcca acgaagaatg tatcgtcaaa gtgatccaag cacactcata gttggagtcg    6000
tactccaaag gcggcaatga cgagtcagac agatactcgt cgacgtttaa acagtgtacg    6060
cagatctact atagaggaac atttaaattg ccccggagaa gacggccagg ccgcctagat    6120
gacaaattca acaactcaca gctgactttc tgccattgcc actagggggg ggccttttta    6180
tatggccaag ccaagctctc cacgtcggtt gggctgcacc caacaataaa tgggtagggt    6240
tgcaccaaca aagggatggg atgggggggta gaagatacga ggataacggg gctcaatggc    6300
acaaataaga acgaatactg ccattaagac tcgtgatcca gcgactgaca ccattgcatc    6360
atctaagggc ctcaaaacta cctcggaact gctgcgctga tctggacacc acagaggttc    6420
cgagcacttt aggttgcacc aaatgtccca ccaggtgcag gcagaaaacg ctggaacagc    6480
gtgtacagtt tgtcttaaca aaaagtgagg gcgctgaggt cgagcagggt ggtgtgactt    6540
gttatagcct ttagagctgc gaaagcgcgt atggattttgg ctcatcaggc cagattgagg    6600
gtctgtggac acatgtcatg ttagtgtact tcaatcgccc cctggatata gccccgacaa    6660
```

-continued

```
taggccgtgg cctcattttt ttgccttccg cacatttcca ttgctcgata cccacacctt    6720
gcttctcctg cacttgccaa ccttaatact ggtttacatt gaccaacatc ttacaagcgg    6780
ggggcttgtc tagggtatat ataaacagtg gctctcccaa tcggttgcca gtctcttttt    6840
tcctttcttt ccccacagat tcgaaatcta aactacacat cacagaattc cgagccgtga    6900
gtatccacga caagatcagt gtcgagacga cgcgttttgt gtaatgacac aatccgaaag    6960
tcgctagcaa cacacactct ctacacaaac taacccagct ctggtaccat gatcacaagt    7020
ttgtacaaaa aagcaggctc cgcggccgcc cccttcacca tggctctggc caacgacgct    7080
ggcgagcgaa tctgggctgc cgtcaccgat cccgaaatcc tcattggcac cttctcctac    7140
ctgctcctga agcctctcct gcgaaactct ggtctcgtgg acgagaagaa aggagcctac    7200
cgaacctcca tgatctggta caacgtcctc ctggctctct tctctgccct gtccttctac    7260
gtgactgcca ccgctctcgg ctgggactac ggtactggag cctggctgcg aagacagacc    7320
ggtgatactc cccagcctct ctttcagtgt ccctctcctg tctgggactc caagctgttc    7380
acctggactg ccaaggcctt ctactattct aagtacgtgg agtacctcga caccgcttgg    7440
ctggtcctca agggcaagcg agtgtccttt ctgcaggcct ccatcacttt ggagctccc    7500 tgggacgtct acctcggcat tcgactgcac aacgagggtg tgtggatctt catgttcttt    7560
aactcgttca ttcacaccat catgtacacc tactatggac tgactgccgc tggctacaag    7620
ttcaaggcca agcctctgat cactgccatg cagatttgcc agttcgtcgg tggctttctc    7680
ctggtctggg actacatcaa cgttccctgc ttcaactctg acaagggcaa gctgttctcc    7740
tgggctttca actacgccta cgtcggatct gtctttctcc tgttctgtca cttcttttac    7800
caggacaacc tggccaccaa gaaatccgct aaggctggta agcagcttta gaagggtggg    7860
cgcgccgacc cagcttt                                                  7877
```

<210> SEQ ID NO 52
<211> LENGTH: 7771
<212> TYPE: DNA
<213> ORGANISM: Artificial Sequence
<220> FEATURE:
<223> OTHER INFORMATION: Plasmid pZUFmEgD9e

<400> SEQUENCE: 52

```
catggaggtg gtgaatgaaa tagtctcaat tgggcaggaa gttttaccca accagttgat      60
tatgcccaac tctggagtga tgccagtcac tgtgaggtgc tttacttgtc catcgcattt     120
gtcatcttga agttcactct tggcccccctt ggtccaaaag gtcagtctcg tatgaagttt     180
gttttcacca attacaacct tctcatgtcc atttattcgt gggatcatt cctctcaatg      240 gcatatgcca tgtacaccat cggtgttatg tctgacaact gcgagaaggc ttttgacaac      300
aacgtcttca ggatcaccac gcagttgttc tatttgagca agttcctgga gtatattgac      360
tccttctatt tgccactgat gggcaagcct ctgacctggt tgcaattctt ccatcatttg      420
ggggcaccga tggatatgtg gctgttctat aattaccgaa atgaagctgt tggatttt      480 gtgctgttga atggtttcat ccactggatc atgtacggtt attattggac cagattgatc      540
aagctgaagt tccccatgcc aaaatccctg attacatcaa tgcagatcat tcaattcaat      600
gttggtttct acattgtctg gaagtacagg aacattccct gttatcgcca agatgggatg      660
aggatgtttg gctggttctt caattacttt tatgttggca cagtcttgtg tttgttcttg      720
aatttctatg tgcaaacgta tatcgtcagg aagcacaagg gagccaaaaa gattcagtga      780
gcggccgcaa gtgtggatgg ggaagtgagt gcccggttct gtgtgcacaa ttggcaatcc      840
```

```
aagatggatg gattcaacac agggatatag cgagctacgt ggtggtgcga ggatatagca    900
acggatattt atgtttgaca cttgagaatg tacgatacaa gcactgtcca agtacaatac    960
taaacatact gtacatactc atactcgtac ccgggcaacg gtttcacttg agtgcagtgg   1020
ctagtgctct tactcgtaca gtgtgcaata ctgcgtatca tagtctttga tgtatatcgt   1080
attcattcat gttagttgcg tacgagccgg aagcataaag tgtaaagcct ggggtgccta   1140
atgagtgagc taactcacat taattgcgtt gcgctcactg cccgctttcc agtcgggaaa   1200
cctgtcgtgc cagctgcatt aatgaatcgg ccaacgcgcg gggagaggcg gtttgcgtat   1260
tgggcgctct tccgcttcct cgctcactga ctcgctgcgc tcggtcgttc ggctgcggcg   1320
agcggtatca gctcactcaa aggcggtaat acggttatcc acagaatcag ggataacgc   1380
aggaaagaac atgtgagcaa aaggccagca aaaggccagg aaccgtaaaa aggccgcgtt   1440
gctggcgttt ttccataggc tccgcccccc tgacgagcat cacaaaaatc gacgctcaag   1500
tcagaggtgg cgaaacccga caggactata agataccag gcgtttcccc ctggaagctc    1560
cctcgtgcgc tctcctgttc cgaccctgcc gcttaccgga tacctgtccg cctttctccc   1620
ttcgggaagc gtggcgcttt ctcatagctc acgctgtagg tatctcagtt cggtgtaggt   1680
cgttcgctcc aagctgggct gtgtgcacga accccccgtt cagcccgacc gctgcgcctt   1740
atccggtaac tatcgtcttg agtccaaccc ggtaagacac gacttatcgc cactggcagc   1800
agccactggt aacaggatta gcagagcgag gtatgtaggc ggtgctacag agttcttgaa   1860
gtggtggcct aactacggct acactagaag gacagtattt ggtatctgcg ctctgctgaa   1920
gccagttacc ttcggaaaaa gagttggtag ctcttgatcc ggcaaacaaa ccaccgctgg   1980
tagcggtggt ttttttgttt gcaagcagca gattacgcgc agaaaaaaag gatctcaaga   2040
agatcctttg atcttttcta cggggtctga cgctcagtgg aacgaaaact cacgttaagg   2100
gattttggtc atgagattat caaaaaggat cttcacctag atccttttaa attaaaaatg   2160
aagttttaaa tcaatctaaa gtatatatga gtaaacttgg tctgacagtt accaatgctt   2220
aatcagtgag gcacctatct cagcgatctg tctatttcgt tcatccatag ttgcctgact   2280
ccccgtcgtg tagataacta cgatacggga gggcttacca tctggcccca gtgctgcaat   2340
gataccgcga acccacgct caccggctcc agatttatca gcaataaacc agccagccgg    2400
aagggccgag cgcagaagtg gtcctgcaac tttatccgcc tccatccagt ctattaattg   2460
ttgccgggaa gctagagtaa gtagttcgcc agttaatagt ttgcgcaacg ttgttgccat   2520
tgctacaggc atcgtggtgt cacgctcgtc gtttggtatg gcttcattca gctccggttc   2580
ccaacgatca aggcgagtta catgatcccc catgttgtgc aaaaaagcgg ttagctcctt   2640
cggtcctccg atcgttgtca gaagtaagtt ggccgcagtg ttatcactca tggttatggc   2700
agcactgcat aattctctta ctgtcatgcc atccgtaaga tgcttttctg tgactggtga   2760
gtactcaacc aagtcattct gagaatagtg tatgcggcga ccgagttgct cttgcccggc   2820
gtcaatacgg gataataccg cgccacatag cagaacttta aaagtgctca tcattggaaa   2880
acgttcttcg gggcgaaaac tctcaaggat cttaccgctg ttgagatcca gttcgatgta   2940
acccactcgt gcacccaact gatcttcagc atcttttact ttcaccagcg tttctgggtg   3000
agcaaaaaca ggaaggcaaa atgccgcaaa aaagggaata aggcgacac ggaaatgttg    3060
aatactcata ctcttccttt ttcaatatta ttgaagcatt tatcagggtt attgtctcat   3120
gagcggatac atatttgaat gtatttagaa aaataaacaa atagggggttc cgcgcacatt   3180
```

```
tccccgaaaa gtgccacctg acgcgccctg tagcggcgca ttaagcgcgg cgggtgtggt   3240
ggttacgcgc agcgtgaccg ctacacttgc cagcgcccta gcgcccgctc ctttcgcttt   3300
cttcccttcc tttctcgcca cgttcgccgg ctttccccgt caagctctaa atcgggggct   3360 cccctttaggg ttccgattta gtgctttacg gcacctcgac cccaaaaaac ttgattaggg   3420
tgatggttca cgtagtgggc catcgccctg atagacggtt tttcgccctt gacgttgga    3480 gtccacgttc tttaatagtg gactcttgtt ccaaactgga caacactca accctatctc    3540 ggtctattct tttgatttat aagggatttt gccgatttcg gcctattggt taaaaaatga   3600
gctgatttaa caaaatttta acgcgaattt taacaaaata ttaacgctta caatttccat   3660
tcgccattca ggctgcgcaa ctgttgggaa gggcgatcgg tgcgggcctc ttcgctatta   3720
cgccagctgg cgaaggggg atgtgctgca aggcgattaa gttgggtaac gccagggttt    3780
tcccagtcac gacgttgtaa aacgacggcc agtgaattgt aatacgactc actatagggc   3840
gaattgggta ccgggccccc cctcgaggtc gatggtgtcg ataagcttga tatcgaattc   3900
atgtcacaca aaccgatctt cgcctcaagg aaacctaatt ctacatccga gagactgccg   3960
agatccagtc tacactgatt aattttcggg ccaataattt aaaaaaatcg tgttatataa   4020
tattatatgt attatatata tacatcatga tgatactgac agtcatgtcc cattgctaaa   4080
tagacagact ccatctgccg cctccaactg atgttctcaa tatttaaggg gtcatctcgc   4140
attgtttaat aataaacaga ctccatctac cgcctccaaa tgatgttctc aaaatatatt   4200
gtatgaactt attttttatta cttagtatta ttagacaact tacttgcttt atgaaaaaca   4260 cttcctatt aggaaacaat ttataatggc agttcgttca tttaacaatt tatgtagaat    4320
aaatgttata aatgcgtatg ggaaatctta aatatggata gcataaatga tatctgcatt   4380
gcctaattcg aaatcaacag caacgaaaaa aatcccttgt acaacataaa tagtcatcga   4440
gaaatatcaa ctatcaaaga acagctattc acacgttact attgagatta ttattggacg   4500
agaatcacac actcaactgt ctttctctct tctagaaata caggtacaag tatgtactat   4560
tctcattgtt catacttcta gtcatttcat cccacatatt ccttggattt ctctccaatg   4620
aatgacattc tatcttgcaa attcaacaat tataataaga tataccaaag tagcggtata   4680
gtggcaatca aaaagcttct ctggtgtgct tctcgtattt atttttattc taatgatcca   4740
ttaaaggtat atatttattt cttgttatat aatcctttg tttattacat gggctggata    4800
cataaaggta ttttgattta atttttttgct taaattcaat cccccctcgt tcagtgtcaa   4860
ctgtaatggt aggaaattac catacttttg aagaagcaaa aaaatgaaa gaaaaaaaa     4920 atcgtatttc caggttagac gttccgcaga atctagaatg cggtatgcgg tacattgttc   4980
ttcgaacgta aaagttgcgc tccctgagat attgtacatt tttgctttta caagtacaag   5040
tacatcgtac aactatgtac tactgttgat gcatccacaa cagtttgttt tgttttttt    5100 tgttttttt ttttctaatg attcattacc gctatgtata cctacttgta cttgtagtaa    5160
gccgggttat tggcgttcaa ttaatcatag acttatgaat ctgcacggtg tgcgctgcga   5220
gttactttta gctatgcat gctacttggg tgtaatattg ggatctgttc ggaaatcaac    5280
ggatgctcaa tcgatttcga cagtaattaa ttaagtcata cacaagtcag ctttcttcga   5340
gcctcatata agtataagta gttcaacgta ttagcactgt acccagcatc tccgtatcga   5400
gaaacacaac aacatgcccc attggacaga tcatgcggat acacaggttg tgcagtatca   5460
tacatactcg atcagacagg tcgtctgacc atcatacaag ctgaacaagc gctccatact   5520
tgcacgctct ctatatacac agttaaatta catatccata gtctaacctc taacagttaa   5580
```

```
tcttctggta agcctcccag ccagccttct ggtatcgctt ggcctcctca ataggatctc    5640
ggttctggcc gtacagacct cggccgacaa ttatgatatc cgttccggta gacatgacat    5700
cctcaacagt tcggtactgc tgtccgagag cgtctccctt gtcgtcaaga cccacccgg    5760 gggtcagaat aagccagtcc tcagagtcgc ccttaggtcg gttctgggca atgaagccaa    5820
ccacaaactc ggggtcggat cgggcaagct caatggtctg cttggagtac tcgccagtgg    5880
ccagagagcc cttgcaagac agctcggcca gcatgagcag acctctggcc agcttctcgt    5940
tgggagaggg gactaggaac tccttgtact gggagttctc gtagtcagag cgtcctcct    6000 tcttctgttc agagacagtt tcctcggcac cagctcgcag gccagcaatg attccggttc    6060
cgggtacacc gtgggcgttg gtgatatcgg accactcggc gattcggtga caccggtact    6120
ggtgcttgac agtgttgcca atatctgcga actttctgtc ctcgaacagg aagaaaccgt    6180
gcttaagagc aagttccttg aggggagca cagtgccggc gtaggtgaag tcgtcaatga    6240
tgtcgatatg ggttttgatc atgcacacat aaggtccgac cttatcggca agctcaatga    6300
gctccttggt ggtggtaaca tccagagaag cacacaggtt ggttttcttg gctgccacga    6360
gcttgagcac tcgagcggca aaggcggact tgtggacgtt agctcgagct tcgtaggagg    6420
gcattttggt ggtgaagagg agactgaaat aaatttagtc tgcagaactt tttatcggaa    6480
ccttatctgg ggcagtgaag tatatgttat ggtaatagtt acgagttagt tgaacttata    6540
gatagactgg actatacggc tatcggtcca aattagaaag aacgtcaatg gctctctggg    6600
cgtcgccttt gccgacaaaa atgtgatcat gatgaaagcc agcaatgacg ttgcagctga    6660
tattgttgtc ggccaaccgc gccgaaaacg cagctgtcag acccacagcc tccaacgaag    6720
aatgtatcgt caaagtgatc caagcacact catagttgga gtcgtactcc aaaggcggca    6780
atgacgagtc agacagatac tcgtcgacgt ttaaacagtg tacgcagatc tactatagag    6840
gaacatttaa attgccccgg agaagacggc caggccgcct agatgacaaa ttcaacaact    6900
cacagctgac tttctgccat tgccactagg ggggggcctt tttatatggc caagccaagc    6960
tctccacgtc ggttgggctg cacccaacaa taaatgggta gggttgcacc aacaaaggga    7020
tgggatgggg ggtagaagat acgaggataa cggggctcaa tggcacaaat aagaacgaat    7080
actgccatta agactcgtga tccagcgact gacaccattg catcatctaa gggcctcaaa    7140
actacctcgg aactgctgcg ctgatctgga caccacagag gttccgagca ctttaggttg    7200
caccaaatgt cccaccaggt gcaggcagaa aacgctggaa cagcgtgtac agtttgtctt    7260
aacaaaaagt gagggcgctg aggtcgagca gggtggtgtg acttgttata gcctttagag    7320
ctgcgaaagc gcgtatggat ttggctcatc aggccagatt gagggtctgt ggacacatgt    7380
catgttagtg tacttcaatc gcccctgga tatagccccg acaataggcc gtggcctcat    7440 tttttttgcct tccgcacatt tccattgctc gatacccaca ccttgcttct cctgcacttg    7500
ccaaccttaa tactggttta cattgaccaa catcttacaa gcgggggct tgtctagggt    7560 atatataaac agtggctctc ccaatcggtt gccagtctct ttttttccttt ctttccccac    7620 agattcgaaa tctaaactac acatcacaga attccgagcc gtgagtatcc acgacaagat    7680
cagtgtcgag acgacgcgtt ttgtgtaatg acacaatccg aaagtcgcta gcaacacaca    7740
ctctctacac aaactaaccc agctctggta c                                   7771
```

<210> SEQ ID NO 53
<211> LENGTH: 7769
<212> TYPE: DNA

<213> ORGANISM: Artificial Sequence
<220> FEATURE:
<223> OTHER INFORMATION: Plasmid pZUFmEgD9eS

<400> SEQUENCE: 53

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaaggatct caccctagat cctttaaat taaaatgaa     1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
```

```
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgcccctagc gcccgctcct ttcgctttct    2520
tcccttcctt tctcgccacg ttcgccggct ttccccgtca agctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa atatatattgt    3420 atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc ccctcgttc agtgtcaact    4080 gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
```

```
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct ggagtactc gccagtggcc    5100
agagagccct tgcaagacag ctcggccagc atgagcagac tctggccag cttcgttg      5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaagtga gggcgctgag gtcgagcagg gtggtgtgac ttgttatagc ctttagagct    6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc gggggcttg tctagggtat    6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
```

```
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acctctccat cgccttcgtc atcctgaagt tcacccttgg tcctctcgga    7140
cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
acctggttgc agttctttca ccatctcgga gctcctatgg acatgtggct gttctacaac    7440
taccgaaacg aagccgtttg gatctttgtg ctgctcaacg gcttcattca ctggatcatg    7500
tacggctact attggacccg actgatcaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggttttttcaa ctacttctac    7680 gttggtactg tcctgtgtct gttcctcaac ttctacgtgc agacctacat cgtccgaaag    7740
cacaagggag ccaaaaagat tcagtgagc                                      7769

<210> SEQ ID NO 54
<211> LENGTH: 7769
<212> TYPE: DNA
<213> ORGANISM: Artificial Sequence
<220> FEATURE:
<223> OTHER INFORMATION: Plasmid pY120

<400> SEQUENCE: 54
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac ccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
```

-continued

```
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccgttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt aatagtggac tcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa atatatttgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
```

```
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg     4320 ttttttttt ttctaatgat tcattaccgc tatgtatacc tacttgtact tgtagtaagc     4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct ggagtactc gccagtggcc     5100 agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
```

```
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc     6180
tccacgtcgg ttgggctgca cccaacaata aatgggtagg gttgcaccaa caaagggatg    6240 ggatggggg tagaagatac gaggataacg gggctcaatg gcacaaataa gaacgaatac     6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480 caaaagtga gggcgctgag gtcgagcagg gtggtgtgac ttgttatagc ctttagagct     6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat     6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtgg tgaatgaaat agtctcaatt    7020
gggcaggaag ttttacccaa agttgattat gcccaactct ggagtgatgc cagtcactgt    7080
gaggtgcttt acttgtccat cgcatttgtc atcttgaagt tcactcttgg ccccctggt     7140 ccaaaaggtc agtctcgtat gaagtttgtt ttcaccaatt acaaccttct catgtccatt    7200
tattcgttgg gatcattcct ctcaatggca tatgccatgt acaccatcgg tgttatgtct    7260
gacaactgcg agaaggcttt tgacaacaac gtcttcagga tcaccacgca gttgttctat    7320
ttgagcaagt tcctggagta tattgactcc ttctatttgc cactgatggg caagcctctg    7380
acctggttgc aattcttcca tcatttgggg gcaccgatgg atatgtggct gttctataat    7440
taccgaaatg aagctgtttg gattttgtg ctgttgaatg gtttcatcca ctggatcatg     7500
tacggttatt attggaccag attgatcaag ctgaagttcc ccatgccaaa atccctgatt    7560
acatcaatgc agatcattca attcaatgtt ggtttctaca ttgtctggaa gtacaggaac    7620
attccctgtt atcgccaaga tgggatgagg atgtttggct ggttcttcaa ttacttttat    7680
gttggcacag tcttgtgttt gttcttgaat ttctatgtgc aaacgtatat cgtcaggaag    7740
cacaagggag ccaaaaagat tcagtgagc                                      7769

<210> SEQ ID NO 55
<211> LENGTH: 7085
<212> TYPE: DNA
<213> ORGANISM: Artificial Sequence
<220> FEATURE:
<223> OTHER INFORMATION: Plasmid pKR72

<400> SEQUENCE: 55
gtacggatcc gtcgacggcg cgcccgatca tccggatata gttcctcctt tcagcaaaaa      60 accctcaag acccgtttag aggccccaag gggttatgct agttattgct cagcggtggc      120
agcagccaac tcagcttcct ttcgggcttt gttagcagcc ggatcgatcc aagctgtacc     180
tcactattcc tttgccctcg acgagtgct ggggcgtcgg tttccactat cggcgagtac      240
```

-continued

| | |
|---|---|
| ttctacacag ccatcggtcc agacggccgc gcttctgcgg gcgatttgtg tacgcccgac | 300 |
| agtcccggct ccggatcgga cgattgcgtc gcatcgaccc tgcgcccaag ctgcatcatc | 360 |
| gaaattgccg tcaaccaagc tctgatagag ttggtcaaga ccaatgcgga gcatatacgc | 420 |
| ccggagccgc ggcgatcctg caagctccgg atgcctccgc tcgaagtagc gcgtctgctg | 480 |
| ctccatacaa gccaaccacg gcctccagaa gaagatgttg cgacctcgt attgggaatc | 540 |
| cccgaacatc gcctcgctcc agtcaatgac cgctgttatg cggccattgt ccgtcaggac | 600 |
| attgttggag ccgaaatccg cgtgcacgag gtgccggact cgggcagt cctcggccca | 660 |
| aagcatcagc tcatcgagag cctgcgcgac ggacgcactg acggtgtcgt ccatcacagt | 720 |
| ttgccagtga tacacatggg gatcagcaat cgcgcatatg aaatcacgcc atgtagtgta | 780 |
| ttgaccgatt ccttgcggtc cgaatgggcc gaacccgctc gtctggctaa gatcggccgc | 840 |
| agcgatcgca tccatagcct ccgcgaccgg ctgcagaaca gcgggcagtt cggtttcagg | 900 |
| caggtcttgc aacgtgacac cctgtgcacg gcgggagatg caataggtca ggctctcgct | 960 |
| gaattcccca atgtcaagca cttccggaat cgggagcgcg gccgatgcaa agtgccgata | 1020 |
| aacataacga tctttgtaga aaccatcggc gcagctattt acccgcagga catatccacg | 1080 |
| ccctcctaca tcgaagctga aagcacgaga ttcttcgccc tccgagagct gcatcaggtc | 1140 |
| ggagacgctg tcgaactttt cgatcagaaa cttctcgaca gacgtcgcgg tgagttcagg | 1200 |
| cttttccatg ggtatatctc cttcttaaag ttaaacaaaa ttatttctag agggaaaccg | 1260 |
| ttgtggtctc cctatagtga gtcgtattaa tttcgcggga tcgagatcga tccaattcca | 1320 |
| atcccacaaa aatctgagct taacagcaca gttgctcctc tcagagcaga atcgggtatt | 1380 |
| caacacccctc atatcaacta ctacgttgtg tataacggtc cacatgccgg tatatacgat | 1440 |
| gactggggtt gtacaaaggc ggcaacaaac ggcgttcccg gagttgcaca caagaaattt | 1500 |
| gccactatta cagaggcaag agcagcagct gacgcgtaca caacaagtca gcaaacagac | 1560 |
| aggttgaact tcatccccaa aggagaagct caactcaagc ccaagagctt tgctaaggcc | 1620 |
| ctaacaagcc caccaaagca aaaagcccac tggctcacgc taggaaccaa aaggcccagc | 1680 |
| agtgatccag ccccaaaaga gatctccttt gccccggaga ttacaatgga cgatttcctc | 1740 |
| tatctttacg atctaggaag gaagttcgaa ggtgaaggtg acgacactat gttcaccact | 1800 |
| gataatgaga aggttagcct cttcaatttc agaaagaatg ctgacccaca gatggttaga | 1860 |
| gaggcctacg cagcaggtct catcaagacg atctacccga gtaacaatct ccaggagatc | 1920 |
| aaataccttc ccaagaaggt taaagatgca gtcaaaagat tcaggactaa ttgcatcaag | 1980 |
| aacacagaga aagacatatt tctcaagatc agaagtacta ttccagtatg gacgattcaa | 2040 |
| ggcttgcttc ataaaccaag gcaagtaata gagattggag tctctaaaaa ggtagttcct | 2100 |
| actgaatcta aggccatgca tgagtctaa gattcaaatc gaggatctaa cagaactcgc | 2160 |
| cgtgaagact ggcgaacagt tcatacagag tcttttacga ctcaatgaca agaagaaaat | 2220 |
| cttcgtcaac atggtggagc acgacactct ggtctactcc aaaaatgtca agatacagt | 2280 |
| ctcagaagac caaagggcta ttgagacttt tcaacaaagg ataatttcgg gaaacctcct | 2340 |
| cggattccat tgcccagcta tctgtcactt catcgaaagg acagtagaaa aggaaggtgg | 2400 |
| ctcctacaaa tgccatcatt gcgataaagg aaaggctatc attcaagatg cctctgccga | 2460 |
| cagtggtccc aaagatggac ccccacccac gaggagcatc gtggaaaaag aagacgttcc | 2520 |
| aaccacgtct tcaaagcaag tggattgatg tgacatctcc actgacgtaa gggatgacgc | 2580 |

```
acaatcccac tatccttcgc aagacccttc ctctatataa ggaagttcat tcatttgga   2640 gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca cttttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat tcatatgcg cgattgctga    3180 tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggttttat gattagagtc ccgcaattat acatttaata cgcgatagaa    3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt ttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
```

```
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aataaaaga    5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
ttcgtccagc aaggctaaac gattgtatag atttatgaca atatttactt ttttatagat   5700
aaatgttata ttataataaa tttatataca tatattatat gttatttatt attattttaa   5760
atccttcaat attttatcaa accaactcat aatttttttt ttatctgtaa gaagcaataa   5820
aattaaatag acccacttta aggatgatcc aacctttata cagagtaaga gagttcaaat   5880
agtacccttt catatacata tcaactaaaa tattagaaat atcatggatc aaaccttata   5940
aagacattaa ataagtggat aagtataata tataaatggg tagtatataa tatataaatg   6000
gatacaaact tctctctttta taattgttat gtctccttaa catcctaata taatacataa   6060
gtgggtaata tataatatat aaatggagac aaacttcttc cattataatt gttatgtctt   6120
cttaacactt atgtctcgtt cacaatgcta aggttagaat tgtttagaaa gtcttatagt   6180
acacatttgt ttttgtacta tttgaagcat tccataagcc gtcacgattc agatgattta   6240
taataataag aggaaattta tcatagaaca ataaggtgca tagatagagt gttaatatat   6300
cataacatcc tttgtttatt catagaagaa gtgagatgga gctcagttat tatactgtta   6360
catggtcgga tacaatattc catgctctcc atgagctctt acacctacat gcatttagt    6420
tcatacttgc ggccgcagta tatcttaaat tctttaatac ggtgtactag gatattgaac   6480
tggttcttga tgatgaaaac ctgggccgag attgcagcta tttatagtca taggtcttgt   6540
taacatgcat ggacatttgg ccacggggtg gcatgcagtt tgacgggtgt tgaaataaac   6600
aaaaatgagg tggcggaaga gaatacgagt ttgaggttgg gttagaaaca acaaatgtga   6660
gggctcatga tgggttgagt tggtgaatgt tttgggctgc tcgattgaca cctttgtgag   6720
tacgtgttgt tgtgcatggc ttttggggtc cagtttttt ttcttgacgc ggcgatcctg    6780
atcagctagt ggataagtga tgtccactgt gtgtgattgc gttttgttt gaattttatg    6840
aacttagaca ttgctatgca aaggatactc tcattgtgtt ttgtcttctt ttgttccttg   6900
gcttttttcctt atgatccaag agactagtca gtgttgtggc attcgagact accaagatta   6960
attatgatgg gggaaggata agtaactgat tagtacggac tgttaccaaa ttaattaata   7020
agcggcaaat gaagggcatg gatcaaaagc ttggatctcc tgcaggatct ggccggccgg   7080
atctc                                                              7085
```

<210> SEQ ID NO 56
<211> LENGTH: 7873
<212> TYPE: DNA
<213> ORGANISM: Artificial Sequence
<220> FEATURE:

<223> OTHER INFORMATION: Plasmid pKR912

<400> SEQUENCE: 56

```
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta acaattcta accttagcat tgtgaacgag     300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttttt agcagtagag caatggttga   1080
ccgtgtgctt agcttctttt attttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac accgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct ccaggggga aacgcctggt atctttatag tcctgtcggg tttcgccacc   2100
tctgacttga gcgtcgattt ttgtgatgct cgtcaggggg cggagccta tggaaaaacg   2160
ccagcaacgc ggcctttta cggttcctgg ccttttgctg ccttttgct cacatgttct   2220
ttcctgcgtt atcccctgat tctgtggata accgtattac cgcctttgag tgagctgata   2280
```

-continued

```
ccgctcgccg cagccgaacg accgagcgca gcgagtcagt gagcgaggaa gcggaagagc    2340
gcccaatacg caaaccgcct ctccccgcgc gttggccgat tcattaatgc aggttgatcg    2400
attcgacatc gatctagtaa catagatgac accgcgcgcg ataatttatc ctagtttgcg    2460
cgctatattt tgttttctat cgcgtattaa atgtataatt gcgggactct aatcataaaa    2520
acccatctca taaataacgt catgcattac atgttaatta ttacatgctt aacgtaattc    2580
aacagaaatt atatgataat catcgcaaga ccggcaacag gattcaatct taagaaactt    2640
tattgccaaa tgtttgaacg atctgcttcg acgcactcct tctttaggta cctcactatt    2700
cctttgccct cggacgagtg ctggggcgtc ggtttccact atcggcgagt acttctacac    2760
agccatcggt ccagacggcc gcgcttctgc gggcgatttg tgtacgcccg acagtcccgg    2820
ctccggatcg gacgattgcg tcgcatcgac cctgcgccca agctgcatca tcgaaattgc    2880
cgtcaaccaa gctctgatag agttggtcaa gaccaatgcg gagcatatac gcccggagcc    2940
gcggcgatcc tgcaagctcc ggatgcctcc gctcgaagta gcgcgtctgc tgctccatac    3000
aagccaacca cggcctccag aagaagatgt tggcgacctc gtattgggaa tccccgaaca    3060
tcgcctcgct ccagtcaatg accgctgtta tgcggccatt gtccgtcagg acattgttgg    3120
agccgaaatc cgcgtgcacg aggtgccgga cttcggggca gtcctcggcc caaagcatca    3180
gctcatcgag agcctgcgcg acggacgcac tgacggtgtc gtccatcaca gtttgccagt    3240
gatacacatg gggatcagca atcgcgcata tgaaatcacg ccatgtagtg tattgaccga    3300
ttccttgcgg tccgaatggg ccgaacccgc tcgtctggct aagatcggcc gcagcgatcg    3360
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540
gatctttgta gaaaccatcg gcgcagctat ttacccgcag gacatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca ggcttttttca    3720 tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgt ggttgaacg tcttctttttt ccacgatgct cctcgtgggt gggggtccat    3960
ctttgggacc actgtcggca gaggcatctt gaatgatagc cttttccttta tcgcaatgat    4020 ggcatttgta ggagccacct tccttttcta ctgtcctttc gatgaagtga cagatagctg    4080
ggcaatggaa tccgaggagg tttcccgaaa ttatcctttg ttgaaaagtc tcaatagccc    4140
tttggtcttc tgagactgta tctttgacat ttttggagta gaccagagtg tcgtgctcca    4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac taccttttta gagactccaa tctctattac ttgccttggt    4380
ttatgaagca agccttgaat cgtccatact ggaatagtac ttctgatctt gagaaatatg    4440
tctttctctg tgttcttgat gcaattagtc ctgaatcttt tgactgcatc tttaaccttc    4500
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
```

```
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg ccttttggtt cctagcgtga gccagtgggc ttttgctt     4800
ggtgggcttg ttagggcctt agcaaagctc ttgggcttga gttgagcttc tcctttgggg    4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggaa caactgtgct gttaagctca    5100
gattttgtg ggattggaat tggatcgatc tcgatcccgc gaaattaata cgactcacta    5160
tagggagacc acaacggttt ccctctagaa ataattttgt ttaactttaa gaaggagata    5220
tacccatgga aaagcctgaa ctcaccgcga cgtctgtcga agtttctgat cgaaaagt     5280
tcgacagcgt ctccgacctg atgcagctct cggagggcga agaatctcgt gctttcagct    5340
tcgatgtagg agggcgtgga tatgtcctgc gggtaaatag ctgcgccgat ggtttctaca    5400
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg gttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg gccgcataac agcggtcatt gactggagcg    5880
aggcgatgtt cggggattcc caatacgagg tcgccaacat cttcttctgg aggccgtggt    5940
tggcttgtat ggagcagcag acgcgctact tcgagcggag gcatccggag cttgcaggat    6000
cgccgcggct ccgggcgtat atgctccgca ttggtcttga ccaactctat cagagcttgg    6060
ttgacggcaa tttcgatgat gcagcttggg cgcagggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg gaaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata ccccttggg gcctctaaac     6360
gggtcttgag gggttttttg ctgaaaggag gaactatatc cggatgatcg ggcgcgccgt    6420
cgacggatcc gtacgagatc cggccggcca gatcctgcag gagatccaag cttttgatcc    6480
atgcccttca tttgccgctt attaattaat ttggtaacag tccgtactaa tcagttactt    6540
atccttcccc catcataatt aatcttggta gtctcgaatg ccacaacact gactagtctc    6600
ttggatcata gaaaaagcc aaggaacaaa agaagacaaa acacaatgag agtatccttt      6660
gcatagcaat gtctaagttc ataaaattca acaaaaacg caatcacaca cagtggacat      6720
cacttatcca ctagctgatc aggatcgccg cgtcaagaaa aaaaaactgg accccaaaag    6780
ccatgcacaa caacacgtac tcacaaaggt gtcaatcgag cagcccaaaa cattcaccaa    6840
ctcaacccat catgagccct cacatttgtt gtttctaacc caacctcaaa ctcgtattct    6900
cttccgccac ctcattttg tttatttcaa cacccgtcaa actgcatgcc accccgtggc     6960
caaatgtcca tgcatgttaa caagacctat gactataaat agctgcaatc tcggcccagg    7020
```

-continued

| | |
|---|---|
| ttttcatcat caagaaccag ttcaatatcc tagtacaccg tattaaagaa tttaagatat | 7080 |
| actgcggccg caccatggag gtggtgaatg aaatagtctc aattgggcag gaagttttac | 7140 |
| ccaaagttga ttatgcccaa ctctggagtg atgccagtca ctgtgaggtg ctttacttgt | 7200 |
| ccatcgcatt tgtcatcttg aagttcactc ttggcccct tggtccaaaa ggtcagtctc | 7260 |
| gtatgaagtt tgttttcacc aattacaacc ttctcatgtc catttattcg ttgggatcat | 7320 |
| tcctctcaat ggcatatgcc atgtacacca tcggtgttat gtctgacaac tgcgagaagg | 7380 |
| cttttgacaa caacgtcttc aggatcacca cgcagttgtt ctatttgagc aagttcctgg | 7440 |
| agtatattga ctccttctat ttgccactga tgggcaagcc tctgacctgg ttgcaattct | 7500 |
| tccatcattt gggggcaccg atggatatgt ggctgttcta taattaccga aatgaagctg | 7560 |
| tttggatttt tgtgctgttg aatggtttca tccactggat catgtacggt tattattgga | 7620 |
| ccagattgat caagctgaag ttccccatgc caaaatccct gattacatca atgcagatca | 7680 |
| ttcaattcaa tgttggtttc tacattgtct ggaagtacag gaacattccc tgttatcgcc | 7740 |
| aagatgggat gaggatgttt ggctggttct tcaattactt ttatgttggc acagtcttgt | 7800 |
| gtttgttctt gaatttctat gtgcaaacgt atatcgtcag gaagcacaag ggagccaaaa | 7860 |
| agattcagtg agc | 7873 |

<210> SEQ ID NO 57
<211> LENGTH: 2540
<212> TYPE: DNA
<213> ORGANISM: Artificial Sequence
<220> FEATURE:
<223> OTHER INFORMATION: Plasmid pKS102

<400> SEQUENCE: 57

| | |
|---|---|
| cgatcatccg gatatagttc ctcctttcag caaaaaaccc ctcaagaccc gtttagaggc | 60 |
| cccaaggggt tatgctagtt attgctcagc ggtggcagca gccaactcag cttcctttcg | 120 |
| ggctttgtta gcagccggat cgatccaagc tgtacctcac tattcctttg ccctcggacg | 180 |
| agtgctgggg cgtcggtttc cactatcggc gagtacttct acacagccat cggtccagac | 240 |
| ggccgcgctt ctgcgggcga tttgtgtacg cccgacagtc ccggctccgg atcggacgat | 300 |
| tgcgtcgcat cgaccctgcg cccaagctgc atcatcgaaa ttgccgtcaa ccaagctctg | 360 |
| atagagttgg tcaagaccaa tgcggagcat atacgcccgg agccgcggcg atcctgcaag | 420 |
| ctccggatgc ctccgctcga gtagcgcgt ctgctgctcc atacaagcca accacggcct | 480 |
| ccagaagaag atgttggcga cctcgtattg ggaatccccg aacatcgcct cgctccagtc | 540 |
| aatgaccgct gttatgcggc cattgtccgt caggacattg ttggagccga atccgcgtg | 600 |
| cacgaggtgc cggacttcgg ggcagtcctc ggcccaaagc atcagctcat cgagagcctg | 660 |
| cgcgacggac gcactgacgg tgtcgtccat cacagtttgc cagtgataca catgggatc | 720 |
| agcaatcgcg catatgaaat cacgccatgt agtgtattga ccgattcctt gcggtccgaa | 780 |
| tgggccgaac ccgctcgtct ggctaagatc ggccgcagcg atcgcatcca tagcctccgc | 840 |
| gaccggctgc agaacagcgg gcagttcggt ttcaggcagg tcttgcaacg tgacaccctg | 900 |
| tgcacggcgg gagatgcaat aggtcaggct ctcgctgaat tccccaatgt caagcacttc | 960 |
| cggaatcggg agcgcggccg atgcaaagtg ccgataaaca taacgatctt tgtagaaacc | 1020 |
| atcggcgcag ctatttaccc gcaggacata tccacgccct cctacatcga agctgaaagc | 1080 |
| acgagattct tcgccctccg agagctgcat caggtcggag acgctgtcga acttttcgat | 1140 |

-continued

| | |
|---|---|
| cagaaacttc tcgacagacg tcgcggtgag ttcaggcttt tccatgggta tatctccttc | 1200 |
| ttaaagttaa acaaaattat ttctagaggg aaaccgttgt ggtctcccta tagtgagtcg | 1260 |
| tattaatttc gcgggatcga gatctgatca acctgcatta atgaatcggc caacgcgcgg | 1320 |
| ggagaggcgg tttgcgtatt gggcgctctt ccgcttcctc gctcactgac tcgctgcgct | 1380 |
| cggtcgttcg gctgcggcga gcggtatcag ctcactcaaa ggcggtaata cggttatcca | 1440 |
| cagaatcagg ggataacgca ggaaagaaca tgtgagcaaa aggccagcaa aaggccagga | 1500 |
| accgtaaaaa ggccgcgttg ctggcgtttt tccataggct ccgcccccct gacgagcatc | 1560 |
| acaaaaatcg acgctcaagt cagaggtggc gaaacccgac aggactataa agataccagg | 1620 |
| cgtttccccc tggaagctcc ctcgtgcgct ctcctgttcc gaccctgccg cttaccggat | 1680 |
| acctgtccgc ctttctccct cgggaagcg tggcgctttc tcaatgctca cgctgtaggt | 1740 |
| atctcagttc ggtgtaggtc gttcgctcca agctgggctg tgtgcacgaa ccccccgttc | 1800 |
| agcccgaccg ctgcgcctta tccggtaact atcgtcttga gtccaacccg gtaagacacg | 1860 |
| acttatcgcc actggcagca gccactggta acaggattag cagagcgagg tatgtaggcg | 1920 |
| gtgctacaga gttcttgaag tggtggccta actacggcta cactagaagg acagtatttg | 1980 |
| gtatctgcgc tctgctgaag ccagttacct tcggaaaaag agttggtagc tcttgatccg | 2040 |
| gcaaacaaac caccgctggt agcggtggtt tttttgtttg caagcagcag attacgcgca | 2100 |
| gaaaaaaagg atctcaagaa gatcctttga tcttttctac ggggtctgac gctcagtgga | 2160 |
| acgaaaactc acgttaaggg attttggtca tgacattaac ctataaaaat aggcgtatca | 2220 |
| cgaggccctt tcgtctcgcg cgtttcggtg atgacggtga aaacctctga cacatgcagc | 2280 |
| tcccggagac ggtcacagct tgtctgtaag cggatgccgg gagcagacaa gcccgtcagg | 2340 |
| gcgcgtcagc gggtgttggc gggtgtcggg gctggcttaa ctatgcggca tcagagcaga | 2400 |
| ttgtactgag agtgcaccat atggacatat tgtcgttaga acgcggctac aattaataca | 2460 |
| taaccttatg tatcatacac atacgattta ggtgacacta tagaacggcg cgccaagctt | 2520 |
| ggatccgtcg acggcgcgcc | 2540 |

<210> SEQ ID NO 58
<211> LENGTH: 4359
<212> TYPE: DNA
<213> ORGANISM: Artificial Sequence
<220> FEATURE:
<223> OTHER INFORMATION: Plasmid pKR197

<400> SEQUENCE: 58

| | |
|---|---|
| cgcgcccgat catccggata tagttcctcc tttcagcaaa aaacccctca agacccgttt | 60 |
| agaggcccca aggggttatg ctagttattg ctcagcggtg gcagcagcca actcagcttc | 120 |
| ctttcgggct ttgttagcag ccggatcgat ccaagctgta cctcactatt cctttgccct | 180 |
| cggacgagtg ctggggcgtc ggtttccact atcggcgagt acttctacac agccatcggt | 240 |
| ccagacggcc gcgcttctgc gggcgatttg tgtacgcccg acagtcccgg ctccggatcg | 300 |
| gacgattgcg tcgcatcgac cctgcgccca agctgcatca tcgaaattgc cgtcaaccaa | 360 |
| gctctgatag agttggtcaa gaccaatgcg gagcatatac gcccggagcc gcggcgatcc | 420 |
| tgcaagctcc ggatgcctcc gctcgaagta gcgcgtctgc tgctccatac aagccaacca | 480 |
| cggcctccag aagaagatgt tggcgacctc gtattgggaa tccccgaaca tcgcctcgct | 540 |
| ccagtcaatg accgctgtta tcggccatt gtccgtcagg acattgttgg agccgaaatc | 600 |
| cgcgtgcacg aggtgccgga cttcggggca gtcctcggcc caaagcatca gctcatcgag | 660 |

-continued

| | |
|---|---|
| agcctgcgcg acggacgcac tgacggtgtc gtccatcaca gtttgccagt gatacacatg | 720 |
| gggatcagca atcgcgcata tgaaatcacg ccatgtagtg tattgaccga ttccttgcgg | 780 |
| tccgaatggg ccgaacccgc tcgtctggct aagatcggcc gcagcgatcg catccatagc | 840 |
| ctccgcgacc ggctgcagaa cagcgggcag ttcggtttca ggcaggtctt gcaacgtgac | 900 |
| accctgtgca cggcgggaga tgcaataggt caggctctcg ctgaattccc caatgtcaag | 960 |
| cacttccgga atcgggagcg cggccgatgc aaagtgccga taaacataac gatctttgta | 1020 |
| gaaaccatcg gcgcagctat ttacccgcag gacatatcca cgccctccta catcgaagct | 1080 |
| gaaagcacga gattcttcgc cctccgagag ctgcatcagg tcggagacgc tgtcgaactt | 1140 |
| ttcgatcaga aacttctcga cagcgtcgc ggtgagttca ggcttttcca tgggtatatc | 1200 |
| tccttcttaa agttaaacaa aattatttct agagggaaac cgttgtggtc tccctatagt | 1260 |
| gagtcgtatt aatttcgcgg gatcgagatc tgatcaacct gcattaatga atcggccaac | 1320 |
| gcgcggggag aggcggtttg cgtattgggc gctcttccgc ttcctcgctc actgactcgc | 1380 |
| tgcgctcggt cgttcggctg cggcgagcgg tatcagctca ctcaaaggcg gtaatacggt | 1440 |
| tatccacaga atcaggggat aacgcaggaa agaacatgtg agcaaaaggc cagcaaaagg | 1500 |
| ccaggaaccg taaaaaggcc gcgttgctgg cgttttttcca taggctccgc cccctgacg | 1560 |
| agcatcacaa aaatcgacgc tcaagtcaga ggtggcgaaa cccgacagga ctataaagat | 1620 |
| accaggcgtt ccccctggaa gctccctcg tgcgctctcc tgttccgacc ctgccgctta | 1680 |
| ccggatacct gtccgccttt ctcccttcgg gaagcgtggc gctttctcaa tgctcacgct | 1740 |
| gtaggtatct cagttcggtg taggtcgttc gctccaagct gggctgtgtg cacgaacccc | 1800 |
| ccgttcagcc cgaccgctgc gccttatccg gtaactatcg tcttgagtcc aacccggtaa | 1860 |
| gacacgactt atcgccactg gcagcagcca ctggtaacag gattagcaga gcgaggtatg | 1920 |
| taggcggtgc tacagagttc ttgaagtggt ggcctaacta cggctacact agaaggacag | 1980 |
| tatttggtat ctgcgctctg ctgaagccag ttaccttcgg aaaaagagtt ggtagctctt | 2040 |
| gatccggcaa acaaaccacc gctggtagcg gtggtttttt tgtttgcaag cagcagatta | 2100 |
| cgcgcagaaa aaaaggatct caagaagatc ctttgatctt ttctacgggg tctgacgctc | 2160 |
| agtggaacga aaactcacgt taagggattt tggtcatgac attaacctat aaaaataggc | 2220 |
| gtatcacgag gccctttcgt ctcgcgcgtt tcggtgatga cggtgaaaac ctctgacaca | 2280 |
| tgcagctccc ggagacggtc acagcttgtc tgtaagcgga tgccgggagc agacaagccc | 2340 |
| gtcagggcgc gtcagcgggt gttggcgggt gtcggggctg gcttaactat gcggcatcag | 2400 |
| agcagattgt actgagagtg caccatatgg acatattgtc gttagaacgc ggctacaatt | 2460 |
| aatacataac cttatgtatc atacacatac gatttaggtg acactataga acggcgcgcc | 2520 |
| aagcttgttg aaacatccct gaagtgtctc atttttatttt atttattctt tgctgataaa | 2580 |
| aaaataaaat aaaagaagct aagcacacgg tcaaccattg ctctactgct aaaagggtta | 2640 |
| tgtgtagtgt tttactgcat aaattatgca gcaaacaaga caactcaaat taaaaaattt | 2700 |
| cctttgcttg ttttttttgtt gtctctgact tgactttctt gtggaagttg gttgtataag | 2760 |
| gattgggaca ccattgtcct tcttaattta attttattct ttgctgataa aaaaaaaaat | 2820 |
| ttcatatagt gttaaataat aatttgttaa ataaccaaaa agtcaaatat gtttactctc | 2880 |
| gtttaaataa ttgagattcg tccagcaagg ctaaacgatt gtatagattt atgacaatat | 2940 |
| ttactttttt atagataaat gttatattat aataaattta tatacatata ttatatgtta | 3000 |

```
tttattatta ttttaaatcc ttcaatattt tatcaaacca actcataatt tttttttat    3060 ctgtaagaag caataaaatt aaatagaccc actttaagga tgatccaacc tttatacaga    3120
gtaagagagt tcaaatagta ccctttcata tacatatcaa ctaaaatatt agaaatatca    3180
tggatcaaac cttataaaga cattaaataa gtggataagt ataatatata aatgggtagt    3240 atataaatata taaatggata caaacttctc tctttataat tgttatgtct ccttaacatc    3300
ctaatataat acataagtgg gtaatatata atatataaat ggagacaaac ttcttccatt    3360
ataattgtta tgtcttctta acacttatgt ctcgttcaca atgctaaggt tagaattgtt    3420
tagaaagtct tatagtacac atttgttttt gtactatttg aagcattcca taagccgtca    3480
cgattcagat gatttataat aataagagga aatttatcat agaacaataa ggtgcataga    3540
tagagtgtta atatatcata acatcccttg tttattcata gaagaagtga gatggagctc    3600
agttattata ctgttacatg gtcggataca atattccatg ctctccatga gctcttacac    3660
ctacatgcat tttagttcat acttgcggcc gcagtatatc ttaaattctt taatacggtg    3720
tactaggata ttgaactggt tcttgatgat gaaaacctgg gccgagattg cagctattta    3780
tagtcatagg tcttgttaac atgcatggac atttggccac ggggtggcat gcagtttgac    3840
gggtgttgaa ataaacaaaa atgaggtggc ggaagagaat acgagtttga ggttgggtta    3900
gaaacaacaa atgtgagggc tcatgatggg ttgagttggt gaatgttttg ggctgctcga    3960
ttgacacctt tgtgagtacg tgttgttgtg catggctttt ggggtccagt ttttttttct    4020
tgacgcggcg atcctgatca gctagtggat aagtgatgtc cactgtgtgt gattgcgttt    4080
ttgtttgaat tttatgaact tagacattgc tatgcaaagg atactctcat tgtgttttgt    4140
cttcttttgt tccttggctt tttcttatga tccaagagac tagtcagtgt tgtggcattc    4200
gagactacca agattaatta tgatggggga aggataagta actgattagt acggactgtt    4260
accaaattaa ttaataagcg gcaaatgaag ggcatggatc aaaagcttgg atctcctgca    4320
ggatctggcc ggccggatct cgtacggatc cgtcgacgg                           4359
```

<210> SEQ ID NO 59
<211> LENGTH: 5147
<212> TYPE: DNA
<213> ORGANISM: Artificial Sequence
<220> FEATURE:
<223> OTHER INFORMATION: Plasmid pKR911

<400> SEQUENCE: 59

```
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta acaattctta accttagcat gtgaacgag     300 acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatatttag ttgatatgta     540 tatgaaaggg tactatttga actctcttac tctgtataaa ggttggatca tcccttaaagt   600 gggtctattt aattttattg cttccttacag ataaaaaaaa aattatgagt tggtttgata    660
aaatattgaa ggatttaaaa taataataaa taacatataa tatatgtata taaatttatt    720
```

```
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taaccctttt agcagtagag caatggttga   1080
ccgtgtgctt agcttctttt attttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct ccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg ccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatca   2400
gatctcgatc ccgcgaaatt aatacgactc actataggga gaccacaacg gtttccctct   2460
agaaataatt ttgtttaact ttaagaagga gatatacccca tggaaaagcc tgaactcacc   2520
gcgacgtctg tcgagaagtt tctgatcgaa aagttcgaca gcgtctccga cctgatgcag   2580
ctctcggagg gcgaagaatc tcgtgctttc agcttcgatg taggagggcg tggatatgtc   2640
ctgcgggtaa atagctgcgc cgatggtttc tacaaagatc gttatgttta tcggcacttt   2700
gcatcggccg cgctcccgat tccggaagtg cttgacattg gggaattcag cgagagcctg   2760
acctattgca tctcccgccg tgcacagggt gtcacgttgc aagacctgcc tgaaaccgaa   2820
ctgcccgctg ttctgcagcc ggtcgcggag gctatggatg cgatcgctgc ggccgatctt   2880
agccagacga gcgggttcgg cccattcgga ccgcaaggaa tcggtcaata cactacatgg   2940
cgtgatttca tatgcgcgat tgctgatccc catgtgtatc actggcaaac tgtgatggac   3000
gacaccgtca gtgcgtccgt cgcgcaggct ctcgatgagc tgatgctttg ggccgaggac   3060
```

| | | | | |
|---|---|---|---|---|
| tgccccgaag | tccggcacct | cgtgcacgcg | gatttcggct | ccaacaatgt cctgacggac | 3120 |
| aatggccgca | taacagcggt | cattgactgg | agcgaggcga | tgttcgggga ttcccaatac | 3180 |
| gaggtcgcca | acatcttctt | ctggaggccg | tggttggctt | gtatggagca gcagacgcgc | 3240 |
| tacttcgagc | ggaggcatcc | ggagcttgca | ggatcgccgc | ggctccgggc gtatatgctc | 3300 |
| cgcattggtc | ttgaccaact | ctatcagagc | ttggttgacg | gcaatttcga tgatgcagct | 3360 |
| tgggcgcagg | gtcgatgcga | cgcaatcgtc | cgatccggag | ccgggactgt cgggcgtaca | 3420 |
| caaatcgccc | gcagaagcgc | ggccgtctgg | accgatggct | gtgtagaagt actcgccgat | 3480 |
| agtggaaacc | gacgcccag | cactcgtccg | agggcaaagg | aatagtgagg tacagcttgg | 3540 |
| atcgatccgg | ctgctaacaa | agcccgaaag | gaagctgagt | tggctgctgc caccgctgag | 3600 |
| caataactag | cataaccct | tggggcctct | aaacgggtct | tgaggggttt tttgctgaaa | 3660 |
| ggaggaacta | tatccggatg | atcgggcgcg | ccgtcgacgg | atccgtacga gatccggccg | 3720 |
| gccagatcct | gcaggagatc | caagcttttg | atccatgccc | ttcatttgcc gcttattaat | 3780 |
| taatttggta | acagtccgta | ctaatcagtt | acttatcctt | ccccccatcat aattaatctt | 3840 |
| ggtagtctcg | aatgccacaa | cactgactag | tctcttggat | cataagaaaa agccaaggaa | 3900 |
| caaagaaga | caaaacacaa | tgagagtatc | ctttgcatag | caatgtctaa gttcataaaa | 3960 |
| ttcaaacaaa | aacgcaatca | cacacagtgg | acatcactta | tccactagct gatcaggatc | 4020 |
| gccgcgtcaa | gaaaaaaaa | ctggaccca | aaagccatgc | acaacaacac gtactcacaa | 4080 |
| aggtgtcaat | cgagcagccc | aaaacattca | ccaactcaac | ccatcatgag ccctcacatt | 4140 |
| tgttgtttct | aacccaacct | caaactcgta | ttctcttccg | ccacctcatt tttgtttatt | 4200 |
| tcaacacccg | tcaaactgca | tgccaccccg | tggccaaatg | tccatgcatg ttaacaagac | 4260 |
| ctatgactat | aaatagctgc | aatctcggcc | caggttttca | tcatcaagaa ccagttcaat | 4320 |
| atcctagtac | accgtattaa | agaatttaag | atatactgcg | gccgcaccat ggaggtggtg | 4380 |
| aatgaaatag | tctcaattgg | gcaggaagtt | tacccaaag | ttgattatgc ccaactctgg | 4440 |
| agtgatgcca | gtcactgtga | ggtgctttac | ttgtccatcg | catttgtcat cttgaagttc | 4500 |
| actcttggcc | cccttggtcc | aaaaggtcag | tctcgtatga | agtttgtttt caccaattac | 4560 |
| aaccttctca | tgtccattta | ttcgttggga | tcattcctct | caatggcata tgccatgtac | 4620 |
| accatcggtg | ttatgtctga | caactgcgag | aaggcttttg | acaacaacgt cttcaggatc | 4680 |
| accacgcagt | tgttctattt | gagcaagttc | ctggagtata | ttgactccct ctatttgcca | 4740 |
| ctgatgggca | agcctctgac | ctggttgcaa | ttcttccatc | atttgggggc accgatggat | 4800 |
| atgtggctgt | tctataatta | ccgaaatgaa | gctgtttgga | ttttttgtgct gttgaatggt | 4860 |
| ttcatccact | ggatcatgta | cggttattat | tggaccagat | tgatcaagct gaagttcccc | 4920 |
| atgccaaaat | ccctgattac | atcaatgcag | atcattcaat | tcaatgttgg tttctacatt | 4980 |
| gtctggaagt | acaggaacat | tccctgttat | cgccaagatg | ggatgaggat gtttggctgg | 5040 |
| ttcttcaatt | acttttatgt | tggcacagtc | ttgtgtttgt | tcttgaattt ctatgtgcaa | 5100 |
| acgtatatcg | tcaggaagca | caagggagcc | aaaaagattc | agtgagc | 5147 |

<210> SEQ ID NO 60
<211> LENGTH: 1266
<212> TYPE: DNA
<213> ORGANISM: Euglena gracilis

<400> SEQUENCE: 60
atgaagtcaa agcgccaagc gcttcccctt acaattgatg gaacaacata tgatgtgtct      60

-continued

```
gcctgggtca atttccaccc tggtggtgcg gaaattatag agaattacca aggaagggat    120
gccactgatg ccttcatggt tatgcactct caagaagcct tcgacaagct caagcgcatg    180
cccaaaatca atcccagttc tgagttgcca ccccaggctg cagtgaatga agctcaagag    240
gatttccgga agctccgaga agagttgatc gcaactggca tgtttgatgc ctccccctc    300 tggtactcat acaaaatcag caccacactg ggccttggag tgctgggtta ttcctgatg    360 gttcagtatc agatgtattt cattggggca gtgttgcttg ggatgcacta tcaacagatg    420
ggctggcttt ctcatgacat tgccaccac cagactttca agaaccggaa ctggaacaac    480
ctcgtgggac tggtatttgg caatggtctg caaggttttt ccgtgacatg gtggaaggac    540
agacacaatg cacatcattc ggcaaccaat gttcaagggc acgaccctga tattgacaac    600
ctccccctct tagcctggtc tgaggatgac gtcacacggg cgtcaccgat tcccgcaag    660 ctcattcagt tccagcagta ctatttcttg gtcatctgta tcttgttgcg gttcatttgg    720
tgtttccaga gcgtgttgac cgtgcgcagt ttgaaggaca gagataacca attctatcgc    780
tctcagtata agaaggaggc cattggcctc gccctgcact ggaccttgaa gaccctgttc    840
cacttattct ttatgcccag catcctcaca tcgctgttgg tgttttcgt tcggagctg    900 gttggcggct tcggcattgc gatcgtggtg ttcatgaacc actacccact ggagaagatc    960
ggggactcag tctgggatgg ccatggattc tcggttggcc agatccatga gaccatgaac    1020
attcggcgag ggattatcac agattggttt tcggaggct tgaattacca gattgagcac    1080
catttgtggc cgaccctccc tcgccacaac ctgacagcgg ttagctacca ggtggaacag    1140
ctgtgccaga agcacaacct gccgtatcgg aacccgctgc cccatgaagg gttggtcatc    1200
ctgctgcgct atctggcggt gttcgcccgg atggcggaga agcaacccgc ggggaaggct    1260
ctataa                                                              1266
```

<210> SEQ ID NO 61
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase ("Eg5" or "EgD8")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US_2005-0287652-A1
<311> PATENT FILING DATE: 2005-06-24
<312> PUBLICATION DATE: 2005-12-29
<313> RELEVANT RESIDUES: (1)..(421)

<400> SEQUENCE: 61

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

```
Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
                 85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 62
<211> LENGTH: 19
<212> TYPE: DNA
<213> ORGANISM: Artificial Sequence
<220> FEATURE:
<223> OTHER INFORMATION: Primer Eg5-1

<400> SEQUENCE: 62
```

```
gaaatgaagt caaagcgcc                                                       19
```

<210> SEQ ID NO 63
<211> LENGTH: 19
<212> TYPE: DNA
<213> ORGANISM: Artificial Sequence
<220> FEATURE:
<223> OTHER INFORMATION: Primer Eg3-3

<400> SEQUENCE: 63

```
ccttatagag ccttccccg                                                       19
```

<210> SEQ ID NO 64
<211> LENGTH: 19
<212> TYPE: DNA
<213> ORGANISM: Artificial Sequence
<220> FEATURE:
<223> OTHER INFORMATION: T7 primer

<400> SEQUENCE: 64

```
ggaaacagct atgaccatg                                                       19
```

<210> SEQ ID NO 65
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 65

```
gtaatacgac tcactatagg gc                                                   22
```

<210> SEQ ID NO 66
<211> LENGTH: 19
<212> TYPE: DNA
<213> ORGANISM: Artificial Sequence
<220> FEATURE:
<223> OTHER INFORMATION: Primer Eg3-2

<400> SEQUENCE: 66

```
aatgttcatg gtctcatgg                                                       19
```

<210> SEQ ID NO 67
<211> LENGTH: 19
<212> TYPE: DNA
<213> ORGANISM: Artificial Sequence
<220> FEATURE:
<223> OTHER INFORMATION: Primer Eg5-2

<400> SEQUENCE: 67

```
ttggcaatgg tctgcaagg                                                       19
```

<210> SEQ ID NO 68
<211> LENGTH: 1272
<212> TYPE: DNA
<213> ORGANISM: Euglena gracilis
<220> FEATURE:
<221> NAME/KEY: misc_feature
<222> LOCATION: (2)..(1270)
<223> OTHER INFORMATION: synthetic delta-8 desaturase CDS,
      codon-optimized for expression in Yarrowia lipolytica ("D8SF" or
      "EgD8S")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24

<312> PUBLICATION DATE: 2006-02-02
<313> RELEVANT RESIDUES: (1)..(1272)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES: (1)..(1272)

<400> SEQUENCE: 68

```
catggtgaag tccaagcgac aggctctgcc cctcaccatc gacgaacta cctacgacgt      60
ctccgcttgg gtgaacttcc accctggtgg agctgaaatc attgagaact accagggacg     120
agatgctact gacgccttca tggttatgca ctctcaggaa gccttcgaca agctcaagcg     180
aatgcccaag atcaacccct cctccgagct gcctcccag gctgccgtca acgaagctca     240
ggaggatttc cgaaagctcc gagaagagct gatcgccact ggcatgtttg acgcctctcc     300
cctctggtac tcgtacaaga tctccaccac cctgggtctt ggcgtgcttg gatacttcct     360
gatggtccag taccagatgt acttcattgg tgctgtgctg ctcggtatgc actaccagca     420
aatgggatgc tgtctcatg acatctgcca ccaccagacc ttcaagaacc gaaactggaa     480
taacctcgtg ggtctggtct ttggcaacgg actccagggc ttctccgtga cctggtggaa     540
ggacagacac aacgcccatc attctgctac caacgttcag ggtcacgatc cgacattga     600
taacctgcct ctgctcgcct ggtccgagga cgatgtcact cgagcttctc ccatctcccg     660
aaagctcatt cagttccaac agtactattt cctggtcatc tgtattctcc tgcgattcat     720
ctggtgtttc cagtctgtgc tgaccgttcg atccctcaag gaccgagaca accagttcta     780
ccgatctcag tacaagaaag aggccattgg actcgctctg cactggactc tcaagaccct     840
gttccacctc ttctttatgc cctccatcct gacctcgctc ctggtgttct tgtttccga     900
gctcgtcggt ggcttcggaa ttgccatcgt ggtcttcatg aaccactacc ctctggagaa     960
gatcggtgat tccgtctggg acggacatgg cttctctgtg ggtcagatcc atgagaccat    1020
gaacattcga cgaggcatca ttactgactg gttctttgga ggcctgaact accagatcga    1080
gcaccatctc tggcccaccc tgcctcgaca caacctcact gccgtttcct accaggtgga    1140
acagctgtgc cagaagcaca acctccccta ccgaaaccct ctgccccatg aaggtctcgt    1200
catcctgctc cgatacctgg ccgtgttcgc tcgaatggcc gagaagcagc ccgctggcaa    1260
ggctctctaa gc                                                        1272
```

<210> SEQ ID NO 69
<211> LENGTH: 422
<212> TYPE: PRT
<213> ORGANISM: Euglena gracilis
<220> FEATURE:
<221> NAME/KEY: MISC_FEATURE
<223> OTHER INFORMATION: synthetic delta-8 desaturase codon-optimized
      for expression in Yarrowia lipolytica ("D8SF" or "EgD8S")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES: (1)..(422)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES: (1)..(422)

<400> SEQUENCE: 69

```
Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Leu Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
```

```
                405                 410                 415
Pro Ala Gly Lys Ala Leu
            420

<210> SEQ ID NO 70
<211> LENGTH: 4826
<212> TYPE: DNA
<213> ORGANISM: Artificial Sequence
<220> FEATURE:
<223> OTHER INFORMATION: Plasmid pKS121
<220> FEATURE:
<221> NAME/KEY: misc_feature
<222> LOCATION: (3711)..(3711)
<223> OTHER INFORMATION: n is a, c, g, or t

<400> SEQUENCE: 70
tcgacggcgc gcccgatcat ccggatatag ttcctccttt cagcaaaaaa cccctcaaga      60
cccgtttaga ggccccaagg ggttatgcta gttattgctc agcggtggca gcagccaact     120
cagcttcctt tcgggctttg ttagcagccg gatcgatcca agctgtacct cactattcct     180
ttgccctcgg acgagtgctg gggcgtcggt ttccactatc ggcgagtact tctacacagc     240
catcggtcca gacggccgcg cttctgcggg cgatttgtgt acgcccgaca gtcccggctc     300
cggatcggac gattgcgtcg catcgaccct gcgcccaagc tgcatcatcg aaattgccgt     360
caaccaagct ctgatagagt tggtcaagac caatgcggag catatacgcc cggagccgcg     420
gcgatcctgc aagctccgga tgcctccgct cgaagtagcg cgtctgctgc tccatacaag     480
ccaaccacgg cctccagaag aagatgttgg cgacctcgta ttgggaatcc ccgaacatcg     540
cctcgctcca gtcaatgacc gctgttatgc ggccattgtc cgtcaggaca ttgttggagc     600
cgaaatccgc gtgcacgagg tgccggactt cggggcagtc tcggcccaa agcatcagct      660 catcgagagc ctgcgcgacg gacgcactga cggtgtcgtc catcacagtt tgccagtgat     720
acacatgggg atcagcaatc gcgcatatga aatcacgcca tgtagtgtat tgaccgattc     780
cttgcggtcc gaatgggccg aacccgctcg tctggctaag atcggccgca gcgatcgcat     840
ccatagcctc cgcgaccggc tgcagaacag cgggcagttc ggtttcaggc aggtcttgca     900
acgtgacacc ctgtgcacgg cgggagatgc aataggtcag gctctcgctg aattccccaa     960
tgtcaagcac ttccggaatc gggagcgcgg ccgatgcaaa gtgccgataa acataacgat    1020
ctttgtagaa accatcggcg cagctattta cccgcaggac atatccacgc cctcctacat    1080
cgaagctgaa agcacgagat tcttcgccct ccgagagctg catcaggtcg agacgctgt     1140 cgaactttc gatcagaaac ttctcgacag acgtcgcggt gagttcaggc ttttccatgg    1200
gtatatctcc ttcttaaagt taaacaaaat tatttctaga gggaaaccgt tgtggtctcc    1260
ctatagtgag tcgtattaat ttcgcgggat cgagatctga tcaacctgca ttaatgaatc    1320
ggccaacgcg cggggagagg cggtttgcgt attgggcgct cttccgcttc ctcgctcact    1380
gactcgctgc gctcggtcgt tcggctgcgg cgagcggtat cagctcactc aaaggcggta    1440
atacggttat ccacagaatc agggg ataac gcaggaaaga acatgtgagc aaaaggccag    1500
caaaaggcca ggaaccgtaa aaaggccgcg ttgctggcgt ttttccatag gctccgcccc    1560
cctgacgagc atcacaaaaa tcgacgctca agtcagaggt ggcgaaaccc gacaggacta    1620
taaagatacc aggcgtttcc ccctggaagc tccctcgtgc gctctcctgt tccgaccctg    1680
ccgcttaccg gatacctgtc cgcctttctc ccttcgggaa gcgtggcgct ttctcaatgc    1740
tcacgctgta ggtatctcag ttcggtgtag gtcgttcgct ccaagctggg ctgtgtgcac    1800
```

```
gaaccccccg ttcagcccga ccgctgcgcc ttatccggta actatcgtct tgagtccaac   1860
ccggtaagac acgacttatc gccactggca gcagccactg gtaacaggat tagcagagcg   1920
aggtatgtag gcggtgctac agagttcttg aagtggtggc ctaactacgg ctacactaga   1980
aggacagtat ttggtatctg cgctctgctg aagccagtta ccttcggaaa aagagttggt   2040
agctcttgat ccggcaaaca accaccgct  ggtagcggtg ttttttttgt ttgcaagcag   2100
cagattacgc gcagaaaaaa aggatctcaa gaagatcctt tgatcttttc tacggggtct   2160
gacgctcagt ggaacgaaaa ctcacgttaa gggattttgg tcatgacatt aacctataaa   2220
aataggcgta tcacgaggcc ctttcgtctc gcgcgtttcg gtgatgacgg tgaaaacctc   2280
tgacacatgc agctcccgga gacggtcaca gcttgtctgt aagcggatgc cgggagcaga   2340
caagcccgtc agggcgcgtc agcgggtgtt ggcgggtgtc ggggctggct taactatgcg   2400
gcatcagagc agattgtact gagagtgcac catatggaca tattgtcgtt agaacgcggc   2460
tacaattaat acataacctt atgtatcata cacatacgat ttaggtgaca ctatagaacg   2520
gcgcgccaag cttggatcct cgaagagaag ggttaataac acattttta  acattttta   2580 cacaaatttt agttatttaa aaatttatta aaaaatttaa ataagaaga  ggaactcttt   2640 aaataaatct aacttacaaa atttatgatt tttaataagt tttcaccaat aaaaaatgtc   2700
ataaaaatat gttaaaaagt atattatcaa tattctcttt atgataaata aaagaaaaa   2760 aaaaataaaa gttaagtgaa atgagattg  aagtgactt  aggtgtgtat aaatatatca   2820
accccgccaa caatttattt aatccaaata tattgaagta tattattcca tagcctttat   2880
ttatttatat atttattata taaaagcttt atttgttcta ggttgttcat gaaatatttt   2940
tttggtttta tctccgttgt aagaaaatca tgtgctttgt gtcgccactc actattgcag   3000
ctttttcatg cattggtcag attgacggtt gattgtattt ttgtttttta tggttttgtg   3060
ttatgactta agtcttcatc tctttatctc ttcatcaggt ttgatggtta cctaatatgg   3120
tccatgggta catgcatggt taaattaggt ggccaacttt gttgtgaacg atagaatttt   3180
ttttatatta agtaaactat ttttatatta tgaaataata ataaaaaaaa tattttatca   3240
ttattaacaa aatcatatta gttaatttgt taactctata ataaagaaa  tactgtaaca   3300 ttcacattac atggtaacat cttttccaccc tttcatttgt ttttttgtttg atgactttt   3360 ttcttgttta aatttatttc ccttctttta aatttggaat acattatcat catatataaa   3420
ctaaaatact aaaacagga  ttacacaaat gataaataat aacacaaata tttataaatc   3480
tagctgcaat atatttaaac tagctatatc gatattgtaa aataaaacta gctgcattga   3540
tactgataaa aaaatatcat gtgctttctg gactgatgat gcagtatact tttgacattg   3600
cctttatttt attttcaga  aaagcttct  tagttctggg ttcttcatta tttgtttccc   3660
atctccattg tgaattgaat catttgcttc gtgtcacaaa tacaatttag ntaggtacat   3720
gcattggtca gattcacggt ttattatgtc atgacttaag ttcatggtag tacattacct   3780
gccacgcatg cattatattg gttagatttg ataggcaaat ttggttgtca acaatataaa   3840
tataaataat gttttatat  tacgaaataa cagtgatcaa acaaacagt  tttatcttta   3900 ttaacaagat tttgttttg  tttgatgacg tttttttaatg tttacgcttt cccccttctt   3960
ttgaatttag aacactttat catcataaaa tcaaatacta aaaaaattac atatttcata   4020
aataataaca caaatatttt taaaaaatct gaaataataa tgaacaatat tacatattat   4080
cacgaaaatt cattaataaa aatattatat aaataaaatg taatagtagt tatatgtagg   4140
aaaaaagtac tgcacgcata atatatacaa aaagattaaa atgaactatt ataaataata   4200
```

-continued

```
acactaaatt aatggtgaat catatcaaaa taatgaaaaa gtaaataaaa tttgtaatta    4260
acttctatat gtattacaca cacaaataat aaataatagt aaaaaaaatt atgataaata    4320
tttaccatct cataagatat ttaaaataat gataaaaata tagattatttt tttatgcaac   4380 tagctagcca aaaagagaac acgggtatat ataaaaagag tacctttaaa ttctactgta    4440
cttcctttat tcctgacgtt tttatatcaa gtggacatac gtgaagattt taattatcag    4500
tctaaatatt tcattagcac ttaatacttt tctgttttat tcctatccta aagtagtcc    4560 cgattctccc aacattgctt attcacacaa ctaactaaga aagtcttcca tagcccccca    4620
agcggccgcg acacaagtgt gagagtacta aataaatgct ttggttgtac gaaatcatta    4680
cactaaataa aataatcaaa gcttatatat gccttccgct aaggccgaat gcaaagaaat    4740
tggttctttc tcgttatctt ttgccacttt tactagtacg tattaattac tacttaatca    4800
tctttgttta cggctcatta tatccg                                         4826

<210> SEQ ID NO 71
<211> LENGTH: 5252
<212> TYPE: DNA
<213> ORGANISM: Artificial Sequence
<220> FEATURE:
<223> OTHER INFORMATION: Plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 71
gtacgtgggc ggatccccg ggctgcagga attcactggc cgtcgtttta caacgtcgtg      60
actgggaaaa ccctggcgtt acccaactta atcgccttgc agcacatccc cctttcgcca    120
gctggcgtaa tagcgaagag gcccgcaccg atcgccctt ccaacagttg cgcagcctga     180
atggcgaatg cgcctgatg cggtattttc tccttacgca tctgtgcggt atttcacacc     240
gcatatggtg cactctcagt acaatctgct ctgatgccgc atagttaagc cagccccgac    300
acccgccaac acccgctgac gcgccctgac gggcttgtct gctcccggca tccgcttaca    360
gacaagctgt gaccgtctcc gggagctgca tgtgtcagag gttttcaccg tcatcaccga    420
aacgcgcgag acgaaagggc ctcgtgatac gcctattttt ataggttaat gtcatgataa    480
taatggtttc ttagacgtca ggtggcactt ttcggggaaa tgtgcgcgga acccctattt    540 gtttatttt ctaaatacat tcaaatatgt atccgctcat gagacaataa ccctgataaa    600
tgcttcaata atattgaaaa aggaagagta tgagtattca acatttccgt gtcgccctta    660 ttccctttt tgcggcattt tgccttcctg tttttgctca cccagaaacg ctggtgaaag    720
taaaagatgc tgaagatcag ttgggtgcac gagtgggtta tcgaactg gatctcaaca    780 gcggtaagat ccttgagagt tttcgccccg aagaacgttt tccaatgatg agcactttta    840
aagttctgct atgtggcgcg gtattatccc gtattgacgc cgggcaagag caactcggtc    900
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
taccaaacga cgagcgtgac accacgatgc ctgtagcaat ggcaacaacg ttgcgcaaac   1200
tattaactgg cgaactactt actctagctt cccggcaaca attaatagac tggatggagg   1260
```

```
cggataaagt tgcaggacca cttctgcgct cggcccttcc ggctggctgg tttattgctg    1320
ataaatctgg agccggtgag cgtgggtctc gcggtatcat tgcagcactg gggccagatg    1380
gtaagccctc ccgtatcgta gttatctaca cgacggggag tcaggcaact atggatgaac    1440
gaaatagaca gatcgctgag ataggtgcct cactgattaa gcattggtaa ctgtcagacc    1500
aagtttactc atatatactt tagattgatt taaaacttca ttttaatttt aaaaggatct    1560
aggtgaagat cctttttgat aatctcatga ccaaaatccc ttaacgtgag ttttcgttcc    1620
actgagcgtc agaccccgta gaaaagatca aaggatcttc ttgagatcct ttttttctgc    1680
gcgtaatctg ctgcttgcaa acaaaaaaac caccgctacc agcggtggtt tgtttgccgg    1740
atcaagagct accaactctt tttccgaagg taactggctt cagcagagcg cagataccaa    1800
atactgtcct tctagtgtag ccgtagttag gccaccactt caagaactct gtagcaccgc    1860
ctacatacct cgctctgcta atcctgttac cagtggctgc tgccagtggc gataagtcgt    1920
gtcttaccgg gttggactca agacgatagt taccggataa ggcgcagcgg tcgggctgaa    1980
cggggggttc gtgcacacag cccagcttgg agcgaacgac ctacaccgaa ctgagatacc    2040
tacagcgtga gctatgagaa agcgccacgc ttcccgaagg gagaaaggcg gacaggtatc    2100
cggtaagcgg cagggtcgga acaggagagc gcacgaggga gcttccaggg ggaaacgcct    2160
ggtatcttta tagtcctgtc gggtttcgcc acctctgact tgagcgtcga ttttgtgat     2220 gctcgtcagg ggggcggagc ctatggaaaa acgccagcaa cgcggccttt ttacggttcc    2280
tggccttttg ctggcctttt gctcacatgt tctttcctgc gttatcccct gattctgtgg    2340
ataaccgtat taccgccttt gagtgagctg ataccgctcg ccgcagccga acgaccgagc    2400
gcagcgagtc agtgagcgag gaagcggaag agcgcccaat acgcaaaccg cctctccccg    2460
cgcgttggcc gattcattaa tgcagctggc acgacaggtt tcccgactgg aaagcgggca    2520
gtgagcgcaa cgcaattaat gtgagttagc tcactcatta ggcacccag gctttacact     2580 ttatgcttcc ggctcgtatg ttgtgtggaa ttgtgagcgg ataacaattt cacacaggaa    2640
acagctatga ccatgattac gccaagcttg catgcctgca ggtcgactcg acgtacgtcc    2700
tcgaagagaa gggttaataa cacatttttt aacattttta acacaaattt tagttattta    2760
aaaatttatt aaaaaattta aaataagaag aggaactctt taaataaatc taacttacaa    2820
aatttatgat ttttaataag ttttcaccaa taaaaaatgt cataaaaata tgttaaaaag    2880
tatattatca atattctctt tatgataaat aaaaagaaaa aaaaaataaa agttaagtga    2940
aaatgagatt gaagtgactt taggtgtgta taaatatatc aaccccgcca acaatttatt    3000
taatccaaat atattgaagt atattattcc atagccttta tttatttata tatttattat    3060
ataaaagctt tatttgttct aggttgttca tgaaatattt ttttggtttt atctccgttg    3120
taagaaaatc atgtgctttg tgtcgccact cactattgca gcttttcat gcattggtca     3180 gattgacggt tgattgtatt tttgttttt atggttttgt gttatgactt aagtcttcat    3240
ctctttatct cttcatcagg tttgatggtt acctaatatg gtccatgggt acatgcatgg    3300
ttaaattagg tggccaactt tgttgtgaac gatagaattt ttttatatt aagtaaacta     3360 tttttatatt atgaaataat aataaaaaaa atattttatc attattaaca aaatcatatt    3420
agttaatttg ttaactctat aataaaagaa atactgtaac attcacatta catggtaaca    3480 tcttttccacc ctttcatttg tttttttgttt gatgacttttt tttcttgttt aaatttattt   3540
cccttctttt aaatttggaa tacattatca tcatatataa actaaaatac taaaaacagg    3600
attacacaaa tgataaataa taacacaaat atttataaat ctagctgcaa tatatttaaa    3660
```

```
ctagctatat cgatattgta aaataaaact agctgcattg atactgataa aaaaatatca   3720
tgtgctttct ggactgatga tgcagtatac ttttgacatt gcctttattt tattttttcag  3780 aaaagctttc ttagttctgg gttcttcatt atttgtttcc catctccatt gtgaattgaa   3840
tcatttgctt cgtgtcacaa atacaattta gntaggtaca tgcattggtc agattcacgg   3900
tttattatgt catgacttaa gttcatggta gtacattacc tgccacgcat gcattatatt   3960
ggttagattt gataggcaaa tttggttgtc aacaatataa atataaataa tgtttttata   4020
ttacgaaata acagtgatca aaacaaacag ttttatcttt attaacaaga ttttgttttt   4080
gtttgatgac gttttttaat gtttacgctt tcccccttct tttgaattta gaacacttta   4140
tcatcataaa atcaaatact aaaaaaatta catatttcat aaataataac acaaatattt   4200
ttaaaaaatc tgaaataata atgaacaata ttacatatta tcacgaaaat tcattaataa   4260
aaatattata taaataaaat gtaatagtag ttatatgtag gaaaaaagta ctgcacgcat   4320
aatatataca aaaagattaa aatgaactat tataaataat aacactaaat taatggtgaa   4380
tcatatcaaa ataatgaaaa agtaaataaa atttgtaatt aacttctata tgtattacac   4440
acacaaataa taaataatag taaaaaaaat tatgataaat atttaccatc tcataagata   4500
tttaaaataa tgataaaaat atagattatt ttttatgcaa ctagctagcc aaaaagagaa   4560
cacgggtata tataaaaga gtacctttaa attctactgt acttccttta ttcctgacgt   4620
ttttatatca agtggacata cgtgaagatt ttaattatca gtctaaatat ttcattagca   4680
cttaatactt ttctgtttta ttcctatcct ataagtagtc ccgattctcc caacattgct   4740
tattcacaca actaactaag aaagtcttcc atagccccc aagcggccgc gacacaagtg    4800
tgagagtact aaataaatgc tttggttgta cgaaatcatt acactaaata aaataatcaa   4860
agcttatata tgccttccgc taaggccgaa tgcaaagaaa ttggttcttt ctcgttatct   4920
tttgccactt ttactagtac gtattaatta ctacttaatc atctttgttt acggctcatt   4980
atatccggtc tagaggatcc aaggccgcga agttaaaagc aatgttgtca cttgtcgtac   5040
taacacatga tgtgatagtt tatgctagct agctataaca taagctgtct ctgagtgtgt   5100
tgtatattaa taaagatcat cactggtgaa tggtgatcgt gtacgtaccc tacttagtag   5160
gcaatggaag cacttagagt gtgctttgtg catggccttg cctctgtttt gagacttttg   5220
taatgttttc gagtttaaat ctttgccttt gc                                 5252

<210> SEQ ID NO 72
<211> LENGTH: 37
<212> TYPE: DNA
<213> ORGANISM: Artificial Sequence
<220> FEATURE:
<223> OTHER INFORMATION: KTi cassette 5' end MCS for pKR457

<400> SEQUENCE: 72
aagcttgcat gcctgcaggt cgactcgacg tacgtcc                            37

<210> SEQ ID NO 73
<211> LENGTH: 282
<212> TYPE: DNA
<213> ORGANISM: Artificial Sequence
<220> FEATURE:
<223> OTHER INFORMATION: KTi cassette 3' end MCS for pKR457 including
      the soy albumin transcription 3' terminator

<400> SEQUENCE: 73
ggtctagagg atccaaggcc gcgaagttaa aagcaatgtt gtcacttgtc gtactaacac    60
```

```
atgatgtgat agtttatgct agctagctat aacataagct gtctctgagt gtgttgtata    120
ttaataaaga tcatcactgg tgaatggtga tcgtgtacgt accctactta gtaggcaatg    180
gaagcactta gagtgtgctt tgtgcatggc cttgcctctg ttttgagact tttgtaatgt    240
tttcgagttt aaatctttgc ctttgcgtac gtgggcggat cc                       282
```

<210> SEQ ID NO 74
<211> LENGTH: 32
<212> TYPE: DNA
<213> ORGANISM: Artificial Sequence
<220> FEATURE:
<223> OTHER INFORMATION: Primer oSalb-12

<400> SEQUENCE: 74

```
tttggatcct ctagacgtac gcaaaggcaa ag                                   32
```

<210> SEQ ID NO 75
<211> LENGTH: 36
<212> TYPE: DNA
<213> ORGANISM: Artificial Sequence
<220> FEATURE:
<223> OTHER INFORMATION: Primer oSalb-13

<400> SEQUENCE: 75

```
aaaggatcca aggccgcgaa gttaaaagca atgttg                               36
```

<210> SEQ ID NO 76
<211> LENGTH: 6559
<212> TYPE: DNA
<213> ORGANISM: Artificial Sequence
<220> FEATURE:
<223> OTHER INFORMATION: Plasmid pKR680
<220> FEATURE:
<221> NAME/KEY: misc_feature
<222> LOCATION: (4340)..(4340)
<223> OTHER INFORMATION: n is a, c, g, or t

<400> SEQUENCE: 76

```
ggccgcgaca caagtgtgag agtactaaat aaatgctttg gttgtacgaa atcattacac    60
taaataaaat aatcaaagct tatatatgcc ttccgctaag gccgaatgca agaaattgg    120 ttctttctcg ttatcttttg ccacttttac tagtacgtat taattactac ttaatcatct    180
ttgtttacgg ctcattatat ccggtctaga ggatccaagg ccgcgaagtt aaaagcaatg    240
ttgtcacttg tcgtactaac acatgatgtg atagtttatg ctagctagct ataacataag    300
ctgtctctga gtgtgttgta tattaataaa gatcatcact ggtgaatggt gatcgtgtac    360
gtaccctact tagtaggcaa tggaagcact tagagtgtgc tttgtgcatg gccttgcctc    420
tgttttgaga cttttgtaat gttttcgagt ttaaatcttt gcctttgcgt acgtgggcgg    480 atccccccggg ctgcaggaat tcactggccg tcgttttaca acgtcgtgac tgggaaaacc    540
ctggcgttac ccaacttaat cgccttgcag cacatccccc tttcgccagc tggcgtaata    600
gcgaagaggc ccgcaccgat cgcccttccc aacagttgcg cagcctgaat ggcgaatggc    660
gcctgatgcg gtattttctc cttacgcatc tgtgcggtat tcacaccgc atatggtgca    720 ctctcagtac aatctgctct gatgccgcat agttaagcca gccccgacac ccgccaacac    780
ccgctgacgc gccctgacgg gcttgtctgc tcccggcatc cgcttacaga caagctgtga    840
ccgtctccgg gagctgcatg tgtcagaggt tttcaccgtc atcaccgaaa cgcgcgagac    900
gaaagggcct cgtgatacgc ctattttat aggttaatgt catgataata atggtttctt    960
```

-continued

```
agacgtcagg tggcactttt cggggaaatg tgcgcggaac ccctatttgt ttattttttct    1020
aaatacattc aaatatgtat ccgctcatga gacaataacc ctgataaatg cttcaataat    1080
attgaaaaag gaagagtatg agtattcaac atttccgtgt cgcccttatt ccctttttg    1140
cggcattttg ccttcctgtt tttgctcacc cagaaacgct ggtgaaagta aaagatgctg    1200
aagatcagtt gggtgcacga gtgggttaca tcgaactgga tctcaacagc ggtaagatcc    1260
ttgagagttt tcgccccgaa gaacgttttc caatgatgag cacttttaaa gttctgctat    1320
gtggcgcggt attatcccgt attgacgccg ggcaagagca actcggtcgc cgcatacact    1380
attctcagaa tgacttggtt gagtactcac cagtcacaga aaagcatctt acggatggca    1440
tgacagtaag agaattatgc agtgctgcca taaccatgag tgataacact gcggccaact    1500
tacttctgac aacgatcgga ggaccgaagg agctaaccgc ttttttgcac aacatggggg    1560
atcatgtaac tcgccttgat cgttgggaac cggagctgaa tgaagccata ccaaacgacg    1620
agcgtgacac cacgatgcct gtagcaatgg caacaacgtt gcgcaaacta ttaactggcg    1680
aactacttac tctagcttcc cggcaacaat taatagactg gatggaggcg gataaagttg    1740
caggaccact tctgcgctcg gcccttccgg ctggctggtt tattgctgat aaatctggag    1800
ccggtgagcg tgggtctcgc ggtatcattg cagcactggg gccagatggt aagccctccc    1860
gtatcgtagt tatctacacg acggggagtc aggcaactat ggatgaacga atagacaga    1920
tcgctgagat aggtgcctca ctgattaagc attggtaact gtcagaccaa gtttactcat    1980
atatacttta gattgattta aaacttcatt tttaatttaa aaggatctag gtgaagatcc    2040
tttttgataa tctcatgacc aaaatccctt aacgtgagtt ttcgttccac tgagcgtcag    2100
accccgtaga aaagatcaaa ggatcttctt gagatccttt ttttctgcgc gtaatctgct    2160
gcttgcaaac aaaaaaacca ccgctaccag cggtggtttg tttgccggat caagagctac    2220
caactctttt tccgaaggta actggcttca gcagagcgca gataccaaat actgtccttc    2280
tagtgtagcc gtagttaggc caccacttca agaactctgt agcaccgcct acatacctcg    2340
ctctgctaat cctgttacca gtggctgctg ccagtggcga taagtcgtgt cttaccgggt    2400
tggactcaag acgatagtta ccggataagg cgcagcggtc gggctgaacg gggggttcgt    2460
gcacacagcc cagcttggag cgaacgacct acaccgaact gagatacccta cagcgtgagc    2520
tatgagaaag cgccacgctt cccgaaggga gaaaggcgga caggtatccg gtaagcggca    2580
gggtcggaac aggagagcgc acgagggagc ttccaggggg aaacgcctgg tatctttata    2640
gtcctgtcgg gtttcgccac ctctgacttg agcgtcgatt tttgtgatgc tcgtcagggg    2700
ggcggagcct atgaaaaaac gccagcaacg cggcctttt acggttcctg gccttttgct    2760
ggccttttgc tcacatgttc tttcctgcgt tatcccctga ttctgtggat aaccgtatta    2820
ccgcctttga gtgagctgat accgctcgcc gcagccgaac gaccgagcgc agcgagtcag    2880
tgagcgagga agcggaagag cgcccaatac gcaaaccgcc tctccccgcg cgttggccga    2940
ttcattaatg cagctggcac gacaggtttc ccgactggaa agcgggcagt gagcgcaacg    3000
caattaatgt gagttagctc actcattagg caccccaggc tttacacttt atgcttccgg    3060
ctcgtatgtt gtgtggaatt gtgagcggat aacaatttca cacaggaaac agctatgacc    3120
atgattacgc caagcttgca tgcctgcagg tcgactcgac gtacgtcctc gaagagaagg    3180
gttaataaca cattttttaa cattttttaac acaaattta gttatttaaa aatttattaa    3240
aaaatttaaa ataagaagag gaactcttta aataaatcta acttacaaaa tttatgattt    3300
ttaataagtt ttcaccaata aaaaatgtca taaaaatatg ttaaaaagta tattatcaat    3360
```

```
attctcttta tgataaataa aaagaaaaaa aaaataaaag ttaagtgaaa atgagattga    3420
agtgactta  ggtgtgtata aatatatcaa ccccgccaac aatttattta atccaaatat    3480
attgaagtat attattccat agcctttatt tatttatata tttattatat aaaagcttta    3540
tttgttctag gttgttcatg aaatattttt ttggttttat ctccgttgta agaaaatcat    3600
gtgctttgtg tcgccactca ctattgcagc ttttcatgc  attggtcaga ttgacggttg    3660
attgtatttt tgttttttat ggttttgtgt tatgacttaa gtcttcatct ctttatctct    3720
tcatcaggtt tgatggttac ctaatatggt ccatgggtac atgcatggtt aaattaggtg    3780
gccaactttg ttgtgaacga tagaattttt tttatattaa gtaaactatt tttatattat    3840
gaaataataa taaaaaaaat attttatcat tattaacaaa atcatattag ttaatttgtt    3900
aactctataa taaaagaaat actgtaacat tcacattaca tggtaacatc tttccaccct    3960
ttcatttgtt ttttgtttga tgactttttt tcttgtttaa atttatttcc cttcttttaa    4020
atttggaata cattatcatc atatataaac taaaatacta aaacaggat  tacacaaatg    4080
ataaataata acacaaatat ttataaatct agctgcaata tatttaaact agctatatcg    4140
atattgtaaa ataaaactag ctgcattgat actgataaaa aaatatcatg tgctttctgg    4200
actgatgatg cagtatactt ttgacattgc ctttatttta tttttcagaa aagctttctt    4260
agttctgggt tcttcattat ttgtttccca tctccattgt gaattgaatc atttgcttcg    4320
tgtcacaaat acaatttagn taggtacatg cattggtcag attcacggtt tattatgtca    4380
tgacttaagt tcatggtagt acattacctg ccacgcatgc attatattgg ttagatttga    4440
taggcaaatt tggttgtcaa caatataaat ataataatg  ttttatatt  acgaaataac    4500
agtgatcaaa acaaacagtt ttatctttat taacaagatt ttgttttgt  ttgatgacgt    4560
tttttaatgt ttacgctttc ccccttcttt tgaatttaga acactttatc atcataaaat    4620
caaatactaa aaaattaca  tatttcataa ataataacac aaatatttt  aaaaaatctg    4680
aaataataat gaacaatatt acatattatc acgaaaattc attaataaaa atattatata    4740
aataaaatgt aatagtagtt atatgtagga aaaaagtact gcacgcataa tatatacaaa    4800
aagattaaaa tgaactatta taaataataa cactaaatta atggtgaatc atatcaaaat    4860
aatgaaaaag taaataaaat ttgtaattaa cttctatatg tattacacac acaaataata    4920
aataatagta aaaaaaatta tgataaatat ttaccatctc ataagatatt taaaataatg    4980
ataaaaatat agattatttt ttatgcaact agctagccaa aaagagaaca cgggtatata    5040
taaaaagagt acctttaaat tctactgtac ttcctttatt cctgacgttt ttatatcaag    5100
tggacatacg tgaagatttt aattatcagt ctaaatattt cattagcact taatactttt    5160
ctgttttatt cctatcctat aagtagtccc gattctccca acattgctta ttcacacaac    5220
taactaagaa agtcttccat agcccccccaa gcggccgcgg gaattcgatt gaatgaagt    5280
caaagcgcca agcgcttccc cttacaattg atggaacaac atatgatgtg tctgcctggg    5340
tcaatttcca ccctggtggt gcggaaatta tagagaatta ccaaggaagg gatgccactg    5400
atgccttcat ggttatgcac tctcaagaag ccttcgacaa gctcaagcgc atgcccaaaa    5460
tcaatcccag ttctgagttg ccaccccagg ctgcagtgaa tgaagctcaa gaggatttcc    5520
ggaagctccg agaagagttg atcgcaactg gcatgtttga tgcctccccc ctctggtact    5580
catacaaaat cagcaccaca ctgggccttg gagtgctggg ttatttcctg atggttcagt    5640
atcagatgta tttcattggg gcagtgttgc ttgggatgca ctatcaacag atgggctggc    5700
```

```
tttctcatga catttgccac caccagactt tcaagaaccg gaactggaac aacctcgtgg   5760
gactggtatt tggcaatggt ctgcaaggtt tttccgtgac atggtggaag acagacaca    5820 atgcacatca ttcggcaacc aatgttcaag ggcacgaccc tgatattgac aacctccccc   5880
tcttagcctg gtctgaggat gacgtcacac gggcgtcacc gatttccgc aagctcattc    5940 agttccagca gtactatttc ttggtcatct gtatcttgtt gcggttcatt tggtgtttcc   6000
agagcgtgtt gaccgtgcgc agtttgaagg acagagataa ccaattctat cgctctcagt   6060
ataagaagga ggccattggc ctcgccctgc actggacctt gaagaccctg ttccacttat   6120
tctttatgcc cagcatcctc acatcgctgt tggtgttttt cgtttcggag ctggttggcg   6180
gcttcggcat tgcgatcgtg gtgttcatga accactaccc actggagaag atcggggact   6240
cagtctggga tggccatgga ttctcggttg gccagatcca tgagaccatg aacattcggc   6300
gagggattat cacagattgg ttttccggag gcttgaatta ccagattgag caccatttgt   6360
ggccgaccct ccctcgccac aacctgacag cggttagcta ccaggtggaa cagctgtgcc   6420
agaagcacaa cctgccgtat cggaacccgc tgccccatga aggggttggtc atcctgctgc   6480 gctatctggc ggtgttcgcc cggatggcgg agaagcaacc cgcggggaag gctctataag   6540
gaatcactag tgaattcgc                                                6559
```

<210> SEQ ID NO 77
<211> LENGTH: 9014
<212> TYPE: DNA
<213> ORGANISM: Artificial Sequence
<220> FEATURE:
<223> OTHER INFORMATION: Plasmid pKR913
<220> FEATURE:
<221> NAME/KEY: misc_feature
<222> LOCATION: (7839)..(7839)
<223> OTHER INFORMATION: n is a, c, g, or t

<400> SEQUENCE: 77

```
gtacgagatc cggccggcca gatcctgcag gagatccaag cttttgatcc atgcccttca     60
tttgccgctt attaattaat ttggtaacag tccgtactaa tcagttactt atccttcccc    120
catcataatt aatcttggta gtctcgaatg ccacaacact gactagtctc ttggatcata    180
agaaaaagcc aaggaacaaa agaagacaaa acacaatgag agtatccttt gcatagcaat    240
gtctaagttc ataaaattca acaaaaacg caatcacaca cagtggacat cacttatcca    300
ctagctgatc aggatcgccg cgtcaagaaa aaaaactgg accccaaaag ccatgcacaa    360 caaacacgtac tcacaaaggt gtcaatcgag cagcccaaaa cattcaccaa ctcaacccat    420
catgagccct cacatttgtt gtttctaacc caacctcaaa ctcgtattct cttccgccac    480
ctcatttttg tttatttcaa cacccgtcaa actgcatgcc accccgtggc caaatgtcca    540
tgcatgttaa caagacctat gactataaat agctgcaatc tcggcccagg ttttcatcat    600
caagaaccag ttcaatatcc tagtacaccg tattaaagaa tttaagatat actgcggccg    660
caccatggag gtggtgaatg aaatagtctc aattgggcag gaagttttac ccaaagttga    720
ttatgcccaa ctctggagtg atgccagtca ctgtgaggtg cttttacttgt ccatcgcatt    780 tgtcatcttg aagttcactc ttggccccct tggtccaaaa ggtcagtctc gtatgaagtt    840
tgttttcacc aattacaacc ttctcatgtc catttattcg ttgggatcat tcctctcaat    900
ggcatatgcc atgtacacca tcggtgttat gtctgacaac tgcgagaagg cttttgacaa    960
caacgtcttc aggatcacca cgcagttgtt ctatttgagc aagttcctgg agtatattga   1020
ctccttctat ttgccactga tgggcaagcc tctgacctgg ttgcaattct tccatcattt   1080
```

```
gggggcaccg atggatatgt ggctgttcta taattaccga aatgaagctg tttggatttt   1140
tgtgctgttg aatggtttca tccactggat catgtacggt tattattgga ccagattgat   1200
caagctgaag ttccccatgc caaaatccct gattacatca atgcagatca ttcaattcaa   1260
tgttggtttc tacattgtct ggaagtacag gaacattccc tgttatcgcc aagatgggat   1320
gaggatgttt ggctggttct tcaattactt ttatgttggc acagtcttgt gtttgttctt   1380
gaatttctat gtgcaaacgt atatcgtcag gaagcacaag ggagccaaaa agattcagtg   1440
agcggccgca agtatgaact aaaatgcatg taggtgtaag agctcatgga gagcatggaa   1500
tattgtatcc gaccatgtaa cagtataata actgagctcc atctcacttc ttctatgaat   1560
aaacaaagga tgttatgata tattaacact ctatctatgc accttattgt tctatgataa   1620
atttcctctt attattataa atcatctgaa tcgtgacggc ttatggaatg cttcaaatag   1680
tacaaaaaca aatgtgtact ataagacttt ctaaacaatt ctaaccttag cattgtgaac   1740
gagacataag tgttaagaag acataacaat tataatggaa gaagtttgtc tccatttata   1800
tattatatat tacccactta tgtattatat taggatgtta aggagacata acaattataa   1860
agagagaagt ttgtatccat ttatatatta tatactaccc atttatatat tatacttatc   1920
cacttattta atgtctttat aaggtttgat ccatgatatt tctaatattt tagttgatat   1980
gtatatgaaa gggtactatt tgaactctct tactctgtat aaaggttgga tcatccttaa   2040
agtgggtcta tttaatttta ttgcttctta cagataaaaa aaaaattatg agttggtttg   2100
ataaaatatt gaaggattta aaataataat aaataacata taatatatgt atataaattt   2160
attataatat aacatttatc tataaaaaag taaatattgt cataaatcta tacaatcgtt   2220
tagccttgct ggacgaatct caattattta aacgagagta aacatatttg acttttggt    2280
tatttaacaa attattattt aacactatat gaaattttt ttttatcag caaagaataa    2340
aattaaatta agaaggacaa tggtgtccca atccttatac aaccaacttc cacaagaaag   2400
tcaagtcaga gacaacaaaa aaacaagcaa aggaaatttt taatttgag ttgtcttgtt    2460
tgctgcataa tttatgcagt aaaacactac acataaccct tttagcagta gagcaatggt   2520
tgaccgtgtg cttagcttct tttatttat tttttatca gcaaagaata aataaaataa     2580
aatgagacac ttcagggatg tttcaacaag cttggcgcgc cgttctatag tgtcacctaa   2640
atcgtatgtg tatgatacat aaggttatgt attaattgta gccgcgttct aacgacaata   2700
tgtccatatg gtgcactctc agtacaatct gctctgatgc cgcatagtta agccagcccc   2760
gacacccgcc aacacccgct gacgcgccct gacgggcttg tctgctcccg gcatccgctt   2820
acagacaagc tgtgaccgtc tccgggagct gcatgtgtca gaggttttca ccgtcatcac   2880
cgaaacgcgc gagacgaaag ggcctcgtga tacgcctatt tttataggtt aatgtcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
taactggctt cagcagagcg cagataccaa atactgtcct tctagtgtag ccgtagttag   3180
gccaccactt caagaactct gtagcaccgc ctacatacct cgctctgcta atcctgttac   3240
cagtggctgc tgccagtggc gataagtcgt gtcttaccgg gttggactca agacgatagt   3300
taccggataa ggcgcagcgg tcgggctgaa cggggggttc gtgcacacag cccagcttgg   3360
agcgaacgac ctacaccgaa ctgagatacc tacagcgtga gcattgagaa agcgccacgc   3420
```

```
ttcccgaagg gagaaaggcg gacaggtatc cggtaagcgg cagggtcgga acaggagagc    3480
gcacgaggga gcttccaggg ggaaacgcct ggtatcttta tagtcctgtc gggtttcgcc    3540
acctctgact tgagcgtcga tttttgtgat gctcgtcagg ggggcggagc ctatggaaaa    3600
acgccagcaa cgcggccttt ttacggttcc tggccttttg ctggccttt gctcacatgt    3660 tctttcctgc gttatcccct gattctgtgg ataaccgtat taccgccttt gagtgagctg    3720
ataccgctcg ccgcagccga acgaccgagc gcagcgagtc agtgagcgag gaagcggaag    3780
agcgcccaat acgcaaaccg cctctccccg cgcgttggcc gattcattaa tgcaggttga    3840
tcagatctcg atcccgcgaa attaatacga ctcactatag ggagaccaca acggtttccc    3900
tctagaaata attttgttta actttaagaa ggagatatac ccatggaaaa gcctgaactc    3960
accgcgacgt ctgtcgagaa gtttctgatc gaaaagttcg acagcgtctc cgacctgatg    4020
cagctctcgg agggcgaaga atctcgtgct ttcagcttcg atgtaggagg gcgtggatat    4080
gtcctgcggg taaatagctg cgccgatggt ttctacaaag atcgttatgt ttatcggcac    4140
tttgcatcgg ccgcgctccc gattccggaa gtgcttgaca ttggggaatt cagcgagagc    4200
ctgacctatt gcatctcccg ccgtgcacag ggtgtcacgt tgcaagacct gcctgaaacc    4260
gaactgcccg ctgttctgca gccggtcgcg gaggctatgg atgcgatcgc tgcggccgat    4320
cttagccaga cgagcgggtt cggcccattc ggaccgcaag gaatcggtca atacactaca    4380
tggcgtgatt tcatatgcgc gattgctgat ccccatgtgt atcactggca aactgtgatg    4440
gacgacaccg tcagtgcgtc cgtcgcgcag gctctcgatg agctgatgct ttgggccgag    4500
gactgccccg aagtccggca cctcgtgcac gcggatttcg ctccaacaa tgtcctgacg    4560 gacaatggcc gcataacagc ggtcattgac tggagcgagg cgatgttcgg ggattcccaa    4620
tacgaggtcg ccaacatctt cttctggagg ccgtggttgg cttgtatgga gcagcagacg    4680
cgctacttcg agcggaggca tccggagctt gcaggatcgc cgcggctccg gcgtatatg    4740 ctccgcattg gtcttgacca actctatcag agcttggttg acggcaattt cgatgatgca    4800
gcttgggcgc agggtcgatg cgacgcaatc gtccgatccg gagccgggac tgtcgggcgt    4860
acacaaatcg cccgcagaag cgcggccgtc tggaccgatg gctgtgtaga agtactcgcc    4920
gatagtggaa accgacgccc cagcactcgt ccgagggcaa aggaatagtg aggtacagct    4980
tggatcgatc cggctgctaa caaagcccga aggaagctg agttggctgc tgccaccgct    5040
gagcaataac tagcataacc ccttggggcc tctaaacggg tcttgagggg ttttttgctg    5100
aaaggaggaa ctatatccgg atgatcgggc gcgccgtcga cggatccgta cgcaaaggca    5160
aagatttaaa ctcgaaaaca ttacaaaagt ctcaaaacag aggcaaggcc atgcacaaag    5220
cacactctaa gtgcttccat tgcctactaa gtagggtacg tacacgatca ccattcacca    5280
gtgatgatct ttattaatat acaacacact cagagacagc ttatgttata gctagctagc    5340
ataaactatc acatcatgtg ttagtacgac aagtgacaac attgctttta acttcgcggc    5400
cttggatcct ctagaccgga tataatgagc cgtaaacaaa gatgattaag tagtaattaa    5460
tacgtactag taaaagtggc aaaagataac gagaaagaac caatttcttt gcattcggcc    5520
ttagcggaag gcatatataa gctttgatta ttttatttag tgtaatgatt tcgtacaacc    5580
aaagcattta tttagtactc tcacacttgt gtcgcggccg cgaattcact agtgattcct    5640
tatagagcct tccccgcggg ttgcttctcc gccatccggg cgaacaccgc cagatagcgc    5700
agcaggatga ccaacccttc atggggcagc gggttccgat acggcaggtt gtgcttctgg    5760
cacagctgtt ccacctggta gctaaccgct gtcaggttgt ggcgagggag ggtcggccac    5820
```

```
aaatggtgct caatctggta attcaagcct ccgaaaaacc aatctgtgat aatccctcgc    5880
cgaatgttca tggtctcatg gatctggcca accgagaatc catggccatc ccagactgag    5940
tccccgatct tctccagtgg gtagtggttc atgaacacca cgatcgcaat gccgaagccg    6000
ccaaccagct ccgaaacgaa aaacaccaac agcgatgtga ggatgctggg cataaagaat    6060
aagtggaaca gggtcttcaa ggtccagtgc agggcgaggc caatggcctc cttcttatac    6120
tgagagcgat agaattggtt atctctgtcc ttcaaactgc gcacggtcaa cacgctctgg    6180
aaacaccaaa tgaaccgcaa caagatacag atgaccaaga aatagtactg ctggaactga    6240
atgagcttgc gggaaatcgg tgacgcccgt gtgacgtcat cctcagacca ggctaagagg    6300
gggaggttgt caatatcagg gtcgtgccct gaacattgg ttgccgaatg atgtgcattg     6360
tgtctgtcct tccaccatgt cacggaaaaa ccttgcagac cattgccaaa taccagtccc    6420
acgaggttgt tccagttccg gttcttgaaa gtctggtggt ggcaaatgtc atgagaaagc    6480
cagcccatct gttgatagtg catcccaagc aacactgccc caatgaaata catctgatac    6540
tgaaccatca ggaaataacc cagcactcca aggcccagtg tggtgctgat tttgtatgag    6600
taccagaggg gggaggcatc aaacatgcca gttgcgatca actcttctcg gagcttccgg    6660
aaatcctctt gagcttcatt cactgcagcc tggggtggca actcagaact gggattgatt    6720
ttgggcatgc gcttgagctt gtcgaaggct tcttgagagt gcataaccat gaaggcatca    6780
gtggcatccc ttccttggta attctctata atttccgcac caccagggtg gaaattgacc    6840
caggcagaca catcatatgt tgttccatca attgtaaggg gaagcgcttg gcgctttgac    6900
ttcatttcaa tcgaattccc gcggccgctt ggggggctat ggaagacttt cttagttagt    6960
tgtgtgaata agcaatgttg ggagaatcgg gactacttat aggataggaa taaaacagaa    7020
aagtattaag tgctaatgaa atatttagac tgataattaa aatcttcacg tatgtccact    7080
tgatataaaa acgtcaggaa taaggaagt acagtagaat ttaaaggtac tcttttata     7140
tatacccgtg ttctcttttt ggctagctag ttgcataaaa aataatctat attttatca    7200
ttatttttaaa tatcttatga gatggtaaat atttatcata atttttttta ctattattta  7260
ttatttgtgt gtgtaataca tatagaagtt aattacaaat tttatttact ttttcattat   7320
tttgatatga ttcaccatta atttagtgtt attatttata atagttcatt ttaatctttt   7380
tgtatatatt atgcgtgcag tactttttc ctacatataa ctactattac attttattta    7440
tataatattt ttattaatga attttcgtga taatatgtaa tattgttcat tattatttca   7500
gattttttaa aaatatttgt gttattattt atgaaatatg taattttttt agtatttgat   7560
tttatgatga taaagtgttc taaattcaaa agaagggga aagcgtaaac attaaaaaac     7620
gtcatcaaac aaaaacaaaa tcttgttaat aaagataaaa ctgtttgttt tgatcactgt   7680
tatttcgtaa tataaaaaca ttatttatat ttatattgtt gacaaccaaa tttgcctatc   7740
aaatctaacc aatataatgc atgcgtggca ggtaatgtac taccatgaac ttaagtcatg   7800
acataataaa ccgtgaatct gaccaatgca tgtacctanc taaattgtat ttgtgacacg   7860
aagcaaatga ttcaattcac aatggagatg ggaaacaaat aatgaagaac ccagaactaa   7920
gaaagctttt ctgaaaaata aaataaaggc aatgtcaaaa gtatactgca tcatcagtcc   7980
agaaagcaca tgatattttt ttatcagtat caatgcagct agttttattt tacaatatcg   8040
atatagctag tttaaatata ttgcagctag atttataaat atttgtgtta ttatttatca   8100
tttgtgtaat cctgttttta gtattttagt ttatatatga tgataatgta ttccaaattt   8160
```

```
aaaagaaggg aaataaattt aaacaagaaa aaaagtcatc aaacaaaaaa caaatgaaag   8220
ggtggaaaga tgttaccatg taatgtgaat gttacagtat ttcttttatt atagagttaa   8280
caaattaact aatatgattt tgttaataat gataaaatat tttttttatt attatttcat   8340
aatataaaaa tagtttactt aatataaaaa aaattctatc gttcacaaca aagttggcca   8400
cctaatttaa ccatgcatgt acccatggac catattaggt aaccatcaaa cctgatgaag   8460
agataaagag atgaagactt aagtcataac acaaaaccat aaaaaacaaa aatacaatca   8520
accgtcaatc tgaccaatgc atgaaaaagc tgcaatagtg agtggcgaca caaagcacat   8580
gattttctta aacggagat aaaaccaaaa aaatatttca tgaacaacct agaacaaata   8640
aagcttttat ataataaata tataaataaa taaaggctat ggaataatat acttcaatat   8700
atttggatta aataaattgt tggcggggtt gatatattta tacacaccta aagtcacttc   8760
aatctcattt tcacttaact tttatttttt ttttcttttt atttatcata aagagaatat   8820
tgataatata cttttaaca tattttatg acattttta ttggtgaaaa cttattaaaa   8880
atcataaatt ttgtaagtta gattattta aagagttcct cttcttattt taaattttt   8940 aataaattt taataacta aaatttgtgt taaaaatgtt aaaaaatgtg ttattaaccc   9000
ttctcttcga ggac   9014

<210> SEQ ID NO 78
<211> LENGTH: 1482
<212> TYPE: DNA
<213> ORGANISM: Mortierella alpina
<220> FEATURE:
<221> NAME/KEY: CDS
<222> LOCATION: (59)..(1399)
<223> OTHER INFORMATION: delta-5 desaturase

<400> SEQUENCE: 78
gcttcctcca gttcatcctc catttcgcca cctgcattct ttacgaccgt taagcaag     58 atg gga acg gac caa gga aaa acc ttc acc tgg gaa gag ctg gcg gcc   106
Met Gly Thr Asp Gln Gly Lys Thr Phe Thr Trp Glu Glu Leu Ala Ala
1               5                   10                  15 cat aac acc aag gac gac cta ctc ttg gcc atc cgc ggc agg gtg tac   154
His Asn Thr Lys Asp Asp Leu Leu Leu Ala Ile Arg Gly Arg Val Tyr
            20                  25                  30 gat gtc aca aag ttc ttg agc cgc cat cct ggt gga gtg gac act ctc   202
Asp Val Thr Lys Phe Leu Ser Arg His Pro Gly Gly Val Asp Thr Leu
        35                  40                  45 ctg ctc gga gct ggc cga gat gtt act ccg gtc ttt gag atg tat cac   250
Leu Leu Gly Ala Gly Arg Asp Val Thr Pro Val Phe Glu Met Tyr His
    50                  55                  60 gcg ttt ggg gct gca gat gcc att atg aag aag tac tat gtc ggt aca   298
Ala Phe Gly Ala Ala Asp Ala Ile Met Lys Lys Tyr Tyr Val Gly Thr
65                  70                  75                  80 ctg gtc tcg aat gag ctg ccc atc ttc ccg gag cca acg gtg ttc cac   346
Leu Val Ser Asn Glu Leu Pro Ile Phe Pro Glu Pro Thr Val Phe His
                85                  90                  95 aaa acc atc aag acg aga gtc gag ggc tac ttt acg gat cgg aac att   394
Lys Thr Ile Lys Thr Arg Val Glu Gly Tyr Phe Thr Asp Arg Asn Ile
            100                 105                 110 gat ccc aag aat aga cca gag atc tgg gga cga tac gct ctt atc ttt   442
Asp Pro Lys Asn Arg Pro Glu Ile Trp Gly Arg Tyr Ala Leu Ile Phe
        115                 120                 125 gga tcc ttg atc gct tcc tac tac gcg cag ctc ttt gtg cct ttc gtt   490
Gly Ser Leu Ile Ala Ser Tyr Tyr Ala Gln Leu Phe Val Pro Phe Val
    130                 135                 140
```

| | | |
|---|---|---|
| gtc gaa cgc aca tgg ctt cag gtg gtg ttt gca atc atc atg gga ttt<br>Val Glu Arg Thr Trp Leu Gln Val Val Phe Ala Ile Ile Met Gly Phe<br>145                          150                      155                  160 | 538 |
| gcg tgc gca caa gtc gga ctc aac cct ctt cat gat gcg tct cac ttt<br>Ala Cys Ala Gln Val Gly Leu Asn Pro Leu His Asp Ala Ser His Phe<br>               165                      170                      175 | 586 |
| tca gtg acc cac aac ccc act gtc tgg aag att ctg gga gcc acg cac<br>Ser Val Thr His Asn Pro Thr Val Trp Lys Ile Leu Gly Ala Thr His<br>     180                      185                      190 | 634 |
| gac ttt ttc aac gga gca tcg tac ctg gtg tgg atg tac caa cat atg<br>Asp Phe Phe Asn Gly Ala Ser Tyr Leu Val Trp Met Tyr Gln His Met<br>         195                      200                      205 | 682 |
| ctc ggc cat cac ccc tac acc aac att gct gga gca gat ccc gac gtg<br>Leu Gly His His Pro Tyr Thr Asn Ile Ala Gly Ala Asp Pro Asp Val<br>210                          215                      220 | 730 |
| tcg acg tct gag ccc gat gtt cgt cgt atc aag ccc aac caa aag tgg<br>Ser Thr Ser Glu Pro Asp Val Arg Arg Ile Lys Pro Asn Gln Lys Trp<br>225                          230                      235                  240 | 778 |
| ttt gtc aac cac atc aac cag cac atg ttt gtt cct ttc ctg tac gga<br>Phe Val Asn His Ile Asn Gln His Met Phe Val Pro Phe Leu Tyr Gly<br>                      245                      250                      255 | 826 |
| ctg ctg gcg ttc aag gtg cgc att cag gac atc aac att ttg tac ttt<br>Leu Leu Ala Phe Lys Val Arg Ile Gln Asp Ile Asn Ile Leu Tyr Phe<br>         260                      265                      270 | 874 |
| gtc aag acc aat gac gct att cgt gtc aat ccc atc tcg aca tgg cac<br>Val Lys Thr Asn Asp Ala Ile Arg Val Asn Pro Ile Ser Thr Trp His<br>275                          280                      285 | 922 |
| act gtg atg ttc tgg ggc ggc aag gct ttc ttt gtc tgg tat cgc ctg<br>Thr Val Met Phe Trp Gly Gly Lys Ala Phe Phe Val Trp Tyr Arg Leu<br>     290                      295                      300 | 970 |
| att gtt ccc ctg cag tat ctg ccc ctg ggc aag gtg ctg ctc ttg ttc<br>Ile Val Pro Leu Gln Tyr Leu Pro Leu Gly Lys Val Leu Leu Leu Phe<br>305                          310                      315                  320 | 1018 |
| acg gtc gcg gac atg gtg tcg tct tac tgg ctg gcg ctg acc ttc cag<br>Thr Val Ala Asp Met Val Ser Ser Tyr Trp Leu Ala Leu Thr Phe Gln<br>                      325                      330                      335 | 1066 |
| gcg aac cac gtt gtt gag gaa gtt cag tgg ccg ttg cct gac gag aac<br>Ala Asn His Val Val Glu Glu Val Gln Trp Pro Leu Pro Asp Glu Asn<br>                  340                      345                      350 | 1114 |
| ggg atc atc caa aag gac tgg gca gct atg cag gtc gag act acg cag<br>Gly Ile Ile Gln Lys Asp Trp Ala Ala Met Gln Val Glu Thr Thr Gln<br>         355                      360                      365 | 1162 |
| gat tac gca cac gat tcg cac ctc tgg acc agc atc act ggc agc ttg<br>Asp Tyr Ala His Asp Ser His Leu Trp Thr Ser Ile Thr Gly Ser Leu<br>370                          375                      380 | 1210 |
| aac tac cag gct gtg cac cat ctg ttc ccc aac gtg tcg cag cac cat<br>Asn Tyr Gln Ala Val His His Leu Phe Pro Asn Val Ser Gln His His<br>385                          390                      395                  400 | 1258 |
| tat ccc gat att ctg gcc atc atc aag aac acc tgc agc gag tac aag<br>Tyr Pro Asp Ile Leu Ala Ile Ile Lys Asn Thr Cys Ser Glu Tyr Lys<br>                  405                      410                      415 | 1306 |
| gtt cca tac ctt gtc aag gat acg ttt tgg caa gca ttt gct tca cat<br>Val Pro Tyr Leu Val Lys Asp Thr Phe Trp Gln Ala Phe Ala Ser His<br>         420                      425                      430 | 1354 |
| ttg gag cac ttg cgt gtt ctt gga ctc cgt ccc aag gaa gag tag<br>Leu Glu His Leu Arg Val Leu Gly Leu Arg Pro Lys Glu Glu<br>                  435                      440                      445 | 1399 |
| aagaaaaaaa gcgccgaatg aagtattgcc cccttttttct ccaagaatgg caaaaggaga | 1459 |

```
tcaagtggac attctctatg aag                                           1482
```

<210> SEQ ID NO 79
<211> LENGTH: 446
<212> TYPE: PRT
<213> ORGANISM: Mortierella alpina

<400> SEQUENCE: 79

| | | | | | | | | | | | | | | |
|---|---|---|---|---|---|---|---|---|---|---|---|---|---|---|
| Met | Gly | Thr | Asp | Gln | Gly | Lys | Thr | Phe | Thr | Trp | Glu | Glu | Leu | Ala | Ala |
| 1 | | | | 5 | | | | | 10 | | | | | 15 | |
| His | Asn | Thr | Lys | Asp | Asp | Leu | Leu | Leu | Ala | Ile | Arg | Gly | Arg | Val | Tyr |
| | | | 20 | | | | | 25 | | | | | 30 | | |
| Asp | Val | Thr | Lys | Phe | Leu | Ser | Arg | His | Pro | Gly | Gly | Val | Asp | Thr | Leu |
| | | 35 | | | | | 40 | | | | | 45 | | | |
| Leu | Leu | Gly | Ala | Gly | Arg | Asp | Val | Thr | Pro | Val | Phe | Glu | Met | Tyr | His |
| 50 | | | | | 55 | | | | | 60 | | | | | |
| Ala | Phe | Gly | Ala | Ala | Asp | Ala | Ile | Met | Lys | Lys | Tyr | Tyr | Val | Gly | Thr |
| 65 | | | | 70 | | | | | 75 | | | | | 80 | |
| Leu | Val | Ser | Asn | Glu | Leu | Pro | Ile | Phe | Pro | Glu | Pro | Thr | Val | Phe | His |
| | | | | 85 | | | | | 90 | | | | | 95 | |
| Lys | Thr | Ile | Lys | Thr | Arg | Val | Glu | Gly | Tyr | Phe | Thr | Asp | Arg | Asn | Ile |
| | | | 100 | | | | | 105 | | | | | 110 | | |
| Asp | Pro | Lys | Asn | Arg | Pro | Glu | Ile | Trp | Gly | Arg | Tyr | Ala | Leu | Ile | Phe |
| | | 115 | | | | | 120 | | | | | 125 | | | |
| Gly | Ser | Leu | Ile | Ala | Ser | Tyr | Tyr | Ala | Gln | Leu | Phe | Val | Pro | Phe | Val |
| 130 | | | | | 135 | | | | | 140 | | | | | |
| Val | Glu | Arg | Thr | Trp | Leu | Gln | Val | Val | Phe | Ala | Ile | Ile | Met | Gly | Phe |
| 145 | | | | 150 | | | | | 155 | | | | | 160 | |
| Ala | Cys | Ala | Gln | Val | Gly | Leu | Asn | Pro | Leu | His | Asp | Ala | Ser | His | Phe |
| | | | | 165 | | | | | 170 | | | | | 175 | |
| Ser | Val | Thr | His | Asn | Pro | Thr | Val | Trp | Lys | Ile | Leu | Gly | Ala | Thr | His |
| | | | 180 | | | | | 185 | | | | | 190 | | |
| Asp | Phe | Phe | Asn | Gly | Ala | Ser | Tyr | Leu | Val | Trp | Met | Tyr | Gln | His | Met |
| | | 195 | | | | | 200 | | | | | 205 | | | |
| Leu | Gly | His | His | Pro | Tyr | Thr | Asn | Ile | Ala | Gly | Ala | Asp | Pro | Asp | Val |
| 210 | | | | | 215 | | | | | 220 | | | | | |
| Ser | Thr | Ser | Glu | Pro | Asp | Val | Arg | Arg | Ile | Lys | Pro | Asn | Gln | Lys | Trp |
| 225 | | | | | 230 | | | | | 235 | | | | | 240 |
| Phe | Val | Asn | His | Ile | Asn | Gln | His | Met | Phe | Val | Pro | Phe | Leu | Tyr | Gly |
| | | | | 245 | | | | | 250 | | | | | 255 | |
| Leu | Leu | Ala | Phe | Lys | Val | Arg | Ile | Gln | Asp | Ile | Asn | Ile | Leu | Tyr | Phe |
| | | | 260 | | | | | 265 | | | | | 270 | | |
| Val | Lys | Thr | Asn | Asp | Ala | Ile | Arg | Val | Asn | Pro | Ile | Ser | Thr | Trp | His |
| | | 275 | | | | | 280 | | | | | 285 | | | |
| Thr | Val | Met | Phe | Trp | Gly | Gly | Lys | Ala | Phe | Phe | Val | Trp | Tyr | Arg | Leu |
| | | 290 | | | | | 295 | | | | | 300 | | | |
| Ile | Val | Pro | Leu | Gln | Tyr | Leu | Pro | Leu | Gly | Lys | Val | Leu | Leu | Leu | Phe |
| 305 | | | | | 310 | | | | | 315 | | | | | 320 |
| Thr | Val | Ala | Asp | Met | Val | Ser | Ser | Tyr | Trp | Leu | Ala | Leu | Thr | Phe | Gln |
| | | | | 325 | | | | | 330 | | | | | 335 | |
| Ala | Asn | His | Val | Val | Glu | Glu | Val | Gln | Trp | Pro | Leu | Pro | Asp | Glu | Asn |
| | | | 340 | | | | | 345 | | | | | 350 | | |
| Gly | Ile | Ile | Gln | Lys | Asp | Trp | Ala | Ala | Met | Gln | Val | Glu | Thr | Thr | Gln |
| | | 355 | | | | | 360 | | | | | 365 | | | |

```
Asp Tyr Ala His Asp Ser His Leu Trp Thr Ser Ile Thr Gly Ser Leu
        370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 80
<211> LENGTH: 69
<212> TYPE: DNA
<213> ORGANISM: Artificial Sequence
<220> FEATURE:
<223> OTHER INFORMATION: Restriction enzyme sites added to pKR287 to
      produce pKR767

<400> SEQUENCE: 80
ccatggtcaa tcaatgagac gccaacttct taatctattg agacctgcag gtctagaagg      60
gcggatccc                                                              69

<210> SEQ ID NO 81
<211> LENGTH: 5561
<212> TYPE: DNA
<213> ORGANISM: Artificial Sequence
<220> FEATURE:
<223> OTHER INFORMATION: Plasmid pKR767

<400> SEQUENCE: 81
catggtcaat caatgagacg ccaacttctt aatctattga gacctgcagg tctagaaggg      60
cggatccccg gtaccgagct cgaattcac tggccgtcgt tttacaacgt cgtgactggg     120
aaaaccctgg cgttacccaa cttaatcgcc ttgcagcaca tccccctttc gccagctggc     180
gtaatagcga agaggcccgc accgatcgcc cttcccaaca gttgcgcagc ctgaatggcg     240
aatggcgcct gatgcggtat tttctcctta cgcatctgtg cggtatttca ccgcatat      300 ggtgcactct cagtacaatc tgctctgatg ccgcatagtt aagccagccc cgacacccgc     360
caacacccgc tgacgcgccc tgacgggctt gtctgctccc ggcatccgct tacagacaag     420
ctgtgaccgt ctccgggagc tgcatgtgtc agaggttttc accgtcatca ccgaaacgcg     480
cgagacgaaa gggcctcgtg atacgcctat ttttataggt taatgtcatg ataataatgg     540
tttcttagac gtcaggtggc acttttcggg gaaatgtgcg cggaacccct atttgtttat     600
ttttctaaat acattcaaat atgtatccgc tcatgagaca ataaccctga taaatgcttc     660
aataatattg aaaaggaag agtatgagta ttcaacattt ccgtgtcgcc cttattccct     720
tttttgcggc attttgcctt cctgtttttg ctcacccaga aacgctggtg aaagtaaaag     780
atgctgaaga tcagttgggt gcacgagtgg gttacatcga actggatctc aacagcggta     840
agatccttga gagttttcgc cccgaagaac gttttccaat gatgagcact tttaaagttc     900
tgctatgtgg cgcggtatta cccgtattga cgccgggca agagcaactc ggtcgccgca     960
tacactattc tcagaatgac ttggttgagt actcaccagt cacagaaaag catcttacgg    1020
atggcatgac agtaagagaa ttatgcagtg ctgccataac catgagtgat aacactgcgg    1080
ccaacttact tctgacaacg atcggaggac cgaaggagct aaccgctttt ttgcacaaca    1140
tgggggatca tgtaactcgc cttgatcgtt gggaaccgga gctgaatgaa gccataccaa    1200
```

```
acgacgagcg tgacaccacg atgcctgtag caatggcaac aacgttgcgc aaactattaa   1260
ctggcgaact acttactcta gcttcccggc aacaattaat agactggatg gaggcggata   1320
aagttgcagg accacttctg cgctcggccc ttccggctgg ctggtttatt gctgataaat   1380
ctggagccgg tgagcgtggg tctcgcggta tcattgcagc actggggcca gatggtaagc   1440
cctcccgtat cgtagttatc tacacgacgg ggagtcaggc aactatggat gaacgaaata   1500
gacagatcgc tgagataggt gcctcactga ttaagcattg gtaactgtca gaccaagttt   1560
actcatatat actttagatt gatttaaaac ttcattttta atttaaaagg atctaggtga   1620
agatccttt tgataatctc atgaccaaaa tcccttaacg tgagttttcg ttccactgag   1680
cgtcagaccc cgtagaaaag atcaaaggat cttcttgaga tccttttttt ctgcgcgtaa   1740
tctgctgctt gcaaacaaaa aaaccaccgc taccagcggt ggtttgtttg ccggatcaag   1800
agctaccaac tctttttccg aaggtaactg gcttcagcag agcgcagata ccaaatactg   1860
tccttctagt gtagccgtag ttaggccacc acttcaagaa ctctgtagca ccgcctacat   1920
acctcgctct gctaatcctg ttaccagtgg ctgctgccag tggcgataag tcgtgtctta   1980
ccgggttgga ctcaagacga tagttaccgg ataaggcgca gcggtcgggc tgaacggggg   2040
gttcgtgcac acagcccagc ttggagcgaa cgacctacac cgaactgaga tacctacagc   2100
gtgagctatg agaaagcgcc acgcttcccg aagggagaaa ggcggacagg tatccggtaa   2160
gcggcagggt cggaacagga gagcgcacga gggagcttcc aggggggaaac gcctggtatc   2220
tttatagtcc tgtcgggttt cgccacctct gacttgagcg tcgatttttg tgatgctcgt   2280
cagggggggcg gagcctatgg aaaaacgcca gcaacgcggc ctttttacgg ttcctggcct   2340
tttgctggcc ttttgctcac atgttctttc ctgcgttatc ccctgattct gtggataacc   2400
gtattaccgc ctttgagtga gctgataccg ctcgccgcag ccgaacgacc gagcgcagcg   2460
agtcagtgag cgaggaagcg gaagagcgcc caatacgcaa accgcctctc cccgcgcgtt   2520
ggccgattca ttaatgcagc tggcacgaca ggtttcccga ctggaaagcg ggcagtgagc   2580
gcaacgcaat taatgtgagt tagctcactc attaggcacc ccaggcttta cactttatgc   2640
ttccggctcg tatgttgtgt ggaattgtga gcggataaca atttcacaca ggaaacagct   2700
atgaccatga ttacgccaag cttgcatgcc tgcaggctag cctaagtacg tactcaaaat   2760
gccaacaaat aaaaaaaaag ttgctttaat aatgccaaaa caaattaata aaacacttac   2820
aacaccggat ttttttttaat taaaatgtgc catttaggat aaatagttaa tatttttaat   2880
aattatttaa aaagccgtat ctactaaaat gattttttatt tggttgaaaa tattaatatg   2940
tttaaatcaa cacaatctat caaaattaaa ctaaaaaaaa aataagtgta cgtggttaac   3000
attagtacag taatataaga ggaaaatgag aaattaagaa attgaaagcg agtctaattt   3060
ttaaattatg aacctgcata tataaaagga agaaagaat ccaggaagaa aagaaatgaa   3120
accatgcatg gtcccctcgt catcacgagt ttctgccatt tgcaatagaa acactgaaac   3180
acctttctct ttgtcactta attgagatgc cgaagccacc tcacaccatg aacttcatga   3240
ggtgtagcac ccaaggcttc catagccatg catactgaag aatgtctcaa gctcagcacc   3300
ctacttctgt gacgtgtccc tcattcacct tcctctcttc cctataaata accacgcctc   3360
aggttctccg cttcacaact caaacattct ctccattggt ccttaaacac tcatcagtca   3420
tcaccgcggc cgcatgggaa cggaccaagg aaaaaccttc acctgggaag agctggcggc   3480
ccataacacc aaggacgacc tactcttggc catccgcggc agggtgtacg atgtcacaaa   3540
```

```
gttcttgagc cgccatcctg gtggagtgga cactctcctg ctcggagctg gccgagatgt    3600
tactccggtc tttgagatgt atcacgcgtt tggggctgca gatgccatta tgaagaagta    3660
ctatgtcggt acactggtct cgaatgagct gcccatcttc ccggagccaa cggtgttcca    3720
caaaaccatc aagacgagag tcgagggcta ctttacggat cggaacattg atcccaagaa    3780
tagaccagag atctggggac gatacgctct tatctttgga tccttgatcg cttcctacta    3840
cgcgcagctc tttgtgcctt tcgttgtcga acgcacatgg cttcaggtgg tgtttgcaat    3900
catcatggga tttgcgtgcg cacaagtcgg actcaaccct cttcatgatg cgtctcactt    3960
ttcagtgacc cacaacccca ctgtctggaa gattctggga gccacgcacg acttttttcaa   4020
cggagcatcg tacctggtgt ggatgtacca acatatgctc ggccatcacc cctacaccaa    4080
cattgctgga gcagatcccg acgtgtcgac gtctgagccc gatgttcgtc gtatcaagcc    4140
caaccaaaag tggtttgtca accacatcaa ccagcacatg tttgttcctt tcctgtacgg    4200
actgctggcg ttcaaggtgc gcattcagga catcaacatt ttgtactttg tcaagaccaa    4260
tgacgctatt cgtgtcaatc ccatctcgac atggcacact gtgatgttct ggggcggcaa    4320
ggctttcttt gtctggtatc gcctgattgt tccctgcag tatctgcccc tgggcaaggt    4380
gctgctcttg ttcacggtcg cggacatggt gtcgtcttac tggctggcgc tgaccttcca    4440
ggcgaaccac gttgttgagg aagttcagtg gccgttgcct gacgagaacg ggatcatcca    4500
aaaggactgg gcagctatgc aggtcgagac tacgcaggat tacgcacacg attcgcacct    4560
ctggaccagc atcactggca gcttgaacta ccaggctgtg caccatctgt tccccaacgt    4620
gtcgcagcac cattatcccg atattctggc catcatcaag aacacctgca gcgagtacaa    4680
ggttccatac cttgtcaagg atacgttttg gcaagcattt gcttcacatt tggagcactt    4740
gcgtgttctt ggactccgtc ccaaggaaga gtaggcggcc gcatttcgca ccaaatcaat    4800
gaaagtaata atgaaaagtc tgaataagaa tacttaggct tagatgcctt tgttacttgt    4860
gtaaaataac ttgagtcatg tacctttggc ggaaacagaa taaataaaag gtgaaattcc    4920
aatgctctat gtataagtta gtaatactta atgtgttcta cggttgtttc aatatcatca    4980
aactctaatt gaaactttag aaccacaaat ctcaatcttt tcttaatgaa atgaaaaatc    5040
ttaattgtac catgttatg ttaaacacct tacaattggt tggagaggag gaccaaccga    5100
tgggacaaca ttgggagaaa gagattcaat ggagatttgg ataggagaac aacattcttt    5160
ttcacttcaa tacaagatga gtgcaacact aaggatatgt atgagacttt cagaagctac    5220
gacaacatag atgagtgagg tggtgattcc tagcaagaaa gacattagag gaagccaaaa    5280
tcgaacaagg aagacatcaa gggcaagaga caggaccatc catctcagga aaaggagctt    5340
tgggatagtc cgagaagttg tacaagaaat tttttggagg gtgagtgatg cattgctggt    5400
gactttaact caatcaaaat tgagaaagaa agaaaaggga gggggctcac atgtgaatag    5460
aagggaaacg ggagaatttt acagttttga tctaatgggc atcccagcta gtggtaacat    5520
attcaccatg tttaaccttc acgtacgtct agaggatccc                           5561
```

<210> SEQ ID NO 82
<211> LENGTH: 8671
<212> TYPE: DNA
<213> ORGANISM: Artificial Sequence
<220> FEATURE:
<223> OTHER INFORMATION: Plasmid pKR328

<400> SEQUENCE: 82

```
ggatctggcc ggccggatct cgtacggatc cgtcgacggc gcgcccgatc atccggatat      60
```

-continued

```
agttcctcct ttcagcaaaa aaccccctcaa gacccgttta gaggcccccaa ggggttatgc    120 tagttattgc tcagcggtgg cagcagccaa ctcagcttcc tttcgggctt tgttagcagc    180
cggatcgatc caagctgtac ctcactattc ctttgccctc ggacgagtgc tggggcgtcg    240
gtttccacta tcggcgagta cttctacaca gccatcggtc cagacggccg cgcttctgcg    300
ggcgatttgt gtacgcccga cagtcccggc tccggatcgg acgattgcgt cgcatcgacc    360
ctgcgcccaa gctgcatcat cgaaattgcc gtcaaccaag ctctgataga gttggtcaag    420
accaatgcgg agcatatacg cccggagccg cggcgatcct gcaagctccg gatgcctccg    480
ctcgaagtag cgcgtctgct gctccataca agccaaccac ggcctccaga agaagatgtt    540
ggcgacctcg tattgggaat ccccgaacat cgcctcgctc cagtcaatga ccgctgttat    600
gcggccattg tccgtcagga cattgttgga gccgaaatcc gcgtgcacga ggtgccggac    660
ttcggggcag cctcggccc aaagcatcag ctcatcgaga gcctgcgcga cggacgcact    720
gacggtgtcg tccatcacag tttgccagtg atacacatgg ggatcagcaa tcgcgcatat    780
gaaatcacgc catgtagtgt attgaccgat tccttgcggt ccgaatgggc cgaacccgct    840
cgtctggcta agatcggccg cagcgatcgc atccatagcc tccgcgaccg gctgcagaac    900
agcgggcagt tcggtttcag gcaggtcttg caacgtgaca ccctgtgcac ggcgggagat    960
gcaataggtc aggctctcgc tgaattcccc aatgtcaagc acttccggaa tcgggagcgc   1020
ggccgatgca aagtgccgat aaacataacg atctttgtag aaaccatcgg cgcagctatt   1080
tacccgcagg acatatccac gccctcctac atcgaagctg aaagcacgag attcttcgcc   1140
ctccgagagc tgcatcaggt cggagacgct gtcgaacttt tcgatcagaa acttctcgac   1200
agacgtcgcg gtgagttcag gctttttccat gggtatatct ccttcttaaa gttaaacaaa   1260
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
ggagttgcac acaagaaatt tgccactatt acagaggcaa gagcagcagc tgacgcgtac   1560
acaacaagtc agcaaacaga caggttgaac ttcatcccca aaggagaagc tcaactcaag   1620
cccaagagct ttgctaaggc cctaacaagc ccaccaaagc aaaaagccca ctggctcacg   1680
ctaggaacca aaaggcccag cagtgatcca gcccccaaaag agatctcctt tgccccggag   1740
attacaatgg acgatttcct ctatctttac gatctaggaa ggaagttcga aggtgaaggt   1800
gacgacacta tgttcaccac tgataatgag aaggttagcc tcttcaattt cagaaagaat   1860
gctgacccac agatggttag agaggcctac gcagcaggtc tcatcaagac gatctacccg   1920
agtaacaatc tccaggagat caaataccct cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtctttacg   2220 actcaatgac aagaagaaaa tcttcgtcaa catggtggag cacgacactc tggtctactc   2280
caaaaatgtc aaagatacag tctcagaaga ccaaagggct attgagactt ttcaacaaag   2340
gataatttcg ggaaacctcc tcggattcca ttgcccagct atctgtcact tcatcgaaag   2400
```

```
gacagtagaa aaggaaggtg gctcctacaa atgccatcat tgcgataaag gaaaggctat    2460
cattcaagat gcctctgccg acagtggtcc caaagatgga cccccaccca cgaggagcat    2520
cgtggaaaaa gaagacgttc caaccacgtc ttcaaagcaa gtggattgat gtgacatctc    2580
cactgacgta agggatgacg cacaatccca ctatccttcg caagaccctt cctctatata    2640
aggaagttca tttcatttgg agaggacacg ctcgagctca tttctctatt acttcagcca    2700
taacaaaaga actcttttct cttcttatta aaccatgaaa aagcctgaac tcaccgcgac    2760
gtctgtcgag aagtttctga tcgaaaagtt cgacagcgtc tccgacctga tgcagctctc    2820
ggagggcgaa gaatctcgtg cttttcagctt cgatgtagga gggcgtggat atgtcctgcg    2880
ggtaaatagc tgcgccgatg gtttctacaa agatcgttat gtttatcggc actttgcatc    2940
ggccgcgctc ccgattccgg aagtgcttga cattggggaa ttcagcgaga gcctgaccta    3000
ttgcatctcc cgccgtgcac agggtgtcac gttgcaagac ctgcctgaaa ccgaactgcc    3060
cgctgttctg cagccggtcg cggaggccat ggatgcgatc gctgcggccg atcttagcca    3120
gacgagcggg ttcggcccat tcggaccgca aggaatcggt caatacacta catggcgtga    3180
tttcatatgc gcgattgctg atccccatgt gtatcactgg caaactgtga tggacgacac    3240
cgtcagtgcg tccgtcgcgc aggctctcga tgagctgatg ctttgggccg aggactgccc    3300
cgaagtccgg cacctcgtgc acgcggattt cggctccaac aatgtcctga cggacaatgg    3360
ccgcataaca gcggtcattg actggagcga ggcgatgttc gggattccc aatacgaggt    3420
cgccaacatc ttcttctgga ggccgtggtt ggcttgtatg gagcagcaga cgcgctactt    3480
cgagcggagg catccggagc ttgcaggatc gccgcggctc cgggcgtata tgctccgcat    3540
tggtcttgac caactctatc agagcttggt tgacggcaat ttcgatgatg cagcttgggc    3600
gcagggtcga tgcgacgcaa tcgtccgatc cggagccggg actgtcgggc gtacacaaat    3660
cgcccgcaga agcgcggccg tctgaccga tggctgtgta gaagtactcg ccgatagtgg    3720
aaaccgacgc cccagcactc gtccgagggc aaaggaatag tgaggtacct aaagaaggag    3780
tgcgtcgaag cagatcgttc aaacatttgg caataaagtt tcttaagatt gaatcctgtt    3840
gccggtcttg cgatgattat catataattt ctgttgaatt acgttaagca tgtaataatt    3900
aacatgtaat gcatgacgtt atttatgaga tgggttttta tgattagagt cccgcaatta    3960
tacatttaat acgcgataga aaacaaaata tagcgcgcaa actaggataa attatcgcgc    4020
gcggtgtcat ctatgttact agatcgatgt cgaatcgatc aacctgcatt aatgaatcgg    4080
ccaacgcgcg gggagaggcg gtttgcgtat tgggcgctct tccgcttcct cgctcactga    4140
ctcgctgcgc tcggtcgttc ggctgcggcg agcggtatca gctcactcaa aggcggtaat    4200
acggttatcc acagaatcag gggataacgc aggaaagaac atgtgagcaa aaggccagca    4260
aaaggccagg aaccgtaaaa aggccgcgtt gctggcgttt ttccataggc tccgcccccc    4320
tgacgagcat cacaaaaatc gacgctcaag tcagaggtgg cgaaacccga caggactata    4380
aagataccag gcgtttcccc ctggaagctc cctcgtgcgc tctcctgttc cgaccctgcc    4440
gcttaccgga tacctgtccg cctttctccc ttcgggaagc gtggcgcttt ctcaatgctc    4500
acgctgtagg tatctcagtt cggtgtaggt cgttcgctcc aagctgggct gtgtgcacga    4560
acccccgtt cagcccgacc gctgcgcctt atccggtaac tatcgtcttg agtccaaccc    4620
ggtaagacac gacttatcgc cactggcagc agccactggt aacaggatta gcagagcgag    4680
gtatgtaggc ggtgctacag agttcttgaa gtggtggcct aactacggct acactagaag    4740
gacagtattt ggtatctgcg ctctgctgaa gccagttacc ttcggaaaaa gagttggtag    4800
```

```
ctcttgatcc ggcaaacaaa ccaccgctgg tagcggtggt ttttttgttt gcaagcagca   4860
gattacgcgc agaaaaaaag gatctcaaga agatcctttg atcttttcta cggggtctga   4920
cgctcagtgg aacgaaaact cacgttaagg gattttggtc atgacattaa cctataaaaa   4980
taggcgtatc acgaggccct ttcgtctcgc gcgtttcggt gatgacggtg aaaacctctg   5040
acacatgcag ctcccggaga cggtcacagc ttgtctgtaa gcggatgccg ggagcagaca   5100
agcccgtcag ggcgcgtcag cgggtgttgg cgggtgtcgg gctggctta actatgcggc    5160
atcagagcag attgtactga gagtgcacca tatggacata ttgtcgttag aacgcggcta   5220
caattaatac ataaccttat gtatcataca catacgattt aggtgacact atagaacggc   5280
gcgccaagct tggatctcct gcagcccggg ggatccgccc acgtacggta ccatctgcta   5340
atatttttaaa tcacatgcaa gagaggaggc atggttccat tttctacctt cacattattt   5400
gagaaaaacg aacttgttct gtgttttatt tttgcccttc acattagtac aacgtggaag   5460
actcatggtt acacagaatc atacataagt acaatgcttg tccctaagaa aacaagcact   5520
cgttgtattg aacctttacg gctcatgcgg ccgcgaattc actagtgatt gaattcgcgg   5580
ccgcttagtc cgacttggcc ttggcggccg cggccgactc tttgagcgtg aagatctgcg   5640
ccgtctcggg cacagcgccg tagttgacaa agaggtgcgc ggtcttgaag aaggccgtga   5700
tgatgggctc gtcgttcctg cgcacgaggt gcgggtacgg ggccgcaaag tgcttggtgg   5760
cttcgttgag cttgtagtgc ggaatgatcg ggaacaagtg gtggacctgg tgcgtgccaa   5820
tgtggtggct caggttgtcc acgaacgcgc cgtacgagcg gtcgacgctc gagaggttgc   5880
ccttgacgta cgtccactcc gagtcgccgt accacggcgt cgcttcgtcg ttgtggtgca   5940
agaaggtcgt aatgacgagg aacgaagcaa agacaaagag cggcgcatag tagtagaggc   6000
ccatgacggc aaagccgagc gagtatgtga ggtacgcgta cgcggcgaag aaggcggccc   6060
agacgccgag cgacacgatg acggccgacg cgcggcgaag gaggagcggg tcccacgggt   6120
caaagtggct catcgtgcgc ggggcatacc cgaccttcaa gtagacaaac cacgcaccgc   6180
cgagcgtgta gacccattgg cgcacgtcct ggaggtcctt gaccgaccgg tgcgggtaaa   6240
agatctcgtc cttatcaatg ttgcccgtgt tcttgtggtg gtggcggtgc gtcacgcgcc   6300
agctctcgaa cggcgtcaaa atcgcagagt gcatgatgca gccgatgata agttgacgc    6360
tgtggtagcg cgagaaggcc gagtggccgc agtcgtggcc gaccgtgaag aagccccaga   6420
agatgacgcc ctgcacgtag atgtaggtgg cgcaaacgag cgcgtggagc agaacgttat   6480
cggcaatgaa cggcgtcgag cgcgccgcgt agagcagcgc cgccgaggcc gacgcgttga   6540
agatcgcgcg ggccgtgtag tagagcgaga ggccgaggtt cgactcaaag cacgcgttcg   6600
ggatcgagtg cttgagctcc gtgagcgtcg ggaactcgac cttcgtctta tcctcagtca   6660
tgcggccgct gaagtattgc ttcttagtta acctttcctt tctctctcag ctatgtgaat   6720
tcattttgct ttcgtcacaa tttatatagt gaaattggat cttggagtt  aacgccttca   6780
caggattatc gtgttagaac aatgcttttt catgttctaa ttagtagtac attacaaatg   6840
tgcactctat tcaataagca tcttttggca cgttaataaa tcatgtgaaa aaaaaatact   6900
actatttcaa agaaagtgtt gtaaaaagaa acgaaagag agctggcttc agttgttgag   6960
acttgtttgc tagtaaaaat ggtgtgaaga gtgattcatg gtgaggtggt ttttcgtccc   7020
tttctgtttg catgaaaaac aaatggcaag agatgacgta ggattccttc ccttaacgat   7080
tatctgtttt taatttcaaa tatacatata ggaatttatg aattactaag gttgtaaaat   7140
```

| | |
|---|---:|
| atgctggtca tttatttatg gctaaaatat tttttttttct cgtaaatata aaaatattta | 7200 |
| aaatttattt ttatcatatt ttttatcctt ataaaattat gtgtacaacc tatataaaaa | 7260 |
| aatatcatat ttaatattga ttatatgttt aatcaatata aaaaatcatt atcatatatt | 7320 |
| tagatttatt cgaatataca tctaaacaaa aaataacata ttttaattt atgaagaaaa | 7380 |
| aaaaatattt tatcctttat ttatttaaga ttaattaata gttatgtatt gtggaaagac | 7440 |
| ttttacacat gcaatagata tactgaatca attagatgcc aatgctgagt tggaaatcac | 7500 |
| ttgaggaggg gaggagactt gccaatgctt ttcagtttca tttaaatgat ttagtggagg | 7560 |
| agatagagta gtgataaagg catgccccaa ttttggagtg tatatatgag tggaaataag | 7620 |
| agagggatag agagaaaaaa taaagagagt aaaaataatt aatgtgaaat gatatgataa | 7680 |
| aaaaataaag aaagagataa agagaaaaat gaaatgagag atagatgaaa tagagagtag | 7740 |
| atacatgttt gtttaggttt ttttttaggaa ataacacatt ttttctcat cacttattac | 7800 |
| tcactgtcaa tttcctctct ttcaatcata atgatatgat ttgtttaaca aaaatgtgaa | 7860 |
| aaaacatata aagtaaaata ttttttataaa ttgataaata aaaatttaca aaatttattt | 7920 |
| cttattaaat tgaatagaaa atgaaagaaa agaaagaaa aagtatatat aaaatgatat | 7980 |
| agctttaaaa agaataaatt tttcatatca gtcttttttt aataatttag aaatatttaa | 8040 |
| gtatatagca aaaatataat gtactttaca tatgcataaa taataatttg aaaatagaac | 8100 |
| taatagaata gagaaaaaag taatatataa attaactata tgaaaatta gaagggacaa | 8160 |
| tattttttaat taagaatata aacaatattt cttttcatgt aatgagggac ggatgtacgg | 8220 |
| ggccagtgtt ggagtcaaag ccaaaatagt cacggggaaa ttaatgcact gcatgactat | 8280 |
| tcgaaaaaat tcactagcct tactagatg ttagattaat agctaggggg tgcagataat | 8340 |
| tttgaaaggc atgaaaaaca ttaatttgta cattgcaagc ttttgatgac aagctttgca | 8400 |
| attgttcaca ctaccttatg ccatttataaa atagagtgat tggcatatga aggaaatcat | 8460 |
| gagagtcgaa gcgaaaaaca aagcttgaga gtgtaggaaa aatacagttt ttttggtaaa | 8520 |
| aatacagtat ttgaatagga gcgaaaaata tcctttcaaa atgatccttt tcttttttt | 8580 |
| ttttttcttt gttgttcttg gtcagttatt caaaggaaaa gggattgaaa taaaaacttg | 8640 |
| catgtgggat cgtacgtcga gtcgacctgc a | 8671 |

<210> SEQ ID NO 83
<211> LENGTH: 9892
<212> TYPE: DNA
<213> ORGANISM: Artificial Sequence
<220> FEATURE:
<223> OTHER INFORMATION: Plasmid pKR886

<400> SEQUENCE: 83

| | |
|---|---:|
| ggtcgactcg acgtacgtct agaggatccg tcgacggcgc gcccgatcat ccggatatag | 60 |
| ttcctccttt cagcaaaaaa cccctcaaga cccgtttaga ggccccaagg ggttatgcta | 120 |
| gttattgctc agcggtggca gcagccaact cagcttcctt tcgggctttg ttagcagccg | 180 |
| gatcgatcca agctgtacct cactattcct ttgccctcgg acgagtgctg gggcgtcggt | 240 |
| ttccactatc ggcgagtact tctacacagc catcggtcca gacggccgcg cttctgcggg | 300 |
| cgatttgtgt acgcccgaca gtcccggctc cggatcggac gattgcgtcg catcgaccct | 360 |
| gcgcccaagc tgcatcatcg aaattgccgt caaccaagct ctgatagagt tggtcaagac | 420 |
| caatgcggag catatacgcc cggagccgcg gcgatcctgc aagctccgga tgcctccgct | 480 |
| cgaagtagcg cgtctgctgc tccatacaag ccaaccacgg cctccagaag aagatgttgg | 540 |

```
cgacctcgta ttgggaatcc ccgaacatcg cctcgctcca gtcaatgacc gctgttatgc    600
ggccattgtc cgtcaggaca ttgttggagc cgaaatccgc gtgcacgagg tgccggactt    660
cggggcagtc ctcggcccaa agcatcagct catcgagagc ctgcgcgacg gacgcactga    720
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
aataggtcag gctctcgctg aattccccaa tgtcaagcac ttccggaatc gggagcgcgg   1020
ccgatgcaaa gtgccgataa acataacgat ctttgtagaa accatcggcg cagctattta   1080
cccgcaggac atatccacgc cctcctacat cgaagctgaa agcacgagat tcttcgccct   1140
ccgagagctg catcaggtcg gagacgctgt cgaacttttc gatcagaaac ttctcgacag   1200
acgtcgcggt gagttcaggc ttttccatgg gtatatctcc ttcttaaagt taaacaaaat   1260
tatttctaga gggaaaccgt tgtggtctcc ctatagtgag tcgtattaat ttcgcgggat   1320
cgagatctga tcaacctgca ttaatgaatc ggccaacgcg cggggagagg cggtttgcgt   1380
attgggcgct cttccgcttc ctcgctcact gactcgctgc gctcggtcgt tcggctgcgg   1440
cgagcggtat cagctcactc aaaggcggta atacggttat ccacagaatc aggggataac   1500
gcaggaaaga acatgtgagc aaaaggccag caaaaggcca ggaaccgtaa aaaggccgcg   1560
ttgctggcgt ttttccatag gctccgcccc cctgacgagc atcacaaaaa tcgacgctca   1620
agtcagaggt ggcgaaaccc gacaggacta taaagatacc aggcgtttcc ccctggaagc   1680
tccctcgtgc gctctcctgt tccgaccctg ccgcttaccg gatacctgtc cgcctttctc   1740
ccttcgggaa gcgtggcgct ttctcaatgc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gtttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggattcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaagaa   2880
```

```
aaacattgat atgtaacctg attccattag cttttgactt cttcaacaga ttctctactt    2940
agatttctaa cagaaatatt attactagca catcattttc agtctcacta cagcaaaaaa    3000
tccaacggca caatacagac aacaggagat atcagactac agagatagat agatgctact    3060
gcatgtagta agttaaataa aaggaaaata aaatgtcttg ctaccaaaac tactacagac    3120
tatgatgctc accacaggcc aaatcctgca actaggacag cattatctta tatatattgt    3180
acaaaacaag catcaaggaa catttggtct aggcaatcag tacctcgttc taccatcacc    3240
ctcagttatc acatccttga aggatccatt actgggaatc atcggcaaca catgctcctg    3300
atggggcaca atgacatcaa gaaggtaggg gccaggggtg tccaacattc tctgaattgc    3360
cgctctaagc tcttccttct tcgtcactcg cgctgccggt atcccacaag catcagcaaa    3420
cttgagcatg tttgggaata tctcgctctc gctagacgga tctccaagat aggtgtgagc    3480
tctattggac ttgtagaacc tatcctccaa ctgaaccacc atacccaaat gctgattgtt    3540
caacaacaat atcttaactg ggagattctc cactcttata gtggccaact cctgaacatt    3600
catgatgaaa ctaccatccc catcaatgtc aaccacaaca ccccagggt tagcaacagc    3660
agcaccaata gccgcaggca atccaaaacc catggctcca agaccccctg aggtcaacca    3720
ctgcctcggt ctcttgtact tgtaaaactg cgcagcccac atttgatgct gcccaacccc    3780
agtactaaca atagcatctc cattagtcaa ctcatcaaga acctcgatag catgctgcgg    3840
agaaatcgcg tcctggaatg tcttgtaacc caatggaaac ttgtgtttct gcacattaat    3900
ctcttctctc caacctccaa gatcaaactt accctccact cctttctcct ccaaaatcat    3960
attaattccc ttcaaggcca acttcaaatc cgcgcaaacc gacacgtgcg cctgcttgtt    4020
cttcccaatc tcggcagaat caatatcaat gtgaacaatc ttagccctac tagcaaaagc    4080
ctcaagcttc ccagtaacac ggtcatcaaa ccttacccca aaggcaagca acaaatcact    4140
attgtcaaca gcatagttag cataaacagt accatgcata cccagcatct gaagggaata    4200
ttcatcacca ataggaaaag ttccaagacc cattaaagtg ctagcaacgg gaataccagt    4260
gagttcaaca aagcgcctca attcagcact ggaattcaaa ctgccaccgc cgacgtagag    4320
aacgggcttt tgggcctcca tgatgagtct gacaatgtgt tccaattggg cctcggcggg    4380
gggcctgggc agcctggcga ggtaaccggg gaggttaacg ggctcgtccc aattaggcac    4440
ggcgagttgc tgctgaacgt cttggggaat gtcgatgagg accggaccgg ggcggccgga    4500
ggtggcgacg aagaaagcct cggcgacgac gcggggatg tcgtcgacgt cgaggatgag    4560
gtagttgtgc ttcgtgatgg atctgctcac ctccacgatc ggggtttctt ggaaggcgtc    4620
ggtgccgatc atccggcggg cgacctggcc ggtgatggcg acgactggga cgctgtccat    4680
taaagcgtcg gcgaggccgc tcacgaggtt ggtggcgccg gggccggagg tggcaatgca    4740
gacgccgggg aggccggagg aacgcgcgta gccttcggcg gcgaagacgc cgccctgctc    4800
gtggcgcggg agcacgttgc ggatggcggc ggagcgcgtg agcgcctggt ggatctccat    4860
cgacgcaccg ccggggtacg cgaacaccgt cgtcacgccc tgcctctcca gcgcctccac    4920
aaggatgtcc gcgcccttgc gaggttcgcc ggaggcgaac cgtgacacga agggctccgt    4980
ggtcggcgct tccttggtga agggcgccgc cgtggggggt ttggagatgg aacatttgat    5040
tttgagagcg tggttgggtt tggtgagggt ttgatgagag agaggagggg tggatctagt    5100
aatgcgtttg gggaaggtgg ggtgtgaaga ggaagaagag aatcgggtgg ttctggaagc    5160
ggtgccgcc attgtgttgt gtggcatggt tatacttcaa aaactgcaca acaagcctag    5220
agttagtacc taaacagtaa atttacaaca gagagcaaag acacatgcaa aaatttcagc    5280
```

```
cataaaaaaa gttataatag aatttaaagc aaaagtttca ttttttaaac atatatacaa    5340
acaaactgga tttgaaggaa gggattaatt ccccctgctca aagtttgaat tcctattgtg   5400
acctatactc gaataaaatt gaagcctaag gaatgtatga gaaacaagaa aacaaaacaa    5460
aactacagac aaacaagtac aattacaaaa ttcgctaaaa ttctgtaatc accaaacccc    5520
atctcagtca gcacaaggcc caaggtttat tttgaaataa aaaaaaagtg attttatttc    5580
tcataagcta aagaaagaa aggcaattat gaaatgattt cgactagatc tgaaagtcca    5640
acgcgtattc cgcagatatt aaagaaagag tagagtttca catggatcct agatggaccc    5700
agttgaggaa aaagcaaggc aaagcaaacc agaagtgcaa gatccgaaat tgaaccacgg    5760
aatctaggat ttggtagagg gagaagaaaa gtaccttgag aggtagaaga aagagaaga    5820 gcagagagat atatgaacga gtgtgtcttg gtctcaactc tgaagcgata cgagtttaga    5880
ggggagcatt gagttccaat ttatagggaa accgggtggc aggggtgagt taatgacgga    5940
aaagccccta agtaacgaga ttggattgtg ggttagattc aaccgtttgc atccgcggct    6000
tagattgggg aagtcagagt gaatctcaac cgttgactga gttgaaaatt gaatgtagca    6060
accaattgag ccaaccccag cctttgccct ttgattttga tttgtttgtt gcatactttt    6120
tatttgtctt ctggttctga ctctctttct ctcgtttcaa tgccaggttg cctactccca    6180
caccactcac aagaagattc tactgttagt attaaatatt ttttaatgta ttaaatgatg    6240
aatgcttttg taaacagaac aagactatgt ctaataagtg tcttgcaaca tttttaaga    6300 aattaaaaaa aatatattta ttatcaaaat caaatgtatg aaaaatcatg aataatataa    6360
ttttatacat ttttttaaaa aatcttttaa tttcttaatt aatatcttaa aaataatgat    6420
taatatttaa cccaaaataa ttagtatgat tggtaaggaa gatatccatg ttatgtttgg    6480
atgtgagttt gatctagagc aaagcttact agagtcgacc tgcaggtcga ctcgacgtac    6540
gatcccacat gcaagttttt atttcaatcc cttttccttt gaataactga ccaagaacaa    6600
caagaaaaaa aaaaaaaaag aaaaggatca ttttgaaagg atatttttcg ctcctattca    6660
aatactgtat ttttaccaaa aaaactgtat ttttcctaca ctctcaagct tgttttttcg    6720
cttcgactct catgatttcc ttcatatgcc aatcactcta tttataaatg gcataaggta    6780
gtgtgaacaa ttgcaaagct tgtcatcaaa agcttgcaat gtacaaatta atgttttca    6840 tgcctttcaa aattatctgc accccctagc tattaatcta acatctaagt aaggctagtg    6900
aattttttcg aatagtcatg cagtgcatta atttccccgt gactattttg gctttgactc    6960
caacactggc cccgtacatc cgtccctcat tacatgaaaa gaaatattgt ttatattctt    7020
aattaaaaat attgtcccctt ctaaattttc atatagttaa ttattatatt acttttttct    7080
ctattctatt agttctattt tcaaattatt atttatgcat atgtaaagta cattatatt    7140 ttgctatata cttaaatatt tctaaattat taaaaaaaga ctgatatgaa aaatttattc    7200
tttttaaagc tatatcattt tatatatact ttttctttc ttttctttca ttttctattc    7260
aatttaataa gaaataaatt ttgtaaattt ttattatcca atttataaaa atattttact    7320
ttatatgttt tttcacattt ttgttaaaca aatcatatca ttatgattga agagaggaa    7380 attgacagtg agtaataagt gatgagaaaa aaatgtgtta tttcctaaaa aaaacctaaa    7440
caaacatgta tctactctct atttcatcta tctctcattt cattttttctc tttatctctt    7500 tcttttatttt tttatcatat catttcacat taattatttt tactctcttt attttttctc    7560
tctatccctc tcttatttcc actcatatat acactccaaa attggggcat gcctttatca    7620
```

```
ctactctatc tcctccacta aatcatttaa atgaaactga aaagcattgg caagtctcct    7680
cccctcctca agtgatttcc aactcagcat tggcatctaa ttgattcagt atatctattg    7740
catgtgtaaa agtctttcca caatacataa ctattaatta atcttaaata aataaaggat    7800
aaaatatttt tttttcttca taaaattaaa atatgttatt ttttgtttag atgtatattc    7860
gaataaatct aaatatatga taatgatttt ttatattgat taaacatata atcaatatta    7920
aatatgatat tttttatat aggttgtaca cataattttta taaggataaa aaatatgata    7980
aaaataaatt ttaaatattt ttatatttac gagaaaaaaa aatattttag ccataaataa    8040
atgaccagca tattttacaa ccttagtaat tcataaattc ctatatgtat atttgaaatt    8100
aaaaacagat aatcgttaag ggaaggaatc ctacgtcatc tcttgccatt tgttttttcat    8160 gcaaacagaa agggacgaaa aaccacctca ccatgaatca ctcttcacac cattttact    8220 agcaaacaag tctcaacaac tgaagccagc tctctttccg tttctttta caacactttc    8280 tttgaaatag tagtatttt ttttcacatg atttattaac gtgccaaaag atgcttattg    8340
aatagagtgc acatttgtaa tgtactacta attagaacat gaaaaagcat tgttctaaca    8400
cgataatcct gtgaaggcgt taactccaaa gatccaattt cactatataa attgtgacga    8460
aagcaaaatg aattcacata gctgagagag aaaggaaagg ttaactaaga agcaatactt    8520
cagcggccgc atgactgagg ataagacgaa ggtcgagttc ccgacgctca cggagctcaa    8580
gcactcgatc ccgaacgcgt gctttgagtc gaacctcggc ctctcgctct actacacggc    8640
ccgcgcgatc ttcaacgcgt cggcctcggc ggcgctgctc tacgcggcgc gctcgacgcc    8700
gttcattgcc gataacgttc tgctccacgc gctcgtttgc gccacctaca tctacgtgca    8760
gggcgtcatc ttctggggct tcttcacggt cggccacgac tgcggccact cggccttctc    8820
gcgctaccac agcgtcaact ttatcatcgg ctgcatcatg cactctgcga ttttgacgcc    8880
gttcgagagc tggcgcgtga cgcaccgcca ccaccacaag aacacgggca acattgataa    8940
ggacgagatc ttttacccgc accggtcggt caaggacctc caggacgtgc gccaatgggt    9000
ctacacgctc ggcggtgcgt ggtttgtcta cttgaaggtc gggtatgccc cgcgcacgat    9060
gagccacttt gacccgtggg acccgctcct ccttcgccgc gcgtcggccg tcatcgtgtc    9120
gctcggcgtc tgggccgcct tcttcgccgc gtacgcgtac ctcacatact cgctcggctt    9180
tgccgtcatg ggcctctact actatgcgcc gctctttgtc tttgcttcgt tcctcgtcat    9240
tacgaccttc ttgcaccaca acgacgaagc gacgccgtgg tacggcgact cggagtggac    9300
gtacgtcaag ggcaacctct cgagcgtcga ccgctcgtac ggcgcgttcg tggacaacct    9360
gagccaccac attggcacgc accaggtcca ccacttgttc ccgatcattc cgcactacaa    9420
gctcaacgaa gccaccaagc actttgcggc gcgtacccg cacctcgtgc gcaggaacga    9480
cgagcccatc atcacggcct tcttcaagac cgcgcacctc tttgtcaact acggcgctgt    9540
gcccgagacg cgcagatct tcacgctcaa agagtcggcc gcggccgcca aggccaagtc    9600
ggactaagcg gccgcgaatt caatcactag tgaattcgcg gccgcatgag ccgtaaaggt    9660
tcaatacaac gagtgcttgt tttcttaggg acaagcattg tacttatgta tgattctgtg    9720
taaccatgag tcttccacgt tgtactaatg tgaagggcaa aaataaaaca cagaacaagt    9780 tcgttttct caaataatgt gaaggtagaa aatggaacca tgcctcctct cttgcatgtg    9840
atttaaaata ttagcagatg gtaccgtacg tgggcggatc ccccgggctg ca            9892
```

<210> SEQ ID NO 84
<211> LENGTH: 9892

<212> TYPE: DNA
<213> ORGANISM: Artificial Sequence
<220> FEATURE:
<223> OTHER INFORMATION: Plasmid pKR886r

<400> SEQUENCE: 84

```
ggtcgactcg acgtacgtct agaggatccg tcgacggcgc gcccgatcat ccggatatag      60
ttcctccttt cagcaaaaaa cccctcaaga cccgtttaga ggccccaagg ggttatgcta     120
gttattgctc agcggtggca gcagccaact cagcttcctt tcgggctttg ttagcagccg     180
gatcgatcca agctgtacct cactattcct ttgccctcgg acgagtgctg gggcgtcggt     240
ttccactatc ggcgagtact tctacacagc catcggtcca gacggccgcg cttctgcggg     300
cgatttgtgt acgcccgaca gtcccggctc cggatcggac gattgcgtcg catcgaccct     360
gcgcccaagc tgcatcatcg aaattgccgt caaccaagct ctgatagagt tggtcaagac     420
caatgcggag catatacgcc cggagccgcg gcgatcctgc aagctccgga tgcctccgct     480
cgaagtagcg cgtctgctgc tccatacaag ccaaccacgg cctccagaag aagatgttgg     540
cgacctcgta ttgggaatcc ccgaacatcg cctcgctcca gtcaatgacc gctgttatgc     600
ggccattgtc cgtcaggaca ttgttggagc cgaaatccgc gtgcacgagg tgccggactt     660
cggggcagtc ctcggcccaa agcatcagct catcgagagc ctgcgcgacg gacgcactga     720
cggtgtcgtc catcacagtt tgccagtgat acacatgggg atcagcaatc gcgcatatga     780
aatcacgcca tgtagtgtat tgaccgattc cttgcggtcc gaatgggccg aacccgctcg     840
tctggctaag atcggccgca gcgatcgcat ccatagcctc cgcgaccggc tgcagaacag     900
cgggcagttc ggtttcaggc aggtcttgca acgtgacacc ctgtgcacgg cgggagatgc     960
aataggtcag gctctcgctg aattccccaa tgtcaagcac ttccggaatc gggagcgcgg    1020
ccgatgcaaa gtgccgataa acataacgat ctttgtagaa accatcggcg cagctattta    1080
cccgcaggac atatccacgc cctcctacat cgaagctgaa agcacgagat tcttcgccct    1140
ccgagagctg catcaggtcg gagacgctgt cgaacttttc gatcagaaac ttctcgacag    1200
acgtcgcggt gagttcaggc ttttccatgg gtatatctcc ttcttaaagt taaacaaaat    1260
tatttctaga gggaaaccgt tgtggtctcc ctatagtgag tcgtattaat ttcgcgggat    1320
cgagatctga tcaacctgca ttaatgaatc ggccaacgcg cggggagagg cggtttgcgt    1380
attgggcgct cttccgcttc ctcgctcact gactcgctgc gctcggtcgt tcggctgcgg    1440
cgagcggtat cagctcactc aaaggcggta atacggttat ccacagaatc agggggataac    1500
gcaggaaaga acatgtgagc aaaaggccag caaaaggcca ggaaccgtaa aaaggccgcg    1560
ttgctggcgt ttttccatag gctccgcccc cctgacgagc atcacaaaaa tcgacgctca    1620
agtcagaggt ggcgaaaccc gacaggacta taaagatacc aggcgtttcc ccctggaagc    1680
tccctcgtgc gctctcctgt tccgaccctg ccgcttaccg gatacctgtc cgcctttctc    1740
ccttcgggaa gcgtggcgct ttctcaatgc tcacgctgta ggtatctcag ttcggtgtag    1800
gtcgttcgct ccaagctggg ctgtgtgcac gaacccccCg ttcagcccga ccgctgcgcc    1860
ttatccggta actatcgtct tgagtccaac ccggtaagac acgacttatc gccactggca    1920
gcagccactg gtaacaggat tagcagagcg aggtatgtag gcggtgctac agagttcttg    1980
aagtggtggc ctaactacgg ctacactaga aggacagtat ttggtatctg cgctctgctg    2040
aagccagtta ccttcggaaa aagagttggt agctcttgat ccggcaaaca aaccaccgct    2100
ggtagcggtg gtttttttgt ttgcaagcag cagattacgc gcagaaaaaa aggatctcaa    2160
```

```
gaagatcctt tgatcttttc tacggggtct gacgctcagt ggaacgaaaa ctcacgttaa    2220
gggattttgg tcatgacatt aacctataaa aataggcgta tcacgaggcc ctttcgtctc    2280
gcgcgtttcg gtgatgacgg tgaaaacctc tgacacatgc agctcccgga gacggtcaca    2340
gcttgtctgt aagcggatgc cgggagcaga caagcccgtc agggcgcgtc agcgggtgtt    2400
ggcgggtgtc ggggctggct taactatgcg gcatcagagc agattgtact gagagtgcac    2460
catatggaca tattgtcgtt agaacgcggc tacaattaat acataacctt atgtatcata    2520
cacatacgat ttaggtgaca ctatagaacg gcgcgccaag ctgggtctag aactagaaac    2580
gtgatgccac ttgttattga agtcgattac agcatctatt ctgttttact atttataact    2640
ttgccatttc tgacttttga aaactatctc tggatttcgg tatcgctttg tgaagatcga    2700
gcaaaagaga cgttttgtgg acgcaatggt ccaaatccgt tctacatgaa caaattggtc    2760
acaatttcca ctaaaagtaa ataaatggca agttaaaaaa ggaatatgca ttttactgat    2820
tgcctaggtg agctccaaga gaagttgaat ctacacgtct accaaccgct aaaaaaagaa    2880
aaacattgat atgtaacctg attccattag cttttgactt cttcaacaga ttctctactt    2940
agatttctaa cagaaatatt attactagca catcattttc agtctcacta cagcaaaaaa    3000
tccaacggca caatacagac aacaggagat atcagactac agagatagat agatgctact    3060
gcatgtagta agttaaataa aaggaaaata aaatgtcttg ctaccaaaac tactacagac    3120
tatgatgctc accacaggcc aaatcctgca actaggacag cattatctta tatatattgt    3180
acaaaacaag catcaaggaa catttggtct aggcaatcag tacctcgttc taccatcacc    3240
ctcagttatc acatccttga aggatccatt actgggaatc atcggcaaca catgctcctg    3300
atggggcaca atgacatcaa gaaggtaggg gccaggggtg tccaacattc tctgaattgc    3360
cgctctaagc tcttccttct tcgtcactcg cgctgccggt atcccacaag catcagcaaa    3420
cttgagcatg tttgggaata tctcgctctc gctagacgga tctccaagat aggtgtgagc    3480
tctattggac ttgtagaacc tatcctccaa ctgaaccacc atacccaaat gctgattgtt    3540
caacaacaat atcttaactg ggagattctc cactcttata gtggccaact cctgaacatt    3600
catgatgaaa ctaccatccc catcaatgtc aaccacaaca gccccagggt tagcaacagc    3660
agcaccaata gccgcaggca atccaaaacc catggctcca agaccccctg aggtcaacca    3720
ctgcctcggt ctcttgtact tgtaaaactg cgcagcccac atttgatgct gcccaacccc    3780
agtactaaca atagcatctc cattagtcaa ctcatcaaga acctcgatag catgctgcgg    3840
agaaatcgcg tcctggaatg tcttgtaacc caatggaaac ttgtgtttct gcacattaat    3900
ctcttctctc caacctccaa gatcaaactt accctccact cctttctcct ccaaaatcat    3960
attaattccc ttcaaggcca acttcaaatc cgcgcaaacc gacacgtgcg cctgcttgtt    4020
cttcccaatc tcggcagaat caatatcaat gtgaacaatc ttagccctac tagcaaaagc    4080
ctcaagcttc ccagtaacac ggtcatcaaa ccttacccca aaggcaagca acaaatcact    4140
attgtcaaca gcatagttag cataaacagt accatgcata cccagcatct gaagggaata    4200
ttcatcacca ataggaaaag ttccaagacc cattaaagtg ctagcaacgg gaataccagt    4260
gagttcaaca aagcgcctca attcagcact ggaattcaaa ctgccaccgc cgacgtagag    4320
aacgggcttt tgggcctcca tgatgagtct gacaatgtgt tccaattggg cctcggcggg    4380
gggcctgggc agcctggcga ggtaaccggg gaggttaacg ggctcgtccc aattaggcac    4440
ggcgagttgc tgctgaacgt ctttgggaat gtcgatgagg accggaccgg ggcggccgga    4500
ggtggcgacg aagaaagcct cggcgacgac gcggggggatg tcgtcgacgt cgaggatgag    4560
```

```
gtagttgtgc ttcgtgatgg atctgctcac ctccacgatc ggggtttctt ggaaggcgtc    4620
ggtgccgatc atccggcggg cgacctggcc ggtgatggcg acgactggga cgctgtccat    4680
taaagcgtcg gcgaggccgc tcacgaggtt ggtggcgccg gggccggagg tggcaatgca    4740
gacgccgggg aggccggagg aacgcgcgta gccttcggcg gcgaagacgc cgccctgctc    4800
gtggcgcggg agcacgttgc ggatggcggc ggagcgcgtg agcgcctggt ggatctccat    4860
cgacgcaccg ccggggtacg cgaacaccgt cgtcacgccc tgcctctcca gcgcctccac    4920
aaggatgtcc gcgcccttgc gaggttcgcc ggaggcgaac cgtgacacga agggctccgt    4980
ggtcggcgct tccttggtga agggcgccgc cgtgggcggt ttggagatgg aacatttgat    5040
tttgagagcg tggttgggtt tggtgagggt tgatgagag agagggaggg tggatctagt    5100
aatgcgtttg gggaaggtgg ggtgtgaaga ggaagaagag aatcgggtgg ttctggaagc    5160
ggtggccgcc attgtgttgt gtggcatggt tatacttcaa aaactgcaca acaagcctag    5220
agttagtacc taaacagtaa atttacaaca gagagcaaag acacatgcaa aaatttcagc    5280
cataaaaaaa gttataatag aatttaaagc aaaagtttca tttttttaaac atatatacaa    5340 acaaactgga tttgaaggaa gggattaatt cccctgctca aagtttgaat tcctattgtg    5400
acctatactc gaataaaatt gaagcctaag gaatgtatga gaaacaagaa aacaaaacaa    5460
aactacagac aaacaagtac aattacaaaa ttcgctaaaa ttctgtaatc accaaacccc    5520
atctcagtca gcacaaggcc caaggtttat tttgaaataa aaaaaagtg attttatttc    5580 tcataagcta aagaaagaa aggcaattat gaaatgattt cgactagatc tgaaagtcca    5640
acgcgtattc cgcagatatt aaagaaagag tagagtttca catggatcct agatggaccc    5700
agttgaggaa aaagcaaggc aaagcaaacc agaagtgcaa gatccgaaat tgaaccacgg    5760
aatctaggat ttggtagagg gagaagaaaa gtaccttgag aggtagaaga gaagagaaga    5820
gcagagagat atatgaacga gtgtgtcttg gtctcaactc tgaagcgata cgagtttaga    5880
ggggagcatt gagttccaat ttataggaa accgggtggc aggggtgagt taatgacgga    5940
aaagccccta agtaacgaga ttggattgtg ggttagattc aaccgtttgc atccgcggct    6000
tagattgggg aagtcagagt gaatctcaac cgttgactga gttgaaaatt gaatgtagca    6060
accaattgag ccaaccccag cctttgccct ttgattttga tttgtttgtt gcatactttt    6120
tatttgtctt ctggttctga ctctctttct ctcgtttcaa tgccaggttg cctactccca    6180
caccactcac aagaagattc tactgttagt attaaatatt ttttaatgta ttaaatgatg    6240
aatgcttttg taaacagaac aagactatgt ctaataagtg tcttgcaaca tttttttaaga   6300 aattaaaaaa aatatattta ttatcaaaat caaatgtatg aaaaatcatg aataatataa    6360
ttttatacat ttttttaaaa aatctttaa tttcttaatt aatatcttaa aaataatgat    6420
taatatttaa cccaaaataa ttagtatgat tggtaaggaa gatatccatg ttatgtttgg    6480
atgtgagttt gatctagagc aaagcttact agagtcgacc tgcagcccgg gggatccgcc    6540
cacgtacggt accatctgct aatattttaa atcacatgca agagaggagg catggttcca    6600
ttttctacct tcacattatt tgagaaaaac gaacttgttc tgtgttttat ttttgccctt    6660
cacattagta caacgtggaa gactcatggt tacacagaat catacataag tacaatgctt    6720
gtccctaaga aaacaagcac tcgttgtatt gaacctttac ggctcatgcg ccgcgaatt    6780 cactagtgat tgaattcgcg ccgcttagt ccgactggc cttggcgcc gcggccgact    6840 cttttgagcgt gaagatctgc gccgtctcgg gcacagcgcc gtagttgaca aagaggtgcg    6900
```

```
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
ggtcgacgct cgagaggttg cccttgacgt acgtccactc cgagtcgccg taccacggcg   7140
tcgcttcgtc gttgtggtgc aagaaggtcg taatgacgag gaacgaagca aagcaaaga    7200
gcggcgcata gtagtagagg cccatgacgg caaagccgag cgagtatgtg aggtacgcgt   7260
acgcggcgaa gaaggcggcc cagacgccga gcgacgcgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagcccag aagatgacgc cctgcacgta gatgtaggtg cgcaaacga    7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
atcatgtgaa aaaaaatac tactatttca aagaaagtgt tgtaaaaaga aacggaaaga    8160
gagctggctt cagttgttga gacttgtttg ctagtaaaaa tggtgtgaag agtgattcat   8220
ggtgaggtgg tttttcgtcc ctttctgttt gcatgaaaaa caaatggcaa gagatgacgt   8280
aggattcctt cccttaacga ttatctgttt ttaatttcaa atatacatat aggaatttat   8340
gaattactaa ggttgtaaaa tatgctggtc atttatttat ggctaaaata ttttttttc    8400
tcgtaaatat aaaatattt aaaatttatt tttatcatat tttttatcct tataaaatta    8460
tgtgtacaac ctatataaaa aaatatcata tttaatattg attatatgtt taatcaatat   8520
aaaaaatcat tatcatatat ttagatttat tcgaatatac atctaaacaa aaataacat    8580
attttaattt tatgaagaaa aaaaaatatt ttatcctta ttttatttaag attaattaat    8640
agttatgtat tgtggaaaga cttttacaca tgcaatagat atactgaatc aattagatgc   8700
caatgctgag ttgaaaatca cttgaggagg ggaggagact tgccaatgct tttcagtttc   8760
atttaaatga tttagtggag gagatagagt agtgataaag gcatgcccca attttggagt   8820
gtatatatga gtgaaataa gagagggata gagagaaaaa ataagagag taaaaataat    8880
taatgtgaaa tgatatgata aaaaaataaa gaaagagata agagaaaaa tgaaatgaga    8940
gatagatgaa atagagagta gatacatgtt tgtttaggtt ttttttagga aataacacat   9000
tttttctca tcacttatta ctcactgtca atttcctctc tttcaatcat aatgatatga    9060
tttgtttaac aaaaatgtga aaaaacatat aaagtaaaat atttttataa attgataaat   9120
aaaaatttac aaaatttatt tcttattaaa ttgaatagaa aatgaaagaa aagaaaagaa   9180
aaagtatata taaaatgata tagctttaaa aagaataaat ttttcatatc agtcttttt    9240
taataatttta gaaatatta agtatatagc aaaaatataa tgtactttac atatgcataa    9300
```

```
ataataattt gaaaatagaa ctaatagaat agagaaaaaa gtaatataat aattaactat    9360
atgaaaattt agaagggaca atatttttaa ttaagaatat aaacaatatt tcttttcatg    9420
taatgaggga cggatgtacg gggccagtgt tggagtcaaa gccaaaatag tcacggggaa    9480
attaatgcac tgcatgacta ttcgaaaaaa ttcactagcc ttacttagat gttagattaa    9540
tagctagggg gtgcagataa ttttgaaagg catgaaaaac attaatttgt acattgcaag    9600
cttttgatga caagctttgc aattgttcac actaccttat gccatttata aatagagtga    9660
ttggcatatg aaggaaatca tgagagtcga agcgaaaaac aaagcttgag agtgtaggaa    9720
aaatacagtt ttttggtaa  aaatacagta tttgaatagg agcgaaaaat atcctttcaa    9780
aatgatcctt ttcttttttt tttttttct  tgttgttctt ggtcagttat tcaaaggaaa    9840
agggattgaa ataaaaactt gcatgtggga tcgtacgtcg agtcgacctg ca            9892
```

<210> SEQ ID NO 85
<211> LENGTH: 6021
<212> TYPE: DNA
<213> ORGANISM: Artificial Sequence
<220> FEATURE:
<223> OTHER INFORMATION: Plasmid pKR271

<400> SEQUENCE: 85

```
ggccgcgaat tcaatcacta gtgaattcgc ggccgcatga gccgtaaagg ttcaatacaa      60
cgagtgcttg ttttcttagg gacaagcatt gtactatgt  atgattctgt gtaaccatga     120
gtcttccacg ttgtactaat gtgaagggca aaaataaaac acagaacaag ttcgtttttc     180
tcaaataatg tgaaggtaga aaatggaacc atgcctcctc tcttgcatgt gatttaaaat     240
attagcagat ggtaccgtac gtgggcggat ccccgggct  gcaggaattc actggccgtc     300
gttttacaac gtcgtgactg gaaaaccct  ggcgttaccc aacttaatcg ccttgcagca     360 catcccctt  tcgccagctg gcgtaatagc gaagaggccc gcaccgatcg cccttcccaa     420
cagttgcgca gcctgaatgg cgaatggcgc ctgatgcggt attttctcct tacgcatctg     480
tgcggtattt cacaccgcat atggtgcact ctcagtacaa tctgctctga tgccgcatag     540
ttaagccagc cccgacaccc gccaacaccc gctgacgcgc cctgacgggc ttgtctgctc     600
ccggcatccg cttacagaca agctgtgacc gtctccggga gctgcatgtg tcagaggttt     660
tcaccgtcat caccgaaacg cgcgagacga agggcctcg  tgatacgcct atttttatag     720
gttaatgtca tgataataat ggtttcttag acgtcaggtg gcacttttcg ggaaatgtg     780 cgcggaaccc ctatttgttt attttttctaa atacattcaa atatgtatcc gctcatgaga    840
caataaccct gataaatgct tcaataatat tgaaaaagga agagtatgag tattcaacat     900
ttccgtgtcg cccttattcc cttttttgcg gcattttgcc ttcctgtttt tgctcaccca     960
gaaacgctgg tgaaagtaaa agatgctgaa gatcagttgg gtgcacgagt gggttacatc    1020
gaactggatc tcaacagcgg taagatcctt gagagttttc gccccgaaga acgttttcca    1080
atgatgagca cttttaaagt tctgctatgt ggcgcggtat tatcccgtat tgacgccggg    1140
caagagcaac tcggtcgccg catacactat tctcagaatg acttggttga gtactcacca    1200
gtcacagaaa agcatcttac ggatggcatg acagtaagag aattatgcag tgctgccata    1260
accatgagtg ataacactgc ggccaactta cttctgacaa cgatcggagg accgaaggag    1320
ctaaccgctt ttttgcacaa catgggggat catgtaactc gccttgatcg ttgggaaccg    1380
gagctgaatg aagccatacc aaacgacgag cgtgacacca cgatgcctgt agcaatggca    1440
```

```
acaacgttgc gcaaactatt aactggcgaa ctacttactc tagcttcccg gcaacaatta    1500
atagactgga tggaggcgga taaagttgca ggaccacttc tgcgctcggc ccttccggct    1560
ggctggttta ttgctgataa atctggagcc ggtgagcgtg ggtctcgcgg tatcattgca    1620
gcactggggc cagatggtaa gccctcccgt atcgtagtta tctacacgac ggggagtcag    1680
gcaactatgg atgaacgaaa tagacagatc gctgagatag gtgcctcact gattaagcat    1740
tggtaactgt cagaccaagt ttactcatat atactttaga ttgatttaaa acttcattttt   1800 taatttaaaa ggatctaggt gaagatcctt tttgataatc tcatgaccaa aatcccttaa    1860
cgtgagtttt cgttccactg agcgtcagac cccgtagaaa agatcaaagg atcttcttga    1920 gatcctttt ttctgcgcgt aatctgctgc ttgcaaacaa aaaaccacc gctaccagcg      1980 gtggtttgtt tgccggatca agagctacca actcttttc cgaaggtaac tggcttcagc     2040
agagcgcaga taccaaatac tgtccttcta gtgtagccgt agttaggcca ccacttcaag    2100
aactctgtag caccgcctac atacctcgct ctgctaatcc tgttaccagt ggctgctgcc    2160
agtggcgata agtcgtgtct taccgggttg gactcaagac gatagttacc ggataaggcg    2220
cagcggtcgg gctgaacggg gggttcgtgc acacagccca gcttggagcg aacgacctac    2280
accgaactga gatacctaca gcgtgagcta tgagaaagcg ccacgcttcc cgaagggaga    2340
aaggcggaca ggtatccggt aagcggcagg gtcggaacag gagagcgcac gagggagctt    2400 ccaggggaa acgcctggta tctttatagt cctgtcgggt ttcgccacct ctgacttgag     2460 cgtcgattt tgtgatgctc gtcagggggg cggagcctat ggaaaaacgc cagcaacgcg    2520
gcctttttac ggttcctggc cttttgctgg ccttttgctc acatgttctt tcctgcgtta    2580
tcccctgatt ctgtggataa ccgtattacc gcctttgagt gagctgatac cgctcgccgc    2640
agccgaacga ccgagcgcag cgagtcagtg agcgaggaag cggaagagcg cccaatacgc    2700
aaaccgcctc tccccgcgcg ttggccgatt cattaatgca gctggcacga caggtttccc    2760
gactggaaag cgggcagtga gcgcaacgca attaatgtga gttagctcac tcattaggca    2820
ccccaggctt tacactttat gcttccggct cgtatgttgt gtggaattgt gagcggataa    2880
caatttcaca caggaaacag ctatgaccat gattacgcca agcttgcatg cctgcaggtc    2940
gactcgacgt acgatcccac atgcaagttt ttatttcaat ccctttttcct ttgataact    3000 gaccaagaac aacaagaaaa aaaaaaaaaa agaaaaggat cattttgaaa ggatattttt    3060
cgctcctatt caaatactgt attttttacca aaaaaactgt attttttccta cactctcaag    3120 cttttgttttt cgcttcgact ctcatgattt ccttcatatg ccaatcactc tatttataaa    3180
tggcataagg tagtgtgaac aattgcaaag cttgtcatca aaagcttgca atgtacaaat    3240
taatgttttt catgcctttc aaaattatct gcacccccta gctattaatc taacatctaa    3300
gtaaggctag tgaatttttt cgaatagtca tgcagtgcat taatttcccc gtgactattt    3360
tggctttgac tccaacactg gccccgtaca tccgtccctc attacatgaa aagaaatatt    3420
gtttatattc ttaattaaaa atattgtccc ttctaaattt tcatatagtt aattattata    3480
ttactttttt ctctattcta ttagttctat tttcaaatta ttatttatgc atatgtaaag    3540
tacattatat ttttgctata tacttaaata tttctaaatt attaaaaaaa gactgatatg    3600 aaaaattat tcttttttaaa gctatatcat tttatatata ctttttcttt tcttttcttt    3660
cattttctat tcaatttaat aagaaataaa ttttgtaaat tttatttat caatttataa    3720 aaatatttta cttatatgt tttttcacat ttttgttaaa caaatcatat cattatgatt    3780
gaaagagagg aaattgacag tgagtaataa gtgatgagaa aaaaatgtgt tatttcctaa    3840
```

-continued

```
aaaaaaccta acaaacatg tatctactct ctatttcatc tatctctcat ttcattttc      3900 tctttatctc tttctttatt tttttatcat atcatttcac attaattatt tttactctct      3960 ttatttttc tctctatccc tctcttattt ccactcatat atacactcca aaattggggc      4020
atgcctttat cactactcta tctcctccac taaatcattt aaatgaaact gaaaagcatt      4080
ggcaagtctc ctcccctcct caagtgattt ccaactcagc attggcatct aattgattca      4140
gtatatctat tgcatgtgta aaagtctttc cacaatacat aactattaat taatcttaaa      4200
taaataaagg ataaaatatt tttttttctt cataaaatta aaatatgtta ttttttgttt      4260
agatgtatat tcgaataaat ctaaatatat gataatgatt tttatattg attaaacata      4320 taatcaatat taaatatgat atttttttat ataggttgta cacataattt tataaggata      4380
aaaaatatga taaaaataaa ttttaaatat tttatatttt acgagaaaaa aaaatatttt      4440
agccataaat aaatgaccag catattttac aaccttagta attcataaat tcctatatgt      4500
atatttgaaa ttaaaaacag ataatcgtta agggaaggaa tcctacgtca tctcttgcca      4560 tttgttttc atgcaaacag aaagggacga aaaaccacct caccatgaat cactcttcac      4620
accattttta ctagcaaaca agtctcaaca actgaagcca gctctctttc cgtttcttt      4680 tacaacactt tctttgaaat agtagtattt tttttcaca tgatttatta acgtgccaaa      4740
agatgcttat tgaatagagt gcacatttgt aatgtactac taattagaac atgaaaaagc      4800
attgttctaa cacgataatc ctgtgaaggc gttaactcca aagatccaat ttcactatat      4860
aaattgtgac gaaagcaaaa tgaattcaca tagctgagag agaaaggaaa ggttaactaa      4920
gaagcaatac ttcagcggcc gcatgactga ggataagacg aaggtcgagt tcccgacgct      4980
cacggagctc aagcactcga tcccgaacgc gtgctttgag tcgaacctcg gcctctcgct      5040
ctactacacg gcccgcgcga tcttcaacgc gtcggcctcg gcggcgctgc tctacgcggc      5100
gcgctcgacg ccgttcattg ccgataacgt tctgctccac gcgctcgttt gcgccaccta      5160
catctacgtg cagggcgtca tcttctgggg cttcttcacg gtcggccacg actgcggcca      5220
ctcggccttc tcgcgctacc acagcgtcaa ctttatcatc ggctgcatca tgcactctgc      5280
gattttgacg ccgttcgaga gctggcgcgt gacgcaccgc caccaccaca agaacacggg      5340
caacattgat aaggacgaga tcttttaccc gcaccggtcg gtcaaggacc tccaggacgt      5400
gcgccaatgg gtctacacgc tcggcggtgc gtggtttgtc tacttgaagg tcgggtatgc      5460
cccgcgcacg atgagccact ttgacccgtg ggacccgctc ctccttcgcc gcgcgtcggc      5520
cgtcatcgtg tcgctcggcg tctgggccgc cttcttcgcc gcgtacgcgt acctcacata      5580
ctcgctcggc tttgccgtca tgggcctcta ctactatgcg ccgctctttg tctttgcttc      5640
gttcctcgtc attacgacct tcttgcacca caacgacgaa gcgacgccgt ggtacggcga      5700
ctcggagtgg acgtacgtca agggcaacct ctcgagcgtc gaccgctcgt acggcgcgtt      5760
cgtggacaac ctgagccacc acattggcac gcaccaggtc caccacttgt tcccgatcat      5820
tccgcactac aagctcaacg aagccaccaa gcactttgcg gccgcgtacc cgcacctcgt      5880
gcgcaggaac gacgagccca tcatcacggc cttcttcaag accgcgcacc tctttgtcaa      5940
ctacggcgct gtgcccgaga cggcgcagat cttcacgctc aaagagtcgg ccgcggccgc      6000
caaggccaag tcggactaag c                                               6021
```

<210> SEQ ID NO 86
<211> LENGTH: 6524
<212> TYPE: DNA

<213> ORGANISM: Artificial Sequence
<220> FEATURE:
<223> OTHER INFORMATION: Plasmid pKR226

<400> SEQUENCE: 86

| | |
|---|---|
| gtacgtctag aggatccgtc gacggcgcgc ccgatcatcc ggatatagtt cctcctttca | 60 |
| gcaaaaaacc cctcaagacc cgtttagagg ccccaagggg ttatgctagt tattgctcag | 120 |
| cggtggcagc agccaactca gcttcctttc gggctttgtt agcagccgga tcgatccaag | 180 |
| ctgtacctca ctattccttt gccctcggac gagtgctggg gcgtcggttt ccactatcgg | 240 |
| cgagtacttc tacacagcca tcggtccaga cggccgcgct tctgcgggcg atttgtgtac | 300 |
| gcccgacagt cccggctccg gatcggacga ttgcgtcgca tcgaccctgc gcccaagctg | 360 |
| catcatcgaa attgccgtca accaagctct gatagagttg gtcaagacca atgcggagca | 420 |
| tatacgcccg gagccgcggc gatcctgcaa gctccggatg cctccgctcg aagtagcgcg | 480 |
| tctgctgctc catacaagcc aaccacggcc tccagaagaa gatgttggcg acctcgtatt | 540 |
| gggaatcccc gaacatcgcc tcgctccagt caatgaccgc tgttatgcgg ccattgtccg | 600 |
| tcaggacatt gttggagccg aaatccgcgt gcacagggtg ccggacttcg ggcagtcct | 660 |
| cggcccaaag catcagctca tcgagagcct gcgcgacgga cgcactgacg gtgtcgtcca | 720 |
| tcacagtttg ccagtgatac acatggggat cagcaatcgc gcatatgaaa tcacgccatg | 780 |
| tagtgtattg accgattcct tgcggtccga atgggccgaa cccgctcgtc tggctaagat | 840 |
| cggccgcagc gatcgcatcc atagcctccg cgaccggctg cagaacagcg ggcagttcgg | 900 |
| tttcaggcag gtcttgcaac gtgacaccct gtgcacggcg ggagatgcaa taggtcaggc | 960 |
| tctcgctgaa ttccccaatg tcaagcactt ccggaatcgg gagcgcggcc gatgcaaagt | 1020 |
| gccgataaac ataacgatct ttgtagaaac catcggcgca gctatttacc cgcaggacat | 1080 |
| atccacgccc tcctacatcg aagctgaaag cacgagattc ttcgccctcc gagagctgca | 1140 |
| tcaggtcgga gacgctgtcg aacttttcga tcagaaactt ctcgacagac gtcgcggtga | 1200 |
| gttcaggctt ttccatgggt atatctcctt cttaaagtta acaaaaatta tttctagagg | 1260 |
| gaaaccgttg tggtctccct atagtgagtc gtattaattt cgcgggatcg agatctgatc | 1320 |
| aacctgcatt aatgaatcgg ccaacgcgcg gggagaggcg gtttgcgtat gggcgctct | 1380 |
| tccgcttcct cgctcactga ctcgctgcgc tcggtcgttc ggctgcggcg agcggtatca | 1440 |
| gctcactcaa aggcggtaat acggttatcc acagaatcag gggataacgc aggaaagaac | 1500 |
| atgtgagcaa aaggccagca aaaggccagg aaccgtaaaa aggccgcgtt gctggcgttt | 1560 |
| ttccataggc tccgcccccc tgacgagcat cacaaaaatc gacgctcaag tcagaggtgg | 1620 |
| cgaaacccga caggactata agataccagg cgtttccccc tggaagctc cctcgtgcgc | 1680 |
| tctcctgttc cgacccrgcc gcttaccgga tacctgtccg cctttctccc ttcgggaagc | 1740 |
| gtggcgcttt ctcaatgctc acgctgtagg tatctcagtt cggtgtaggt cgttcgctcc | 1800 |
| aagctgggct gtgtgcacga accccccgtt cagcccgacc gctgcgcctt atccggtaac | 1860 |
| tatcgtcttg agtccaaccc ggtaagacac gacttatcgc cactggcagc agccactggt | 1920 |
| aacaggatta gcagagcgag gtatgtaggc ggtgctacag agttcttgaa gtggtggcct | 1980 |
| aactacggct acactagaag gacagtattt ggtatctgcg ctctgctgaa gccagttacc | 2040 |
| ttcggaaaaa gagttggtag ctcttgatcc ggcaaacaaa ccaccgctgg tagcggtggt | 2100 |
| ttttttgttt gcaagcagca gattacgcgc agaaaaaaag gatctcaaga agatcctttg | 2160 |
| atcttttcta cggggtctga cgctcagtgg aacgaaaact cacgttaagg gattttggtc | 2220 |

```
atgacattaa cctataaaaa taggcgtatc acgaggccct ttcgtctcgc gcgtttcggt    2280
gatgacggtg aaaacctctg acacatgcag ctcccggaga cggtcacagc ttgtctgtaa    2340
gcggatgccg ggagcagaca agcccgtcag ggcgcgtcag cgggtgttgg cgggtgtcgg    2400
ggctggctta actatgcggc atcagagcag attgtactga gagtgcacca tatggacata    2460
ttgtcgttag aacgcggcta caattaatac ataaccttat gtatcataca catacgattt    2520
aggtgacact atagaacggc gcgccaagct gggtctagaa ctagaaacgt gatgccactt    2580
gttattgaag tcgattacag catctattct gttttactat ttataacttt gccatttctg    2640
acttttgaaa actatctctg gatttcggta tcgctttgtg aagatcgagc aaaagagacg    2700
ttttgtggac gcaatggtcc aaatccgttc tacatgaaca aattggtcac aatttccact    2760
aaaagtaaat aaatggcaag ttaaaaaagg aatatgcatt ttactgattg cctaggtgag    2820
ctccaagaga agttgaatct acacgtctac caaccgctaa aaaagaaaa acattgatat    2880
gtaacctgat tccattagct tttgacttct tcaacagatt ctctacttag atttctaaca    2940
gaaatattat tactagcaca tcattttcag tctcactaca gcaaaaaatc caacggcaca    3000
atacagacaa caggagatat cagactacag agatagatag atgctactgc atgtagtaag    3060
ttaaataaaa ggaaaataaa atgtcttgct accaaaacta ctacagacta tgatgctcac    3120
cacaggccaa atcctgcaac taggacagca ttatcttata tatattgtac aaaacaagca    3180
tcaaggaaca tttggtctag gcaatcagta cctcgttcta ccatcaccct cagttatcac    3240
atccttgaag gatccattac tgggaatcat cggcaacaca tgctcctgat ggggcacaat    3300
gacatcaaga aggtaggggc caggggtgtc caacattctc tgaattgccg ctctaagctc    3360
ttccttcttc gtcactcgcg ctgccggtat cccacaagca tcagcaaact tgagcatgtt    3420
tgggaatatc tcgctctcgc tagacggatc tccaagatag gtgtgagctc tattggactt    3480
gtagaaccta tcctccaact gaaccaccat acccaaatgc tgattgttca acaacaatat    3540
cttaactggg agattctcca ctcttatagt ggccaactcc tgaacattca tgatgaaact    3600
accatcccca tcaatgtcaa ccacaacagc cccagggtta gcaacagcag caccaatagc    3660
cgcaggcaat ccaaaaccca tggctccaag acccctgag gtcaaccact gcctcggtct    3720
cttgtacttg taaaactgcg cagcccacat ttgatgctgc ccaaccccag tactaacaat    3780
agcatctcca ttagtcaact catcaagaac ctcgatagca tgctgcggag aaatcgcgtc    3840
ctggaatgtc ttgtaaccca atggaaactt gtgtttctgc acattaatct cttctctcca    3900
acctccaaga tcaaacttac cctccactcc tttctcctcc aaaatcatat taattcccct    3960
caaggccaac ttcaaatccg cgcaaaccga cacgtgcgcc tgcttgttct tcccaatctc    4020
ggcagaatca atatcaatgt gaacaatctt agccctacta gcaaaagcct caagcttccc    4080
agtaacacgg tcatcaaacc ttaccccaaa ggcaagcaac aaatcactat tgtcaacagc    4140
atagttagca taaacagtac catgcatacc cagcatctga agggaatatt catcaccaat    4200
aggaaaagtt ccaagaccca ttaaagtgct agcaacggga ataccagtga gttcaacaaa    4260
gcgcctcaat tcagcactgg aattcaaact gccaccgccg acgtagagaa cgggcttttg    4320
ggcctccatg atgagtctga caatgtgttc caattgggcc tcggcggggg gcctgggcag    4380
cctggcgagg taaccgggga ggttaacggg ctcgtcccaa ttaggcacgg cgagttgctg    4440
ctgaacgtct ttgggaatgt cgatgaggac cggaccgggg cggccggagg tggcgacgaa    4500
gaaagcctcg gcgacgacgc gggggatgtc gtcgacgtcg aggatgaggt agttgtgctt    4560
```

```
cgtgatggat ctgctcacct ccacgatcgg ggtttcttgg aaggcgtcgg tgccgatcat    4620
ccggcgggcg acctggccgg tgatggcgac gactgggacg ctgtccatta aagcgtcggc    4680
gaggccgctc acgaggttgg tggcgccggg gccggaggtg gcaatgcaga cgccggggag    4740
gccggaggaa cgcgcgtagc cttcggcggc gaagacgccg ccctgctcgt ggcgcgggag    4800
cacgttgcgg atggcggcgg agcgcgtgag cgcctggtgg atctccatcg acgcaccgcc    4860
ggggtacgcg aacaccgtcg tcacgccctg cctctccagc gcctccacaa ggatgtccgc    4920
gcccttgcga ggttcgccgg aggcgaaccg tgacacgaag ggctccgtgg tcggcgcttc    4980
cttggtgaag ggcgccgccg tgggggggttt ggagatggaa catttgattt tgagagcgtg    5040
gttgggtttg gtgagggttt gatgagagag agggagggtg gatctagtaa tgcgtttggg    5100
gaaggtgggg tgtgaagagg aagaagagaa tcgggtggtt ctggaagcgg tggccgccat    5160
tgtgttgtgt ggcatggtta tacttcaaaa actgcacaac aagcctagag ttagtaccta    5220
aacagtaaat ttacaacaga gagcaaagac acatgcaaaa atttcagcca taaaaaaagt    5280
tataatagaa tttaaagcaa aagtttcatt ttttaaacat atatacaaac aaactggatt    5340
tgaaggaagg gattaattcc cctgctcaaa gtttgaattc ctattgtgac ctatactcga    5400
ataaaattga agcctaagga atgtatgaga aacaagaaaa caaaacaaaa ctacagacaa    5460
acaagtacaa ttacaaaatt cgctaaaatt ctgtaatcac caaacccat ctcagtcagc    5520 acaaggccca aggtttattt tgaaataaaa aaaagtgat tttatttctc ataagctaaa    5580
agaaagaaag gcaattatga aatgatttcg actagatctg aaagtccaac gcgtattccg    5640
cagatattaa agaaagagta gagtttcaca tggatcctag atggacccag ttgaggaaaa    5700
agcaaggcaa agcaaaccag aagtgcaaga tccgaaattg aaccacggaa tctaggattt    5760
ggtagaggga gaagaaaagt accttgagag gtagaagaga agagaagagc agagagatat    5820
atgaacgagt gtgtcttggt ctcaactctg aagcgatacg agtttagagg ggagcattga    5880
gttccaattt atagggaaac cgggtggcag gggtgagtta atgacggaaa agcccctaag    5940
taacgagatt ggattgtggg ttagattcaa ccgtttgcat ccgcggctta gattggggaa    6000
gtcagagtga atctcaaccg ttgactgagt tgaaaattga atgtagcaac caattgagcc    6060
aaccccagcc tttgcccttt gattttgatt tgtttgttgc atacttttta tttgtcttct    6120
ggttctgact ctcttttctct cgtttcaatg ccaggttgcc tactcccaca ccactcacaa    6180
gaagattcta ctgttagtat taaatatttt ttaatgtatt aaatgatgaa tgcttttgta    6240
aacagaacaa gactatgtct aataagtgtc ttgcaacatt ttttaagaaa ttaaaaaaaa    6300
tatatttatt atcaaaatca aatgtatgaa aaatcatgaa taatataatt ttatacattt    6360
ttttaaaaaa tcttttaatt tcttaattaa tatcttaaaa ataatgatta atatttaacc    6420
caaaataatt agtatgattg gtaaggaaga tatccatgtt atgtttggat gtgagtttga    6480
tctagagcaa agcttactag agtcgacctg caggtcgact cgac                    6524
```

<210> SEQ ID NO 87
<211> LENGTH: 13514
<212> TYPE: DNA
<213> ORGANISM: Artificial Sequence
<220> FEATURE:
<223> OTHER INFORMATION: Plasmid pKR275
<220> FEATURE:
<221> NAME/KEY: misc_feature
<222> LOCATION: (1192)..(1192)
<223> OTHER INFORMATION: n is a, c, g, or t
<220> FEATURE:
<221> NAME/KEY: misc_feature
<222> LOCATION: (2675)..(2675)
<223> OTHER INFORMATION: n is a, c, g, or t

<400> SEQUENCE: 87

| | | | | | |
|---|---|---|---|---|---|
| ggtcgactcg | acgtacgtcc | tcgaagagaa | gggttaataa | cacatttttt | aacattttta | 60 |
| acacaaattt | tagttattta | aaaatttatt | aaaaaattta | aataagaag | aggaactctt | 120 |
| taaataaatc | taacttacaa | aatttatgat | ttttaataag | ttttcaccaa | taaaaaatgt | 180 |
| cataaaaata | tgttaaaaag | tatattatca | atattctctt | tatgataaat | aaaaagaaaa | 240 |
| aaaaaataaa | agtaagtga | aaatgagatt | gaagtgactt | taggtgtgta | taaatatatc | 300 |
| aaccccgcca | acaatttatt | taatccaaat | atattgaagt | atattattcc | atagcctta | 360 |
| tttatttata | tatttattat | ataaaagctt | tatttgttct | aggttgttca | tgaaatattt | 420 |
| ttttggtttt | atctccgttg | taagaaaatc | atgtgctttg | tgtcgccact | cactattgca | 480 |
| gcttttcat | gcattggtca | gattgacggt | tgattgtatt | tttgtttttt | atggttttgt | 540 |
| gttatgactt | aagtcttcat | ctctttatct | cttcatcagg | tttgatggtt | acctaatatg | 600 |
| gtccatgggt | acatgcatgg | ttaaattagg | tggccaactt | tgttgtgaac | gatagaattt | 660 |
| tttttatatt | aagtaaacta | ttttatatt | atgaaataat | aataaaaaaa | atattttatc | 720 |
| attattaaca | aaatcatatt | agttaatttg | ttaactctat | aataaaagaa | atactgtaac | 780 |
| attcacatta | catggtaaca | tcttcccacc | ctttcatttg | ttttttgttt | gatgacttt | 840 |
| tttcttgttt | aaatttattt | cccttctttt | aaatttggaa | tacattatca | tcatatataa | 900 |
| actaaaatac | taaaaacagg | attacacaaa | tgataaaata | taacacaaat | atttataaat | 960 |
| ctagctgcaa | tatatttaaa | ctagctatat | cgatattgta | aaataaaact | agctgcattg | 1020 |
| atactgataa | aaaaatatca | tgtgctttct | ggactgatga | tgcagtatac | ttttgacatt | 1080 |
| gcctttattt | tattttcag | aaaagcttc | ttagttctgg | gttcttcatt | atttgtttcc | 1140 |
| catctccatt | gtgaattgaa | tcatttgctt | cgtgtcacaa | atacaattta | gntaggtaca | 1200 |
| tgcattggtc | agattcacgg | tttattatgt | catgacttaa | gttcatggta | gtacattacc | 1260 |
| tgccacgcat | gcattatatt | ggttagattt | gataggcaaa | tttggttgtc | aacaatataa | 1320 |
| atataaataa | tgtttttata | ttacgaaata | acagtgatca | aaacaaacag | ttttatcttt | 1380 |
| attaacaaga | ttttgttttt | gttgatgac | gtttttaat | gtttacgctt | tccccttct | 1440 |
| tttgaattta | gaacacttta | tcatcataaa | atcaaatact | aaaaaaatta | catatttcat | 1500 |
| aaataataac | acaaatattt | ttaaaaatc | tgaaataata | atgaacaata | ttacatatta | 1560 |
| tcacgaaaat | tcattaataa | aaatattata | taaataaaat | gtaatagtag | ttatatgtag | 1620 |
| gaaaaaagta | ctgcacgcat | aatatataca | aaaagattaa | aatgaactat | tataaataat | 1680 |
| aacactaaat | taatggtgaa | tcatatcaaa | ataatgaaaa | agtaaataaa | atttgtaatt | 1740 |
| aacttctata | tgtattacac | acacaaataa | taaataatag | taaaaaaaat | tatgataaat | 1800 |
| atttaccatc | tcataagata | tttaaaataa | tgataaaaat | atagattatt | ttttatgcaa | 1860 |
| ctagctagcc | aaaagagaa | cacgggtata | tataaaaaga | gtacctttaa | attctactgt | 1920 |
| acttcctta | ttcctgacgt | ttttatatca | agtggacata | cgtgaagatt | ttaattatca | 1980 |
| gtctaaatat | ttcattagca | cttaatactt | ttctgtttta | ttcctatcct | ataagtagtc | 2040 |
| ccgattctcc | caacattgct | tattcacaca | actaactaag | aaagtcttcc | atagccccc | 2100 |
| aagcggccgc | ctctctctct | ctctcttctc | tcttttctc | cccctctctc | cggcgatggt | 2160 |
| tgttgctatg | gaccaacgca | ccaatgtgaa | cggagatccc | ggcgccggag | accggaagaa | 2220 |

```
agaagaaagg tttgatccga gtgcacaacc accgttcaag atcggagata taagggcggc   2280
gattcctaag cactgttggg ttaagagtcc tttgagatca atgagttacg tcgtcagaga   2340
cattatcgcc gtcgcggctt tggccatcgc tgccgtgtat gttgatagct ggttcctttg   2400
gcctctttat tgggccgccc aaggaacact tttctgggcc atctttgttc tcggccacga   2460
ctgtggacat gggagtttct cagacattcc tctactgaat agtgtggttg gtcacattct   2520
tcattctttc atcctcgttc cttaccatgg ttggagaata agccaccgga cacaccacca   2580
gaaccatggc catgttgaaa cgacgagtc atgggttccg ttaccagaaa gggtgtacaa    2640
gaaattgccc cacagtactc ggatgctcag atacnctgtc cctctcccca tgctcgcata   2700
tcctctctat ttgtgctaca gaagtcctgg aaaagaagga tcacatttta acccatacag   2760
tagtttattt gctccaagcg agagaaagct tattgcaact tcaactactt gttggtccat   2820
aatgttcgtc agtcttatcg ctctatcttt cgtcttcggt ccactcgcgg ttcttaaagt   2880
ctacggtgta ccgtacatta tctttgtgat gtggttggat gctgtcacgt atttgcatca   2940
tcatggtcac gatgagaagt tgccttggta tagaggcaag gaatggagtt atctacgtgg   3000
aggattaaca acaattgata gagattacgg aatctttaac aacattcatc acgacattgg   3060
aactcacgtg atccatcatc tcttcccaca aatccctcac tatcacttgg tcgacgccac   3120
gaaagcagct aaacatgtgt tgggaagata ctacagagaa ccaaagacgt caggagcaat   3180
accgatccac ttggtggaga gtttggtcgc aagtattaag aaagatcatt acgtcagcga   3240
cactggtgat attgtcttct acgagacaga tccagatctc tacgtttacg cttctgacaa   3300
atctaaaatc aattaatctc catttgttta gctctattag gaataaacca gcccactttt   3360
aaaattttta ttcttgttg tttttaagtt aaaagtgtac tcgtgaaact cttttttttt   3420
tcttttttt tattaatgta tttacattac aaggcgtaaa gcggccgcga cacaagtgtg   3480
agagtactaa ataaatgctt tggttgtacg aaatcattac actaaataaa ataatcaaag   3540
cttatatatg ccttccgcta aggccgaatg caaagaaatt ggttctttct cgttatcttt   3600
tgccactttt actagtacgt attaattact acttaatcat ctttgtttac ggctcattat   3660
atccgtacgt ctagaggatc cgtcgacggc gcgcccgatc atccggatat agttcctcct   3720
ttcagcaaaa aaccccctcaa gacccgttta gaggccccaa ggggttatgc tagttattgc   3780
tcagcggtgg cagcagccaa ctcagcttcc tttcgggctt tgttagcagc cggatcgatc   3840
caagctgtac ctcactattc ctttgccctc ggacgagtgc tggggcgtcg gtttccacta   3900
tcggcgagta cttctacaca gccatcggtc cagacgccg cgcttctgcg ggcgatttgt    3960
gtacgcccga cagtcccggc tccggatcgg acgattgcgt cgcatcgacc ctgcgcccaa   4020
gctgcatcat cgaaattgcc gtcaaccaag ctctgataga gttggtcaag accaatgcgg   4080
agcatatacg cccggagccg cggcgatcct gcaagctccg gatgcctccg ctcgaagtag   4140
cgcgtctgct gctccataca agccaaccac ggcctccaga agaagatgtt ggcgacctcg   4200
tattgggaat ccccgaacat cgcctcgctc cagtcaatga ccgctgttat gcggccattg   4260
tccgtcagga cattgttgga gccgaaatcc gcgtgcacga ggtgccggac ttcggggcag   4320
tcctcggccc aaagcatcag ctcatcgaga gcctgcgcga cggacgcact gacggtgtcg   4380
tccatcacag tttgccagtg atacacatgg ggatcagcaa tcgcgcatat gaaatcacgc   4440
catgtagtgt attgaccgat tccttgcggt ccgaatgggc cgaacccgct cgtctggcta   4500
agatcggccg cagcgatcgc atccatagcc tccgcgaccg gctgcagaac agcgggcagt   4560
tcggtttcag gcaggtcttg caacgtgaca ccctgtgcac ggcgggagat gcaataggtc   4620
```

```
aggctctcgc tgaattcccc aatgtcaagc acttccggaa tcgggagcgc ggccgatgca    4680
aagtgccgat aaacataacg atctttgtag aaaccatcgg cgcagctatt tacccgcagg    4740
acatatccac gccctcctac atcgaagctg aaagcacgag attcttcgcc ctccgagagc    4800
tgcatcaggt cggagacgct gtcgaacttt tcgatcagaa acttctcgac agacgtcgcg    4860
gtgagttcag gcttttccat gggtatatct ccttcttaaa gttaaacaaa attatttcta    4920
gagggaaacc gttgtggtct ccctatagtg agtcgtatta atttcgcggg atcgagatct    4980
gatcaacctg cattaatgaa tcggccaacg cgcggggaga ggcggtttgc gtattgggcg    5040
ctcttccgct tcctcgctca ctgactcgct gcgctcggtc gttcggctgc ggcgagcggt    5100
atcagctcac tcaaaggcgg taatacggtt atccacagaa tcaggggata acgcaggaaa    5160
gaacatgtga gcaaaaggcc agcaaaaggc caggaaccgt aaaaaggccg cgttgctggc    5220 gttttccat aggctccgcc cccctgacga gcatcacaaa aatcgacgct caagtcagag    5280
gtggcgaaac ccgacaggac tataaagata ccaggcgttt ccccctggaa gctccctcgt    5340
gcgctctcct gttccgaccc tgccgcttac cggatacctg tccgcctttc tcccttcggg    5400
aagcgtggcg ctttctcaat gctcacgctg taggtatctc agttcggtgt aggtcgttcg    5460
ctccaagctg ggctgtgtgc acgaaccccc cgttcagccc gaccgctgcg ccttatccgg    5520
taactatcgt cttgagtcca acccggtaag acacgactta tcgccactgg cagcagccac    5580
tggtaacagg attagcagag cgaggtatgt aggcggtgct acagagttct tgaagtggtg    5640
gcctaactac ggctacacta aggacagt atttggtatc tgcgctctgc tgaagccagt    5700
taccttcgga aaaagagttg gtagctcttg atccggcaaa caaaccaccg ctggtagcgg    5760 tggtttttt gtttgcaagc agcagattac gcgcagaaaa aaaggatctc aagaagatcc    5820
tttgatcttt tctacggggt ctgacgctca gtggaacgaa aactcacgtt aagggatttt    5880
ggtcatgaca ttaacctata aaaataggcg tatcacgagg ccctttcgtc tcgcgcgttt    5940
cggtgatgac ggtgaaaacc tctgacacat gcagctcccg gagacggtca gcttgtct    6000 gtaagcggat gccgggagca gacaagcccg tcagggcgcg tcagcgggtg ttggcgggtg    6060
tcggggctgg cttaactatg cggcatcaga gcagattgta ctgagagtgc accatatgga    6120
catattgtcg ttagaacgcg gctacaatta atacataacc ttatgtatca tacacatacg    6180
atttaggtga cactatagaa cggcgcgcca agctgggtct agaactagaa acgtgatgcc    6240
acttgttatt gaagtcgatt acagcatcta ttctgtttta ctatttataa ctttgccatt    6300
tctgactttt gaaaactatc tctggatttc ggtatcgctt tgtgaagatc gagcaaaaga    6360
gacgttttgt ggacgcaatg gtccaaatcc gttctacatg aacaaattgg tcacaatttc    6420
cactaaaagt aaataaatgg caagttaaaa aaggaatatg catttactg attgcctagg    6480 tgagctccaa gagaagttga atctacacgt ctaccaaccg ctaaaaaaag aaaaacattg    6540
atatgtaacc tgattccatt agcttttgac ttcttcaaca gattctctac ttagatttct    6600
aacagaaata ttattactag cacatcattt tcagtctcac tacagcaaaa atccaacgg    6660 cacaatacag acaacaggag atatcagact acagagatag atagatgcta ctgcatgtag    6720
taagttaaat aaaaggaaaa taaaatgtct tgctaccaaa actactacag actatgatgc    6780
tcaccacagg ccaaatcctg caactaggac agcattatct tatatatatt gtacaaaaca    6840
agcatcaagg aacatttggt ctaggcaatc agtacctcgt tctaccatca ccctcagtta    6900
tcacatcctt gaaggatcca ttactgggaa tcatcggcaa cacatgctcc tgatgggca    6960
```

-continued

```
caatgacatc aagaaggtag gggccagggg tgtccaacat tctctgaatt gccgctctaa    7020
gctcttcctt cttcgtcact cgcgctgccg gtatcccaca agcatcagca aacttgagca    7080
tgtttgggaa tatctcgctc tcgctagacg gatctccaag ataggtgtga gctctattgg    7140
acttgtagaa cctatcctcc aactgaacca ccatacccaa atgctgattg ttcaacaaca    7200
atatcttaac tgggagattc tccactctta tagtggccaa ctcctgaaca ttcatgatga    7260
aactaccatc cccatcaatg tcaaccacaa cagccccagg gttagcaaca gcagcaccaa    7320
tagccgcagg caatccaaaa cccatggctc caagaccccc tgaggtcaac cactgcctcg    7380
gtctcttgta cttgtaaaac tgcgcagccc acatttgatg ctgcccaacc ccagtactaa    7440
caatagcatc tccattagtc aactcatcaa gaacctcgat agcatgctgc ggagaaatcg    7500
cgtcctggaa tgtcttgtaa cccaatggaa acttgtgttt ctgcacatta atctcttctc    7560
tccaacctcc aagatcaaac ttaccctcca ctcctttctc ctccaaaatc atattaattc    7620
ccttcaaggc caacttcaaa tccgcgcaaa ccgacacgtg cgcctgcttg ttcttcccaa    7680
tctcggcaga atcaatatca atgtgaacaa tcttagccct actagcaaaa gcctcaagct    7740
tcccagtaac acggtcatca aaccttaccc caaaggcaag caacaaatca ctattgtcaa    7800
cagcatagtt agcataaaca gtaccatgca tacccagcat ctgaagggaa tattcatcac    7860
caataggaaa agttccaaga cccattaaag tgctagcaac gggaatacca gtgagttcaa    7920
caaagcgcct caattcagca ctggaattca aactgccacc gccgacgtag agaacgggct    7980
tttgggcctc catgatgagt ctgacaatgt gttccaattg ggcctcggcg gggggcctgg    8040
gcagcctggc gaggtaaccg gggaggttaa cgggctcgtc ccaattaggc acggcgagtt    8100
gctgctgaac gtctttggga atgtcgatga ggaccggacc ggggcggccg gaggtggcga    8160
cgaagaaagc ctcggcgacg acgcggggga tgtcgtcgac gtcgaggatg aggtagttgt    8220
gcttcgtgat ggatctgctc acctccacga tcggggtttc ttggaaggcg tcggtgccga    8280
tcatccggcg ggcgacctgg ccggtgatgg cgacgactgg gacgctgtcc attaaagcgt    8340
cggcgaggcc gctcacgagg ttggtggcgc cggggccgga ggtggcaatg cagacgccgg    8400
ggaggccgga ggaacgcgcg tagccttcgg cggcgaagac gccgccctgc tcgtggcgcg    8460
ggagcacgtt gcggatggcg gcggagcgcg tgagcgcctg gtggatctcc atcgacgcac    8520
cgccggggta cgcgaacacc gtcgtcacgc cctgcctctc cagcgcctcc acaaggatgt    8580
ccgcgccctt gcgaggttcg ccggaggcga accgtgacac gaagggctcc gtggtcggcg    8640
cttccttggt gaagggcgcc gccgtggggg gtttggagat ggaacatttg atttttgagag    8700
cgtggttggg tttggtgagg gtttgatgag agagagggag ggtggatcta gtaatgcgtt    8760
tggggaaggt ggggtgtgaa gaggaagaag agaatcgggt ggttctggaa gcggtggccg    8820
ccattgtgtt gtgtggcatg gttatacttc aaaaactgca caacaagcct agagttagta    8880
cctaaacagt aaatttacaa cagagagcaa agacacatgc aaaaatttca gccataaaaa    8940
aagttataat agaatttaaa gcaaaagttt cattttttaa acatatatac aaacaaactg    9000
gatttgaagg aagggattaa ttcccctgct caaagtttga attcctattg tgacctatac    9060
tcgaataaaa ttgaagccta aggaatgtat gagaaacaag aaaacaaaac aaaactacag    9120
acaaacaagt acaattacaa aattcgctaa aattctgtaa tcaccaaacc ccatctcagt    9180
cagcacaagg cccaaggttt atttttgaaat aaaaaaaaag tgattttatt tctcataagc    9240
taaaagaaag aaaggcaatt atgaaatgat ttcgactaga tctgaaagtc caacgcgtat    9300
tccgcagata ttaaagaaag agtagagttt cacatggatc ctagatggac ccagttgagg    9360
```

-continued

```
aaaaagcaag gcaaagcaaa ccagaagtgc aagatccgaa attgaaccac ggaatctagg    9420
atttggtaga gggagaagaa aagtaccttg agaggtagaa gagaagagaa gagcagagag    9480
atatatgaac gagtgtgtct tggtctcaac tctgaagcga tacgagttta gaggggagca    9540
ttgagttcca atttataggg aaaccgggtg gcaggggtga gttaatgacg gaaaagcccc    9600
taagtaacga gattggattg tgggttagat tcaaccgttt gcatccgcgg cttagattgg    9660
ggaagtcaga gtgaatctca accgttgact gagttgaaaa ttgaatgtag caaccaattg    9720
agccaacccc agcctttgcc ctttgatttt gatttgtttg ttgcatactt tttatttgtc    9780
ttctggttct gactctcttt ctctcgtttc aatgccaggt tgcctactcc cacaccactc    9840
acaagaagat tctactgtta gtattaaata tttttaatg tattaaatga tgaatgcttt     9900
tgtaaacaga acaagactat gtctaataag tgtcttgcaa cattttttaa gaaattaaaa    9960
aaaatatatt tattatcaaa atcaaatgta tgaaaaatca tgaataatat aatttttatac  10020
atttttttaa aaaatctttt aatttcttaa ttaatatctt aaaaataatg attaatattt   10080
aacccaaaat aattagtatg attggtaagg aagatatcca tgttatgttt ggatgtgagt   10140
ttgatctaga gcaaagctta ctagagtcga cctgcaggtc gactcgacgt acgatcccac   10200
atgcaagttt ttatttcaat ccctttttcct ttgaataact gaccaagaac aacaagaaaa  10260
aaaaaaaaaa agaaaaggat cattttgaaa ggatattttt cgctcctatt caaatactgt   10320
attttttacca aaaaaactgt atttttccta cactctcaag ctttgttttt cgcttcgact  10380
ctcatgattt ccttcatatg ccaatcactc tatttataaa tggcataagg tagtgtgaac   10440
aattgcaaag cttgtcatca aaagcttgca atgtacaaat taatgttttt catgcctttc   10500
aaaattatct gcaccccccta gctattaatc taacatctaa gtaaggctag tgaatttttt   10560
cgaatagtca tgcagtgcat taatttcccc gtgactattt tggctttgac tccaacactg   10620
gccccgtaca tccgtccctc attacatgaa aagaaatatt gtttatattc ttaattaaaa   10680
atattgtccc ttctaaattt tcatatagtt aattattata ttactttttt ctctattcta   10740
ttagttctat tttcaaatta ttatttatgc atatgtaaag tacattatat ttttgctata   10800
tacttaaata tttctaaatt attaaaaaaa gactgatatg aaaaatttat tctttttaaa   10860
gctatatcat tttatatata cttttttctttt tcttttcttt cattttctat tcaatttaat  10920
aagaaataaa ttttgtaaat tttatttat caatttataa aaatatttta ctttatatgt   10980
tttttcacat ttttgttaaa caaatcatat cattatgatt gaaagagagg aaattgacag   11040
tgagtaataa gtgatgagaa aaaaatgtgt tatttcctaa aaaaaaccta aacaaacatg   11100
tatctactct ctatttcatc tatctctcat ttcattttc tcttatctc tttctttatt    11160
tttttatcat atcatttcac attaattatt tttactctct ttatttttttc tctctatccc  11220
tctcttattt ccactcatat atacactcca aaattggggc atgcctttat cactactcta   11280
tctcctccac taaatcattt aaatgaaact gaaaagcatt ggcaagtctc ctcccctcct   11340
caagtgattt ccaactcagc attggcatct aattgattca gtatatctat tgcatgtgta   11400
aaagtctttc cacaatacat aactattaat taatcttaaa taaataaagg ataaaatatt   11460
ttttttttctt cataaaatta aaatatgtta tttttttgttt agatgtatat tcgaataaat  11520
ctaaatatat gataatgatt tttatattg attaaacata taatcaatat taaatatgat   11580
atttttttat ataggttgta cacataattt tataaggata aaaaatatga taaaaatataaa 11640
ttttaaatat ttttatattt acgagaaaaa aaaatatttt agccataaat aaatgaccag   11700
```

```
catattttac aaccttagta attcataaat tcctatatgt atatttgaaa ttaaaaacag    11760
ataatcgtta agggaaggaa tcctacgtca tctcttgcca tttgttttc atgcaaacag    11820 aaagggacga aaaaccacct caccatgaat cactcttcac accatttta ctagcaaaca    11880 agtctcaaca actgaagcca gctctctttc cgtttcttt tacaacactt tctttgaaat    11940
agtagtattt tttttcaca tgatttatta acgtgccaaa agatgcttat tgaatagagt    12000
gcacatttgt aatgtactac taattagaac atgaaaagc attgttctaa cacgataatc    12060
ctgtgaaggc gttaactcca aagatccaat ttcactatat aaattgtgac gaaagcaaaa    12120
tgaattcaca tagctgagag agaaaggaaa ggttaactaa gaagcaatac ttcagcggcc    12180
gcatgactga ggataagacg aaggtcgagt tcccgacgct cacggagctc aagcactcga    12240
tcccgaacgc gtgctttgag tcgaacctcg gcctctcgct ctactacacg gcccgcgcga    12300
tcttcaacgc gtcggcctcg gcggcgctgc tctacgcggc gcgctcgacg ccgttcattg    12360
ccgataacgt tctgctccac gcgctcgttt gcgccaccta catctacgtg cagggcgtca    12420
tcttctgggg cttcttcacg gtcggccacg actgcggcca ctcggccttc tcgcgctacc    12480
acagcgtcaa ctttatcatc ggctgcatca tgcactctgc gattttgacg ccgttcgaga    12540
gctggcgcgt gacgcaccgc caccaccaca agaacacggg caacattgat aaggacgaga    12600
tcttttaccc gcaccggtcg gtcaaggacc tccaggacgt gcgccaatgg gtctacacgc    12660
tcggcggtgc gtggtttgtc tacttgaagg tcgggtatgc cccgcgcacg atgagccact    12720
ttgacccgtg ggaccccgct ctccttcgcc gcgcgtcggc cgtcatcgtg tcgctcggcg    12780
tctgggccgc cttcttcgcc gcgtacgcgt acctcacata ctcgctcggc tttgccgtca    12840
tgggcctcta ctactatgcg ccgctctttg tctttgcttc gttcctcgtc attacgacct    12900
tcttgcacca caacgacgaa gcgacgccgt ggtacggcga ctcggagtgg acgtacgtca    12960
agggcaacct ctcgagcgtc gaccgctcgt acggcgcgtt cgtggacaac ctgagccacc    13020
acattggcac gcaccaggtc caccacttgt tcccgatcat tccgcactac aagctcaacg    13080
aagccaccaa gcactttgcg gccgcgtacc cgcacctcgt gcgcaggaac gacgagccca    13140
tcatcacggc cttcttcaag accgcgcacc tctttgtcaa ctacggcgct gtgcccgaga    13200
cggcgcagat cttcacgctc aaagagtcgg ccgcggccgc caaggccaag tcggactaag    13260
cggccgcatg agccgtaaag gttcaataca acgagtgctt gttttcttag ggacaagcat    13320
tgtacttatg tatgattctg tgtaaccatg agtcttccac gttgtactaa tgtgaagggc    13380
aaaaataaaa cacagaacaa gttcgttttt ctcaaataat gtgaaggtag aaaatggaac    13440
catgcctcct ctcttgcatg tgatttaaaa tattagcaga tggtaccgta cgtgggcgga    13500
tcccccgggc tgca                                                     13514
```

<210> SEQ ID NO 88
<211> LENGTH: 12323
<212> TYPE: DNA
<213> ORGANISM: Artificial Sequence
<220> FEATURE:
<223> OTHER INFORMATION: Plasmid pKR329
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (2684)..(2684)
<223> OTHER INFORMATION: n is a, c, g, or t

<400> SEQUENCE: 88

-continued

```
ggatctggcc ggccggatct cgtacgtcct cgaagagaag ggttaataac acatttttta      60
acatttttaa cacaaatttt agttatttaa aaatttatta aaaaatttaa aataagaaga     120
ggaactcttt aaataaatct aacttacaaa atttatgatt tttaataagt tttcaccaat     180
aaaaaatgtc ataaaaatat gttaaaaagt atattatcaa tattctcttt atgataaata     240
aaaagaaaaa aaaaataaaa gttaagtgaa aatgagattg aagtgacttt aggtgtgtat     300
aaatatatca accccgccaa caatttattt aatccaaata tattgaagta tattattcca     360
tagcctttat ttatttatat atttattata taaaagcttt atttgttcta ggttgttcat     420
gaaatatttt tttggtttta tctccgttgt aagaaaatca tgtgctttgt gtcgccactc     480
actattgcag cttttttcatg cattggtcag attgacggtt gattgtattt ttgttttta    540
tggttttgtg ttatgactta agtcttcatc tctttatctc ttcatcaggt ttgatggtta     600
cctaatatgg tccatgggta catgcatggt taaattaggt ggccaacttt gttgtgaacg     660
atagaatttt ttttatatta agtaaactat ttttatatta tgaaataata ataaaaaaaa     720
tattttatca ttattaacaa aatcatatta gttaatttgt taactctata ataaagaaa      780
tactgtaaca ttcacattac atggtaacat ctttccaccc tttcatttgt tttttgtttg     840
atgacttttt ttcttgttta aatttatttc ccttctttta aatttggaat acattatcat     900
catatataaa ctaaaatact aaaaacagga ttacacaaat gataaataat aacacaaata     960
tttataaatc tagctgcaat atatttaaac tagctatatc gatattgtaa aataaaacta    1020
gctgcattga tactgataaa aaaatatcat gtgctttctg gactgatgat gcagtatact    1080
tttgacattg cctttatttt atttttcaga aaagctttct tagttctggg ttcttcatta    1140
tttgtttccc atctccattg tgaattgaat catttgcttc gtgtcacaaa tacaatttag    1200
ntaggtacat gcattggtca gattcacggt ttattatgtc atgacttaag ttcatggtag    1260
tacattacct gccacgcatg cattatattg gttagatttg ataggcaaat ttggttgtca    1320
acaatataaa tataaataat gttttatat tacgaaataa cagtgatcaa aacaaacagt    1380
tttatcttta ttaacaagat tttgtttttg tttgatgacg tttttaatg tttacgcttt     1440
cccccttctt ttgaatttag aacactttat catcataaaa tcaaatacta aaaaaattac    1500
atatttcata aataataaca caaatatttt taaaaaatct gaaataataa tgaacaatat    1560
tacatattat cacgaaaatt cattaataaa aatattatat aaataaaatg taatagtagt    1620
tatatgtagg aaaaaagtac tgcacgcata atatatacaa aaagattaaa atgaactatt    1680
ataaataata acactaaatt aatggtgaat catatcaaaa taatgaaaaa gtaaataaaa    1740
tttgtaatta acttctatat gtattacaca cacaaataaa aaataatagt aaaaaaaatt    1800
atgataaata tttaccatct cataagatat ttaaaataat gataaaaata tagattattt    1860
tttatgcaac tagctagcca aaaagagaac acgggtatat ataaaaagag tacctttaaa    1920
ttctactgta cttcctttat tcctgacgtt tttatatcaa gtggacatac gtgaagattt    1980
taattatcag tctaaatatt tcattagcac ttaaactttt tctgttttat tcctatccta    2040
taagtagtcc cgattctccc aacattgctt attcacacaa ctaactaaga aagtcttcca    2100
tagcccccca agcggccgcc tctctctctc tctcttctct ctttctctcc ccctctctcc    2160
ggcgatggtt gttgctatgg accaacgcac caatgtgaac ggagatcccg cgccggaga    2220
ccggaagaaa gaagaaaggt ttgatccgag tgcacaacca ccgttcaaga tcggagatat    2280
aagggcggcg attcctaagc actgttgggt taagagtcct ttgagatcaa tgagttacgt    2340
```

```
cgtcagagac attatcgccg tcgcggcttt ggccatcgct gccgtgtatg ttgatagctg    2400
gttcctttgg cctctttatt gggccgccca aggaacactt ttctgggcca tctttgttct    2460
cggccacgac tgtggacatg ggagtttctc agacattcct ctactgaata gtgtggttgg    2520
tcacattctt cattctttca tcctcgttcc ttaccatggt tggagaataa gccaccggac    2580
acaccaccag aaccatggcc atgttgaaaa cgacgagtca tgggttccgt taccagaaag    2640
ggtgtacaag aaattgcccc acagtactcg gatgctcaga tacnctgtcc ctctcccat    2700 gctcgcatat cctctctatt tgtgctacag aagtcctgga aagaaggat cacattttaa    2760 cccatacagt agtttatttg ctccaagcga gagaaagctt attgcaactt caactacttg    2820
ttggtccata atgttcgtca gtcttatcgc tctatctttc gtcttcggtc cactcgcggt    2880
tcttaaagtc tacggtgtac cgtacattat ctttgtgatg tggttggatg ctgtcacgta    2940
tttgcatcat catggtcacg atgagaagtt gccttggtat agaggcaagg aatggagtta    3000
tctacgtgga ggattaacaa caattgatag agattacgga atctttaaca acattcatca    3060
cgacattgga actcacgtga tccatcatct cttcccacaa atccctcact atcacttggt    3120
cgacgccacg aaagcagcta acatgtgtt gggaagatac tacagagaac caaagacgtc    3180
aggagcaata ccgatccact tggtggagag tttggtcgca agtattaaga aagatcatta    3240
cgtcagcgac actggtgata ttgtcttcta cgagacagat ccagatctct acgtttacgc    3300
ttctgacaaa tctaaaatca attaatctcc atttgtttag ctctattagg aataaaccag    3360
cccactttta aaatttttat ttcttgttgt ttttaagtta aaagtgtact cgtgaaactc    3420
tttttttttt ctttttttt attaatgtat ttacattaca aggcgtaaag cggccgcgac    3480
acaagtgtga gagtactaaa taaatgcttt ggttgtacga aatcattaca ctaaataaaa    3540
taatcaaagc ttatatatgc cttccgctaa ggccgaatgc aaagaaattg gttctttctc    3600
gttatctttt gccactttta ctagtacgta ttaattacta cttaatcatc tttgtttacg    3660
gctcattata tccgtacgga tccgtcgacg gcgcgcccga tcatccggat atagttcctc    3720
ctttcagcaa aaaaccccctc aagacccgtt tagaggcccc aaggggttat gctagttatt    3780
gctcagcggt ggcagcagcc aactcagctt cctttcgggc tttgttagca gccggatcga    3840
tccaagctgt acctcactat tcctttgccc tcggacgagt gctggggcgt cggtttccac    3900
tatcggcgag tacttctaca cagccatcgg tccagacggc cgcgcttctg cgggcgattt    3960
gtgtacgccc gacagtcccg gctccggatc ggacgattgc gtcgcatcga ccctgcgccc    4020
aagctgcatc atcgaaattg ccgtcaacca agctctgata gagttggtca agaccaatgc    4080
ggagcatata cgcccggagc cgcggcgatc ctgcaagctc cggatgcctc cgctcgaagt    4140
agcgcgtctg ctgctccata caagccaacc acggcctcca gaagaagatg ttggcgacct    4200
cgtattggga atccccgaac atcgcctcgc tccagtcaat gaccgctgtt atgcggccat    4260
tgtccgtcag gacattgttg gagccgaaat ccgcgtgcac gaggtgccgg acttcggggc    4320
agtcctcggc ccaaagcatc agctcatcga gagcctgcgc gacggacgca ctgacggtgt    4380
cgtccatcac agtttgccag tgatacacat ggggatcagc aatcgcgcat atgaaatcac    4440
gccatgtagt gtattgaccg attccttgcg gtccgaatgg gccgaacccg ctcgtctggc    4500
taagatcggc cgcagcgatc gcatccatag cctccgcgac cggctgcaga acagcgggca    4560
gttcggtttc aggcaggtct tgcaacgtga caccctgtgc acggcgggag atgcaatagg    4620
tcaggctctc gctgaattcc ccaatgtcaa gcacttccgg aatcgggagc gcggccgatg    4680
caaagtgccg ataaacataa cgatctttgt agaaaccatc ggcgcagcta tttacccgca    4740
```

```
ggacatatcc acgccctcct acatcgaagc tgaaagcacg agattcttcg ccctccgaga    4800
gctgcatcag gtcggagacg ctgtcgaact tttcgatcag aaacttctcg acagacgtcg    4860
cggtgagttc aggcttttcc atgggtatat ctccttctta agttaaaca aaattatttc     4920 tagagggaaa ccgttgtggt ctccctatag tgagtcgtat taatttcgcg ggatcgagat    4980
cgatccaatt ccaatcccac aaaaatctga gcttaacagc acagttgctc ctctcagagc    5040
agaatcgggt attcaacacc ctcatatcaa ctactacgtt gtgtataacg gtccacatgc    5100
cggtatatac gatgactggg gttgtacaaa ggcggcaaca aacggcgttc ccggagttgc    5160
acacaagaaa tttgccacta ttacagaggc aagagcagca gctgacgcgt acacaacaag    5220
tcagcaaaca gacaggttga acttcatccc caaaggagaa gctcaactca gcccaagag    5280 ctttgctaag gccctaacaa gcccaccaaa gcaaaaagcc cactggctca cgctaggaac    5340
caaaaggccc agcagtgatc cagccccaaa agagatctcc tttgccccgg agattacaat    5400
ggacgatttc ctctatcttt acgatctagg aaggaagttc gaaggtgaag gtgacgacac    5460
tatgttcacc actgataatg agaaggttag cctcttcaat ttcagaaaga atgctgaccc    5520
acagatggtt agagaggcct acgcagcagg tctcatcaag acgatctacc cgagtaacaa    5580
tctccaggag atcaaatacc ttcccaagaa ggttaaagat gcagtcaaaa gattcaggac    5640
taattgcatc aagaacacag agaaagacat atttctcaag atcagaagta ctattccagt    5700
atggacgatt caaggcttgc ttcataaacc aaggcaagta atagagattg gagtctctaa    5760
aaaggtagtt cctactgaat ctaaggccat gcatggagtc taagattcaa atcgaggatc    5820
taacagaact cgccgtgaag actggcgaac agttcataca gagtcttttta cgactcaatg    5880 acaagaagaa aatcttcgtc aacatggtgg agcacgacac tctggtctac tccaaaaatg    5940
tcaaagatac agtctcagaa gaccaaaggg ctattgagac ttttcaacaa aggataattt    6000
cgggaaacct cctcggattc cattgcccag ctatctgtca cttcatcgaa aggacagtag    6060
aaaaggaagg tggctcctac aaatgccatc attgcgataa aggaaaggct atcattcaag    6120
atgcctctgc cgacagtggt cccaaagatg gaccccccacc cacgaggagc atcgtggaaa    6180
aagaagacgt tccaaccacg tcttcaaagc aagtggattg atgtgacatc tccactgacg    6240
taagggatga cgcacaatcc cactatcctt cgcaagaccc ttcctctata taggaagtt     6300 catttcattt ggagaggaca cgctcgagct catttctcta ttacttcagc cataacaaaa    6360
gaactctttt ctcttcttat taaaccatga aaaagcctga actcaccgcg acgtctgtcg    6420
agaagtttct gatcgaaaag ttcgacagcg tctccgacct gatgcagctc tcggagggcg    6480
aagaatctcg tgctttcagc ttcgatgtag gagggcgtgg atatgtcctg cgggtaaata    6540
gctgcgccga tggtttctac aaagatcgtt atgtttatcg gcactttgca tcggccgcgc    6600
tcccgattcc ggaagtgctt gacattgggg aattcagcga gagcctgacc tattgcatct    6660
cccgccgtgc acagggtgtc acgttgcaag acctgcctga aaccgaactg cccgctgttc    6720
tgcagccggt cgcggaggcc atggatgcga tcgctgcggc cgatcttagc cagacgagcg    6780
ggttcggccc attcggaccg caaggaatcg gtcaatacac tacatggcgt gatttcatat    6840
gcgcgattgc tgatccccat gtgtatcact ggcaaactgt gatggacgac accgtcagtg    6900
cgtccgtcgc gcaggctctc gatgagctga tgctttgggc cgaggactgc cccgaagtcc    6960
ggcacctcgt gcacgcggat ttcggctcca acaatgtcct gacggacaat ggccgcataa    7020
cagcggtcat tgactggagc gaggcgatgt tcggggattc ccaatacgag gtcgccaaca    7080
```

```
tcttcttctg gaggccgtgg ttggcttgta tggagcagca gacgcgctac ttcgagcgga    7140
ggcatccgga gcttgcagga tcgccgcggc tccgggcgta tatgctccgc attggtcttg    7200
accaactcta tcagagcttg gttgacggca atttcgatga tgcagcttgg gcgcagggtc    7260
gatgcgacgc aatcgtccga tccggagccg ggactgtcgg gcgtacacaa atcgcccgca    7320
gaagcgcggc cgtctggacc gatggctgtg tagaagtact cgccgatagt ggaaaccgac    7380
gccccagcac tcgtccgagg gcaaaggaat agtgaggtac ctaaagaagg agtgcgtcga    7440
agcagatcgt tcaaacattt ggcaataaag tttcttaaga ttgaatcctg ttgccggtct    7500
tgcgatgatt atcatataat ttctgttgaa ttacgttaag catgtaataa ttaacatgta    7560
atgcatgacg ttatttatga gatgggtttt tatgattaga gtcccgcaat tatacattta    7620
atacgcgata gaaaacaaaa tatagcgcgc aaactaggat aaattatcgc gcgcggtgtc    7680
atctatgtta ctagatcgat gtcgaatcga tcaacctgca ttaatgaatc ggccaacgcg    7740
cggggagagg cggtttgcgt attgggcgct cttccgcttc ctcgctcact gactcgctgc    7800
gctcggtcgt tcggctgcgg cgagcggtat cagctcactc aaaggcggta atacggttat    7860
ccacagaatc aggggataac gcaggaaaga acatgtgagc aaaaggccag caaaaggcca    7920
ggaaccgtaa aaaggccgcg ttgctggcgt ttttccatag gctccgcccc cctgacgagc    7980
atcacaaaaa tcgacgctca agtcagaggt ggcgaaaccc gacaggacta taaagatacc    8040
aggcgtttcc ccctggaagc tccctcgtgc gctctcctgt tccgaccctg ccgcttaccg    8100
gatacctgtc cgcctttctc ccttcgggaa gcgtggcgct ttctcaatgc tcacgctgta    8160
ggtatctcag ttcggtgtag gtcgttcgct ccaagctggg ctgtgtgcac gaaccccccg    8220
ttcagcccga ccgctgcgcc ttatccggta actatcgtct tgagtccaac ccggtaagac    8280
acgacttatc gccactggca gcagccactg gtaacaggat tagcagagcg aggtatgtag    8340
gcggtgctac agagttcttg aagtggtggc ctaactacgg ctacactaga aggacagtat    8400
ttggtatctg cgctctgctg aagccagtta ccttcggaaa aagagttggt agctcttgat    8460
ccggcaaaca aaccaccgct ggtagcggtg gttttttttgt ttgcaagcag cagattacgc    8520
gcagaaaaaa aggatctcaa gaagatcctt tgatcttttc tacggggtct gacgctcagt    8580
ggaacgaaaa ctcacgttaa gggattttgg tcatgacatt aacctataaa aataggcgta    8640
tcacgaggcc ctttcgtctc gcgcgtttcg gtgatgacgg tgaaaacctc tgacacatgc    8700
agctcccgga gacggtcaca gcttgtctgt aagcggatgc cgggagcaga caagcccgtc    8760
agggcgcgtc agcgggtgtt ggcgggtgtc ggggctggct taactatgcg gcatcagagc    8820
agattgtact gagagtgcac catatggaca tattgtcgtt agaacgcggc tacaattaat    8880
acataacctt atgtatcata cacatacgat ttaggtgaca ctatagaacg gcgcgccaag    8940
cttggatctc ctgcagcccg ggggatccgc ccacgtacgg taccatctgc taatattta    9000
aatcacatgc aagagaggag gcatggttcc attttctacc ttcacattat ttgagaaaaa    9060
cgaacttgtt ctgtgtttta tttttgccct tcacattagt acaacgtgga agactcatgg    9120
ttacacagaa tcatacataa gtacaatgct tgtccctaag aaaacaagca ctcgttgtat    9180
tgaacccttta cggctcatgc ggccgcgaat tcactagtga ttgaattcgc ggccgcttag    9240
tccgacttgg ccttggcggc gcggccgac tctttgagcg tgaagatctg cgccgtctcg    9300
ggcacagcgc cgtagttgac aaagaggtgc gcggtcttga agaaggccgt gatgatgggc    9360
tcgtcgttcc tgcgcacgag gtgcgggtac gcggccgcaa agtgcttggt ggcttcgttg    9420
agcttgtagt gcggaatgat cgggaacaag tggtggacct ggtgcgtgcc aatgtggtgg    9480
```

```
ctcaggttgt ccacgaacgc gccgtacgag cggtcgacgc tcgagaggtt gcccttgacg    9540
tacgtccact ccgagtcgcc gtaccacggc gtcgcttcgt cgttgtggtg caagaaggtc    9600
gtaatgacga ggaacgaagc aaagacaaag agcggcgcat agtagtagag gcccatgacg    9660
gcaaagccga gcgagtatgt gaggtacgcg tacgggcga agaaggcggc ccagacgccg    9720
agcgacacga tgacggccga cgcgcggcga aggaggagcg ggtcccacgg gtcaaagtgg    9780
ctcatcgtgc gcggggcata cccgaccttc aagtagacaa accacgcacc gccgagcgtg    9840
tagacccatt ggcgcacgtc ctggaggtcc ttgaccgacc ggtgcgggta aaagatctcg    9900
tccttatcaa tgttgcccgt gttcttgtgg tggtggcggt gcgtcacgcg ccagctctcg    9960
aacggcgtca aaatcgcaga gtgcatgatg cagccgatga taaagttgac gctgtggtag   10020
cgcgagaagg ccgagtggcc gcagtcgtgg ccgaccgtga agaagcccca gaagatgacg   10080
ccctgcacgt agatgtaggt ggcgcaaacg agcgcgtgga gcagaacgtt atcggcaatg   10140
aacggcgtcg agcgcgccgc gtagagcagc gccgccgagg ccgacgcgtt gaagatcgcg   10200
cgggccgtgt agtagagcga gaggccgagg ttcgactcaa agcacgcgtt cgggatcgag   10260
tgcttgagct ccgtgagcgt cgggaactcg accttcgtct tatcctcagt catgcggccg   10320
ctgaagtatt gcttcttagt taaccttttcc tttctctctc agctatgtga attcattttg   10380
ctttcgtcac aatttatata gtgaaattgg atctttggag ttaacgcctt cacaggatta   10440
tcgtgttaga acaatgcttt ttcatgttct aattagtagt acattacaaa tgtgcactct   10500
attcaataag catcttttgg cacgttaata aatcatgtga aaaaaaata ctactatttc    10560 aaagaaagtg ttgtaaaaag aaacggaaag agagctggct tcagttgttg agacttgttt   10620
gctagtaaaa atggtgtgaa gagtgattca tggtgaggtg gtttttcgtc cctttctgtt   10680
tgcatgaaaa acaaatggca agagatgacg taggattcct tcccttaacg attatctgtt   10740
tttaatttca aatatacata taggaattta tgaattacta aggttgtaaa atatgctggt   10800
catttattta tggctaaaat atttttttt ctcgtaaata taaaaatatt taaaatttat    10860
ttttatcata ttttttatcc ttataaaatt atgtgtacaa cctatataaa aaatatcat    10920 atttaatatt gattatatgt ttaatcaata taaaaaatca ttatcatata tttagattta   10980
ttcgaatata catctaaaca aaaaataaca tattttaatt ttatgaagaa aaaaaaatat   11040
tttatccttt atttatttaa gattaattaa tagttatgta ttgtggaaag acttttacac   11100
atgcaataga tatactgaat caattagatg ccaatgctga gttggaaatc acttgaggag   11160
gggaggagac ttgccaatgc ttttcagttt catttaaatg atttagtgga ggagatagag   11220
tagtgataaa ggcatgcccc aattttggag tgtatatatg agtggaaata agagagggat   11280
agagagaaaa aataaagaga gtaaaaataa ttaatgtgaa atgatatgat aaaaaaataa   11340
agaaagagat aaagagaaaa atgaaatgag agatagatga aatagagagt agatacatgt   11400
ttgtttaggt ttttttttagg aaataacaca ttttttttctc atcacttatt actcactgtc   11460
aatttcctct ctttcaatca taatgatatg atttgtttaa caaaaatgtg aaaaaacata   11520
taaagtaaaa tattttttata aattgataaa taaaaattta caaaatttat ttcttattaa   11580
attgaataga aaatgaaaga aaagaaaaga aaagtatat ataaaatgat atagctttaa    11640
aaagaataaa ttttttcatat cagtcttttt ttaataattt agaaatattt aagtatatag   11700
caaaaatata atgtacttta catatgcata aataataatt tgaaaataga actaatagaa   11760
tagagaaaaa agtaatataa taattaacta tatgaaaatt tagaagggac aatattttta   11820
```

```
attaagaata taaacaatat ttcttttcat gtaatgaggg acggatgtac ggggccagtg    11880
ttggagtcaa agccaaaata gtcacgggga aattaatgca ctgcatgact attcgaaaaa    11940
attcactagc cttacttaga tgttagatta atagctaggg ggtgcagata attttgaaag    12000
gcatgaaaaa cattaatttg tacattgcaa gcttttgatg acaagctttg caattgttca    12060
cactacctta tgccatttat aaatagagtg attggcatat gaaggaaatc atgagagtcg    12120
aagcgaaaaa caaagcttga gagtgtagga aaaatacagt ttttttggta aaaatacagt    12180
atttgaatag gagcgaaaaa tatcctttca aaatgatcct tttctttttt tttttttttc    12240
ttgttgttct tggtcagtta ttcaaaggaa aagggattga aataaaaact tgcatgtggg    12300
atcgtacgtc gagtcgacct gca                                            12323

<210> SEQ ID NO 89
<211> LENGTH: 12456
<212> TYPE: DNA
<213> ORGANISM: Artificial Sequence
<220> FEATURE:
<223> OTHER INFORMATION: Plasmid pKR585
<220> FEATURE:
<221> NAME/KEY: misc_feature
<222> LOCATION: (1201)..(1201)
<223> OTHER INFORMATION: n is a, c, g, or t

<400> SEQUENCE: 89
ggatctggcc ggccggatct cgtacgtcct cgaagagaag ggttaataac acattttta     60 acattttaa cacaaatttt agttatttaa aaatttatta aaaaatttaa aataagaaga    120
ggaactcttt aaataaatct aacttacaaa atttatgatt tttaataagt tttcaccaat    180
aaaaaatgtc ataaaaatat gttaaaaagt atattatcaa tattctcttt atgataaata    240
aaaagaaaaa aaaaataaaa gttaagtgaa aatgagattg aagtgacttt aggtgtgtat    300
aaatatatca accccgccaa caatttattt aatccaaata tattgaagta tattattcca    360
tagcctttat ttatttatat atttattata taaaagcttt atttgttcta ggttgttcat    420
gaaatatttt tttggtttta tctccgttgt aagaaaatca tgtgctttgt gtcgccactc    480
actattgcag cttttttcatg cattggtcag attgacggtt gattgtattt ttgttttta    540 tggttttgtg ttatgactta agtcttcatc tctttatctc ttcatcaggt ttgatggtta    600
cctaatatgg tccatgggta catgcatggt taaattaggt ggccaacttt gttgtgaacg    660
atagaatttt ttttatatta agtaaactat tttatatta tgaaataata ataaaaaaaa    720
tattttatca ttattaacaa aatcatatta gttaatttgt taactctata ataaaagaaa    780
tactgtaaca ttcacattac atggtaacat cttttccaccc ttttcatttgt tttttgtttg    840 atgactttt ttcttgttta aatttatttc ccttctttta aatttggaat acattatcat    900
catatataaa ctaaaatact aaaaacagga ttacacaaat gataaataat aacacaaata    960
tttataaatc tagctgcaat atatttaaac tagctatatc gatattgtaa aataaaacta   1020
gctgcattga tactgataaa aaaatatcat gtgctttctg gactgatgat gcagtatact   1080
tttgacattg cctttatttt atttttcaga aaagctttct tagttctggg ttcttcatta   1140
tttgtttccc atctccattg tgaattgaat catttgcttc gtgtcacaaa tacaatttag   1200
ntaggtacat gcattggtca gattcacggt ttattatgtc atgacttaag ttcatggtag   1260
tacattacct gccacgcatg cattatattg gttagatttg ataggcaaat tggttgtca    1320 acaatataaa tataaataat gttttatat tacgaaataa cagtgatcaa acaaacagt    1380 tttatcttta ttaacaagat tttgttttg tttgatgacg ttttttaatg tttacgcttt    1440
```

-continued

```
cccccttctt ttgaatttag aacactttat catcataaaa tcaaatacta aaaaaattac    1500
atatttcata aataataaca caaatatttt taaaaaatct gaaataataa tgaacaatat    1560
tacatattat cacgaaaatt cattaataaa aatattatat aaataaaatg taatagtagt    1620
tatatgtagg aaaaaagtac tgcacgcata atatatacaa aaagattaaa atgaactatt    1680
ataaataata acactaaatt aatggtgaat catatcaaaa taatgaaaaa gtaaataaaa    1740
tttgtaatta acttctatat gtattacaca cacaaataat aaataatagt aaaaaaaatt    1800
atgataaata tttaccatct cataagatat ttaaaataat gataaaaata tagattattt    1860
tttatgcaac tagctagcca aaaagagaac acgggtatat ataaaaagag tacctttaaa    1920
ttctactgta cttcctttat tcctgacgtt tttatatcaa gtggacatac gtgaagattt    1980
taattatcag tctaaatatt tcattagcac ttaatacttt tctgttttat tcctatccta    2040
taagtagtcc cgattctccc aacattgctt attcacacaa ctaactaaga aagtcttcca    2100
tagcccccca agcggccgca caatggcgac tcgacagcga actgccacca ctgttgtggt    2160
cgaggacctt cccaaggtca ctcttgaggc caagtctgaa cctgtgttcc ccgatatcaa    2220
gaccatcaag gatgccattc ccgcgcactg cttccagccc tcgctcgtca cctcattcta    2280
ctacgtcttc cgcgattttg ccatggtctc tgccctcgtc tgggctgctc tcacctacat    2340
ccccagcatc cccgaccaga ccctccgcgt cgcagcttgg atggtctacg gcttcgtcca    2400
gggtctgttc tgcaccggtg tctggattct cggccatgag tgcggccacg gtgctttctc    2460
tctccacgga aaggtcaaca atgtgaccgg ctggttcctc cactcgttcc tcctcgtccc    2520
ctacttcagc tggaagtact ctcaccaccg ccaccaccgc ttcaccggcc acatggatct    2580
cgacatggct ttcgtcccca agactgagcc caagccctcc aagtcgctca tgattgctgg    2640
cattgacgtc gccgagcttg ttgaggacac ccccgctgct cagatggtca agctcatctt    2700
ccaccagctt ttcggatggc aggcgtacct cttcttcaac gctagctctg caagggcag     2760 caagcagtgg gagcccaaga ctggcctctc caagtggttc cgagtcagtc acttcgagcc    2820
taccagcgct gtcttccgcc caacgaggc catcttcatc ctcatctccg atatcggtct     2880
tgctctaatg ggaactgctc tgtactttgc ttccaagcaa gttggtgttt cgaccattct    2940
cttcctctac cttgttccct acctgtgggt tcaccactgg ctcgttgcca ttacctacct    3000
ccaccaccac cacaccgagc tccctcacta caccgctgag ggctggacct acgtcaaggg    3060
agctctcgcc actgtcgacc gtgagtttgg cttcatcgga aagcacctct ccacggtat     3120 cattgagaag cacgttgttc accatctctt ccctaagatc cccttctaca aggctgacga    3180
ggccaccgag gccatcaagc ccgtcattgg cgaccactac tgccacgacg accgaagctt    3240
cctgggccag ctgtggacca tcttcggcac gctcaagtac gtcgagcacg accctgcccg    3300
acccggtgcc atgcgatgga caaggacta ggctaggcgg ccgcgacaca agtgtgagag     3360
tactaaataa atgctttggt tgtacgaaat cattcacta aataaaataa tcaaagctta     3420
tatatgcctt ccgctaaggc cgaatgcaaa gaaattggtt ctttctcgtt atcttttgcc    3480
acttttacta gtacgtatta attactactt aatcatcttt gtttacggct cattatatcc    3540
ggtctagagg atccaaggcc gcgaagttaa aagcaatgtt gtcacttgtc gtactaacac    3600
atgatgtgat agtttatgct agctagctat aacataagct gtctctgagt gtgttgtata    3660
ttaataaaga tcatcactgg tgaatggtga tcgtgtacgt accctactta gtaggcaatg    3720
gaagcactta gagtgtgctt tgtgcatggc cttgcctctg ttttgagact tttgtaatgt    3780
```

```
tttcgagttt aaatctttgc ctttgcgtac ggatccgtcg acggcgcgcc cgatcatccg   3840
gatatagttc ctcctttcag caaaaaaccc ctcaagaccc gtttagaggc cccaagggggt  3900
tatgctagtt attgctcagc ggtggcagca gccaactcag cttcctttcg ggctttgtta   3960
gcagccggat cgatccaagc tgtacctcac tattcctttg ccctcggacg agtgctgggg   4020
cgtcggtttc cactatcggc gagtacttct acacagccat cggtccagac ggccgcgctt   4080
ctgcgggcga tttgtgtacg cccgacagtc ccggctccgg atcggacgat tgcgtcgcat   4140
cgaccctgcg cccaagctgc atcatcgaaa ttgccgtcaa ccaagctctg atagagttgg   4200
tcaagaccaa tgcggagcat atacgcccgg agccgcggcg atcctgcaag ctccggatgc   4260
ctccgctcga agtagcgcgt ctgctgctcc atacaagcca accacggcct ccagaagaag   4320
atgttggcga cctcgtattg gaatccccg aacatcgcct cgctccagtc aatgaccgct    4380
gttatgcggc cattgtccgt caggacattg ttggagccga atccgcgtg cacgaggtgc    4440
cggacttcgg ggcagtcctc ggcccaaagc atcagctcat cgagagcctg cgcgacggac   4500
gcactgacgg tgtcgtccat cacagtttgc cagtgataca catgggatc agcaatcgcg    4560
catatgaaat cacgccatgt agtgtattga ccgattcctt gcggtccgaa tgggccgaac   4620
ccgctcgtct ggctaagatc ggccgcagcg atcgcatcca tagcctccgc gaccggctgc   4680
agaacagcgg gcagttcggt ttcaggcagg tcttgcaacg tgacaccctg tgcacggcgg   4740
gagatgcaat aggtcaggct ctcgctgaat tccccaatgt caagcacttc cggaatcggg   4800
agcgcggcc atgcaaagtg ccgataaaca taacgatctt tgtagaaacc atcggcgcag   4860
ctatttaccc gcaggacata tccacgccct cctacatcga agctgaaagc acgagattct   4920
tcgccctccg agagctgcat caggtcggag acgctgtcga acttttcgat cagaaacttc   4980
tcgacagacg tcgcggtgag ttcaggcttt tccatgggta tatctccttc ttaaagttaa   5040
acaaaattat ttctagaggg aaaccgttgt ggtctcccta tagtgagtcg tattaatttc   5100
gcgggatcga gatcgatcca attccaatcc cacaaaaatc tgagcttaac agcacagttg   5160
ctcctctcag agcagaatcg ggtattcaac accctcatat caactactac gttgtgtata   5220
acggtccaca tgccggtata tacgatgact ggggttgtac aaaggcggca acaaacggcg   5280
ttcccggagt tgcacacaag aaatttgcca ctattacaga ggcaagagca gcagctgacg   5340
cgtacacaac aagtcagcaa acagacaggt tgaacttcat ccccaaagga gaagctcaac   5400
tcaagcccaa gagctttgct aaggccctaa caagcccacc aaagcaaaaa gcccactggc   5460
tcacgctagg aaccaaaagg cccagcagtg atccagcccc aaaagagatc tcctttgccc   5520
cggagattac aatggacgat ttcctctatc tttacgatct aggaaggaag ttcgaaggtg   5580
aaggtgacga cactatgttc accactgata atgagaaggt tagcctcttc aatttcagaa   5640
agaatgctga cccacagatg gttagagagg cctacgcagc aggtctcatc aagacgatct   5700
acccgagtaa caatctccag gagatcaaat accttcccaa gaaggttaaa gatgcagtca   5760
aaagattcag gactaattgc atcaagaaca cagagaaaga catatttctc aagatcagaa   5820
gtactattcc agtatggacg attcaaggct tgcttcataa accaaggcaa gtaatagaga   5880
ttggagtctc taaaaaggta gttcctactg aatctaaggc catgcatgga gtctaagatt   5940
caaatcgagg atctaacaga actcgccgtg aagactggcg aacagttcat acagagtctt   6000
ttacgactca atgacaagaa gaaaatcttc gtcaacatgg tggagcacga cactctggtc   6060
tactccaaaa atgtcaaaga tacagtctca gaagaccaaa gggctattga acttttcaa   6120
caaaggataa tttcgggaaa cctcctcgga ttccattgcc cagctatctg tcacttcatc   6180
```

```
gaaaggacag tagaaaagga aggtggctcc tacaaatgcc atcattgcga taaaggaaag    6240
gctatcattc aagatgcctc tgccgacagt ggtcccaaag atggacccc  acccacgagg    6300 agcatcgtgg aaaaagaaga cgttccaacc acgtcttcaa agcaagtgga ttgatgtgac    6360
atctccactg acgtaaggga tgacgcacaa tcccactatc cttcgcaaga cccttcctct    6420
atataaggaa gttcatttca tttggagagg acacgctcga gctcatttct ctattacttc    6480
agccataaca aaagaactct tttctcttct tattaaacca tgaaaagcc  tgaactcacc    6540 gcgacgtctg tcgagaagtt tctgatcgaa aagttcgaca gcgtctccga cctgatgcag    6600
ctctcggagg gcgaagaatc tcgtgctttc agcttcgatg taggagggcg tggatatgtc    6660
ctgcgggtaa atagctgcgc cgatggtttc tacaaagatc gttatgttta tcggcacttt    6720
gcatcggccg cgctcccgat tccggaagtg cttgacattg gggaattcag cgagagcctg    6780
acctattgca tctcccgccg tgcacagggt gtcacgttgc aagacctgcc tgaaaccgaa    6840
ctgcccgctg ttctgcagcc ggtcgcggag gccatggatg cgatcgctgc ggccgatctt    6900
agccagacga gcgggttcgg cccattcgga ccgcaaggaa tcggtcaata cactacatgg    6960
cgtgatttca tatgcgcgat tgctgatccc catgtgtatc actggcaaac tgtgatggac    7020
gacaccgtca gtgcgtccgt cgcgcaggct ctcgatgagc tgatgctttg ggccgaggac    7080
tgccccgaag tccggcacct cgtgcacgcg gatttcggct ccaacaatgt cctgacggac    7140
aatggccgca taacagcggt cattgactgg agcgaggcga tgttcgggga ttcccaatac    7200
gaggtcgcca acatcttctt ctggaggccg tggttggctt gtatgagca  gcagacgcgc    7260 tacttcgagc ggaggcatcc ggagcttgca ggatcgccgc ggctccgggc gtatatgctc    7320
cgcattggtc ttgaccaact ctatcagagc ttggttgacg gcaatttcga tgatgcagct    7380
tgggcgcagg gtcgatgcga cgcaatcgtc cgatccggag ccgggactgt cgggcgtaca    7440
caaatcgccc gcagaagcgc ggccgtctgg accgatggct gtgtagaagt actcgccgat    7500
agtggaaacc gacgccccag cactcgtccg agggcaaagg aatagtgagg tacctaaaga    7560
aggagtgcgt cgaagcagat cgttcaaaca tttggcaata aagtttctta agattgaatc    7620
ctgttgccgg tcttgcgatg attatcatat aatttctgtt gaattacgtt aagcatgtaa    7680
taattaacat gtaatgcatg acgttattta tgagatgggt ttttatgatt agagtcccgc    7740
aattatacat ttaatacgcg atagaaaaca aaatatagcg cgcaaactag gataaattat    7800
cgcgcgcggt gtcatctatg ttactagatc gatgtcgaat cgatcaacct gcattaatga    7860
atcggccaac gcgcggggag aggcggtttg cgtattgggc gctcttccgc ttcctcgctc    7920
actgactcgc tgcgctcggt cgttcggctg cggcgagcgg tatcagctca ctcaaaggcg    7980
gtaatacggt tatccacaga atcaggggat aacgcaggaa agaacatgtg agcaaaaggc    8040
cagcaaaagg ccaggaaccg taaaaaggcc gcgttgctgg cgttttttcc ataggctccgc   8100 cccctgacg  agcatcacaa aaatcgacgc tcaagtcaga ggtggcgaaa cccgacagga    8160
ctataaagat accaggcgtt tcccctggaa gctccctcg  tgcgctctcc tgttccgacc    8220
ctgccgctta ccggatacct gtccgccttt ctcccttcgg gaagcgtggc gctttctcaa    8280
tgctcacgct gtaggtatct cagttcggtg taggtcgttc gctccaagct gggctgtgtg    8340
cacgaacccc ccgttcagcc cgaccgctgc gccttatccg gtaactatcg tcttgagtcc    8400
aacccggtaa gacacgactt atcgccactg gcagcagcca ctggtaacag gattagcaga    8460
gcgaggtatg taggcggtgc tacagagttc ttgaagtggt ggcctaacta cggctacact    8520
```

```
agaaggacag tatttggtat ctgcgctctg ctgaagccag ttaccttcgg aaaaagagtt    8580
ggtagctctt gatccggcaa acaaaccacc gctggtagcg gtggttttt tgtttgcaag     8640
cagcagatta cgcgcagaaa aaaggatct caagaagatc ctttgatctt ttctacgggg     8700
tctgacgctc agtggaacga aaactcacgt taagggattt tggtcatgac attaacctat    8760
aaaaataggc gtatcacgag gccctttcgt ctcgcgcgtt tcggtgatga cggtgaaaac    8820
ctctgacaca tgcagctccc ggagacggtc acagcttgtc tgtaagcgga tgccgggagc    8880
agacaagccc gtcagggcgc gtcagcgggt gttggcgggt gtcggggctg gcttaactat    8940
gcggcatcag agcagattgt actgagagtg caccatatgg acatattgtc gttagaacgc    9000
ggctacaatt aatacataac cttatgtatc atacacatac gatttaggtg acactataga    9060
acggcgcgcc aagcttggat ctcctgcagc ccggggggatc cgcccacgta cggtaccatc    9120
tgctaatatt ttaaatcaca tgcaagagag gaggcatggt tccatttttct accttcacat    9180
tatttgagaa aaacgaactt gttctgtgtt ttatttttgc ccttcacatt agtacaacgt    9240
ggaagactca tggttacaca gaatcataca taagtacaat gcttgtccct aagaaaacaa    9300
gcactcgttg tattgaacct ttacggctca tgccggccgcg aattcactag tgattgaatt    9360
cgcggccgct tagtccgact tggccttggc ggccgcggcc gactctttga gcgtgaagat    9420
ctgcgccgtc tcgggcacag cgccgtagtt gacaaagagg tgcgcggtct tgaagaaggc    9480
cgtgatgatg ggctcgtcgt tcctgcgcac gaggtgcggg tacgcggccg caaagtgctt    9540
ggtggcttcg ttgagcttgt agtgcggaat gatcgggaac aagtggtgga cctggtgcgt    9600
gccaatgtgg tggctcaggt tgtccacgaa cgcgccgtac gagcggtcga cgctcgagag    9660
gttgcccttg acgtacgtcc actccgagtc gccgtaccac ggcgtcgctt cgtcgttgtg    9720
gtgcaagaag gtcgtaatga cgaggaacga agcaaagaca aagagcggcg catagtagta    9780
gaggcccatg acggcaaagc cgagcgagta tgtgaggtac gcgtacgcgg cgaagaaggc    9840
ggcccagacg ccgagcgaca cgatgacggc cgacgcgcgg cgaaggagga gcgggtccca    9900
cgggtcaaag tggctcatcg tgcgcggggc ataccccgacc ttcaagtaga caaaccacgc    9960
accgccgagc gtgtagaccc attggcgcac gtcctggagg tccttgaccg accggtgcgg   10020
gtaaaagatc tcgtccttat caatgttgcc cgtgttcttg tggtggtggc ggtgcgtcac   10080
gcgccagctc tcgaacggcg tcaaaatcgc agagtgcatg atgcagccga tgataaagtt   10140
gacgctgtgg tagcgcgaga aggccgagtg gccgcagtcg tggccgaccg tgaagaagcc   10200
ccagaagatg acgccctgca cgtagatgta ggtggcgcaa acgagcgcgt ggagcagaac   10260
gttatcggca tgaacggcg tcgagcgcgc cgcgtagagc agcgccgccg aggccgacgc   10320
gttgaagatc gcgcgggccg tgtagtagag cgagaggccg aggttcgact caaagcacgc   10380
gttcgggatc gagtgcttga gctccgtgag cgtcgggaac tcgaccttcg tcttatcctc   10440
agtcatgcgc ccgctgaagt attgcttctt agttaacctt tcctttctct ctcagctatg   10500
tgaattcatt ttgctttcgt cacaatttat atagtgaaat tggatctttg gagttaacgc   10560
cttcacagga ttatcgtgtt agaacaatgc tttttcatgt tctaattagt agtacattac   10620
aaatgtgcac tctattcaat aagcatcttt tggcacgtta ataaatcatg tgaaaaaaaa   10680
atactactat ttcaaagaaa gtgttgtaaa aagaaacgga aagagagctg gcttcagttg   10740
ttgagacttg tttgctagta aaatggtgt gaagagtgat tcatggtgag gtggttttc     10800
gtcccttttct gtttgcatga aaacaaatg gcaagagatg acgtaggatt ccttcccta    10860
acgattatct gttttaatt tcaaatatac atataggaat ttatgaatta ctaaggttgt   10920
```

-continued

```
aaaatatgct ggtcatttat ttatggctaa atatttttt tttctcgtaa atataaaaat    10980
atttaaaatt tatttttatc atattttta tccttataaa attatgtgta caacctatat    11040
aaaaaaatat catatttaat attgattata tgtttaatca atataaaaaa tcattatcat    11100
atatttagat ttattcgaat atacatctaa acaaaaaata acatatttta attttatgaa    11160
gaaaaaaaaa tattttatcc tttatttatt taagattaat taatagttat gtattgtgga    11220 aagacttta cacatgcaat agatatactg aatcaattag atgccaatgc tgagttggaa    11280
atcacttgag gagggagga gacttgccaa tgcttttcag tttcatttaa atgatttagt    11340
ggaggagata gagtagtgat aaaggcatgc cccaattttg gagtgtatat atgagtggaa    11400
ataagagagg gatagagaga aaaaataaag agagtaaaaa taattaatgt gaaatgatat    11460
gataaaaaaa taagaaaga gataaagaga aaaatgaaat gagagataga tgaaatagag    11520
agtagataca tgtttgttta ggttttttt aggaaataac acattttttt ctcatcactt    11580
attactcact gtcaatttcc tctctttcaa tcataatgat atgatttgtt taacaaaaat    11640
gtgaaaaaac atataagta aaatatttt ataaattgat aaataaaaat ttacaaaatt    11700
tatttcttat taaattgaat agaaaatgaa agaaagaaa agaaaagta tatataaaat    11760 gatatagctt taaaaagaat aaattttca tatcagtctt ttttaataa tttagaaata    11820 tttaagtata tagcaaaaat ataatgtact ttacatatgc ataaataata atttgaaaat    11880
agaactaata gaatagagaa aaagtaata taataattaa ctatatgaaa atttagaagg    11940
gacaatattt ttaattaaga atataaacaa tatttctttt catgtaatga gggacggatg    12000
tacggggcca gtgttggagt caaagccaaa atagtcacgg ggaaattaat gcactgcatg    12060
actattcgaa aaaattcact agccttactt agatgttaga ttaatagcta ggggggtgcag    12120 ataattttga aaggcatgaa aaacattaat ttgtacattg caagctttg atgacaagct    12180 ttgcaattgt tcacactacc ttatgccatt tataaataga gtgattggca tatgaaggaa    12240
atcatgagag tcgaagcgaa aaacaaagct tgagagtgta ggaaaaatac agttttttg    12300 gtaaaaatac agtatttgaa taggagcgaa aaatatcctt tcaaaatgat ccttttcttt    12360
tttttttttt ttcttgttgt tcttggtcag ttattcaaag gaaagggat tgaaataaaa    12420 acttgcatgt gggatcgtac gtcgagtcga cctgca                              12456
```

<210> SEQ ID NO 90
<211> LENGTH: 9088
<212> TYPE: DNA
<213> ORGANISM: Artificial Sequence
<220> FEATURE:
<223> OTHER INFORMATION: Plasmid pKR578
<220> FEATURE:
<221> NAME/KEY: misc_feature
<222> LOCATION: (6951)..(6951)
<223> OTHER INFORMATION: n is a, c, g, or t

<400> SEQUENCE: 90

```
ggccgcgaca caagtgtgag agtactaaat aaatgctttg gttgtacgaa atcattacac      60
taaataaaat aatcaaagct tatatatgcc ttccgctaag gccgaatgca agaaattgg     120 ttctttctcg ttatcttttg ccacttttac tagtacgtat taattactac ttaatcatct    180
ttgtttacgg ctcattatat ccggtctaga ggatccaagg ccgcgaagtt aaaagcaatg    240
ttgtcacttg tcgtactaac acatgatgtg atagttatg ctagctagct ataacataag    300
ctgtctctga gtgtgttgta tattaataaa gatcatcact ggtgaatggt gatcgtgtac    360
```

-continued

```
gtaccctact tagtaggcaa tggaagcact tagagtgtgc tttgtgcatg gccttgcctc    420
tgttttgaga cttttgtaat gttttcgagt ttaaatcttt gcctttgcgt acggatccgt    480
cgacggcgcg cccgatcatc cggatatagt tcctcctttc agcaaaaaac ccctcaagac    540
ccgtttagag gccccaaggg gttatgctag ttattgctca gcggtggcag cagccaactc    600
agcttccttt cgggctttgt tagcagccgg atcgatccaa gctgtacctc actattcctt    660
tgccctcgga cgagtgctgg ggcgtcggtt ccactatcg gcgagtactt ctacacagcc    720
atcggtccag acggccgcgc ttctgcgggc gatttgtgta cgcccgacag tcccggctcc    780
ggatcggacg attgcgtcgc atcgaccctg cgcccaagct gcatcatcga aattgccgtc    840
aaccaagctc tgatagagtt ggtcaagacc aatgcggagc atatacgccc ggagccgcgg    900
cgatcctgca agctccggat gcctccgctc gaagtagcgc gtctgctgct ccatacaagc    960
caaccacggc ctccagaaga gatgttggc gacctcgtat tgggaatccc cgaacatcgc   1020
ctcgctccag tcaatgaccg ctgttatgcg gccattgtcc gtcaggacat tgttggagcc   1080
gaaatccgcg tgcacgaggt gccggacttc ggggcagtcc tcggcccaaa gcatcagctc   1140
atcgagagcc tgcgcgacgg acgcactgac ggtgtcgtcc atcacagttt gccagtgata   1200
cacatgggga tcagcaatcg cgcatatgaa atcacgccat gtagtgtatt gaccgattcc   1260
ttgcggtccg aatgggccga acccgctcgt ctggctaaga tcggccgcag cgatcgcatc   1320
catagcctcc gcgaccggct gcagaacagc gggcagttcg gtttcaggca ggtcttgcaa   1380
cgtgacaccc tgtgcacggc gggagatgca ataggtcagg ctctcgctga attccccaat   1440
gtcaagcact tccggaatcg ggagcgcggc cgatgcaaag tgccgataaa cataacgatc   1500
tttgtagaaa ccatcggcgc agctatttac ccgcaggaca tatccacgcc ctcctacatc   1560
gaagctgaaa gcacgagatt cttcgccctc cgagagctgc atcaggtcgg agacgctgtc   1620 gaactttcg atcagaaact tctcgacaga cgtcgcggtg agttcaggct tttccatggg   1680
tatatctcct tcttaaagtt aaacaaaatt atttctagag ggaaaccgtt gtggtctccc   1740
tatagtgagt cgtattaatt tcgcgggatc gagatcgatc caattccaat cccacaaaaa   1800
tctgagctta acagcacagt tgctcctctc agagcagaat cgggtattca acaccctcat   1860
atcaactact acgttgtgta taacggtcca catgccggta tatcgatgac ctggggttgt   1920
acaaaggcgg caacaaacgg cgttcccgga gttgcacaca agaaatttgc cactattaca   1980
gaggcaagag cagcagctga cgcgtacaca acaagtcagc aaacagacag gttgaacttc   2040
atccccaaag gagaagctca actcaagccc aagagctttg ctaaggccct aacaagccca   2100
ccaaagcaaa aagcccactg gctcacgcta ggaaccaaaa ggcccagcag tgatccagcc   2160
ccaaaagaga tctcctttgc cccggagatt acaatggacg atttcctcta tctttacgat   2220
ctaggaagga agttcgaagg tgaaggtgac gacactatgt tcaccactga taatgagaag   2280
gttagcctct tcaatttcag aaagaatgct gacccacaga tggttagaga ggcctacgca   2340
gcaggtctca tcaagacgat ctacccgagt aacaatctcc aggagatcaa ataccttccc   2400
aagaaggtta aagatgcagt caaaagattc aggactaatt gcatcaagaa cacagagaaa   2460
gacatatttc tcaagatcag aagtactatt ccagtatgga cgattcaagg cttgcttcat   2520
aaaccaaggc aagtaataga gattggagtc tctaaaaagg tagttcctac tgaatctaag   2580
gccatgcatg gagtctaaga ttcaaatcga ggatctaaca gaactcgccg tgaagactgg   2640
cgaacagttc atacagagtc ttttacgact caatgacaag aagaaaatct tcgtcaacat   2700
ggtggagcac gacactctgg tctactccaa aaatgtcaaa gatacagtct cagaagacca   2760
```

```
aagggctatt gagactttc aacaaaggat aatttcggga aacctcctcg gattccattg    2820
cccagctatc tgtcacttca tcgaaaggac agtagaaaag gaaggtggct cctacaaatg    2880
ccatcattgc gataaaggaa aggctatcat tcaagatgcc tctgccgaca gtggtcccaa    2940
agatggaccc ccacccacga ggagcatcgt ggaaaaagaa gacgttccaa ccacgtcttc    3000
aaagcaagtg gattgatgtg acatctccac tgacgtaagg gatgacgcac aatcccacta    3060
tccttcgcaa gaccctcct ctatataagg aagttcattt catttggaga ggacacgctc    3120
gagctcattt ctctattact tcagccataa caaaagaact cttttctctt cttattaaac    3180
catgaaaaag cctgaactca ccgcgacgtc tgtcgagaag tttctgatcg aaaagttcga    3240
cagcgtctcc gacctgatgc agctctcgga gggcgaagaa tctcgtgctt tcagcttcga    3300
tgtaggaggg cgtggatatg tcctgcgggt aaatagctgc gccgatggtt tctacaaaga    3360
tcgttatgtt tatcggcact ttgcatcggc cgcgctcccg attccggaag tgcttgacat    3420
tggggaattc agcgagagcc tgacctattg catctcccgc cgtgcacagg gtgtcacgtt    3480
gcaagacctg cctgaaaccg aactgcccgc tgttctgcag ccggtcgcgg aggccatgga    3540
tgcgatcgct gcggccgatc ttagccagac gagcgggttc ggcccattcg gaccgcaagg    3600
aatcggtcaa tacactacat ggcgtgattt catatgcgcg attgctgatc ccatgtgta    3660
tcactggcaa actgtgatgg acgaccacgt cagtgcgtcc gtcgcgcagg ctctcgatga    3720
gctgatgctt tgggccgagg actgccccga agtccggcac ctcgtgcacg cggatttcgg    3780
ctccaacaat gtcctgacgg acaatggccg cataacagcg gtcattgact ggagcgaggc    3840
gatgttcggg gattcccaat acgaggtcgc caacatcttc ttctggaggc cgtggttggc    3900
ttgtatggag cagcagacgc gctacttcga gcggaggcat ccggagcttg caggatcgcc    3960
gcggctccgg gcgtatatgc tccgcattgg tcttgaccaa ctctatcaga gcttggttga    4020
cggcaatttc gatgatgcag cttgggcgca gggtcgatgc gacgcaatcg tccgatccgg    4080
agccgggact gtcgggcgta cacaaatcgc ccgcagaagc gcggccgtct ggaccgatgg    4140
ctgtgtagaa gtactcgccg atagtggaaa ccgacgcccc agcactcgtc cgagggcaaa    4200
ggaatagtga ggtacctaaa gaaggagtgc gtcgaagcag atcgttcaaa catttggcaa    4260
taaagttct taagattgaa tcctgttgcc ggtcttgcga tgattatcat ataatttctg    4320
ttgaattacg ttaagcatgt aataattaac atgtaatgca tgacgttatt tatgagatgg    4380
gttttatga ttagagtccc gcaattatac atttaatacg cgatagaaaa caaaatatag    4440
cgcgcaaact aggataaatt atcgcgcgcg gtgtcatcta tgttactaga tcgatgtcga    4500
atcgatcaac ctgcattaat gaatcggcca acgcgcgggg agaggcggtt tgcgtattgg    4560
gcgctcttcc gcttcctcgc tcactgactc gctgcgctcg gtcgttcggc tgcggcgagc    4620
ggtatcagct cactcaaagg cggtaatacg gttatccaca gaatcagggg ataacgcagg    4680
aaagaacatg tgagcaaaag gccagcaaaa ggccaggaac cgtaaaaagg ccgcgttgct    4740
ggcgttttc cataggctcc gcccccctga cgagcatcac aaaaatcgac gctcaagtca    4800
gaggtggcga aacccgacag gactataaag ataccaggcg tttccccctg gaagctccct    4860
cgtgcgctct cctgttccga ccctgccgct taccggatac ctgtccgcct ttctcccttc    4920
gggaagcgtg gcgctttctc aatgctcacg ctgtaggtat ctcagttcgg tgtaggtcgt    4980
tcgctccaag ctgggctgtg tgcacgaacc ccccgttcag cccgaccgct gcgccttatc    5040
cggtaactat cgtcttgagt ccaacccggt aagacacgac ttatcgccac tggcagcagc    5100
```

```
cactggtaac aggattagca gagcgaggta tgtaggcggt gctacagagt tcttgaagtg    5160
gtggcctaac tacggctaca ctagaaggac agtatttggt atctgcgctc tgctgaagcc    5220
agttaccttc ggaaaaagag ttggtagctc ttgatccggc aaacaaacca ccgctggtag    5280
cggtggtttt tttgtttgca agcagcagat tacgcgcaga aaaaaggat ctcaagaaga     5340 tcctttgatc ttttctacgg ggtctgacgc tcagtggaac gaaaactcac gttaagggat    5400
tttggtcatg acattaacct ataaaaatag gcgtatcacg aggccctttc gtctcgcgcg    5460
tttcggtgat gacggtgaaa acctctgaca catgcagctc ccggagacgg tcacagcttg    5520
tctgtaagcg gatgccggga gcagacaagc ccgtcagggc gcgtcagcgg gtgttggcgg    5580 gtgtcgggc tggcttaact atgcggcatc agagcagatt gtactgagag tgcaccatat    5640
ggacatattg tcgttagaac gcggctacaa ttaatacata accttatgta tcatacacat    5700
acgatttagg tgacactata gaacggcgcg ccaagcttgg atctcctgca ggatctggcc    5760
ggccggatct cgtacgtcct cgaagagaag ggttaataac acatttttta acattttaa    5820 cacaattttt agttatttaa aaatttatta aaaatttaa ataagaaga ggaactcttt     5880 aaataaatct aacttacaaa atttatgatt tttaataagt tttccaccaat aaaaaatgtc   5940 ataaaaatat gttaaaaagt atattatcaa tattctcttt atgataaata aaagaaaaa    6000 aaaaataaaa gttaagtgaa aatgagattg aagtgacttt aggtgtgtat aaatatatca    6060
accccgccaa caatttattt aatccaaata tattgaagta tattattcca tagcctttat    6120
ttatttatat atttattata taaaagcttt atttgttcta ggttgttcat gaaatatttt    6180
tttggtttta tctccgttgt aagaaaatca tgtgctttgt gtcgccactc actattgcag    6240 cttttttcatg cattggtcag attgacggtt gattgtattt ttgttttta tggttttgtg    6300 ttatgactta agtcttcatc tctttatctc ttcatcaggt ttgatggtta cctaatatgg    6360
tccatgggta catgcatggt taaattaggt ggccaactttt gttgtgaacg atagaattt    6420 ttttatatta agtaaactat ttttatatta tgaaataata ataaaaaaaa tattttatca    6480
ttattaacaa aatcatatta gttaatttgt taactctata ataaaagaaa tactgtaaca    6540
ttcacattac atggtaacat ctttccaccc tttcatttgt tttttgtttg atgacttttt    6600
ttcttgttta aatttatttc ccttctttta aatttggaat acattatcat catatataaa    6660
ctaaaatact aaaacagga ttacacaaat gataaataat aacacaaata tttataaatc     6720
tagctgcaat atatttaaac tagctatatc gatattgtaa aataaaacta gctgcattga    6780
tactgataaa aaaatatcat gtgctttctg gactgatgat gcagtatact tttgacattg    6840 ccttttatttt attttcaga aaagcttct tagttctggg ttcttcatta tttgtttccc     6900
atctccattg tgaattgaat catttgcttc gtgtcacaaa tacaatttag ntaggtacat    6960
gcattggtca gattcacggt ttattatgtc atgacttaag ttcatggtag tacattacct    7020
gccacgcatg cattatattg gttagatttg ataggcaaat ttggttgtca acaatataaa    7080
tataaataat gttttatat tacgaaataa cagtgatcaa acaaacagt tttatctta      7140 ttaacaagat tttgttttg tttgatgacg tttttaatg tttacgcttt cccccttctt     7200
ttgaatttag aacactttat catcataaaa tcaaatacta aaaaattac atatttcata    7260 aataataaca caaatatttt taaaaatctc gaaataataa tgaacaatat tacatattat   7320
cacgaaaatt cattaataaa aatattatat aaataaaatg taatagtagt tatatgtagg    7380
aaaaaagtac tgcacgcata atatatacaa aaagattaaa atgaactatt ataaataata    7440
acactaaatt aatggtgaat catatcaaaa taatgaaaaa gtaaataaaa tttgtaatta    7500
```

| | | | | |
|---|---|---|---|---|
| acttctatat | gtattacaca | cacaaataat | aaataatagt | aaaaaaaatt atgataaata | 7560 |
| tttaccatct | cataagatat | ttaaaataat | gataaaaata | tagattatttt tttatgcaac | 7620 |
| tagctagcca | aaaagagaac | acgggtatat | ataaaaagag | tacctttaaa ttctactgta | 7680 |
| cttcctttat | tcctgacgtt | tttatatcaa | gtggacatac | gtgaagattt taattatcag | 7740 |
| tctaaatatt | tcattagcac | ttaatacttt | tctgttttat | tcctatccta taagtagtcc | 7800 |
| cgattctccc | aacattgctt | attcacacaa | ctaactaaga | aagtcttcca tagcccccca | 7860 |
| agcggccgca | caatggcgac | tcgacagcga | actgccacca | ctgttgtggt cgaggacctt | 7920 |
| cccaaggtca | ctcttgaggc | caagtctgaa | cctgtgttcc | ccgatatcaa gaccatcaag | 7980 |
| gatgccattc | ccgcgcactg | cttccagccc | tcgctcgtca | cctcattcta ctacgtcttc | 8040 |
| cgcgattttg | ccatggtctc | tgccctcgtc | tgggctgctc | tcacctacat ccccagcatc | 8100 |
| cccgaccaga | ccctccgcgt | cgcagcttgg | atggtctacg | gcttcgtcca gggtctgttc | 8160 |
| tgcaccggtg | tctggattct | cggccatgag | tgcggccacg | gtgctttctc tctccacgga | 8220 |
| aaggtcaaca | atgtgaccgg | ctggttcctc | cactcgttcc | tcctcgtccc ctacttcagc | 8280 |
| tggaagtact | ctcaccaccg | ccaccaccgc | ttcaccggcc | acatggatct cgacatggct | 8340 |
| ttcgtcccca | agactgagcc | caagccctcc | aagtcgctca | tgattgctgg cattgacgtc | 8400 |
| gccgagcttg | ttgaggacac | ccccgctgct | cagatggtca | agctcatctt ccaccagctt | 8460 |
| ttcggatggc | aggcgtacct | cttcttcaac | gctagctctg | gcaagggcag caagcagtgg | 8520 |
| gagcccaaga | ctggcctctc | caagtggttc | cgagtcagtc | acttcgagcc taccagcgct | 8580 |
| gtcttccgcc | ccaacgaggc | catcttcatc | ctcatctccg | atatcggtct tgctctaatg | 8640 |
| ggaactgctc | tgtactttgc | ttccaagcaa | gttggtgttt | cgaccattct cttcctctac | 8700 |
| cttgttccct | acctgtgggt | tcaccactgg | ctcgttgcca | ttacctacct ccaccaccac | 8760 |
| cacaccgagc | tccctcacta | caccgctgag | ggctggacct | acgtcaaggg agctctcgcc | 8820 |
| actgtcgacc | gtgagtttgg | cttcatcgga | aagcacctct | ccacggtat cattgagaag | 8880 |
| cacgttgttc | accatctctt | ccctaagatc | cccttctaca | aggctgacga ggccaccgag | 8940 |
| gccatcaagc | ccgtcattgg | cgaccactac | tgccacgacg | accgaagctt cctgggccag | 9000 |
| ctgtggacca | tcttcggcac | gctcaagtac | gtcgagcacg | accctgcccg acccggtgcc | 9060 |
| atgcgatgga | acaaggacta | ggctaggc | | | 9088 |

<210> SEQ ID NO 91
<211> LENGTH: 10309
<212> TYPE: DNA
<213> ORGANISM: Artificial Sequence
<220> FEATURE:
<223> OTHER INFORMATION: Plasmid pKR667
<220> FEATURE:
<221> NAME/KEY: misc_feature
<222> LOCATION: (7704)..(7704)
<223> OTHER INFORMATION: n is a, c, g, or t

<400> SEQUENCE: 91

| | | | | |
|---|---|---|---|---|
| gtacgtctag | aggatccgtc | gacggcgcgc | ccgatcatcc | ggatatagtt cctcctttca | 60 |
| gcaaaaaacc | cctcaagacc | cgtttagagg | ccccaagggg | ttatgctagt tattgctcag | 120 |
| cggtggcagc | agccaactca | gcttcctttc | gggctttgtt | agcagccgga tcgatccaag | 180 |
| ctgtacctca | ctattccttt | gccctcggac | gagtgctggg | gcgtcggttt ccactatcgg | 240 |
| cgagtacttc | tacacagcca | tcggtccaga | cggccgcgct | tctgcgggcg atttgtgtac | 300 |

-continued

```
gcccgacagt cccggctccg gatcggacga ttgcgtcgca tcgaccctgc gcccaagctg      360
catcatcgaa attgccgtca accaagctct gatagagttg gtcaagacca atgcggagca      420
tatacgcccg gagccgcggc gatcctgcaa gctccggatg cctccgctcg aagtagcgcg      480
tctgctgctc catacaagcc aaccacggcc tccagaagaa gatgttggcg acctcgtatt      540
gggaatcccc gaacatcgcc tcgctccagt caatgaccgc tgttatgcgg ccattgtccg      600
tcaggacatt gttggagccg aaatccgcgt gcacgaggtg ccggacttcg gggcagtcct      660
cggcccaaag catcagctca tcgagagcct gcgcgacgga cgcactgacg gtgtcgtcca      720
tcacagtttg ccagtgatac acatggggat cagcaatcgc gcatatgaaa tcacgccatg      780
tagtgtattg accgattcct tgcggtccga atgggccgaa cccgctcgtc tggctaagat      840
cggccgcagc gatcgcatcc atagcctccg cgaccggctg cagaacagcg ggcagttcgg      900
tttcaggcag gtcttgcaac gtgacaccct gtgcacggcg ggagatgcaa taggtcaggc      960
tctcgctgaa ttccccaatg tcaagcactt ccggaatcgg gagcgcggcc gatgcaaagt     1020
gccgataaac ataacgatct ttgtagaaac catcggcgca gctatttacc cgcaggacat     1080
atccacgccc tcctacatcg aagctgaaag cacgagattc ttcgccctcc gagagctgca     1140
tcaggtcgga gacgctgtcg aacttttcga tcagaaactt ctcgacagac gtcgcggtga     1200
gttcaggctt ttccatgggt atatctcctt cttaaagtta aacaaaatta tttctagagg     1260
gaaaccgttg tggtctccct atagtgagtc gtattaattt cgcgggatcg agatctgatc     1320
aacctgcatt aatgaatcgg ccaacgcgcg gggagaggcg gtttgcgtat tgggcgctct     1380
tccgcttcct cgctcactga ctcgctgcgc tcggtcgttc ggctgcggcg agcggtatca     1440
gctcactcaa aggcggtaat acggttatcc acagaatcag gggataacgc aggaaagaac     1500
atgtgagcaa aaggccagca aaaggccagg aaccgtaaaa aggccgcgtt gctggcgttt     1560
ttccataggc tccgcccccc tgacgagcat cacaaaaatc gacgctcaag tcagaggtgg     1620
cgaaacccga caggactata aagataccag gcgtttcccc ctggaagctc cctcgtgcgc     1680
tctcctgttc cgaccctgcc gcttaccgga tacctgtccg cctttctccc ttcgggaagc     1740
gtggcgcttt ctcaatgctc acgctgtagg tatctcagtt cggtgtaggt cgttcgctcc     1800
aagctgggct gtgtgcacga accccccgtt cagcccgacc gctgcgcctt atccggtaac     1860
tatcgtcttg agtccaaccc ggtaagacac gacttatcgc cactggcagc agccactggt     1920
aacaggatta gcagagcgag gtatgtaggc ggtgctacag agttcttgaa gtggtggcct     1980
aactacggct acactagaag gacagtattt ggtatctgcg ctctgctgaa gccagttacc     2040
ttcggaaaaa gagttggtag ctcttgatcc ggcaaacaaa ccaccgctgg tagcggtggt     2100
ttttttgttt gcaagcagca gattacgcgc agaaaaaaag gatctcaaga agatcctttg     2160
atcttttcta cggggtctga cgctcagtgg aacgaaaact cacgttaagg gattttggtc     2220
atgacattaa cctataaaaa taggcgtatc acgaggccct ttcgtctcgc gcgtttcggt     2280
gatgacggtg aaaacctctg acacatgcag ctcccggaga cggtcacagc ttgtctgtaa     2340
gcggatgccg ggagcagaca agcccgtcag gcgcgtcag cgggtgttgg cgggtgtcgg      2400
ggctggctta actatgcggc atcagagcag attgtactga gagtgcacca tatggacata     2460
ttgtcgttag aacgcggcta caattaatac ataaccttat gtatcataca catacgattt     2520
aggtgacact atagaacggc gcgccaagct gggtctagaa ctagaaacgt gatgccactt     2580
gttattgaag tcgattacag catctattct gttttactat ttataacttt gccatttctg     2640
acttttgaaa actatctctg gatttcggta tcgctttgtg aagatcgagc aaaagagacg     2700
```

```
ttttgtggac gcaatggtcc aaatccgttc tacatgaaca aattggtcac aatttccact    2760
aaaagtaaat aaatggcaag ttaaaaaagg aatatgcatt ttactgattg cctaggtgag    2820
ctccaagaga agttgaatct acacgtctac caaccgctaa aaaagaaaa acattgatat     2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtagggc cagggggtgtc caacattctc tgaattgccg ctctaagctc    3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag acccctgag gtcaaccact gcctcggtct    3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag gctccgtgg tcggcgcttc     4980
cttggtgaag ggcgccgccg tggggggttt ggagatggaa catttgattt tgagagcgtg   5040
```

```
gttgggtttg gtgagggttt gatgagagag agggagggtg gatctagtaa tgcgtttggg    5100
gaaggtgggg tgtgaagagg aagaagagaa tcgggtggtt ctggaagcgg tggccgccat    5160
tgtgttgtgt ggcatggtta tacttcaaaa actgcacaac aagcctagag ttagtaccta    5220
aacagtaaat ttacaacaga gagcaaagac acatgcaaaa atttcagcca taaaaaaagt    5280
tataatagaa tttaaagcaa aagtttcatt ttttaaacat atatacaaac aaactggatt    5340
tgaaggaagg gattaattcc cctgctcaaa gtttgaattc ctattgtgac ctatactcga    5400
ataaaattga agcctaagga atgtatgaga aacaagaaaa caaaacaaaa ctacagacaa    5460
acaagtacaa ttacaaaatt cgctaaaatt ctgtaatcac caaaccccat ctcagtcagc    5520
acaaggccca aggtttattt tgaaataaaa aaaagtgat tttatttctc ataagctaaa    5580
agaaagaaag gcaattatga aatgatttcg actagatctg aaagtccaac gcgtattccg    5640
cagatattaa agaaagagta gagtttcaca tggatcctag atggacccag ttgaggaaaa    5700
agcaaggcaa agcaaaccag aagtgcaaga tccgaaattg aaccacggaa tctaggattt    5760
ggtagaggga gaagaaaagt accttgagag gtagaagaga agagaagagc agagagatat    5820
atgaacgagt gtgtcttggt ctcaactctg aagcgatacg agtttagagg ggagcattga    5880
gttccaattt atagggaaac cgggtggcag gggtgagtta atgacggaaa agcccctaag    5940
taacgagatt ggattgtggg ttagattcaa ccgtttgcat ccgcggctta gattggggaa    6000
gtcagagtga atctcaaccg ttgactgagt tgaaaattga atgtagcaac caattgagcc    6060
aaccccagcc tttgcccttt gattttgatt tgtttgttgc atactttta tttgtcttct    6120 ggttctgact ctctttctct cgtttcaatg ccaggttgcc tactcccaca ccactcacaa    6180
gaagattcta ctgttagtat taaatatttt ttaatgtatt aaatgatgaa tgcttttgta    6240
aacagaacaa gactatgtct aataagtgtc ttgcaacatt ttttaagaaa ttaaaaaaaa    6300
tatatttatt atcaaaatca aatgtatgaa aaatcatgaa taatataatt ttatacattt    6360
ttttaaaaaa tcttttaatt tcttaattaa tatcttaaaa ataatgatta atatttaacc    6420
caaaataatt agtatgattg gtaaggaaga tatccatgtt atgtttggat gtgagtttga    6480
tctagagcaa agcttactag agtcgacctg caggtcgact cgacgtacgt cctcgaagag    6540
aagggttaat aacacatttt ttaacatttt taacacaaat tttagttatt taaaaattta    6600
ttaaaaaatt taaaataaga agaggaactc tttaaataaa tctaacttac aaaatttatg    6660 attttttaata agttttcacc aataaaaaat gtcataaaaa tatgttaaaa agtatattat    6720
caatattctc tttatgataa ataaaaagaa aaaaaaaata aaagttaagt gaaaatgaga    6780
ttgaagtgac tttaggtgtg tataaatata tcaacccccgc caacaattta tttaatccaa    6840
atatattgaa gtatattatt ccatagcctt tatttattta tatatttatt atataaaagc    6900
tttatttgtt ctaggttgtt catgaaatat ttttttggtt ttatctccgt tgtaagaaaa    6960
tcatgtgctt tgtgtcgcca ctcactattg cagcttttc atgcattggt cagattgacg    7020
gttgattgta ttttgtttt ttatggtttt gtgttatgac ttaagtcttc atctctttat    7080
ctcttcatca ggtttgatgg ttacctaata tggtccatgg gtacatgcat ggttaaatta    7140
ggtggccaac tttgttgtga acgatagaat tttttttata ttaagtaaac tatttttata    7200
ttatgaaata ataataaaaa aaatatttta tcattattaa caaaatcata ttagttaatt    7260
tgttaactct ataataaaag aaatactgta acattcacat tacatggtaa catctttcca    7320 cccttcatt tgttttttgt ttgatgactt ttttcttgt ttaaatttat ttcccttctt    7380
ttaaatttgg aatacattat catcatatat aaactaaaat actaaaaaca ggattacaca    7440
```

```
aatgataaat aataacacaa atatttataa atctagctgc aatatattta aactagctat    7500
atcgatattg taaaataaaa ctagctgcat tgatactgat aaaaaaatat catgtgcttt    7560
ctggactgat gatgcagtat acttttgaca ttgcctttat tttattttc agaaaagctt    7620
tcttagttct gggttcttca ttatttgttt cccatctcca ttgtgaattg aatcatttgc    7680
ttcgtgtcac aaatacaatt tagntaggta catgcattgg tcagattcac ggtttattat    7740
gtcatgactt aagttcatgg tagtacatta cctgccacgc atgcattata ttggttagat    7800
ttgataggca aatttggttg tcaacaatat aaatataaat aatgttttta tattacgaaa    7860
taacagtgat caaacaaac agttttatct ttattaacaa gattttgttt ttgtttgatg     7920
acgttttta atgtttacgc ttcccccctt cttttgaatt tagaacactt tatcatcata     7980
aaatcaaata ctaaaaaat tacatatttc ataataata acacaaatat ttttaaaaaa     8040
tctgaaataa taatgaacaa tattacatat tatcacgaaa attcattaat aaaaatatta    8100
tataaataaa atgtaatagt agttatatgt aggaaaaaag tactgcacgc ataatatata    8160
caaaagatt aaaatgaact attataaata ataacactaa attaatggtg aatcatatca     8220
aaataatgaa aaagtaaata aaatttgtaa ttaacttcta tatgtattac acacacaaat    8280
aataaataat agtaaaaaaa attatgataa atatttacca tctcataaga tatttaaaat    8340
aatgataaaa atatagatta tttttatgc aactagctag ccaaaaagag aacacgggta     8400
tatataaaaa gagtaccttt aaattctact gtacttcctt tattcctgac gtttttatat    8460
caagtggaca tacgtgaaga ttttaattat cagtctaaat atttcattag cacttaatac    8520
ttttctgttt tattcctatc ctataagtag tcccgattct cccaacattg cttattcaca    8580
caactaacta agaaagtctt ccatagcccc ccaagcggcc gcacaatggc gactcgacag    8640
cgaactgcca ccactgttgt ggtcgaggac cttcccaagg tcactcttga ggccaagtct    8700
gaacctgtgt tccccgatat caagaccatc aaggatgcca ttcccgcgca ctgcttccag    8760
ccctcgctcg tcacctcatt ctactacgtc ttccgcgatt ttgccatggt ctctgccctc    8820
gtctgggctg ctctcaccta catccccagc atccccgacc agaccctccg cgtcgcagct    8880
tggatggtct acggcttcgt ccagggtctg ttctgcaccg gtgtctggat tctcggccat    8940
gagtgcggcc acggtgcttt ctctctccac ggaaaggtca acaatgtgac cggctggttc    9000
ctccactcgt tcctcctcgt cccctacttc agctggaagt actctcacca ccgccaccac    9060
cgcttcaccg gccacatgga tctcgacatg gctttcgtcc ccaagactga gcccaagccc    9120
tccaagtcgc tcatgattgc tggcattgac gtcgccgagc ttgttgagga cacccccgct    9180
gctcagatgg tcaagctcat cttccaccag cttttcggat ggcaggcgta cctcttcttc    9240
aacgctagct ctggcaaggg cagcaagcag tgggagccca agactggcct ctccaagtgg    9300
ttccgagtca gtcacttcga gcctaccagc gctgtcttcc gccccaacga ggccatcttc    9360
atcctcatct ccgatatcgg tcttgctcta atgggaactg ctctgtactt tgcttccaag    9420
caagttggtg tttcgaccat tctcttcctc taccttgttc cctacctgtg ggttcaccac    9480
tggctcgttg ccattaccta cctccaccac caccacaccg agctccctca ctacaccgct    9540
gagggctgga cctacgtcaa gggagctctc gccactgtcg accgtgagtt tggcttcatc    9600
ggaaagcacc tcttccacgg tatcattgag aagcacgttg ttcaccatct cttccctaag    9660
atccccttct acaaggctga cgaggccacc gaggccatca gcccgtcat ggcgaccac     9720
tactgccacg acgaccgaag cttcctgggc cagctgtgga ccatcttcgg cacgctcaag    9780
```

```
tacgtcgagc acgaccctgc ccgacccggt gccatgcgat ggaacaagga ctaggctagg    9840
cggccgcgac acaagtgtga gagtactaaa taaatgcttt ggttgtacga aatcattaca    9900
ctaaataaaa taatcaaagc ttatatatgc cttccgctaa ggccgaatgc aaagaaattg    9960
gttctttctc gttatctttt gccacttttca ctagtacgta ttaattacta cttaatcatc   10020
tttgtttacg gctcattata tccggtctag aggatccaag gccgcgaagt taaaagcaat   10080
gttgtcactt gtcgtactaa cacatgatgt gatagtttat gctagctagc tataacataa   10140
gctgtctctg agtgtgttgt atattaataa agatcatcac tggtgaatgg tgatcgtgta   10200
cgtaccctac ttagtaggca atggaagcac ttagagtgtg ctttgtgcat ggccttgcct   10260
ctgttttgag acttttgtaa tgttttcgag tttaaatctt tgcctttgc               10309
```

<210> SEQ ID NO 92
<211> LENGTH: 12403
<212> TYPE: DNA
<213> ORGANISM: Artificial Sequence
<220> FEATURE:
<223> OTHER INFORMATION: Plasmid pKR873

<400> SEQUENCE: 92

```
ggtcgactcg acgtacgaaa ccaactgcgt ttggggctcc agattaaacg acgccgtttc      60
gttcctttcg cttcacggct taacgatgtc gtttctgtct gtgcccaaaa aataaaggca     120
tttgttattt gcaccagata tttactaagt gcaccctagt ttgacaagta ggcgataatt     180
acaaatagat gcggtgcaaa taataaattt tgaaggaaat aattacaaaa gaacagaact     240
tatatttact ttattttaaa aaactaaaat gaaagaacaa aaaagtaaa aaatacaaaa      300 aatgtgcttt aaccactttc attatttgtt acagaaagta tgattctact caaattgatc     360
tgttgtatct ggtgctgcct tgtcacactg gcgatttcaa tcccctaaag atatggtgca     420
aactgcgaag tgatcaatat ctgctcggtt aatttagatt aattaataat attcaacgtg     480
atgtaccaaa aaaagacaat tttttgctcc attgacaaat taaacctcat caaggtaatt     540
tccaaaccta taagcaaaaa aatttcacat taattggccc gcaatcctat tagtcttatt     600
atactagagt aggaaaaaaa acaattacac aacttgtctt attattctct atgctaatga     660 atattttttcc cttttgttag aaatcagtgt ttcctaattt attgagtatt aattccactc    720
accgcatata tttaccgttg aataagaaaa ttttacacat aattcttttt aagataaata     780
atttttttat actagatctt atatgattac gtgaagccaa gtgggttata ctaatgatat     840
ataatgtttg atagtaatca gtttataaac caaatgcatg gaaatgttac gtggaagcac     900
gtaaattaac aagcattgaa gcaaatgcag ccaccgcacc aaaaccaccc cacttcactt     960
ccacgtacca tattccatgc aactacaaca ccctaaaact tcaataaatg cccccaccttt   1020 cacttcactt cacccatcaa tagcaagcgg ccgcacaatg gcgactcgac agcgaactgc    1080
caccactgtt gtggtcgagg accttcccaa ggtcactctt gaggcaagt ctgaacctgt     1140 gttccccgat atcaagacca tcaaggatgc cattcccgcg cactgcttcc agccctcgct    1200
cgtcacctca ttctactacg tcttccgcga ttttgccatg gtctctgccc tcgtctgggc    1260
tgctctcacc tacatcccca gcatccccga ccagaccctc cgcgtcgcag cttggatggt    1320
ctacggcttc gtccagggtc tgttctgcac cggtgtctgg attctcggcc atgagtgcgg    1380
ccacggtgct ttctctctcc acggaaaggt caacaatgtg accggctggt tcctccactc    1440
gttcctcctc gtcccctact tcagctggaa gtactctcac caccgccacc accgcttcac    1500
cggccacatg gatctcgaca tggctttcgt ccccaagact gagcccaagc cctccaagtc    1560
```

```
gctcatgatt gctggcattg acgtcgccga gcttgttgag gacaccccg ctgctcagat    1620
ggtcaagctc atcttccacc agcttttcgg atggcaggcg tacctcttct tcaacgctag    1680
ctctggcaag ggcagcaagc agtgggagcc caagactggc ctctccaagt ggttccgagt    1740
cagtcacttc gagcctacca gcgctgtctt ccgccccaac gaggccatct tcatcctcat    1800
ctccgatatc ggtcttgctc taatgggaac tgctctgtac tttgcttcca agcaagttgg    1860
tgtttcgacc attctcttcc tctaccttgt tccctacctg tgggttcacc actggctcgt    1920
tgccattacc tacctccacc accaccacac cgagctccct cactacaccg ctgagggctg    1980
gacctacgtc aagggagctc tcgccactgt cgaccgtgag tttggcttca tcggaaagca    2040
cctcttccac ggtatcattg agaagcacgt tgttcaccat ctcttcccta agatcccctt    2100
ctacaaggct gacgaggcca ccgaggccat caagcccgtc attggcgacc actactgcca    2160
cgacgaccga agcttcctgg gccagctgtg gaccatcttc ggcacgctca agtacgtcga    2220
gcacgaccct gcccgacccg gtgccatgcg atggaacaag gactaggcta ggcggccgcg    2280
aagttaaaag caatgttgtc acttgtcgta ctaacacatg atgtgatagt ttatgctagc    2340
tagctataac ataagctgtc tctgagtgtg ttgtatatta ataaagatca tcactggtga    2400
atggtgatcg tgtacgtacc ctacttagta ggcaatggaa gcacttagag tgtgctttgt    2460
gcatggcctt gcctctgttt tgagactttt gtaatgtttt cgagtttaaa tctttgcctt    2520
tgcgtacgtc tagaggatcc gtcgacggcg cgcccgatca tccgatata gttcctcctt    2580
tcagcaaaaa accccctcaag acccgtttag aggccccaag gggttatgct agttattgct    2640
cagcggtggc agcagccaac tcagcttcct ttcgggcttt gttagcagcc ggatcgatcc    2700
aagctgtacc tcactattcc tttgccctcg acgagtgct ggggcgtcgg tttccactat    2760
cggcgagtac ttctacacag ccatcggtcc agacggccgc gcttctgcgg gcgatttgtg    2820
tacgcccgac agtcccggct ccggatcgga cgattgcgtc gcatcgaccc tgcgcccaag    2880
ctgcatcatc gaaattgccg tcaaccaagc tctgatagag ttggtcaaga ccaatgcgga    2940
gcatatacgc ccggagccgc ggcgatcctg caagctccgg atgcctccgc tcgaagtagc    3000
gcgtctgctg ctccatacaa gccaaccacg gcctccagaa gaagatgttg gcgacctcgt    3060
attgggaatc cccgaacatc gcctcgctcc agtcaatgac cgctgttatg cggccattgt    3120
ccgtcaggac attgttggag ccgaaatccg cgtgcacgag gtgccggact cggggcagt    3180
cctcggccca agcatcagc tcatcgagag cctgcgcgac ggacgcactg acggtgtcgt    3240
ccatcacagt ttgccagtga tacacatggg gatcagcaat cgcgcatatg aaatcacgcc    3300
atgtagtgta ttgaccgatt ccttgcggtc cgaatgggcc gaacccgctc gtctggctaa    3360
gatcggccgc agcgatcgca tccatagcct ccgcgaccgg ctgcagaaca gcgggcagtt    3420
cggtttcagg caggtcttgc aacgtgacac cctgtgcacg gcgggagatg caataggtca    3480
ggctctcgct gaattcccca atgtcaagca cttccggaat cgggagcgcg gccgatgcaa    3540
agtgccgata aacataacga tctttgtaga aaccatcggc gcagctattt acccgcagga    3600
catatccacg ccctcctaca tcgaagctga agcacgaga ttcttcgccc tccgagagct    3660
gcatcaggtc ggagacgctg tcgaactttt cgatcagaaa cttctcgaca gacgtcgcgg    3720
tgagttcagg cttttccatg gtatatctc cttcttaaag ttaaacaaaa ttatttctag    3780
agggaaaccg ttgtggtctc cctatagtga gtcgtattaa tttcgcggga tcgagatctg    3840
atcaacctgc attaatgaat cggccaacgc gcggggagag gcggtttgcg tattgggcgc    3900
```

```
tcttccgctt cctcgctcac tgactcgctg cgctcggtcg ttcggctgcg gcgagcggta    3960
tcagctcact caaaggcggt aatacggtta tccacagaat caggggataa cgcaggaaag    4020
aacatgtgag caaaaggcca gcaaaaggcc aggaaccgta aaaaggccgc gttgctggcg    4080 ttttccata ggctccgccc ccctgacgag catcacaaaa atcgacgctc aagtcagagg    4140
tggcgaaacc cgacaggact ataaagatac caggcgtttc ccctggaag ctccctcgtg    4200 cgctctcctg ttccgaccct gccgcttacc ggatacctgt ccgcctttct ccttcggga    4260 agcgtggcgc tttctcaatg ctcacgctgt aggtatctca gttcggtgta ggtcgttcgc    4320
tccaagctgg gctgtgtgca cgaaccccc gttcagcccg accgctgcgc cttatccggt    4380
aactatcgtc ttgagtccaa cccggtaaga cacgacttat cgccactggc agcagccact    4440
ggtaacagga ttagcagagc gaggtatgta ggcggtgcta cagagttctt gaagtggtgg    4500
cctaactacg gctacactag aaggacagta tttggtatct gcgctctgct gaagccagtt    4560
accttcggaa aaagagttgg tagctcttga tccggcaaac aaaccaccgc tggtagcggt    4620
ggtttttttg tttgcaagca gcagattacg cgcagaaaaa aaggatctca agaagatcct    4680
ttgatctttt ctacggggtc tgacgctcag tggaacgaaa actcacgtta agggattttg    4740
gtcatgacat aacctataa aaataggcgt atcacgaggc cctttcgtct cgcgcgtttc    4800
ggtgatgacg gtgaaaacct ctgacacatg cagctcccgg agacggtcac agcttgtctg    4860
taagcggatg ccgggagcag acaagcccgt cagggcgcgt cagcgggtgt tggcgggtgt    4920
cggggctggc ttaactatgc ggcatcagag cagattgtac tgagagtgca ccatatggac    4980
atattgtcgt tagaacgcgg ctacaattaa tacataacct tatgtatcat acacatacga    5040
tttaggtgac actatagaac ggcgcgccaa gctgggtcta gaactagaaa cgtgatgcca    5100
cttgttattg aagtcgatta cagcatctat tctgttttac tatttataac tttgccattt    5160
ctgacttttg aaaactatct ctggatttcg gtatcgcttt gtgaagatcg agcaaaagag    5220
acgttttgtg gacgcaatgg tccaaatccg ttctacatga acaaattggt cacaatttcc    5280
actaaaagta aataaatggc aagttaaaaa aggaatatgc atttactga ttgcctaggt    5340 gagctccaag agaagttgaa tctacacgtc taccaaccgc taaaaaaaga aaacattga    5400 tatgtaacct gattccatta gcttttgact tcttcaacag attctctact tagatttcta    5460
acagaaatat tattactagc acatcatttt cagtctcact acagcaaaaa atccaacggc    5520
acaatacaga caacaggaga tatcagacta cagagataga tagatgctac tgcatgtagt    5580
aagttaaata aaggaaaat aaaatgtctt gctaccaaaa ctactacaga ctatgatgct    5640
caccacaggc caaatcctgc aactaggaca gcattatctt atatatattg tacaaaacaa    5700
gcatcaagga acatttggtc taggcaatca gtacctcgtt ctaccatcac cctcagttat    5760
cacatccttg aaggatccat tactgggaat catcggcaac acatgctcct gatggggcac    5820
aatgacatca agaaggtagg ggccaggggt gtccaacatt tctgaattg ccgctctaag    5880 ctcttccttc ttcgtcactc gcgctgccgg tatcccacaa gcatcagcaa acttgagcat    5940
gtttgggaat atctcgctct cgctagacgg atctccaaga taggtgtgag ctctattgga    6000
cttgtagaac ctatcctcca actgaaccac catacccaaa tgctgattgt caacaacaa    6060 tatcttaact gggagattct ccactctat agtggccaac tcctgaacat tcatgatgaa    6120
actaccatcc ccatcaatgt caaccacaac agccccaggg ttagcaacag cagcaccaat    6180
agccgcaggc aatccaaaac ccatggctcc aagacccct gaggtcaacc actgcctcgg    6240
tctcttgtac ttgtaaaact gcgcagccca catttgatgc tgcccaaccc cagtactaac    6300
```

```
aatagcatct ccattagtca actcatcaag aacctcgata gcatgctgcg gagaaatcgc   6360
gtcctggaat gtcttgtaac ccaatggaaa cttgtgtttc tgcacattaa tctcttctct   6420
ccaacctcca agatcaaact taccctccac tcctttctcc tccaaaatca tattaattcc   6480
cttcaaggcc aacttcaaat ccgcgcaaac cgacacgtgc gcctgcttgt tcttcccaat   6540
ctcggcagaa tcaatatcaa tgtgaacaat cttagcccta ctagcaaaag cctcaagctt   6600
cccagtaaca cggtcatcaa accttacccc aaaggcaagc aacaaatcac tattgtcaac   6660
agcatagtta gcataaacag taccatgcat acccagcatc tgaagggaat attcatcacc   6720
aataggaaaa gttccaagac ccattaaagt gctagcaacg ggaataccag tgagttcaac   6780
aaagcgcctc aattcagcac tggaattcaa actgccaccg ccgacgtaga gaacgggctt   6840
ttgggcctcc atgatgagtc tgacaatgtg ttccaattgg gcctcggcgg ggggcctggg   6900
cagcctggcg aggtaaccgg ggaggttaac gggctcgtcc caattaggca cggcgagttg   6960
ctgctgaacg tctttgggaa tgtcgatgag gaccggaccg gggcggccgg aggtggcgac   7020
gaagaaagcc tcggcgacga cgcggggggat gtcgtcgacg tcgaggatga ggtagttgtg   7080
cttcgtgatg gatctgctca cctccacgat cggggtttct tggaaggcgt cggtgccgat   7140
catccggcgg gcgacctggc cggtgatggc gacgactggg acgctgtcca ttaaagcgtc   7200
ggcgaggccg ctcacgaggt tggtggcgcc ggggccggag gtggcaatgc agacgccggg   7260
gaggccggag gaacgcgcgt agccttcggc ggcgaagacg ccgccctgct cgtggcgcgg   7320
gagcacgttg cggatggcgg cggagcgcgt gagcgcctgg tggatctcca tcgacgcacc   7380
gccggggtac gcgaacaccg tcgtcacgcc ctgcctctcc agcgcctcca caaggatgtc   7440
cgcgcccttg cgaggttcgc cggaggcgaa ccgtgacacg aagggctccg tggtcggcgc   7500
ttccttggtg aagggcgccg ccgtgggggg tttggagatg gaacatttga ttttgagagc   7560
gtggttgggt ttggtgaggg tttgatgaga gagagggagg gtggatctag taatgcgttt   7620
ggggaaggtg gggtgtgaag aggaagaaga gaatcgggtg gttctggaag cggtggccgc   7680
cattgtgttg tgtggcatgg ttatacttca aaaactgcac aacaagccta gagttagtac   7740
ctaaacagta aatttacaac agagagcaaa gacacatgca aaaatttcag ccataaaaaa   7800
agttataata gaatttaaag caaaagtttc attttttaaa catatataca aacaaactgg   7860
atttgaagga agggattaat tcccctgctc aaagtttgaa ttcctattgt gacctatact   7920
cgaataaaat tgaagcctaa ggaatgtatg agaaacaaga aaacaaaaca aaactacaga   7980
caaacaagta caattacaaa attcgctaaa attctgtaat caccaaaccc catctcagtc   8040
agcacaaggc ccaaggttta ttttgaaata aaaaaaaagt gattttatt ctcataagct    8100 aaaagaaaga aaggcaatta tgaaatgatt tcgactagat ctgaaagtcc aacgcgtatt   8160
ccgcagatat taaagaaaga gtagagtttc acatggatcc tagatggacc cagttgagga   8220
aaaagcaagg caaagcaaac cagaagtgca agatccgaaa ttgaaccacg gaatctagga   8280
tttggtagag ggagaagaaa agtaccttga gaggtagaag agaagagaag agcagagaga   8340
tatatgaacg agtgtgtctt ggtctcaact ctgaagcgat acgagtttag aggggagcat   8400
tgagttccaa tttataggga aaccgggtgg caggggtgag ttaatgacgg aaaagcccct   8460
aagtaacgag attggattgt gggttagatt caaccgtttg catccgcggc ttagattggg   8520
gaagtcagag tgaatctcaa ccgttgactg agttgaaaat tgaatgtagc aaccaattga   8580 gccaaccccca gcctttgccc tttgattttg atttgtttgt tgcatacttt ttatttgtct   8640
```

```
tctggttctg actctctttc tctcgtttca atgccaggtt gcctactccc acaccactca   8700
caagaagatt ctactgttag tattaaatat tttttaatgt attaaatgat gaatgctttt   8760
gtaaacagaa caagactatg tctaataagt gtcttgcaac atttttttaag aaattaaaaa   8820
aaatatattt attatcaaaa tcaaatgtat gaaaaatcat gaataatata attttataca   8880
ttttttaaa aaatcttta atttcttaat taatatctta aaaataatga ttaaatttta   8940
acccaaaata attagtatga ttggtaagga agatatccat gttatgtttg gatgtgagtt   9000
tgatctagag caaagcttac tagagtcgac ctgcagcccg ggggatccgc ccacgtacgg   9060
taccatctgc taatatttta aatcacatgc aagagaggag gcatggttcc attttctacc   9120
ttcacattat ttgagaaaaa cgaacttgtt ctgtgtttta ttttgccct tcacattagt   9180
acaacgtgga agactcatgg ttacacagaa tcatacataa gtacaatgct tgtccctaag   9240
aaaacaagca ctcgttgtat tgaacctttta cggctcatgc ggccgcgaat tcactagtga   9300
ttgaattcgc ggccgcttag tccgacttgg ccttggcggc cgcggccgac tctttgagcg   9360
tgaagatctg cgccgtctcg ggcacagcgc cgtagttgac aaagaggtgc gcggtcttga   9420
agaaggccgt gatgatgggc tcgtcgttcc tgcgcacgag gtgcgggtac gcggccgcaa   9480
agtgcttggt ggcttcgttg agcttgtagt gcggaatgat cgggaacaag tggtggacct   9540
ggtgcgtgcc aatgtggtgg ctcaggttgt ccacgaacgc gccgtacgag cggtcgacgc   9600
tcgagaggtt gcccttgacg tacgtccact ccgagtcgcc gtaccacggc gtcgcttcgt   9660
cgttgtggtg caagaaggtc gtaatgacga ggaacgaagc aaagacaaag agcggcgcat   9720
agtagtagag gcccatgacg gcaaagccga gcgagtatgt gaggtacgcg tacgcggcga   9780
agaaggcggc ccagacgccg agcgacacga tgacggccga cgcgcggcga aggaggagcg   9840
ggtcccacgg gtcaaagtgg ctcatcgtgc gcggggcata cccgaccttc aagtagacaa   9900
accacgcacc gccgagcgtg tagacccatt ggcgcacgtc ctggaggtcc ttgaccgacc   9960
ggtgcgggta aaagatctcg tccttatcaa tgttgcccgt gttcttgtgg tggtggcggt  10020
gcgtcacgcg ccagctctcg aacggcgtca aatcgcaga gtgcatgatg cagccgatga  10080
taaagttgac gctgtggtag cgcgagaagg ccgagtggcc gcagtcgtgg ccgaccgtga  10140
agaagcccca gaagatgacg ccctgcacgt agatgtaggt ggcgcaaacg agcgcgtgga  10200
gcagaacgtt atcggcaatg aacggcgtcg agcgcgccgc gtagagcagc gccgccgagg  10260
ccgacgcgtt gaagatcgcg cgggccgtgt agtagagcga gaggccgagg ttcgactcaa  10320
agcacgcgtt cgggatcgag tgcttgagct ccgtgagcgt cgggaactcg accttcgtct  10380
tatcctcagt catgcggccg ctgaagtatt gcttcttagt taacctttcc tttctctctc  10440
agctatgtga attcattttg ctttcgtcac aatttatata gtgaaattgg atctttggag  10500
ttaacgcctt cacaggatta tcgtgttaga acaatgcttt ttcatgttct aattagtagt  10560
acattacaaa tgtgcactct attcaataag catcttttgg cacgttaata aatcatgtga  10620
aaaaaaaata ctactatttc aaagaaagtg ttgtaaaaag aaacggaaag agagctggct  10680
tcagttgttg agacttgttt gctagtaaaa atggtgtgaa gagtgattca tggtgaggtg  10740
gtttttcgtc cctttctgtt tgcatgaaaa acaaatggca agagatgacg taggattcct  10800
tcccttaacg attatctgtt tttaatttca aatatacata taggaattta tgaattacta  10860
aggttgtaaa atatgctggt cattatttta tggctaaaat attttttttt ctcgtaaata  10920
taaaaatatt taaaatttat ttttatcata ttttttatcc ttataaaatt atgtgtacaa  10980
cctatataaa aaaatatcat atttaatatt gattatatgt ttaatcaata taaaaaatca  11040
```

```
ttatcatata tttagattta ttcgaatata catctaaaca aaaaataaca tattttaatt   11100
ttatgaagaa aaaaaaatat tttatccttt atttatttaa gattaattaa tagttatgta   11160
ttgtggaaag acttttacac atgcaataga tatactgaat caattagatg ccaatgctga   11220
gttggaaatc acttgaggag gggaggagac ttgccaatgc ttttcagttt catttaaatg   11280
atttagtgga ggagatagag tagtgataaa ggcatgcccc aattttggag tgtatatatg   11340
agtggaaata agagagggat agagagaaaa aataaagaga gtaaaaataa ttaatgtgaa   11400
atgatatgat aaaaaaataa agaaagagat aaagagaaaa atgaaatgag agatagatga   11460
aatagagagt agatacatgt ttgtttaggt ttttttttagg aaataacaca tttttttctc   11520
atcacttatt actcactgtc aatttcctct ctttcaatca taatgatatg atttgtttaa   11580
caaaaatgtg aaaaaacata taaagtaaaa tatttttata aattgataaa taaaaattta   11640
caaaatttat ttcttattaa attgaataga aaatgaaaga aagaaaaga aaagtatat    11700 ataaaatgat atagctttaa aaagaataaa tttttcatat cagtcttttt ttaataattt   11760
agaaatattt aagtatatag caaaaatata atgtacttta catatgcata aataataatt   11820
tgaaaataga actaatagaa tagagaaaaa agtaatataa taattaacta tatgaaaatt   11880
tagaagggac aatattttta attaagaata taaacaatat ttcttttcat gtaatgaggg   11940
acggatgtac ggggccagtg ttggagtcaa agccaaaata gtcacgggga aattaatgca   12000
ctgcatgact attcgaaaaa attcactagc cttacttaga tgttagatta atagctaggg   12060
ggtgcagata attttgaaag gcatgaaaaa cattaatttg tacattgcaa gcttttgatg   12120
acaagctttg caattgttca cactaccttta tgccatttat aaatagagtg attggcatat   12180
gaaggaaatc atgagagtcg aagcgaaaaa caaagcttga gagtgtagga aaaatacagt   12240 tttttttggta aaaatacagt atttgaatag gagcgaaaaa tatcctttca aaatgatcct   12300 tttcttttt tttttttttc ttgttgttct tggtcagtta ttcaaaggaa aagggattga   12360
aataaaaact tgcatgtggg atcgtacgtc gagtcgacct gca                   12403
```

<210> SEQ ID NO 93
<211> LENGTH: 3983
<212> TYPE: DNA
<213> ORGANISM: Artificial Sequence
<220> FEATURE:
<223> OTHER INFORMATION: Plasmid pKR132

<400> SEQUENCE: 93

```
ctagagtcga cctgcaggca tgcaagcttg gcgtaatcat ggtcatagct gtttcctgtg     60
tgaaattgtt atccgctcac aattccacac aacatacgag ccggaagcat aaagtgtaaa    120
gcctggggtg cctaatgagt gagctaactc acattaattg cgttgcgctc actgcccgct    180
ttccagtcgg gaaacctgtc gtgccagctg cattaatgaa tcggccaacg cgcgggaga     240 ggcggtttgc gtattgggcg ctcttccgct tcctcgctca ctgactcgct gcgctcggtc    300
gttcggctgc ggcgagcggt atcagctcac tcaaaggcgg taatacggtt atccacagaa    360
tcaggggata acgcaggaaa gaacatgtga gcaaaaggcc agcaaaaggc caggaaccgt    420
aaaaaggccg cgttgctggc gtttttccat aggctccgcc cccctgacga gcatcacaaa    480
aatcgacgct caagtcagag gtggcgaaac ccgacaggac tataaagata ccaggcgttt    540 cccccctggaa gctccctcgt gcgctctcct gttccgaccc tgccgcttac cggatacctg    600
tccgcctttc tcccttcggg aagcgtggcg ctttctcata gctcacgctg taggtatctc    660
```

```
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
tcgccactgg cagcagccac tggtaacagg attagcagag cgaggtatgt aggcggtgct    840
acagagttct tgaagtggtg gcctaactac ggctacacta aaggacagt  atttggtatc    900 tgcgctctgc tgaagccagt taccttcgga aaaagagttg gtagctcttg atccggcaaa    960
caaaccaccg ctggtagcgg tggtttttt  gtttgcaagc agcagattac gcgcagaaaa   1020
aaaggatctc aagaagatcc tttgatcttt tctacggggt ctgacgctca gtggaacgaa   1080
aactcacgtt aagggatttt ggtcatgaga ttatcaaaaa ggatcttcac ctagatcctt   1140
ttaaattaaa aatgaagttt taaatcaatc taaagtatat atgagtaaac ttggtctgac   1200
agttaccaat gcttaatcag tgaggcacct atctcagcga tctgtctatt tcgttcatcc   1260
atagttgcct gactccccgt cgtgtagata actacgatac gggagggctt accatctggc   1320
cccagtgctg caatgatacc gcgagaccca cgctcaccgg ctccagattt atcagcaata   1380
aaccagccag ccggaagggc cgagcgcaga agtggtcctg caactttatc cgcctccatc   1440
cagtctatta attgttgccg ggaagctaga gtaagtagtt cgccagttaa tagtttgcgc   1500
aacgttgttg ccattgctac aggcatcgtg gtgtcacgct cgtcgtttgg tatggcttca   1560
ttcagctccg gttcccaacg atcaaggcga gttacatgat cccccatgtt gtgcaaaaaa   1620
gcggttagct ccttcggtcc tccgatcgtt gtcagaagta agttggccgc agtgttatca   1680
ctcatggtta tggcagcact gcataattct cttactgtca tgccatccgt aagatgcttt   1740
tctgtgactg gtgagtactc aaccaagtca ttctgagaat agtgtatgcg gcgaccgagt   1800
tgctcttgcc cggcgtcaat acgggataat accgcgccac atagcagaac tttaaaagtg   1860
ctcatcattg gaaaacgttc ttcggggcga aaactctcaa ggatcttacc gctgttgaga   1920
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc ctttttcaat attattgaag catttatcag   2100
ggttattgtc tcatgagcgg atacatattt gaatgtattt agaaaaataa acaaataggg   2160
gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag gttttccca  gtcacgacgt   2640 tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat tgttatttg  caccagatat   2820 ttactaagtc cacccctagtt tgacaagtag gcgataatta caaatagatg cggtgcaaat   2880
aataaatttt gaaggaaata attacaaaag aacagaactt atatttactt tattttaaaa   2940
aactaaaatg aaagaacaaa aaaagtaaaa aatacaaaaa atgtgcttta accactttca   3000
ttatttgtta cagaaagtat gattctactc aaattgatct gttgtatctg gtgctgcctt   3060
```

```
gtcacactgg cgatttcaat cccctaaaga tatggtgcaa actgcgaagt gatcaatatc    3120
tgctcggtta atttagatta attaataata ttcaacgtga tgtaccaaaa aaagacaatt    3180
ttttgctcca ttgacaaatt aaacctcatc aaggtaattt ccaaacctat aagcaaaaaa    3240
atttcacatt aattggcccg caatcctatt agtcttatta tactagagta ggaaaaaaaa    3300
caattacaca acttgtctta ttattctcta tgctaatgaa tattttttccc ttttgttaga    3360 aatcagtgtt tcctaattta ttgagtatta attccactca ccgcatatat ttaccgttga    3420
ataagaaaat tttacacata attcttttta agataaataa ttttttttata ctagatctta    3480 tatgattacg tgaagccaag tgggttatac aatgatata taatgtttga tagtaatcag     3540
tttataaacc aaatgcatgg aaatgttacg tggaagcacg taaattaaca agcattgaag    3600
caaatgcagc caccgcacca aaaccacccc acttcacttc cacgtaccat attccatgca    3660
actacaacac cctaaaactt caataaatgc ccccaccttc acttcacttc acccatcaat    3720
agcaagcggc cgcgaagtta aaagcaatgt tgtcacttgt cgtactaaca catgatgtga    3780
tagtttatgc tagctagcta taacataagc tgtctctgag tgtgttgtat attaataaag    3840
atcatcactg gtgaatggtg atcgtgtacg taccctactt agtaggcaat ggaagcactt    3900
agagtgtgct ttgtgcatgg ccttgcctct gttttgagac ttttgtaatg ttttcgagtt    3960
taaatctttg cctttgcgta cgt                                            3983

<210> SEQ ID NO 94
<211> LENGTH: 33
<212> TYPE: DNA
<213> ORGANISM: Artificial Sequence
<220> FEATURE:
<223> OTHER INFORMATION: Primer oSAlb-9

<400> SEQUENCE: 94
ttctagacgt acgaaaccaa ctgcgtttgg ggc                                  33

<210> SEQ ID NO 95
<211> LENGTH: 35
<212> TYPE: DNA
<213> ORGANISM: Artificial Sequence
<220> FEATURE:
<223> OTHER INFORMATION: Primer oSAlb-2

<400> SEQUENCE: 95
aatctagacg tacgcaaagg caaagattta aactc                                35

<210> SEQ ID NO 96
<211> LENGTH: 4268
<212> TYPE: DNA
<213> ORGANISM: Artificial Sequence
<220> FEATURE:
<223> OTHER INFORMATION: Plasmid pKR160

<400> SEQUENCE: 96
aatctagacg tacgcaaagg caaagattta aactcgaaaa cattacaaaa gtctcaaaac     60
agaggcaagg ccatgcacaa agcacactct aagtgcttcc attgcctact aagtagggta    120
cgtacacgat caccattcac cagtgatgat ctttattaat atacaacaca ctcagagaca    180
gcttatgtta tagctagcta gcataaacta tcacatcatg tgttagtacg acaagtgaca    240
acattgcttt taacttcgcg gccgcttgct attgatgggt gaagtgaagt gaaggtgggg    300
gcatttattg aagtttttagg gtgttgtagt tgcatggaat atggtacgtg gaagtgaagt    360
```

-continued

```
ggggtggttt tggtgcggtg gctgcatttg cttcaatgct tgttaattta cgtgcttcca      420
cgtaacattt ccatgcattt ggtttataaa ctgattacta tcaaacatta tatatcatta      480
gtataaccca cttggcttca cgtaatcata aagatctag tataaaaaaa ttatttatct       540
taaaaagaat tatgtgtaaa attttcttat tcaacggtaa atatatgcgg tgagtggaat      600
taatactcaa taaattagga aacactgatt tctaacaaaa gggaaaaata ttcattagca      660
tagagaataa taagacaagt tgtgtaattg tttttttttcc tactctagta taataagact     720
aataggattg cgggccaatt aatgtgaaat ttttttgctt ataggtttgg aaattacctt      780
gatgaggttt aatttgtcaa tggagcaaaa aattgtcttt ttttggtaca tcacgttgaa      840
tattattaat taatctaaat taaccgagca gatattgatc acttcgcagt ttgcaccata      900
tctttagggg attgaaatcg ccagtgtgac aaggcagcac cagatacaac agatcaattt     960
gagtagaatc atactttctg taacaaataa tgaaagtggt taaagcacat ttttgtatt      1020 ttttactttt tttgttcttt cattttagtt ttttaaaata aagtaaatat aagttctgtt     1080
cttttgtaat tatttccttc aaaatttatt atttgcaccg catctatttg taattatcgc     1140
ctacttgtca aactagggtg cacttagtaa atatctggtg caaataacaa atgcctttat     1200
tttttgggca cagacagaaa cgacatcgtt aagccgtgaa gcgaaggaa cgaaacggcg       1260 tcgtttaatc tggagcccca aacgcagttg gtttcgtacg tctagaaggg ctagagcggc     1320
cgccaccgcg gtggagctcc agcttttgtt ccctttagtg agggttaatt gcgcgcttgg     1380
cgtaatcatg gtcatagctg tttcctgtgt gaaattgtta tccgctcaca attccacaca     1440
acatacgagc cggaagcata aagtgtaaag cctggggtgc ctaatgagtg agctaactca     1500
cattaattgc gttgcgctca ctgcccgctt tccagtcggg aaacctgtcg tgccagctgc     1560
attaatgaat cggccaacgc gcggggagag gcggtttgcg tattgggcgc tcttccgctt     1620
cctcgctcac tgactcgctg cgctcggtcg ttcggctgcg gcgagcggta tcagctcact     1680
caaaggcggt aatacggtta tccacagaat caggggataa cgcaggaaag aacatgtgag     1740
caaaaggcca gcaaaaggcc aggaaccgta aaaaggccgc gttgctggcg ttttttccata   1800 ggctccgccc ccctgacgag catcacaaaa atcgacgctc aagtcagagg tggcgaaacc   1860
cgacaggact ataaagatac caggcgtttc cccctggaag ctccctcgtg cgctctcctg     1920
ttccgaccct gccgcttacc ggatacctgt ccgcctttct cccttcggga agcgtggcgc   1980
tttctcatag ctcacgctgt aggtatctca gttcggtgta ggtcgttcgc tccaagctgg   2040
gctgtgtgca cgaaccccc gttcagcccg accgctgcgc cttatccggt aactatcgtc     2100
ttgagtccaa cccggtaaga cacgacttat cgccactggc agcagccact ggtaacagga    2160
ttagcagagc gaggtatgta ggcggtgcta cagagttctt gaagtggtgg cctaactacg    2220
gctacactag aaggacagta tttggtatct gcgctctgct gaagccagtt accttcggaa    2280
aaagagttgg tagctcttga tccggcaaac aaaccaccgc tggtagcggt ggtttttttg    2340
tttgcaagca gcagattacg cgcagaaaaa aaggatctca agaagatcct ttgatctttt    2400
ctacggggtc tgacgctcag tggaacgaaa actcacgtta agggattttg gtcatgagat    2460
tatcaaaaag gatcttcacc tagatccttt taaattaaaa atgaagtttt aaatcaatct    2520
aaagtatata tgagtaaact tggtctgaca gttaccaatg cttaatcagt gaggcaccta    2580
tctcagcgat ctgtctattt cgttcatcca tagttgcctg actccccgtc gtgtagataa    2640
ctacgatacg ggagggctta ccatctggcc ccagtgctgc aatgataccg cgagacccac    2700
gctcaccggc tccagattta tcagcaataa accagccagc cggaagggcc gagcgcagaa    2760
```

-continued

```
gtggtcctgc aactttatcc gcctccatcc agtctattaa ttgttgccgg gaagctagag    2820
taagtagttc gccagttaat agtttgcgca acgttgttgc cattgctaca ggcatcgtgg    2880
tgtcacgctc gtcgtttggt atggcttcat tcagctccgg ttcccaacga tcaaggcgag    2940
ttacatgatc ccccatgttg tgcaaaaaag cggttagctc cttcggtcct ccgatcgttg    3000
tcagaagtaa gttggccgca gtgttatcac tcatggttat ggcagcactg cataattctc    3060
ttactgtcat gccatccgta agatgctttt ctgtgactgg tgagtactca accaagtcat    3120
tctgagaata gtgtatgcgg cgaccgagtt gctcttgccc ggcgtcaata cgggataata    3180
ccgcgccaca tagcagaact ttaaaagtgc tcatcattgg aaaacgttct cggggcgaaa    3240
aactctcaag gatcttaccg ctgttgagat ccagttcgat gtaacccact cgtgcaccca    3300
actgatcttc agcatctttt actttcacca gcgtttctgg gtgagcaaaa acaggaaggc    3360
aaaatgccgc aaaaaaggga ataagggcga cacggaaatg ttgaatactc atactcttcc    3420
tttttcaata ttattgaagc atttatcagg gttattgtct catgagcgga tacatatttg    3480
aatgtattta gaaaaataaa caaatagggg ttccgcgcac atttccccga aaagtgccac    3540
ctaaattgta agcgttaata ttttgttaaa attcgcgtta aattttttgtt aaatcagctc    3600 attttttaac caataggccg aaatcggcaa aatcccttat aaatcaaaag aatagaccga    3660
gatagggttg agtgttgttc cagtttggaa caagagtcca ctattaaaga acgtggactc    3720
caacgtcaaa gggcgaaaaa ccgtctatca gggcgatggc ccactacgtg aaccatcacc    3780
ctaatcaagt tttttggggt cgaggtgccg taaagcacta atcggaacc ctaaagggag    3840 cccccgattt agagcttgac ggggaaagcc ggcgaacgtg gcgagaaagg aagggaagaa    3900
agcgaaagga gcgggcgcta gggcgctggc aagtgtagcg gtcacgctgc gcgtaaccac    3960
cacacccgcc gcgcttaatg cgccgctaca gggcgcgtcc cattcgccat tcaggctgcg    4020
caactgttgg gaagggcgat cggtgcgggc ctcttcgcta ttacgccagc tggcgaaagg    4080
gggatgtgct gcaaggcgat taagttgggt aacgccaggg ttttcccagt cacgacgttg    4140
taaaacgacg gccagtgagc gcgcgtaata cgactcacta gggcgaat tgggtaccgg    4200 gccccccctc gaggtcgacg gtatcgataa gcttgatatc gaattcctgc agcccggggg    4260
atccgccc                                                              4268
```

<210> SEQ ID NO 97
<211> LENGTH: 4990
<212> TYPE: DNA
<213> ORGANISM: Artificial Sequence
<220> FEATURE:
<223> OTHER INFORMATION: Plasmid pKR124
<220> FEATURE:
<221> NAME/KEY: misc_feature
<222> LOCATION: (1186)..(1186)
<223> OTHER INFORMATION: n is a, c, g, or t

<400> SEQUENCE: 97

```
ctagacgtac gtcctcgaag agaagggtta ataacacatt ttttaacatt tttaacacaa      60
attttagtta tttaaaaatt tattaaaaaa tttaaaataa gaagaggaac tctttaaata     120
aatctaactt acaaaattta tgatttttaa taagttttca ccaataaaaa atgtcataaa     180
aatatgttaa aaagtatatt atcaatattc tctttatgat aaataaaaag aaaaaaaaaa     240
taaaagttaa gtgaaaatga gattgaagtg acttaggtg tgtataaata tatcaacccc     300
gccaacaatt tatttaatcc aaatatattg aagtatatta ttccatagcc tttatttatt     360
```

```
tatatattta ttatataaaa gctttatttg ttctaggttg ttcatgaaat attttttgg      420 ttttatctcc gttgtaagaa aatcatgtgc tttgtgtcgc cactcactat tgcagctttt      480
tcatgcattg gtcagattga cggttgattg tattttgtt ttttatggtt ttgtgttatg      540
acttaagtct tcatctcttt atctcttcat caggtttgat ggttacctaa tatggtccat      600
gggtacatgc atggttaaat taggtggcca actttgttgt gaacgataga attttttta      660 tattaagtaa actatttta tattatgaaa taataataaa aaaatatttt tatcattatt      720
aacaaaatca tattagttaa tttgttaact ctataataaa agaaatactg taacattcac      780
attacatggt aacatctttc caccctttca tttgtttttt gtttgatgac ttttttttctt      840 gtttaaattt atttccctttc ttttaaattt ggaatacatt atcatcatat ataaactaaa      900
atactaaaaa caggattaca caaatgataa ataataacac aaatatttat aaatctagct      960
gcaatatatt taaactagct atatcgatat tgtaaaataa aactagctgc attgatactg     1020
ataaaaaaat atcatgtgct ttctggactg atgatgcagt atactttga cattgccttt     1080 attttattttt tcagaaaagc tttcttagtt ctgggttctt cattatttgt ttcccatctc     1140
cattgtgaat tgaatcattt gcttcgtgtc acaaatacaa tttagntagg tacatgcatt     1200
ggtcagattc acggtttatt atgtcatgac ttaagttcat ggtagtacat tacctgccac     1260
gcatgcatta tattggttag atttgatagg caaatttggt tgtcaacaat ataaatataa     1320
ataatgtttt tatattacga ataacagtg atcaaaacaa acagttttat ctttattaac     1380
aagattttgt ttttgtttga tgacgttttt taatgtttac gctttccccc ttcttttgaa     1440
tttagaacac tttatcatca taaaatcaaa tactaaaaaa attacatatt tcataaataa     1500
taacacaaat atttttaaaa aatctgaaat aataatgaac aatattacat attatcacga     1560
aaattcatta ataaaaatat tatataaata aaatgtaata gtagttatat gtaggaaaaa     1620
agtactgcac gcataatata tacaaaaaga ttaaaatgaa ctattataaa taataacact     1680
aaattaatgg tgaatcatat caaaataatg aaaaagtaaa taaaattttgt aattaacttc     1740 tatatgtatt acacacacaa ataataaata atagtaaaaa aaattatgat aaatattttac     1800 catctcataa gatatttaaa ataatgataa aaatatagat tattttttat gcaactagct     1860
agccaaaaag agaacacggg tatatataaa aagagtacct ttaaattcta ctgtacttcc     1920
tttattcctg acgtttttat atcaagtgga catacgtgaa gattttaatt atcagtctaa     1980
atatttcatt agcacttaat acttttctgt tttattccta tcctataagt agtcccgatt     2040
ctcccaacat tgcttattca cacaactaac taagaaagtc ttccatagcc ccccaagcgg     2100
ccgcgacaca agtgtgagag tactaaataa atgctttggt tgtacgaaat cattacacta     2160
aataaaataa tcaaagctta tatatgcctt ccgctaaggc cgaatgcaaa gaaattggtt     2220 cttttctcgtt atcttttgcc acttttacta gtacgtatta attactactt aatcatctttt     2280 gtttacggct cattatatcc gtacgtcgag tcgacctgca ggcatgcaag cttggcgtaa     2340
tcatggtcat agctgtttcc tgtgtgaaat tgttatccgc tcacaattcc acacaacata     2400
cgagccggaa gcataaagtg taaagcctgg ggtgcctaat gagtgagcta actcacatta     2460
attgcgttgc gctcactgcc cgctttccag tcgggaaacc tgtcgtgcca gctgcattaa     2520
tgaatcggcc aacgcgcggg gagaggcggt ttgcgtattg ggcgctcttc cgcttcctcg     2580
ctcactgact cgctgcgctc ggtcgttcgg ctgcggcgag cggtatcagc tcactcaaag     2640
gcggtaatac ggttatccac agaatcaggg gataacgcag gaaagaacat gtgagcaaaa     2700
ggccagcaaa aggccaggaa ccgtaaaaag gccgcgttgc tggcgttttt ccataggctc     2760
```

```
cgcccccctg acgagcatca caaaaatcga cgctcaagtc agaggtggcg aaacccgaca    2820
ggactataaa gataccaggc gtttccccct ggaagctccc tcgtgcgctc tcctgttccg    2880
accctgccgc ttaccggata cctgtccgcc tttctccctt cgggaagcgt ggcgctttct    2940
catagctcac gctgtaggta tctcagttcg gtgtaggtcg ttcgctccaa gctgggctgt    3000
gtgcacgaac cccccgttca gcccgaccgc tgcgccttat ccggtaacta tcgtcttgag    3060
tccaacccgg taagacacga cttatcgcca ctggcagcag ccactggtaa caggattagc    3120
agagcgaggt atgtaggcgg tgctacagag ttcttgaagt ggtggcctaa ctacggctac    3180
actagaagga cagtatttgg tatctgcgct ctgctgaagc cagttacctt cggaaaaaga    3240
gttggtagct cttgatccgg caaacaaacc accgctggta cggtggtttt tttgtttgc    3300
aagcagcaga ttacgcgcag aaaaaaagga tctcaagaag atcctttgat cttttctacg    3360
gggtctgacg ctcagtggaa cgaaaactca cgttaaggga ttttggtcat gagattatca    3420
aaaaggatct tcacctagat ccttttaaat taaaaatgaa gttttaaatc aatctaaagt    3480
atatatgagt aaacttggtc tgacagttac caatgcttaa tcagtgaggc acctatctca    3540
gcgatctgtc tatttcgttc atccatagtt gcctgactcc ccgtcgtgta gataactacg    3600
atacgggagg gcttaccatc tggccccagt gctgcaatga taccgcgaga cccacgctca    3660
ccggctccag atttatcagc aataaaccag ccagccggaa gggccgagcg cagaagtggt    3720
cctgcaactt tatccgcctc catccagtct attaattgtt gccgggaagc tagagtaagt    3780
agttcgccag ttaatagttt gcgcaacgtt gttgccattg ctacaggcat cgtggtgtca    3840
cgctcgtcgt ttggtatggc ttcattcagc tccggttccc aacgatcaag gcgagttaca    3900
tgatccccca tgttgtgcaa aaaagcggtt agctccttcg gtcctccgat cgttgtcaga    3960
agtaagttgg ccgcagtgtt atcactcatg gttatggcag cactgcataa ttctcttact    4020
gtcatgccat ccgtaagatg cttttctgtg actggtgagt actcaaccaa gtcattctga    4080
gaatagtgta tgcggcgacc gagttgctct tgcccggcgt caatacggga taataccgcg    4140
ccacatagca gaactttaaa agtgctcatc attggaaaac gttcttcggg gcgaaaactc    4200
tcaaggatct taccgctgtt gagatccagt tcgatgtaac ccactcgtgc acccaactga    4260
tcttcagcat cttttacttt caccagcgtt tctgggtgag caaaaacagg aaggcaaaat    4320
gccgcaaaaa agggaataag ggcgacacgg aaatgttgaa tactcatact cttccttttt    4380
caatattatt gaagcattta tcagggttat tgtctcatga gcggatacat atttgaatgt    4440
atttagaaaa ataaacaaat aggggttccg cgcacatttc cccgaaaagt gccacctgac    4500
gtctaagaaa ccattattat catgacatta acctataaaa ataggcgtat cacgaggccc    4560
tttcgtctcg cgcgtttcgg tgatgacggt gaaaacctct gacacatgca gctcccggag    4620
acggtcacag cttgtctgta agcggatgcc gggagcagac aagcccgtca gggcgcgtca    4680
gcgggtgttg gcgggtgtcg ggctggctt aactatgcgg catcagagca gattgtactg    4740
agagtgcacc atatgcggtg tgaaataccg cacagatgcg taaggagaaa ataccgcatc    4800
aggcgccatt cgccattcag gctgcgcaac tgttgggaag ggcgatcggt gcgggcctct    4860
tcgctattac gccagctggc gaaaggggga tgtgctgcaa ggcgattaag ttgggtaacg    4920
ccagggtttt cccagtcacg acgttgtaaa acgacggcca gtgaattcga gctcggtacc    4980
cggggatcct                                                           4990

<210> SEQ ID NO 98
```

<211> LENGTH: 3982
<212> TYPE: DNA
<213> ORGANISM: Artificial Sequence
<220> FEATURE:
<223> OTHER INFORMATION: Plasmid pKR163

<400> SEQUENCE: 98

| | | | | | |
|---|---|---|---|---|---|
| gtacgaaacc | aactgcgttt | ggggctccag | attaaacgac | gccgtttcgt | tcctttcgct | 60 |
| tcacggctta | acgatgtcgt | ttctgtctgt | gcccaaaaaa | taaaggcatt | tgttatttgc | 120 |
| accagatatt | tactaagtgc | accctagttt | gacaagtagg | cgataattac | aaatagatgc | 180 |
| ggtgcaaata | ataaattttg | aaggaaataa | ttacaaaaga | acagaactta | tatttacttt | 240 |
| attttaaaaa | actaaaatga | agaacaaaa | aagtaaaaa | atacaaaaaa | tgtgctttaa | 300 |
| ccactttcat | tatttgttac | agaaagtatg | attctactca | aattgatctg | ttgtatctgg | 360 |
| tgctgccttg | tcacactggc | gatttcaatc | ccctaaagat | atggtgcaaa | ctgcgaagtg | 420 |
| atcaatatct | gctcggttaa | tttagattaa | ttaataatat | tcaacgtgat | gtaccaaaaa | 480 |
| aagacaattt | tttgctccat | tgacaaatta | aacctcatca | aggtaatttc | caaacctata | 540 |
| agcaaaaaaa | tttcacatta | attggcccgc | aatcctatta | gtcttattat | actagagtag | 600 |
| gaaaaaaac | aattacacaa | cttgtcttat | tattctctat | gctaatgaat | attttttccct | 660 |
| tttgttagaa | atcagtgttt | cctaatttat | tgagtattaa | ttccactcac | cgcatatatt | 720 |
| taccgttgaa | taagaaaatt | ttacacataa | ttcttttttaa | gataaataat | tttttttatac | 780 |
| tagatcttat | atgattacgt | gaagccaagt | gggttatact | aatgatatat | aatgtttgat | 840 |
| agtaatcagt | ttataaacca | aatgcatgga | aatgttacgt | ggaagcacgt | aaattaacaa | 900 |
| gcattgaagc | aaatgcagcc | accgcaccaa | aaccacccca | cttcacttcc | acgtaccata | 960 |
| ttccatgcaa | ctacaacacc | ctaaaacttc | aataaatgcc | cccaccttca | cttcacttca | 1020 |
| cccatcaata | gcaagcggcc | gcgaagttaa | aagcaatgtt | gtcacttgtc | gtactaacac | 1080 |
| atgatgtgat | agtttatgct | agctagctat | aacataagct | gtctctgagt | gtgttgtata | 1140 |
| ttaataaaga | tcatcactgg | tgaatggtga | tcgtgtacgt | accctactta | gtaggcaatg | 1200 |
| gaagcactta | gagtgtgctt | tgtgcatggc | cttgcctctg | ttttgagact | tttgtaatgt | 1260 |
| tttcgagttt | aaatctttgc | ctttgcgtac | gtcgagtcga | cctgcaggca | tgcaagcttg | 1320 |
| gcgtaatcat | ggtcatagct | gtttcctgtg | tgaaattgtt | atccgctcac | aattccacac | 1380 |
| aacatacgag | ccggaagcat | aaagtgtaaa | gcctggggtg | cctaatgagt | gagctaactc | 1440 |
| acattaattg | cgttgcgctc | actgcccgct | ttccagtcgg | gaaacctgtc | gtgccagctg | 1500 |
| cattaatgaa | tcggccaacg | cgcggggaga | ggcggtttgc | gtattgggcg | ctcttccgct | 1560 |
| tcctcgctca | ctgactcgct | gcgctcggtc | gttcggctgc | ggcgagcggt | atcagctcac | 1620 |
| tcaaaggcgg | taatacggtt | atccacagaa | tcaggggata | acgcaggaaa | gaacatgtga | 1680 |
| gcaaaaggcc | agcaaaaggc | caggaaccgt | aaaaaggccg | cgttgctggc | gtttttccat | 1740 |
| aggctccgcc | cccctgacga | gcatcacaaa | aatcgacgct | caagtcagag | gtggcgaaac | 1800 |
| ccgacaggac | tataaagata | ccaggcgttt | ccccctggaa | gctccctcgt | gcgctctcct | 1860 |
| gttccgaccc | tgccgcttac | cggatacctg | tccgcctttc | tcccttcggg | aagcgtggcg | 1920 |
| ctttctcata | gctcacgctg | taggtatctc | agttcggtgt | aggtcgttcg | ctccaagctg | 1980 |
| ggctgtgtgc | acgaaccccc | cgttcagccc | gaccgctgcg | ccttatccgg | taactatcgt | 2040 |
| cttgagtcca | acccggtaag | acacgactta | tcgccactgg | cagcagccac | tggtaacagg | 2100 |
| attagcagag | cgaggtatgt | aggcggtgct | acagagttct | tgaagtggtg | gcctaactac | 2160 |

```
ggctacacta aaggacagt atttggtatc tgcgctctgc tgaagccagt taccttcgga    2220
aaaagagttg gtagctcttg atccggcaaa caaaccaccg ctggtagcgg tggttttttt    2280
gtttgcaagc agcagattac gcgcagaaaa aaaggatctc aagaagatcc tttgatcttt    2340
tctacggggt ctgacgctca gtggaacgaa aactcacgtt aagggatttt ggtcatgaga    2400
ttatcaaaaa ggatcttcac ctagatcctt ttaaattaaa aatgaagttt taaatcaatc    2460
taaagtatat atgagtaaac ttggtctgac agttaccaat gcttaatcag tgaggcacct    2520
atctcagcga tctgtctatt tcgttcatcc atagttgcct gactccccgt cgtgtagata    2580
actacgatac gggagggctt accatctggc cccagtgctg caatgatacc gcgagaccca    2640
cgctcaccgg ctccagattt atcagcaata aaccagccag ccggaagggc cgagcgcaga    2700
agtggtcctg caactttatc cgcctccatc cagtctatta attgttgccg ggaagctaga    2760
gtaagtagtt cgccagttaa tagtttgcgc aacgttgttg ccattgctac aggcatcgtg    2820
gtgtcacgct cgtcgtttgg tatggcttca ttcagctccg gttcccaacg atcaaggcga    2880
gttacatgat cccccatgtt gtgcaaaaaa gcggttagct ccttcggtcc tccgatcgtt    2940
gtcagaagta agttggccgc agtgttatca ctcatggtta tggcagcact gcataattct    3000
cttactgtca tgccatccgt aagatgcttt tctgtgactg gtgagtactc aaccaagtca    3060
ttctgagaat agtgtatgcg gcgaccgagt tgctcttgcc cggcgtcaat acgggataat    3120
accgcgccac atagcagaac tttaaaagtg ctcatcattg gaaaacgttc ttcggggcga    3180
aaactctcaa ggatcttacc gctgttgaga tccagttcga tgtaacccac tcgtgcaccc    3240
aactgatctt cagcatcttt tactttcacc agcgtttctg ggtgagcaaa aacaggaagg    3300
caaaatgccg caaaaaaggg aataagggcg acacggaaat gttgaatact catactcttc    3360 cttttcaat attattgaag catttatcag ggttattgtc tcatgagcgg atacatattt    3420
gaatgtattt agaaaaataa acaaataggg gttccgcgca catttccccg aaaagtgcca    3480
cctgacgtct aagaaaccat tattatcatg acattaacct ataaaaatag gcgtatcacg    3540 aggcccttc gtctcgcgcg tttcggtgat gacggtgaaa acctctgaca catgcagctc    3600
ccggagacgg tcacagcttg tctgtaagcg gatgccggga gcagacaagc ccgtcagggc    3660
gcgtcagcgg gtgttggcgg gtgtcgggc tggcttaact atgcggcatc agagcagatt    3720
gtactgagag tgcaccatat gcggtgtgaa ataccgcaca gatgcgtaag gagaaaatac    3780
cgcatcaggc gccattcgcc attcaggctg cgcaactgtt gggaagggcg atcggtgcgg    3840
gcctcttcgc tattacgcca gctggcgaaa gggggatgtg ctgcaaggcg attaagttgg    3900
gtaacgccag ggttttccca gtcacgacgt tgtaaaacga cggccagtga attcgagctc    3960
ggtacccggg gatcctctag ac    3982
```

<210> SEQ ID NO 99
<211> LENGTH: 8878
<212> TYPE: DNA
<213> ORGANISM: Artificial Sequence
<220> FEATURE:
<223> OTHER INFORMATION: Plasmid pY34

<400> SEQUENCE: 99

```
ggccgcacag gccgcacaat ggcgactcga cagcgaactg ccaccactgt tgtggtcgag      60
gaccttccca aggtcactct tgaggccaag tctgaacctg tgttcccga tatcaagacc     120 atcaaggatg ccattcccgc gcactgcttc agccctcgc tcgtcacctc attctactac     180
```

-continued

| | |
|---|---|
| gtcttccgcg attttgccat ggtctctgcc ctcgtctggg ctgctctcac ctacatcccc | 240 |
| agcatccccg accagaccct ccgcgtcgca gcttggatgg tctacggctt cgtccagggt | 300 |
| ctgttctgca ccggtgtctg gattctcggc catgagtgcg gccacggtgc tttctctctc | 360 |
| cacggaaagg tcaacaatgt gaccggctgg ttcctccact cgttcctcct cgtccctac | 420 |
| ttcagctgga agtactctca ccaccgccac caccgcttca ccggccacat ggatctcgac | 480 |
| atggctttcg tccccaagac tgagcccaag ccctccaagt cgctcatgat tgctggcatt | 540 |
| gacgtcgccg agcttgttga ggacaccccc gctgctcaga tggtcaagct catcttccac | 600 |
| cagcttttcg gatggcaggc gtacctcttc ttcaacgcta gctctggcaa gggcagcaag | 660 |
| cagtgggagc ccaagactgg cctctccaag tggttccgag tcagtcactt cgagcctacc | 720 |
| agcgctgtct tccgccccaa cgaggccatc ttcatcctca tctccgatat cggtcttgct | 780 |
| ctaatgggaa ctgctctgta ctttgcttcc aagcaagttg gtgtttcgac cattctcttc | 840 |
| ctctaccttg ttccctacct gtgggttcac cactggctcg ttgccattac ctacctccac | 900 |
| caccaccaca ccgagctccc tcactacacc gctgagggct ggacctacgt caagggagct | 960 |
| ctcgccactg tcgaccgtga gtttggcttc atcggaaagc acctcttcca cggtatcatt | 1020 |
| gagaagcacg ttgttcacca tctcttccct aagatcccct tctacaaggc tgacgaggcc | 1080 |
| accgaggcca tcaagcccgt cattggcgac cactactgcc acgacgaccg aagcttcctg | 1140 |
| ggccagctgt ggaccatctt cggcacgctc aagtacgtcg agcacgaccc tgcccgaccc | 1200 |
| ggtgccatgc gatggaacaa ggactaggct aggcggccgc caccgcgccc cgagattccg | 1260 |
| gcctcttcgg ccgccaagcg acccgggtgg acgtctagag gtacctagca attaacagat | 1320 |
| agtttgccgg tgataattct cttaacctcc cacactcctt tgacataacg atttatgtaa | 1380 |
| cgaaactgaa atttgaccag atattgtgtc cgcggtggag ctccagcttt tgttcccttt | 1440 |
| agtgagggtt aatttcgagc ttggcgtaat catggtcata gctgtttcct gtgtgaaatt | 1500 |
| gttatccgct cacaattcca cacaacgtac gagccggaag cataaagtgt aaagcctggg | 1560 |
| gtgcctaatg agtgagctaa ctcacattaa ttgcgttgcg ctcactgccc gctttccagt | 1620 |
| cgggaaacct gtcgtgccag ctgcattaat gaatcggcca acgcgcgggg agaggcggtt | 1680 |
| tgcgtattgg gcgctcttcc gcttcctcgc tcactgactc gctgcgctcg tcgttcggc | 1740 |
| tgcggcgagc ggtatcagct cactcaaagg cggtaatacg ttatccaca gaatcagggg | 1800 |
| ataacgcagg aaagaacatg tgagcaaaag gccagcaaaa ggccaggaac cgtaaaaagg | 1860 |
| ccgcgttgct ggcgtttttc cataggctcc gcccccctga cgagcatcac aaaaatcgac | 1920 |
| gctcaagtca gaggtggcga aacccgacag gactataaag ataccaggcg tttccccctg | 1980 |
| gaagctccct cgtgcgctct cctgttccga ccctgccgct taccggatac ctgtccgcct | 2040 |
| ttctcccttc gggaagcgtg gcgctttctc atagctcacg ctgtaggtat ctcagttcgg | 2100 |
| tgtaggtcgt tcgctccaag ctgggctgtg tgcacgaacc ccccgttcag cccgaccgct | 2160 |
| gcgccttatc cggtaactat cgtcttgagt ccaacccggt aagacacgac ttatcgccac | 2220 |
| tggcagcagc cactggtaac aggattagca gagcgaggta tgtaggcggt gctacagagt | 2280 |
| tcttgaagtg gtggcctaac tacggctaca ctagaaggac agtatttggt atctgcgctc | 2340 |
| tgctgaagcc agttaccttc ggaaaaagag ttggtagctc ttgatccggc aaacaaacca | 2400 |
| ccgctggtag cggtggtttt tttgtttgca agcagcagat tacgcgcaga aaaaaggat | 2460 |
| ctcaagaaga tccttgatc ttttctacgg gtctgacgc tcagtggaac gaaaactcac | 2520 |
| gttaagggat tttggtcatg agattatcaa aaaggatctt cacctagatc ctttaaatt | 2580 |

```
aaaaatgaag ttttaaatca atctaaagta tatatgagta aacttggtct gacagttacc    2640
aatgcttaat cagtgaggca cctatctcag cgatctgtct atttcgttca tccatagttg    2700
cctgactccc cgtcgtgtag ataactacga tacgggaggg cttaccatct ggccccagtg    2760
ctgcaatgat accgcgagac ccacgctcac cggctccaga tttatcagca ataaaccagc    2820
cagccggaag ggccgagcgc agaagtggtc ctgcaacttt atccgcctcc atccagtcta    2880
ttaattgttg ccgggaagct agagtaagta gttcgccagt taatagtttg cgcaacgttg    2940
ttgccattgc tacaggcatc gtggtgtcac gctcgtcgtt tggtatggct tcattcagct    3000
ccggttccca acgatcaagg cgagttacat gatcccccat gttgtgcaaa aaagcggtta    3060
gctccttcgg tcctccgatc gttgtcagaa gtaagttggc cgcagtgtta tcactcatgg    3120
ttatggcagc actgcataat tctcttactg tcatgccatc cgtaagatgc ttttctgtga    3180
ctggtgagta ctcaaccaag tcattctgag aatagtgtat gcggcgaccg agttgctctt    3240
gcccggcgtc aatacgggat aataccgcgc cacatagcag aactttaaaa gtgctcatca    3300
ttggaaaacg ttcttcgggg cgaaaactct caaggatctt accgctgttg agatccagtt    3360
cgatgtaacc cactcgtgca cccaactgat cttcagcatc ttttactttc accagcgttt    3420
ctgggtgagc aaaaacagga aggcaaaatg ccgcaaaaaa gggaataagg gcgacacgga    3480
aatgttgaat actcatactc ttcctttttc aatattattg aagcatttat cagggttatt    3540
gtctcatgag cggatacata tttgaatgta tttagaaaaa taaacaaata ggggttccgc    3600
gcacatttcc ccgaaaagtg ccacctgacg cgccctgtag cggcgcatta gcgcggcgg     3660
gtgtggtggt tacgcgcagc gtgaccgcta cacttgccag cgccctagcg cccgctcctt    3720
tcgctttctt cccttccttt ctcgccacgt tcgccggctt tccccgtcaa gctctaaatc    3780
gggggctccc tttagggttc cgatttagtg ctttacggca cctcgacccc aaaaaacttg    3840
attagggtga tggttcacgt agtgggccat cgccctgata cggttttt cgcccttga     3900
cgttggagtc cacgttcttt aatagtggac tcttgttcca aactggaaca cactcaacc     3960
ctatctcggt ctattctttt gatttataag ggattttgcc gatttcggcc tattggttaa    4020
aaaatgagct gatttaacaa aaatttaacg cgaattttaa caaaatatta cgcttacaa     4080
tttccattcg ccattcaggc tgcgcaactg ttgggaaggg cgatcggtgc gggcctcttc    4140
gctattacgc cagctggcga aggggggatg tgctgcaagg cgattaagtt gggtaacgcc    4200
agggttttcc cagtcacgac gttgtaaaac gacggccagt gaattgtaat acgactcact    4260
atagggcgaa ttgggtaccg gccccccct cgaggtcgat ggtgtcgata agcttgatat     4320
cgaattcatg tcacacaaac cgatcttcgc ctcaaggaaa cctaattcta catccgagag    4380
actgccgaga tccagtctac actgattaat tttcgggcca ataatttaaa aaaatcgtgt    4440
tatataaatat tatatgtatt atatatatac atcatgatga tactgacagt catgtcccat    4500
tgctaaatag acagactcca tctgccgcct ccaactgatg ttctcaatat ttaagggtc     4560
atctcgcatt gtttaataat aaacagactc catctaccgc ctccaaatga tgttctcaaa    4620
atatattgta tgaacttatt tttattactt agtattatta gacaacttac ttgctttatg    4680
aaaaacactt cctatttagg aaacaattta taatggcagt tcgttcattt aacaatttat    4740
gtagaataaa tgttataaat gcgtatggga atcttaaat atggatagca taaatgatat     4800
ctgcattgcc taattcgaaa tcaacagcaa cgaaaaaaat cccttgtaca acataaaatag   4860
tcatcgagaa atatcaacta tcaaagaaca gctattcaca cgttactatt gagattatta    4920
```

-continued

```
ttggacgaga atcacacact caactgtctt tctctcttct agaaatacag gtacaagtat    4980
gtactattct cattgttcat acttctagtc atttcatccc acatattcct tggatttctc    5040
tccaatgaat gacattctat cttgcaaatt caacaattat aataagatat accaaagtag    5100
cggtatagtg gcaatcaaaa agcttctctg gtgtgcttct cgtatttatt tttattctaa    5160
tgatccatta aaggtatata tttatttctt gttatataat cctttttgttt attacatggg   5220 ctggatacat aaaggtattt tgatttaatt ttttgcttaa attcaatccc ccctcgttca    5280
gtgtcaactg taatggtagg aaattaccat acttttgaag aagcaaaaaa aatgaaagaa    5340
aaaaaaaatc gtatttccag gttagacgtt ccgcagaatc tagaatgcgg tatgcggtac    5400
attgttcttc gaacgtaaaa gttgcgctcc ctgagatatt gtacattttt gcttttacaa    5460
gtacaagtac atcgtacaac tatgtactac tgttgatgca tccacaacag tttgttttgt    5520
ttttttttgt tttttttttt tctaatgatt cattaccgct atgtatacct acttgtactt    5580
gtagtaagcc gggttattgg cgttcaatta atcatagact tatgaatctg cacggtgtgc    5640
gctgcgagtt acttttagct tatgcatgct acttgggtgt aatattggga tctgttcgga    5700
aatcaacgga tgctcaaccg atttcgacag taataatttg aatcgaatcg gagcctaaaa    5760
tgaacccgag tatatctcat aaaattctcg gtgagaggtc tgtgactgtc agtacaaggt    5820
gccttcatta tgccctcaac cttaccatac ctcactgaat gtagtgtacc tctaaaaatg    5880
aaatacagtg ccaaaagcca aggcactgag ctcgtctaac ggacttgata tacaaccaat    5940
taaaacaaat gaaagaaat acagttcttt gtatcatttg taacaattac cctgtacaaa     6000
ctaaggtatt gaaatcccac aatattccca aagtccaccc ctttccaaat tgtcatgcct    6060
acaactcata taccaagcac taacctacca aacaccacta aaaccccaca aaatatatct    6120
taccgaatat acagtaacaa gctaccacca cactcgttgg gtgcagtcgc cagcttaaag    6180
atatctatcc acatcagcca caactcccct cctttaataa accgactaca cccttggcta    6240
ttgaggttat gagtgaatat actgtagaca agacactttc aagaagactg tttccaaaac    6300
gtaccactgt cctccactac aaacacaccc aatctgcttc ttctagtcaa ggttgctaca    6360
ccggtaaatt ataaatcatc atttcattag cagggcaggg ccctttttat agagtcttat    6420
acactagcgg accctgccgg tagaccaacc cgcaggcgcg tcagtttgct ccttccatca    6480
atgcgtcgta gaaacgactt actccttctt gagcagctcc ttgaccttgt tggcaacaag    6540
tctccgacct cggaggtgga ggaagagcct ccgatatcgg cggtagtgat accagcctcg    6600
acggactcct tgacggcagc ctcaacagcg tcaccggcgg gcttcatgtt aagagagaac    6660
ttgagcatca tggcggcaga cagaatggtg gcaatggggt tgaccttctg cttgccgaga    6720
tcgggggcag atccgtgaca gggctcgtac agaccgaacg cctcgttggt gtcgggcaga    6780
gaagccagag aggcggaggg cagcagaccc agagaaccgg ggatgacgga ggcctcgtcg    6840
gagatgatat cgccaaacat gttggtggtg atgatgatac cattcatctt ggagggctgc    6900
ttgatgagga tcatggcggc cgagtcgatc agctggtggt tgagctcgag ctgggggaat    6960
tcgtccttga ggactcgagt gacagtcttt cgccaaagtc gagaggaggc cagcacgttg    7020
gccttgtcaa gagaccacac gggaagaggg gggttgtgct gaagggccag gaaggcggcc    7080
attcgggcaa ttcgctcaac ctcaggaacg gagtaggtct cggtgtcgga agcgacgcca    7140
gatccgtcat cctcctttcg ctctccaaag tagataccctc cgacgagctc tcggacaatg    7200
atgaagtcgg tgccctcaac gtttcggatg ggggagagat cggcgagctt gggcgacagc    7260
agctggcagg gtcgcaggtt ggcgtacagg ttcaggtcct ttcgcagctt gaggagaccc    7320
```

```
tgctcgggtc gcacgtcggt tcgtccgtcg ggagtggtcc atacggtgtt ggcagcgcct    7380
ccgacagcac cgagcataat agagtcagcc tttcggcaga tgtcgagagt agcgtcggtg    7440
atgggctcgc cctccttctc aatggcagct cctccaatga gtcggtcctc aaacacaaac    7500
tcggtgccgg aggcctcagc aacagacttg agcaccttga cggcctcggc aatcacctcg    7560
gggccacaga gtcgccgcc gagaagaaca atcttcttgg agtcagtctt ggtcttctta    7620
gtttcgggtt ccattgtgga tgtgtgtggt tgtatgtgtg atgtggtgtg tggagtgaaa    7680
atctgtggct ggcaaacgct cttgtatata tacgcacttt tgcccgtgct atgtggaaga    7740
ctaaacctcc gaagattgtg actcaggtag tgcggtatcg gctagggacc caaaccttgt    7800
cgatgccgat agcgctatcg aacgtacccc agccggccgg gagtatgtcg gaggggacat    7860
acgagatcgt caagggtttg tggccaactg gtatttaaat gatgtcgacg cagtaggatg    7920
tcctgcacgg gtcttttgt ggggtgtgga gaaaggggtg cttggagatg gaagccggta    7980
gaaccgggct gcttgtgctt ggagatggaa gccggtagaa ccgggctgct tgggggatt    8040 tggggccgct gggctccaaa gaggggtagg catttcgttg gggttacgta attgcggcat    8100
ttgggtcctg cgcgcatgtc ccattggtca gaattagtcc ggataggaga cttatcagcc    8160
aatcacagcg ccggatccac ctgtaggttg ggttgggtgg gagcacccct ccacagagta    8220
gagtcaaaca gcagcagcaa catgatagtt ggggtgtgc gtgttaaagg aaaaaaaga    8280 agcttgggtt atattcccgc tctatttaga ggttgcggga tagacgccga cggagggcaa    8340
tggcgccatg gaaccttgcg gatatcgata cgccgcggcg gactgcgtcc gaaccagctc    8400
cagcagcgtt ttttccgggc cattgagccg actgcgaccc cgccaacgtg tcttggccca    8460
cgcactcatg tcatgttggt gttgggaggc cacttttaa gtagcacaag gcacctagct    8520
cgcagcaagg tgtccgaacc aaagaagcgg ctgcagtggt gcaaacgggg cggaaacggc    8580
gggaaaaagc cacgggggca cgaattgagg cacgccctcg aatttgagac gagtcacggc    8640
cccattcgcc cgcgcaatgg ctcgccaacg cccggtcttt tgcaccacat caggttaccc    8700
caagccaaac ctttgtgtta aaagcttaa catattatac cgaacgtagg tttgggcggg    8760
cttgctccgt ctgtccaagg caacatttat ataagggtct gcatcgccgg ctcaattgaa    8820 tctttttct tcttctcttc tctatattca ttcttgaatt aaacacacat caatccgc    8878
```

<210> SEQ ID NO 100
<211> LENGTH: 5207
<212> TYPE: DNA
<213> ORGANISM: Artificial Sequence
<220> FEATURE:
<223> OTHER INFORMATION: Plasmid pKR863

<400> SEQUENCE: 100

```
ggccgcgaag ttaaaagcaa tgttgtcact tgtcgtacta acacatgatg tgatagttta     60
tgctagctag ctataacata agctgtctct gagtgtgttg tatattaata aagatcatca    120
ctggtgaatg tgatcgtgt acgtacccta cttagtaggc aatggaagca cttagagtgt    180
gctttgtgca tggccttgcc tctgttttga gacttttgta atgttttcga gtttaaatct    240
ttgcctttgc gtacgtcgag tcgacctgca ggcatgcaag cttggcgtaa tcatggtcat    300
agctgtttcc tgtgtgaaat tgttatccgc tcacaattcc acacaacata cgagccgaa    360 gcataaagtg taaagcctgg ggtgcctaat gagtgagcta actcacatta attgcgttgc    420
gctcactgcc cgctttccag tcgggaaacc tgtcgtgcca gctgcattaa tgaatcggcc    480
```

-continued

```
aacgcgcggg gagaggcggt ttgcgtattg ggcgctcttc cgcttcctcg ctcactgact       540
cgctgcgctc ggtcgttcgg ctgcggcgag cggtatcagc tcactcaaag gcggtaatac       600
ggttatccac agaatcaggg gataacgcag gaaagaacat gtgagcaaaa ggccagcaaa       660
aggccaggaa ccgtaaaaag gccgcgttgc tggcgttttt ccataggctc cgcccccctg       720
acgagcatca aaaaatcga cgctcaagtc agaggtggcg aaacccgaca ggactataaa       780
gataccaggc gtttccccct ggaagctccc tcgtgcgctc tcctgttccg accctgccgc       840
ttaccggata cctgtccgcc tttctccctt cgggaagcgt ggcgctttct catagctcac       900
gctgtaggta tctcagttcg gtgtaggtcg ttcgctccaa gctgggctgt gtgcacgaac       960
cccccgttca gcccgaccgc tgcgccttat ccggtaacta tcgtcttgag tccaacccgg      1020
taagacacga cttatcgcca ctggcagcag ccactggtaa caggattagc agagcgaggt      1080
atgtaggcgg tgctacagag ttcttgaagt ggtggcctaa ctacggctac actagaagga      1140
cagtatttgg tatctgcgct ctgctgaagc cagttacctt cggaaaaaga gttggtagct      1200
cttgatccgg caaacaaacc accgctggta gcggtggttt ttttgtttgc aagcagcaga      1260
ttacgcgcag aaaaaaagga tctcaagaag atcctttgat cttttctacg ggtctgacg       1320 ctcagtggaa cgaaaactca cgttaaggga ttttggtcat gagattatca aaaaggatct      1380
tcacctagat ccttttaaat taaaaatgaa gttttaaatc aatctaaagt atatatgagt      1440
aaacttggtc tgacagttac caatgcttaa tcagtgaggc acctatctca gcgatctgtc      1500
tatttcgttc atccatagtt gcctgactcc ccgtcgtgta gataactacg atacgggagg      1560
gcttaccatc tggccccagt gctgcaatga taccgcgaga cccacgctca ccggctccag      1620
atttatcagc aataaaccag ccagccggaa gggccgagcg cagaagtggt cctgcaactt      1680
tatccgcctc catccagtct attaattgtt gccgggaagc tagagtaagt agttcgccag      1740
ttaatagttt gcgcaacgtt gttgccattg ctacaggcat cgtggtgtca cgctcgtcgt      1800
ttggtatggc ttcattcagc tccggttccc aacgatcaag gcgagttaca tgatccccca      1860
tgttgtgcaa aaaagcggtt agctccttcg gtcctccgat cgttgtcaga agtaagttgg      1920
ccgcagtgtt atcactcatg gttatggcag cactgcataa ttctcttact gtcatgccat      1980
ccgtaagatg cttttctgtg actggtgagt actcaaccaa gtcattctga agtagtgta       2040 tgcggcgacc gagttgctct tgcccggcgt caatacggga taataccgcg ccacatagca      2100
gaactttaaa agtgctcatc attggaaaac gttcttcggg gcgaaaactc tcaaggatct      2160
taccgctgtt gagatccagt tcgatgtaac ccactcgtgc acccaactga tcttcagcat      2220
cttttacttt caccagcgtt tctgggtgag caaaaacagg aaggcaaaat gccgcaaaaa      2280
agggaataag ggcgacacgg aaatgttgaa tactcatact cttcctttt caatattatt      2340 gaagcattta tcagggttat tgtctcatga gcggatacat atttgaatgt atttagaaaa      2400
ataaacaaat aggggttccg cgcacatttc cccgaaaagt gccacctgac gtctaagaaa      2460
ccattattat catgacatta acctataaaa ataggcgtat cacgaggccc tttcgtctcg      2520
cgcgtttcgg tgatgacggt gaaaacctct gacacatgca gctcccggag acggtcacag      2580
cttgtctgta agcggatgcc gggagcagac aagcccgtca gggcgcgtca gcgggtgttg      2640
gcgggtgtcg ggctggctt aactatgcgg catcagagca gattgtactg agagtgcacc       2700
atatgcggtg tgaaataccg cacagatgcg taaggagaaa ataccgcatc aggcgccatt      2760
cgccattcag gctgcgcaac tgttgggaag ggcgatcggt gcgggcctct tcgctattac      2820
gccagctggc gaaaggggga tgtgctgcaa ggcgattaag ttgggtaacg ccagggtttt      2880
```

```
cccagtcacg acgttgtaaa acgacggcca gtgaattcga gctcggtacc cggggatcct    2940
ctagacgtac gaaaccaact gcgtttgggg ctccagatta acgacgccg  tttcgttcct    3000
ttcgcttcac ggcttaacga tgtcgtttct gtctgtgccc aaaaaataaa ggcatttgtt    3060
atttgcacca gatatttact aagtgcaccc tagtttgaca agtaggcgat aattacaaat    3120
agatgcggtg caataataa  attttgaagg aaataattac aaaagaacag aacttatatt    3180
tactttattt taaaaaacta aaatgaaaga acaaaaaaag taaaaaatac aaaaaatgtg    3240
ctttaaccac tttcattatt tgttacagaa agtatgattc tactcaaatt gatctgttgt    3300
atctggtgct gccttgtcac actggcgatt tcaatcccct aaagatatgg tgcaaactgc    3360
gaagtgatca atatctgctc ggttaattta gattaattaa taatattcaa cgtgatgtac    3420
caaaaaaga  caatttttg  ctccattgac aaattaaacc tcatcaaggt aatttccaaa    3480
cctataagca aaaaaattc  acattaattg gcccgcaatc ctattagtct tattatacta    3540
gagtaggaaa aaaaacaatt acacaacttg tcttattatt ctctatgcta atgaatattt    3600
ttccctttg  ttagaaatca gtgtttccta atttattgag tattaattcc actcaccgca    3660
tatatttacc gttgaataag aaaatttac  acataattct ttttaagata aataattttt    3720
ttatactaga tcttatatga ttacgtgaag ccaagtgggt tatactaatg atatataatg    3780
tttgatagta atcagtttat aaaccaaatg catggaaatg ttacgtggaa gcacgtaaat    3840
taacaagcat tgaagcaaat gcagccaccg caccaaaacc accccacttc acttccacgt    3900
accatattcc atgcaactac aacaccctaa aacttcaata aatgccccca ccttcacttc    3960
acttcaccca tcaatagcaa gcggccgcac aatggcgact cgacagcgaa ctgccaccac    4020
tgttgtggtc gaggaccttc ccaaggtcac tcttgaggcc aagtctgaac ctgtgttccc    4080
cgatatcaag accatcaagg atgccattcc cgcgcactgc ttccagccct cgctcgtcac    4140
ctcattctac tacgtcttcc gcgattttgc catggtctct gccctcgtct gggctgctct    4200
cacctacatc cccagcatcc ccgaccagac cctccgcgtc gcagcttgga tggtctacgg    4260
cttcgtccag ggtctgttct gcaccggtgt ctggattctc ggccatgagt gcggccacgg    4320
tgctttctct ctccacggaa aggtcaacaa tgtgaccggc tggttcctcc actcgttcct    4380
cctcgtcccc tacttcagct ggaagtactc tcaccaccgc caccaccgct tcaccggcca    4440
catggatctc gacatggctt tcgtccccaa gactgagccc aagccctcca gtcgctcat     4500
gattgctggc attgacgtcg ccgagcttgt tgaggacacc cccgctgctc agatggtcaa    4560
gctcatcttc caccagcttt tcggatggca ggcgtacctc ttcttcaacg ctagctctgg    4620
caagggcagc aagcagtggg agcccaagac tggcctctcc aagtggttcc gagtcagtca    4680
cttcgagcct accagcgctg tcttccgccc caacgaggcc atcttcatcc tcatctccga    4740
tatcggtctt gctctaatgg gaactgctct gtactttgct tccaagcaag ttggtgtttc    4800
gaccattctc ttcctctacc ttgttcccta cctgtgggtt caccactggc tcgttgccat    4860
tacctacctc caccaccacc acaccgagct ccctcactac accgctgagg ctgaccta     4920
cgtcaaggga gctctcgcca ctgtcgaccg tgagtttggc ttcatcggaa agcacctctt    4980
ccacggtatc attgagaagc acgttgttca ccatctcttc cctaagatcc ccttctacaa    5040
ggctgacgag gccaccgagg ccatcaagcc cgtcattggc gaccactact gccacgacga    5100
ccgaagcttc ctgggccagc tgtgaccat  cttcggcacg ctcaagtacg tcgagcacga    5160
ccctgcccga cccggtgcca tgcgatggaa caaggactag gctaggc                  5207
```

<210> SEQ ID NO 101
<211> LENGTH: 9035
<212> TYPE: DNA
<213> ORGANISM: Artificial Sequence
<220> FEATURE:
<223> OTHER INFORMATION: Plasmid pKR869

<400> SEQUENCE: 101

| | | | | | |
|---|---|---|---|---|---|
| gtacgtctag | aggatccgtc | gacggcgcgc | ccgatcatcc | ggatatagtt | cctcctttca | 60 |
| gcaaaaaacc | cctcaagacc | cgtttagagg | ccccaagggg | ttatgctagt | tattgctcag | 120 |
| cggtggcagc | agccaactca | gcttcctttc | gggctttgtt | agcagccgga | tcgatccaag | 180 |
| ctgtacctca | ctattccttt | gccctcggac | gagtgctggg | gcgtcggttt | ccactatcgg | 240 |
| cgagtacttc | tacacagcca | tcggtccaga | cggccgcgct | tctgcgggcg | atttgtgtac | 300 |
| gcccgacagt | cccggctccg | gatcggacga | ttgcgtcgca | tcgaccctgc | gcccaagctg | 360 |
| catcatcgaa | attgccgtca | accaagctct | gatagagttg | gtcaagacca | atgcggagca | 420 |
| tatacgcccg | gagccgcggc | gatcctgcaa | gctccggatg | cctccgctcg | aagtagcgcg | 480 |
| tctgctgctc | catacaagcc | aaccacggcc | tccagaagaa | gatgttggcg | acctcgtatt | 540 |
| gggaatcccc | gaacatcgcc | tcgctccagt | caatgaccgc | tgttatgcgg | ccattgtccg | 600 |
| tcaggacatt | gttggagccg | aaatccgcgt | gcacgaggtg | ccggacttcg | ggcagtcct | 660 |
| cggcccaaag | catcagctca | tcgagagcct | gcgcgacgga | cgcactgacg | tgtcgtcca | 720 |
| tcacagtttg | ccagtgatac | acatggggat | cagcaatcgc | gcatatgaaa | tcacgccatg | 780 |
| tagtgtattg | accgattcct | tgcggtccga | atgggccgaa | cccgctcgtc | tggctaagat | 840 |
| cggccgcagc | gatcgcatcc | atagcctccg | cgaccggctg | cagaacagcg | ggcagttcgg | 900 |
| tttcaggcag | gtcttgcaac | gtgacaccct | gtgcacggcg | ggagatgcaa | taggtcaggc | 960 |
| tctcgctgaa | ttccccaatg | tcaagcactt | ccggaatcgg | gagcgcggcc | gatgcaaagt | 1020 |
| gccgataaac | ataacgatct | tgtagaaac | catcggcgca | gctatttacc | cgcaggacat | 1080 |
| atccacgccc | tcctacatcg | aagctgaaag | cacgagattc | ttcgccctcc | gagagctgca | 1140 |
| tcaggtcgga | gacgctgtcg | aacttttcga | tcagaaactt | ctcgacagac | gtcgcggtga | 1200 |
| gttcaggctt | ttccatgggt | atatctcctt | cttaaagtta | aacaaaatta | tttctagagg | 1260 |
| gaaaccgttg | tggtctccct | atagtgagtc | gtattaattt | cgcgggatcg | agatctgatc | 1320 |
| aacctgcatt | aatgaatcgg | ccaacgcgcg | gggagaggcg | gtttgcgtat | gggcgctct | 1380 |
| tccgcttcct | cgctcactga | ctcgctgcgc | tcggtcgttc | ggctgcggcg | agcggtatca | 1440 |
| gctcactcaa | aggcggtaat | acggttatcc | acagaatcag | gggataacgc | aggaaagaac | 1500 |
| atgtgagcaa | aaggccagca | aaaggccagg | aaccgtaaaa | aggccgcgtt | gctggcgttt | 1560 |
| ttccataggc | tccgcccccc | tgacgagcat | cacaaaaatc | gacgctcaag | tcagaggtgg | 1620 |
| cgaaacccga | caggactata | aagataccag | gcgtttcccc | ctggaagctc | cctcgtgcgc | 1680 |
| tctcctgttc | cgaccctgcc | gcttaccgga | tacctgtccg | cctttctccc | ttcgggaagc | 1740 |
| gtggcgcttt | ctcaatgctc | acgctgtagg | tatctcagtt | cggtgtaggt | cgttcgctcc | 1800 |
| aagctgggct | gtgtgcacga | accccccgtt | cagcccgacc | gctgcgcctt | atccggtaac | 1860 |
| tatcgtcttg | agtccaaccc | ggtaagacac | gacttatcgc | cactggcagc | agccactggt | 1920 |
| aacaggatta | gcagagcgag | gtatgtaggc | ggtgctacag | agttcttgaa | gtggtggcct | 1980 |
| aactacggct | acactagaag | gacagtattt | ggtatctgcg | ctctgctgaa | gccagttacc | 2040 |
| ttcggaaaaa | gagttggtag | ctcttgatcc | ggcaaacaaa | ccaccgctgg | tagcggtggt | 2100 |

```
tttttttgttt gcaagcagca gattacgcgc agaaaaaaag gatctcaaga agatcctttg    2160
atctttctta cggggtctga cgctcagtgg aacgaaaact cacgttaagg gattttggtc    2220
atgacattaa cctataaaaa taggcgtatc acgaggccct ttcgtctcgc gcgtttcggt    2280
gatgacggtg aaaacctctg acacatgcag ctcccggaga cggtcacagc ttgtctgtaa    2340
gcggatgccg ggagcagaca gcccgtcag ggcgcgtcag cgggtgttgg cgggtgtcgg     2400
ggctggctta actatgcggc atcagagcag attgtactga gagtgcacca tatggacata    2460
ttgtcgttag aacgcggcta caattaatac ataaccttat gtatcataca catacgattt    2520
aggtgacact atagaacggc gcgccaagct gggtctagaa ctagaaacgt gatgccactt    2580
gttattgaag tcgattacag catctattct gttttactat ttataacttt gccatttctg    2640
acttttgaaa actatctctg gatttcggta tcgctttgtg aagatcgagc aaaagagacg    2700
ttttgtggac gcaatggtcc aaatccgttc tacatgaaca aattggtcac aatttccact    2760
aaaagtaaat aaatggcaag ttaaaaaagg aatatgcatt ttactgattg cctaggtgag    2820
ctccaagaga agttgaatct acacgtctac caaccgctaa aaaagaaaa acattgatat     2880 gtaacctgat tccattagct tttgacttct tcaacagatt ctctacttag atttctaaca    2940
gaaatattat tactagcaca tcattttcag tctcactaca gcaaaaaatc caacggcaca    3000
atacagacaa caggagatat cagactacag agatagatag atgctactgc atgtagtaag    3060
ttaaataaaa ggaaaataaa atgtcttgct accaaaacta ctacagacta tgatgctcac    3120
cacaggccaa atcctgcaac taggacagca ttatcttata tatattgtac aaaacaagca    3180
tcaaggaaca tttggtctag gcaatcagta cctcgttcta ccatcaccct cagttatcac    3240
atccttgaag gatccattac tgggaatcat cggcaacaca tgctcctgat ggggcacaat    3300
gacatcaaga aggtaggggc caggggtgtc caacattctc tgaattgccg ctctaagctc    3360
ttccttcttc gtcactcgcg ctgccggtat cccacaagca tcagcaaact tgagcatgtt    3420
tgggaatatc tcgctctcgc tagacggatc tccaagatag gtgtgagctc tattggactt    3480
gtagaaccta tcctccaact gaaccaccat acccaaatgc tgattgttca acaacaatat    3540
cttaactggg agattctcca ctcttatagt ggccaactcc tgaacattca tgatgaaact    3600
accatcccca tcaatgtcaa ccacaacagc cccagggtta gcaacagcag caccaatagc    3660
cgcaggcaat ccaaaaccca tggctccaag accccctgag gtcaaccact gcctcggtct    3720
cttgtacttg taaaactgcg cagcccacat ttgatgctgc ccaaccccag tactaacaat    3780
agcatctcca ttagtcaact catcaagaac ctcgatagca tgctgcggag aaatcgcgtc    3840
ctggaatgtc ttgtaaccca atggaaactt gtgtttctgc acattaatct cttctctcca    3900
acctccaaga tcaaacttac cctccactcc tttctcctcc aaaatcatat taattccctt    3960
caaggccaac ttcaaatccg cgcaaaccga cacgtgcgcc tgcttgttct tcccaatctc    4020
ggcagaatca atatcaatgt gaacaatctt agccctacta gcaaaagcct caagcttccc    4080
agtaacacgg tcatcaaacc ttaccccaaa ggcaagcaac aaatcactat tgtcaacagc    4140
atagttagca taaacagtac catgcatacc cagcatctga agggaatatt catcaccaat    4200
aggaaaagtt ccaagaccca ttaaagtgct agcaacggga ataccagtga gttcaacaaa    4260
gcgcctcaat tcagcactgg aattcaaact gccaccgccg acgtagagaa cgggcttttg    4320
ggcctccatg atgagtctga caatgtgttc caattgggcc tcggcggggg gcctgggcag    4380
cctggcgagg taaccgggga ggttaacggg ctcgtcccaa ttaggcacgg cgagttgctg    4440
```

```
ctgaacgtct ttgggaatgt cgatgaggac cggaccgggg cggccggagg tggcgacgaa    4500
gaaagcctcg gcgacgacgc gggggatgtc gtcgacgtcg aggatgaggt agttgtgctt    4560
cgtgatggat ctgctcacct ccacgatcgg ggtttcttgg aaggcgtcgg tgccgatcat    4620
ccggcgggcg acctggccgg tgatggcgac gactgggacg ctgtccatta aagcgtcggc    4680
gaggccgctc acgaggttgg tggcgccggg gccggaggtg gcaatgcaga cgccggggag    4740
gccggaggaa cgcgcgtagc cttcggcggc gaagacgccg ccctgctcgt ggcgcggag    4800
cacgttgcgg atggcggcgg agcgcgtgag cgcctggtgg atctccatcg acgcaccgcc    4860
ggggtacgcg aacaccgtcg tcacgccctg cctctccagc gcctccacaa ggatgtccgc    4920
gcccttgcga ggttcgccgg aggcgaaccg tgacacgaag gctccgtgg tcggcgcttc     4980
cttggtgaag ggcgccgccg tggggggttt ggagatggaa catttgattt tgagagcgtg    5040
gttgggtttg gtgagggttt gatgagagag agggagggtg gatctagtaa tgcgtttggg    5100
gaaggtgggg tgtgaagagg aagaagagaa tcggtggtt ctggaagcgg tggccgccat     5160
tgtgttgtgt ggcatggtta acttcaaaa actgcacaac aagcctagag ttagtaccta     5220
aacagtaaat ttacaacaga gagcaaagac acatgcaaaa atttcagcca taaaaaaagt    5280
tataatagaa tttaaagcaa aagtttcatt ttttaaacat atatacaaac aaactggatt    5340
tgaaggaagg gattaattcc cctgctcaaa gtttgaattc ctattgtgac ctatactcga    5400
ataaaattga agcctaagga atgtatgaga acaagaaaa caaaacaaaa ctacagacaa      5460
acaagtacaa ttacaaaatt cgctaaaatt ctgtaatcac caaacccat ctcagtcagc      5520
acaaggccca aggtttattt tgaaataaaa aaaaagtgat tttatttctc ataagctaaa    5580
agaaagaaag gcaattatga aatgatttcg actagatctg aaagtccaac gcgtattccg    5640
cagatattaa agaaagagta gagtttcaca tggatcctag atggacccag ttgaggaaaa    5700
agcaaggcaa agcaaaccag aagtgcaaga tccgaaattg aaccacggaa tctaggattt    5760
ggtagaggga gaagaaaagt accttgagag gtagaagaga agagaagagc agagagatat    5820
atgaacgagt gtgtcttggt ctcaactctg aagcgatacg agtttagagg ggagcattga    5880
gttccaattt atagggaaac cgggtggcag gggtgagtta atgacggaaa agcccctaag    5940
taacgagatt ggattgtggg ttagattcaa ccgtttgcat ccgcggctta gattggggaa    6000
gtcagagtga atctcaaccg ttgactgagt tgaaaattga atgtagcaac caattgagcc    6060
aaccccagcc tttgcccttt gattttgatt tgtttgttgc atactttta tttgtcttct      6120
ggttctgact ctctttctct cgtttcaatg ccaggttgcc tactcccaca ccactcacaa    6180
gaagattcta ctgttagtat taaatatttt ttaatgtatt aaatgatgaa tgcttttgta    6240
aacagaacaa gactatgtct aataagtgtc ttgcaacatt ttttaagaaa ttaaaaaaaa    6300
tatatttatt atcaaaatca aatgtatgaa aaatcatgaa taatataatt ttatacattt    6360
ttttaaaaaa tcttttaatt tcttaattaa tatcttaaaa ataatgatta atatttaacc    6420
caaaataatt agtatgattg gtaaggaaga tatccatgtt atgtttggat gtgagtttga    6480
tctagagcaa agcttactag agtcgacctg caggtcgact cgacgtacga aaccaactgc    6540
gtttggggct ccagattaaa cgacgccgtt tcgttccttt cgcttcacgg cttaacgatg    6600
tcgtttctgt ctgtgcccaa aaaataaagg catttgttat ttgcaccaga tatttactaa    6660
gtgcacccta gtttgacaag taggcgataa ttacaaatag atgcggtgca ataataaat     6720
tttgaaggaa ataattacaa aagaacagaa cttatattta cttatattta aaaaactaaa   6780
atgaaagaac aaaaaaagta aaaaatacaa aaaatgtgct ttaaccactt tcattatttg    6840
```

-continued

```
ttacagaaag tatgattcta ctcaaattga tctgttgtat ctggtgctgc cttgtcacac    6900
tggcgatttc aatcccctaa agatatggtg caaactgcga agtgatcaat atctgctcgg    6960
ttaatttaga ttaattaata atattcaacg tgatgtacca aaaaaagaca attttttgct    7020
ccattgacaa attaaacctc atcaaggtaa tttccaaacc tataagcaaa aaaatttcac    7080
attaattggc ccgcaatcct attagtctta ttatactaga gtaggaaaaa aaacaattac    7140
acaacttgtc ttattattct ctatgctaat gaatatttt ccctttttgtt agaaatcagt    7200 gtttcctaat ttattgagta ttaattccac tcaccgcata tatttaccgt tgaataagaa    7260
aattttacac ataattcttt ttaagataaa taatttttt atactagatc ttatatgatt    7320
acgtgaagcc aagtgggtta tactaatgat atataatgtt tgatagtaat cagtttataa    7380
accaaatgca tggaaatgtt acgtggaagc acgtaaatta acaagcattg aagcaaatgc    7440
agccaccgca ccaaaaccac cccacttcac ttccacgtac catattccat gcaactacaa    7500
caccctaaaa cttcaataaa tgcccccacc ttcacttcac ttcacccatc aatagcaagc    7560
ggccgcacaa tggcgactcg acagcgaact gccaccactg ttgtggtcga ggaccttccc    7620
aaggtcactc ttgaggccaa gtctgaacct gtgttccccg atatcaagac catcaaggat    7680
gccattcccg cgcactgctt ccagccctcg ctcgtcacct cattctacta cgtcttccgc    7740
gattttgcca tggtctctgc cctcgtctgg gctgctctca cctacatccc cagcatcccc    7800
gaccagaccc tccgcgtcgc agcttggatg gtctacggct tcgtccaggg tctgttctgc    7860
accggtgtct ggattctcgg ccatgagtgc ggccacggtg cttctctctct ccacggaaag    7920 gtcaacaatg tgaccggctg gttcctccac tcgttcctcc tcgtccccta cttcagctgg    7980
aagtactctc accaccgcca ccaccgcttc accggccaca tggatctcga catggctttc    8040
gtccccaaga ctgagcccaa gccctccaag tcgctcatga ttgctggcat tgacgtcgcc    8100
gagcttgttg aggacacccc cgctgctcag atggtcaagc tcatcttcca ccagcttttc    8160
ggatggcagg cgtacctctt cttcaacgct agctctggca agggcagcaa gcagtgggag    8220
cccaagactg gcctctccaa gtggttccga gtcagtcact tcgagcctac cagcgctgtc    8280
ttccgcccca acgaggccat cttcatcctc atctccgata tcggtcttgc tctaatggga    8340
actgctctgt actttgcttc caagcaagtt ggtgtttcga ccattctctt cctctaccct    8400
gttccctacc tgtgggttca ccactggctc gttgccatta cctacctcca ccaccaccac    8460
accgagctcc ctcactacac cgctgagggc tggacctacg tcaagggagc tctcgccact    8520
gtcgaccgtg agtttggctt catcggaaag cacctcttcc acggtatcat tgagaagcac    8580
gttgttcacc atctcttccc taagatcccc ttctacaagg ctgacgaggc caccgaggcc    8640
atcaagcccg tcattggcga ccactactgc cacgacgacc gaagcttcct gggccagctg    8700
tggaccatct tcggcacgct caagtacgtc gagcacgacc ctgcccgacc cggtgccatg    8760
cgatggaaca aggactaggc taggcggccg cgaagttaaa agcaatgttg tcacttgtcg    8820
tactaacaca tgatgtgata gtttatgcta gctagctata acataagctg tctctgagtg    8880
tgttgtatat taataaagat catcactggt gaatggtgat cgtgtacgta ccctacttag    8940
taggcaatgg aagcacttag agtgtgcttt gtgcatggcc ttgcctctgt tttgagactt    9000
ttgtaatgtt ttcgagttta aatctttgcc tttgc                              9035
```

<210> SEQ ID NO 102
<211> LENGTH: 5108
<212> TYPE: DNA

<213> ORGANISM: Artificial Sequence
<220> FEATURE:
<223> OTHER INFORMATION: Plasmid pKR270

<400> SEQUENCE: 102

```
ggccgcattt cgcaccaaat caatgaaagt aataatgaaa agtctgaata agaatactta      60
ggcttagatg cctttgttac ttgtgtaaaa taacttgagt catgtacctt tggcggaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat     240
cttttcttaa tgaaatgaaa atcttaatt gtaccatgtt tatgttaaac accttacaat      300
tggttggaga ggaggaccaa ccgatgggac aacattggga gaaagagatt caatggagat     360
ttggatagga gaacaacatt ctttttcact tcaatacaag atgagtgcaa cactaaggat     420
atgtatgaga ctttcagaag ctacgacaac atagatgagt gaggtggtga ttcctagcaa     480
gaaagacatt agaggaagcc aaaatcgaac aaggaagaca tcaagggcaa gagacaggac     540
catccatctc aggaaaagga gctttgggat agtccgagaa gttgtacaag aaattttttg     600
gagggtgagt gatgcattgc tggtgacttt aactcaatca aaattgagaa agaaagaaaa     660
gggaggggc tcacatgtga atagaaggga aacgggagaa ttttacagtt ttgatctaat      720
gggcatccca gctagtggta acatattcac catgtttaac cttcacgtac gtctagagga     780
tccccgggta ccgagctcga attcactggc cgtcgtttta caacgtcgtg actgggaaaa     840
ccctggcgtt acccaactta tcgccttgc agcacatccc cctttcgcca gctggcgtaa      900
tagcgaagag gcccgcaccg atcgcccttc ccaacagttg cgcagcctga atggcgaatg     960
gcgcctgatg cggtattttc tccttacgca tctgtgcggt atttcacacc gcatatggtg    1020
cactctcagt acaatctgct ctgatgccgc atagttaagc cagccccgac acccgccaac    1080
acccgctgac gcgccctgac gggcttgtct gctcccggca tccgcttaca gacaagctgt    1140
gaccgtctcc gggagctgca tgtgtcagag gttttcaccg tcatcaccga aacgcgcgag    1200
acgaaagggc ctcgtgatac gcctattttt ataggttaat gtcatgataa taatggtttc    1260
ttagacgtca ggtggcactt tcggggaaa tgtgcgcgga accccatttt gtttattttt     1320
ctaaatacat tcaaatatgt atccgctcat gagacaataa ccctgataaa tgcttcaata    1380
atattgaaaa aggaagagta tgagtattca acatttccgt gtcgccctta ttccctttt     1440
tgcggcattt tgccttcctg tttttgctca cccagaaacg ctggtgaaag taaaagatgc    1500
tgaagatcag ttgggtgcac gagtgggtta catcgaactg gatctcaaca gcggtaagat    1560
ccttgagagt tttcgccccg aagaacgttt tccaatgatg agcacttta aagttctgct     1620
atgtggcgcg gtattatccc gtattgacgc cgggcaagag caactcggtc gccgcataca    1680
ctattctcag aatgacttgg ttgagtactc accagtcaca gaaaagcatc ttacggatgg    1740
catgacagta agagaattat gcagtgctgc cataaccatg agtgataaca ctgcggccaa    1800
cttacttctg acaacgatcg gaggaccgaa ggagctaacc gcttttttgc acaacatggg    1860
ggatcatgta actcgccttg atcgttggga accggagctg aatgaagcca taccaaacga    1920
cgagcgtgac accacgatgc ctgtagcaat ggcaacaacg ttgcgcaaac tattaactgg    1980
cgaactactt actctagctt cccggcaaca attaatagac tggatggagg cggataaagt    2040
tgcaggacca cttctgcgct cggcccttcc ggctggctgg tttattgctg ataaatctgg    2100
agccggtgag cgtgggtctc gcggtatcat tgcagcactg gggccagatg gtaagccctc    2160
ccgtatcgta gttatctaca cgacggggag tcaggcaact atggatgaac gaaatagaca    2220
```

```
gatcgctgag ataggtgcct cactgattaa gcattggtaa ctgtcagacc aagtttactc    2280
atatatactt tagattgatt taaaacttca tttttaattt aaaaggatct aggtgaagat    2340 ccttttgat aatctcatga ccaaaatccc ttaacgtgag ttttcgttcc actgagcgtc     2400 agacccgta gaaaagatca aaggatcttc ttgagatcct ttttttctgc gcgtaatctg    2460
ctgcttgcaa acaaaaaaac caccgctacc agcggtggtt tgtttgccgg atcaagagct    2520
accaactctt tttccgaagg taactggctt cagcagagcg cagataccaa atactgtcct    2580
tctagtgtag ccgtagttag gccaccactt caagaactct gtagcaccgc ctacatacct    2640
cgctctgcta atcctgttac cagtggctgc tgccagtggc gataagtcgt gtcttaccgg    2700
gttggactca agacgatagt taccggataa ggcgcagcgg tcgggctgaa cggggggttc    2760
gtgcacacag cccagcttgg agcgaacgac ctacaccgaa ctgagatacc tacagcgtga    2820
gctatgagaa agcgccacgc ttcccgaagg gagaaaggcg gacaggtatc cggtaagcgg    2880
cagggtcgga acaggagagc gcacgaggga gcttccaggg ggaaacgcct ggtatcttta    2940
tagtcctgtc gggtttcgcc acctctgact tgagcgtcga tttttgtgat gctcgtcagg    3000
ggggcggagc ctatggaaaa acgccagcaa cgcggccttt ttacggttcc tggccttttg    3060
ctggcctttt gctcacatgt tctttcctgc gttatcccct gattctgtgg ataaccgtat    3120
taccgccttt gagtgagctg ataccgctcg ccgcagccga acgaccgagc gcagcgagtc    3180
agtgagcgag gaagcggaag agcgcccaat acgcaaaccg cctctccccg cgcgttggcc    3240
gattcattaa tgcagctggc acgacaggtt tcccgactgg aaagcgggca gtgagcgcaa    3300
cgcaattaat gtgagttagc tcactcatta ggcaccccag gctttacact ttatgcttcc    3360
ggctcgtatg ttgtgtggaa ttgtgagcgg ataacaattt cacacaggaa acagctatga    3420
ccatgattac gccaagcttg catgcctgca ggctagccta agtacgtact caaaatgcca    3480
acaaataaaa aaaagttgc tttaataatg ccaaaacaaa ttaataaaac acttacaaca    3540
ccggattttt tttaattaaa atgtgccatt taggataaat agttaatatt tttaataatt    3600
atttaaaaag ccgtatctac taaaatgatt tttatttggt tgaaatatt aatatgttta    3660 aatcaacaca atctatcaaa attaaactaa aaaaaaata agtgtacgtg gttaacatta    3720
gtacagtaat ataagaggaa aatgagaaat taagaaattg aaagcgagtc taattttttaa    3780 attatgaacc tgcatatata aaaggaaaga aagaatccag gaagaaaaga aatgaaacca    3840
tgcatggtcc cctcgtcatc acgagtttct gccatttgca atagaaacac tgaaacacct    3900
ttctctttgt cacttaattg agatgccgaa gccacctcac accatgaact tcatgaggtg    3960
tagcacccaa ggcttccata gccatgcata ctgaagaatg tctcaagctc agcaccctac    4020
ttctgtgacg tgtccctcat tcaccttcct ctcttcccta taaataacca cgcctcaggt    4080
tctccgcttc acaactcaaa cattctctcc attggtcctt aaacactcat cagtcatcac    4140
cgcggccgca tggagtcgat tgcgccattc ctcccatcaa agatgccgca agatctgttt    4200
atggaccttg ccaccgctat cggtgtccgg gccgcgccct atgtcgatcc tctcgaggcc    4260
gcgctggtgg cccaggccga gaagtacatc cccacgattg tccatcacac gcgtgggttc    4320
ctggtcgcgg tggagtcgcc tttgcccgt gagctgccgt tgatgaaccc gttccacgtg    4380
ctgttgatcg tgctcgctta tttggtcacg gtctttgtgg gcatgcagat catgaagaac    4440
tttgagcggt tcgaggtcaa gacgttttcg ctcctgcaca acttttgtct ggtctcgatc    4500
agcgcctaca tgtgcggtgg gatcctgtac gaggcttatc aggccaacta tggactgttt    4560
```

```
gagaacgctg ctgatcatac cttcaagggt cttcctatgg ccaagatgat ctggctcttc    4620
tacttctcca agatcatgga gtttgtcgac accatgatca tggtcctcaa gaagaacaac    4680
cgccagatct ccttcttgca cgtttaccac cacagctcca tcttcaccat ctggtggttg    4740
gtcacctttg ttgcacccaa cggtgaagcc tacttctctg ctgcgttgaa ctcgttcatc    4800
catgtgatca tgtacggcta ctacttcttg tcggccttgg gcttcaagca ggtgtcgttc    4860
atcaagttct acatcacgcg ctcgcagatg acacagttct gcatgatgtc ggtccagtct    4920
tcctgggaca tgtacgccat gaaggtcctt ggccgccccg ataccccctt cttcatcacg    4980
gctctgcttt ggttctacat gtggaccatg ctcggtctct tctacaactt ttacagaaag    5040
aacgccaagt tggccaagca ggccaaggcc gacgctgcca aggagaaggc aaggaagttg    5100
cagtaagc                                                            5108
```

<210> SEQ ID NO 103
<211> LENGTH: 39
<212> TYPE: DNA
<213> ORGANISM: Artificial Sequence
<220> FEATURE:
<223> OTHER INFORMATION: Smart(TM) IV oligonucleotide

<400> SEQUENCE: 103

```
aagcagtggt atcaacgcag agtggccatt acggccggg                             39
```

<210> SEQ ID NO 104
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 104

```
attctagagg ccgaggcggc cgacatgttt tttttttttt tttttttttt tttttttvn      59
```

<210> SEQ ID NO 105
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 105

```
aagcagtggt atcaacgcag agt                                             23
```

<210> SEQ ID NO 106
<211> LENGTH: 20
<212> TYPE: DNA
<213> ORGANISM: Artificial Sequence
<220> FEATURE:
<223> OTHER INFORMATION: Primer EuEF3
<220> FEATURE:
<221> NAME/KEY: misc_feature
<222> LOCATION: (3)..(3)
<223> OTHER INFORMATION: n is a, c, g, or t

<400> SEQUENCE: 106
ytncarttyt tycaycaytt                                              20

<210> SEQ ID NO 107
<211> LENGTH: 7
<212> TYPE: PRT
<213> ORGANISM: Artificial Sequence
<220> FEATURE:
<223> OTHER INFORMATION: Primer EuEF3 (translation)

<400> SEQUENCE: 107

Leu Gln Phe Phe His His Leu
1               5

<210> SEQ ID NO 108
<211> LENGTH: 20
<212> TYPE: DNA
<213> ORGANISM: Artificial Sequence
<220> FEATURE:
<223> OTHER INFORMATION: Primer EuER3

<400> SEQUENCE: 108
ttraaytgda tdatytgcat                                              20

<210> SEQ ID NO 109
<211> LENGTH: 7
<212> TYPE: PRT
<213> ORGANISM: Artificial Sequence
<220> FEATURE:
<223> OTHER INFORMATION: Primer EuER3 (translation)

<400> SEQUENCE: 109

Met Gln Ile Ile Gln Phe Asn
1               5

<210> SEQ ID NO 110
<211> LENGTH: 22
<212> TYPE: DNA
<213> ORGANISM: Artificial Sequence
<220> FEATURE:
<223> OTHER INFORMATION: Primer 389Elo-5-1

<400> SEQUENCE: 110
gaatgaaccc attcaaaaac ac                                           22

<210> SEQ ID NO 111
<211> LENGTH: 22
<212> TYPE: DNA
<213> ORGANISM: Artificial Sequence
<220> FEATURE:
<223> OTHER INFORMATION: Primer 389Elo-5-2

<400> SEQUENCE: 111
gatccaaata gattccccag aa                                           22

<210> SEQ ID NO 112
<211> LENGTH: 22
<212> TYPE: DNA
<213> ORGANISM: Artificial Sequence
<220> FEATURE:
<223> OTHER INFORMATION: Primer DNR CDS 5'-2

<400> SEQUENCE: 112
caacgcagag tggccattac gg                                           22

<210> SEQ ID NO 113
<211> LENGTH: 21

```
<212> TYPE: DNA
<213> ORGANISM: Artificial Sequence
<220> FEATURE:
<223> OTHER INFORMATION: Primer 389Elo-5-4

<400> SEQUENCE: 113
gtaaacttca agatcacgaa g                                              21

<210> SEQ ID NO 114
<211> LENGTH: 22
<212> TYPE: DNA
<213> ORGANISM: Artificial Sequence
<220> FEATURE:
<223> OTHER INFORMATION: Primer 389Elo-3-1

<400> SEQUENCE: 114
gttcattcac tttgttatgt ac                                             22

<210> SEQ ID NO 115
<211> LENGTH: 22
<212> TYPE: DNA
<213> ORGANISM: Artificial Sequence
<220> FEATURE:
<223> OTHER INFORMATION: Primer 389Elo-3-2

<400> SEQUENCE: 115
ctggactcgg ctgatgaagt tc                                             22

<210> SEQ ID NO 116
<211> LENGTH: 29
<212> TYPE: DNA
<213> ORGANISM: Artificial Sequence
<220> FEATURE:
<223> OTHER INFORMATION: Primer 389ELO-F

<400> SEQUENCE: 116
aagatcccat ggctgcggtg atagaggtc                                      29

<210> SEQ ID NO 117
<211> LENGTH: 37
<212> TYPE: DNA
<213> ORGANISM: Artificial Sequence
<220> FEATURE:
<223> OTHER INFORMATION: Primer 389ELO-R1

<400> SEQUENCE: 117
aagatcgcgg ccgcctattg gaccttttta tctgcag                             37

<210> SEQ ID NO 118
<211> LENGTH: 7222
<212> TYPE: DNA
<213> ORGANISM: Artificial Sequence
<220> FEATURE:
<223> OTHER INFORMATION: Plasmid pFBAIN-MOD1

<400> SEQUENCE: 118
catggatcca ggcctgttaa cggccattac ggcctgcagg atccgaaaaa acctcccaca     60 cctcccctg aacctgaaac ataaaatgaa tgcaattgtt gttgttaact tgtttattgc     120
agcttataat ggttacaaat aaagcaatag catcacaaat ttcacaaata aagcattttt    180
ttcactgcat tctagttgtg gtttgtccaa actcatcaat gtatcttatc atgtctgcgg    240
ccgcaagtgt ggatgggaa gtgagtgccc ggttctgtgt gcacaattgg caatccaaga    300
tggatggatt caacacaggg atatagcgag ctacgtggtg gtgcgaggat atagcaacgg    360
```

```
atatttatgt ttgacacttg agaatgtacg atacaagcac tgtccaagta caatactaaa    420
catactgtac atactcatac tcgtacccgg gcaacggttt cacttgagtg cagtggctag    480
tgctcttact cgtacagtgt gcaatactgc gtatcatagt ctttgatgta tatcgtattc    540
attcatgtta gttgcgtacg agccggaagc ataaagtgta aagcctgggg tgcctaatga    600
gtgagctaac tcacattaat tgcgttgcgc tcactgcccg ctttccagtc gggaaacctg    660
tcgtgccagc tgcattaatg aatcggccaa cgcgcgggga gaggcggttt gcgtattggg    720
cgctcttccg cttcctcgct cactgactcg ctgcgctcgg tcgttcggct gcggcgagcg    780
gtatcagctc actcaaaggc ggtaatacgg ttatccacag aatcagggga taacgcagga    840
aagaacatgt gagcaaaagg ccagcaaaag gccaggaacc gtaaaaaggc cgcgttgctg    900
gcgtttttcc ataggctccg ccccctgac gagcatcaca aaaatcgacg ctcaagtcag    960
aggtggcgaa acccgacagg actataaaga taccaggcgt ttccccctgg aagctccctc   1020
gtgcgctctc ctgttccgac cctgccgctt accggatacc tgtccgcctt tctcccttcg   1080
ggaagcgtgg cgctttctca tagctcacgc tgtaggtatc tcagttcggt gtaggtcgtt   1140
cgctccaagc tgggctgtgt gcacgaaccc cccgttcagc ccgaccgctg cgccttatcc   1200
ggtaactatc gtcttgagtc caacccggta agacacgact tatcgccact ggcagcagcc   1260
actggtaaca ggattagcag agcgaggtat gtaggcggtg ctacagagtt cttgaagtgg   1320
tggcctaact acggctacac tagaaggaca gtatttggta tctgcgctct gctgaagcca   1380
gttaccttcg gaaaaagagt tggtagctct tgatccggca aacaaaccac cgctggtagc   1440
ggtggttttt ttgtttgcaa gcagcagatt acgcgcagaa aaaaggatc tcaagaagat   1500
cctttgatct tttctacggg gtctgacgct cagtggaacg aaaactcacg ttaagggatt   1560
ttggtcatga gattatcaaa aaggatcttc acctagatcc ttttaaatta aaaatgaagt   1620
tttaaatcaa tctaaagtat atatgagtaa acttggtctg acagttacca atgcttaatc   1680
agtgaggcac ctatctcagc gatctgtcta tttcgttcat ccatagttgc ctgactcccc   1740
gtcgtgtaga taactacgat acgggagggc ttaccatctg gccccagtgc tgcaatgata   1800
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata taccgcgcc acatagcaga actttaaaag tgctcatcat ggaaaacgt   2340
tcttcggggc gaaaactctc aaggatctta ccgctgttga tccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct ccttttttca atattattga agcatttatc agggttattg tctcatgagc   2580
ggatacatat ttgaatgtat ttagaaaaat aaacaaatag gggttccgcg cacatttccc   2640
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
```

```
ccttcctttc tcgccacgtt cgccggcttt ccccgtcaag ctctaaatcg ggggctccct      2820
ttagggttcc gatttagtgc tttacggcac ctcgacccca aaaaacttga ttagggtgat      2880
ggttcacgta gtgggccatc gccctgatag acggtttttc gcccttttgac gttggagtcc    2940
acgttcttta atagtggact cttgttccaa actggaacaa cactcaaccc tatctcggtc     3000
tattcttttg atttataagg gattttgccg atttcggcct attggttaaa aaatgagctg     3060
atttaacaaa aatttaacgc gaattttaac aaaatattaa cgcttacaat ttccattcgc     3120
cattcaggct gcgcaactgt tgggaagggc gatcggtgcg ggcctcttcg ctattacgcc     3180
agctggcgaa agggggatgt gctgcaaggc gattaagttg ggtaacgcca gggttttccc    3240
agtcacgacg ttgtaaaacg acggccagtg aattgtaata cgactcacta tagggcgaat    3300
tgggtaccgg gccccccctc gaggtcgatg gtgtcgataa gcttgatatc gaattcatgt    3360
cacacaaacc gatcttcgcc tcaaggaaac ctaattctac atccgagaga ctgccgagat    3420
ccagtctaca ctgattaatt ttcgggccaa taatttaaaa aaatcgtgtt atataatatt     3480
atatgtatta tatatataca tcatgatgat actgacagtc atgtcccatt gctaaataga    3540
cagactccat ctgccgcctc caactgatgt tctcaatatt taaggggtca tctcgcattg    3600
tttaataata aacagactcc atctaccgcc tccaaatgat gttctcaaaa tatattgtat    3660
gaacttattt ttattactta gtattattag acaacttact tgctttatga aaacacttc     3720
ctatttagga aacaatttat aatggcagtt cgttcattta acaatttatg tagaataaat    3780
gttataaatg cgtatgggaa atcttaaata tggatagcat aaatgatatc tgcattgcct    3840
aattcgaaat caacagcaac gaaaaaaatc ccttgtacaa cataaatagt catcgagaaa    3900
tatcaactat caaagaacag ctattcacac gttactattg agattattat tggacgagaa    3960
tcacacactc aactgtcttt ctctcttcta gaaatacagg tacaagtatg tactattctc    4020
attgttcata cttctagtca tttcatccca catattcctt ggatttctct ccaatgaatg    4080
acattctatc ttgcaaattc aacaattata ataagatata ccaaagtagc ggtatagtgg    4140
caatcaaaaa gcttctctgg tgtgcttctc gtatttattt ttattctaat gatccattaa    4200
aggtatatat ttatttcttg ttatataatc cttttgttta ttacatgggc tggatacata    4260
aaggtatttt gatttaattt tttgcttaaa ttcaatcccc cctcgttcag tgtcaactgt    4320
aatggtagga aattaccata cttttgaaga agcaaaaaaa atgaaagaaa aaaaaaatcg    4380
tatttccagg ttagacgttc cgcagaatct agaatgcggt atgcgtaca ttgttcttcg     4440
aacgtaaaag ttgcgctccc tgagatattg tacatttttg cttttacaag tacaagtaca    4500
tcgtacaact atgtactact gttgatgcat ccacaacagt ttgttttgtt ttttttttgtt  4560
ttttttttt ctaatgattc attaccgcta tgtatacctaa cttgtacttg tagtaagccg    4620
ggttattggc gttcaattaa tcatagactt atgaatctgc acggtgtgcg ctgcgagtta    4680
cttttagctt atgcatgcta cttgggtgta atattgggat ctgttcggaa atcaacggat    4740
gctcaatcga tttcgacagt aattaattaa gtcatacaca agtcagcttt cttcgagcct    4800
catataagta taagtagttc aacgtattag cactgtaccc agcatctccg tatcgagaaa    4860
cacaacaaca tgccccattg gacagatcat gcggatacac aggttgtgca gtatcataca    4920
tactcgatca gacaggtcgt ctgaccatca tacaagctga acaagcgctc catacttgca    4980
cgctctctat atacacagtt aaattacata tccatagtct aacctctaac agttaatctt    5040
ctggtaagcc tcccagccag ccttctggta tcgcttggcc tcctcaatag gatctcggtt    5100
```

```
ctggccgtac agacctcggc cgacaattat gatatccgtt ccggtagaca tgacatcctc    5160
aacagttcgg tactgctgtc cgagagcgtc tcccttgtcg tcaagaccca ccccgggggt    5220
cagaataagc cagtcctcag agtcgcccct aggtcggttc tgggcaatga agccaaccac    5280
aaactcgggg tcggatcggg caagctcaat ggtctgcttg gagtactcgc cagtggccag    5340
agagcccttg caagacagct cggccagcat gagcagacct ctggccagct tctcgttggg    5400
agagggact aggaactcct tgtactggga gttctcgtag tcagagacgt cctccttctt    5460
ctgttcagag acagtttcct cggcaccagc tcgcaggcca gcaatgattc cggttccggg    5520
tacaccgtgg gcgttggtga tatcggacca ctcggcgatt cggtgacacc ggtactggtg    5580
cttgacagtg ttgccaatat ctgcgaactt tctgtcctcg aacaggaaga aaccgtgctt    5640
aagagcaagt tccttgaggg ggagcacagt gccggcgtag gtgaagtcgt caatgatgtc    5700
gatatgggtt ttgatcatgc acacataagg tccgacctta tcggcaagct caatgagctc    5760
cttggtggtg gtaacatcca gagaagcaca caggttggtt ttcttggctg ccacgagctt    5820
gagcactcga gcggcaaagg cggacttgtg gacgttagct cgagcttcgt aggagggcat    5880
tttggtggtg aagaggagac tgaaataaat ttagtctgca gaacttttta tcggaacctt    5940
atctggggca gtgaagtata tgttatggta atagttacga gttagttgaa cttatagata    6000
gactggacta tacggctatc ggtccaaatt agaaagaacg tcaatggctc tctgggcgtc    6060
gcctttgccg acaaaaatgt gatcatgatg aaagccagca atgacgttgc agctgatatt    6120
gttgtcggcc aaccgcgccg aaaacgcagc tgtcagaccc acagcctcca acgaagaatg    6180
tatcgtcaaa gtgatccaag cacactcata gttggagtcg tactccaaag gcggcaatga    6240
cgagtcagac agatactcgt cgaaaacagt gtacgcagat ctactataga ggaacattta    6300
aattgccccg gagaagacgg ccaggccgcc tagatgacaa attcaacaac tcacagctga    6360
ctttctgcca ttgccactag gggggggcct ttttatatgg ccaagccaag ctctccacgt    6420
cggttgggct gcacccaaca ataaatgggt agggttgcac caacaaaggg atgggatggg    6480
gggtagaaga tacgaggata acggggctca atggcacaaa taagaacgaa tactgccatt    6540
aagactcgtg atccagcgac tgacaccatt gcatcatcta agggcctcaa aactacctcg    6600
gaactgctgc gctgatctgg acaccacaga ggttccgagc actttaggtt gcaccaaatg    6660
tcccaccagg tgcaggcaga aaacgctgga acagcgtgta cagtttgtct taacaaaaag    6720
tgagggcgct gaggtcgagc agggtggtgt gacttgttat agcctttaga gctgcgaaag    6780
cgcgtatgga tttggctcat caggccagat tgagggtctg tggacacatg tcatgttagt    6840
gtacttcaat cgcccctgg atatagcccc gacaataggc cgtggcctca tttttttgcc    6900
ttccgcacat ttccattgct cggtacccac accttgcttc cctgcactt gccaacctta    6960
atactggttt acattgacca acatcttaca agcgggggc ttgtctaggg tatatataaa    7020
cagtggctct cccaatcggt tgccagtctc ttttttcctt tctttcccca cagattcgaa    7080
atctaaacta cacatcacag aattccgagc cgtgagtatc cacgacaaga tcagtgtcga    7140
gacgacgcgt tttgtgtaat gacacaatcc gaaagtcgct agcaacacac actctctaca    7200
caaactaacc cagctctggt ac                                             7222

<210> SEQ ID NO 119
<211> LENGTH: 7779
<212> TYPE: DNA
<213> ORGANISM: Artificial Sequence
<220> FEATURE:
<223> OTHER INFORMATION: Plasmid pFBAIN-389Elo
```

<400> SEQUENCE: 119

```
ggccgcaagt gtggatgggg aagtgagtgc ccggttctgt gtgcacaatt ggcaatccaa        60
gatggatgga ttcaacacag ggatatagcg agctacgtgg tggtgcgagg atatagcaac       120
ggatatttat gtttgacact tgagaatgta cgatacaagc actgtccaag tacaatacta       180
aacatactgt acatactcat actcgtaccc gggcaacgtt tcacttgag tgcagtggct        240
agtgctctta ctcgtacagt gtgcaatact gcgtatcata gtctttgatg tatatcgtat       300
tcattcatgt tagttgcgta cgagccggaa gcataaagtg taaagcctgg ggtgcctaat       360
gagtgagcta actcacatta attgcgttgc gctcactgcc cgctttccag tcgggaaacc       420
tgtcgtgcca gctgcattaa tgaatcggcc aacgcgcggg gagaggcggt ttgcgtattg       480
ggcgctcttc cgcttcctcg ctcactgact cgctgcgctc ggtcgttcgg ctgcggcgag       540
cggtatcagc tcactcaaag gcggtaatac ggttatccac agaatcaggg gataacgcag       600
gaaagaacat gtgagcaaaa ggccagcaaa aggccaggaa ccgtaaaaag gccgcgttgc       660
tggcgttttt ccataggctc cgcccccctg acgagcatca aaaaatcga cgctcaagtc       720
agaggtggcg aaacccgaca ggactataaa gataccaggc gtttccccct ggaagctccc       780
tcgtgcgctc tcctgttccg accctgccgc ttaccggata cctgtccgcc tttctccctt       840
cgggaagcgt ggcgctttct catagctcac gctgtaggta tctcagttcg gtgtaggtcg       900
ttcgctccaa gctgggctgt gtgcacgaac cccccgttca gcccgaccgc tgcgccttat       960
ccggtaacta tcgtcttgag tccaacccgg taagacacga cttatcgcca ctggcagcag      1020
ccactggtaa caggattagc agagcgaggt atgtaggcgg tgctacagag ttcttgaagt      1080
ggtggcctaa ctacggctac actagaagga cagtatttgg tatctgcgct ctgctgaagc      1140
cagttacctt cggaaaaaga gttggtagct cttgatccgg caaacaaacc accgctggta      1200
gcggtggttt ttttgtttgc aagcagcaga ttacgcgcag aaaaaaagga tctcaagaag      1260
atcctttgat cttttctacg gggtctgacg ctcagtggaa cgaaaactca cgttaaggga      1320
ttttggtcat gagattatca aaaaggatct cacctagat ccttttaaat taaaaatgaa      1380
gttttaaatc aatctaaagt atatatgagt aaacttggtc tgacagttac caatgcttaa      1440
tcagtgaggc acctatctca gcgatctgtc tatttcgttc atccatagtt gcctgactcc      1500
ccgtcgtgta gataactacg atacgggagg gcttaccatc tggccccagt gctgcaatga      1560
taccgcgaga cccacgctca ccggctccag atttatcagc aataaaccag ccagccggaa      1620
gggccgagcg cagaagtggt cctgcaactt tatccgcctc catccagtct attaattgtt      1680
gccgggaagc tagagtaagt agttcgccag ttaatagttt gcgcaacgtt gttgccattg      1740
ctacaggcat cgtggtgtca cgctcgtcgt ttggtatggc ttcattcagc tccggttccc      1800
aacgatcaag gcgagttaca tgatccccca tgttgtgcaa aaaagcggtt agctccttcg      1860
gtcctccgat cgttgtcaga agtaagttgg ccgcagtgtt atcactcatg gttatggcag      1920
cactgcataa ttctcttact gtcatgccat ccgtaagatg cttttctgtg actggtgagt      1980
actcaaccaa gtcattctga aatagtgta tgcggcgacc gagttgctct tgcccggcgt      2040
caatacggga taataccgcg ccacatagca gaactttaaa agtgctcatc attggaaaac      2100
gttcttcggg gcgaaaactc tcaaggatct taccgctgtt gagatccagt tcgatgtaac      2160
ccactcgtgc acccaactga tcttcagcat cttttacttt caccagcgtt tctgggtgag      2220
caaaaacagg aaggcaaaat gccgcaaaaa agggaataag ggcgacacgg aaatgttgaa      2280
```

```
tactcatact cttcctttt caatattatt gaagcattta tcagggttat tgtctcatga      2340
gcggatacat atttgaatgt atttagaaaa ataaacaaat aggggttccg cgcacatttc      2400
cccgaaaagt gccacctgac gcgccctgta gcggcgcatt aagcgcggcg ggtgtggtgg      2460
ttacgcgcag cgtgaccgct acacttgcca gcgccctagc gcccgctcct ttcgctttct      2520
tcccttcctt tctcgccacg ttcgccggct tccccgtca agctctaaat cgggggctcc      2580
ctttagggtt ccgatttagt gctttacggc acctcgaccc caaaaaactt gattagggtg      2640
atggttcacg tagtgggcca tcgccctgat agacggtttt tcgccctttg acgttggagt      2700
ccacgttctt aatagtgga ctcttgttcc aaactggaac aacactcaac cctatctcgg      2760
tctattcttt tgatttataa gggattttgc cgatttcggc ctattggtta aaaaatgagc      2820
tgatttaaca aaaatttaac gcgaatttta acaaaatatt aacgcttaca atttccattc      2880
gccattcagg ctgcgcaact gttgggaagg gcgatcggtg cgggcctctt cgctattacg      2940
ccagctggcg aaagggggat gtgctgcaag gcgattaagt tgggtaacgc cagggttttc      3000
ccagtcacga cgttgtaaaa cgacggccag tgaattgtaa tacgactcac tatagggcga      3060
attgggtacc gggccccccc tcgaggtcga tggtgtcgat aagcttgata tcgaattcat      3120
gtcacacaaa ccgatcttcg cctcaaggaa acctaattct acatccgaga gactgccgag      3180
atccagtcta cactgattaa ttttcgggcc aataatttaa aaaaatcgtg ttatataata      3240
ttatatgtat tatatatata catcatgatg atactgacag tcatgtccca ttgctaaata      3300
gacagactcc atctgccgcc tccaactgat gttctcaata tttaagggggt catctcgcat      3360 tgtttaataa taaacagact ccatctaccg cctccaaatg atgttctcaa aatatattgt      3420
atgaacttat ttttattact tagtattatt agacaactta cttgctttat gaaaaacact      3480
tcctatttag gaaacaattt ataatggcag ttcgttcatt taacaattta tgtagaataa      3540
atgttataaa tgcgtatggg aaatcttaaa tatggatagc ataaatgata tctgcattgc      3600
ctaattcgaa atcaacagca acgaaaaaaa tcccttgtac aacataaata gtcatcgaga      3660
aatatcaact atcaaagaac agctattcac acgttactat tgagattatt attggacgag      3720
aatcacacac tcaactgtct ttctctcttc tagaaataca ggtacaagta tgtactattc      3780
tcattgttca tacttctagt catttcatcc cacatattcc ttggatttct ctccaatgaa      3840
tgacattcta tcttgcaaat tcaacaatta taataagata taccaaagta gcggtatagt      3900
ggcaatcaaa aagcttctct ggtgtgcttc tcgtatttat ttttattcta atgatccatt      3960
aaaggtatat atttatttct tgttatataa tccttttgtt tattacatgg gctggataca      4020
taaaggtatt ttgatttaat ttttgctta aattcaatcc cccctcgttc agtgtcaact      4080
gtaatggtag gaaattacca tacttttgaa gaagcaaaaa aaatgaaaga aaaaaaaat      4140 cgtatttcca ggttagacgt tccgcagaat ctagaatgcg gtatgcggta cattgttctt      4200
cgaacgtaaa agttgcgctc cctgagatat tgtacatttt tgcttttaca agtacaagta      4260
catcgtacaa ctatgtacta ctgttgatgc atccacaaca gtttgttttg ttttttttg      4320 ttttttttt ttctaatgat tcattaccgc tatgtatacc tacttgtact tgtagtaagc      4380
cgggttattg gcgttcaatt aatcatagac ttatgaatct gcacggtgtg cgctgcgagt      4440 tactttagc ttatgcatgc tacttgggtg taatattggg atctgttcgg aaatcaacgg      4500
atgctcaatc gatttcgaca gtaattaatt aagtcataca caagtcagct ttcttcgagc      4560
ctcatataag tataagtagt tcaacgtatt agcactgtac ccagcatctc cgtatcgaga      4620
aacacaacaa catgccccat tggacagatc atgcggatac acaggttgtg cagtatcata      4680
```

```
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc aacgaagaa    5940
tgtatcgtca aagtgatcca agcacactca tagttggagt cgtactccaa aggcggcaat   6000
gacgagtcag acagatactc gtcgaaaaca gtgtacgcag atctactata gaggaacatt   6060
taaattgccc cggagaagac ggccaggccg cctagatgac aaattcaaca actcacagct   6120
gactttctgc cattgccact aggggggggc cttttatat ggccaagcca agctctccac    6180
gtcggttggg ctgcacccaa caataaatgg gtagggttgc accaacaaag ggatgggatg   6240
gggggtagaa gatacgagga taacggggct caatggcaca ataagaacg aatactgcca    6300
ttaagactcg tgatccagcg actgacacca ttgcatcatc taagggcctc aaaactacct   6360
cggaactgct gcgctgatct ggacaccaca gaggttccga gcactttagg ttgcaccaaa   6420
tgtcccacca ggtgcaggca gaaaacgctg aacagcgtg tacagtttgt cttaacaaaa    6480
agtgagggcg ctgaggtcga gcagggtggt gtgacttgtt atagccttta gagctgcgaa   6540
agcgcgtatg gatttggctc atcaggccag attgagggtc tgtggacaca tgtcatgtta   6600
gtgtacttca atcgcccct ggatatagcc ccgacaatag gccgtggcct cattttttg     6660
ccttccgcac atttccattg ctcggtaccc acaccttgct tctcctgcac ttgccaacct   6720
taatactggt ttacattgac caacatctta caagcggggg gcttgtctag ggtatatata   6780
aacagtggct ctcccaatcg gttgccagtc tcttttttcc tttctttccc cacagattcg   6840
aaatctaaac tacacatcac agaattccga gccgtgagta tccacgacaa gatcagtgtc   6900
gagacgacgc gttttgtgta atgacacaat ccgaaagtcg ctagcaacac acactctcta   6960
cacaaactaa cccagctctg gtaccatggc tgcggtgata gaggtcgcca acgagtttgt   7020
```

| | | | | |
|---|---|---|---|---|
| agccatcacg | gcagaaacgc | tccccaaagt | tgactatcaa | cgactatggc gagacattta | 7080 |
| cagttgtgag | ctactgtatt | tctccattgc | cttcgtgatc | ttgaagttta cgttgggcga | 7140 |
| gttgagcgac | agcggaaaaa | agattttgag | agtgttgttc | aagtggtaca atctcttcat | 7200 |
| gtccgtgttc | tccttggtgt | ctttcctttg | catgggctat | gccatttata ccgtgggcct | 7260 |
| atactctaac | gaatgcgaca | gggctttcga | caactcgttg | ttccgctttg caacaaaggt | 7320 |
| gttctactac | agtaagtttt | tggagtacat | cgactctttt | tatcttccgc tcatggccaa | 7380 |
| gccgctgtct | ttcctgcaat | tcttccatca | cttgggagcc | cccatggaca tgtggctctt | 7440 |
| tgtccaatat | tctggggaat | ctatttggat | cttttgtgttt | ttgaatgggt tcattcactt | 7500 |
| tgttatgtac | gggtactact | ggactcggct | gatgaagttc | aatttcccaa tgcccaagca | 7560 |
| gttgattacc | gcgatgcaga | tcacgcagtt | caacgttggt | ttctacctcg tgtggtggta | 7620 |
| caaagatatt | ccctgctacc | gaaaggatcc | catgcgaatg | ttggcctgga tcttcaatta | 7680 |
| ctggtatgtt | gggactgtct | tgctgctgtt | cattaatttc | ttcgtcaaat cctatgtgtt | 7740 |
| cccaaagccg | aagactgcag | ataaaaaggt | ccaataggc | | 7779 |

<210> SEQ ID NO 120
<211> LENGTH: 3511
<212> TYPE: DNA
<213> ORGANISM: Artificial Sequence
<220> FEATURE:
<223> OTHER INFORMATION: Plasmid pE389S

<400> SEQUENCE: 120

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcaggcgcg tcagcgggtg | 120 |
| ttggcgggtg | tcgggctgg | cttaactatg | cggcatcaga | gcagattgta ctgagagtgc | 180 |
| accatatgcg | gtgtgaaata | ccgcacagat | gcgtaaggag | aaaataccgc atcaggcgcc | 240 |
| attcgccatt | caggctgcgc | aactgttggg | aagggcgatc | ggtgcgggcc tcttcgctat | 300 |
| tacgccagct | ggcgaaaggg | ggatgtgctg | caaggcgatt | aagttgggta acgccagggt | 360 |
| tttcccagtc | acgacgttgt | aaaacgacgg | ccagtgaatt | cgagctcggt acctcgcgaa | 420 |
| tgcatctaga | tccatggctg | ccgtcatcga | ggtggccaac | gagttcgtcg ctatcactgc | 480 |
| cgagacccctt | cccaaggtgg | actatcagcg | actctggcga | gacatctact cctgcgagct | 540 |
| cctgtacttc | tccattgctt | tcgtcatcct | caagtttacc | cttggcgagc tctcggattc | 600 |
| tggcaaaaag | attctgcgag | tgctgttcaa | gtggtacaac | ctcttcatgt ccgtcttttc | 660 |
| gctggtgtcc | ttcctctgta | tgggttacgc | catctacacc | gttggactgt actccaacga | 720 |
| atgcgacaga | gctttcgaca | acagcttgtt | ccgatttgcc | accaaggtct tctactattc | 780 |
| caagtttctg | gagtacatcg | actctttcta | ccttcccctc | atggccaagc tctgtccctt | 840 |
| tctgcagttc | tttcatcact | tgggagctcc | tatggacatg | tggctcttcg tgcagtactc | 900 |
| tggcgaatcc | atttggatct | ttgtgttcct | gaacggattc | attcactttg tcatgtacgg | 960 |
| ctactattgg | acacggctga | tgaagttcaa | ctttcccatg | cccaagcagc tcattaccgc | 1020 |
| aatgcagatc | acccagttca | acgttggctt | ctacctcgtg | tggtggtaca aggacattcc | 1080 |
| ctgttaccga | aaggatccca | tgcgaatgct | ggcctgatc | ttcaactact ggtacgtcgg | 1140 |
| taccgttctt | ctgctcttca | tcaacttctt | tgtcaagtcc | tacgtgtttc ccaagcctaa | 1200 |
| gactgccgac | aaaaaggtcc | agtagcggcc | gcatcggatc | ccgggcccgt cgactgcaga | 1260 |
| ggcctgcatg | caagcttggc | gtaatcatgg | tcatagctgt | ttcctgtgtg aaattgttat | 1320 |

-continued

```
ccgctcacaa ttccacacaa catacgagcc ggaagcataa agtgtaaagc ctggggtgcc      1380
taatgagtga gctaactcac attaattgcg ttgcgctcac tgcccgcttt ccagtcggga      1440
aacctgtcgt gccagctgca ttaatgaatc ggccaacgcg cggggagagg cggtttgcgt      1500
attgggcgct cttccgcttc ctcgctcact gactcgctgc gctcggtcgt tcggctgcgg      1560
cgagcggtat cagctcactc aaaggcggta atacggttat ccacagaatc agggaataac      1620
gcaggaaaga acatgtgagc aaaaggccag caaaaggcca ggaaccgtaa aaaggccgcg      1680
ttgctggcgt ttttccatag gctccgcccc cctgacgagc atcacaaaaa tcgacgctca      1740
agtcagaggt ggcgaaaccc gacaggacta taaagatacc aggcgtttcc ccctggaagc      1800
tccctcgtgc gctctcctgt tccgaccctg ccgcttaccg gatacctgtc cgcctttctc      1860
ccttcgggaa gcgtggcgct ttctcatagc tcacgctgta ggtatctcag ttcggtgtag      1920
gtcgttcgct ccaagctggg ctgtgtgcac gaaccccccg ttcagcccga ccgctgcgcc      1980
ttatccggta actatcgtct tgagtccaac ccggtaagac acgacttatc gccactggca      2040
gcagccactg gtaacaggat tagcagagcg aggtatgtag gcggtgctac agagttcttg      2100
aagtggtggc ctaactacgg ctacactaga agaacagtat ttggtatctg cgctctgctg      2160
aagccagtta ccttcggaaa aagagttggt agctcttgat ccggcaaaca aaccaccgct      2220
ggtagcggtg gtttttttgt ttgcaagcag cagattacgc gcagaaaaaa aggatctcaa      2280
gaagatcctt tgatctttc tacggggtct gacgctcagt ggaacgaaaa ctcacgttaa      2340
gggattttgg tcatgagatt atcaaaaagg atcttcacct agatcctttt aaattaaaaa      2400
tgaagtttta aatcaatcta agtatatat gagtaaactt ggtctgacag ttaccaatgc      2460
ttaatcagtg aggcacctat ctcagcgatc tgtctatttc gttcatccat agttgcctga      2520
ctccccgtcg tgtagataac tacgatacgg gagggcttac catctggccc cagtgctgca      2580
atgataccgc gagacccacg ctcaccggct ccagatttat cagcaataaa ccagccagcc      2640
ggaagggccg agcgcagaag tggtcctgca actttatccg cctccatcca gtctattaat      2700
tgttgccggg aagctagagt aagtagttcg ccagttaata gtttgcgcaa cgttgttgcc      2760
attgctacag gcatcgtggt gtcacgctcg tcgtttggta tggcttcatt cagctccggt      2820
tcccaacgat caaggcgagt tacatgatcc cccatgttgt gcaaaaaagc ggttagctcc      2880
ttcggtcctc cgatcgttgt cagaagtaag ttggccgcag tgttatcact catggttatg      2940
gcagcactgc ataattctct tactgtcatg ccatccgtaa gatgcttttc tgtgactggt      3000
gagtactcaa ccaagtcatt ctgagaatag tgtatgcggc gaccgagttg ctcttgcccg      3060
gcgtcaatac gggataatac cgcgccacat agcagaactt taaaagtgct catcattgga      3120
aaacgttctt cggggcgaaa actctcaagg atcttaccgc tgttgagatc cagttcgatg      3180
taacccactc gtgcacccaa ctgatcttca gcatctttta ctttcaccag cgtttctggg      3240
tgagcaaaaa caggaaggca aaatgccgca aaaagggaa taagggcgac acggaaatgt      3300
tgaatactca tactcttcct ttttcaatat tattgaagca tttatcaggg ttattgtctc      3360
atgagcggat acatatttga atgtatttag aaaaataaac aaataggggt tccgcgcaca      3420
tttccccgaa aagtgccacc tgacgtctaa gaaaccatta ttatcatgac attaacctat      3480
aaaaataggc gtatcacgag gccctttcgt c                                    3511
```

<210> SEQ ID NO 121
<211> LENGTH: 8165
<212> TYPE: DNA

<213> ORGANISM: Artificial Sequence
<220> FEATURE:
<223> OTHER INFORMATION: Plasmid pZUF17

<400> SEQUENCE: 121

| | | | | |
|---|---|---|---|---|
| gtacgagccg gaagcataaa gtgtaaagcc tggggtgcct aatgagtgag ctaactcaca | 60 |
| ttaattgcgt tgcgctcact gcccgctttc cagtcgggaa acctgtcgtg ccagctgcat | 120 |
| taatgaatcg gccaacgcgc ggggagaggc ggtttgcgta ttgggcgctc ttccgcttcc | 180 |
| tcgctcactg actcgctgcg ctcggtcgtt cggctgcggc gagcggtatc agctcactca | 240 |
| aaggcggtaa tacggttatc cacagaatca ggggataacg caggaaagaa catgtgagca | 300 |
| aaaggccagc aaaaggccag gaaccgtaaa aaggccgcgt tgctggcgtt tttccatagg | 360 |
| ctccgccccc ctgacgagca tcacaaaaat cgacgctcaa gtcagaggtg gcgaaacccg | 420 |
| acaggactat aaagatacca ggcgtttccc cctggaagct ccctcgtgcg ctctcctgtt | 480 |
| ccgaccctgc cgcttaccgg atacctgtcc gcctttctcc cttcgggaag cgtggcgctt | 540 |
| tctcatagct cacgctgtag gtatctcagt tcggtgtagg tcgttcgctc caagctgggc | 600 |
| tgtgtgcacg aaccccccgt tcagcccgac cgctgcgcct tatccggtaa ctatcgtctt | 660 |
| gagtccaacc cggtaagaca cgacttatcg ccactggcag cagccactgg taacaggatt | 720 |
| agcagagcga ggtatgtagg cggtgctaca gagttcttga agtggtggcc taactacggc | 780 |
| tacactagaa ggacagtatt tggtatctgc gctctgctga agccagttac cttcggaaaa | 840 |
| agagttggta gctcttgatc cggcaaacaa accaccgctg gtagcggtgg tttttttgtt | 900 |
| tgcaagcagc agattacgcg cagaaaaaaa ggatctcaag aagatccttt gatcttttct | 960 |
| acggggtctg acgctcagtg gaacgaaaac tcacgttaag ggattttggt catgagatta | 1020 |
| tcaaaaagga tcttcaccta gatcctttta aattaaaaat gaagttttaa atcaatctaa | 1080 |
| agtatatatg agtaaacttg gtctgacagt taccaatgct taatcagtga ggcacctatc | 1140 |
| tcagcgatct gtctatttcg ttcatccata gttgcctgac tccccgtcgt gtagataact | 1200 |
| acgatacggg agggcttacc atctggcccc agtgctgcaa tgataccgcg agacccacgc | 1260 |
| tcaccggctc cagatttatc agcaataaac cagccagccg aagggccga gcgcagaagt | 1320 |
| ggtcctgcaa ctttatccgc ctccatccag tctattaatt gttgccggga agctagagta | 1380 |
| agtagttcgc cagttaatag tttgcgcaac gttgttgcca ttgctacagg catcgtggtg | 1440 |
| tcacgctcgt cgtttggtat ggcttcattc agctccggtt cccaacgatc aaggcgagtt | 1500 |
| acatgatccc ccatgttgtg caaaaaagcg gttagctcct tcggtcctcc gatcgttgtc | 1560 |
| agaagtaagt tggccgcagt gttatcactc atggttatgg cagcactgca taattctctt | 1620 |
| actgtcatgc catccgtaag atgcttttct gtgactggtg agtactcaac caagtcattc | 1680 |
| tgagaatagt gtatgcggcg accgagttgc tcttgcccgg cgtcaatacg ggataatacc | 1740 |
| gcgccacata gcagaacttt aaaagtgctc atcattggaa aacgttcttc ggggcgaaaa | 1800 |
| ctctcaagga tcttaccgct gttgagatcc agttcgatgt aacccactcg tgcacccaac | 1860 |
| tgatcttcag catcttttac tttcaccagc gtttctgggt gagcaaaaac aggaaggcaa | 1920 |
| aatgccgcaa aaagggaat aagggcgaca cggaaatgtt gaatactcat actcttcctt | 1980 |
| tttcaatatt attgaagcat ttatcagggt tattgtctca tgagcggata catatttgaa | 2040 |
| tgtatttaga aaaataaaca ataggggtt ccgcgcacat ttccccgaaa agtgccacct | 2100 |
| gacgcgccct gtagcggcgc attaagcgcg gcgggtgtgg tggttacgcg cagcgtgacc | 2160 |
| gctacacttg ccagcgccct agcgcccgct cctttcgctt tcttcccttc ctttctcgcc | 2220 |

-continued

| | | | | | |
|---|---|---|---|---|---|
| acgttcgccg | gctttccccg | tcaagctcta | aatcggggc | tccctttagg | gttccgattt | 2280 |
| agtgctttac | ggcacctcga | ccccaaaaaa | cttgattagg | gtgatggttc | acgtagtggg | 2340 |
| ccatcgccct | gatagacggt | ttttcgccct | ttgacgttgg | agtccacgtt | ctttaatagt | 2400 |
| ggactcttgt | tccaaactgg | aacaacactc | aaccctatct | cggtctattc | ttttgattta | 2460 |
| taagggattt | tgccgatttc | ggcctattgg | ttaaaaaatg | agctgattta | acaaaaattt | 2520 |
| aacgcgaatt | ttaacaaaat | attaacgctt | acaatttcca | ttcgccattc | aggctgcgca | 2580 |
| actgttggga | agggcgatcg | gtgcgggcct | cttcgctatt | acgccagctg | gcgaaagggg | 2640 |
| gatgtgctgc | aaggcgatta | agttgggtaa | cgccagggtt | ttcccagtca | cgacgttgta | 2700 |
| aaacgacggc | cagtgaattg | taatacgact | cactataggg | cgaattgggt | accgggcccc | 2760 |
| ccctcgaggt | cgatggtgtc | gataagcttg | atatcgaatt | catgtcacac | aaaccgatct | 2820 |
| tcgcctcaag | gaaacctaat | tctacatccg | agagactgcc | gagatccagt | ctacactgat | 2880 |
| taattttcgg | gccaataatt | taaaaaaatc | gtgttatata | atattatatg | tattatatat | 2940 |
| atacatcatg | atgatactga | cagtcatgtc | ccattgctaa | atagacagac | tccatctgcc | 3000 |
| gcctccaact | gatgttctca | atatttaagg | ggtcatctcg | cattgtttaa | taataaacag | 3060 |
| actccatcta | ccgcctccaa | atgatgttct | caaaatatat | tgtatgaact | tatttttatt | 3120 |
| acttagtatt | attagacaac | ttacttgctt | tatgaaaaac | acttcctatt | taggaaacaa | 3180 |
| tttataatgg | cagttcgttc | atttaacaat | ttatgtagaa | taaatgttat | aaatgcgtat | 3240 |
| gggaaatctt | aaatatggat | agcataaatg | atatctgcat | tgcctaattc | gaaatcaaca | 3300 |
| gcaacgaaaa | aaatcccttg | tacaacataa | atagtcatcg | agaaatatca | actatcaaag | 3360 |
| aacagctatt | cacacgttac | tattgagatt | attattggac | gagaatcaca | cactcaactg | 3420 |
| tctttctctc | ttctagaaat | acaggtacaa | gtatgtacta | ttctcattgt | tcatacttct | 3480 |
| agtcatttca | tcccacatat | tccttggatt | tctctccaat | gaatgacatt | ctatcttgca | 3540 |
| aattcaacaa | ttataataag | atataccaaa | gtagcggtat | agtggcaatc | aaaaagcttc | 3600 |
| tctggtgtgc | ttctcgtatt | tatttttatt | ctaatgatcc | attaaaggta | tatatttatt | 3660 |
| tcttgttata | taatccttttt | gtttattaca | tgggctggat | acataaaggt | attttgattt | 3720 |
| aattttttgc | ttaaattcaa | tccccctcg | ttcagtgtca | actgtaatgg | taggaaatta | 3780 |
| ccatactttt | gaagaagcaa | aaaaaatgaa | agaaaaaaaa | aatcgtatt | ccaggttaga | 3840 |
| cgttccgcag | aatctagaat | gcggtatgcg | gtacattgtt | cttcgaacgt | aaaagttgcg | 3900 |
| ctccctgaga | tattgtacat | ttttgctttt | acaagtacaa | gtacatcgta | caactatgta | 3960 |
| ctactgttga | tgcatccaca | acagtttgtt | ttgtttttttt | ttgtttttttt | tttttctaat | 4020 |
| gattcattac | cgctatgtat | acctacttgt | acttgtagta | agccgggtta | ttggcgttca | 4080 |
| attaatcata | gacttatgaa | tctgcacggt | gtgcgctgcg | agttacttttt | agcttatgca | 4140 |
| tgctacttgg | gtgtaatatt | gggatctgtt | cggaaatcaa | cggatgctca | atcgatttcg | 4200 |
| acagtaatta | attaagtcat | acacaagtca | gctttcttcg | agcctcatat | aagtataagt | 4260 |
| agttcaacgt | attagcactg | tacccagcat | ctccgtatcg | agaaacacaa | caacatgccc | 4320 |
| cattggacag | atcatgcgga | tacacaggtt | gtgcagtatc | atacatactc | gatcagacag | 4380 |
| gtcgtctgac | catcatacaa | gctgaacaag | cgctccatac | ttgcacgctc | tctatataca | 4440 |
| cagttaaatt | acatatccat | agtctaacct | ctaacagtta | atcttctggt | aagcctccca | 4500 |
| gccagccttc | tggtatcgct | tggcctcctc | aataggatct | cggttctggc | cgtacagacc | 4560 |

```
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg ccagagagc ccttgcaaga     4800 cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag aagaaaccg tgcttaagag caagttcctt     5100 gaggggagc acagtgccgg cgtaggtgaa gtcgtcaatg atgtcgatat gggttttgat     5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg ggcagtgaa     5400 gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880 ggggccttt tatatggcca agccaagctc tccacgtcgg ttgggctgca cccaacaata     5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata     6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc gggggcttg tctagggtat atataaacag tggctctccc aatcggttgc     6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
```

| | |
|---|---:|
| gctccacgct ctggtttgcg ccacctacat ctacgtgcag ggtgtcatct tctggggttt | 7020 |
| ctttaccgtc ggtcacgact gtggtcactc tgccttctcc cgataccact ccgtcaactt | 7080 |
| catcattggc tgcatcatgc actctgccat tctgactccc ttcgagtcct ggcgagtgac | 7140 |
| ccaccgacac catcacaaga acactggcaa cattgataag gacgagatct tctaccctca | 7200 |
| tcggtccgtc aaggacctcc aggacgtgcg acaatgggtc tacaccctcg gaggtgcttg | 7260 |
| gtttgtctac ctgaaggtcg gatatgctcc tcgaaccatg tcccactttg acccctggga | 7320 |
| ccctctcctg cttcgacgag cctccgctgt catcgtgtcc ctcggagtct gggctgcctt | 7380 |
| cttcgctgcc tacgcctacc tcacatactc gctcggcttt gccgtcatgg gcctctacta | 7440 |
| ctatgctcct ctctttgtct ttgcttcgtt cctcgtcatt actaccttct tgcatcacaa | 7500 |
| cgacgaagct actccctggt acggtgactc ggagtggacc tacgtcaagg gcaacctgag | 7560 |
| ctccgtcgac cgatcgtacg gagctttcgt ggacaacctg tctcaccaca ttggcaccca | 7620 |
| ccaggtccat cacttgttcc ctatcattcc ccactacaag ctcaacgaag ccaccaagca | 7680 |
| ctttgctgcc gcttaccctc acctcgtgag acgtaacgac gagcccatca ttactgcctt | 7740 |
| cttcaagacc gctcacctct ttgtcaacta cggagctgtg cccgagactg ctcagatttt | 7800 |
| caccctcaaa gagtctgccg ctgcagccaa ggccaagagc gactaagcgg ccgcaagtgt | 7860 |
| ggatggggaa gtgagtgccc ggttctgtgt gcacaattgg caatccaaga tggatggatt | 7920 |
| caacacaggg atatagcgag ctacgtggtg gtgcgaggat atagcaacgg atatttatgt | 7980 |
| ttgacacttg agaatgtacg atacaagcac tgtccaagta caatactaaa catactgtac | 8040 |
| atactcatac tcgtacccgg gcaacggttt cacttgagtg cagtggctag tgctcttact | 8100 |
| cgtacagtgt gcaatactgc gtatcatagt ctttgatgta tatcgtattc attcatgtta | 8160 |
| gttgc | 8165 |

<210> SEQ ID NO 122
<211> LENGTH: 7879
<212> TYPE: DNA
<213> ORGANISM: Artificial Sequence
<220> FEATURE:
<223> OTHER INFORMATION: Plasmid pZUFE389S

<400> SEQUENCE: 122

| | |
|---|---:|
| catggctgcc gtcatcgagg tggccaacga gttcgtcgct atcactgccg agacccttcc | 60 |
| caaggtggac tatcagcgac tctggcgaga catctactcc tgcgagctcc tgtacttctc | 120 |
| cattgctttc gtcatcctca agtttaccct tggcgagctc tcggattctg gcaaaaagat | 180 |
| tctgcgagtg ctgttcaagt ggtacaacct cttcatgtcc gtcttttcgc tggtgtcctt | 240 |
| cctctgtatg ggttacgcca tctacaccgt tggactgtac tccaacgaat gcgacagagc | 300 |
| tttcgacaac agcttgttcc gatttgccac caaggtcttc tactattcca gttctggaa | 360 |
| gtacatcgac tctttctacc ttcccctcat ggccaagcct ctgtcctttc tgcagttctt | 420 |
| tcatcacttg ggagctccta tggacatgtg gctcttcgtg cagtactctg gcgaatccat | 480 |
| ttggatcttt gtgttcctga acggattcat tcactttgtc atgtacggct actattggac | 540 |
| acggctgatg aagttcaact ttcccatgcc caagcagctc attaccgcaa tgcagatcac | 600 |
| ccagttcaac gttggcttct acctcgtgtg gtggtacaag acattccct gttaccgaaa | 660 |
| ggatcccatg cgaatgctgg cctggatctt caactactgg tacgtcggta ccgttcttct | 720 |
| gctcttcatc aacttctttg tcaagtccta cgtgtttccc aagcctaaga ctgccgacaa | 780 |

-continued

```
aaaggtccag tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacgggtct gacgctcagt ggaacgaaaa   2100
ctcacgttaa gggattttgg tcatgagatt atcaaaaagg atcttcacct agatcctttt   2160
aaattaaaaa tgaagtttta atcaatcta agtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaagggaa taagggcgac   3060 acggaaatgt tgaatactca tactcttcct ttttcaatat tattgaagca tttatcaggg   3120
ttattgtctc atgagcggat acatatttga atgtatttag aaaaataaac aaatagggt   3180
```

```
tccgcgcaca tttccccgaa aagtgccacc tgacgcgccc tgtagcggcg cattaagcgc  3240
ggcgggtgtg gtggttacgc gcagcgtgac cgctacactt gccagcgccc tagcgcccgc  3300
tcctttcgct ttcttccctt cctttctcgc cacgttcgcc ggctttcccc gtcaagctct  3360
aaatcggggg ctcccttttag ggttccgatt tagtgcttta cggcacctcg accccaaaaa  3420
acttgattag ggtgatggtt cacgtagtgg gccatcgccc tgatagacgg ttttcgccc  3480
tttgacgttg gagtccacgt tctttaatag tggactcttg ttccaaactg gaacaacact  3540
caaccctatc tcggtctatt cttttgattt ataagggatt ttgccgattt cggcctattg  3600
gttaaaaaat gagctgattt aacaaaaatt taacgcgaat tttaacaaaa tattaacgct  3660
tacaatttcc attcgccatt caggctgcgc aactgttggg aagggcgatc ggtgcgggcc  3720
tcttcgctat tacgccagct ggcgaaaggg ggatgtgctg caaggcgatt aagttgggta  3780
acgccagggt tttcccagtc acgacgttgt aaaacgacgg ccagtgaatt gtaatacgac  3840
tcactatagg gcgaattggg taccgggccc ccctcgagg tcgatggtgt cgataagctt  3900
gatatcgaat tcatgtcaca caaaccgatc ttcgcctcaa ggaaacctaa ttctacatcc  3960
gagagactgc cgagatccag tctacactga ttaatttcg ggccaataat ttaaaaaaat  4020
cgtgttatat aatattatat gtattatata tacatcat gatgactg acagtcatgt  4080
cccattgcta aatagacaga ctccatctgc cgcctccaac tgatgttctc aatatttaag  4140
gggtcatctc gcattgttta ataataaaca gactccatct accgcctcca aatgatgttc  4200
tcaaaatata ttgtatgaac ttatttttat tacttagtat tattagacaa cttacttgct  4260
ttatgaaaaa cacttcctat ttaggaaaca atttataatg gcagttcgtt catttaacaa  4320
tttatgtaga ataaatgtta taaatgcgta tgggaaatct taaatatgga tagcataaat  4380
gatatctgca ttgcctaatt cgaaatcaac agcaacgaaa aaaatcccctt gtacaacata  4440
aatagtcatc gagaaatatc aactatcaaa gaacagctat tcacacgtta ctattgagat  4500
tattattgga cgagaatcac acactcaact gtctttctct cttctagaaa tacaggtaca  4560
agtatgtact attctcattg ttcatacttc tagtcatttc atcccacata ttccttggat  4620
ttctctccaa tgaatgacat tctatcttgc aaattcaaca attataataa gatataccaa  4680
agtagcggta tagtggcaat caaaaagctt ctctggtgtg cttctcgtat ttattttat  4740
tctaatgatc cattaaaggt atatatttat ttcttgttat ataatccttt tgtttattac  4800
atgggctgga tacataaagg tatttttgatt taattttttg cttaaattca atccccctc  4860
gttcagtgtc aactgtaatg gtaggaaatt accatacttt tgaagaagca aaaaaaatga  4920
aagaaaaaaa aaatcgtatt tccaggttag acgttccgca gaatctagaa tgcggtatgc  4980
ggtacattgt tcttcgaacg taaaagttgc gctccctgag atattgtaca tttttgcttt  5040
tacaagtaca agtacatcgt acaactatgt actactgttg atgcatccac aacagtttgt  5100
tttgtttttt tttgttttt tttttctaa tgattcatta ccgctatgta tacctacttg  5160
tacttgtagt aagccgggtt attggcgttc aattaatcat agacttatga atctgcacgg  5220
tgtgcgctgc gagttacttt tagcttatgc atgctacttg ggtgtaatat tgggatctgt  5280
tcggaaatca acggatgctc aatcgatttc gacagtaatt aattaagtca tacacaagtc  5340
agctttcttc gagcctcata taagtataag tagttcaacg tattagcact gtacccagca  5400
tctccgtatc gagaaacaca acaacatgcc ccattggaca gatcatgcgg atacacaggt  5460
tgtgcagtat catacatact cgatcagaca ggtcgtctga ccatcataca agctgaacaa  5520
```

```
gcgctccata cttgcacgct ctctatatac acagttaaat tacatatcca tagtctaacc    5580
tctaacagtt aatcttctgg taagcctccc agccagcctt ctggtatcgc ttggcctcct    5640
caataggatc tcggttctgg ccgtacagac ctcggccgac aattatgata tccgttccgg    5700
tagacatgac atcctcaaca gttcggtact gctgtccgag agcgtctccc ttgtcgtcaa    5760
gacccacccc gggggtcaga ataagccagt cctcagagtc gcccttaggt cggttctggg    5820
caatgaagcc aaccacaaac tcggggtcgg atcgggcaag ctcaatggtc tgcttggagt    5880
actcgccagt ggccagagag cccttgcaag acagctcggc cagcatgagc agacctctgg    5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgaggggag cacagtgccg gcgtaggtga    6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
cttcgtagga gggcattttg gtggtgaaga ggagactgaa ataaatttag tctgcagaac    6480
ttttttatcgg aaccttatct ggggcagtga agtatatgtt atggtaatag ttacgagtta    6540
gttgaactta tagatagact ggactatacg gctatcggtc caaattagaa agaacgtcaa    6600
tggctctctg ggcgtcgcct ttgccgacaa aaatgtgatc atgatgaaag ccagcaatga    6660
cgttgcagct gatattgttg tcggccaacc gcgccgaaaa cgcagctgtc agacccacag    6720
cctccaacga agaatgtatc gtcaaagtga tccaagcaca ctcatagttg gagtcgtact    6780
ccaaaggcgg caatgacgag tcagacagat actcgtcgac tcaggcgacg acggaattcc    6840
tgcagcccat ctgcagaatt caggagagac cgggttggcg gcgtatttgt gtcccaaaaa    6900
acagccccaa ttgccccgga gaagacggcc aggccgccta gatgacaaat tcaacaactc    6960
acagctgact ttctgccatt gccactaggg gggggccttt ttatatggcc aagccaagct    7020
ctccacgtcg gttgggctgc acccaacaat aaatgggtag ggttgcacca acaaagggat    7080
gggatggggg gtagaagata cgaggataac ggggctcaat ggcacaaata agaacgaata    7140
ctgccattaa gactcgtgat ccagcgactg acaccattgc atcatctaag ggcctcaaaa    7200
ctacctcgga actgctgcgc tgatctggac accagagagg ttccgagcac tttaggttgc    7260
accaaatgtc ccaccaggtg caggcagaaa acgctggaac agcgtgtaca gtttgtctta    7320
acaaaaagtg agggcgctga ggtcgagcag ggtggtgtga cttgttatag cctttagagc    7380
tgcgaaagcg cgtatggatt tggctcatca ggccagattg agggtctgtg gacacatgtc    7440
atgttagtgt acttcaatcg ccccctggat atagccccga caataggccg tggcctcatt    7500
ttttttgcctt ccgcacattt ccattgctcg gtacccacac cttgcttctc ctgcacttgc    7560
caaccttaat actggtttac attgaccaac atcttacaag cgggggggctt gtctagggta    7620
tatataaaca gtggctctcc caatcggttg ccagtctctt ttttccttc tttccccaca    7680
gattcgaaat ctaaactaca catcacacaa tgcctgttac tgacgtcctt aagcgaaagt    7740
ccggtgtcat cgtcggcgac gatgtccgag ccgtgagtat ccacgacaag atcagtgtcg    7800
agacgacgcg ttttgtgtaa tgacacaatc cgaaagtcgc tagcaacaca cactctctac    7860
acaaactaac ccagctctc                                                 7879
```

```
<210> SEQ ID NO 123
<211> LENGTH: 13
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = L or F
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 123

Tyr Asn Xaa Xaa Xaa Xaa Xaa Xaa Ser Xaa Xaa Ser Phe
1               5                   10

<210> SEQ ID NO 124
<211> LENGTH: 15
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X = E or D
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: X = T or S
<220> FEATURE:
<221> NAME/KEY: misc_feature
<222> LOCATION: (13)..(14)
<223> OTHER INFORMATION: Xaa can be any naturally occurring amino acid

<400> SEQUENCE: 124

Phe Tyr Xaa Ser Lys Xaa Xaa Xaa Tyr Xaa Asp Xaa Xaa Xaa Leu
1               5                   10                  15

<210> SEQ ID NO 125
<211> LENGTH: 9
<212> TYPE: PRT
<213> ORGANISM: Artificial Sequence
<220> FEATURE:
<223> OTHER INFORMATION: delta-9 elongase motif
<220> FEATURE:
<221> NAME/KEY: MISC_FEATURE
<222> LOCATION: (2)..(2)
<223> OTHER INFORMATION: X = Q or H
<220> FEATURE:
```

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 125

Leu Xaa Xaa Phe His His Xaa Gly Ala
1               5

<210> SEQ ID NO 126
<211> LENGTH: 14
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X = K or R or N

<400> SEQUENCE: 126

Met Tyr Xaa Tyr Tyr Xaa Xaa Xaa Xaa Xaa Xaa Xaa Xaa Phe
1               5                   10

<210> SEQ ID NO 127
<211> LENGTH: 8
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = I or L or M
<220> FEATURE:
<221> NAME/KEY: misc_feature
<222> LOCATION: (6)..(7)
<223> OTHER INFORMATION: Xaa can be any naturally occurring amino acid

<400> SEQUENCE: 127

Lys Xaa Leu Xaa Thr Xaa Xaa Gln
1               5

<210> SEQ ID NO 128
<211> LENGTH: 7
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

-continued

```
<400> SEQUENCE: 128

Trp Xaa Phe Asn Tyr Xaa Tyr
1               5

<210> SEQ ID NO 129
<211> LENGTH: 9
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 129

Tyr Xaa Gly Xaa Val Xaa Xaa Leu Phe
1               5
```

DELTA-9 ELONGASES AND THEIR USE IN MAKING POLYUNSATURATED FATTY ACIDS

This application claims the benefit of U.S. Provisional Application No. 60/739,989, filed Nov. 23, 2005, the entire content of which is herein incorporated by reference.

FIELD OF THE INVENTION

This invention is in the field of biotechnology. More specifically, this invention pertains to the identification of nucleic acid fragments encoding Δ9 fatty acid elongase enzymes and the use of these elongases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs has cardiovascular protective effects (Dyerberg, J. et al., *Amer. J. Clin. Nutr.*, 28:958-966 (1975); Dyerberg, J. et al., *Lancet*, 2(8081):117-119 (Jul. 15, 1978); Shimokawa, H., *World Rev. Nutr. Diet*, 88:100-108 (2001); von Schacky, C. and Dyerberg, J., *World Rev. Nutr. Diet*, 88:90-99 (2001)). Numerous other studies document wide-ranging health benefits conferred by administration of ω-3 and/or ω-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production. Although the natural PUFA-producing abilities of the host organisms are sometimes specific to a given methodology, genetic engineering has also proven that the natural abilities of some hosts (even those natively limited to LA and ALA fatty acid production) can be substantially enhanced to produce high-levels of various long-chain ω-3/ω-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the Δ9 elongase/Δ8 desaturase pathway (which operates in some organisms, such as euglenoid species and which is characterized by the production of eicosadienoic acid [EDA; 20:2 ω-6] and/or eicosatrienoic acid [ETrA; 20:3 ω-3]) or the Δ6 desaturase/Δ6 elongase pathway (which is predominantly found in algae, mosses, fungi, nematodes and humans and which is characterized by the production of gamma-linoleic acid [GLA; 18:3 ω-6] and/or stearidonic acid [STA; 18:4 ω-3]) (FIG. 1).

For the purposes herein, the present application focuses on use of the Δ9 elongase/Δ8 desaturase pathway, and more specifically, on the use of Δ9 elongase enzymes. Most Δ9 elongase enzymes identified so far have the ability to convert both LA to EDA and ALA to ETrA (wherein DGLA and ETA are subsequently synthesized from EDA and ETrA, respectively, following reaction with a Δ8 desaturase; ARA and EPA are subsequently synthesized from DGLA and ETA, respectively, following reaction with a Δ5 desaturase; and, DHA synthesis requires subsequent expression of an additional $C_{20/22}$ elongase and a Δ4 desaturase).

In spite of the need for new methods for the production of ARA, EPA and DHA, few Δ9 elongase enzymes have been identified. For example, only a single Δ9 elongase is presently known prior to the Applicants' invention herein. Specifically, PCT Publications No. WO 2002/077213, No. WO 2005/083093, No. WO 2005/012316 and No. WO 2004/057001 describe a Δ9 elongase from *Isochrysis galbana* and its use (see also GenBank Accession No. AAL37626). Thus, there is need for the identification and isolation of additional genes encoding Δ9 elongases that will be suitable for heterologous expression in a variety of host organisms for use in the production of ω-3/ω-6 fatty acids.

Elongases which have been identified in the past differ in terms of the substrates upon which they act. They are present in both animals and plants. Those found in mammals can act upon saturated, monounsaturated and polyunsaturated fatty acids. However, those found in plants are specific for saturated and monounsaturated fatty acids. Thus, there is a need for a PUFA-specific elongase to produce PUFAs in plants.

The elongation process in plants involves a four-step process initiated by the crucial step of condensation of malonate and a fatty acid with release of a carbon dioxide molecule. The substrates in fatty acid elongation are CoA-thioesters. The condensation step is mediated by a 3-ketoacyl synthase, which is generally rate-limiting to the overall cycle of four reactions and provides some substrate specificity. The product of one elongation cycle regenerates a fatty acid that has been extended by two carbon atoms (Browse et al., *Trends in Biochemical Sciences*, 27(9):467-473 (September 2002); Napier, *Trends in Plant Sciences*, 7(2):51-54 (February 2002)).

Based on the utility of expressing Δ9 elongases in conjunction with Δ8 desaturases, there has also been considerable effort to identify and characterize Δ8 desaturases from various sources. Most efforts thus far have focused on the isolation and characterization of Δ8 desaturases from *Euglena gracilis*; and, several sequence variations of *E. gracilis* Δ8 desaturases have been reported (see, e.g., Wallis et al., *Arch. Biochem. and Biophys.*, 365(2):307-316 (May 1999); PCT Publication No. WO 2000/34439; U.S. Pat. No. 6,825,017; PCT Publication No. WO 2004/057001; U.S. application Ser. No. 11/166,003 filed Jun. 24, 2005 (PCT Publications No. WO 2006/012325 and No. WO 2006/012326; published Feb. 2, 2006)). More recently, PCT Publication No. WO 2005/103253 (published Apr. 22, 2005) discloses amino acid and nucleic acid sequences for a Δ8 desaturase enzyme from *Pavlova salina*. Sayanova et al. (*FEBS Lett.*, 580:1946-1952 (2006)) describes the isolation and characterization of a cDNA from the free living soil amoeba *Acanthamoeba castellanii* that, when expressed in *Arabidopsis*, encodes a $C_{20}$ Δ8 desaturase. Also, commonly owned, co-pending application having Provisional Application No. 60/795,810 (filed Apr. 28, 2006) discloses amino acid and nucleic acid sequences for a Δ8 desaturase enzyme from *Pavlova lutheri* (CCMP459), while commonly owned, co-pending application having U.S. Provisional Application No. 60/853,563 filed Oct. 23, 2006, discloses Δ8 desaturases from the euglenoids *Tetruetreptia pomquetensis* CCMP1491, *Eutreptiella* sp. CCMP389 and *Eutreptiella* cf_*gymnastica* CCMP1594.

The following commonly owned patent applications relate to the production of PUFAs in oleaginous yeasts (i.e., *Yar-* rowia lipolytica), including: PCT Publication No. WO 2004/101757 and PCT Publication No. WO 2004/101753 (both published Nov. 25, 2004); U.S. application Ser. No. 11/265,761 (filed Nov. 2, 2005; corresponding to PCT Publication No. WO 2006/052870); U.S. application Ser. No. 11/264,784 (filed Nov. 1, 2005; corresponding to PCT Publication No. WO 2006/055322); and U.S. application Ser. No. 11/264,737 (filed Nov. 1, 2005; corresponding to PCT Publication No. WO 2006/052871).

Additionally, PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are commonly owned and copending applications.

Applicants have solved the stated problem by isolating the genes encoding Δ9 elongase from *Euglena gracilis* and *Eutreptiella* sp. CCMP389.

SUMMARY OF THE INVENTION

The present invention relates to new genetic constructs encoding polypeptides having Δ9 elongase activity, and their use in plants, algae, bacteria, yeast and fungi for the production of PUFAs.

Accordingly the invention provides an isolated polynucleotide selected from the group consisting of:
  (a) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;
  (b) an isolated nucleic acid sequence comprising a nucleotide sequence encoding a polypeptide having Δ9 elongase activity, wherein the nucleotide sequence has at least 70% sequence identity, based on the BLASTN method of alignment, when compared to a nucleotide sequence as set forth in SEQ ID NO:1, SEQ ID NO:3, SEQ ID NO:4 or SEQ ID NO:6;
  (c) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; or
  (d) a complement of the nucleotide sequence of (a), (b) or (c), wherein the complement and the nucleotide sequence consist of the same number of nucleotides and are 100% complementary.

Additionally invention provides polypeptides encoded by the isolated nucleic acid sequences of the invention. Specifically the invention provides a Δ9 elongase polypeptide wherein the amino acid sequence of the polypeptide is selected from the group consisting of:
  (a) an amino acid sequence as set forth in SEQ ID NO:2 or SEQ ID NO:5; and
  (b) an amino acid sequence that differs from the amino acid sequences in (a) by at least one conservative amino acid substitution.

In another embodiment the invention provides host cells transformed with the isolated nucleic acid sequences of the invention, where preferred host cells are microbial species as for example algae, bacterial, yeast, oomycetes and fungi.

In another embodiment the invention provides a method for the production of eicosadienoic acid comprising:
  a) providing an isolated transformed yeast host cell comprising:
    i) an isolated polynucleotide sequence encoding a polypeptide having Δ9 elongase activity, selected from the group consisting of:
      (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;
      (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and
    (ii) a source of linoleic acid;
  b) growing the yeast host cell of step (a) under conditions wherein the nucleic acid sequence encoding the Δ9 elongase polypeptide is expressed and the linoleic acid is converted to eicosadienoic acid; and,
  c) optionally recovering the eicosadienoic acid of step (b).

In an alternate embodiment the invention provides a method for the production of eicosatrienoic acid comprising:
  a) providing an isolated transformed yeast host cell comprising:
    i) an isolated polynucleotide sequence encoding a polypeptide having Δ9 elongase activity, selected from the group consisting of:
      (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;
      (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and
    (ii) a source of α-linolenic acid;
  b) growing the host cell of step (a) under conditions wherein the nucleic acid sequence encoding the Δ9 elongase polypeptide is expressed and the α-linolenic acid is converted to eicosatrienoic acid; and,
  c) optionally recovering the eicosatrienoic acid of step (b).

In another embodiment the invention provides microbial oils produced by the transformed hosts of the invention.

In a separate embodiment the invention provides a food product comprising the microbial oils of the invention.

In another embodiment the invention provides an animal feed comprising the oils of the invention.

BIOLOGICAL DEPOSITS

The following plasmids have been deposited with the American Type Culture Collection (ATCC), 10801 University Boulevard, Manassas, Va. 20110-2209, and bear the following designations, Accession Numbers and dates of deposit (Table 1).

TABLE 1

ATCC Deposits

| Plasmid | Accession Number | Date of Deposit |
|---|---|---|
| pKR72 | PTA-6019 | May 28, 2004 |
| pKR275 | PTA-4989 | Jan. 30, 2003 |
| pKR585 | PTA-6279 | Nov. 4, 2004 |
| pKR578 | PTA-6280 | Nov. 4, 2004 |

BRIEF DESCRIPTION OF THE DRAWINGS AND SEQUENCE LISTINGS

FIG. 1 illustrates the ω-3/ω-6 fatty acid biosynthetic pathway providing for the conversion of myristic acid through various intermediates to DHA.

FIG. 2 shows a Clustal V alignment (with default parameters) of the amino acid sequence of the *Euglena gracilis* Δ9 elongase of the instant invention (SEQ ID NO:2), the amino acid sequence of the *Eutreptiella* sp. CCMP389 Δ9 elongase of the instant invention (SEQ ID NO:5) and the amino acid sequence of the long-chain PUFA elongation enzyme from *Isochrysis galbana* (NCBI Accession No. AAL37626 (GI 17226123)) (SEQ ID NO:8).

FIG. 4 shows a Clustal V alignment (with default parameters) of the amino acid sequence of the *Euglena gracilis* Δ9 elongase of the instant invention (SEQ ID NO:2) and the amino acid sequence of the long-chain PUFA elongation enzyme from *Isochrysis galbana* (NCBI Accession No. AAL37626 (GI 17226123)) (SEQ ID NO:8).

FIG. 6 are the results of functional analysis of the *Euglena gracilis* Δ9 elongase (EgD9e) in *Saccharomyces cerevisiae*.

Figure 10:
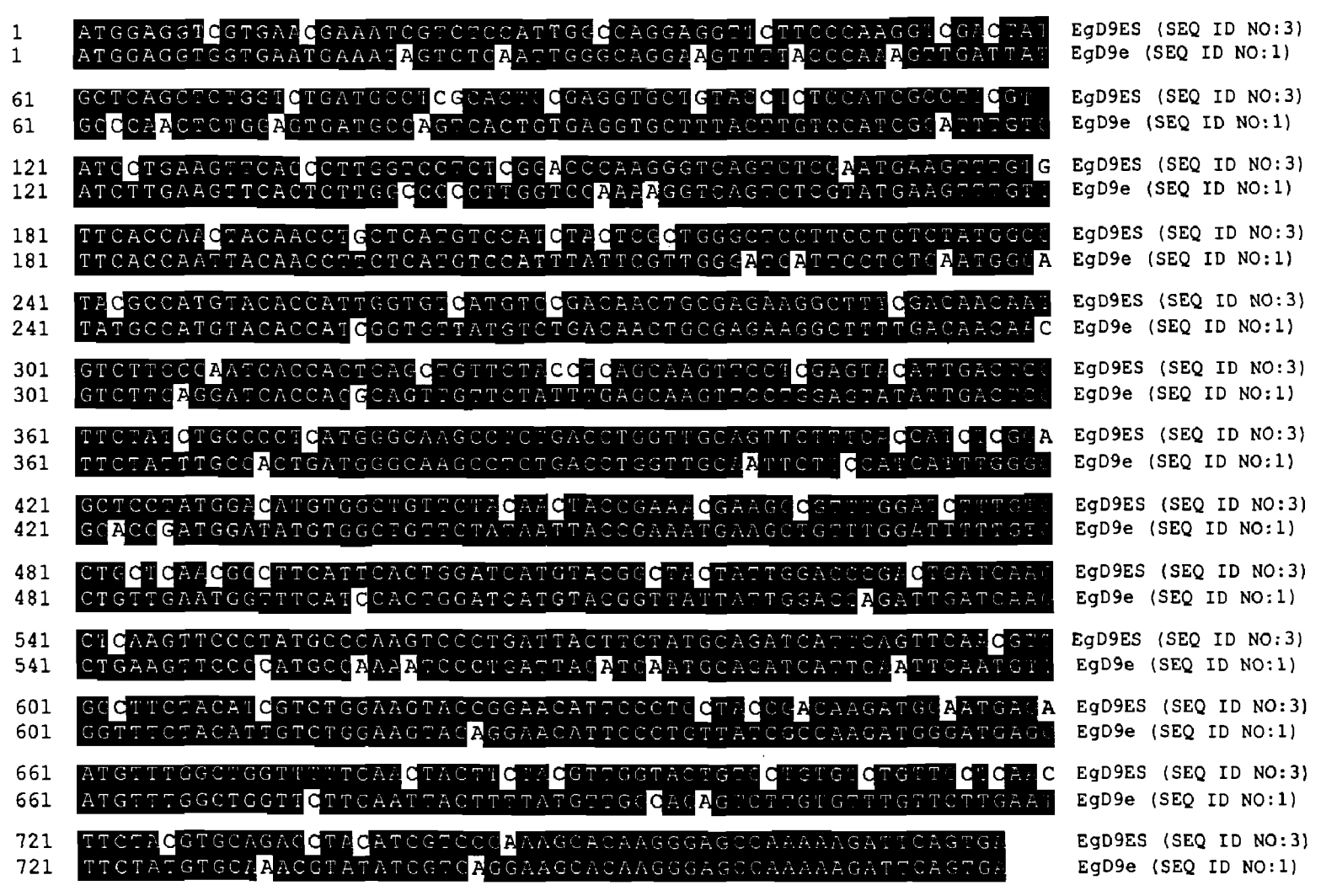

FIG. 10 shows a comparison of the DNA sequences of the *Euglena gracilis* Δ9 elongase gene (EgD9e; SEQ ID NO:1) and the synthetic gene (EgD9eS; SEQ ID NO:3) codon-optimized for expression in *Yarrowia lipolytica*.

Figure 11A:
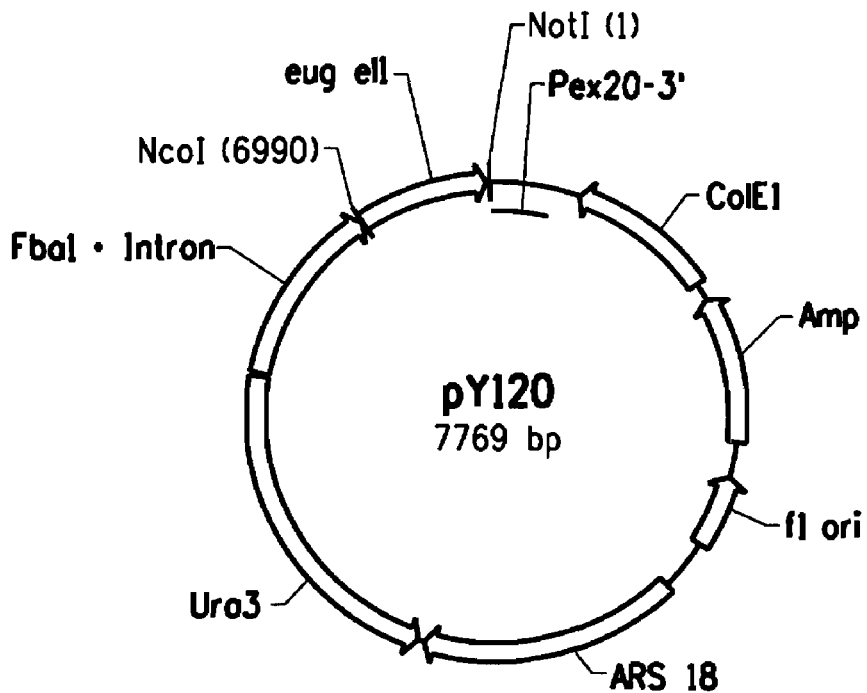
Figure 11B:
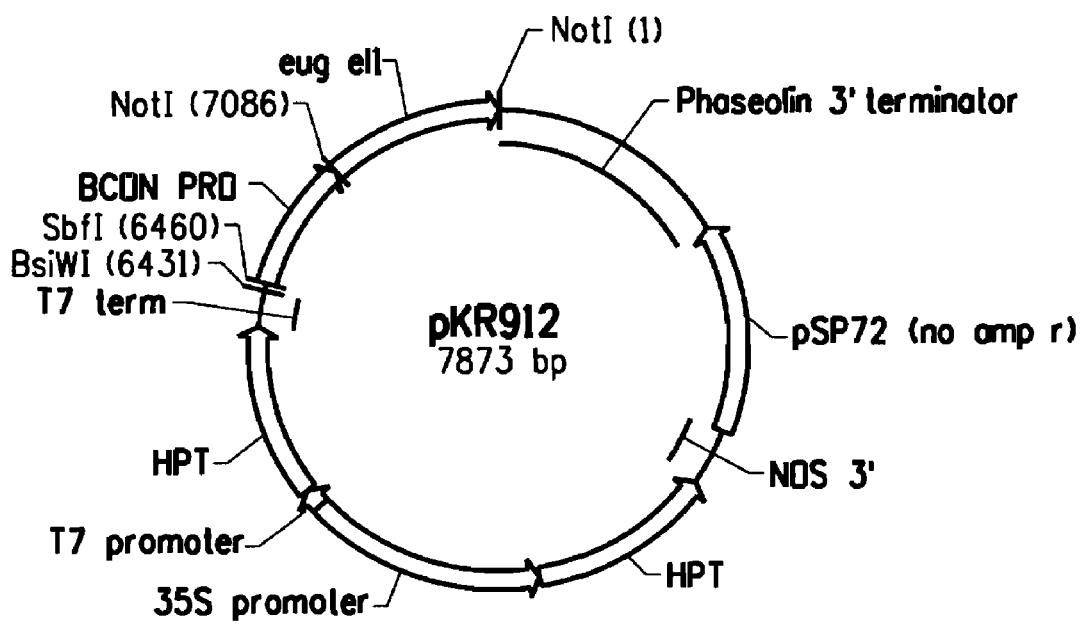

FIG. 11A is a map of plasmid pY120, while FIG. 11B is a map of plasmid pKR912.

Figure 12A:
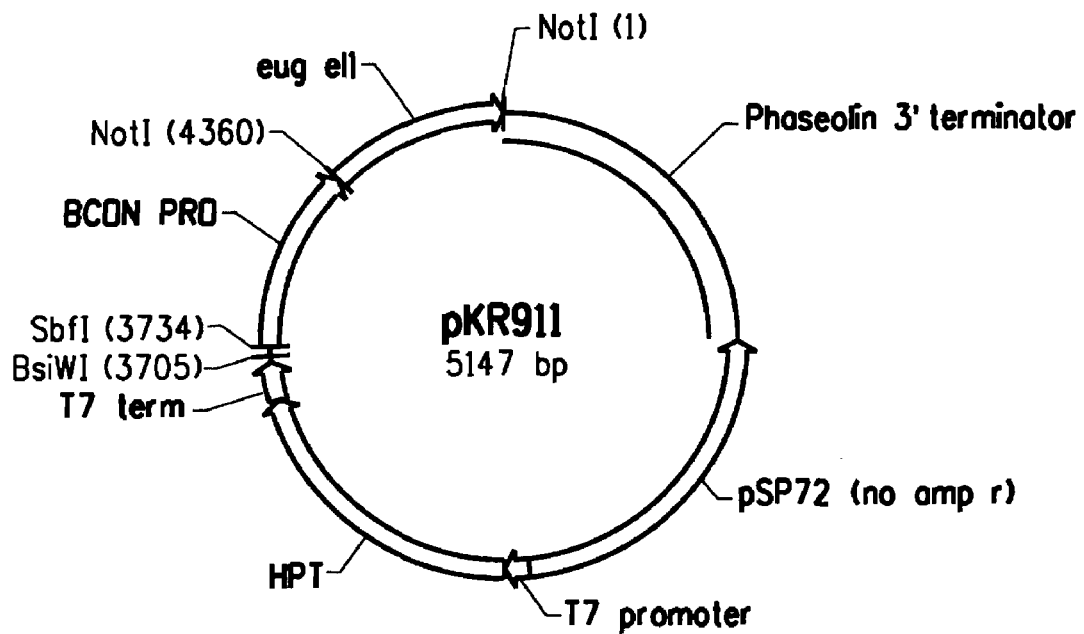
Figure 12B:
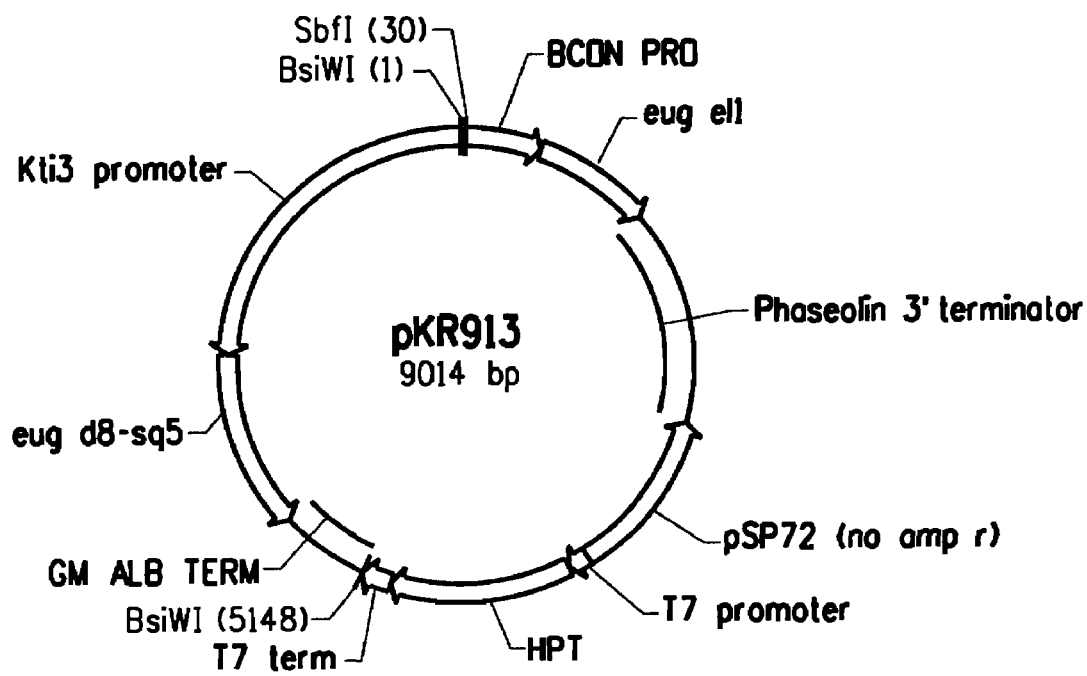

FIG. 12A is a map of plasmid pKR911, while FIG. 12B is a map of plasmid pKR913.

Figure 13A:
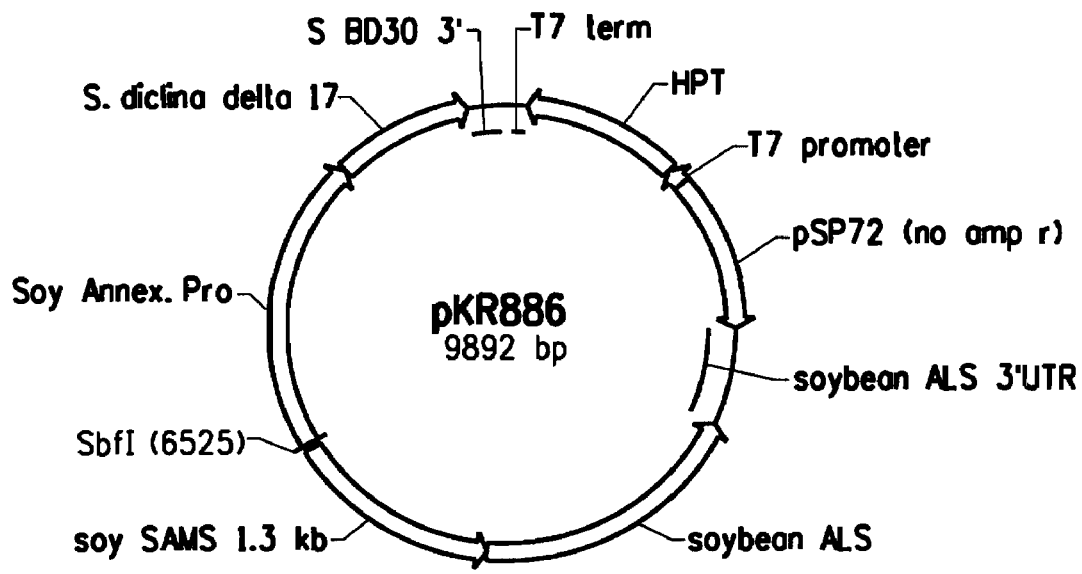
Figure 13B:
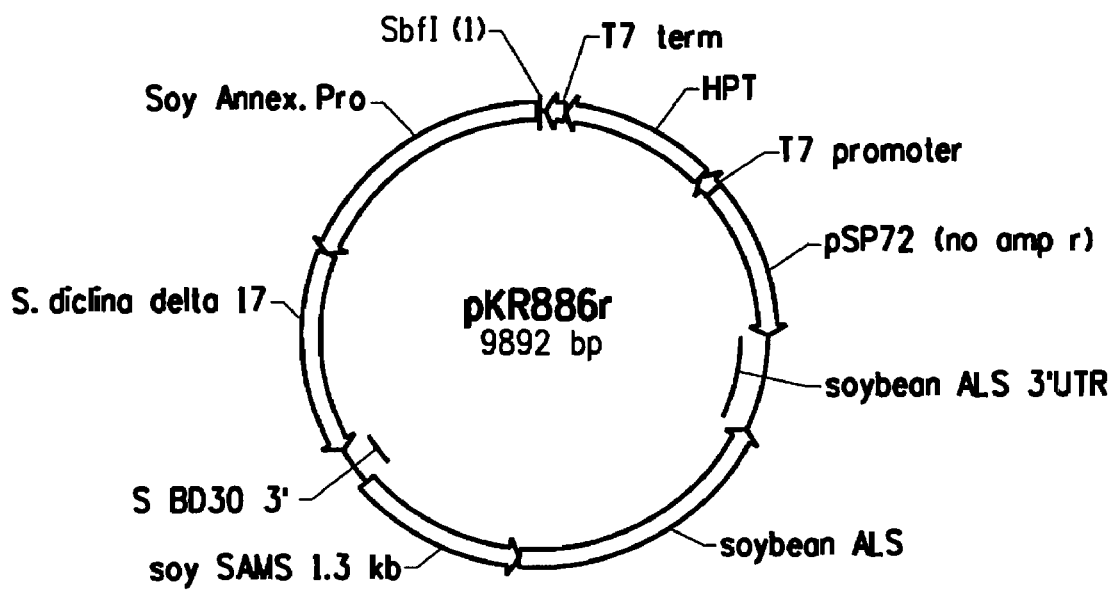

FIG. 13A is a map of plasmid pKR886, while FIG. 13B is a map of plasmid pKR886r.

Figure 14A:
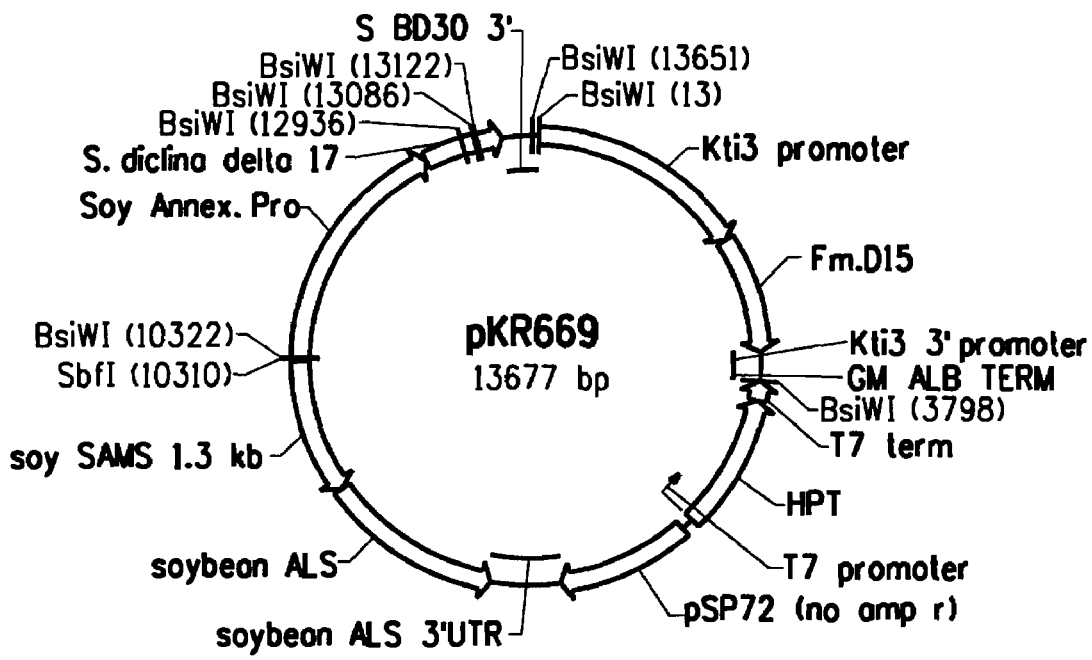
Figure 14B:
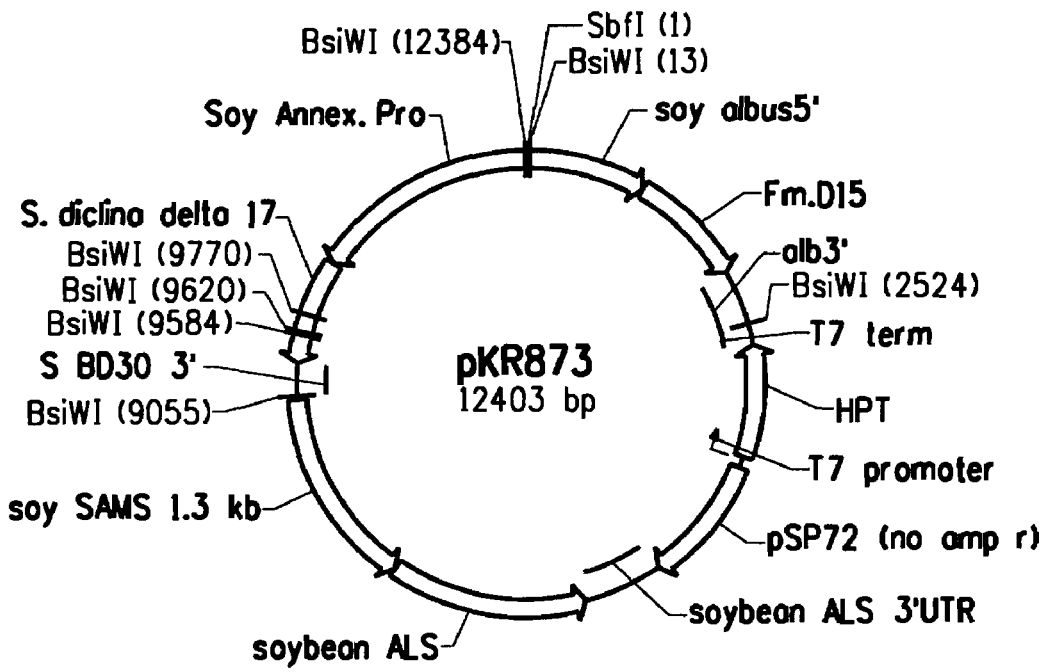

FIG. 14A is a map of plasmid pKR669, while FIG. 14B is a map of plasmid pKR873.

Figure 15A:
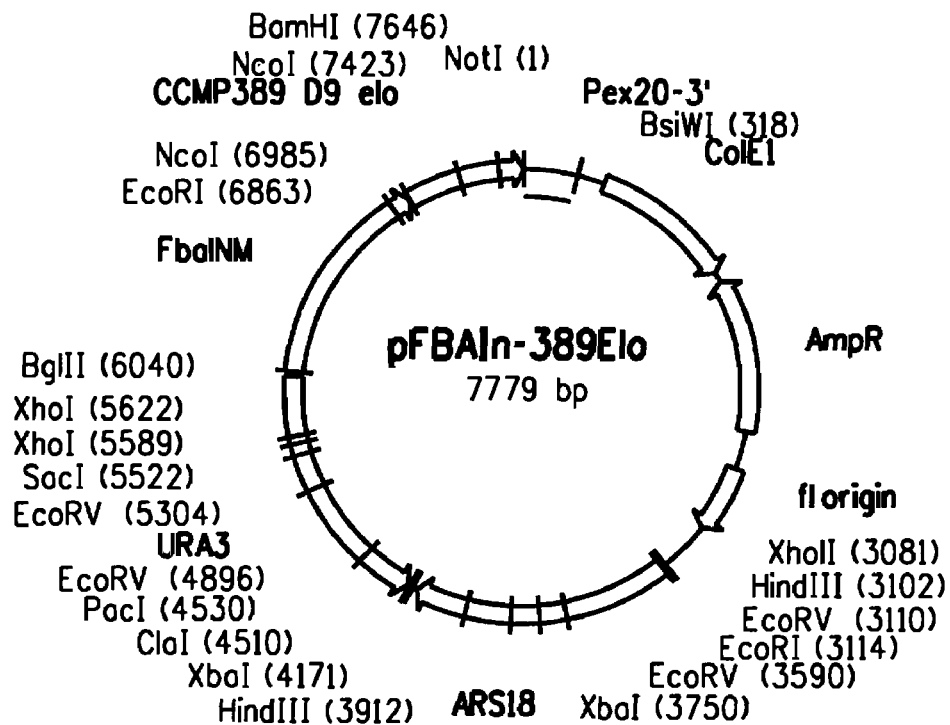
Figure 15B:
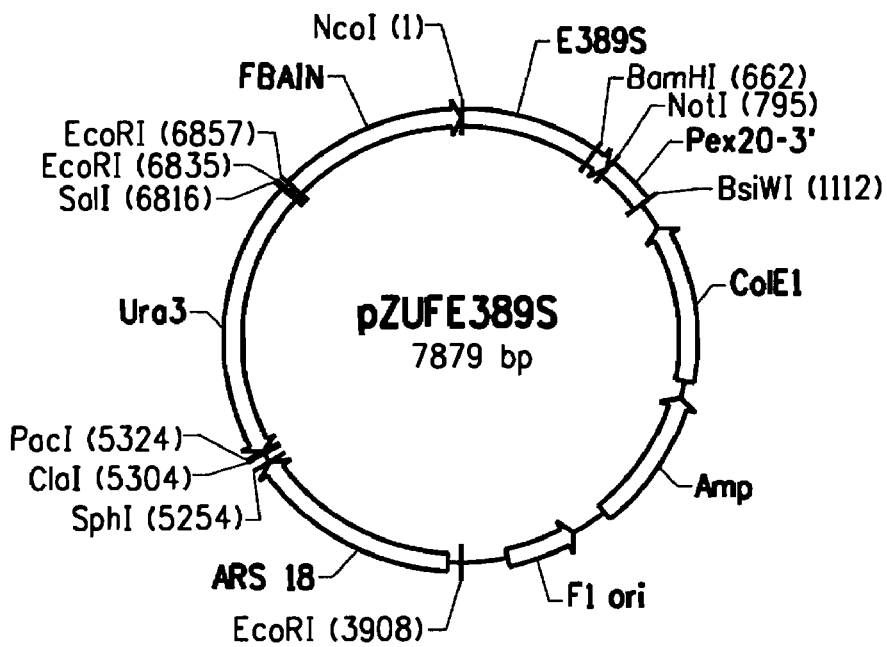

FIG. 15A is a plasmid map of pFBAIN-389Elo, while FIG. 15B is a plasmid map of pZUFE389S.

Figure 16:
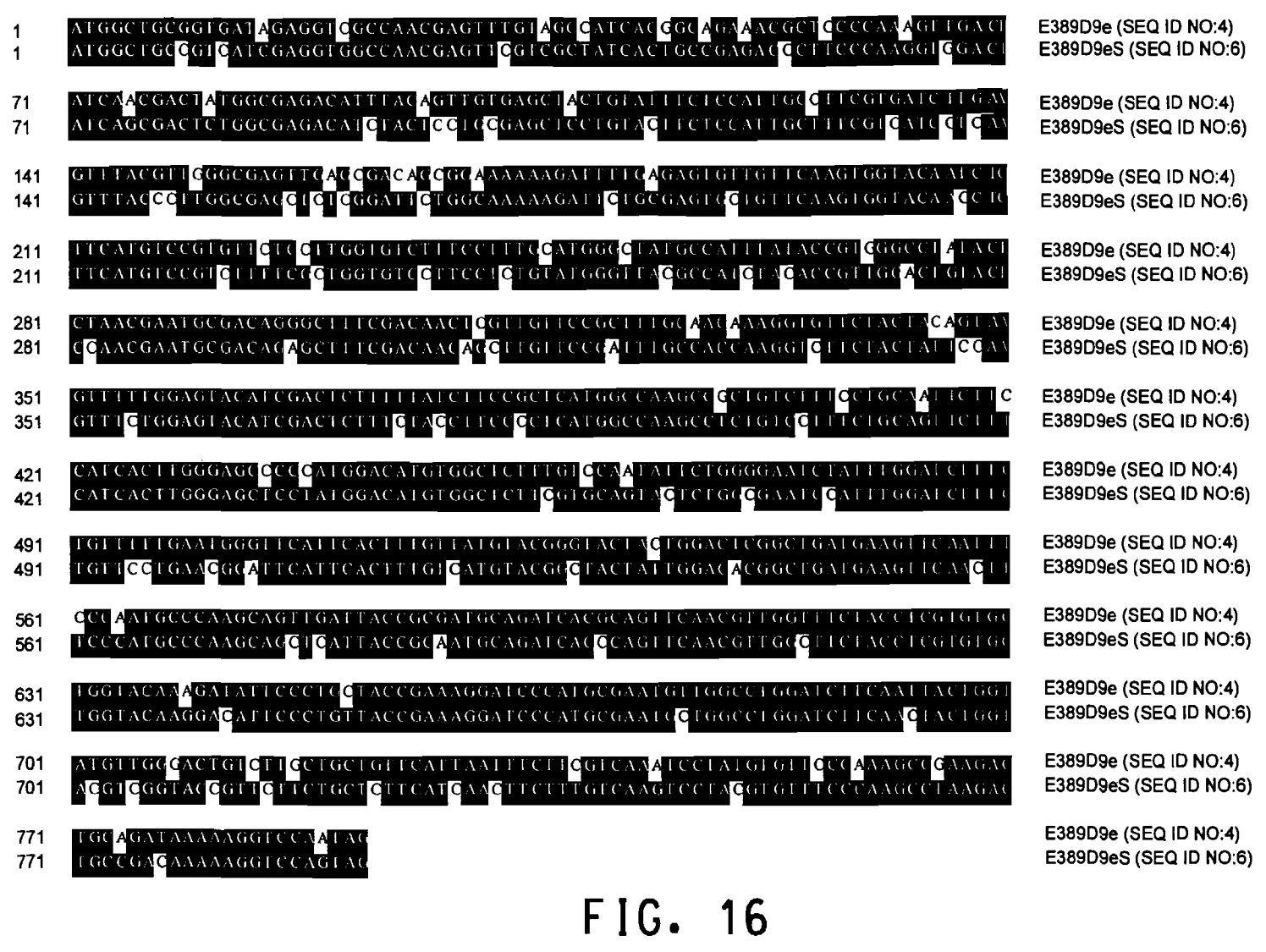

FIG. 16 shows a comparison of the DNA sequences of the *Eutreptiella* sp. CCMP389 Δ9 elongase gene (E389D9e; SEQ ID NO:4) and the synthetic gene (E389D9eS; SEQ ID NO:6) codon-optimized for expression in *Y. lipolytica*.

The invention can be more fully understood from the following detailed description and the accompanying drawings and Sequence Listing, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence Listing", and CRF. The disks contain the following file: CL3600_10.26.2006.ST25 having the following size: 483,000 bytes and which was created Nov. 15, 2006.

SEQ ID NOs:1-17, 21, 22, 45-48, 51-61, 68-71, 76-79, 81-93, 96-102 and 118-129 are ORFs encoding genes or proteins (or portions thereof), or plasmids, as identified in Table 2.

TABLE 2

Summary Of Nucleic Acid And Protein SEQ ID Numbers

| Description and Abbreviation | Nucleic acid SEQ ID NO. | Protein SEQ ID NO. |
|---|---|---|
| *Euglena gracilis* Δ9 elongase (EgD9e; clone eeg1c.pk001.n5.f)) | 1 (777 bp) | 2 (258 AA) |
| Synthetic Δ9 elongase, derived from *Euglena gracilis*, codon-optimized for expression in *Yarrowia lipolytica* (EgD9eS) | 3 (777 bp) | 2 (258 AA) |
| *Eutreptiella* sp. CCMP389 Δ9 elongase (E389D9e) | 4 (792 bp) | 5 (263 AA) |
| Synthetic Δ9 elongase, derived from *Eutreptiella* sp. CCMP389, codon-optimized for expression in *Yarrowia lipolytica* (E389D9eS) | 6 (792 bp) | 5 (263 AA) |
| *Isochrysis galbana* Δ9 elongase (IgD9e; NCBI Accession No. AAL37626 [GI17226123], locus AAL37626, CDS AF390174; GenBank Accession No. AF390174) (CDS = nucleotides 2-793) | 7 (1064 bp) | 8 (263 AA) |
| Synthetic Δ9 elongase, derived from *Isochrysis galbana*, codon-optimized for expression in *Yarrowia lipolytica* (IgD9eS) (equivalent to coding sequence of SEQ ID NOs: 51 and 50 in PCT Publication No. WO 2006/052870) | 9 (792 bp) | 8 (263 AA) |
| *Euglena gracilis* EgD9e - 5' sequence of the cDNA insert from clone eeg1c.pk001.n5.f. | 10 (757 bp) | — |
| *Euglena gracilis* EgD9e - 3' sequence of the cDNA insert from clone eeg1c.pk001.n5.f. | 11 (774 bp) | — |
| *Euglena gracilis* EgD9e - sequence aligned from SEQ ID NO: 10 and SEQ ID NO: 11 (full cDNA sequence excluding polyA tail) | 12 (1201 bp) | — |
| *Eutreptiella* sp. CCMP389 E389D9e - internal cDNA fragment | 13 (200 bp) | — |
| *Eutreptiella* sp. CCMP389 E389D9e - 5' cDNA fragment #1 | 14 (406 bp) | — |
| *Eutreptiella* sp. CCMP389 E389D9e - 5' cDNA fragment #2 | 15 (197 bp) | — |
| *Eutreptiella* sp. CCMP389 E389D9e - 3' cDNA fragment | 16 (920 bp) | — |

TABLE 2-continued

Summary Of Nucleic Acid And Protein SEQ ID Numbers

| Description and Abbreviation | Nucleic acid SEQ ID NO. | Protein SEQ ID NO. |
|---|---|---|
| *Eutreptiella* sp. CCMP389 E389D9e - complete assembled contig | 17 (1504 bp) | — |
| Plasmid pY119 | 21 (8306 bp) | — |
| Plasmid pDMW263 | 22 (9472 bp) | — |
| Plasmid pY115 | 45 (7783 bp) | — |
| Plasmid pDMW237 | 46 (7879 bp) | — |
| Plasmid pBY1 | 47 (8704 bp) | — |
| Plasmid pBY2 | 48 (8145 bp) | — |
| Plasmid pBY1-FAE | 51 (7877 bp) | — |
| Plasmid pZuFmEgD9E | 52 (7771 bp) | — |
| Plasmid pZuFmEgD9ES | 53 (7769 bp) | — |
| Plasmid pY120 | 54 (7769 bp) | — |
| Plasmid pKR72 | 55 (7085 bp) | — |
| Plasmid pKR912 | 56 (7873 bp) | — |
| Plasmid pKS102 | 57 (2540 bp) | — |
| Plasmid pKR197 | 58 (4359 bp) | — |
| Plasmid pKR911 | 59 (5147 bp) | — |
| *Euglena gracilis* Δ8 desaturase (EgD8) (equivalent to coding sequence of SEQ ID NOs: 1 and 2 in PCT Publications No. WO 2006/012325 and No. WO 2006/012326 [U52005-0287652-A1]) | 60 (1266 bp) | 61 (421 AA) |
| Synthetic Δ8 desaturase, derived from *Euglena gracilis*, codon-optimized for expression in *Yarrowia lipolytica* (EgD8S) (equivalent to SEQ ID NOs: 112 and 113 in PCT Publication No. WO 2006/012326) | 68 (1272 bp) | 69 (422 AA) |
| Plasmid pKS121 | 70 (4826 bp) | — |
| Plasmid pKR457 | 71 (5252 bp) | — |
| Plasmid pKR680 | 76 (6559 bp) | — |
| Plasmid pKR913 | 77 (9014 bp) | — |
| *Mortierella alpina* Δ5 desaturase | 78 (1482 bp) | 79 (446 AA) |
| Plasmid pKR767 | 81 (5561 bp) | — |
| Plasmid pKR328 | 82 (8671 bp) | — |
| Plasmid pKR886 | 83 (9892 bp) | — |
| Plasmid pKR886r | 84 (9892 bp) | — |
| Plasmid pKR271 | 85 (6021 bp) | — |
| Plasmid pKR226 | 86 (6524 bp) | — |
| Plasmid pKR275 | 87 (13,514 bp) | — |
| Plasmid pKR329 | 88 (12,323 bp) | — |
| Plasmid pKR585 | 89 (12,456 bp) | — |
| Plasmid pKR578 | 90 (9088 bp) | — |
| Plasmid pKR667 | 91 (10,309 bp) | — |
| Plasmid pKR873 | 92 (12,403 bp) | — |
| Plasmid pKR132 | 93 (3983 bp) | — |
| Plasmid pKR160 | 96 (4268 bp) | — |
| Plasmid pKR124 | 97 (4990 bp) | — |
| Plasmid pKR163 | 98 (3982 bp) | — |
| Plasmid pY34 | 99 (8878 bp) | — |
| Plasmid pKR863 | 100 (5207 bp) | — |
| Plasmid pKR869 | 101 (9035 bp) | — |
| Plasmid pKR270 | 102 (5108 bp) | — |
| Plasmid pFBAIN-MOD-1 | 118 (7222 bp) | — |
| Plasmid pFBAIN-389EIo | 119 (7779 bp) | — |
| Plasmid pE389S | 120 (3511 bp) | — |
| Plasmid pZUF17 | 121 (8165 bp) | — |
| Plasmid pZUFE389S | 122 (7879 bp) | — |
| Δ9 Elongase Motif #1 | — | 123 |
| Δ9 Elongase Motif #2 | — | 124 |
| Δ9 Elongase Motif #3 | — | 125 |
| Δ9 Elongase Motif #4 | — | 126 |
| Δ9 Elongase Motif #5 | — | 127 |
| Δ9 Elongase Motif #6 | — | 128 |
| Δ9 Elongase Motif #7 | — | 129 |

SEQ ID NO:18 is the M13F universal primer used for sequencing the *Euglena gracilis* cDNA library eeg1c.

SEQ ID NOs:19 and 20 correspond to primers oEugEL1-1 and oEugEL1-2, respectively, used for amplifying EgD9e from clone eeg1c.pk001.n5.f.

SEQ ID NOs:23-38 correspond to primers IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A and IL3-8B, respectively, used for amplification of IgD9eS.

SEQ ID NOs:39-42 correspond to primers IL3-1F, IL3-4R, IL3-5F and IL3-8R, respectively, used for amplification of IgD9eS.

SEQ ID NO:43 is the 417 bp NcoI/PstI fragment from pT9(1-4).

SEQ ID NO:44 is the 377 bp PstI/Not1 fragment from pT9(5-8).

SEQ ID NOs:49 and 50 correspond to primers ig-s and ig-as, respectively, used for amplifying IgD9eS from vector pY115.

SEQ ID NOs:62 and 63 correspond to primers Eg5-1 and Eg3-3, respectively, used for amplifying EgD8 from cDNA.

SEQ ID NOs:64-67 correspond to primers T7, M13-28Rev, Eg3-2 and Eg5-2, respectively, used for sequencing EgD8.

SEQ ID NO:72 is the sequence of the KTi cassette 5' end multiple cloning site (MCS) for pKR457.

SEQ ID NO:73 is the sequence of the KTi cassette 3' end multiple cloning site (MCS) for pKR457 including the soy albumin transcription 3' terminator.

SEQ ID NOs:74 and 75 correspond to primers oSalb-12 and oSalb-13, respectively, used for amplifying the soy albumin transcription terminator from soy genomic DNA.

SEQ ID NO:80 corresponds to restriction sites added to pKR287 to produce pKR767.

SEQ ID NOs:94 and 95 correspond to primers oSAlb-9 and oSAlb-2, respectively, used for creation of restriction sites during production of pKR160.

SEQ ID NOs:103-105 correspond to SMART™ IV oligonucleotide primer, CDSIII/3' PCR primer and 5'-PCR primer, respectively, used for *Eutreptiella* sp. CCMP389 cDNA synthesis.

SEQ ID NO:106 is the nucleotide sequence of degenerate primer EuEF3, which encodes the peptide set forth in SEQ ID NO:107. Similarly, SEQ ID NO:108 is the nucleotide sequence of degenerate primer EuER3, which encodes the peptide set forth in SEQ ID NO:109.

SEQ ID NOs:110-113 correspond to primers 389Elo-5-1, 389Elo-5-2, DNR CDS 5'-2 and 389Elo-5-4, respectively, used for PCR amplification of the 5'-end of cDNA encoding E389D9e.

SEQ ID NOs:114 and 115 correspond to primers 389Elo-3-1 and 389Elo-3-2, respectively, used for PCR amplification of the 3'-end of cDNA encoding E389D9e.

SEQ ID NOs:116 and 117 correspond to primers 389ELO-F and 389ELO-R1, respectively, used for amplification of the full length cDNA encoding E389D9e.

DETAILED DESCRIPTION OF THE INVENTION

All patents, patent applications, and publications cited herein are incorporated by reference in their entirety. This specifically includes the following commonly owned and copending applications: U.S. patent application Ser. No. 10/840,478, Ser. No. 10/840,579 and Ser. No. 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,109 and Ser. No. 10/985,691 (filed Nov. 10, 2004), U.S. patent application Ser. No. 10/987,548 (filed Nov. 12, 2004), U.S. patent application Ser. No. 11/024,545 and Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/251,466 (filed Oct. 14, 2005), U.S. patent application Ser. No. 11/254,173 and No. 11/253,882 (filed Oct. 19, 2005), U.S. patent application Ser. No. 11/264,784 and No. 11/264,737 (filed Nov. 1, 2005), U.S. patent application Ser. No. 11/265,761 (filed Nov. 2, 2005), U.S. Patent Application No. 60/739,989 (filed Nov. 23, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. Patent Application No. 60/801,172 (filed May 17, 2006), U.S. Patent Application No. 60/801,119 (filed May 17, 2006), U.S. Patent Application No. 60/853,563 (filed Oct. 23, 2006), U.S. Patent Application No. 60/855,177 (filed Oct. 30, 2006). This additionally includes the following commonly owned and copending applications: U.S. patent application Ser. No. 10/776,311, concerning the production of PUFAs in plants; and, U.S. patent application Ser. No. 10/776,889, concerning annexin promoters and their use in expression of transgenes in plants.

The invention provides novel *Euglena gracilis* and *Eutreptiella* sp. CCMP389 Δ9 elongase enzymes and genes encoding the same that may be used for the manipulation of biochemical pathways for the production of healthful PUFAs.

PUFAs, or derivatives thereof, made by the methodology disclosed herein can be used as dietary substitutes, or supplements and infant formulas, and for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Definitions

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is the number of carbon (C) atoms in the particular fatty acid and Y is the number of double bonds. The number following the fatty acid designation indicates the position of the double bond from the carboxyl end of the fatty acid with the "c" affix for the cis-configuration of the double bond [e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)]. Unless otherwise specified 18:1, 18:2 and 18:3 refer to oleic, LA and ALA fatty acids. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 3. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and each compounds' chemical name.

TABLE 3

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| Gamma-linolenic | GLA | cis-6,9,12-octadecatrienoic | 18:3 ω-6 |
| Eicosadienoic | EDA | cis-11,14-eicosadienoic | 20:2 ω-6 |
| Dihomo-gamma-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| Alpha-linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Juniperonic | JUP | cis-5,11,14,17-eicosatrienoic | 20:4b ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,6,19-docosahexaenoic | 22:6 ω-3 |

The term "essential fatty acid" refers to a particular PUFA that an organism must ingest in order to survive, being unable to synthesize the particular essential fatty acid de novo. For example, mammals can not synthesize the essential fatty acid LA. Other essential fatty acids include, but are not limited to, GLA, DGLA, ARA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publications No. WO 2005/003322 and No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
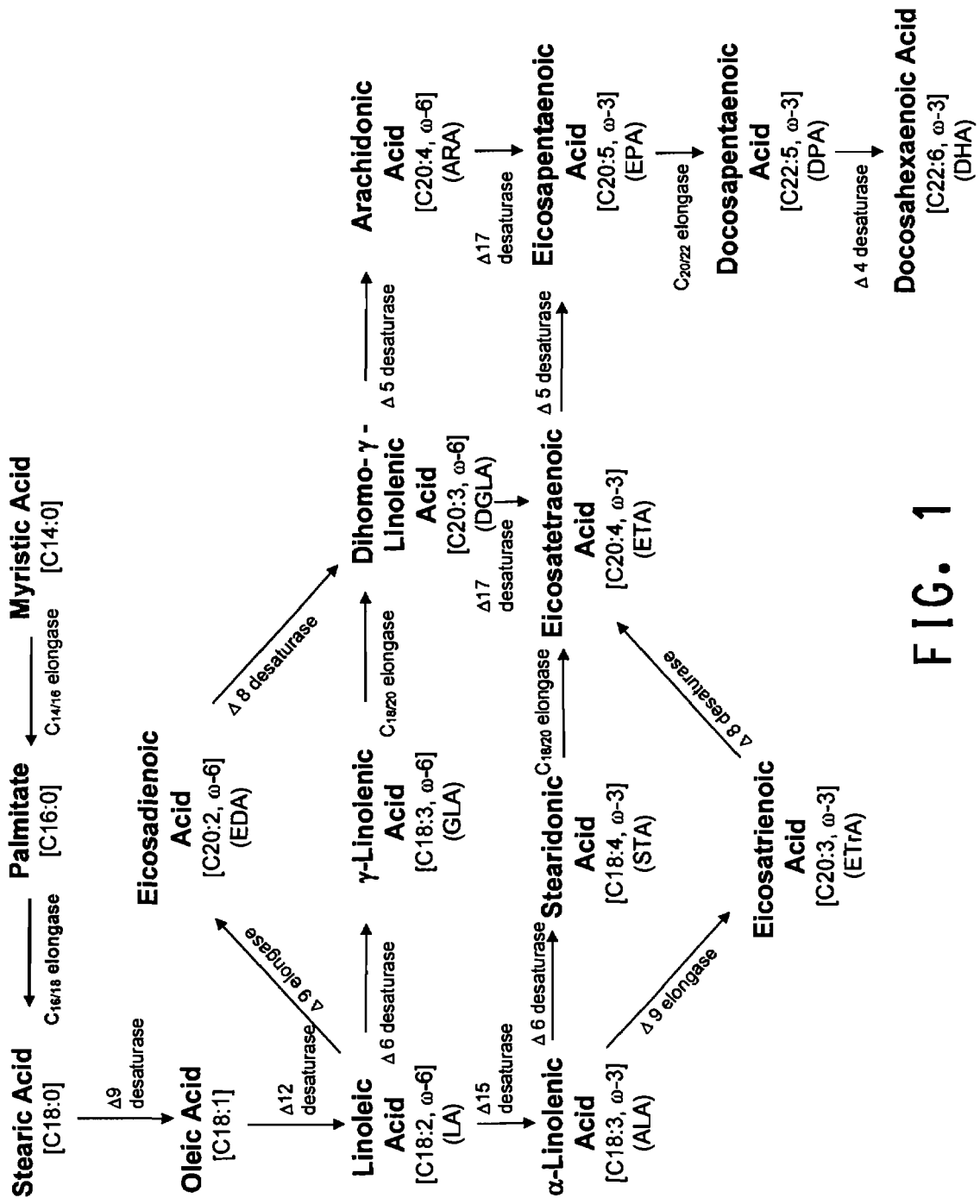

The term "omega-3/omega-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids.

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all of the PUFA biosynthetic pathway enzyme genes are required, as a number of fatty acid products will only require the expression of a subset of the genes of this pathway.

The term "Δ9 elongase/Δ8 desaturase pathway" refers to a biosynthetic pathway for production of long-chain PUFAs. This pathway, at a minimum, comprises a Δ9 elongase and a Δ8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Desaturases of interest include, for example: (1) Δ8 desaturases that will desaturate a fatty acid between the eighth and ninth carbon atom numbered from the carboxyl-terminal end of the molecule and that can, for example, catalyze the conversion of EDA to DGLA and/or ETrA to ETA; (2) Δ5 desaturases that catalyze the conversion of DGLA to ARA and/or ETA to EPA; (3) Δ6 desaturases that catalyze the conversion of LA to GLA and/or ALA to STA; (4) Δ4 desaturases that catalyze the conversion of DPA to DHA; (5) Δ12 desaturases that catalyze the conversion of oleic acid to LA; (6) Δ15 desaturases that catalyze the conversion of LA to ALA and/or GLA to STA; (7) Δ17 desaturases that catalyze the conversion of ARA to EPA and/or DGLA to ETA; and (8) Δ9 desaturases that catalyze the conversion of palmitate to palmitoleic acid (16:1) and/or stearate to oleic acid (18:1). In the art, Δ15 and Δ17 desaturases are also occasionally referred to as "omega-3 desaturases", "ω-3 desaturases", and/or "ω-3 desaturases", based on their ability to convert ω-6 fatty acids into their ω-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "EgD8" refers to a Δ8 desaturase enzyme (SEQ ID NO:61) isolated from *Euglena gracilis*, encoded by SEQ ID NO:60 herein. EgD8 is 100% identical and functionally equivalent to "Eg5", as described in PCT Publications No. WO 2006/012325 and No. WO 2006/012326 [SEQ ID NO:2 of U.S. Publication No. 2005-0287652-A1].

Similarly, the term "EgD8S" refers to a synthetic Δ8 desaturase derived from *Euglena gracilis* that is codon-optimized for expression in *Yarrowia lipolytica* herein (i.e., SEQ ID NOs:68 and 69). EgD8S is 100% identical and functionally equivalent to "D8SF", as described in PCT Publications No. WO 2006/012325 and No. WO 2006/012326.

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell*, 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example: a $C_{14/16}$ elongase will utilize a $C_{14}$ substrate (e.g., myristic acid); a $C_{16/18}$ elongase will utilize a $C_{16}$ substrate (e.g., palmitate); a $C_{18/20}$ elongase (also known as a Δ6 elongase as the terms can be used interchangeably) will utilize a $C_{18}$ substrate (e.g., GLA, STA); and a $C_{20/22}$ elongase will utilize a $C_{20}$ substrate (e.g., EPA). In like manner, and of particular interest herein, a "Δ9 elongase" is able to catalyze the conversion of LA and ALA to EDA and ETrA, respectively. It is important to note that some elongases have broad specificity and thus a single enzyme may be capable of catalyzing several elongase reactions. Thus, for example, a Δ9 elongase may also act as a $C_{16/18}$ elongase, $C_{18/20}$ elongase and/or $C_{20/22}$ elongase and may have alternate, but not preferred, specificities for Δ5 and Δ6 fatty acids such as EPA and/or GLA, respectively. In preferred embodiments, it is desirable to empirically determine the specificity of a fatty acid elongase by transforming a suitable host with the gene for the fatty acid elongase and determining its effect on the fatty acid profile of the host.

For the purposes herein, the term "EgD9e" refers to a Δ9 elongase enzyme (SEQ ID NO:2) isolated from *Euglena gracilis* encoded by SEQ ID NO:1. In contrast, the term "EgD9eS" refers to a synthetic Δ9 elongase derived from *Euglena gracilis* that is codon-optimized for expression in *Yarrowia lipolytica* (i.e., SEQ ID NOs:3 and 2).

The term "E389D9e" refers to a Δ9 elongase enzyme (SEQ ID NO:5) isolated from *Eutreptiella* sp. CCMP389, encoded by SEQ ID NO:4. In contrast, the term "E389D9eS" refers to a synthetic Δ9 elongase derived from *Eutreptiella* sp. CCMP389 that is codon-optimized for expression in *Yarrowia lipolytica* (i.e., SEQ ID NOs:6 and 5).

The term "IgD9e" refers to a Δ9 elongase enzyme (SEQ ID NO:8; NCBI Accession No. AAL37626 [GI 17226123], locus AAL37626, CDS AF390174; GenBank Accession No. AF390174) isolated from *Isochrysis galbana*, encoded by SEQ ID NO:7. In contrast, the term "IgD9eS" refers to a synthetic Δ9 elongase derived from *Isochrysis galbana* that is codon-optimized for expression in *Yarrowia lipolytica* (i.e., SEQ ID NOs:9 and 8). Synthesis and functional analysis of IgD9eS is described in PCT Publication No. WO 2006/052870 (wherein IgD9eS is equivalent to SEQ ID NOs:51 and 50 therein).

The term "amino acid" will refer to the basic chemical structural unit of a protein or polypeptide. Amino acids are identified by either the one-letter code or the three-letter codes for amino acids, in conformity with the IUPAC-IYUB standards described in *Nucleic Acids Research*, 13:3021-3030 (1985) and in the *Biochemical Journal*, 219 (2):345-373 (1984), which are herein incorporated by reference.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: His [H], Arg [R], Lys [K];
4. Large aliphatic, nonpolar residues: Met [M], Leu [L], Ile [I], Val M (Cys [C]); and,
5. Large aromatic residues: Phe [F], Tyr [Y], Trp [W].

Conservative amino acid substitutions generally maintain: 1.) the structure of the polypeptide backbone in the area of the substitution; 2.) the charge or hydrophobicity of the molecule at the target site; or 3.) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1.) a hydrophilic residue is substituted for/by a hydrophobic residue (e.g., Ser or Thr for/by Leu, Ile, Val); 2.) a Cys or Pro is substituted for/by any other residue; 3.) a residue having an electropositive side chain is substituted for/by an electronegative residue (e.g., Lys, Arg or His for/by Asp or Glu); or, 4.) a residue having a bulky side chain is substituted for/by one not having a side chain (e.g., Phe for/by Gly). Sometimes, non-conservative amino acid substitutions between two of the five groups will not affect the activity of the encoded protein.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. For the purposes herein, the following Table describes motifs of the present invention which are indicative of a protein having Δ9 elongase activity.

TABLE 4

Summary Of Δ9 Elongase Motifs

| Description | Sequence | Protein SEQ ID NO. |
|---|---|---|
| Δ9 Elongase Motif #1 | Y N X (L or F) X X X X S X X S F | 123 |
| Δ9 Elongase Motif #2 | F Y X S K X X (E or D) Y X D (T or S) X X L | 124 |
| Δ9 Elongase Motif #3 | L (Q or H) X F H H X G A | 125 |
| Δ9 Elongase Motif #4 | M Y X Y Y X X X X X X X (K or R or N) F | 126 |
| Δ9 Elongase Motif #5 | K X L (I or L or M) T X X Q | 127 |
| Δ9 Elongase Motif #6 | W X F N Y X Y | 128 |
| Δ9 Elongase Motif #7 | Y X G X V X X L F | 129 |

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Other exemplary stringent hybridization conditions include 0.1×SSC, 0.1% SDS, 65° C. and washed with 2×SSC, 0.1% SDS followed by 0.1×SSC, 0.1% SDS.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.*, 138:267-284 (1984): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*, 5:151-153 (1989); Higgins, D. G. et al., *Comput. Appl. Biosci.*, 8:189-191 (1992)) and found in the MegAlign™ program of the LASERGENE bioinformatics computing suite (supra). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

The term "genome" as it applies to a plant cells encompasses not only chromosomal DNA found within the nucleus, but organelle DNA found within subcellular components (e.g., mitochondrial, plastid) of the cell.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants*, 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.*, 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell*, 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementary of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described below.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.).

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus it is preferable if multiple events are screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acids, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on over-expression of a nucleic acid sequence having homology to an endogenous mRNA, in the sense orientation, which results in the reduction of all RNA having homology to the overex-pressed sequence (Vaucheret et al., *Plant J.*, 16:651-659 (1998); Gura, *Nature*, 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050; PCT Publication No. WO 02/00904). This increases the frequency of co-suppression in the recovered transgenic plants. Another variation describes the use of plant viral sequences to direct the suppression, or "silencing", of proximal mRNA encoding sequences (PCT Publication No. WO 98/36083). Both of these co-suppressing phenomena have not been elucidated mechanistically, although genetic evidence has begun to unravel this complex situation (Elmayan et al., *Plant Cell,* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). A class of plants identified as oleaginous are commonly referred to as "oilseed" plants. Examples of oilseed plants include, but are not limited to: soybean (*Glycine* and *Soja* sp.), flax (*Linum* sp.), rapeseed (*Brassica* sp.), maize, cotton, safflower (*Carthamus* sp.) and sunflower (*Helianthus* sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Eutreptiella, Euglena* and *Tetruetreptia.*

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long-chain $\omega$-3/$\omega$-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific $\omega$-3/$\omega$-6 fatty acid.

Specifically, all pathways require the initial conversion of oleic acid to LA, the first of the $\omega$-6 fatty acids, by a $\Delta 12$ desaturase. Then, using the "$\Delta 9$ elongase/$\Delta 8$ desaturase pathway", long-chain $\omega$-6 fatty acids are formed as follows: (1) LA is converted to EDA by a $\Delta 9$ elongase; (2) EDA is converted to DGLA by a $\Delta 8$ desaturase; and (3) DGLA is converted to ARA by a $\Delta 5$ desaturase. Alternatively, the "$\Delta 9$ elongase/$\Delta 8$ desaturase pathway" can be utilized for formation of long-chain $\omega$-3 fatty acids as follows: (1) LA is converted to ALA, the first of the $\omega$-3 fatty acids, by a $\Delta 15$ desaturase; (2) ALA is converted to ETrA by a $\Delta 9$ elongase; (3) ETrA is converted to ETA by a $\Delta 8$ desaturase; (4) ETA is converted to EPA by a $\Delta 5$ desaturase; (5) EPA is converted to DPA by a $C_{20/22}$ elongase; and (6) DPA is converted to DHA by a $\Delta 4$ desaturase. Optionally, $\omega$-6 fatty acids may be converted to $\omega$-3 fatty acids; for example, ETA and EPA are produced from DGLA and ARA, respectively, by $\Delta 17$ desaturase activity.

Alternate pathways for the biosynthesis of $\omega$-3/$\omega$-6 fatty acids utilize a $\Delta 6$ desaturase and $C_{18/20}$ elongase (i.e., the "$\Delta 6$ desaturase/$\Delta 6$ elongase pathway"). More specifically, LA and ALA may be converted to GLA and STA, respectively, by a $\Delta 6$ desaturase; then, a $C_{18/20}$ elongase converts GLA to DGLA and/or STA to ETA.

It is contemplated that the particular functionalities required to be introduced into a specific host organism for production of a $\omega$-3/$\omega$-6 fatty acids will depend on the host cell (and its native PUFA profile and/or desaturase/elongase profile), the availability of substrate, and the desired end product(s). For example, expression of the $\Delta 9$ elongase/$\Delta 8$ desaturase pathway may be preferred in some embodiments, as opposed to expression of the Δ6 desaturase/Δ6 elongase pathway, since PUFAs produced via the former pathway are devoid of GLA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., Δ6 desaturases, $C_{18/20}$ elongases, Δ5 desaturases, Δ117 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Δ9 Elongases

In the present invention, nucleotide sequences encoding Δ9 elongases have been isolated from *Euglena gracilis* (designated herein as "EgD9e") and *Eutreptiella* sp. CCMP389 (designated herein as "E389D9e").

Comparison of the EgD9e nucleotide base and deduced amino acid sequences to public databases reveals that the most similar known sequences (i.e., IgD9e) are about 31.8% identical to the amino acid sequence of EgD9e reported herein over a length of 258 amino acids using a Clustal V analysis.

Comparison of the E389D9e nucleotide base and deduced amino acid sequences to public databases reveals that the most similar known sequences (i.e., IgD9e) are about 33.1% identical to the amino acid sequence of E389D9e reported herein over a length of 263 amino acids using a Clustal V analysis.

For reference, comparison of the novel EgD9e and E389D9e protein sequences described herein as SEQ ID NO:2 and SEQ ID NO:5 share 65.1% identity using a Clustal V analysis.

Within the context of the present invention preferred amino acid fragments are at least about 70%-85% identical to the EgD9e and E389D9e sequences herein, where those sequences that are at least about 85%-90% identical are particularly suitable and those sequences that are at least about 90%-95% identical are most preferred. Preferred EgD9e and E389D9e encoding nucleic acid sequences corresponding to the instant ORFs are those encoding active proteins and which are at least about 70%-85% identical to the nucleic acid sequences of EgD9e and E389D9e reported herein, respectively, where those sequences that are at least 85%-90% identical are particularly suitable and those sequences that are at least about 90%-95% identical are most preferred.

In alternate embodiments, the instant EgD9e and E389D9e sequences can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In one preferred embodiment of the invention, EgD9e and E389D9e were codon-optimized for expression in *Yarrowia lipolytica*. This was possible by first determining the *Y. lipolytica* codon usage profile (see PCT Publication No. WO 04/101757) and identifying those codons that were preferred. Further optimization of gene expression in *Y. lipolytica* was achieved by determining the consensus sequence around the 'ATG' initiation codon.

Optimization of EgD9e resulted in modification of 117 bp of the 777 bp coding region (15.1%) and optimization of 106 codons. None of the modifications in the codon-optimized gene ("EgD9eS"; SEQ ID NO:3) changed the amino acid sequence of the encoded protein (SEQ ID NO:2). As described in Example 8, the codon-optimized gene was about 16.2% more efficient elongating LA to EDA than the wild-type EgD9e gene, when expressed in *Y. lipolytica*.

Similarly, optimization of E389D9e resulted in modification of 128 bp of the 792 bp coding region (16.2%) and optimization of 113 codons. None of the modifications in the codon-optimized gene ("E389D9eS"; SEQ ID NO:6) changed the amino acid sequence of the encoded protein (SEQ ID NO:5). As described in Example 24, the codon-optimized gene elongated LA to EDA with similar efficiency as the wildtype gene, when expressed in *Y. lipolytica*.

Thus, the present invention concerns an isolated polynucleotide sequence encoding a polypeptide having Δ9 elongase activity, selected from the group consisting of:

(a) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);

(b) an isolated nucleic acid sequence comprising a nucleotide sequence encoding a polypeptide having Δ9 elongase activity, wherein the nucleotide sequence has at least 70% sequence identity, based on the BLASTN method of alignment, when compared to a nucleotide sequence as set forth in SEQ ID NO:1 (EgD9e), SEQ ID NO:3 (EgD9eS), SEQ ID NO:4 (E389D9e) or SEQ ID NO:6 (E389D9eS); and (c) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1×SSC, 0.1% SDS; and, (d) a complement of the nucleotide sequence of (a), (b) or (c), wherein the complement and the nucleotide sequence consist of the same number of nucleotides and are 100% complementary.

One skilled in the art would be able to use the teachings herein to create various other codon-optimized Δ9 elongase proteins suitable for optimal expression in alternate hosts (i.e., other than *Yarrowia lipolytica*), based on the wildtype EgD9e and/or E389D9e sequence. This alternate host organism may include, but is not limited to, a plant or plant part. Accordingly, the instant invention relates to any codon-optimized Δ9 elongase protein that is derived from either the wildtype EgD9e (i.e., encoded by SEQ ID NO:2) or the wildtype E389D9e (i.e., encoded by SEQ ID NO:5). This includes, but is not limited to: the nucleotide sequence set forth in SEQ ID NO:3 (which encodes a synthetic Δ9 elongase protein (i.e., EgD9eS)) and the nucleotide sequence set forth in SEQ ID NO:6 (which encodes a synthetic Δ9 elongase protein (i.e., E389D9eS)), both of which were codon-optimized for expression in *Yarrowia lipolytica*.

In another aspect this invention concerns an isolated nucleic acid fragment comprising a nucleic acid sequence encoding a Δ9 elongase, excluding SEQ ID NO:8 (i.e., "IgD9e", the Δ9 elongase from *Isochrysis galbana* (NCBI Accession No. AAL37626 (GI 17226123)), wherein the amino acid sequence comprising said Δ9 elongase contains at least one of the following amino acid sequence motifs selected from the group consisting of:

a) Y N X (L or F) X X X X S X X S F;  (SEQ ID NO: 123)

b) F Y X S K X X (E or D) Y X D (T or S) X X L;  (SEQ ID NO: 124)

c) L (Q or H) X F H H X G A;  (SEQ ID NO: 125)

d) M Y X Y Y X X X X X X (K or R or N) F;  (SEQ ID NO: 126)

e) K X L (I or L or M) T X X Q;  (SEQ ID NO: 127)

f) W X F N Y X Y;  (SEQ ID NO: 128)
and g) Y X G X V X X L F;  (SEQ ID NO: 129)

wherein X can be any amino acid.

Figure 2:
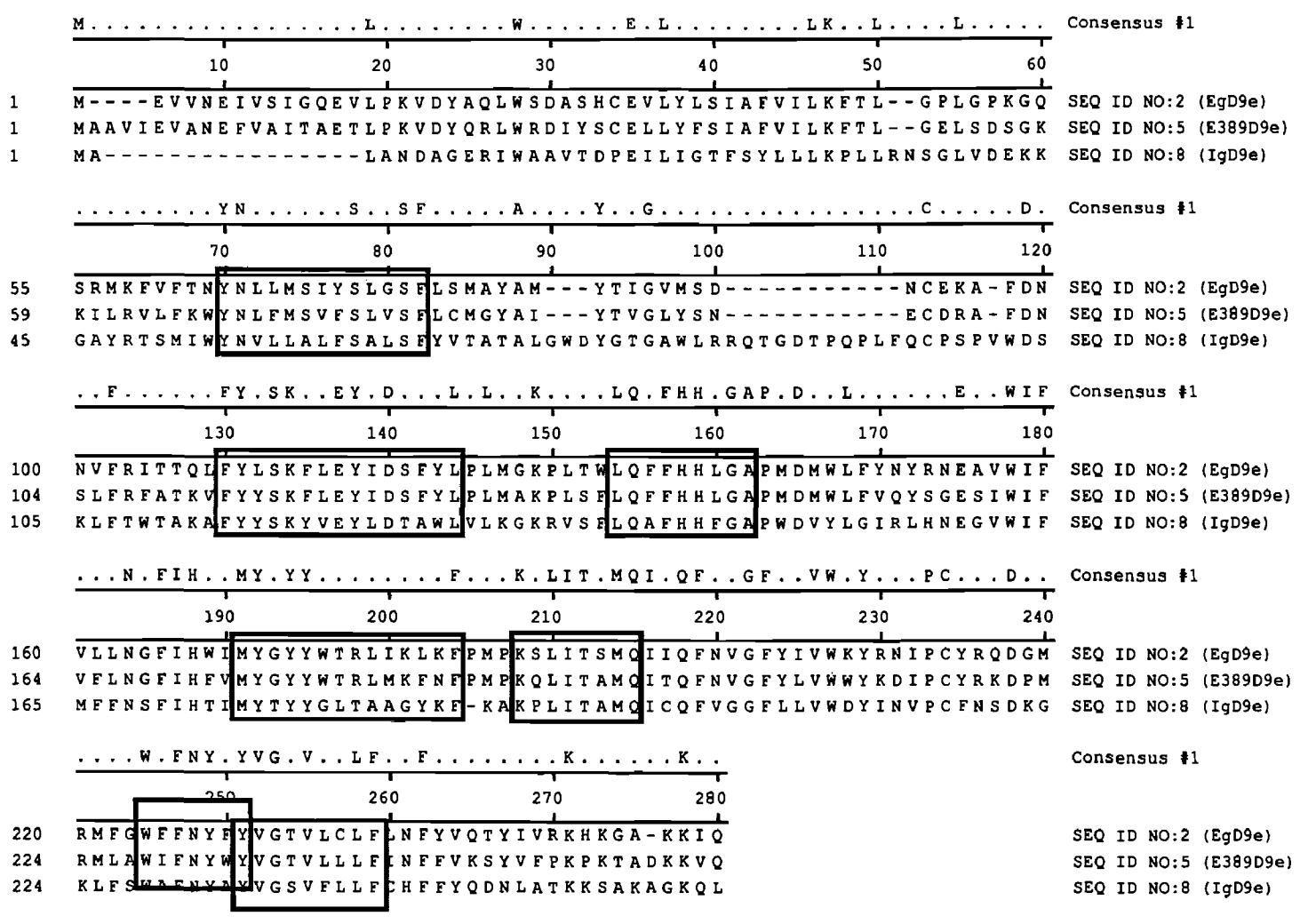

The underlined amino acids may be unique to Δ9 elongases. FIG. 2 sets forth a comparison of the Δ9 elongases of the present invention with a Δ9 elongase from *Isochrysis galbana* using a Clustal V alignment (with default parameters). Specifically, SEQ ID NO:2 (EgD9e), SEQ ID NO:5 (E389D9e) and SEQ ID NO:8 (IgD9e) were compared. Regions comprising the motifs of the invention are shown in boxes.

Identification and Isolation of Homologs

Any of the instant elongase sequences (i.e., EgD9e, EgD9eS, E389D9e, E389D9eS) or portions thereof may be used to search for Δ9 elongase homologs in the same or other bacterial, algal, fungal, euglenoid or plant species using sequence analysis software. In general, such computer software matches similar sequences by assigning degrees of homology to various substitutions, deletions and other modifications.

Alternatively, any of the instant elongase sequences or portions thereof may also be employed as hybridization reagents for the identification of Δ9 elongase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ9 elongase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA,* 82:1074 (1985); or strand displacement amplification (SDA), Walker, et al., *Proc. Natl. Acad. Sci. USA,* 89:392 (1992)]; and 3.) methods of library construction and screening by complementation.

For example, genes encoding similar proteins or polypeptides to the Δ9 elongases described herein could be isolated directly by using all or a portion of the instant nucleic acid fragments as DNA hybridization probes to screen libraries from e.g., any desired yeast or fungus using methodology well known to those skilled in the art (wherein those organisms producing EDA and/or ETrA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach,* K. E. Davis Ed., (1986) pp 33-50, IRL: Herndon, V A; and Rychlik, W., In *Methods in Molecular Biology,* White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA,* 86:5673 (1989); Loh et al., *Science,* 243:217 (1989)).

In other embodiments, any of the Δ9 elongase nucleic acid fragments described herein (or any homologs identified thereof) may be used for creation of new and improved fatty acid elongases. As is well known in the art, in vitro mutagenesis and selection, chemical mutagenesis, "gene shuffling" methods or other means can be employed to obtain mutations of naturally occurring elongase genes (wherein such mutations may include deletions, insertions and point mutations, or combinations thereof). This would permit production of a polypeptide having elongase activity, respectively, in vivo with more desirable physical and kinetic parameters for function in the host cell such as a longer half-life or a higher rate of production of a desired PUFA. Or, if desired, the regions of a polypeptide of interest (i.e., a Δ9 elongase) important for enzymatic activity can be determined through routine mutagenesis, expression of the resulting mutant polypeptides and determination of their activities. An overview of these techniques is described in PCT Publication No. WO 2004/101757. All such mutant proteins and nucleotide sequences encoding them that are derived from EgD9e, EgD9eS, E389D9e and E389D9eS are within the scope of the present invention.

Alternatively, improved fatty acids may be synthesized by domain swapping, wherein a functional domain from any of the Δ9 elongase nucleic acid fragments described herein are exchanged with a functional domain in an alternate elongase gene to thereby result in a novel protein.

Methods for Production of Various ω-3 and/or ω-6 Fatty Acids

It is expected that introduction of chimeric genes encoding the Δ9 elongases described herein (i.e., EgD9e, EgD9eS, E389D9e, E389D9eS or other mutant enzymes, codon-optimized enzymes or homologs thereof), under the control of the appropriate promoters will result in increased production of EDA and/or ETrA in the transformed host organism, respectively. As such, the present invention encompasses a method for the direct production of PUFAs comprising exposing a fatty acid substrate (i.e., LA and/or ALA) to the elongase enzymes described herein (e.g., EgD9e, EgD9eS, E389D9e, E389D9eS), such that the substrate is converted to the desired fatty acid product (i.e., EDA and/or ETrA).

More specifically, it is an object of the present invention to provide a method for the production of EDA in a host cell (e.g., oleaginous yeast, soybean), wherein the host cell comprises:

a) an isolated polynucleotide sequence encoding a polypeptide having Δ9 elongase activity, selected from the group consisting of:
(1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);

(2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1× SSC, 0.1% SDS; and b) a source of LA;

wherein the host cell is grown under conditions such that the Δ9 elongase is expressed and the LA is converted to EDA, and wherein the EDA is optionally recovered.

In alternate embodiments of the present invention, the Δ9 elongase may be used for the conversion of ALA to ETrA. Accordingly the invention provides a method for the production of ETrA, wherein the host cell comprises:

a) an isolated polynucleotide sequence encoding a polypeptide having Δ9 elongase activity, selected from the group consisting of:

(1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);

(2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1× SSC, 0.1% SDS; and b) a source of ALA;

wherein the host cell is grown under conditions such that the Δ9 elongase is expressed and the ALA is converted to ETrA, and wherein the ETrA is optionally recovered.

Alternatively, each Δ9 elongase gene and its corresponding enzyme product described herein can be used indirectly for the production of various ω-6 and ω-3 PUFAs, including e.g., DGLA, ETA, ARA, EPA, DPA and/or DHA (FIG. 1; see PCT Publication No. WO 2004/101757). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ9 elongases described herein (e.g., EgD9e, EgD9eS, E389D9e, E389D9eS or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ15 desaturases, Δ9 desaturases, Δ12 desaturases, $C_{14/16}$ elongases, $C_{16/18}$ elongases, Δ5 desaturases, Δ8 desaturases, Δ4 desaturases, $C_{20/22}$ elongases) to result in higher levels of production of longer-chain ω-3/ω-6 fatty acids (e.g., ARA, EPA, DPA and DHA).

In preferred embodiments, the Δ9 elongases of the present invention will minimally be expressed in conjunction with a Δ8 desaturase (e.g., a Δ8 desaturase as set forth in SEQ ID NO:61 [EgD8] or a codon-optimized Δ8 desaturase as set forth in SEQ ID NO:69 [EgD8S]). However, the particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ9 elongase, based on the complete sequences described herein, the complement of those complete sequences, substantial portions of those sequences, codon-optimized elongases derived therefrom and those sequences that are substantially homologous thereto.

Plant Expression Systems, Cassettes & Vectors, and Transformation

In one embodiment, this invention concerns a recombinant construct comprising any one of the Δ9 elongase polynucleotides of the invention operably linked to at least one regulatory sequence suitable for expression in a plant.

A promoter is a DNA sequence that directs the cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the Δ9 elongase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the α-prime subunit of β-conglycinin promoter, the Kunitz trypsin inhibitor 3 promoter, the annexin promoter, the Gly1 promoter, the beta subunit of beta-conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.*, 37:275-285 (1998); Battraw and Hall, *Plant Mol. Biol.*, 15:527-538 (1990); Holtorf et al., *Plant Mol. Biol.*, 29:637-646 (1995); Jefferson et al., *EMBO J.*, 6:3901-3907 (1987); Wilmink et al., *Plant Mol. Biol.*, 28:949-955 (1995)); (2) the *Arabidopsis* oleosin promoters (Plant et al., *Plant Mol. Biol.*, 25:193-205 (1994); Li, Texas A&M University Ph.D. dissertation, pp. 107-128 (1997)); (3) the *Arabidopsis* ubiquitin extension protein promoters (Callis et al., *J. Biol. Chem.*, 265(21):12486-93 (1990)); (4) a tomato ubiquitin gene promoter (Rollfinke et al., *Gene*, 211 (2):267-76 (1998)); (5) a soybean heat shock protein promoter (Schoffl et al., *Mol. Gen. Genet.*, 217(2-3): 246-53 (1989)); and, (6) a maize H3 histone gene promoter (Atanassova et al., *Plant Mol. Biol.*, 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.*, 10:112-122 (1989); Ellerstrom et al., *Plant Mol. Biol.*, 32:1019-1027 (1996); Keddie et al., *Plant Mol. Biol.*, 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific Δ9 elongase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual*; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*, John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: 1.) the entire complement of genetic material (genes and non-coding sequences) that is present in each cell of an organism, or virus or organelle; and/or 2.) a complete set of chromosomes inherited as a (haploid) unit from one parent.

Thus, this invention also concerns a method for transforming a cell, comprising transforming a cell with a recombinant construct of the invention and selecting those cells transformed with said recombinant construct.

Also of interest is a method for producing a transformed plant comprising transforming a plant cell with the Δ9 elongase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. Nos. 5,004,863; 5,159,135); soybean (U.S. Pat. Nos. 5,569,834; 5,416,011); *Brassica* (U.S. Pat. No. 5,463,174); peanut (Cheng et al., *Plant Cell Rep.*, 15:653-657 (1996); McKently et al., *Plant Cell Rep.*, 14:699-703 (1995)); papaya (Ling, K. et al., *Bio/technology*, 9:752-758 (1991)); and pea (Grant et al., *Plant Cell Rep.*, 15:254-258 (1995)). For a review of other commonly used methods of plant transformation see Newell, C. A. (*Mol. Biotechnol.*, 16:53-65 (2000)). One of these methods of transformation uses *Agrobacterium rhizogenes* (Tepfler, M. and Casse-Delbart, F., *Microbiol. Sci.*, 4:24-28 (1987)). Transformation of soybeans using direct delivery of DNA has been published using PEG fusion (PCT Publication No. WO 92/17598), electroporation (Chowrira, G. M. et al., *Mol. Biotechnol.*, 3:17-23 (1995); Christou, P. et al., *Proc. Natl. Acad. Sci. USA*, 84:3962-3966 (1987)), microinjection, or particle bombardment (McCabe, D. E. et al., *Bio/Technology*, 6:923 (1988); Christou et al., *Plant Physiol.*, 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and five or more carbon-carbon double bonds include, but are not limited to, ω-3 fatty acids such as EPA, DPA and DHA. Seeds obtained from such plants are also within the scope of this invention, as well as oil obtained from such seeds.

Thus, in one embodiment this invention concerns an oilseed plant comprising:
  a) a first recombinant DNA construct comprising an isolated polynucleotide encoding a Δ9 elongase polypeptide, operably linked to at least one regulatory sequence; and,
  b) at least one additional recombinant DNA construct comprising an isolated polynucleotide, operably linked to at least one regulatory sequence, encoding a polypeptide selected from the group consisting of: a Δ4 desaturase, a Δ5 desaturase, a Δ6 desaturase, a Δ8 desaturase, a Δ9 desaturase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase.

Such additional desaturases are discussed, for example, in U.S. Pat. No. 6,075,183, No. 5,968,809, No. 6,136,574, No. 5,972,664, No. 6,051,754, No. 6,410,288 and PCT Publications No. WO 98/46763, No. WO 98/46764, No. WO 00/12720 and No. WO 00/40705.

The choice of combination of cassettes used depends in part on the PUFA profile and/or desaturase/elongase profile of the oilseed plant cells to be transformed and the long-chain PUFA(s) which is to be expressed.

In another aspect, this invention concerns a method for making long-chain PUFAs in a plant cell comprising:
  (a) transforming a cell with a recombinant construct of the invention; and,
  (b) selecting those transformed cells that make long-chain PUFAs.

In still another aspect, this invention concerns a method for producing at least one PUFA in a soybean cell comprising:
  (a) transforming a soybean cell with a first recombinant DNA construct comprising:
    (i) an isolated polynucleotide encoding a Δ9 elongase polypeptide, operably linked to at least one regulatory sequence; and,
    (ii) at least one additional recombinant DNA construct comprising an isolated polynucleotide, operably linked to at least one regulatory sequence, encoding a polypeptide selected from the group consisting of: a Δ4 desaturase, a Δ5 desaturase, a Δ6 desaturase, a Δ8 desaturase, a Δ9 desaturase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase;
  (b) regenerating a soybean plant from the transformed cell of step (a); and,
  (c) selecting those seeds obtained from the plants of step (b) having an altered level of PUFAs when compared to the level in seeds obtained from a nontransformed soybean plant.

In particularly preferred embodiments, the at least one additional recombinant DNA construct encodes a polypeptide having Δ8 desaturase activity, e.g., the Δ8 desaturase isolated and/or derived from *Euglena gracilis* and set forth in SEQ ID NOs:61 and 69.

Microbial Expression Systems, Cassettes & Vectors, and Transformation

The Δ9 elongase genes and gene products described herein (i.e., EgD9e, EgD9eS, E389D9e, E389D9eS, or other mutant enzymes, codon-optimized enzymes or homologs thereof) may also be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant Δ9 elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication No. WO 2004/101757 [U.S. Publication 2005-0136519-A1] and PCT Publication No. WO 2006/052870 [U.S. Publication 2006-0115881-A1] for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and 6.) the codon usage within the cloned gene, such that its frequency approaches the frequency of preferred codon usage of the host cell. Each of these types of modifications are encompassed in the present invention, as means to further optimize expression of the Δ9 elongases described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.*, 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast*, 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Yarrowia lipolytica*, thereby permitting high-level gene expression. Unfortunately, however, not all strains of *Yarrowia lipolytica* possess zeta regions (e.g., the strain identified as ATCC Accession No. #20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.*, 48(2): 232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication No. WO 2004/101757 [U.S. Publication 2005-0136519-A1] and PCT Publication No. WO 2006/052870 [U.S. Publication 2006-0115881-A1]. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura− mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura-phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant Δ9 elongases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes described in the instant invention have been isolated for expression in an oleaginous yeast (and in particular *Yarrowia lipolytica*); however, it is contemplated that because transcription, translation and the protein biosynthetic apparatus are highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida revkaufi*, *C. pulcherrima*, *C. tropicalis*, *C. utilis*, *Trichosporon pullans*, *T. cutaneum*, *Rhodotorula glutinus*, *R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (PCT Publication No. WO 2006/055322), No. 11/265,761 (PCT Publication No. WO 2006/052870) and No. 11/264,737 (PCT Publication No. WO 2006/052871), respectively.

Other preferred microbial hosts include oleaginous bacteria, algae and other fungi; and, within this broad group of microbial hosts, of particular interest are microorganisms that synthesize ω-3ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ9 elongase genes under the control of inducible or regulated promoters could yield a transformant organism capable of synthesizing increased quantities of EDA; this could be converted to increased quantities of DGLA if a Δ8 desaturase gene was co-expressed. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either EDA or ETrA, respectively, comprising:

a) providing an oleaginous yeast comprising:
  (i) a first recombinant DNA construct comprising an isolated polynucleotide encoding a Δ9 elongase polypeptide, operably linked to at least one regulatory sequence; and,
  (ii) a source of elongase substrate consisting of either LA or ALA, respectively; and,
b) growing the yeast of step (a) in the presence of a suitable fermentable carbon source wherein the gene encoding a Δ9 elongase polypeptide is expressed and LA is converted to EDA or ALA is converted to ETrA, respectively; and,
c) optionally recovering the EDA or ETrA, respectively, of step (b).

Substrate feeding may be required.

In some preferred embodiments, the nucleotide sequence of the gene encoding a Δ9 elongase is selected from the group consisting of SEQ ID NO:1 and SEQ ID NO:4. In alternate preferred embodiments, the nucleotide sequence of the gene encoding a Δ9 elongase polypeptide is set forth in SEQ ID NO:3 (wherein at least 106 codons have been optimized for expression in *Yarrowia* relative to SEQ ID NO:1). And, in other preferred embodiments, the nucleotide sequence of the gene encoding a Δ9 elongase polypeptide is set forth in SEQ ID NO:6 (wherein at least 113 codons have been optimized for expression in *Yarrowia* relative to SEQ ID NO:4).

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the Δ9 elongases described herein.

Specifically, in one embodiment this invention concerns an oleaginous yeast comprising:

a) a first recombinant DNA construct comprising an isolated polynucleotide encoding a Δ9 elongase polypeptide, operably linked to at least one regulatory sequence; and, b) at least one additional recombinant DNA construct comprising an isolated polynucleotide, operably linked to at least one regulatory sequence, encoding a polypeptide selected from the group consisting of: a Δ4 desaturase, a Δ5 desaturase, Δ6 desaturase, a Δ9 desaturase, a Δ12 desaturase, a Δ15 desaturase, a Δ17 desaturase, a Δ8 desaturase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having Δ8 desaturase activity, e.g., the Δ8 desaturase isolated and/or derived from *Euglena gracilis* and set forth in SEQ ID NOs:61 and 69.

Metabolic Engineering of ω-3 and/or ω-6 Fatty Acid Biosynthesis in Microbes

Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of ω-6 and/or ω-3 fatty acids. Introducing and/or amplifying genes encoding Δ9 desaturases and/or Δ12 desaturases may accomplish this. To maximize production of ω-6 unsaturated fatty acids, it is well known to one skilled in the art that production is favored in a host microorganism that is substantially free of ALA; thus, preferably, the host is selected or obtained by removing or inhibiting Δ15 or ω-3 type desaturase activity that permits conversion of LA to ALA. The endogenous desaturase activity can be reduced or eliminated by, for example: (1) providing a cassette for transcription of antisense sequences to the Δ15 desaturase transcription product; (2) disrupting the Δ15 desaturase gene through insertion, substitution and/or deletion of all or part of the target gene; or (3) using a host cell which naturally has [or has been mutated to have] low or no Δ15 desaturase activity. Inhibition of undesired desaturase pathways can also be accomplished through the use of specific desaturase inhibitors such as those described in U.S. Pat. No. 4,778,630.

Alternatively, it may be desirable to maximize production of ω-3 fatty acids (and minimize synthesis of ω-6 fatty acids). In this example, one could utilize a host microorganism wherein the Δ12 desaturase activity that permits conversion of oleic acid to LA is removed or inhibited; subsequently, appropriate expression cassettes would be introduced into the host, along with appropriate substrates (e.g., ALA) for conversion to ω-3 fatty acid derivatives of ALA (e.g., STA, ETrA, ETA, EPA, DPA, DHA).

In alternate embodiments, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the Δ9 elongase/Δ8 desaturase biosynthetic pathway are introduced into oleaginous yeasts for the production of ω-3 and/or ω-6 fatty acids. It will be particularly useful to express the present Δ9 elongase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and the most economical yield of desired PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. The carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

Methods of isolating seed oils are well known in the art (Young et al., Processing of Fats and Oils, In *The Lipid Handbook*, Gunstone et al., eds., Chapter 5, pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in the Table below.

TABLE 5

Generalized Steps For Soybean Oil And Byproduct Production

| Process Step | Process | Impurities Removed And/Or By-Products Obtained |
|---|---|---|
| # 1 | Soybean seed | |
| # 2 | Oil extraction | Meal |
| # 3 | Degumming | Lecithin |
| # 4 | Alkali or physical refining | Gums, free fatty acids, pigments |
| # 5 | Water washing | Soap |

TABLE 5-continued

Generalized Steps For Soybean Oil And Byproduct Production

| Process Step | Process | Impurities Removed And/Or By-Products Obtained |
|---|---|---|
| # 6 | Bleaching | Color, soap, metal |
| # 7 | (Hydrogenation) | |
| # 8 | (Winterization) | Stearine |
| # 9 | Deodorization | Free fatty acids, tocopherols, sterols, volatiles |
| # 10 | Oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., anti-sticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which, in turn, alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating ω-3 and/or ω-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing ω-3 and/or ω-6 fatty acids described herein will be suitable for use in a variety of food and feed products including, but not limited to: food analogs, meat products, cereal products, snack foods, baked foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to: imitation milk and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking, i.e., to dry or harden by subjecting to heat. Examples of a baked good product include, but are not limited to: bread, cakes, doughnuts, bars, pastas, bread crumbs, baked snacks, mini-biscuits, mini-crackers, mini-cookies and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks; fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ [Mead Johnson & Company] and Similac Advance™ [Ross Products Division, Abbott Laboratories]). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example: chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and includes functional foods, medical foods, medical nutritionals, infant formulas and dietary supplements. Additionally, plant/seed oils, altered seeds and microbial oils of the invention may be used in standard pharmaceutical compositions. For example, the oils of the invention could readily be incorporated into the any of the above mentioned food products, to thereby produce, e.g., a functional or medical food. More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited herein, it is expected that the oils of the invention can be used within pet food products, ruminant and poultry food products and aquacultural food products. Pet food products are those products intended to be fed to a pet [e.g., a dog, cat, bird, reptile, rodent]; these products can include the cereal and health food products above, as well as meat and meat byproducts, soy protein products and grass and hay products (e.g., alfalfa, timothy, oat or brome grass, vegetables). Ruminant and poultry food products are those wherein the product is intended to be fed to e.g., turkeys, chickens, cattle and swine. As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms, animals and/or plants in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM"

means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains with ATCC Accession Nos. #20362, #76982 and #90812 were purchased from the American Type Culture Collection (Rockville, Md.). *Y. lipolytica* strains were typically grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

*Euglena gracilis* Growth Conditions, Lipid Profile and mRNA Isolation

The present Example describes the growth of *Euglena gracilis*, culture lipid analysis and mRNA isolation.

Growth and Lipid Analysis

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (Catalog No. U126-01, Difco Laboratories, Detroit, Mich.), 2 g of Bacto® tryptone (Catalog No. 0123-17-3, Difco Laboratories), 2 g of Bacto® yeast extract (Catalog No. 0127-17-9, Difco Laboratories) in 970 mL of water. After filter sterilizing, 30 mL of soil-water supernatant (Catalog No. 15-3790, Carolina Biological Supply Company, Burlington, N.C.) was aseptically added to produce the final Eg medium. *Euglena gracilis* cultures were grown at 23° C. with a 16 h light, 8 h dark cycle for 2 weeks with no agitation.

Figure 3:
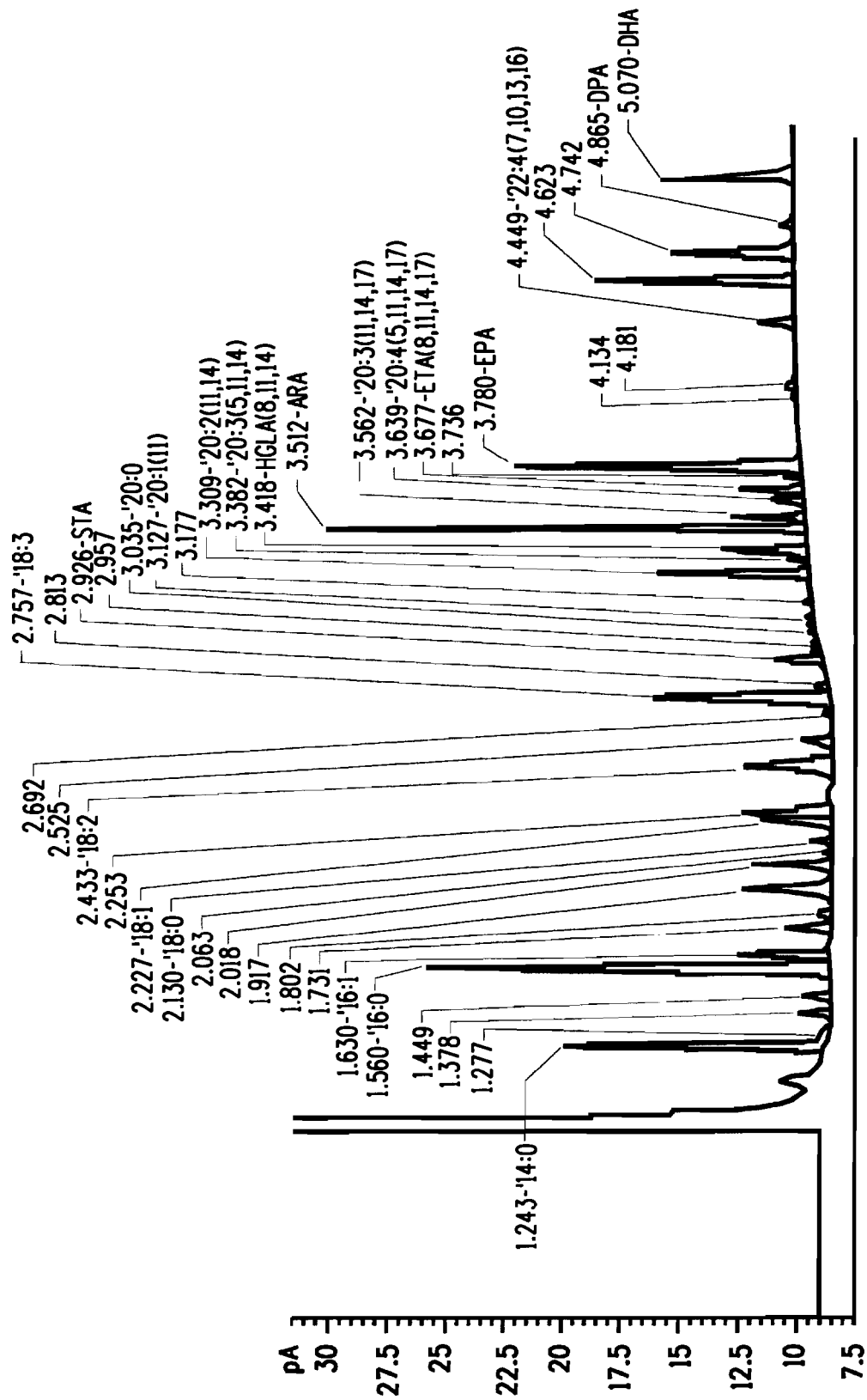
FIG. 3 shows a chromatogram of the lipid profile of an *Euglena gracilis* cell extract (Example 1).

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog No. U-99-A, Nu-Chek Prep, Inc.) and the resulting chromatogram is shown in FIG. 3.

Preparation of mRNA from *Euglena gracilis*

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 μg of mRNA was obtained.

Example 2

*Euglena gracilis* cDNA Synthesis, Library Construction and Sequencing

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 3.2 μg of mRNA (Example 1) using the Biotin-attB2-Oligo(dT) primer. After synthesis of the first and second strand, the attB1 adapter was added, ligated and the cDNA was size fractionated using column chromatography. DNA from fractions 7 and 8 (size ranging from ~800-1500 bp) was concentrated, recombined into pDONR™ 222 and transformed into *E. coli* ElectroMAX™ DH10B™ T1 Phage-Resistant cells (Invitrogen Corporation). The *Euglena gracilis* library was named "eeg1c".

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 µg/mL kanamycin (replicated plates). Plasmids then were isolated, using the Templiphi DNA sequencing template amplification kit method (Amersham Biosciences) following the manufacturer's protocol. Briefly, the Templiphi method uses bacteriophage φ29 DNA polymerase to amplify circular single-stranded or double-stranded DNA by isothermal rolling circle amplification (Dean et al., *Genome Res.,* 11:1095-1099 (2001); Nelson et al., *Biotechniques,* 32:S44-S47 (2002)). After growing 20 h at 37° C., cells from the replicated plate were added to 5 µL of dilution buffer and denatured at 95° C. for 3 min to partially lyse cells and release the denatured template. Templiphi premix (5 µL) was then added to each sample and the resulting reaction mixture was incubated at 30° C. for 16 h, then at 65° C. for 10 min to inactivate the φ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:18), and the ABI Big-Dye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Example 3

Identification of Δ9 Elongase Enzyme Homologs from *Euglena gracilis* cDNA Library eeg1c cDNA clones encoding long-chain polyunsaturated fatty acid elongation enzyme homologs (i.e., LC-PUFA ELO homologs or Δ9 elongases) were identified by conducting BLAST (Basic Local Alignment Search Tool; Altschul et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.,* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequences from clone eeg1c.pk001.n5.f revealed similarity of the protein encoded by the cDNA to IgD9e (i.e., the long-chain PUFA elongation enzyme from *Isochrysis galbana* set forth herein as SEQ ID NO:8; NCBI Accession No. AAL37626 (GI 17226123), locus AAL37626, CDS AF390174; Qi et al., *FEBS Lett.* 510(3):159-165 (2002)). The sequence of a portion of the cDNA insert from clone eeg1c.pk001.n5.f is shown in SEQ ID NO:10 (5' end of cDNA insert).

Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones. The 3' end sequence is shown in SEQ ID NO:11.

Both the 5' and 3' sequences were aligned using Sequencher™ (Version 4.2, Gene Codes Corporation, Ann Arbor, Mich.) and the resulting sequence for the cDNA is shown in SEQ ID NO:12. Sequence for the coding sequence from the cDNA in eeg1c.pk001.n5.f and the corresponding deduced amino acid sequence is shown in SEQ ID NO:1 and SEQ ID NO:2, respectively. On the basis of the homologies reported above, the *Euglena gracilis* gene product of the cDNA insert of eeg1c.pk001.n5.1 was hypothesized to encode a Δ9 elongase and was thus designated as "EgD9e".

The amino acid sequence set forth in SEQ ID NO:2 (i.e., EgD9e) was evaluated by BLASTP, yielding a pLog value of 38.70 (E value of 2e-39) versus IgD9e (SEQ ID NO:8). EgD9e is 39.4% identical to IgD9e using the Jotun Hein method. Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). EgD9e (SEQ ID NO:2) is 31.8% identical to IgD9e (SEQ ID NO:8) using the Clustal V method (FIG. 4). Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v6.1 program of the LASERGENE bioinformatics computing suite with the default parameters for pairwise alignment (KTUPLE=1, GAP PENALTY=3, WINDOW=5, DIAGONALS SAVED=5 and GAP LENGTH PENALTY=10).

BLAST scores and probabilities indicated that the instant nucleic acid fragment (SEQ ID NO:12) encoded an entire *Euglena gracilis* Δ9 elongase.

Example 4

Functional Analysis of the *Euglena gracilis* Δ9 Elongase (EgD9e) in *Saccharomyces cerevisiae*

The present Example describes functional analysis of EgD9e in *Saccharomyces cerevisiae*. This required: (1) cloning of EgD9e into yeast expression vector pY-75 to produce pY119; (2) comparison of lipid profiles within transformant organisms comprising pY-75 and pY119, after substrate feeding; and (3) comparison of lipid profiles within transformant organisms comprising pY-75 and pY119, after no substrate feeding.

Construction of Plasmids pY-75 (Control) and pY119, Comprising EgD9e

The yeast episomal plasmid (YEp)-type vector pRS425 (Christianson et al., *Gene,* 110:119-122 (1992)) contains sequences from the *Saccharomyces cerevisiae* 2µ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the SacII and SpeI sites of pRS425 in the same way as described by Jia et al. (*Physiol. Genomics*, 3:83-92 (2000)) to produce pGPD-425. A NotI site was introduced into the BamHI site of pGPD-425, thus producing a NotI site flanked by BamHI sites, and this plasmid was called pY-75.

Figure 5:
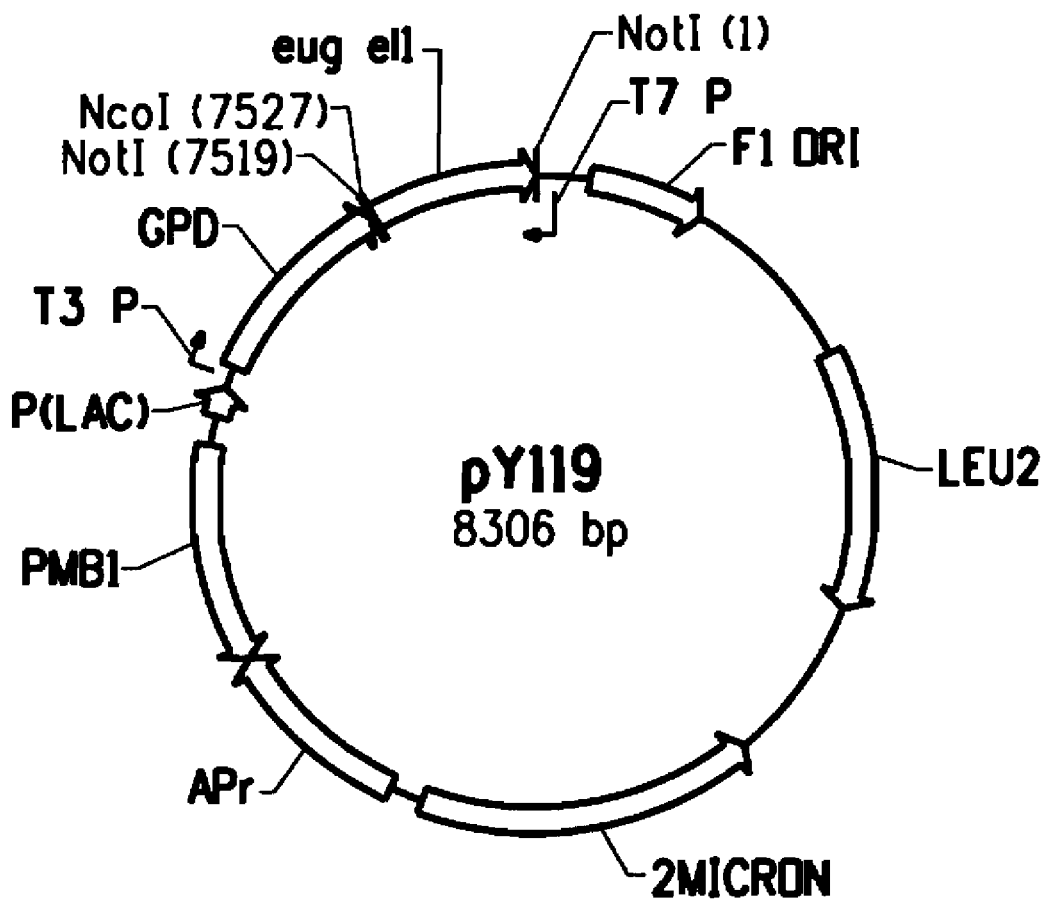
FIG. 5 is a map of plasmid pY119.

EgD9e was amplified from eeg1c.pk001.n5.f with oligonucleotide primers oEugEL1-1 (SEQ ID NO:19) and oEugEL1-2 (SEQ ID NO:20) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906. EgD9e was released from pKR906 by digestion with NotI and cloned into the NotI site of pY-75 to produce pY119 (SEQ ID NO:21; FIG. 5). EgD9e is labeled as "eug el1" in FIG. 5.

Functional Analysis of EgD9e Elongase Activity by Substrate Feeding

Plasmids pY119 and pY-75 were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants from each plate were inoculated into 2 mL of DOB medium supplemented with CSM-leu (Qbiogene) and 0.2% tergitol. Cells were grown for 1 day at 30° C. after which 0.1 mL was transferred to 3 mL of the same medium supplemented with either LA [18:2(9,12)], ALA [18:3(9,12,15)], GLA [18:3(6,9,12)], STA [18:4(6,9,12,15)], ARA [20:4(5,8,11,14)] or EPA [20:5(5,8,11,14,17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G., and Nishida I., *Arch Biochem Biophys.*, 276(1):38-46 (1990)) with 500 µL of 1% sodium methoxide for 30 min at 50° C. after which 500 µL of 1 M sodium chloride and 100 µL of heptane were added. After thorough mixing and centrifugation, fatty acid methyl esters (FAMEs) were analyzed by GC as described in Example 1.

Results for feeding cells containing pY75 (vector control) or pY119 (3 independent transformants, designated as pY119-5, pY119-6 and pY119-8) are shown in FIG. 6. Fatty acids are identified as 16:0 (palmitate), 16:1(9) (palmitoleic acid), 18:0, 18:1(9) (oleic acid), LA, GLA, ALA, STA, EDA, DGLA, ARA, ETrA, ETA, EPA, 22:2(13,16) (docosadienoic acid), 22:4(7,10,13,16) (adrenic acid), DPA and 24:1 (nervonic acid). The elongation efficiency ("% Elo") was calculated for each fatty acid ("FA") fed as: [% FA$_{product}$/(% FA$_{product}$+% FA$_{substrate}$)*100].

The data in FIG. 6 demonstrated that the cloned EgD9e efficiently elongated LA and ALA to EDA and ETrA, respectively.

Functional Analysis of EgD9e Elongase Activity without Substrate Feeding

Additionally, FAMEs from cells where no fatty acid had been fed were analyzed by GC using slightly different temperature profiles in order to achieve separation of oleic acid [OA-18:1(9)] and vaccenic acid [VA-18:1(11)], the product of palmitoleic acid [PA-16:1(9)] elongation. Fatty acid methyl esters (3 µL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 200° C. for 2.7 min, increase to 240° C. at 20° C./min and then hold for an additional 2.3 min. Results are shown in Table 6.

TABLE 6

| Lipid Profiles Having No Exogenous Fatty Acid Added | | | | | | | |
|---|---|---|---|---|---|---|---|
| Sample Name | 16:0 | 16:1 (9) | 18:0 | 18:1 (9) | 18:1 (11) | % Elo 16:0 | % Elo 16:1 |
| pY75 | 13.1 | 54.7 | 3.5 | 27.6 | 1.2 | 20.9 | 2.1 |
| pY119-5 | 12.9 | 55.6 | 3.6 | 26.0 | 1.8 | 21.6 | 3.2 |
| pY119-6 | 13.4 | 54.0 | 3.6 | 27.3 | 1.6 | 21.2 | 3.0 |
| pY119-8 | 12.7 | 53.3 | 3.5 | 29.0 | 1.5 | 21.7 | 2.8 |

Based on the results shown above, EgD9e may act as both a $C_{16/18}$ elongase and a $C_{18/20}$ elongase, in addition to its primary role as a Δ9 elongase that is capable of catalyzing the elongation of LA and ALA to EDA and ETrA, respectively.

Example 5

Construction of *Yarrowia lipolytica* Expression Vector pY115, Comprising a Synthetic Δ9 Elongase Gene (Derived from *Isochrysis galbana*), Codon-Optimized for Expression in *Yarrowia lipolytica* (IgD9eS)

The present Example describes the construction of *Yarrowia lipolytica* expression vector pY115, comprising a chimeric FBAINm::IgD9eS::Pex20 gene, wherein IgD9eS is a synthetic Δ9 elongase derived from *Isochrysis galbana* and codon-optimized for expression in *Yarrowia lipolytica*. Plasmid pY115 indirectly enabled the Δ9 elongase activity of IgD9eS to be compared to the Δ9 elongase activity of EgD9e, as described in Examples 6 and 7, infra.

Figure 8:
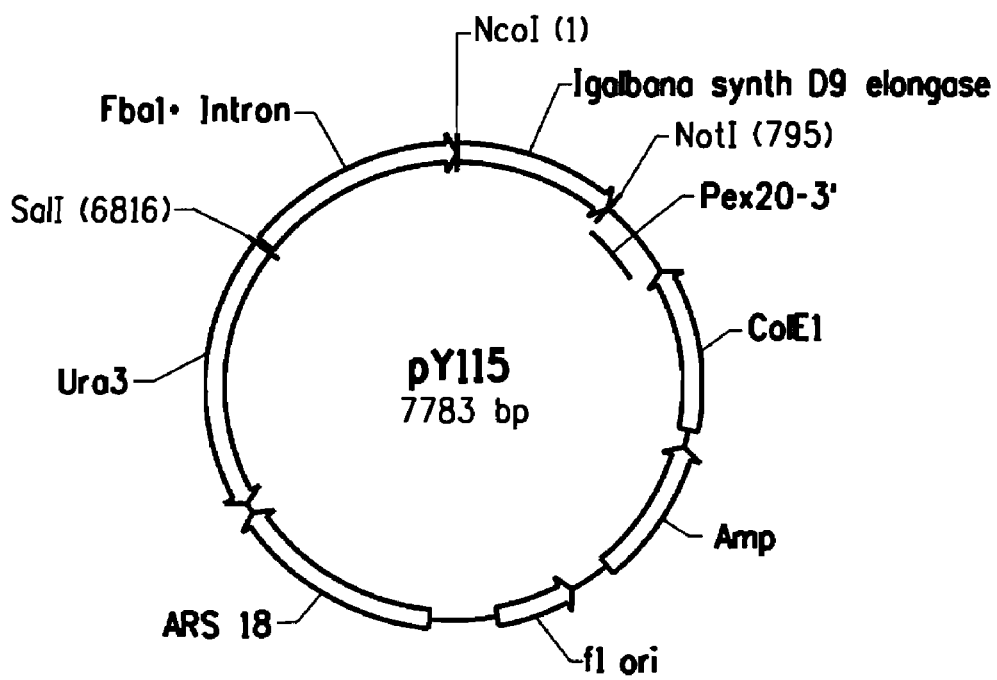
FIG. 8 is a map of plasmid pY115.

Construction of plasmid pY115 (SEQ ID NO:45; FIG. 8) required: (1) construction of pDMW263; (2) synthesis of IgD9eS and creation of plasmid pDMW237; and (3) ligation of fragments from plasmids pDMW263 and pDMW237.

Construction of pDMW263

Figure 7A:
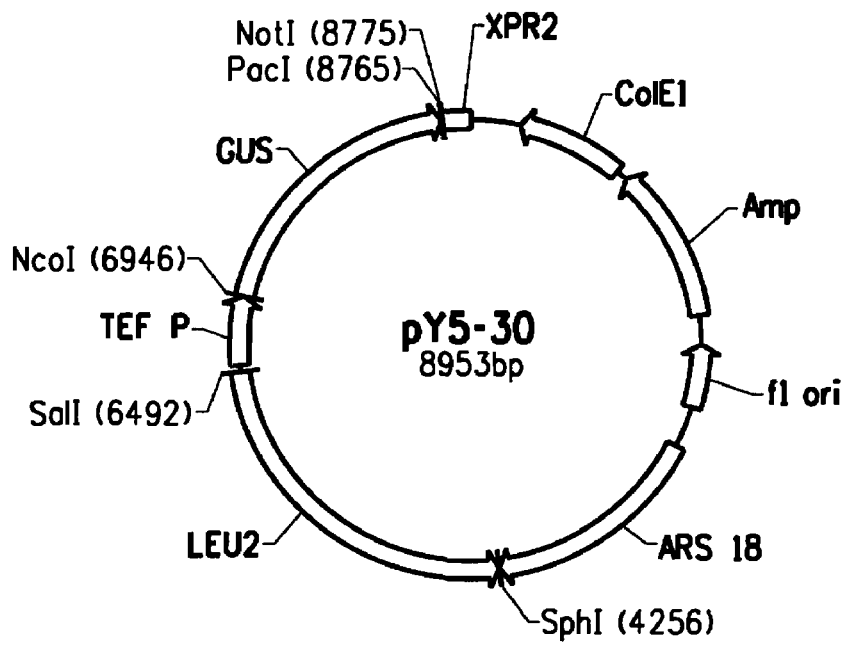
FIG. 7A is a map of plasmid pY5-30.

Plasmid pY5-30 (FIG. 7A; previously described in PCT Publication No. WO 05/003310 [the contents of which are hereby incorporated by reference]) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (Amp$^R$), for selection in *E. coli*; a *Yarrowia* LEU2 gene, for selection in *Yarrowia*; and a chimeric TEF::GUS::XPR gene.

Figure 7B:
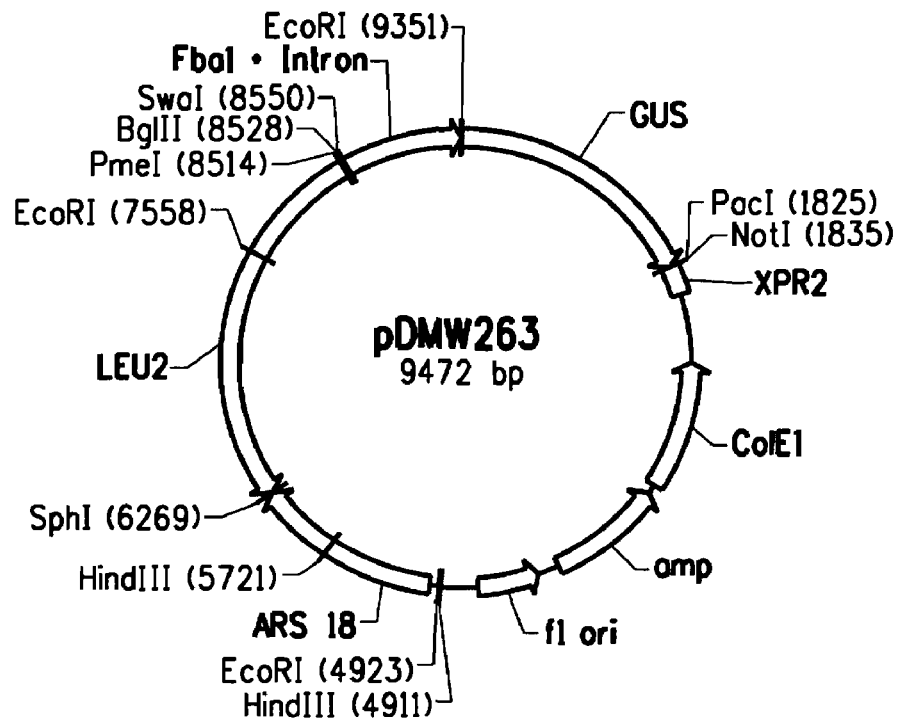
FIG. 7B is a map of plasmid pDMW263.

Plasmid pDMW263 (SEQ ID NO:22; FIG. 7B) was created from pY5-30, by replacing the TEF promoter with the *Yarrowia lipolytica* FBAINm promoter (PCT Publication No. WO 05/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 7 summarizes the components of pDMW263.

TABLE 7

Components of Plasmid pDMW263 (SEQ ID NO: 22)

| RE Sites and Nucleotides Within SEQ ID NO: 22 | Description of Fragment and Chimeric Gene Components |
|---|---|
| 4992-4296 SalI/SacII (8505-2014) | ARS18 sequence (GenBank Accession No. A17608) FBAINm::GUS::XPR, comprising: FBAINm: FBAINm promoter (PCT Publication No. WO 2005/049805; labeled as "Fba1 + intron" in FIG. 7B) GUS: *E. coil* gene encoding β-glucuronidase (Jefferson, R. A. Nature. 14:342:837-838 (1989) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

In Vitro Synthesis of IgD9eS

The codon usage of the Δ9 elongase gene of *Isochrysis galbana* (IgD9e; SEQ ID NOs:7 and 8) was optimized for expression in *Yarrowia lipolytica*, in a manner similar to that described in PCT Publication No. WO 2004/101753 (US-2004-0253621-A1) and as described in PCT Publication No. WO 2006/052870 (US-2006-0115881-A1), each incorporated by reference in their entirety herein. Specifically, a codon-optimized Δ9 elongase gene (designated "IgD9eS"; SEQ ID NO:9) was designed, based on the coding sequence of IgD9e (SEQ ID NO:7), according to the *Yarrowia* codon usage pattern, the consensus sequence around the ATG translation initiation codon, and the general rules of RNA stability (Guhaniyogi, G. and J. Brewer, *Gene*, 265(1-2):11-23 (2001)). In addition to modification of the translation initiation site, 127 bp of the 792 bp coding region were modified (16.0%), and 122 codons were optimized. None of the modifications in the codon-optimized gene changed the amino acid sequence of the encoded protein (SEQ ID NO:8).

More specifically, eight pairs of oligonucleotides were designed to extend the entire length of IgD9eS (e.g., IL3-1A, IL3-1B, IL3-2A, IL3-2B, IL3-3A, IL3-3B, IL3-4A, IL34B, IL3-5A, IL3-5B, IL3-6A, IL3-6B, IL3-7A, IL3-7B, IL3-8A and IL3-8B, corresponding to SEQ ID NOs:23-38). Each pair of sense (A) and anti-sense (B) oligonucleotides were complementary, with the exception of a 4 bp overhang at each 5'-end. Additionally, primers IL3-1F, IL34R, IL3-5F and IL3-8R (SEQ ID NOs:39-42) also introduced NcoI, PstI, PstI and NotI restriction sites, respectively, for subsequent subcloning.

Each oligonucleotide (100 ng) was phosphorylated at 37° C. for 1 h in a volume of 20 µL containing 50 mM Tris-HCl (pH 7.5), 10 mM MgCl$_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min) and 4° C. (15 min). Thus, IL3-1A (SEQ ID NO:23) was annealed to IL3-1B (SEQ ID NO:24) to produce the double-stranded product "IL3-1AB". Similarly, IL3-2A (SEQ ID NO:25) was annealed to IL3-2B (SEQ ID NO:26) to produce the double-stranded product "IL3-2AB", etc.

Two separate pools of annealed, double-stranded oligonucleotides were then ligated together, as shown below: Pool 1 (comprising IL3-1AB, IL3-2AB, IL3-3AB and IL34AB); and Pool 2 (comprising IL3-5AB, IL3-6AB, IL3-7AB and IL3-8AB). Each pool of annealed oligonucleotides was mixed in a volume of 20 µL with 10 U of T4 DNA ligase and the ligation reaction was incubated overnight at 16° C.

The product of each ligation reaction was then used as template to amplify the designed DNA fragment by PCR. Specifically, using the ligated "Pool 1" mixture (e.g., IL3-1AB, IL3-2AB, IL3-3AB and IL34AB) as template, and oligonucleotides IL3-1F and IL34R (SEQ ID NOs:39 and 40) as primers, the first portion of IgD9eS was amplified by PCR. The 417 bp PCR fragment was subcloned into the pGEM-T easy vector (Promega) to generate pT9(1-4) (SEQ ID NO:43).

Using the ligated "Pool 2" mixture (e.g., IL3-5AB, IL3-6AB, IL3-7AB and IL3-8AB) as the template, and oligonucleotides IL3-5F and IL3-8R (SEQ ID NOs:41 and 42) as primers, the second portion of IgD9eS was amplified similarly by PCR and cloned into the pGEM-T-easy vector to generate pT9(5-8) (SEQ ID NO:44).

Figure 7C:
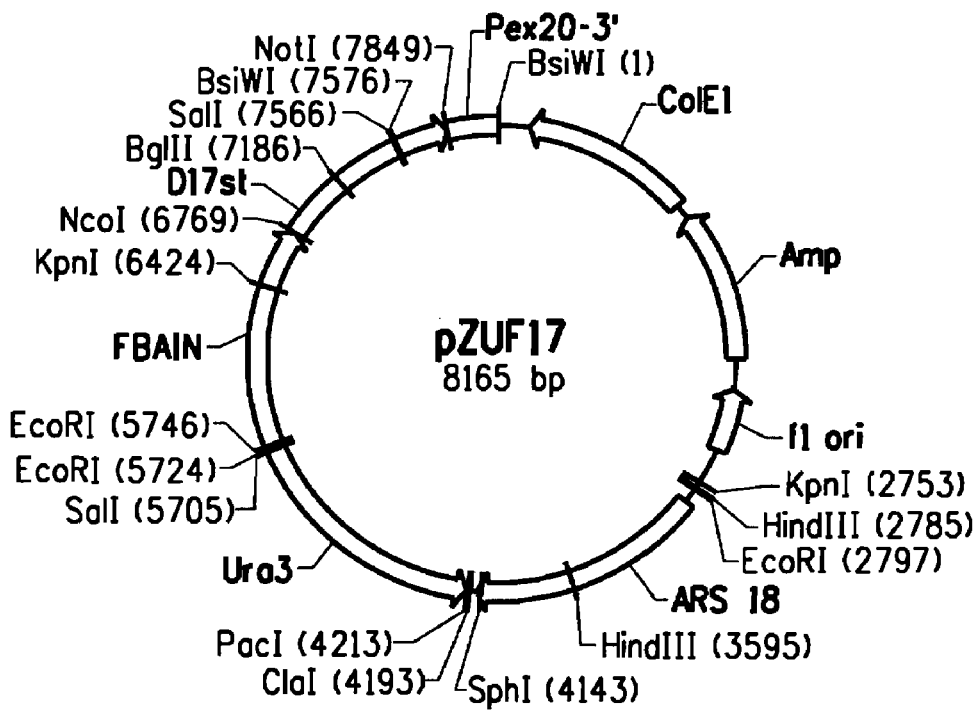
FIG. 7C is a plasmid map of pZUF17.

*E. coli* was transformed separately with pT9(1-4) (SEQ ID NO:43) and pT9(5-8) (SEQ ID NO:44) and the plasmid DNA was isolated from ampicillin-resistant transformants. Plasmid DNA was purified and digested with the appropriate restriction endonucleases to liberate the 417 bp NcoI/PstI fragment of pT9(1-4) and the 377 bp PstI/Not1 fragment of pT9(5-8). These two fragments were then combined and directionally ligated together with Nco1/Not1digested pZUF17 (SEQ ID NO:121; FIG. 7C) to generate pDMW237 (SEQ ID NO:46). Thus, the synthetically produced IgD9eS gene was flanked by a FBAIN promoter and *Yarrowia* Pex20 terminator within expression vector pDMW237.

Final Construction of *Yarrowia lipolytica* Expression Vector pY115

The NcoI/SalI DNA fragment from pDMW263 (containing the *Yarrowia lipolytica* FBAINm promoter) was cloned into the NcoI/SalI DNA fragment of pDMW237 (containing IgD9eS), to produce pY115 (SEQ ID NO:45; FIG. 8), comprising a chimeric FBAINm::IgD9eS::Pex20 gene. FBAINm is labeled as "Fba1+Intron" and IgD9eS is labeled as "*I galbana* synth D9 elongas" in FIG. 8.

Example 6

Construction of *Yarrowia lipolytica* Expression Vectors pBY2 (Comprising EgD9e) and pBY1-FAE (Comprising IgD9eS)

The present Example describes synthesis of *Yarrowia lipolytica* expression vectors pBY2 (comprising a chimeric FBAINm::EgD9e::Pex20 gene) and pBY1-FAE (comprising a chimeric FBAINm::IgD9eS::Pex20 gene). Delta-9 elongase activity of IgD9eS was compared to that of EgD9e when expressed in *Yarrowia lipolytica*, as described in Example 7 (infra).

Construction of *Yarrowia lipolytica* Expression Vector pBY2

Figure 9A:
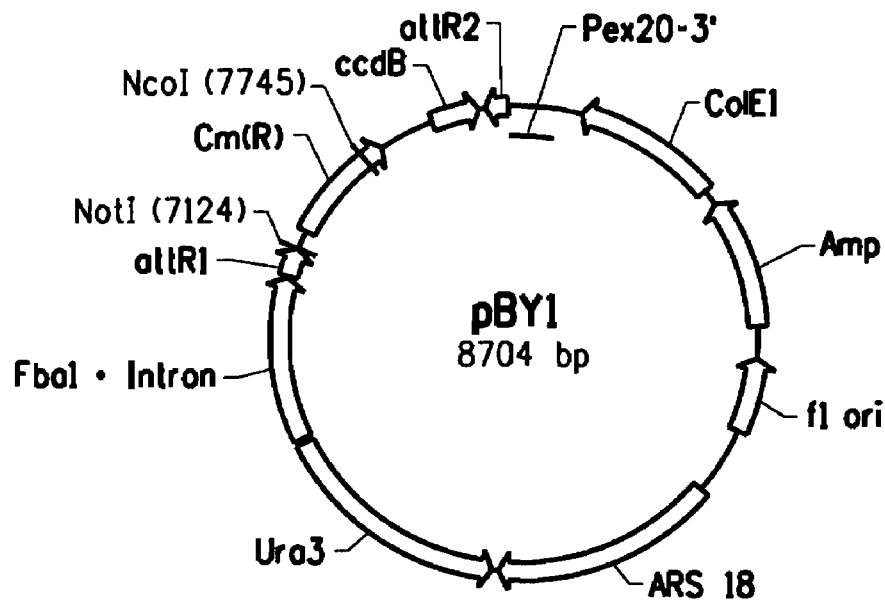
FIG. 9A is a map of *Yarrowia lipolytica* Gateway® destination vector pBY1.

Plasmid pY115 (SEQ ID NO:45; Example 5) was digested with NcoI/NotI and the resulting DNA ends were filled using Klenow. After filling to form blunt ends, the DNA fragments were treated with calf intestinal alkaline phosphatase and separated using agarose gel electrophoresis. The 6989 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6989 bp fragment was ligated with cassette rfA using the Gateway Vector Conversion System (Catalog No. 11823-029, Invitrogen Corporation) following the manufacturer's protocol to form *Yarrowia lipolytica* Gateway® destination vector pBY1 (SEQ ID NO:47; FIG. 9A).

Figure 9B:
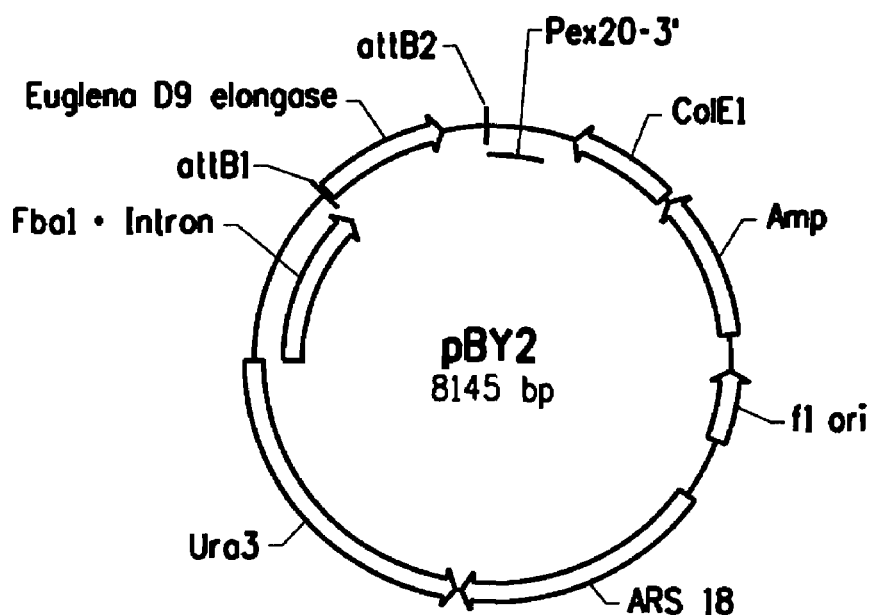
FIG. 9B is a map of plasmid pBY2.

Plasmid was purified from *Euglena gracilis* clone eeg1c.pk001.n5.f (Examples 2 and 3) using the QIAprep® Spin Miniprep Kit (Qiagen Inc., Valencia, Calif.) following the manufacturer's protocol. Using the Gateway® LR Clonase™ II enzyme mix (Catalog No. 11791-020, Invitrogen Corporation) and following the manufacturer's protocol, the cDNA from eeg1c.pk001.n5.f was transferred to pBY1 to form pBY2 (SEQ ID NO:48; FIG. 9B). Since sequencing was performed with the WobbleT primer, the full sequence of the 3' end of eeg1c.pk001.n5.f (i.e., containing the polyA tail) was not known. Based on restriction digest and agarose gel analysis, the poly A tail appeared to be less than 100 bp long.

Construction of Yarrowia lipolytica Expression Vector pBY1-FAE

Figure 9C:
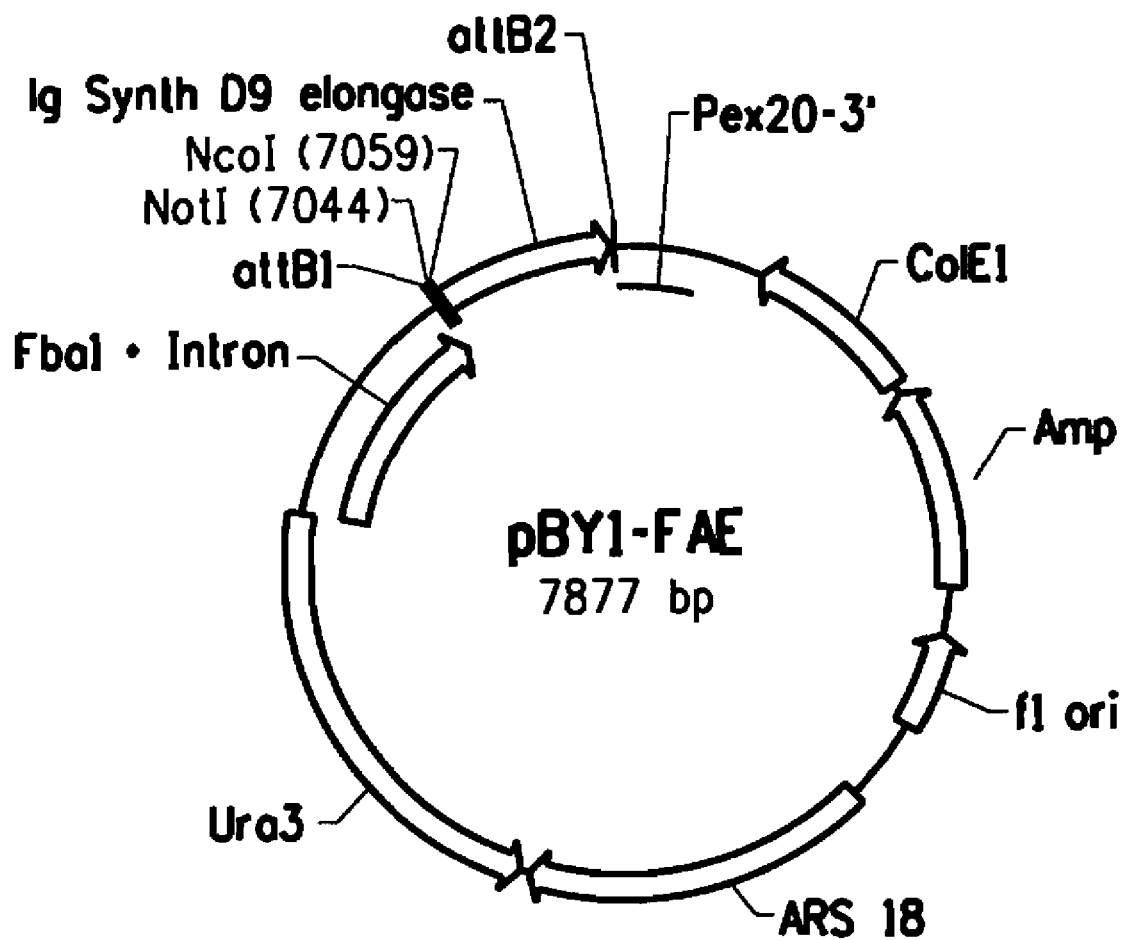
FIG. 9C is a map of plasmid pBY1-FAE.

IgD9eS was amplified from pY115 (SEQ ID NO:45; Example 5) with oligonucleotide primers ig-s (SEQ ID NO:49) and ig-as (SEQ ID NO:50) using AccuPrime™ Taq Polymerase High Fidelity (Catalog No. 12346-086, Invitrogen Corporation) following the manufacturer's protocol. The resulting DNA fragment was cloned into pENTR™/D-TOPO® using the pENTR™ Directional TOPO® Cloning Kit (Invitrogen Corporation), following the manufacturer's protocol, to produce pENTR-FAE. Plasmid pENTR-FAE was purified using the QIAprep® Spin Miniprep Kit (Qiagen Inc., Valencia, Calif.) following the manufacturer's protocol as above. Using the Gateway® LR Clonase™ II enzyme mix (Catalog No. 11791-020, Invitrogen Corporation) and following the manufacturer's protocol, the CDS for IgD9eS was transferred to pBY1 to form pBY1-FAE (SEQ ID NO:51; FIG. 9C).

Vector Transformation into Escherichia coli

Following creation of pBY2 and pBY1-FAE, each vector was transformed into E. coli DH10B™ (Invitrogen Corporation) cells. The transformant cells were grown and pBY2 and pBY1-FAE were isolated using the QIAprep® Spin Miniprep Kit (Qiagen Inc., Valencia, Calif.).

out amino acid, 20 g/L glucose) containing 250 mg/L 5-FOA (Zymo Research). Plates were incubated at 28° C. and four of the resulting colonies were patched separately onto minimal medium plates containing 200 mg/mL 5-FOA and minimal medium plates lacking uracil and uridine to confirm uracil Ura3 auxotrophy. Subsequently, Yarrowia lipolytica strain Y2224 was grown at 28° C. on YPD agar.

Functional Analysis of Yarrowia lipolytica Transformants Comprising pBY1-FAE and pBY2 pBY1-FAE (comprising a chimeric FBAINm::IgD9eS::Pex20 gene) and pBY2 (comprising a chimeric FBAINm::EgD9e::Pex20 gene) were transformed into Yarrowia lipolytica strain Y2224 as described in the General Methods. The cells were plated onto minimal media plates lacking uracil and maintained at 30° C. for 2 to 3 days.

Single colonies of transformants were then grown in 3 mL minimal medium lacking uracil at 30° C. to an $OD_{600}$~1.0. As a control, Y2224 was also grown in a similar way on minimal media supplemented with uracil. Cells were subsequently washed with water, collected by centrifugation and lipids transesterified as described supra. FAMEs from cells containing pBY1-FAE, pBY2 or no expression vector were analyzed by GC, using the methodology described in Example 4 (i.e., for S. cerevisiae cells containing pY119). Results for the average of three replications of each are shown in Table 8. Fatty acids are identified as 16:0 (palmitate), 16:1(9) (palmitoleic acid), 17:1(9), 18:0, 18:1(9) (oleic acid), LA and EDA. Elongation Efficiency ("% Elo LA") was calculated as described in Example 4.

TABLE 8

Comparison Of Lipid Profiles Of Yarrowia Expressing EgD9e And IgD9eS

| Sample Name | Δ9 Elongase | 16:0 | 16:1 (9) | 17:1 (9) | 18:0 | 18:1 (9) | LA | EDA | % Elo LA |
|---|---|---|---|---|---|---|---|---|---|
| Y2224-1 | None | 13.4 | 12.6 | 0.8 | 2.8 | 43.1 | 27.2 | 0.1 | 0.2 |
| Y2224-2 | None | 12.2 | 12.3 | 0.8 | 2.3 | 46.1 | 26.2 | 0.1 | 0.2 |
| Y2224-3 | None | 11.7 | 10.8 | 1.1 | 2.8 | 48.4 | 25.0 | 0.1 | 0.2 |
| pBY1-FAE-1 | IgD9eS | 11.9 | 11.9 | 0.8 | 3.1 | 50.6 | 20.2 | 1.6 | 7.5 |
| pBY1-FAE-2 | IgD9eS | 12.9 | 11.4 | 0.9 | 3.6 | 46.7 | 23.0 | 1.4 | 5.9 |
| pBY1-FAE-3 | IgD9eS | 12.1 | 12.5 | 0.8 | 3.2 | 50.0 | 19.8 | 1.6 | 7.4 |
| pBY2-1 | EgD9e | 12.3 | 11.7 | 0.8 | 3.4 | 48.4 | 21.1 | 2.2 | 9.5 |
| pBY2-2 | EgD9e | 12.1 | 12.5 | 0.8 | 3.2 | 50.1 | 19.1 | 2.3 | 10.6 |
| pBY2-3 | EgD9e | 12.1 | 12.2 | 0.8 | 3.3 | 50.0 | 19.4 | 2.1 | 9.9 |

Example 7

Functional Analysis of EgD9e in Yarrowia lipolytica Strain Y2224

The present Example describes functional analysis of EgD9e in Yarrowia lipolytica strain Y2224. This required: (1) construction of strain Y2224 (i.e., a FOA resistant mutant from an autonomous mutation of the Ura3 gene of wildtype Yarrowia strain ATCC #20362); and, (2) comparison of lipid profiles within transformant organisms of Yarrowia lipolytica strain Y2224 that were comprising either pBY2 (expressing EgD9e) or pBY1-FAE (expressing IgD9eS).

Generation of Yarrowia lipolytica Strain Y2224

Strain Y2224 was isolated in the following manner: Yarrowia lipolytica ATCC #20362 cells from a YPD agar plate were streaked onto a minimal medium plate (75 mg/L each of uracil and uridine, 6.7 g/L YNB with ammonia sulfate, with- As shown in Table 8, the results demonstrated that EgD9e functioned with greater substrate conversion efficiency than IgD9eS, when converting LA to EDA.

Example 8

Construction and Functional Analysis of Yarrowia lipolytica Expression Vector pZuFmEgD9ES, Comprising a Synthetic Δ9 Elongase Gene (Derived from Euglena gracilis), Codon-Optimized for Expression in Yarrowia lipolytica (EgD9eS)

The present Example describes the expression of Yarrowia lipolytica vector pZuFmEgD9ES, comprising a chimeric FBAINm::EgD9ES::Pex20 gene, wherein EgD9eS is a synthetic Δ9 elongase derived from Euglena gracilis and codon-optimized for expression in Yarrowia. This analysis therefore required: (1) synthesis of EgD9eS; (2) construction and transformation of pZuFmEgD9ES into *Yarrowia lipolytica* strain Y2224; and (3) analysis of lipid profiles within transformant organisms of *Yarrowia lipolytica* strain Y2224 that were comprising pZuFmEgD9ES (expressing EgD9eS).

Synthesis of EgD9eS

The codon usage of the Δ9 elongase gene of *Euglena gracilis* (EgD9e; SEQ ID NOs:1 and 2) was optimized for expression in *Yarrowia lipolytica*, in a manner similar to that described in Example 5 and PCT Publication No. WO 2004/101753. Specifically, a codon-optimized Δ9 elongase gene (designated "EgD9eS"; SEQ ID NO:3) was designed, based on the coding sequence of EgD9e (i.e., from clone eeg1c.pk001.n5.f), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 117 bp of the 777 bp coding region were modified (15.1%) and 106 codons were optimized. FIG. 10 shows a comparison of the nucleotide sequences of EgD9e and EgD9eS. None of the modifications in the codon-optimized gene changed the amino acid sequence of the encoded protein (SEQ ID NO:2). The designed EgD9eS gene was synthesized by GenScript Corporation (Piscataway, N.J.) and cloned into pUC57 (GenBank Accession No. Y14837) to generate pEgD9S.

Generation of Construct pZuFmEgD9E (Comprising EgD9E) and pZuFmEgD9ES (Comprising EgD9ES)

Plasmid pZuFmEgD9ES (SEQ ID NO:53), comprising a chimeric FBAINm::EgD9ES::Pex20 gene, was constructed by replacing the Nco I/Not I fragment of pZUF17 (FIG. 7C; SEQ ID NO:121) with the Nco I/Not I fragment from pEgD9S comprising EgD9eS. The product of this ligation was auto-replicating expression vector pZuFmEgD9ES, which thereby contained the following components:

TABLE 9

Components Of Plasmid pZuFmEgD9ES (SEQ ID NO: 53)

| RE Sites And Nucleotides Within SEQ ID NO: 53 | Description Of Fragment And Chimeric Gene Components |
|---|---|
| Swa I/BsiW I (6067-318) | FBAINm::EgD9eS::Pex20, comprising: FBAINm: *Yarrowia lipolytica* FBAINm promoter (PCT Publication No. WO 2005/049805) EgD9eS: codon-optimized Δ9 elongase (SEQ ID NO: 3, described herein as EgD9eS), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | Ampicillin-resistance gene (Amp$^R$) for selection in *E. coli* |
| 3183-4487 | *Yarrowia* autonomous replication sequence (ARS18; GenBank Accession No. A17608) |
| 6020-4533 | *Yarrowia* Ura 3 gene (GenBank Accession No. AJ306421) |

Plasmid pZuFmEgD9E (SEQ ID NO:52), comprising a chimeric FBAINm::EgD9E::Pex20 gene, was synthesized in a similar manner using the pZUF17 plasmid backbone.

Functional Analysis of *Yarrowia lipolytica* Transformants Comprising pZuFmEgD9E and pZuFmEgD9ES Plasmid pZuFmEgD9E and pZuFmEgD9ES (comprising a chimeric FBAINm::EgD9e::Pex20 gene and FBAINm::EgD9eS::Pex20 gene, respectively) were transformed into strain Y2224 (the FOA resistant mutant from an autonomous mutation of the Ura3 gene of wildtype *Yarrowia* strain ATCC #20362; Example 7), as described in the General Methods. The transformants were selected on MM plates. After 2 days growth at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by transesterification, and subsequently analyzed with a Hewlett-Packard 6890 GC.

GC analyses showed that there were about 3.2% EDA (C20:2) of total lipids produced in all seven transformants with pZuFmEgD9E, wherein the average conversion efficiency of LA (C18:2) to EDA in these seven strains was determined to be about 18.3% (average; calculated as described in Example 4).

In contrast, GC analyses showed that there were about 3.6% EDA (C20:2) of total lipids produced in all seven transformants with pZuFmEgD9ES, wherein the average conversion efficiency of LA (C18:2) to EDA in these seven strains was determined to be about 20.1% (average). Thus, the experimental data demonstrated that the synthetic *Euglena gracilis* Δ9 elongase codon-optimized for expression in *Yarrowia lipolytica* (i.e., EgD9eS; SEQ ID NO:3) was about 16.2% more efficient elongating LA to EDA than the wildtype EgD9e gene (i.e., SEQ ID NO:1).

Example 9

Construction of *Yarrowia lipolytica* Expression Vector pY120 for Expression of the *Euglena gracilis* Δ9 Elongase (EgD9e)

The present Example describes construction of *Yarrowia lipolytica* vector pY120 for expression of EgD9e. Specifically, the NcoI/NotI DNA fragment from pKR906 (comprising EgD9e; from Example 4) was cloned into the NcoI/NotI DNA fragment from pY115 (FIG. 8; Example 5; comprising the *Yarrowia lipolytica* FBAINm promoter) to produce pY120 (SEQ ID NO:54; FIG. 11A). In this Figure, EgD9e is labeled as "eug el1".

Example 10

Construction of Soybean Expression Vector pKR912 for Expression of the *Euglena qracilis* Δ9 Elongase (EgD9e)

The present Example describes construction of soybean vector pKR912 for expression of EgD9e.

A starting plasmid pKR72 (ATCC Accession No. PTA-6019; SEQ ID NO:55), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene,* 25:179-188 (1983)), flanked by the T7 promoter and transcription terminator (T7prom/ HPT/T7term cassette), and a bacterial origin of replication (ori) for selection and replication in bacteria (e.g., *E. coli*). In addition, pKR72 also contains the HPT gene, flanked by the 35S promoter (Odell et al., *Nature,* 313:810-812 (1985)) and NOS 3' transcription terminator (Depicker et al., *J. Mol. Appl. Genet.,* 1:561-570 (1982)) (35S/HPT/NOS3' cassette) for selection in plants such as soybean. pKR72 also contains a NotI restriction site, flanked by the promoter for the α' subunit of β-conglycinin ("BCON Pro"; Beachy et al., *EMBO J.,* 4:3047-3053 (1985)) and the 3' transcription termination region of the phaseolin gene (Doyle et al., *J. Biol. Chem.,* 261:9228-9238 (1986)), thus allowing for strong tissue-specific expression in the seeds of soybean of genes cloned into the NotI site.

EgD9e was released from pKR906 (Example 4) by digestion with NotI and cloned into the NotI site of pKR72 to produce pKR912 (SEQ ID NO:56). A schematic depiction of pKR912 is shown in FIG. 11B; EgD9e is labeled as "eug el1" therein.

Example 11

Construction of Soybean Intermediate Cloning Vector pKR911 for Expression of the *Euglena gracilis* Δ9 Elongase (EgD9e)

The present Example describes construction of soybean vector pKR911 for expression of EgD9e.

Vector pKS102 (SEQ ID NO:57), previously described in PCT Publication No. WO 02/00905 (the contents of which are hereby incorporated by reference), contains a T7prom/HPT/ T7term cassette (described in Example 10), and a bacterial origin of replication (ori) for selection and replication in bacteria (e.g., *E. coli*).

Vector pKR197 (SEQ ID NO:58), previously described in PCT Publication No. WO 04/071467 (the contents of which are hereby incorporated by reference), was constructed by combining the AscI fragment from plasmid pKS102 (SEQ ID NO:57), containing the T7prom/HPT/T7term cassette and bacterial ori, with the AscI fragment of plasmid pKR72 (described in Example 10), containing the βcon/NotI/Phas cassette.

EgD9e was released from pKR906 (Example 4) by digestion with NotI and cloned into the NotI site of pKR197 to produce intermediate cloning vector pKR911 (SEQ ID NO:59). A schematic depiction of pKR911 is shown in FIG. 12A; EgD9e is labeled as "eug el1" therein.

Example 12 cDNA Synthesis and PCR of *Euglena gracilis* Δ8 Desaturase (EgD8)

The present Example describes the isolation of a Δ8 desaturase (designated as "EgD8") from *Euglena gracilis*, as disclosed in U.S. patent application Ser. No. 11/166,003 and No. 11/166,993 (corresponding with PCT Publications No. WO 06/012325 and No. WO 06/012326 [the contents of which are hereby incorporated by reference]). The isolation of this gene was desirable to enable co-expression of EgD9e and EgD8, to thereby permit expression of a Δ9 elongase/Δ8 desaturase pathway and enable accumulation of DGLA and/ or ETA from LA and/or ALA.

*Euglena gracilis* cDNA was synthesized from 765 ng of mRNA (Example 1) using the SuperScript™ Choice System for cDNA synthesis (Invitrogen™ Life Technologies, Carlsbad, Calif.) with the provided oligo(dT) primer according to the manufacturer's protocol. The synthesized cDNA was dissolved in 20 μL of water.

The *Euglena gracilis* Δ8 desaturase was amplified from cDNA using the conditions described below. Specifically, cDNA (1 μL) was combined with 50 pmol of Eg5-1 (SEQ ID NO:62), 50 pmol of Eg3-3 (SEQ ID NO:63), 1 μL of PCR nucleotide mix (10 mM, Promega, Madison, Wis.), 5 L of 10×PCR buffer (Invitrogen Corporation), 1.5 μL of MgCl$_2$ (50 mM, Invitrogen Corporation), 0.5 μL of Taq polymerase (Invitrogen Corporation) and water to 50 μL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 μL and a DNA band with molecular weight around 1.3 kB was observed. The remaining 45 μL of product was separated by agarose gel electrophoresis and the DNA band was purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using T7 (SEQ ID NO:64), M13-28Rev (SEQ ID NO:65), Eg3-2 (SEQ ID NO:66) and Eg5-2 (SEQ ID NO:67).

Thus, a DNA sequence for the *Euglena gracilis* Δ8 desaturase (i.e., Eg5) was obtained (SEQ ID NO:60). Translation of Eg5 gave rise to the protein sequence set forth in SEQ ID NO:61. For the purposes herein, "Eg5" is referred to throughout the remainder of this specification as "EgD8".

Although not detailed herein, a synthetic version of EgD8 was also created that was codon-optimized for expression in *Yarrowia lipolytica* (as disclosed in U.S. patent application Ser. No. 11/166,003 and No. 11/166,993 (corresponding with PCT Publications No. WO 06/012325 and No. WO 06/012326)), using the methodology described in Example 5, supra. This gene, designated as EgD8S, is described herein as SEQ ID NOs:68 and 69.

Example 13

Construction of Soybean Expression Vector pKR913 for Co-Expression of EgD9e and EgD8

The present Example describes construction of soybean vector pKR913 for co-expression of EgD9e and EgD8.

Vector pKS121 (SEQ ID NO:70), which was previously described in PCT Publication No. WO 02/00904 (the contents of which are hereby incorporated by reference), contains a NotI site flanked by the Kunitz soybean Trypsin Inhibitor (KTi) promoter (Jofuku et al., *Plant Cell,* 1:1079-1093 (1989)) and the KTi 3' termination region, the isolation of which is described in U.S. Pat. No. 6,372,965 (KTi/NotI/ KTi3' cassette).

Vector pKR457 (SEQ ID NO:71), which was previously described in PCT Publication No. WO 05/047479 (the contents of which are hereby incorporated by reference), is a derivative of pKS121 where the restriction sites upstream and downstream of the KTi/NotI/KTi3' cassette have been altered through a number of subcloning steps. Vector pKR457 also contains the soy albumin transcription terminator (GM-ALB TERM), which was previously described in PCT Publication No. WO 04/071467 (the contents of which are hereby incorporated by reference), downstream of the KTi terminator to lengthen and strengthen termination of transcription. In pKR457, the BamHI site upstream of the KTi promoter in the KTi/NotI/KTi3' cassette was removed and a new sequence (SEQ ID NO:72) was added containing a BsiWI, SalI, SbfI and HindIII site with the BsiWI site being closest to the 5' end of the KTi promoter.

In addition, the SalI site downstream of the KTi terminator in the KTi/NotI/KTi3' cassette from pKS121 was removed and a new sequence (SEQ ID NO:73) added containing an XbaI (closest to 3' end of KTi terminator), a BamHI site, the soy albumin transcription terminator sequence, a BsiWI site and another BamHI site. The albumin transcription terminator had been previously amplified from soy genomic DNA using primer oSalb-12 (SEQ ID NO:74), designed to introduce a BsiWI site at the 3' end of the terminator, and primer oSalb-13 (SEQ ID NO:75), designed to introduce a BamHI site at the 5' end of the terminator.

EgD8 (SEQ ID NO:60) was released from the pGEM®-T Easy Vector described in Example 12 by digestion with NotI and cloned into the NotI site of pKR457 to produce pKR680 (SEQ ID NO:76). Plasmid pKR680 was then digested with BsiWI and the fragment containing EgD8 was cloned into the BsiWI site of pKR911 (SEQ ID NO:59; Example 11) to produce pKR913 (SEQ ID NO:77). A schematic depiction of pKR913 is shown in FIG. 12B. EgD9e is labeled as "eug el1" and EgD8 is labeled as eug d8-sq5 therein.

Example 14

Construction of a Soybean Expression Vector for Co-Expression of EgD9e and EgD8

The present Example describes construction of a soybean vector for co-expression of EgD9e and EgD8. Specifically, plasmid pKR680 (SEQ ID NO:76; Example 13) is digested with BsiWI and the fragment containing EgD8 (SEQ ID NO:60) is cloned into the BsiWI site of pKR912 (SEQ ID NO:56; Example 10). In this way, EgD8 is co-expressed with EgD9e behind strong, seed-specific promoters.

Example 15

Construction of a Vector for Co-Expression of EgD9e and EgD8 with the *Mortierella alpina* Δ5 Desaturase (Mad5)

The present Example describes construction of a soybean vector for co-expression of EgD9e and EgD8, in addition with other PUFA genes (i.e., a Δ5 desaturase).

A soybean expression vector containing EgD8 (SEQ ID NO:60), EgD9e (SEQ ID NO:1) and the *Mortierella alpina* Δ5 desaturase (SEQ ID NO:78; "Mad5"), which is described in U.S. Pat. No. 6,075,183 and PCT Publication Nos. WO 04/071467 and WO 05/0479479 (the contents of which are hereby incorporated by reference), all under the control of strong seed-specific promoters, is constructed in the following way.

Through a number of sub-cloning steps, a sequence of DNA (SEQ ID NO:80) is effectively added into the SmaI site of vector pKR287 (which is described in PCT Publication No. WO 04/071467, the contents of which are hereby incorporated by reference), to produce pKR767 (SEQ ID NO:81). In this way, a SbfI restriction site is added to the 3' end of the leg1A transcription terminator of the Gy1/Mad5/legA2 cassette, which is described in PCT Publication Nos. WO 04/071467 and WO 05/0479479.

The Gy1/Mad5/legA2 cassette is released from pKR767 by digestion with SbfI and the resulting fragment is cloned into the SbfI site of the vector described in Example 14 to produce a new vector that co-expresses all three genes (i.e., EgD9e, EgD8 and Mad5) under control of strong seed-specific promoters.

Example 16

Co-Expressing a Soybean Expression Vector Comprising EgD9e, EgD8 and Mad5 with the *Saprolegnia diclina* Δ17 Desaturase (SdD17)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase). Whole plasmids, or purified AscI fragments from the plasmids containing the appropriate gene combinations, are used (as could any combination of either fragment of plasmid).

For instance, the vector described in Example 15 could be co-transformed with pKR328 (SEQ ID NO:82, described in PCT Publication No. WO 04/071467) containing the *Saprolegnia diclina* Δ17 desaturase (SdD17) under control of the annexin promoter and having a hygromycin resistance gene for selection in plants.

Similarly, the vector described in Example 15, could be co-transformed with pKR886 or pKR886r (FIG. 13A and FIG. 13B, respectively), two vectors similar to pKR328 but having the SAMS/ALS/ALS3' cassette (which is described in PCT Publication No. WO 04/071467) for selection in plants. Specifically, vectors pKR886 (SEQ ID NO:83) and pKR886r (SEQ ID NO:84) are made by cloning the PstI fragment, containing the Ann/Sdd17/BD30 cassette from pKR271 (SEQ ID NO:85, which is described in PCT Publication No. WO 04/071467) into the SbfI site of pKR226 (SEQ ID NO:86, which is described in PCT Publication No. WO 04/071467).

Example 17

Co-Expressing a Soybean Expression Vector Comprising EgD9e, EgD8 and Mad5 with SdD17 and *Arabidopsis* Fad3

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and Fad3).

The vector described in Example 15 could be co-transformed into soybeans with either pKR275 (SEQ ID NO:87, which is described in PCT Publication No. WO 04/071467 and has ATCC Accession Number PTA-4989) or pKR329 (SEQ ID NO:88, which is described in PCT Publication No. WO 04/07146). Plasmids pKR275 and pKR329 have ALS or hygromycin selection, respectively, and contain the KTi/Fad3/KTi3' gene cassette (which is described in PCT Publication No. WO 04/071467) in addition to the Ann/Sdd17/BD30 cassette. In this way, the *Arabidopsis* Fad3 gene could be co-expressed with the *Saprolegnia diclina* Δ17 desaturase (SdD17) behind strong, seed-specific promoters.

Example 18

Co-Expressing a Soybean Expression Vector Comprising EgD9e, EgD8 and Mad5 with SdD17 and *Fusarium moniliforme* Δ15 Desaturase (FmD15)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and a Δ15 desaturase).

The vector described in Example 15 could be co-transformed into soybeans with pKR585 (SEQ ID NO:89, which is described in PCT Publication No. WO 05/0479479 and has ATCC Accession No. PTA-6019), having hygromycin selection and containing the *Fusarium moniliforme* Δ15 desaturase (FmD15) under control of the KTi promoter.

The vector described in Example 15 could also be co-transformed into soybeans with pKR669, having ALS selection and containing the *Fusarium moniliforme* Δ15 desaturase under control of the KTi promoter in addition to the Ann/Sdd17/BD30 cassette. Plasmid pKR669 is produced in the following way. The KTi promoter:FmD15:KTi terminator cassette is released from plasmid pKR578 (SEQ ID NO:90, which is described in PCT Publication No. WO 05/0479479 and has ATCC Accession No. PTA-6280) by digestion with BsiWI and is cloned into the BsiWI site of plasmid pKR226 (SEQ ID NO:86, which is described in PCT Publication No. WO 04/071467), containing the ALS gene for selection, the T7prom/HPT/T7term cassette and the bacterial ori region, to produce pKR667 (SEQ ID NO:91). Plasmid pKR271 (SEQ ID NO:85, which is described in PCT Publication No. WO 04/071467) is digested with PstI and the fragment containing the *Saprolegnia diclina* Δ17 desaturase is cloned into the SbfI site of pKR667 to produce pKR669. In this way, the *Fusarium moniliforme* Δ15 desaturase could be co-expressed with the *Saprolegnia diclina* Δ17 desaturase behind strong, seed-specific promoters. A schematic depiction of pKR669 is shown in FIG. 14A.

The vector described in Example 15 could also be co-transformed into soybeans with pKR873 (SEQ ID NO:92), having ALS selection and containing the *Fusarium moniliforme* Δ15 desaturase (FmD15) under control of the soy albumin promoter (which is described in PCT Publication No. WO 04/071467) in addition to the Ann/Sdd17/BD30 cassette. Specifically, plasmid pKR873 is produced in the following way. The SA/NotI/SA3' cassette is amplified from plasmid pKR132 (SEQ ID NO:93, which is described in PCT Publication No. WO 04/071467) using PCR. Primer oSAlb-9 (SEQ ID NO:94) is designed to introduce XbaI and BsiWI sites at the 5' end of the promoter and primer oSAlb-2 (SEQ ID NO:95) is designed to introduce BsiWI and XbaI sites at the 3' end of the terminator. The resulting PCR fragment is subsequently cloned into pCR-Script AMP SK(+) (Stratagene Company, San Diego, Calif.) to produce pKR160 (SEQ ID NO:96). Plasmid pKR160 is then digested with BsiWI and the SA/NotI/SA3' cassette ligated into the BsiWI site of pKR124 (SEQ ID NO:97, which is described in PCT Publication No. WO 05/0479479) to produce pKR163 (SEQ ID NO:98). The NotI fragment from pY34 (SEQ ID NO:99, which is described in PCT Publication No. WO 05/0479479), containing the *Fusarium moniliforme* Δ15 desaturase, is cloned into the NotI site of pKR163 (SEQ ID NO:98) to produce pKR863 (SEQ ID NO:100). The SA/FmD15/SA3' cassette is released from plasmid pKR863 by digestion with BsiWI and is cloned into the BsiWI site of plasmid pKR226 (SEQ ID NO:86, which is described in PCT Publication No. WO 04/071467), containing the ALS gene for selection, the T7prom/HPT/T7term cassette and the bacterial ori region, to produce pKR869 (SEQ ID NO:101). Plasmid pKR271 (SEQ ID NO:85, which is described in PCT Publication No. WO 04/071467) is digested with PstI and the fragment containing the *Saprolegnia diclina* Δ17 desaturase is cloned into the SbfI site of pKR869 (SEQ ID NO:101) to thereby produce pKR873 (SEQ ID NO:92). In this way, the *Fusarium moniliforme* Δ15 desaturase could be co-expressed with the *Saprolegnia diclina* Δ17 desaturase behind strong, seed-specific promoters. A schematic depiction of pKR873 is shown in FIG. 14B.

Example 19

Co-Expressing a Soybean Expression Vector Comprising EgD9e, EgD8 and Mad5 with SdD17 and *Mortierella alpina* Elongase (MaELO)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and an elongase).

The vector described in Example 15 could also be co-transformed into soybeans with a vector having ALS selection and containing the *Mortierella alpina* elongase (which is described in PCT Publication Nos. WO 04/071467 and WO 00/12720) under control of the soy albumin promoter (which is described in PCT Publication No. WO 04/071467) in addition to the Ann/Sdd17/BD30 cassette. This plasmid could be produced in a similar way as described supra. For instance, the NotI fragment from pKR270 (SEQ ID NO:102, which is described in PCT Publication No. WO 04/071467), containing the *Mortierella alpina* elongase ("Maelo"), could be cloned into the NotI site of pKR163 (SEQ ID NO:98) to produce a vector having the SA/Maelo/SA3' cassette. The SA/Maelo/SA3' cassette could be released from that plasmid by digestion with BsiWI and could be cloned into the BsiWI site of plasmid pKR226 (SEQ ID NO:86, which is described in PCT Publication No. WO 04/071467), containing the ALS gene for selection, the T7prom/HPT/T7term cassette and the bacterial ori region, to produce a new plasmid. Plasmid pKR271 (SEQ ID NO:85, which is described in PCT Publication No. WO 04/071467) could then be digested with PstI and the fragment containing the *Saprolegnia diclina* Δ17 desaturase could be cloned into the SbfI site of the new plasmid containing the SA/Maelo/SA3' cassette. In this way, the *Mortierella alpina* elongase could be co-expressed with the *Saprolegnia diclina* Δ17 desaturase behind strong, seed-specific promoters.

Example 20

Co-Expressing a Soybean Expression Vector Comprising EgD9e, EgD8 and Mad5 with $C_{20/22}$ Elongases and Δ4 Desaturases The present Example describes a means of co-transforming the soybean expression vector described in Example 15 (expressing EgD9e, EgD8 and Mad5), along with other vectors expressing multiple different seed-specific promoter/ long chain PUFA-biosynthetic gene combinations (e.g., expressing $C_{20/22}$ elongases and Δ4 desaturases).

$C_{20/22}$ elongases (also identified as Δ5 elongases and/or EPA elongases) and/or Δ4 desaturases can also be co-expressed in soybean expression vectors similar to those described herein. For instance, a Δ4 desaturase from *Schizochytrium aggregatum* (described in PCT Publication No. WO 02/090493) or a Δ5 elongase from *Pavlova* (described in PCT Publication No. WO 04/071467), can be cloned into suitable soybean expression vectors such as those described in PCT Publication No. WO 04/071467. PCR primers designed to introduce NotI sites at the 5' and 3' ends of the Δ4 desaturase or Δ5 elongase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in PCT Publication No. WO 04/071467 or PCT Publication No. WO 05/047479, but not limited to these, should yield vectors suitable for expression and co-expression of the Δ4 desaturase and or Δ5 elongase in soybean.

Example 21

Preparation of *Eutreptiella* sp. CCMP389 Genomic DNA, RNA and cDNA

The present Example describes the preparation of genomic DNA, RNA and cDNA from *Eutreptiella* sp. CCMP389, which had been purchased from The Provasoli-Guillard National Center for Culture of Marine Phytoplankton (CCMP) (Bigelow Laboratory for Ocean Sciences, West Boothbay Harbor, Me.).

Preparation of RNA and Genomic DNA from *Eutreptiella* sp. CCMP389

Total RNA and genomic DNA were isolated from 1 liter of culture using Trizol reagent (Invitrogen, Carlsbad, Calif.), according to the manufacturer's protocol. Specifically, the cell pellet was resuspended in 0.75 mL of Trizol reagent, mixed with 0.5 mL of 0.5 mm glass beads, and homogenized in a Biospec mini beadbeater (Bartlesville, Okla.) at the highest setting for 3 min. The mixtures were centrifuged in an Eppendorf centrifuge for 30 sec at 14,000 rpm to remove debris and glass beads. The supernatant was extracted with 150 µl of 24:1 chloroform:isoamyl alcohol (Invitrogen). The upper aqueous phase was used for RNA isolation and the lower organic phase was used for DNA isolation.

For RNA isolation, the aqueous phase was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air-dried. In this way, 360 µg of total RNA were obtained.

For genomic DNA isolation, the lower organic phase was mixed with 75 µl of ethanol and incubated at room temperature for 5 min. The sample was then centrifuged at 5,000 rpm for 2 min in an Eppendorf centrifuge. The pellet was washed with 0.75 mL of 0.1 M sodium citrate:10% ethanol twice. Each time, the sample was incubated for 15 min at room temperature in the wash solution, followed by centrifugation at 5,000 rpm for 5 min at 4° C. The pellet was air-dried and re-dissolved in 300 µl of 8 mM NaOH. The pH of the sample was adjusted to 7.5 with 1 M HEPES. The genomic DNA was then further purified with a Qiagen PCR purification kit (Valencia, Calif.) exactly as described in the manufacturer's protocol. Thus, 40 µg of genomic DNA was isolated.

Preparation of cDNA from *Eutreptiella* sp. CCMP389

Double-stranded cDNA was generated, using the Creator™ SMART™ cDNA Library Construction Kit from BD Bioscience Clontech (Palo Alto, Calif.). Specifically, for first strand cDNA synthesis, 1 µl of the total RNA sample (1.2 µg) was mixed individually with 1 µl of SMART™ IV oligonucleotide (SEQ ID NO:103), 1 µl CDSIII/3' PCR primer (SEQ ID NO:104) and 2 µl of water. The mixture was heated to 75° C. for 5 min and cooled on ice for 5 min. To the sample was added 2 µl of 5× first strand buffer, 1 µl 20 mM DTT, 1 µl of dNTP mix (10 mM each of dATP, dCTP, dGTP and dTTP) and 1 µl of PowerScript reverse transcriptase. The sample was incubated at 42° C. for 1 hr.

The first strand cDNA synthesis mixture was used as template for amplification. Specifically, the reaction mixture contained 2 µl of the above first strand cDNA sample, 80 µl of water, 10 µl of 10× Advantage 2 PCR buffer, 2 µl 50×dNTP mix (10 mM each of dATP, dCTP, dGTP and dTTP), 2 µl of 5'-PCR primer (SEQ ID NO:105), 2 µl CDSIII/3'-PCR primer (SEQ ID NO:104) and 2 µl 50× Advantage 2 polymerase mix. PCR amplification was performed using the following conditions: 95° C. for 1 min, followed by 20 cycles of 95° C. for 10 sec and 68° C. for 6 min. Amplification products were purified with a Qiagen PCR purification kit following the manufacturer's protocol exactly. Purified products were eluted with 50 µl of water.

Example 22

Isolation of the Full-Length Δ9 Elongase from *Eutreptiella* sp. CCMP389

The present Example describes the identification of a partial cDNA fragment encoding a Δ9 elongase from *Eutreptiella* sp. CCMP389, by use of primers derived from conserved regions of the *Euglena gracilis* (EgD9e; Example 3) and *I. galbana* (IgD9e) Δ9 elongase sequences. Then, based on the sequence of the partial cDNA fragment, the 5' and 3' ends of the gene were isolated. This enabled assembly of a contig (SEQ ID NO:17), extending 51 bases upstream of the *Eutreptiella* sp. CCMP389 Δ9 elongase translation initiation 'ATG' codon and 662 bp beyond the Δ9 elongase termination codon.

Identification of a cDNA Fragment Encoding a Partial Δ9 Elongase from *Eutreptiella* sp. CCMP389

*Eutreptiella* sp. CCMP389 was analyzed for the presence of a Δ9 elongase. Design of degenerate primers suitable to isolate the *Eutreptiella* sp. CCMP389 Δ9 elongase was based on the identification of several stretches of conserved amino acid sequences common to both EgD9e (SEQ ID NO:2) and IgD9e (SEQ ID NO:8), when an alignment of the two elongases was produced using the method of Clustal W (slow, accurate, Gonnet option; Thompson et al., *Nucleic Acids Res.*, 22:4673-4680 (1994)) of the MegAlign™ program of DNASTAR software (Clustal W alignment not shown herein, in lieu of Clustal V alignment of EgD9e and IgD9e provided as FIG. 4).

Based on this alignment, the following set of degenerate oligonucleotides were designed to amplify a portion of the coding region of the Δ9 elongase gene from *Eutreptiella* sp. CCMP389, as shown in Table 10.

TABLE 10

Degenerate Oligonucleotides Used To Amplify The Δ9 Elongase Gene From *Eutreptiella* sp. CCMP389

| Primer | Nucleotide Sequence | Amino Acid Sequence | Position Within SEQ ID NO: 2 (EgD9e) |
|---|---|---|---|
| EuEF3 | YTNCARTTYTTYCAYCA YTT (SEQ ID NO: 106) | LQFFHHL (SEQ ID NO: 107) | 150-156 |
| EuER3 | TTRAAYTGDATDATYTG CAT (SEQ ID NO: 108) | MQIIQFN (SEQ ID NO: 109) | 210-216 |

[Note: The nucleic acid degeneracy code used for SEQ ID NOs: 106 and 108 was as follows: R = A/G; Y = C/T; D = G/A/T; and N = A/C/T/G.]

The reaction mixture contained 1 µl of 1:20 diluted cDNA, 5 µl each of the forward and reverse primers (20 µM), 14 µl water and 25 µl of TaKaRa ExTaq 2× premix (TaKaRa Bio, Mountain View, Calif.). PCR amplification was performed using the following parameters: 94° C. for 1 min, then 35 cycles of 94° C. for 20 sec, 55° C. for 20 sec, and 72° C. for 1 min, followed by a final elongation cycle at 72° C. for 5 min.

Agarose gel analysis of the PCR products showed that a ~200 bp fragment was obtained. The fragments were purified with a Qiagen PCR purification kit, cloned into pCR2.1-TOPO (Invitrogen) and sequenced. The resultant sequence (SEQ ID NO:13), when translated, had homology with the known Δ9 elongase from *Isochrysis galbana* (IgD9e; SEQ ID NO:8), based on BLAST program analysis (Basic Local Alignment Search Tool; Altschul, S. F., et al., *J. Mol. Biol.*, 215:403-410 (1993); Example 3).

Isolation of the 5'-End Sequence of the *Eutreptiella* sp. CCMP389 Δ9 Elongase

Double-stranded cDNA of *Eutreptiella* sp. CCMP389 (Example 21) was used as template in two separate rounds of PCR amplification. In the first round of PCR amplification, the oligonucleotide primers consisted of a gene specific oligonucleotide (i.e., 389Elo-5-1 [SEQ ID NO:110]) and the generic oligonucleotide 5'-PCR primer (SEQ ID NO:105) from the BD-Clontech Creator™ SMART™ cDNA Library Kit. The PCR amplifications were carried out in a 50 µl total volume, comprising: 1 µl of 1:10 diluted *Eutreptiella* sp. CCMP389 cDNA as template, 1 µl of each primer (20 µM), 22 µl water and 25 µl TaKaRa ExTaq 2× premix. Amplification was carried out at 94° C. for 90 sec, then 30 cycles of 94° C. for 30 sec, 55° C. for 30 sec and 72° C. for 1 min, followed by a final elongation cycle at 72° C. for 7 min.

The second round of PCR amplification used 1 µl of diluted product (1:50) from the first round PCR reaction as template. Primers consisted of a gene specific oligonucleotide (i.e., 389Elo-5-2 (SEQ ID NO:111)) and the oligonucleotide DNR CDS 5'-2 (SEQ ID NO:112). Amplification was conducted as described above.

The products of the second round PCR reaction were electrophoresed in 1% (w/v) agarose and appeared as a diffused band spanning the size range of 200 to 800 bp. Products between 400 bp to 600 bp were isolated using a Qiagen Gel purification kit according to the manufacturer's protocol, cloned into pCR2.1-TOPO (Invitrogen), and transformed into *E. coli*. Transformants were selected on LB agar containing ampicillin (100 µg/mL).

Sequence analysis of the plasmid DNA from one transformant comprising the 5' region of the putative Δ9 elongase cDNA revealed a fragment of 406 bp (i.e., 5'-cDNA fragment 1; SEQ ID NO:14). This fragment extended to near the gene's 'ATG' translation initiation codon, but neither the start codon nor the first 20 to 30 amino acids were included in SEQ ID NO:14.

An additional oligonucleotide (i.e., 389Elo-54 (SEQ ID NO:113)) was then designed to obtain the complete 5' end of the gene by PCR, based on the sequence of 5'-cDNA fragment 1 (SEQ ID NO:14). The reaction mixture and amplification conditions were identical to those used for the second round of PCR above, except that primer 389Elo-5-2 was replaced with 389Elo-5-4. When analyzed by agarose gel electrophoresis, PCR products again appeared as a diffused band between 200 and 800 bp and fragments with a size of 200 to 500 bp were isolated, cloned and transformed as described above.

Sequence analysis of the plasmid DNA from one transformant comprising the 5' region of the putative Δ9 elongase cDNA revealed a fragment of 197 bp (5'-cDNA fragment 2; SEQ ID NO:15). This included the 5'-end of the cDNA and 51 bp of upstream untranslated region.

Isolation of the 3'-End of the *Eutreptiella* sp. CCMP389 Δ9 Elongase

The 3' end of the putative Δ9 delta elongase was also isolated by PCR amplification using cDNA as template. The methodology was as described above for isolation of the 5' end; however, the primers used on both the first and second round of PCR amplification were as shown below in Table 11 and were 10 µM instead of 20 µM. Additionally, the final elongation cycle at 72° C. was decreased from 7 min to 5 min.

TABLE 11

Oligonucleotide Primers Used For 3' cDNA Isolation

| PCR Amplification | Gene Specific Oligonucleotide | Generic Oligonucleotide |
|---|---|---|
| 1st Round | 389EIo-3-1 (SEQ ID NO: 114) | CDSIII/3' PCR primer (SEQ ID NO: 104) |
| 2nd Round | 389EIo-3-2 (SEQ ID NO: 115) | CDSIII/3' PCR primer (SEQ ID NO: 104) |

*CDSIII/3' PCR primer was supplied in Clontech's Creator ™ SMART ™ cDNA Library Construction Kit.

A ~1 kB DNA fragment was generated from the $2^{nd}$ round PCR amplication, which was purified with a Qiagen PCR purification kit, cloned into pCR2.1-TOPO, transformed and sequenced. Sequence analysis of several clones showed that the ~1 kB DNA fragment contained the 3'-region of the putative Δ9 elongase cDNA, including the polyA tail. The 920 bp assembled contig sequence of the 3'-region is shown as SEQ ID NO:16.

Assembly of the Full-Length Δ9 Elongase Sequence from *Eutreptiella* sp. CCMP389

Assembly of the original partial cDNA fragment (SEQ ID NO:13), the two 5' cDNA fragments (SEQ ID NOs:14 and 15) and 3'-cDNA fragment (SEQ ID NO:16) resulted in the complete sequence of the Δ9 elongase from *Eutreptiella* sp. CCMP389, plus 51 bp of 5' untranslated region and 662 bp of 3' untranslated region (SEQ ID NO:17; 1504 bp). The coding region is 792 bp long and encodes a protein of 263 amino acids (SEQ ID NO:5). SEQ ID NO:4 is the nucleotide sequence of the coding sequence of *Eutreptiella* sp. CCMP389 Δ9 elongase (designated herein as E389D9e).

Comparison of the Δ9 Elongase Sequence of *Eutreptiella* sp. CCMP389 (E389D9e) to Known a 9 Elongases Identity of SEQ ID NO:5 (i.e., E389D9e) was determined by conducting BLAST searches for similarity to sequences contained in the BLAST "nr" database (Example 3). The results of the BLAST comparison summarizing the sequence to which SEQ ID NO:5 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, the amino acid fragment described herein as SEQ ID NO:5 shared 38% identity and 56% similarity with IgD9e, the Δ9 elongase of *Isochrysis galbana* (SEQ ID NO:8), with an expectation value of 2E43. Similarly, E389D9e is 33.1% identical to IgD9e using the Clustal V method and E389D9e is 65.1% identical to EgD9e using the Clustal V method (FIG. 2). Sequence percent identity calculations performed by the Clustal V method (Higgins, D. G. and Sharp, P. M., *Comput. Appl. Biosci.*, 5:151-153 (1989); Higgins et al., *Comput. Appl. Biosci.*, 8:189-191 (1992)) were done using the MegAlign™ v6.1 program of the LASERGENE bioinformatics computing suite with the default parameters for pairwise alignment (KTUPLE=1, GAP PENALTY=3, WINDOW=5, DIAGONALS SAVED=5 and GAP LENGTH PENALTY=10).

Example 23

Construction and Functional Analysis of *Yarrowia lipolytica* Expression Vector pFBAIN-389Elo (Comprising the *Eutreptiella* sp. CCMP389 Δ9 Elongase (E389D9e)) in *Yarrowia lipolytica* Strain Y2224

The present Example describes synthesis of *Yarrowia lipolytica* expression vector pFBAIN-389Elo (comprising a chimeric FBAINm::E389D9e::Pex20 gene). Delta-9 elongase activity of E389D9e when expressed in *Yarrowia lipolytica* strain Y2224 was subsequently determined.

Construction of *Yarrowia lipolytica* Expression Vector pFBAIN-389Elo

Oligonucleotides 389Elo-F and 389Elo-R1 (SEQ ID NOs: 116 and 117, respectively) were used as primers to amplify the full length cDNA of E389D9e (SEQ ID NO:4). The PCR reactions, with *Eutreptiella* sp. CCMP389 cDNA (Example 21) as template, were individually carried out in a 50 µl total volume comprising: 1 µl each of 20 µM forward and reverse primers, 1 µl cDNA, 10 µl 5×PCR buffer, 1 µl dNTP mix (10 µM each), 35 µl water and 1 µl Phusion polymerase (New England Biolabs, Inc., Ipswich, Mass.). Amplification was carried out at 98° C. for 1 min, then 30 cycles of 98° C. for 10 sec, 55° C. for 10 sec, and 72° C. for 30 sec, followed by a final elongation cycle at 72° C. for 5 min. The PCR product was digested with NcoI and EarI to generate a ~210 bp fragment that contained the 5' region of the Δ9 elongase cDNA. It was also digested with EarI and NotI to generate a ~600 bp fragment that contained the 3' region of the cDNA. The NcoI/EarI and the EarI/NotI digested fragments were purified following gel electrophoresis in 1% (w/v) agarose.

The NcoI/EarI and the EarI/NotI Δ9 elongase digested fragments were directionally ligated with NcoI/NotI digested pFBAIN-MOD-1 (SEQ ID NO:118), such that the E389D9e gene was under the control of the *Y. lipolytica* FBAINm promoter and the PEX20-3' terminator region. Specifically, the ligation reaction contained: 10 µl 2× ligation buffer, 1 µl T4 DNA ligase (Promega), 4 µl each of the ~210 bp and the ~600 bp fragment (~300 ng each), and 1 µl pFBAIN-MOD-1 (~150 ng). The reaction mixture was incubated at room temperature for 2 hrs and used to transform *E. coli* Top10 competent cells (Invitrogen). Plasmid DNA from transformants was recovered using a Qiagen Miniprep kit. Correct clones were identified by restriction mapping and the final construct was designated "pFBAIN-389Elo".

Thus, pFBAIN-389Elo (FIG. 15A; SEQ ID NO:119) thereby contained the following components:

TABLE 12

Components Of Plasmid pFBAIN-389Elo (SEQ ID NO: 119)

| RE Sites And Nucleotides Within SEQ ID NO: 119 | Description Of Fragment And Chimeric Gene Components |
|---|---|
| BglII-BsiWI (6040-301) | FBAINm::E389D9e:: Pex20, comprising: FBAINm: *Yarrowia lipolytica* FBAINm promoter (PCT Publication No. WO 2005/049805) E389D9e: *Eutreptiella* sp. CCMP389 Δ9 elongase (SEQ ID NO: 4 described herein) Pex20: Pex20 terminator sequence of *Yarrowia* Pex20 gene (GenBank Accession No. AF054613) |
| PacI-BglII (4533-6040) | *Yarrowia* Ura 3 gene (GenBank Accession No. AJ306421) |
| (3123-4487) | *Yarrowia* autonomous replication sequence (ARS18; GenBank Accession No. A17608) |
| (2464-2864) | f1 origin |
| (1424-2284) | Ampicillin-resistance gene (Amp$^R$) for selection in *E. coli* |
| (474-1354) | ColE1 plasmid origin of replication |

Functional Analysis of *Yarrowia lipolytica* Transformants Comprising pFBAIN-389Elo Five (5) individual clones of pFBAIN-389Elo (comprising E389D9e) and control plasmid pFBAIN-MOD-1 were transformed into *Yarrowia lipolytica* strain Y2224 (Example 7) as described in the General Methods. The cells were plated onto MM plates lacking uracil and maintained at 30° C. for 2 to 3 days. Then, cells from each plate were scraped off, lipids were extracted, and fatty acid methyl esters were prepared by transesterification, and subsequently analyzed with a Hewlett-Packard 6890 GC.

GC analyses showed that EDA was produced in all five of the transformants comprising pFBAIN-389Elo, while no EDA was produced in the control strain (Table 13). Fatty acids are identified as 18:2 (LA) and 20:2 (EDA); and the composition of each is presented as a % of the total fatty acids. The conversion efficiency was calculated according to the following formula: ([product]/[substrate+product])*100, where 'product' includes the immediate product and all products in the pathway derived from it.

TABLE 13

Lipid Composition In *Yarrowia lipolytica* Strain Y2224 Engineered To Over-Express *Eutreptiella* sp. CCMP389 Δ9 Elongase (E389D9e)

| Plasmid | Clone | C18:2 | C20:2 | Conversion Efficiency |
|---|---|---|---|---|
| pFBAIN-MOD-1 | 1 | 17.4 | 0 | 0 |
| pFBAIN-389EIo | 1 | 13.49 | 2.16 | 13.80 |
|  | 2 | 13.16 | 1.79 | 11.97 |
|  | 3 | 14.11 | 1.92 | 11.98 |
|  | 4 | 15.55 | 0.78 | 4.78 |
|  | 5 | 13.24 | 1.79 | 11.91 |

The results shown above confirmed that the cloned cDNA from *Eutreptiella* sp. CCMP389, described herein as SEQ ID NOs:4 and 5, efficiently desaturated LA to EDA and thus functioned as a Δ9 elongase.

Example 24

Construction and Functional Analysis of *Yarrowia lipolytica* Expression Vector pZUFE389S, Comprising a Synthetic Δ9 Elongase Gene (Derived from *Eutreptiella* sp. CCMP389), Codon-Optimized for Expression in *Yarrowia lipolytica* (E389D9eS)

The present Example describes the functional expression of *Yarrowia lipolytica* vector pZUFE389S, comprising a chimeric FBAIN::E389D9eS::Pex20 gene, wherein E389D9eS is a synthetic Δ9 elongase derived from *Eutreptiella* sp. CCMP389 and codon-optimized for expression in *Yarrowia*. This analysis therefore required: (1) synthesis of E389D9eS; (2) construction and transformation of pZUFE389S into *Yarrowia lipolytica* strain Y2224; and (3) analysis of lipid profiles within transformant organisms of *Yarrowia lipolytica* strain Y2224 that were comprising pZUFE389S (expressing E389D9eS).

Synthesis of E389D9eS

The codon usage of the Δ9 elongase gene of *Eutreptiella* sp. CCMP389 (E389D9e; SEQ ID NOs:4 and 5) was optimized for expression in *Yarrowia lipolytica*, in a manner similar to that described in Example 5, Example 8 and PCT Publication No. WO 2004/101753. Specifically, a codon-optimized Δ9 elongase gene (designated "E389D9eS", SEQ ID NO:6) was designed, based on the coding sequence of E389D9e (SEQ ID NO:4), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 128 bp of the 792 bp coding region (including the stop codon) were modified (16.2%) and 113 codons were optimized. The GC content was increased from 45.7% within the wildtype gene (i.e., E389D9e) to 50.1% within the synthetic gene (i.e., E389D9eS). A NcoI site and NotI sites were incorporated around the translation initiation codon and after the stop codon of E389D9eS, respectively. FIG. 16 shows a comparison of the nucleotide sequences of E389D9e and E389D9eS. None of the modifications in the codon-optimized gene changed the amino acid sequence of the encoded protein (SEQ ID NO:5).

The designed E389D9eS gene (SEQ ID NO:6) was synthesized by GenScript Corporation (Piscataway, N.J.) and cloned into pUC57 (GenBank Accession No. Y14837) to generate pE389S (SEQ ID NO:120).

Generation of Construct pZUFE389S, Comprising E389D9eS

Plasmid pZUFE389S (FIG. 15B; SEQ ID NO:122) was constructed by replacing the Nco I/Not I fragment of pZUF17 (FIG. 7C; SEQ ID NO:121) with the Nco I/Not I fragment from pE389S (SEQ ID NO:120) comprising E389D9eS. The product of this ligation was pZUFE389S, which thereby contained the following components:

TABLE 14

Components Of Plasmid pZUFE389S (SEQ ID NO: 122)

| RE Sites And Nucleotides Within SEQ ID NO: 122 | Description Of Fragment And Chimeric Gene Components |
|---|---|
| EcoR I/BsiW I (6857-1112) | FBAIN::E389D9eS::Pex20, comprising: FBAIN: *Yarrowia lipolytica* FBAIN promoter (PCT Publication No. WO 2005/049805) E389D9eS: codon-optimized Δ9 elongase (SEQ ID NO: 6), derived from *Eutreptiella* sp. CCMP389 Pex20: Pex20 terminator sequence of *Yarrowia* Pex20 gene (GenBank Accession No. AF054613) |
| 2148-1268 | ColE1 plasmid origin of replication |
| 3078-2218 | Ampicillin-resistance gene (Amp$^R$) for selection in *E. coli* |
| 3977-5281 | *Yarrowia* autonomous replication sequence (ARS18; GenBank Accession No. A17608) |
| 6835-5324 | *Yarrowia* Ura 3 gene (GenBank Accession No. AJ306421) |

Functional Analysis of *Yarrowia lipolytica* Transformants Comprising pZUFE389S

Plasmid pZUFE389S was transformed into strain Y2224 (the FOA resistant mutant from an autonomous mutation of the Ura3 gene of wildtype *Yarrowia* strain ATCC #20362; Example 7), as described in the General Methods. The transformants were selected on MM plates. After 2 days growth at 30° C., transformants were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.2% C20:2 (EDA) of total lipids produced in all 12 transformants, wherein the conversion efficiency of C18:2 to C20:2 in these 12 strains was determined to be about 12% (average; calculated as described in Example 23).

Example 25

Construction of Alternate Soybean Expression Vectors for Expression of *Euglena gracilis* (EgD9e or EgD9eS) and/or *Eutreptiella* sp. CCMP389 (E389D9e or E389D9eS) Δ9 Elongases It will be appreciated by the skilled person that the above Examples are intended to be illustrative but are not limiting. For example, any of the soybean expression vectors created above in Examples 10, 11 and 13-15 for expression of EgD9e could be readily modified to instead enable expression (or co-expression) of EgD9eS, E389D9e and/or E389D9eS using methods similar to, but not limited to, the methods described herein. PCR primers designed to introduce NotI sites at the 5' and 3' ends of the Δ9 elongase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in PCT Publication Nos. WO 2004/071467 or WO 2005/047479 (but not limited to these), would yield vectors suitable for expression of Δ9 elongases in soybean.

Furthermore, in addition to the genes, promoters, terminators and gene cassettes described herein, one skilled in the art can appreciate that other promoter/gene/terminator cassette combinations can be synthesized in a way similar to, but not limited to, that described herein for expression of EgD9e, EgD9eS, E389D9e and/or E389D9eS. Similarly, it may be desirable to express other PUFA genes (such as those described below in Table 17), for co-expression with any of the Δ9 elongases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 15) and a transcription terminator (such as those listed in, but not limited to, Table 16) is used to clone the desired gene. NotI sites can be added to a gene of interest such as those listed in, but not limited to, Table 17 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations (along with suitable selectable marker cassettes), in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 15

Seed-specific Promoters

| Promoter | Organism | Promoter Reference |
|---|---|---|
| Beta-conglycinin α'-subunit | soybean | Beachy et al., EMBO J., 4: 3047-3053 (1985) |
| kunitz trypsin inhibitor | soybean | Jofuku et al., Plant Cell, 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet., 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet., 225: 148-157 (1991) |

TABLE 16

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 17

PUFA Biosynthetic Pathway Genes

| Gene | Organism | Reference |
|---|---|---|
| Δ6 desaturase | Saprolegnia diclina | WO 2002/081668 |
| Δ6 desaturase | Mortierella alpina | U.S. Pat. No. 5,968,809 |
| elongase | Mortierella alpina | WO 2000/12720; U.S. Pat. No. 6,403,349 |
| Δ5 desaturase | Mortierella alpina | U.S. Pat. No. 6,075,183 |
| Δ5 desaturase | Saprolegnia diclina | WO 2002/081668 |
| Δ15 desaturase | Fusarium moniliforme | WO 2005/047479 |
| Δ17 desaturase | Saprolegnia diclina | WO 2002/081668 |
| elongase | Thraustochytrium aureum | WO 2002/08401; U.S. Pat. No. 6,677,145 |
| elongase | Pavlova sp. | Pereira et al., Biochem. J., 384: 357-366 (2004) |
| Δ4 desaturase | Schizochytrium aggregatum | WO 2002/090493 |
| Δ9 elongase | Isochrysis galbana | WO 2002/077213 |
| Δ8 desaturase | Euglena gracilis | WO 2000/34439; U.S. Pat. No. 6,825,017; WO 2004/057001; WO 2006/012325 |
| Δ8 desaturase | Acanthamoeba castellanii | Sayanova et al., FEBS Lett., 580: 1946-1952 (2006) |
| Δ8 desaturase | Pavlova salina | WO 2005/103253 |
| Δ8 desaturase | Pavlova lutheri | U.S. Provisional Application No. 60/795,810 |
| Δ8 desaturase | Tetruetreptia pomquetensis CCMP1491 | U.S. Provisional Application No. 60/853,563 |
| Δ8 desaturase | Eutreptiella sp. CCMP389 | U.S. Provisional Application No. 60/853,563 |
| Δ8 desaturase | Eutreptiella cf_gymnastica CCMP1594 | U.S. Provisional Application No. 60/853,563 |

Example 26

Transformation of Somatic Soybean Embryo Cultures

Culture Conditions:

Soybean embryogenic suspension cultures (cv. Jack) can be maintained in 35 mL liquid medium SB196 (see recipes below) on rotary shaker, 150 rpm, 26° C. with cool white fluorescent lights on 16:8 h day/night photoperiod at light intensity of 60-85 μE/m2/s. Cultures are subcultured every seven days to two weeks by inoculating approximately 35 mg of tissue into 35 mL of fresh liquid SB196 (the preferred subculture interval is every seven days).

Soybean embryogenic suspension cultures can be transformed with the plasmids and DNA fragments described earlier by the method of particle gun bombardment (Klein et al., Nature (London), 327:70-73 (1987); U.S. Pat. No. 4,945,050). A DuPont Biolistic™ PDS1000/HE instrument (helium retrofit) would be used for all transformations.

Soybean Embryogenic Suspension Culture Initiation:

Soybean cultures are initiated twice each month with five-seven days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for eight weeks. After this time, secondary embryos are cut and placed into SB196 liquid media for seven days.

Preparation of DNA for Bombardment:

Either an intact plasmid or a DNA plasmid fragment containing the genes of interest and the selectable marker gene can be used for bombardment. Fragments from plasmids such pKR274 (ATCC Accession No. PTA-4988), pKR685 (ATCC Accession No. PTA-6047) or pKR681 (ATCC Accession No. PTA-6046) and/or other expression plasmids can be obtained by gel isolation of digested plasmids. In each case, 100 µg of plasmid DNA can be used in 0.5 mL of the specific enzyme mix described below. Plasmids could be digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 h. The resulting DNA fragments could be separated by gel electrophoresis on 1% SeaPlaque® GTG agarose (BioWhitaker Molecular Applications) and the DNA fragments containing PUFA biosynthetic genes could be cut from the agarose gel. DNA can be purified from the agarose using the GELase® digesting enzyme following the manufacturer's protocol. Alternatively, whole plasmids or a combination of whole plasmid with fragment could be used.

A 50 µL aliquot of sterile distilled water containing 3 mg of gold particles (3 mg gold) can be added to 5 µL of a 1 µg/µL DNA solution (either intact plasmid or DNA fragment prepared as described above), 50 µL 2.5 M $CaCl_2$ and 20 µL of 0.1 M spermidine. The mixture is shaken 3 min on level 3 of a vortex shaker and spun for 10 sec in a bench microfuge. After a wash with 400 µL 100% ethanol, the pellet is suspended by sonication in 40 µL of 100% ethanol. Five µL of DNA suspension is dispensed to each flying disk of the Biolistic PDS1000/HE instrument disk. Each 5 µL aliquot contained approximately 0.375 mg gold per bombardment (e.g., per disk).

Tissue Preparation and Bombardment with DNA:

Approximately 150-200 mg of seven day old embryonic suspension cultures are placed in an empty, sterile 60×15 mm petri dish and the dish is covered with plastic mesh. Tissue is bombarded one or two shots per plate with the membrane rupture pressure set at 1100 PSI and the chamber evacuated to a vacuum of 27-28 inches of mercury. Tissue is placed approximately 3.5 inches from the retaining/stopping screen.

Selection of Transformed Embryos:

Transformed embryos are selected either using hygromycin (i.e., when the hygromycin B phosphotransferase (HPT) gene was used as the selectable marker) or chlorsulfuron (i.e., when the acetolactate synthase (ALS) gene was used as the selectable marker).

Hygromycin (HPT) Selection:

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection:

Following bombardment, the tissue is divided between two flasks with fresh SB196 media and cultured as described above. Six to seven days post-bombardment, the SB196 is exchanged with fresh SB196 containing selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue needs to be regenerated.

Embryo Maturation:

Transformed embryogenic clusters from production transformation were cultured for four-six weeks (one-three weeks for model system) in multiwell plates as described above at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2 s$. After this time embryo clusters were removed to a solid agar media, SB166, for one-two weeks (1 week for model system) and then subcultured to SB103 medium for 3-4 weeks to mature embryos. After maturation on plates in SB103, individual embryos were removed from the clusters, dried and screened for alterations in their fatty acid compositions as described supra. When desired, plants were obtained from some events as described below.

Alternatively, in some model system experiments, embryos were matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters were removed to 35 mL of SB228 (SHaM liquid media) in a 250 mL Erlenmeyer flask. Tissue was maintained in SHaM liquid media on a rotary shaker at 130 rpm and 26° C. with cool white fluorescent lights on a 16:8 hr day/night photoperiod at a light intensity of 60-85 µE/m2/s for 2-3 weeks as embryos matured. Embryos grown for 2-3 weeks in SHaM liquid media were equivalent in size and fatty acid content to embryos cultured on SB166/SB103 for 5-8 weeks.

After maturation in SHaM liquid media, individual embryos were removed from the clusters, dried and screened for alterations in their fatty acid compositions as described supra. When desired, plants were obtained from some events as described below.

Embryo Desiccation and Germination:

Matured individual embryos can be desiccated by placing them into an empty, small petri dish (35×10 mm) for approximately four-seven days. The plates are sealed with fiber tape (creating a small humidity chamber). Desiccated embryos can be planted into SB71-4 medium where they are left to germinate under the same culture conditions described above. Germinated plantlets are removed from germination medium and rinsed thoroughly with water and then planted in Redi-Earth in a 24-cell pack tray, covered with clear plastic dome. After two weeks the dome is removed and plants hardened off for a further week. If plantlets look hardy, they are transplanted to a 10 inch pot of Redi-Earth with up to 3 plantlets per pot. After ten to sixteen weeks, mature seeds can be harvested, chipped and analyzed for fatty acids as described above.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

| FN Lite Stock Solutions | | |
|---|---|---|
| Stock Number | 1000 mL | 500 mL |
| 1 - MS Fe EDTA 100x Stock | | |
| $Na_2$ EDTA* | 3.724 g | 1.862 g |
| $FeSO_4$—$7H_2O$ | 2.784 g | 1.392 g |
| 2 - MS Sulfate 100x stock | | |
| $MgSO_4$—$7H_2O$ | 37.0 g | 18.5 g |
| $MnSO_4$—$H_2O$ | 1.69 g | 0.845 g |
| $ZnSO_4$—$7H_2O$ | 0.86 g | 0.43 g |
| $CuSO_4$—$5H_2O$ | 0.0025 g | 0.00125 g |
| 3 - FN Lite Halides 100x Stock | | |
| $CaCl_2$—$2H_2O$ | 30.0 g | 15.0 g |
| KI | 0.083 g | 0.0715 g |
| $CoCl_2$—$6H_2O$ | 0.0025 g | 0.00125 g |
| 4 - FN Lite P, B, Mo 100x Stock | | |
| $KH_2PO_4$ | 18.5 g | 9.25 g |
| $H_3BO_3$ | 0.62 g | 0.31 g |
| $Na_2MoO_4$—$2H_2O$ | 0.025 g | 0.0125 g |

*Add first, dissolve in dark bottle while stirring

SB1 Solid Medium (per liter): 1 package MS salts (Gibco/BRL—Cat. No. 11117-066), 1 mL B5 vitamins 1000× stock, 31.5 g sucrose, 2 mL 2,4-D (20 mg/L final concentration), pH 5.7, 8 g TC agar SB 166 Solid Medium (per liter): 1 package MS salts (Gibco/BRL—Cat. No. 11117-066), 1 mL B5 vitamins 1000× stock, 60 g maltose, 750 mg $MgCl_2$ hexahydrate, 5 g activated charcoal, pH 5.7, 2 g gelrite SB 103 Solid Medium (per liter): 1 package MS salts (Gibco/BRL—Cat. No. 11117-066), 1 mL B5 vitamins 1000× stock, 60 g maltose, 750 mg MgCl2 hexahydrate, pH 5.7, 2 g gelrite SB 71-4 Solid Medium (per liter): 1 bottle Gamborg's B5 salts w/sucrose (Gibco/BRL—Cat. No. 21153-036), pH 5.7, 5 g TC agar 2,4-D Stock: Obtain premade from Phytotech Cat. No. D 295—concentration 1 mg/mL B5 Vitamins Stock (per 100 mL): 10 g myo-inositol, 100 mg nicotinic acid, 100 mg pyridoxine HCl, 1 g thiamine. Store aliquots at −20° C.; if the solution does not dissolve quickly enough, apply a low level of heat via the hot stir plate.

Chlorsulfuron Stock: 1 mg/mL in 0.01 N Ammonium Hydroxide

To induce somatic embryos, cotyledons, 3-5 mm in length dissected from surface sterilized, immature seeds of the soybean cultivar A2872, can be cultured in the light or dark at 26° C. on an appropriate agar medium for six-ten weeks. Somatic embryos, which produce secondary embryos, are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 h day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al., Nature (London), 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al., Nature, 313:810-812 (1985)), the hygromycin B phosphotransferase gene from plasmid pJR225 (from E. coli; Gritz et al., Gene, 25:179-188 (1983)) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 sec and the supernatant removed. The DNA-coated particles are then washed once in 400 µL 70% ethanol and resuspended in 40 µL of anhydrous ethanol. The DNA/particle suspension can be sonicated three times for one sec each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately five-ten plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

What is claimed is:

1. An isolated polynucleotide selected from the group consisting of:
   (a) an isolated nucleic acid sequence comprising a nucleotide sequence encoding a polypeptide having Δ9 elongase activity, wherein the polypeptide has at least 95% amino acid identity, based on the Clustal V method of alignment, when compared to an amino acid sequence as set forth in SEQ ID NO:2 or SEQ ID NO:5;
   (b) an isolated nucleic acid sequence comprising a nucleotide sequence encoding a polypeptide having Δ9 elongase activity, wherein the nucleotide sequence has at least 95% sequence identity, based on the BLASTN method of alignment, when compared to a nucleotide sequence as set forth in SEQ ID NO:1, SEQ ID NO:3, SEQ ID NO:4 or SEQ ID NO:6;
   (c) an isolated nucleic acid sequence comprising a nucleotide sequence encoding a polypeptide having Δ9 elongase activity, wherein the nucleotide sequence hybridizes with the nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; or
   (d) a complement of the nucleotide sequence of (a), (b) or (c), wherein the complement and the nucleotide sequence consist of the same number of nucleotides and are 100% complementary.

2. The polynucleotide of claim 1 wherein the nucleotide sequence comprises SEQ ID NO:1, SEQ ID NO:3, SEQ ID NO:4 or SEQ ID NO:6.

3. The polynucleotide of claim 2 selected from the group consisting of SEQ ID NO:1, SEQ ID NO:3, SEQ ID NO:4 or SEQ ID NO:6.

4. An isolated transformed host cell comprising the isolated nucleic acid sequence of claim 1.

5. The transformed host cell of claim 4 wherein the host cell is selected from the group consisting of: algae, bacteria, yeast, oomycetes, plants and fungi.

6. The transformed host cell of claim 5 wherein the host cell is a fungus selected from the group consisting of: *Thraustochytrium* sp., *Schizochytrium* sp. and *Mortierella* sp.

7. The transformed host cell of claim 5 wherein the yeast is an oleaginous yeast.

8. The transformed host cell of claim 7 wherein the oleaginous yeast is selected from the group consisting of: *Yarrowia, Candida, Rhodotorula, Rhodosporidium, Cryptococcus, Trichosporon* and *Lipomyces*.

9. The transformed host cell of claim 8 wherein the yeast is a *Yarrowia* sp.

10. The transformed yeast of claim 9 wherein the *Yarrowia* sp. Is selected from the group consisting of *Yarrowia lipolytica* ATCC #20362, *Yarrowia lipolytica* ATCC #8862, *Yarrowia lipolytica* ATCC #18944, *Yarrowia lipolytica* ATCC #76982 and *Yarrowia lipolytica* LGAM S(7)1.

11. A method for the production of eicosadienoic acid comprising:
   a) providing an isolated transformed yeast host cell comprising:
      (i) an isolated polynucleotide sequence encoding a polypeptide having Δ9 elongase activity, selected from the group consisting of:
         (1) an isolated nucleic acid sequence comprising a nucleotide sequence encoding a polypeptide having Δ9 elongase activity, wherein the polypeptide has at least 95% amino acid identity, based on the Clustal V method of alignment, when compared to an amino acid sequence as set forth in SEQ ID NO:2 or SEQ ID NO:5;
         (2) an isolated nucleic acid sequence comprising a nucleotide sequence encoding a polypeptide having Δ9 elongase activity, wherein the nucleotide sequence hybridizes with a the nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and (ii) a source of linoleic acid;

b) growing the yeast host cell of step (a) under conditions wherein the nucleic acid sequence encoding the Δ9 elongase polypeptide is expressed and the linoleic acid is converted to eicosadienoic acid; and, c) optionally recovering the eicosadienoic acid of step (b).

12. A method for the production of eicosatrienoic acid comprising:

a) providing an isolated transformed yeast host cell comprising:

(i) an isolated polynucleotide sequence encoding a polypeptide having Δ9 elongase activity, selected from the group consisting of:

(1) an isolated nucleic acid sequence comprising a nucleotide sequence encoding a polypeptide having Δ9 elongase activity, wherein the polypeptide has at least 95% amino acid identity, based on the Clustal V method of alignment, when compared to an amino acid sequence as set forth in SEQ ID NO:2 or SEQ ID NO:5;

(2) an isolated nucleic acid sequence comprising a nucleotide sequence encoding a polypeptide having Δ9 elongase activity, wherein the nucleotide sequence hybridizes with the nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and (ii) a source of -linolenic acid;

b) growing the host cell of step (a) under conditions wherein the nucleic acid sequence encoding the Δ9 elongase polypeptide is expressed and the -linolenic acid is converted to eicosatrienoic acid; and, c) optionally recovering the eicosatrienoic acid of step (b).

13. A method according to either of claims 11 or 12 wherein the isolated polynucleotide sequence encoding the Δ9 elongase polypeptide encodes a polypeptide comprising the amino acid sequence as set forth in SEQ ID NO:2 or SEQ ID NO:5.

14. A method according to claim 13 wherein the isolated polynucleotide sequence encoding the Δ9 elongase polypeptide is selected from the group consisting of:

a) SEQ ID NO:5, wherein at least 113 codons are codon-optimized for expression in *Yarrowia*; and, b) SEQ ID NO:2, wherein at least 106 codons are codon-optimized for expression in *Yarrowia*.

* * * * *

UNITED STATES PATENT AND TRADEMARK OFFICE
CERTIFICATE OF CORRECTION

PATENT NO. : 7,645,604 B2  
APPLICATION NO. : 11/601564  
DATED : January 12, 2010  
INVENTOR(S) : Damude et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this

Sixteenth Day of November, 2010

David J. Kappos  
*Director of the United States Patent and Trademark Office*